US011180782B2

(12) United States Patent
Kumaran et al.

(10) Patent No.: US 11,180,782 B2
(45) Date of Patent: Nov. 23, 2021

(54) METHODS FOR PRODUCTION OF OXYGENATED TERPENES

(71) Applicants: GIVAUDAN SA, Vernier (CH); MANUS BIOSYNTHESIS, INC., Cambridge, MA (US)

(72) Inventors: Ajikumar Parayil Kumaran, Cambridge, MA (US); Chin Giaw Lim, Allston, MA (US); Liwei Li, Arlington, MA (US); Souvik Ghosh, Cambridge, MA (US); Christopher Pirie, Cambridge, MA (US); Anthony Qualley, Beavercreek, OH (US); Geoff Marshall-Hill, Buckinghamshire (GB); Martin Preininger, Neuss (DE)

(73) Assignees: Givaudan SA, Vernier (CH); Manus Biosynthesis, Inc., Cambridge, MA (US)

( * ) Notice: Subject to any disclaimer, the term of this patent is extended or adjusted under 35 U.S.C. 154(b) by 58 days.

(21) Appl. No.: 16/669,051

(22) Filed: Oct. 30, 2019

(65) Prior Publication Data

US 2020/0224224 A1 Jul. 16, 2020

Related U.S. Application Data

(62) Division of application No. 15/505,022, filed as application No. PCT/US2015/046421 on Aug. 21, 2015, now Pat. No. 10,501,760.

(60) Provisional application No. 62/040,284, filed on Aug. 21, 2014.

(51) Int. Cl.

| | |
|---|---|
| ***C12P 7/26*** | (2006.01) |
| ***C12N 9/02*** | (2006.01) |
| ***A01N 27/00*** | (2006.01) |
| ***C12P 5/00*** | (2006.01) |
| ***A23L 27/12*** | (2016.01) |

(52) U.S. Cl.

CPC ................ *C12P 7/26* (2013.01); *A01N 27/00* (2013.01); *A23L 27/13* (2016.08); *C12N 9/0073* (2013.01); *C12P 5/002* (2013.01); *C12Y 114/13078* (2013.01); *A23V 2002/00* (2013.01); *C07K 2319/03* (2013.01)

(58) Field of Classification Search

None

See application file for complete search history.

(56) References Cited

U.S. PATENT DOCUMENTS

| | | | |
|---|---|---|---|
| 5,847,226 A | 12/1998 | Muller et al. | |
| 6,200,786 B1 | 3/2001 | Huang et al. | |
| 6,890,960 B1 | 5/2005 | Henderson et al. | |
| 7,211,420 B1 | 5/2007 | Wong et al. | |
| 7,273,735 B2 | 9/2007 | Schalk et al. | |
| 8,097,442 B2 | 1/2012 | Hitchman et al. | |
| 8,415,136 B1 | 4/2013 | Gardner et al. | |
| 8,512,988 B2 | 8/2013 | Ajikumar et al. | |
| 8,927,241 B2 | 1/2015 | Ajikumar et al. | |
| 9,284,570 B2 | 3/2016 | Stephanopoulos et al. | |
| 9,359,624 B2 | 6/2016 | Ajikumar et al. | |
| 9,494,130 B2 | 8/2016 | Ajikumar et al. | |
| 9,796,980 B2 | 10/2017 | Ajikumar et al. | |
| 9,957,527 B2 | 5/2018 | Ajikumar et al. | |
| 10,774,314 B2 * | 9/2020 | Donald | C12P 19/56 |
| 2011/0189717 A1 | 8/2011 | Ajikumar et al. | |
| 2012/0107893 A1 | 5/2012 | Ajikumar et al. | |
| 2012/0164678 A1 | 6/2012 | Stephanopoulos et al. | |
| 2012/0246767 A1 | 9/2012 | Amick et al. | |
| 2017/0002366 A1 | 1/2017 | Ajikumar et al. | |
| 2017/0002382 A1 | 1/2017 | Ajikumar et al. | |
| 2017/0332673 A1 | 11/2017 | Philippe et al. | |
| 2018/0135081 A1 | 5/2018 | Kumaran et al. | |
| 2018/0251738 A1 | 9/2018 | Donald et al. | |
| 2018/0327789 A1 | 11/2018 | Kumaran et al. | |

FOREIGN PATENT DOCUMENTS

| | | |
|---|---|---|
| JP | 2004067723 | 3/2004 |
| WO | 2006079020 | 7/2006 |
| WO | 2011060057 | 5/2011 |
| WO | 2016029187 | 2/2016 |

OTHER PUBLICATIONS

Database WPI Week 200423, Thomson Scientific, London, GB: AN 2004-244290, XP002752397, & JP 2004 067723 (Hasegawa Co. Ltd.) Mar. 4, 2004.

International Search Report and Written Opinion dated Dec. 14, 2015 for international application PCT/US2015/046369.

International Search Report and Written Opinion dated Mar. 22, 2016 for international application PCT/US2015/046421.

International Search Report and Written Opinion for International application PCT/US2016/047692.

"Beta-Nootkaton", Product information from Pubchem, downloaded from pubchem.ncbi.nim.nih.gov/compound/Nootkatol (Year: 2018).

"Predicted: en-kaurene oxidase, chloroplastic-like [*Malus domestica*]", Database Genpept XP002752377, Jun. 20, 2014.

Ajikumar, et al., "Isoprenoid Pathway Optimization for Taxol Precursor Overproduction in *Escherichia Coli*", Science, 2010, vol. 1, No. 330 (6000), pp. 1-11.

Chang, et al., "Engineering *Escherichia Coli*for Production of Functionalized Terpenoids Using Plant P450s", Nature, 2007, Chemical Biology, vol. 3, No. 5, pp. 274-277.

Drew, et al., "Transcritome Analysis of Thapsia laciniata Rouy Provides Insights into Terpenoid Biosynthesis and Diversity in Apiaceae", 2013 International Journal of Molecular Sciences, 2013, vol. 14, pp. 9080-9098.

(Continued)

*Primary Examiner* — Anand U Desai
(74) *Attorney, Agent, or Firm* — Stoel Rives LLP

(57) ABSTRACT

The present disclosure relates to methods for producing oxygenated terpenoids, and preparation of compositions and formulations thereof. Polynucleotides, derivative enzymes, and host cells for use in such methods are also provided.

20 Claims, 76 Drawing Sheets

Specification includes a Sequence Listing.

(56) References Cited

OTHER PUBLICATIONS

Hotze, et al., "Cinnamate 4-hydroxylase from Catharanthus Roseuseand and Strategy for the Functional Expression of Plant Cytochrome P.450 Proteins as Translational Fusions with P450 Reductase in *Escherichia Coli*", FEBS Letters, 1995, vol. 374, pp. 345-350.
Humphrey, et al., "Spatial organization of four enzymes from Stevia rebaudiana that are involved in steviol glycoside synthesis", Plant Molecular Biology (2006) 61:47-62.
Humphrey, et al., "Subname: full-ent-kaurene oxidase CYP701A5", UNIPROT Database, Feb. 19, 2014.
Humphrey, et al., "Subname: Full-kaurene oxidase", UNIPROT Database, Jul. 9, 2014.
King, "Production of Bioactive Diterpenoids in the Euphorbiaceae Depends on Evolutionary Conserved Gene Clusters", The Plant Cell, 2014, vol. 26, pp. 3286-3298.
Kumaran, et al., Notice of Allowance dated Apr. 4, 2019 for U.S. Appl. No. 15/505,022.
Kumaran, et al., Office Action dated Mar. 19, 2019 for U.S. Appl. No. 15/505,503.
Kumaran, et al., Office Action dated Nov. 23, 2018 for U.S. Appl. No. 15/505,022.
Kumaran, et al., Restriction Requirement dated Dec. 20, 2018 for U.S. Appl. No. 15/505,503.
Kumaran, et al., Restriction Requirement dated Oct. 9, 2018 for U.S. Appl. No. 15/505,022.
Lange, et al., "Isoprenoid Biosynthesis: The Evolution of Two Ancient and Distinct Pathways Across Genomes", PNAS 97:13172-13177,2000 (Year 2000).
Leonard, et al., "Functional Expression of a P450 Flavonoid Hydroxy Lase for the Biosynthesis of Plant-Specific Hydroxlated Flavonols in *Escherichia Coli*", Metabolic Engineering, 2007, vol. 8, pp. 172-181.
Schuckel, et al., "A gene-fusion approach to enabling plant cytochromes P450 for Biocatalysis", Chembiochem, vol. 13, No. 18, Nov. 5, 2012, pp. 2758-2763.
Seifert, et al., "Rational design of a minimal and highly enriched CYP102A1 mutant library with improved regio-, stereo, and chemoselectivity", Chembiochem, vol. 10, No. 5,Mar. 23, 2009.
Sing, "Chemistry of Terpenoids and Carotenoids", Discovery Publishing House, New Delhi, 2007, pp. 3 and 4 (Year: 2007).
Wriessn Egger, et al., "Production of the sesquiterpenoid (+)-nootkalone by metabolic engineering of Pichia pastoris". Metabolic Engineering, vol. 24, Apr. 16, 2014, pp. 18-29.

* cited by examiner

>VvVS [Vitis vinifera]

MSTQVSASSLAQIPQPKNRPVANFHPNIWGDQFITYTPEDKVTRACKEEQIEDLKKEV
KRKLTAAAVANPSQLLNFIDAVQRLGVAYHFEQEIEEALQHICNSFHDCNDMDGDLYN
IALGFRLLRQQGYTISCDIFNKFTDERGRFKEALISDVRGMLGLYEAAHLRVHGEDIL
AKALAFTTTHLKAMVESLGYHLAEQVAHALNRPIRKGLERLEARWYISVYQDEAFHDK
TLLELAKLDFNLVQSLHKEELSNLARWWKELDFATKLPFARDRLVEGYFWMHGVYFEP
QYLRGRRILTKVIAMTSILDDIHDAYGTPEELKLFIEAIERWDINSINQLPEYMKLCY
VALLDVYKEIEEEMEKEGNQYRVHYAKEVMKNQVRAYFAEAKWLHEEHVPAFEEYMRV
ALASSGYCLLATTSFVGMGEIATKEAFDWVTSDPKIMSSSNFITRLMDDIKSHKFEQK
RGHVTSAVECYMKQYGVSEEQVYSEFQKQIENAWLDINQECLKPTAVSMPLLARLLNF
TRTMDVIYKEQDSYTHVGKVMRDNIASVFINAVI (SEQ ID NO: 1)

ATGGCTACGCAGGTCTCAGCCTCGTCACTGGCACAAATCCCGCAGCCGAAAAATCGTC
CGGTGGCGAACTTCCATCCGAATATCTGGGGTGACCAGTTTATCACGTATACCCCGGA
AGATAAAGTGACCCGTGCGTGCAAGGAAGAACAAATTGAAGACCTGAAAAAGGAAGTC
AAACGCAAGCTGACCGCAGCAGCAGTGGCAAACCCGTCTCAGCTGCTGAATTTTATCG
ATGCGGTTCAACGTCTGGGCGTCGCCTATCATTTCGAACAGGAAATTGAAGAAGCACT
GCAACATATCTGCAACAGCTTTCACGATTGTAATGATATGGACGGCGATCTGTATAAC
ATTGCTCTGGGTTTCCGTCTGCTGCGCCAGCAAGGCTACACGATTTCCTGTGACATCT
TTAATAAATTCACCGATGAACGTGGTCGCTTTAAGGAAGCGCTGATCTCAGACGTTCG
TGGCATGCTGGGTCTGTATGAAGCTGCGCATCTGCGCGTCCACGGCGAAGATATTCTG
GCCAAAGCACTGGCTTTCACCACGACCCACCTGAAGGCGATGGTCGAATCTCTGGGTT
ACCATCTGGCAGAACAGGTGGCACACGCCCTGAACCGTCCGATCCGCAAAGGCCTGGA
ACGTCTGGAAGCGCGCTGGTATATTAGTGTGTACCAGGACGAAGCATTTCATGATAAA
ACCCTGCTGGAACTGGCTAAGCTGGATTTCAACCTGGTTCAATCTCTGCACAAAGAAG
AACTGAGTAATCTGGCCCGTTGGTGGAAAGAACTGGACTTTGCGACCAAGCTGCCGTT
CGCCCGTGATCGCCTGGTTGAAGGCTATTTTTGGATGCATGGTGTCTATTTCGAACCG
CAGTACCTGCGCGGTCGTCGCATTCTGACGAAAGTGATCGCAATGACCTCGATTCTGG
ATGACATCCACGACGCTTACGGCACCCCGGAAGAACTGAAACTGTTTATTGAAGCGAT
CGAACGTTGGGATATTAACAGCATCAATCAGCTGCCGGAATATATGAAACTGTGCTAC
GTGGCCCTGCTGGATGTTTACAAGGAAATCGAAGAAGAAATGGAAAAGGAAGGTAACC
AGTATCGTGTTCATTACGCGAAAGAAGTCATGAAGAATCAAGTGCGCGCCTACTTTGC
AGAAGCTAAATGGCTGCATGAAGAACACGTGCCGGCGTTCGAAGAATATATGCGCGTT
GCGCTGGCCAGCTCTGGCTACTGTCTGCTGGCCACGACCTCTTTTGTGGGCATGGGTG
AAATTGCAACGAAAGAAGCGTTTGACTGGGTTACCAGTGATCCGAAGATTATGAGTTC
CTCAAACTTTATCACCCGTCTGATGGATGACATTAAATCCCATAAGTTCGAACAGAAA
CGCGGTCACGTCACCTCAGCCGTGGAATGCTATATGAAACAGTACGGCGTTTCGGAAG
AACAAGTCTATAGCGAATTTCAGAAACAAATCGAAAACGCATGGCTGGATATTAATCA
GGAATGTCTGAAACCGACGGCAGTCTCCATGCCGCTGCTGGCTCGTCTGCTGAATTTT
ACGCGCACGATGGATGTGATCTATAAAGAACAGGATTCGTACACCCATGTGGGCAAGG
TTATGCGCGATAACATTGCAAGCGTGTTCATTAATGCTGTTATCTAA (SEQ ID
NO: 2)

FIG. 3A

>Vv1M1 | engineered valencene synthase

MATQVSASSLAQIPQPKNRPVANFHPNIWGDQFITYTPEDKVTRACKEEQIEDLKKEV
KRKLTAAAVANPSQLLNFIDAVQRLGVAYHFEQEIEEALQHICNSFHDCNDMDGDLYN
IALGFRLLRQQGYTISCDIFNKFTDERGRFKEALISDVRGMLGLYEAAHLRVHGEDIL
AKALAFTTTHLKAMVESLGYHLAEQVAHALNRPIRKGLERLEARWYISVYQDEAFHDK
TLLELAKLDFNLVQSLHKEELSNLARWWKELDFATKLPFARDRLVEGYFWMHGVYFEP
QYLRGRRILTKVIAMTSILDDIHDAYGSPEELKLFIEAIEKWDESSINQLPEYMKLCF
VALIDVYNEIEEEMEKEGNQYRIHYLKEVMKNQVRAYFAEAKWLHDEHVPAFEEYMRV
ALASSGYCLLAVTSFVGMGEIVTKEAFDWVTSDPKLMSSSNFITRLMDDIKSHKFEQK
RGHVTSAVECYMKQYGVTEEQVYSEFKKQIENAWLDINQECLKPTAVPMPLLARLLNF
TRTMDVIYKEQDSYTHVGKVMRDNIASVFINPVI (SEQ ID NO: 3)

ATGGCAACCCAGGTGAGTGCAAGCAGCCTGGCCCAAATCCCTCAGCCGAAAAACCGCC
CGGTTGCAAACTTCCACCCTAATATCTGGGGCGATCAGTTCATCACCTATACCCCGGA
AGATAAAGTGACAAGGGCCTGCAAAGAGGAGCAGATCGAGGACCTGAAAAAAGAGGTG
AAGCGCAAGCTGACCGCAGCCGCAGTGGCAAACCCGAGCCAACTGTTAAACTTCATCG
ATGCCGTGCAGCGCCTGGGCGTTGCCTATCACTTCGAGCAGGAAATCGAAGAAGCCCT
ACAGCACATCTGTAACAGCTTCCACGATTGTAACGACATGGATGGCGACTTATACAAC
ATAGCATTAGGTTTCCGCTTACTGCGTCAGCAGGGCTACACCATAAGCTGCGACATCT
TTAACAAGTTTACCGACGAGCGCGGTCGTTTTAAAGAGGCGCTGATTAGCGACGTTCG
CGGCATGTTAGGTCTGTACGAAGCCGCACATCTGCGCGTGCACGGCGAAGACATTCTG
GCGAAGGCGCTGGCATTCACAACCACACACCTGAAGGCAATGGTGGAAAGTCTGGGCT
ACCACTTAGCCGAGCAGGTTGCCCATGCACTGAATCGCCCGATTCGTAAGGGCCTGGA
ACGCCTGGAAGCCCGCTGGTACATCAGTGTTTATCAGGATGAAGCCTTTCATGATAAG
ACCCTGCTGGAGCTGGCAAAGCTGGATTTCAACCTGGTTCAGAGCCTGCATAAGGAAG
AGCTGAGCAACCTGGCCCGTTGGTGGAAGGAGCTGGATTTCGCAACCAAGCTGCCGTT
CGCCAGGGACAGGTTAGTTGAAGGCTACTTCTGGATGCACGGCGTTTACTTCGAGCCG
CAATACCTGCGTGGCCGCCGCATCCTGACGAAGGTGATCGCCATGACCAGCATTCTGG
ACGACATCCACGATGCGTACGGGAGCCCTGAGGAGTTAAAGCTGTTCATCGAGGCAAT
CGAGAAGTGGGATGAGAGTAGCATCAACCAACTGCCGGAGTATATGAAACTGTGCTTC
GTGGCCCTGATTGATGTTTACAATGAGATTGAAGAGGAGATGGAGAAAGAGGGGAACC
AGTACCGCATCCACTACCTGAAAGAGGTGATGAAGAATCAGGTGCGCGCATACTTCGC
AGAGGCCAAATGGCTGCATGATGAGCATGTTCCTGCCTTCGAGGAGTACATGCGCGTG
GCATTAGCCAGCAGTGGTTACTGTCTGTTAGCCGTTACGAGCTTCGTGGGTATGGGCG
AGATCGTGACCAAAGAGGCATTCGACTGGGTGACGAGCGACCCGAAGCTGATGAGCAG
CAGCAACTTCATCACCCGTCTGATGGACGACATCAAGAGCCACAAGTTCGAGCAGAAA
CGCGGTCACGTTACCAGCGCCGTGGAGTGCTACATGAAGCAGTACGGCGTGACAGAGG
AGCAAGTGTACAGCGAGTTCAAGAAACAAATCGAGAACGCCTGGCTGGACATCAACCA
AGAGTGCCTGAAACCGACCGCAGTGCCGATGCCTCTGTTAGCCCGTCTGCTGAATTTC
ACACGCACGATGGACGTTATCTACAAGGAGCAGGATAGCTACACCCACGTTGGTAAGG
TGATGCGCGACAACATCGCCAGTGTGTTCATCAACCCGGTGATCTAA (SEQ ID
NO: 4)

FIG. 3A (Cont'd)

>Vv2M1 | engineered valencene synthase
MATQVSASSLAQIPQPKNRPVANFHPNIWGDQFITYTPEDKVTRACKEEQIEDLKKEV
KRKLTAAAVANPSQLLNFIDAVQRLGVAYHFEQEIEEALQHICNSFHDCNDMDGDLYN
IALGFRLLRQQGYTISCDIFNKFTDERGRFKEALISDVRGMLGLYEAAHLRVHGEDIL
AKALAFTTTHLKAMVESLGYHLAEQVAHALNRPIRKGLERLEARWYISVYQDEAFHDK
TLLELAKLDFNLVQSLHKEELSNLARWWKELDFATKLPFARDRLVEGYFWMHGVYFEP
QYLRGRRILTKVIALTSILDDIHDAYGTPEELKLFIEAIEKWDESSINQLPEYMKLCY
VALLDVYNEIEEEMEKEGNQYRIHYLKEVMKNQVRAYFAEAKWLHDEHVPAFEEYMRV
ALASSGYCLLAVTSFVGMGEIVTKEAFDWVTSDPRIMSSSNFITRLMDDIKSHKFEQK
RGHVTSAVECYMKQYAVTEEQVYSEFKKQIENAWLDINQECLKPTAVPMPLLARLLNF
TRTMDVIYKEQDSYTHVGKTMRDNIASVFINPVI (SEQ ID NO: 5)

ATGGCAACCCAGGTGAGTGCAAGCAGCCTGGCCCAAATCCCTCAGCCGAAAAACCGCC
CGGTTGCAAACTTCCACCCTAATATCTGGGGCGATCAGTTCATCACCTATACCCCGGA
AGATAAAGTGACAAGGGCCTGCAAAGAGGAGCAGATCGAGGACCTGAAAAAAGAGGTG
AAGCGCAAGCTGACCGCAGCCGCAGTGGCAAACCCGAGCCAACTGTTAAACTTCATCG
ATGCCGTGCAGCGCCTGGGCGTTGCCTATCACTTCGAGCAGGAAATCGAAGAAGCCCT
ACAGCACATCTGTAACAGCTTCCACGATTGTAACGACATGGATGGCGACTTATACAAC
ATAGCATTAGGTTTCCGCTTACTGCGTCAGCAGGGCTACACCATAAGCTGCGACATCT
TTAACAAGTTTACCGACGAGCGCGGTCGTTTTAAAGAGGCGCTGATTAGCGACGTTCG
CGGCATGTTAGGTCTGTACGAAGCCGCACATCTGCGCGTGCACGGCGAAGACATTCTG
GCGAAGGCGCTGGCATTCACAACCACACACCTGAAGGCAATGGTGGAAAGTCTGGGCT
ACCACTTAGCCGAGCAGGTTGCCCATGCACTGAATCGCCCGATTCGTAAGGGCCTGGA
ACGCCTGGAAGCCCGCTGGTACATCAGTGTTTATCAGGATGAAGCCTTTCATGATAAG
ACCCTGCTGGAGCTGGCAAAGCTGGATTTCAACCTGGTTCAGAGCCTGCATAAGGAAG
AGCTGAGCAACCTGGCCCGTTGGTGGAAGGAGCTGGATTTCGCAACCAAGCTGCCGTT
CGCCAGGGACAGGTTAGTTGAAGGCTACTTCTGGATGCACGGCGTTTACTTCGAGCCG
CAATACCTGCGTGGCCGCCGCATCCTGACGAAGGTGATCGCCCTGACCAGCATTCTGG
ACGACATCCACGATGCGTACGGGACCCCTGAGGAGTTAAAGCTGTTCATCGAGGCAAT
CGAGAAGTGGGATGAGAGTAGCATCAACCAACTGCCGGAGTATATGAAACTGTGCTAT
GTGGCCCTGCTGGATGTTTACAATGAGATTGAAGAGGAGATGGAGAAAGAGGGGAACC
AGTACCGCATCCACTACCTGAAAGAGGTGATGAAGAATCAGGTGCGCGCATACTTCGC
AGAGGCCAAATGGCTGCATGATGAGCATGTTCCTGCCTTCGAGGAGTACATGCGCGTG
GCATTAGCCAGCAGTGGTTACTGTCTGTTAGCCGTTACGAGCTTCGTGGGTATGGGCG
AGATCGTGACCAAAGAGGCATTCGACTGGGTGACGAGCGACCCGCGTATTATGAGCAG
CAGCAACTTCATCACCCGTCTGATGGACGACATCAAGAGCCACAAGTTCGAGCAGAAA
CGCGGTCACGTTACCAGCGCCGTGGAGTGCTACATGAAGCAGTACGCAGTGACAGAGG
AGCAAGTGTACAGCGAGTTCAAGAAACAAATCGAGAACGCCTGGCTGGACATCAACCA
AGAGTGCCTGAAACCGACCGCAGTGCCGATGCCTCTGTTAGCCCGTCTGCTGAATTTC
ACACGCACGATGGACGTTATCTACAAGGAGCAGGATAGCTACACCCACGTTGGTAAGA
CCATGCGCGACAACATCGCCAGTGTGTTCATCAACCCGGTGATCTAA (SEQ ID
NO: 6)

*FIG. 3A (Cont'd)*

>Vv1M5 | engineered valencene synthase

MATQVSASSLAQIPQPKNRPVANFHPNIWGDQFITYTPEDKVTRAKKEEQIEDLKKEV
KRKLTAAAVANPSQLLNFIDAVQRLGVAYHFEQEIEEALQHICNSFHDCNDMDGDLYN
IALGFRLLRQQGYTISCDIFNKFTDERGRFKEALISDVRGMLGLYEAAHLRVHGEDIL
AKALAFTTTHLKAMVESLGYHLAEQVAHALNRPIRKGLERLEARWYISVYQDEAFHDK
TLLELAKLDFNLVQSLHKEELSNLARWWKELDFATKLPFARDRLVEGYFWMMGVYFEP
QYLRGRRILTKVIAMTSILDDIHDAYGSPEELKLFIEAIEKWDESSINQLPEYMKLCF
VALIDVYNEIEEEMEKEGNQYRIHYLKEVMKNQVRAYFAEAKWLHDEHVPAFEEYMRV
ALASSGYCLLAVTSFVGMGEIVTKEAFDWVTSDPKLMSSSNTITRLMDDIKSHKFEQK
RGHVTSAVECYMKQYGVTEEQVYSEFKKQIENAWLDINQECLKPTAVPMPLLARLLNF
TRTMDVIYKEEDSYTHVGKVMRDNIASVFINPVI (SEQ ID NO: 7)

ATGGCAACCCAGGTGAGTGCAAGCAGCCTGGCCCAAATCCCTCAGCCGAAAAACCGCC
CGGTTGCAAACTTCCACCCTAATATCTGGGGCGATCAGTTCATCACCTATACCCCGGA
AGATAAAGTGACAAGGGCCAAAAAAGAGGAGCAGATCGAGGACCTGAAAAAAGAGGTG
AAGCGCAAGCTGACCGCAGCCGCAGTGGCAAACCCGAGCCAACTGTTAAACTTCATCG
ATGCCGTGCAGCGCCTGGGCGTTGCCTATCACTTCGAGCAGGAAATCGAAGAAGCCCT
ACAGCACATCTGTAACAGCTTCCACGATTGTAACGACATGGATGGCGACTTATACAAC
ATAGCATTAGGTTTCCGCTTACTGCGTCAGCAGGGCTACACCATAAGCTGCGACATCT
TTAACAAGTTTACCGACGAGCGCGGTCGTTTTAAAGAGGCGCTGATTAGCGACGTTCG
CGGCATGTTAGGTCTGTACGAAGCCGCACATCTGCGCGTGCACGGCGAAGACATTCTG
GCGAAGGCGCTGGCATTCACAACCACACACCTGAAGGCAATGGTGGAAAGTCTGGGCT
ACCACTTAGCCGAGCAGGTTGCCCATGCACTGAATCGCCCGATTCGTAAGGGCCTGGA
ACGCCTGGAAGCCCGCTGGTACATCAGTGTTTATCAGGATGAAGCCTTTCATGATAAG
ACCCTGCTGGAGCTGGCAAAGCTGGATTTCAACCTGGTTCAGAGCCTGCATAAGGAAG
AGCTGAGCAACCTGGCCCGTTGGTGGAAGGAGCTGGATTTCGCAACCAAGCTGCCGTT
CGCCAGGGACAGGTTAGTTGAAGGCTACTTCTGGATGATGGGCGTTTACTTCGAGCCG
CAATACCTGCGTGGCCGCCGCATCCTGACGAAGGTGATCGCCATGACCAGCATTCTGG
ACGACATCCACGATGCGTACGGGAGCCCTGAGGAGTTAAAGCTGTTCATCGAGGCAAT
CGAGAAGTGGGATGAGAGTAGCATCAACCAACTGCCGGAGTATATGAAACTGTGCTTC
GTGGCCCTGATTGATGTTTACAATGAGATTGAAGAGGAGATGGAGAAAGAGGGGAACC
AGTACCGCATCCACTACCTGAAAGAGGTGATGAAGAATCAGGTGCGCGCATACTTCGC
AGAGGCCAAATGGCTGCATGATGAGCATGTTCCTGCCTTCGAGGAGTACATGCGCGTG
GCATTAGCCAGCAGTGGTTACTGTCTGTTAGCCGTTACGAGCTTCGTGGGTATGGGCG
AGATCGTGACCAAAGAGGCATTCGACTGGGTGACGAGCGACCCGAAGCTGATGAGCAG
CAGCAACACCATCACCCGTCTGATGGACGACATCAAGAGCCACAAGTTCGAGCAGAAA
CGCGGTCACGTTACCAGCGCCGTGGAGTGCTACATGAAGCAGTACGGCGTGACAGAGG
AGCAAGTGTACAGCGAGTTCAAGAAACAAATCGAGAACGCCTGGCTGGACATCAACCA
AGAGTGCCTGAAACCGACCGCAGTGCCGATGCCTCTGTTAGCCCGTCTGCTGAATTTC
ACACGCACGATGGACGTTATCTACAAGGAGGAAGATAGCTACACCCACGTTGGTAAGG
TGATGCGCGACAACATCGCCAGTGTGTTCATCAACCCGGTGATCTAA (SEQ ID
NO: 8)

*FIG. 3A (Cont'd)*

>Vv2M5 | engineered valencene synthase
MATQVSASSLAQIPQPKNRPVANFHPNIWGDQFITYTPEDKVTRAKKEEQIEDLKKEV
KRKLTAAAVANPSQLLNFIDAVQRLGVAYHFEQEIEEALQHICNSFHDCNDMDGDLYN
IALGFRLLRQQGYTISCDIFNKFTDERGRFKEALISDVRGMLGLYEAAHLRVHGEDIL
AKALAFTTTHLKAMVESLGYHLAEQVAHALNRPIRKGLERLEARWYISVYQDEAFHDK
TLLELAKLDFNLVQSLHKEELSNLARWWKELDFATKLPFARDRLVEGYFWMMGVYFEP
QYLRGRRILTKVIALTSILDDIHDAYGTPEELKLFIEAIEKWDESSINQLPEYMKLCY
VALLDVYNEIEEEMEKEGNQYRIHYLKEVMKNQVRAYFAEAKWLHDEHVPAFEEYMRV
ALASSGYCLLAVTSFVGMGEIVTKEAFDWVTSDPRIMSSSNTITRLMDDIKSHKFEQK
RGHVTSAVECYMKQYAVTEEQVYSEFKKQIENAWLDINQECLKPTAVPMPLLARLLNF
TRTMDVIYKEEDSYTHVGKTMRDNIASVFINPVI (SEQ ID NO: 9)

ATGGCAACCCAGGTGAGTGCAAGCAGCCTGGCCCAAATCCCTCAGCCGAAAAACCGCC
CGGTTGCAAACTTCCACCCTAATATCTGGGGCGATCAGTTCATCACCTATACCCCGGA
AGATAAAGTGACAAGGGCCAAAAAAGAGGAGCAGATCGAGGACCTGAAAAAAGAGGTG
AAGCGCAAGCTGACCGCAGCCGCAGTGGCAAACCCGAGCCAACTGTTAAACTTCATCG
ATGCCGTGCAGCGCCTGGGCGTTGCCTATCACTTCGAGCAGGAAATCGAAGAAGCCCT
ACAGCACATCTGTAACAGCTTCCACGATTGTAACGACATGGATGGCGACTTATACAAC
ATAGCATTAGGTTTCCGCTTACTGCGTCAGCAGGGCTACACCATAAGCTGCGACATCT
TTAACAAGTTTACCGACGAGCGCGGTCGTTTTAAAGAGGCGCTGATTAGCGACGTTCG
CGGCATGTTAGGTCTGTACGAAGCCGCACATCTGCGCGTGCACGGCGAAGACATTCTG
GCGAAGGCGCTGGCATTCACAACCACACACCTGAAGGCAATGGTGGAAAGTCTGGGCT
ACCACTTAGCCGAGCAGGTTGCCCATGCACTGAATCGCCCGATTCGTAAGGGCCTGGA
ACGCCTGGAAGCCCGCTGGTACATCAGTGTTTATCAGGATGAAGCCTTTCATGATAAG
ACCCTGCTGGAGCTGGCAAAGCTGGATTTCAACCTGGTTCAGAGCCTGCATAAGGAAG
AGCTGAGCAACCTGGCCCGTTGGTGGAAGGAGCTGGATTTCGCAACCAAGCTGCCGTT
CGCCAGGGACAGGTTAGTTGAAGGCTACTTCTGGATGATGGGCGTTTACTTCGAGCCG
CAATACCTGCGTGGCCGCCGCATCCTGACGAAGGTGATCGCCCTGACCAGCATTCTGG
ACGACATCCACGATGCGTACGGGACCCCTGAGGAGTTAAAGCTGTTCATCGAGGCAAT
CGAGAAGTGGGATGAGAGTAGCATCAACCAACTGCCGGAGTATATGAAACTGTGCTAT
GTGGCCCTGCTGGATGTTTACAATGAGATTGAAGAGGAGATGGAGAAAGAGGGGAACC
AGTACCGCATCCACTACCTGAAAGAGGTGATGAAGAATCAGGTGCGCGCATACTTCGC
AGAGGCCAAATGGCTGCATGATGAGCATGTTCCTGCCTTCGAGGAGTACATGCGCGTG
GCATTAGCCAGCAGTGGTTACTGTCTGTTAGCCGTTACGAGCTTCGTGGGTATGGGCG
AGATCGTGACCAAAGAGGCATTCGACTGGGTGACGAGCGACCCGCGTATTATGAGCAG
CAGCAACACCATCACCCGTCTGATGGACGACATCAAGAGCCACAAGTTCGAGCAGAAA
CGCGGTCACGTTACCAGCGCCGTGGAGTGCTACATGAAGCAGTACGCAGTGACAGAGG
AGCAAGTGTACAGCGAGTTCAAGAAACAAATCGAGAACGCCTGGCTGGACATCAACCA
AGAGTGCCTGAAACCGACCGCAGTGCCGATGCCTCTGTTAGCCCGTCTGCTGAATTTC
ACACGCACGATGGACGTTATCTACAAGGAGGAAGATAGCTACACCCACGTTGGTAAGA
CCATGCGCGACAACATCGCCAGTGTGTTCATCAACCCGGTGATCTAA (SEQ ID
NO: 10)

FIG. 3A (Cont'd)

>VS2 | engineered valencene synthase

MATQVSASSLAQIPQPKNRPVANFHPNIWGDQFITYTPEDKVTRAKKEEQIEDLKKEVK
RKLTAAAVANPSQLLNFIDAVQRLGVAYHFEQEIEEALQHICNSFHDCNDMDGDLYNIA
LGFRLLRQQGYTISCDIFNKFTDERGRFKEALISDVRGMLGLYEAAHLRVHGEDILAKA
LAFTTTHLKAMVESLGYHLAEQVAHALNRPIRKGLERLEARWYISVYQDEAFHDKTLLE
LAKLDFNLVQSLHKEELSNLARWWKELDFATKLPFARDRLVEGYFWMMGVYFEPQYLRG
RRILTKVIALTSILDDIHDAYGTPEELKLFIEAIEKWDESSINQLPEYMKLCYVALLDV
YNEIEEEMEKEGNQYRIHYLKEVMKNQVRAYFAEAKWLHDEHVPAFEEYMRVALASSGY
CLLAVTSFVGMGEIVTKEAFDWVTSDPRIMSSSNTITRLMDDIKSHKFEQKRGHVTSAV
ECYMKQYAVTEEQVYSEFKKQIENAWLDINQECLKPTAVPMPLLARLLNFTRTMDVIYK
EEDSYTHVGKTMRDNIASVFINPVI (SEQ ID NO: 11)

ATGGCAACCCAGGTGAGCGCCAGTAGCCTGGCACAAATCCCGCAGCCTAAAAACCGCC
CTGTTGCCAATTTCCATCCGAACATCTGGGGCGACCACTTTATCACCTACACCCCGGA
AGACAAAGTGACCCGCGCCAAAAAAGAAGAGAGGATTGAAGATCTGAAGGAAGAAGTG
AAACGCAAACTGACCGCAGCCGCCGTGGCCAATCCGAGTCAACTGCTGAACTTCATTG
ATGCAGTTCAGCGCCTGGGCGTTGCCTATCACTTTGAGCAGGAGATCGAGGAGGCATT
ACAGCATATTTGTAATAGCTTTCACGACTGCAATGATATGGATGGCGACCTGTATAAT
ATCGCCCTGCTATTTCGTCTGCTGCGCCAACAGGGTTACACAATCAGTTGCGACATCT
TTAACAAGTTCACCGATGAAGAGGGCCGCTTTAAAGAAGCCCTGATTAGCGACGTGCG
CGGTATGTTAGGCCTGTATGAAGCAGCCCACCTGCGCGTTCACGGCGAAGACATCCTG
GCAGAGGCACTGGCCTTTACAACCACCCACCTGAAAGCAATGGTTGAATCGCTGGGCT
ACCATCTGGCCGAGCAAGTGAGGCACGCCTTAAACCGTCCGATCCGTAAAGGCATGGA
ACGTCTGGAAGCACGTTGGTACATCAGCATATACCAGGATGAGGCCTTTCATGACAAA
ACCCTGCTGGAGCTGGCCAAACTGGACTTCAACCTGGTGCAGAGCCTGCACAAAGAAG
AGCTGAGCAATCTGGCACGCTGGTGGAAGGAGCTGGATTTTGCCACCAAACTGCCTTT
TGCCCGCGACCGTTTAGTTGAAGGCTACTTTTGGATGATGGGTGTGTATTTTGAGCCG
CAGTATCTGCGTGGCCGTCGCATCCTGACAAAGGTGATCGCCCTGACCAGCATCATTG
ACGACATCCACGATGCCTATGGCACCCCGGAGGAACTGAAACTGTTTATCGAGGCCAT
CGAAAAATGGGACGAGAGCAGCATCAACCAACTGCCTGAGTACATGAAGCTGTGCTAT
GTGGCCCTGCTGGACGTGTATAATGAAATCGAAGAGGAGATGGAAAAGGAGGGCAACC
AATACCGTATCCACTACCTGAAGGAGGTTATGAAAAACCAGGTGCGTGCCTACTTTGC
AGAGGCAAAATGGCTGCACGATGAGCATGTGCCGGCCTTTGAAGAATACATGCGCGTT
GCCCTGGCCAGCAGTGGTTATTGTCTGCTGGCCGTTACAAGTTTTGTGGGCATGGGCG
AGATCGTGACAAAGGAAGCCTTTGACTGGGTTACAAGCGACCCGCGCATCATAAGCAG
CAGCAACACAATTACACGCCTGATGGACGACATTAAAAGCCATAAATTTGAACAGAAA
CGCGGTCATGTGACCAGCGCCGTGGAATGCTACATGAAACAGTACGCCGTGACCGAAG
AGCAGGTTTACGAGGAATTTAAAAAACAGATTGAAAACGCATGGCTGGACATTAATCA
GGAGTGTCTGAAGCCGACCGCAGTGCCGATGCCGCTGTTAGCACGCCTGCTGAATTTC
ACCCGCACAATGGATGTGATTTATAAAGAAGAAGACAGCTATACCCATGTGGGCAAGA
CCATGCGCGACAACATCGCCAGCGTGTTTATCAACCCTGTGATCTAA (SEQ ID
NO: 120)

FIG. 3A (Cont'd)

>CsVS | Citrus sinensis valencene synthase

MASGETFRPTADFHPSLWRNHFLKGASDFKTVDHTATQERHEALKEEVRRMITDAEDKP
VQKLRLIDEVQRLGVAYHFEKEIGDAIQKLCPIYIDSNRADLHTVSLHFRLLRQQGIKI
SCDVFEKFKDDEGRFKSSLINDVQGMLSLYEAAYMAVRGEHILDEAIAFTTTHLKSLVA
QDHVTPKLAEQINHALYRPLRKTLPRLEARYFMSMINSTSDHLCNKTLLNFAKLDFNIL
LELHKEELNELTKWWKDLDFTTKLPYARDRLVELYFWDLGTYFEPQYAFGRKIMTQLNY
ILSIIDDTYDAYGTLEELSLFTEAVQRWNIEAVDMLPEYMKLIYRTLLDAFNEIEEDMA
KQGRSHCVRYAKEENQKVIGAYSVQAKWFSEGYVPTIEEYMPIALTSCAYTFVITNSFL
GMGDFATKEVFEWISNNPKVVKAASVICRLMDDMQGHEFEQKRGHVASAIECYTKQHGV
SKEEAIKMFEEEVANAWKDINEELMMKPTVVARPLLGTILNLARAIDFIYKEDDGYTHS
YLIKDQIASVLGDHVPF (SEQ ID NO: 12)

ATGGCCTCCGGCGAAACCTTCCGTCCGACCGCAGACTTCCATCCGTCACTGTGGCGTA
ATCACTTCCTGAAAGGCGCAAGCGACTTCAAAACGGTGGATCATACGGCAACCCAGGA
ACGTCACGAAGCTCTGAAGGAAGAAGTCCGTCGCATGATTACCGATGCCGAAGACAAA
CCGGTGCAGAAGCTGCGTCTGATCGATGAAGTTCAACGCCTGGGCGTCGCGTATCATT
TTGAAAAAGAAATTGGTGACGCCATCCAGAAGCTGTGCCCGATTTACATCGATAGCAA
CCGCGCAGACCTGCATACCGTGTCTCTGCACTTTCGTCTGCTGCGCCAGCAAGGCATC
AAGATCAGCTGTGATGTTTTCGAAAAGTTCAAGGATGACGAAGGCCGTTTCAAAAGCT
CTCTGATTAATGATGTTCAGGGTATGCTGTCTCTGTATGAAGCGGCCTACATGGCGGT
CCGCGGTGAACATATTCTGGATGAAGCGATCGCCTTTACCACGACCCATCTGAAAAGC
CTGGTGGCCCAGGACCACGTTACGCCGAAGCTGGCGGAACAAATTAACCACGCCCTGT
ATCGTCCGCTGCGCAAAACCCTGCCGCGTCTGGAAGCACGCTACTTCATGAGCATGAT
TAATAGTACGTCCGATCATCTGTGCAACAAAACCCTGCTGAATTTTGCTAAGCTGGAC
TTCAACATCCTGCTGGAACTGCACAAAGAAGAACTGAATGAACTGACCAAATGGTGGA
AGGATCTGGACTTTACGACCAAACTGCCGTATGCACGTGATCGCCTGGTTGAACTGTA
CTTCTGGGACCTGGGCACGTATTTTGAACCGCAGTACGCTTTCGGTCGTAAAATTATG
ACCCAACTGAACTATATCCTGTCAATTATCGATGACACGTATGATGCGTACGGCACCC
TGGAAGAACTGTCGCTGTTTACGGAAGCGGTGCAGCGTTGGAATATTGAAGCCGTTGA
TATGCTGCCGGAATATATGAAACTGATTTACCGCACCCTGCTGGATGCATTCAACGAA
ATCGAAGAAGACATGGCTAAACAAGGTCGTAGTCATTGCGTGCGCTATGCGAAAGAAG
AAAATCAGAAGGTTATTGGCGCGTACTCAGTCCAAGCCAAATGGTTTTCGGAAGGTTA
TGTTCCGACGATTGAAGAATACATGCCGATCGCACTGACCTCATGTGCTTATACGTTT
GTGATCACCAACTCGTTCCTGGGCATGGGTGATTTTGCCACCAAAGAAGTTTTCGAAT
GGATTAGCAACAATCCGAAAGTGGTTAAGGCAGCTTCTGTCATCTGCCGTCTGATGGA
TGACATGCAGGGCCATGAATTTGAACAAAAACGCGGTCACGTTGCAAGTGCTATTGAA
TGTTATACCAAGCAGCACGGCGTCTCCAAAGAAGAAGCAATTAAGATGTTCGAAGAAG
AAGTGGCGAACGCCTGGAAAGATATCAATGAAGAACTGATGATGAAGCCGACGGTCGT
GGCACGTCCGCTGCTGGGCACCATCCTGAATCTGGCACGCGCTATCGATTTCATCTAC
AAAGAAGATGACGGCTACACCCATAGTTACCTGATTAAGGATCAGATCGCCTCCGTCC
TGGGTGACCACGTGCCGTTCTAA (SEQ ID NO: 119)

FIG. 3A (Cont'd)

```
Vv2M5    MATQVSASSLAQIPQPKNRPVANFHPNIWGDQFITYTPEDK-VTRAKKEEQIEDLKKEVK  59
VS2      MATQVSASSLAQIPQPKNRPVANFHPNIWGDQFITYTPEDK-VTRAKKEEQIEDLKKEVK  59
VvVS     MSTQVSASSLAQIPQPKNRPVANFHPNIWGDQFITYTPEDK-VTRACKEEQIEDLKKEVK  59
CsVS     MASGETF-----------RPTADFHPSLWRNHFLKGASDFKTVDHTATQERHEALKEEVR  49
         *::   :           **.*:***.:* ::*:. :.: * * :: .:*: * **:**:

Vv2M5    RKLTAAAVANPSQLLNFIDAVQRLGVAYHFEQEIEEALQHICNSFHDCNDMDGDLYNIAL  119
VS2      RKLTAAAVANPSQLLNFIDAVQRLGVAYHFEQEIEEALQHICNSFHDCNDMDGDLYNIAL  119
VvVS     RKLTAAAVANPSQLLNFIDAVQRLGVAYHFEQEIEEALQHICNSFHDCNDMDGDLYNIAL  119
CsVS     RMITDAEDK-PVQKLRLIDEVQRLGVAYHFEKEIGDAIQKLCPIYIDSNRAD--LHTVSL  106
         * :* *    * * *.:** ***********:** :*:*::*  : *.*  *  *:.::*

Vv2M5    GFRLLRQQGYTISCDIFNKFTDERGRFKEALISDVRGMLGLYEAAHLRVHGEDILAKALA  179
VS2      GFRLLRQQGYTISCDIFNKFTDERGRFKEALISDVRGMLGLYEAAHLRVHGEDILAKALA  179
VvVS     GFRLLRQQGYTISCDIFNKFTDERGRFKEALISDVRGMLGLYEAAHLRVHGEDILAKALA  179
CsVS     HFRLLRQQGIKISCDVFEKFKDDEGRFKSSLINDVQGMLSLYEAAYMAVRGEHILDEAIA  166
          ******** .****:*:**.*:.****.:**.**:***.*****:: *:**.** :*:*

Vv2M5    FTTTHLKAMVES--LGYHLAEQVAHALNRPIRKGLERLEARWYISVY--QDEAFHDKTLL  235
VS2      FTTTHLKAMVES--LGYHLAEQVAHALNRPIRKGLERLEARWYISVY--QDEAFHDKTLL  235
VvVS     FTTTHLKAMVES--LGYHLAEQVAHALNRPIRKGLERLEARWYISVY--QDEAFHDKTLL  235
CsVS     FTTTHLKSLVAQDHVTPKLAEQINHALYRPLRKTLPRLEARYFMSMLNSTSDHLCNKTLL  226
         *******::*  .  :  :****: *** **:** * *****:::*:     .: : :****

Vv2M5    ELAKLDFNLVQSLHKEELSNLARWWKELDFATKLPFARDRLVEGYFWMMGVYFEPQYLRG  295
VS2      ELAKLDFNLVQSLHKEELSNLARWWKELDFATKLPFARDRLVEGYFWMMGVYFEPQYLRG  295
VvVS     ELAKLDFNLVQSLHKEELSNLARWWKELDFATKLPFARDRLVEGYFWMHGVYFEPQYLRG  295
CsVS     NFAKLDFNILLELHKEELNELTKWWKDLDFTTKLPYARDRLVELYFWDLGTYFEPQYAFG  286
         ::******:: .******.:*::***:***:****:******* *** *.******  *

Vv2M5    RRILTKVIALTSILDDIHDAYGTPEELKLFIEAIEKWDESSINQLPEYMKLCYVALLDVY  355
VS2      RRILTKVIALTSILDDIHDAYGTPEELKLFIEAIEKWDESSINQLPEYMKLCYVALLDVY  355
VvVS     RRILTKVIAMTSILDDIHDAYGTPEELKLFIEAIERWDINSINQLPEYMKLCYVALLDVY  355
CsVS     RKIMTQLNYILSIIDDTYDAYGTLEELSLFTEAVQRWNIEAVDMLPEYMKLIYRTLLDAF  346
         *:*:*::  : **:** :***** ***.** **::*:  .:: ******* * :***.:

Vv2M5    NEIEEEMEKEGNQYRIHYLKEVMKNQVRAYFAEAKWLHDEHVPAFEEYMRVALASSGYCL  415
VS2      NEIEEEMEKEGNQYRIHYLKEVMKNQVRAYFAEAKWLHDEHVPAFEEYMRVALASSGYCL  415
VvVS     KEIEEEMEKEGNQYRVHYAKEVMKNQVRAYFAEAKWLHEEHVPAFEEYMRVALASSGYCL  415
CsVS     NEIEEDMAKQGRSHCVRYAKEENQKVIGAYSVQAKWFSEGYVPTIEEYMPIALTSCAYTF  406
         :****:* *:*..: ::* **   :: : ** .:***: : :**:**** :**:*..* :

Vv2M5    LAVTSFVGMGEIVTKEAFDWVTSDPRIMSSSNTITRLMDDIKSHKFEQKRGHVTSAVECY  475
VS2      LAVTSFVGMGEIVTKEAFDWVTSDPRIMSSSNTITRLMDDIKSHKFEQKRGHVTSAVECY  475
VvVS     LATTSFVGMGEIATKEAFDWVTSDPKIMSSSNFITRLMDDIKSHKFEQKRGHVTSAVECY  475
CsVS     VITNSFLGMGDFATKEVFEWISNNPKVVKAASVICRLMDDMQGHEFEQKRGHVASAIECY  466
         : ..**:****::.***.*:*:::.:*:::.::. * *****::.*:*********:**:***

Vv2M5    MKQYAVTEEQVYSEFKKQIENAWLDINQEC-LKPTAVPMPLLARLLNFTRTMDVIYKEED  534
VS2      MKQYAVTEEQVYSEFKKQIENAWLDINQEC-LKPTAVPMPLLARLLNFTRTMDVIYKEED  534
VvVS     MKQYGVSEEQVYSEFQKQIENAWLDINQEC-LKPTAVSMPLLARLLNFTRTMDVIYKEQD  534
CsVS     TKQHGVSKEEAIKMFEEEVANAWKDINEELMMKPTVVARPLLGTILNLARAIDFIYKEDD  526
          **:.*::*:. . *:::: *** ***:*  :***.*. ***. :**::*::*:*.****:*

Vv2M5    SYTHVGKTMRDNIASVFINPVI-  556
VS2      SYTHVGKTMRDNIASVFINPVI-  556
VvVS     SYTHVGKVMRDNIASVFINAVI-  556
CsVS     GYTHS-YLIKDQIASVLGDHVPF  548
         .***    ::*:****: : *
```

FIG. 3B

>ZzHO [Zingiber zerumbet]
MEAISLFSPFFFITLFLGFFITLLIKRSSRSSVHKQQVLLASLPPSPPRLPLIGNIHQLVGG
NPHRILLQLARTHGPLICLRLGQVDQVVASSVEAVEEIIKRHDLKFADRPRDLTFSRIFFYD
GNAVVMTPYGGEWKQMRKIYAMELLNSRRVKSFAAIREDVARKLTGEIAHKAFAQTPVINLS
EMVMSMINAIVIRVAFGDKCKQQAYFLHLVKEAMSYVSSFSVADMYPSLKFLDTLTGLKSKL
EGVHGKLDKVFDEIIAQRQAALAAEQAEEDLIIDVLLKLKDEGNQEFPITYTSVKAIVMEIF
LAGTETSSSVIDWVMSELIKNPKAMEKVQKEMREAMQGKTKLEESDIPKFSYLNLVIKETLR
LHPPGPLLFPRECRETCEVMGYRVPAGARLLINAFALSRDEKYWGSDAESFKPERFEGISVD
FKGSNFEFMPFGAGRRICPGMTFGISSVEVALAHLLFHFDWQLPQGMKIEDLDMMEVSGMSA
TRRSPLLVLAKLIIPLP (SEQ ID No: 13 | Wild Type)

MALLLAVFFFFITLFLGFFITLLIKRS*SR*SSVHKQQVLLASLPPSPPRLPLIGNIHQLVGGN
PHRILLQLARTHGPLICLRLGQVDQVVASSVEAVEEIIKRHDLKFADRPRDLTF*SR*IFFYDG
NAVVMTPYGGEWKQMRKIYAMELLN*SR*RVKSFAAIREDVARKLTGEIAHKAFAQTPVINLSE
MVMSMINAIVIRVAFGDKCKQQAYFLHLVKEAMSYVSSFSVADMYPSLKFLDTLTGLKSKLE
GVHGKLDKVFDEIIAQRQAALAAEQAEEDLIIDVLLKLKDEGNQEFPITYTSVKAIVMEIFL
AGTETSSSVIDWVMSELIKNPKAMEKVQKEMREAMQGKTKLEESDIPKFSYLNLVIKETLRL
HPPGPLLFPRECRETCEVMGYRVPAGARLLINAFAL*SR*DEKYWGSDAESFKPERFEGISVDF
KGSNFEFMPFGAGRRICPGMTFGISSVEVALAHLLFHFDWQLPQGMKIEDLDMMEVSGMSAT
RRSPLLVLAKLIIPLP (SEQ ID NO: 14)

ATGGCTCTGTTATTAGCAGTGTTCTTCTTTTTCATTACGCTGTTTCTGGGTTTCTTTATTAC
GCTGCTGATTAAACGCTCGTCCCGTAGCTCTGTCCATAAACAGCAAGTGCTGCTGGCCTCTC
TGCCGCCGAGTCCGCCGCGCCTGCCGCTGATTGGCAACATCCATCAACTGGTGGGCGGCAAC
CCGCATCGTATTCTGCTGCAACTGGCGCGTACCCACGGCCCGCTGATCTGCCTGCGTCTGGG
TCAGGTTGATCAAGTGGTTGCAAGTTCCGTGGAAGCTGTTGAAGAAATTATCAAACGTCACG
ACCTGAAATTTGCAGATCGTCCGCGCGACCTGACCTTTAGCCGTATTTTCTTTTATGATGGT
AACGCTGTCGTGATGACGCCGTACGGCGGTGAATGGAAACAGATGCGTAAAATCTATGCAAT
GGAACTGCTGAACAGCCGTCGTGTGAAATCTTTTGCGGCCATTCGTGAAGACGTTGCACGCA
AACTGACCGGCGAAATCGCTCACAAAGCATTCGCTCAGACGCCGGTCATTAACCTGTCTGAA
ATGGTGATGAGTATGATCAATGCGATTGTCATCCGCGTGGCCTTTGGTGATAAATGTAAACA
GCAAGCATACTTCCTGCATCTGGTGAAAGAAGCTATGTCCTATGTTTCATCGTTTTCAGTCG
CGGATATGTACCCGTCCCTGAAATTCCTGGACACCCTGACGGGCCTGAAAAGCAAACTGGAA
GGCGTTCACGGTAAACTGGATAAAGTCTTCGACGAAATCATCGCACAGCGTCAAGCAGCGCT
GGCGGCGGAACAGGCTGAAGAAGATCTGATTATCGACGTGCTGCTGAAACTGAAAGATGAAG
GCAACCAGGAATTTCCGATTACCTATACGTCAGTTAAAGCGATTGTCATGGAAATCTTCCTG
GCCGGCACCGAAACCAGCAGCAGCGTGATTGACTGGGTTATGAGTGAACTGATCAAAAACCC
GAAAGCGATGGAAAAAGTGCAGAAAGAAATGCGTGAAGCCATGCAAGGCAAAACCAAACTGG
AAGAATCGGATATTCCGAAATTTAGCTACCTGAATCTGGTTATCAAAGAAACCCTGCGTCTG
CATCCGCCGGGTCCGCTGCTGTTCCCGCGTGAATGCCGCGAAACCTGCGAAGTGATGGGCTA
TCGTGTTCCGGCGGGTGCCCGCCTGCTGATTAACGCATTTGCTCTGTCTCGTGATGAAAAAT
ACTGGGGTTCCGACGCCGAATCATTTAAACCGGAACGCTTTGAAGGCATCTCTGTGGATTTC
AAAGGTAGTAATTTTGAATTTATGCCGTTCGGCGCGGGCCGTCGTATTTGTCCGGGCATGAC
CTTTGGTATCTCCTCAGTTGAAGTCGCGCTGGCCCATCTGCTGTTTCACTTCGATTGGCAAC
TGCCGCAAGGCATGAAAATTGAAGATCTGGACATGATGGAAGTCTCGGGTATGAGCGCAACC
CGTCGTAGCCCGCTGCTGGTTCTGGCCAAACTGATTATCCCGCTGCCG (SEQ ID NO:
15)

*FIG. 4A*

>BsGAO [Barnadesia spinosa]

MELTLTTSLGLAVFVFILFKLLTGSKSTKNSLPEAWRLPIIGHMHHLVGTLPHRGVTDMARK
YGSLMHLQLGEVSTIVVSSPRWAKEVLTTYDITFANRPETLTGEIVAYHNTDIVLSPYGEYW
RQLRKLCTLELLSAKKVKSFQSLREEECWNLVKEVRSSGSGSPVDLSESIFKLIATILSRAA
FGKGIKDQREFTEIVKEILRLTGGFDVADIFPSKKILHHLSGKRAKLTNIHNKLDSLINNIV
SEHPGSRTSSSQESLLDVLLRLKDSAELPLTSDNVKAVILDMFGAGTDTSSATIEWAISELI
RCPRAMEKVQTELRQALNGKERIQEEDIQELSYLKLVIKETLRLHPPLPLVMPRECREPCVL
AGYEIPTKTKLIVNVFAINRDPEYWKDAETFMPERFENSPINIMGSEYEYLPFGAGRRMCPG
AALGLANVELPLAHILYYFNWKLPNGARLDELDMSECFGATVQRKSELLLVPTAYKTANNSA
(SEQ ID No: 16 | Wild Type)

MALLLAVFLGLAVFVFILFKLLTGSKSTKNSLPEAWRLPIIGHMHHLVGTLPHRGVTDMARK
YGSLMHLQLGEVSTIVVSSPRWAKEVLTTYDITFANRPETLTGEIVAYHNTDIVLSPYGEYW
RQLRKLCTLELLSAKKVKSFQSLREEECWNLVKEVRSSGSGSPVDLSESIFKLIATIL*SR*AA
FGKGIKDQREFTEIVKEILRLTGGFDVADIFPSKKILHHLSGKRAKLTNIHNKLDSLINNIV
SEHPG*SR*TSSSQESLLDVLLRLKDSAELPLTSDNVKAVILDMFGAGTDTSSATIEWAISELI
RCPRAMEKVQTELRQALNGKERIQEEDIQELSYLKLVIKETLRLHPPLPLVMPRECREPCVL
AGYEIPTKTKLIVNVFAINRDPEYWKDAETFMPERFENSPINIMGSEYEYLPFGAGRRMCPG
AALGLANVELPLAHILYYFNWKLPNGARLDELDMSECFGATVQRKSELLLVPTAYKTANNSA
(SEQ ID NO: 17)

ATGGCTCTGTTATTAGCAGTTTTCCTGGGCCTGGCTGTCTTCGTCTTTATCCTGTTCAAACT
GCTGACCGGCTCAAAATCAACCAAAAATTCACTGCCGGAAGCATGGCGTCTGCCGATCATTG
GCCACATGCATCACCTGGTTGGCACGCTGCCGCATCGCGGTGTGACCGACATGGCGCGTAAA
TACGGCAGCCTGATGCATCTGCAACTGGGCGAAGTGAGCACCATTGTCGTCTCATCGCCGCG
TTGGGCAAAAGAAGTGCTGACGACGTATGATATTACCTTTGCGAATCGCCCGGAAACCCTGA
CCGGCGAAATTGTTGCGTACCACAACACGGATATTGTGCTGTCACCGTATGGCGAATACTGG
CGCCAACTGCGTAAACTGTGCACGCTGGAACTGCTGAGCGCCAAAAAAGTGAAAAGTTTTCA
GTCGCTGCGTGAAGAAGAATGCTGGAATCTGGTGAAAGAAGTGCGTTCGAGCGGCTCAGGTT
CCCCGGTCGATCTGTCGGAATCCATCTTTAAACTGATTGCAACCATTCTGAGCCGCGCAGCG
TTTGGCAAAGGTATCAAAGATCAGCGTGAATTTACCGAAATTGTGAAAGAAATCCTGCGCCT
GACGGGCGGTTTTGATGTGGCGGATATTTTCCCGTCCAAAAAGATCCTGCACCACCTGAGCG
GCAAACGTGCGAAACTGACCAACATCCACAACAAACTGGATTCCCTGATTAATAACATTGTT
TCTGAACATCCGGGTTCGCGTACCTCGTCGAGCCAGGAAAGCCTGCTGGATGTGCTGCTGCG
CCTGAAAGATTCCGCGGAACTGCCGCTGACCTCGGACAATGTTAAAGCCGTGATCCTGGATA
TGTTCGGTGCGGGCACGGATACGTCGAGCGCCACGATTGAATGGGCGATCAGCGAACTGATC
CGCTGCCCGCGTGCAATGGAAAAAGTGCAAACGGAACTGCGTCAAGCGCTGAATGGTAAAGA
ACGCATTCAGGAAGAAGATATTCAGGAACTGTCCTATCTGAAACTGGTCATTAAAGAAACCC
TGCGCCTGCATCCGCCGCTGCCGCTGGTGATGCCGCGTGAATGTCGTGAACCGTGTGTCCTG
GCGGGTTACGAAATCCCGACCAAAACGAAACTGATTGTGAATGTCTTTGCCATCAATCGTGA
CCCGGAATACTGGAAAGATGCAGAAACCTTCATGCCGGAACGCTTTGAAAACAGCCCGATTA
ACATCATGGGTAGTGAATATGAATACCTGCCGTTTGGCGCAGGCCGCCGTATGTGTCCGGGT
GCAGCTCTGGGTCTGGCGAATGTGGAACTGCCGCTGGCGCACATCCTGTATTATTTTAACTG
GAAACTGCCGAATGGCGCTCGCCTGGATGAACTGGATATGTCGGAATGCTTTGGCGCGACGG
TCCAACGCAAAAGCGAACTGCTGCTGGTCCCGACGGCATACAAAACGGCAAACAACTCCGCA
(SEQ ID NO: 18)

FIG. 4A (Cont'd)

>HmPO [Hyoscyamus muticus]

MQFFSLVSIFLFLSFLFLLRKWKNSNSQSKKLPPGPWKLPLLGSMLHMVGGLPHHVLRDLAK
KYGPLMHLQLGEVSAVVVTSPDMAKEVLKTHDIAFASRPKLLAPEIVCYNRSDIAFCPYGDY
WRQMRKICVLEVLSAKNVRSFSSIRRDEVLRLVNFVRSSTSEPVNFTERLFLFTSSMTCRSA
FGKVFKEQETFIQLIKEVIGLAGGFDVADIFPSLKFLHVLTGMEGKIMKAHHKVDAIVEDVI
NEHKKNLAMGKTNGALGGEDLIDVLLRLMNDGGLQFPITNDNIKAIIFDMFAAGTETSSSTL
VWAMVQMMRNPTILAKAQAEVREAFKGKETFDENDVEELKYLKLVIKETLRLHPPVPLLVPR
ECREETEINGYTIPVKTKVMVNVWALGRDPKYWDDADNFKPERFEQCSVDFIGNNFEYLPFG
GGRRICPGISFGLANVYLPLAQLLYHFDWKLPTGMEPKDLDLTELVGVTAARKSDLMLVATP
YQPSRE (SEQ ID NO: 19 | Wild Type)

MALLLAVFFFSLVSIFLFLSFLFLLRKWKNSNSQSKKLPPGPWKLPLLGSMLHMVGGLPHHV
LRDLAKKYGPLMHLQLGEVSAVVVTSPDMAKEVLKTHDIAFASRPKLLAPEIVCYNRSDIAF
CPYGDYWRQMRKICVLEVLSAKNVRSFSSIRRDEVLRLVNFVRSSTSEPVNFTERLFLFTSS
MTCRSAFGKVFKEQETFIQLIKEVIGLAGGFDVADIFPSLKFLHVLTGMEGKIMKAHHKVDA
IVEDVINEHKKNLAMGKTNGALGGEDLIDVLLRLMNDGGLQFPITNDNIKAIIFDMFAAGTE
TSSSTLVWAMVQMMRNPTILAKAQAEVREAFKGKETFDENDVEELKYLKLVIKETLRLHPPV
PLLVPRECREETEINGYTIPVKTKVMVNVWALGRDPKYWDDADNFKPERFEQCSVDFIGNNF
EYLPFGGGRRICPGISFGLANVYLPLAQLLYHFDWKLPTGMEPKDLDLTELVGVTAARKSDL
MLVATPYQPSRE (SEQ ID NO: 20)

ATGGCTCTGTTATTAGCAGTTTTCTTCTTCTCCCTGGTCTCAATCTTTCTGTTCCTGTCCTT
TCTGTTCCTGCTGCGTAAATGGAAAAACTCAAACTCCCAATCGAAAAAACTGCCGCCGGGTC
CGTGGAAACTGCCGCTGCTGGGCTCTATGCTGCACATGGTTGGCGGCCTGCCGCATCACGTT
CTGCGTGATCTGGCGAAAAAATATGGTCCGCTGATGCATCTGCAACTGGGCGAAGTCTCCGC
CGTGGTTGTCACCTCACCGGATATGGCAAAAGAAGTGCTGAAAACGCATGACATTGCGTTCG
CCTCCCGTCCGAAACTGCTGGCCCCGGAAATTGTGTGCTACAACCGCTCAGATATTGCATTT
TGTCCGTATGGTGACTACTGGCGTCAAATGCGCAAAATTTGCGTCCTGGAAGTGCTGTCGGC
CAAAAATGTGCGCAGCTTTAGCTCTATTCGTCGTGATGAAGTTCTGCGTCTGGTTAACTTCG
TCCGCAGTTCCACCTCGGAGCCGGTGAATTTTACGGAACGTCTGTTTCTGTTCACCTCATCG
ATGACCTGCCGTAGCGCATTTGGTAAAGTTTTCAAAGAACAGGAAACCTTCATTCAACTGAT
CAAAGAAGTCATTGGCCTGGCCGGCGGTTTTGATGTGGCAGACATCTTTCCGAGTCTGAAAT
TCCTGCATGTTCTGACCGGCATGGAAGGCAAAATTATGAAAGCTCATCACAAAGTCGATGCG
ATTGTGGAAGACGTTATCAACGAACACAAGAAAAACCTGGCGATGGGCAAAACGAACGGCGC
ACTGGGCGGTGAAGATCTGATCGACGTTCTGCTGCGTCTGATGAATGATGGCGGCCTGCAAT
TTCCGATCACCAACGATAATATCAAAGCTATTATCTTTGATATGTTTGCGGCGGGCACCGAA
ACCAGCAGCAGCACCCTGGTGTGGGCGATGGTGCAGATGATGCGTAACCCGACGATTCTGGC
AAAAGCTCAAGCGGAAGTGCGCGAAGCCTTCAAAGGCAAAGAAACCTTTGATGAAAATGACG
TTGAAGAACTGAAATATCTGAAACTGGTCATCAAAGAAACGCTGCGTCTGCATCCGCCGGTT
CCGCTGCTGGTCCCGCGTGAATGCCGCGAAGAAACCGAAATTAACGGTTATACCATCCCGGT
TAAAACGAAAGTGATGGTTAATGTCTGGGCTCTGGGCCGTGATCCGAAATACTGGGATGACG
CGGACAACTTTAAACCGGAACGCTTTGAACAGTGCTCTGTGGATTTCATCGGCAACAACTTT
GAATATCTGCCGTTTGGCGGTGGCCGTCGCATTTGTCCGGGTATCAGCTTCGGCCTGGCTAA
TGTTTATCTGCCGCTGGCGCAACTGCTGTACCACTTTGATTGGAAACTGCCGACCGGCATGG
AACCGAAAGATCTGGACCTGACCGAACTGGTGGGCGTTACGGCAGCTCGTAAATCTGATCTG
ATGCTGGTTGCGACCCCGTACCAGCCGAGCCGTGAA (SEQ ID NO: 21)

*FIG. 4A (Cont'd)*

>LsGAO [Lactuca sativa]
MELSITTSIALATIVFFLYKLATRPKSTKKQLPEASRLPIIGHMHHLIGTMPHRGVMDLARK
HGSLMHLQLGEVSTIVVSSPKWAKEILTTYDITFANRPETLTGEIIAYHNTDIVLAPYGEYW
RQLRKLCTLELLSVKKVKSFQSIREEECWNLVKEVKESGSGKPINLSESIFTMIATILSRAA
FGKGIKDQREFTEIVKEILRQTGGFDVADIFPSKKFLHHLSGKRARLTSIHKKLDNLINNIV
AEHHVSTSSKANETLLDVLLRLKDSAEFPLTADNVKAIILDMFGAGTDTSSATVEWAISELI
RCPRAMEKVQAELRQALNGKEKIQEEDIQDLAYLNLVIRETLRLHPPLPLVMPRECREPVNL
AGYEIANKTKLIVNVFAINRDPEYWKDAEAFIPERFENNPNNIMGADYEYLPFGAGRRMCPG
AALGLANVQLPLANILYHFNWKLPNGASHDQLDMTESFGATVQRKTELLLVPSF (SEQ ID NO: 22 | Wild Type)

MALLLAVFIALATIVFFLYKLATRPKSTKKQLPEA*SR*LPIIGHMHHLIGTMPHRGVMDLARK
HGSLMHLQLGEVSTIVVSSPKWAKEILTTYDITFANRPETLTGEIIAYHNTDIVLAPYGEYW
RQLRKLCTLELLSVKKVKSFQSIREEECWNLVKEVKESGSGKPINLSESIFTMIATIL*SR*AA
FGKGIKDQREFTEIVKEILRQTGGFDVADIFPSKKFLHHLSGKRARLTSIHKKLDNLINNIV
AEHHVSTSSKANETLLDVLLRLKDSAEFPLTADNVKAIILDMFGAGTDTSSATVEWAISELI
RCPRAMEKVQAELRQALNGKEKIQEEDIQDLAYLNLVIRETLRLHPPLPLVMPRECREPVNL
AGYEIANKTKLIVNVFAINRDPEYWKDAEAFIPERFENNPNNIMGADYEYLPFGAGRRMCPG
AALGLANVQLPLANILYHFNWKLPNGASHDQLDMTESFGATVQRKTELLLVPSF (SEQ ID NO: 23)

ATGGCTCTGTTATTAGCAGTTTTCATCGCACTGGCTACCATCGTCTTCTTCCTGTATAAACT
GGCAACGCGCCCGAAATCTACCAAAAAACAACTGCCGGAAGCGAGCCGTCTGCCGATTATCG
GCCACATGCATCACCTGATTGGCACCATGCCGCACCGTGGTGTCATGGATCTGGCCCGCAAA
CATGGCTCGCTGATGCATCTGCAACTGGGCGAAGTGAGCACCATTGTGGTTAGCTCTCCGAA
ATGGGCAAAAGAAATTCTGACCACCTATGATATTACCTTTGCTAACCGCCCGGAAACCCTGA
CGGGCGAAATTATCGCGTACCATAATACGGACATTGTGCTGGCCCCGTATGGTGAATACTGG
CGTCAACTGCGTAAACTGTGCACCCTGGAACTGCTGTCCGTTAAAAAAGTCAAATCATTTCA
ATCGATTCGTGAAGAAGAATGTTGGAACCTGGTGAAAGAAGTTAAAGAAAGCGGCTCTGGTA
AACCGATTAATCTGAGTGAATCCATCTTCACCATGATTGCGACGATCCTGAGTCGTGCGGCC
TTTGGCAAAGGTATTAAAGATCAGCGCGAATTTACCGAAATTGTCAAAGAAATCCTGCGTCA
AACGGGCGGTTTCGATGTGGCAGACATTTTTCCGAGCAAAAAATTCCTGCATCACCTGTCTG
GCAAACGTGCTCGCCTGACCAGTATCCATAAAAAACTGGATAACCTGATCAACAATATCGTC
GCGGAACATCATGTGAGCACCAGCAGCAAAGCGAATGAAACGCTGCTGGATGTTCTGCTGCG
CCTGAAAGACAGTGCCGAATTTCCGCTGACCGCAGACAACGTCAAAGCTATTATCCTGGATA
TGTTCGGTGCAGGCACCGATACCAGCAGCGCAACGGTGGAATGGGCCATTAGCGAACTGATC
CGTTGCCCGCGCGCAATGGAAAAAGTTCAGGCAGAACTGCGTCAAGCTCTGAACGGTAAAGA
AAAAATCCAGGAAGAAGATATTCAAGACCTGGCCTATCTGAATCTGGTGATTCGTGAAACCC
TGCGTCTGCACCCGCCGCTGCCGCTGGTTATGCCGCGTGAATGCCGTGAGCCGGTGAACCTG
GCGGGCTATGAAATCGCCAATAAAACCAAACTGATCGTCAATGTGTTTGCGATTAACCGTGA
CCCGGAATACTGGAAAGACGCGGAAGCCTTTATCCCGGAACGTTTTGAAAACAATCCGAACA
ATATCATGGGTGCAGATTATGAATACCTGCCGTTTGGCGCTGGTCGTCGCATGTGTCCGGGC
GCAGCTCTGGGTCTGGCAAACGTTCAACTGCCGCTGGCGAACATTCTGTACCATTTCAACTG
GAAACTGCCGAATGGCGCGTCCCACGATCAACTGGACATGACCGAATCATTTGGTGCCACCG
TGCAACGTAAAACGGAACTGCTGCTGGTTCCGAGCTTC (SEQ ID NO: 24)

FIG. 4A (Cont'd)

>NtEAO [Nicotiani tabacum]
MQFFSLVSIFLFLSFLFLLRKWKNSNSQSKKLPPGPWKIPILGSMLHMIGGEPHHVLRDLAK
KYGPLMHLQLGEISAVVVTSRDMAKEVLKTHDVVFASRPKIVAMDIICYNQSDIAFSPYGDH
WRQMRKICVMELLNAKNVRSFSSIRRDEVVRLIDSIRSDSSSGELVNFTQRIIWFASSMTCR
SAFGQVLKGQDIFAKKIREVIGLAEGFDVVDIFPTYKFLHVLSGMKRKLLNAHLKVDAIVED
VINEHKKNLAAGKSNGALGGEDLIDVLLRLMNDTSLQFPITNDNIKAVIVDMFAAGTETSST
TTVWAMAEMMKNPSVFTKAQAEVREAFRDKVSFDENDVEELKYLKLVIKETLRLHPPSPLLV
PRECREDTDINGYTIPAKTKVMVNVWALGRDPKYWDDAESFKPERFEQCSVDFFGNNFEFLP
FGGGRRICPGMSFGLANLYLPLAQLLYHFDWKLPTGIMPRDLDLTELSGITIARKGGLYLNA
TPYQPSRE (SEQ ID NO: 25 | Wild Type)

MALLLAVFFFSLVSIFLFLSFLFLLRKWKNSNSQSKKLPPGPWKIPILGSMLHMIGGEPHHV
LRDLAKKYGPLMHLQLGEISAVVVT*SR*DMAKEVLKTHDVVFA*SR*PKIVAMDIICYNQSDIAF
SPYGDHWRQMRKICVMELLNAKNVRSFSSIRRDEVVRLIDSIRSDSSSGELVNFTQRIIWFA
SSMTCRSAFGQVLKGQDIFAKKIREVIGLAEGFDVVDIFPTYKFLHVLSGMKRKLLNAHLKV
DAIVEDVINEHKKNLAAGKSNGALGGEDLIDVLLRLMNDTSLQFPITNDNIKAVIVDMFAAG
TETSSTTTVWAMAEMMKNPSVFTKAQAEVREAFRDKVSFDENDVEELKYLKLVIKETLRLHP
PSPLLVPRECREDTDINGYTIPAKTKVMVNVWALGRDPKYWDDAESFKPERFEQCSVDFFGN
NFEFLPFGGGRRICPGMSFGLANLYLPLAQLLYHFDWKLPTGIMPRDLDLTELSGITIARKG
GLYLNATPYQPSRE (SEQ ID NO: 26)

ATGGCTCTGTTATTAGCAGTTTTCTTCTTCTCCCTGGTCTCAATCTTCCTGTTCCTGTCCTT
TCTGTTCCTGCTGCGTAAATGGAAAAACTCTAATAGCCAATCCAAAAAACTGCCGCCGGGTC
CGTGGAAAATTCCGATCCTGGGCTCTATGCTGCACATGATTGGCGGTGAACCGCATCATGTG
CTGCGTGATCTGGCGAAAAAATATGGTCCGCTGATGCATCTGCAACTGGGCGAAATCTCTGC
GGTGGTTGTCACGAGTCGTGACATGGCCAAAGAAGTGCTGAAAACCCATGATGTGGTTTTTG
CATCTCGCCCGAAAATCGTTGCTATGGATATTATCTGCTATAACCAGTCGGACATCGCGTTC
AGCCCGTACGGTGATCACTGGCGTCAAATGCGCAAAATTTGTGTCATGGAACTGCTGAACGC
CAAAAATGTGCGCAGTTTTAGCTCTATTCGTCGTGATGAAGTCGTGCGTCTGATTGATTCCA
TCCGCTCAGACAGTTCCTCAGGCGAACTGGTGAATTTTACGCAGCGTATTATCTGGTTCGCA
TCGAGCATGACCTGCCGCTCGGCTTTTGGTCAGGTTCTGAAAGGCCAAGATATTTTTGCGAA
GAAAATTCGTGAAGTGATCGGTCTGGCCGAAGGCTTCGATGTTGTGGATATTTTTCCGACCT
ATAAATTCCTGCATGTCCTGAGCGGTATGAAACGCAAACTGCTGAACGCGCACCTGAAAGTT
GATGCCATTGTCGAAGACGTGATCAACGAACATAAGAAAAACCTGGCGGCGGGTAAATCCAA
CGGCGCACTGGGCGGTGAAGATCTGATTGACGTGCTGCTGCGTCTGATGAATGATACCAGCC
TGCAATTTCCGATCACCAACGACAACATTAAAGCGGTGATCGTTGATATGTTCGCGGCGGGC
ACCGAAACCTCTAGTACCACGACCGTTTGGGCGATGGCCGAAATGATGAAAAACCCGTCGGT
GTTTACCAAAGCACAAGCGGAAGTGCGTGAAGCGTTTCGTGATAAAGTTAGCTTCGATGAAA
ATGATGTGGAAGAACTGAAATACCTGAAACTGGTGATTAAAGAAACGCTGCGTCTGCATCCG
CCGAGCCCGCTGCTGGTTCCGCGTGAATGCCGTGAAGATACCGACATTAACGGTTATACGAT
CCCGGCAAAAACCAAAGTCATGGTGAATGTTTGGGCTCTGGGCCGTGACCCGAAATACTGGG
ATGACGCAGAATCCTTTAAACCGGAACGCTTTGAACAGTGCTCAGTGGATTTCTTTGGTAAC
AACTTTGAATTTCTGCCGTTTGGCGGTGGCCGTCGCATTTGTCCGGGTATGTCCTTCGGCCT
GGCGAACCTGTATCTGCCGCTGGCCCAACTGCTGTACCACTTTGATTGGAAACTGCCGACGG
GTATTATGCCGCGTGATCTGGACCTGACGGAACTGTCTGGCATTACCATCGCACGCAAAGGT
GGCCTGTATCTGAATGCTACCCCGTACCAGCCGAGTCGTGAA (SEQ ID NO: 27)

*FIG. 4A (Cont'd)*

>CpVO [Citrus x paradisi]
MELPLKSIALTIVIVTVLTWAWRVLNWVWLRPKKLEKFLRQQGLKGNSYRLLFGDLKENSIE
LKEAKARPLSLDDDIAIRVNPFLHKLVNDYGKNSFMWFGPTPRVNIMNPDQIKAIFTKINDF
QKVNSIPLARLLIVGLATLEGEKWAKHRKLINPAFHQEKLKLMLPAFYLSCIEIITKWEKQM
SVEGSSELDVWPYLANLTSDVISRTAFGSSYEEGRRIFQLQAELAELTMQVFRSVHIPGWRF
LPTKRNRRMKEIDKEIRASLMGIIKNREKAMRAGEAANNDLLGILMETSFREIEEHGNNKNV
GFSMNDVIEECKLFYFAGQETTSVLLNWTMVLLSKHQDWQERARQEVLQVFGNNKPDYDGLN
HLKIVQMILYEVLRLYPPVTVLSRAVFKETKLGNLTLPAGVQIGLPMILVHQDPELWGDDAV
EFKPERFAEGISKAAKNQVSYFPFALGPRICVGQNFALVEAKMATAMILQNYSFELSPSYVH
APTAVPTLHPELGTQLILRKLWCKNN (SEQ ID NO: 28 | Wild Type)

MALLLAVFIALTIVIVTVLTWAWRVLNWVWLRPKKLEKFLRQQGLKGNSYRLLFGDLKENSI
ELKEAKARPLSLDDDIAIRVNPFLHKLVNDYGKNSFMWFGPTPRVNIMNPDQIKAIFTKIND
FQKVNSIPLARLLIVGLATLEGEKWAKHRKLINPAFHQEKLKLMLPAFYLSCIEIITKWEKQ
MSVEGSSELDVWPYLANLTSDVI*SR*TAFGSSYEEGRRIFQLQAELAELTMQVFRSVHIPGWR
FLPTKRNRRMKEIDKEIRASLMGIIKNREKAMRAGEAANNDLLGILMETSFREIEEHGNNKN
VGFSMNDVIEECKLFYFAGQETTSVLLNWTMVLLSKHQDWQERARQEVLQVFGNNKPDYDGL
NHLKIVQMILYEVLRLYPPVTVLSRAVFKETKLGNLTLPAGVQIGLPMILVHQDPELWGDDA
VEFKPERFAEGISKAAKNQVSYFPFALGPRICVGQNFALVEAKMATAMILQNYSFELSPSYV
HAPTAVPTLHPELGTQLILRKLWCKNN (SEQ ID NO: 29)

ATGGCTCTGTTATTAGCAGTTTTCATTGCTCTGACGATTGTTATTGTTACGGTGCTGACCTG
GGCGTGGCGTGTGCTGAACTGGGTTTGGCTGCGTCCGAAAAAACTGGAAAAATTTCTGCGCC
AGCAAGGCCTGAAGGGTAACAGCTATCGTCTGCTGTTCGGCGATCTGAAAGAAAATTCTATT
GAACTGAAAGAAGCGAAAGCCCGTCCGCTGAGTCTGGATGACGATATTGCAATCCGCGTTAA
CCCGTTTCTGCATAAACTGGTCAACGATTACGGCAAAAATTCTTTTATGTGGTTCGGTCCGA
CCCCGCGCGTGAACATTATGAACCCGGATCAGATTAAAGCGATCTTTACGAAAATCAACGAT
TTCCAAAAAGTTAATAGCATTCCGCTGGCGCGTCTGCTGATCGTCGGCCTGGCCACCCTGGA
AGGTGAAAAATGGGCAAAACATCGCAAACTGATTAACCCGGCTTTTCACCAAGAAAAACTGA
AACTGATGCTGCCGGCGTTCTATCTGTCCTGCATCGAAATTATCACGAAATGGGAAAAACAG
ATGTCAGTGGAAGGTAGCTCTGAACTGGACGTTTGGCCGTATCTGGCCAATCTGACCAGCGA
TGTTATTTCTCGTACGGCATTTGGCAGTTCCTACGAAGAAGGTCGTCGCATCTTCCAGTTAC
AGGCGGAACTGGCCGAACTGACCATGCAGGTTTTTCGTTCTGTCCATATTCCGGGCTGGCGT
TTCCTGCCGACGAAACGCAACCGTCGCATGAAAGAAATTGACAAAGAAATCCGCGCCAGTCT
GATGGGTATTATCAAAAATCGTGAAAAAGCAATGCGCGCTGGCGAAGCGGCCAACAATGATC
TGCTGGGTATTCTGATGGAAACCAGCTTTCGTGAAATCGAAGAACACGGCAACAATAAAAAC
GTCGGTTTCAGCATGAATGACGTGATCGAAGAATGTAAACTGTTTTATTTCGCTGGCCAGGA
AACCACGTCAGTTCTGCTGAACTGGACGATGGTGCTGCTGTCGAAACATCAGGATTGGCAAG
AACGTGCCCGCCAGGAAGTCCTGCAAGTGTTTGGCAACAATAAACCGGACTACGATGGTCTG
AACCACCTGAAAATTGTGCAGATGATCCTGTATGAAGTTCTGCGTCTGTATCCGCCGGTGAC
GGTGCTGAGCCGTGCGGTGTTTAAAGAAACCAAACTGGGTAATCTGACGCTGCCGGCAGGCG
TCCAGATTGGTCTGCCGATGATCCTGGTGCACCAGGACCCGGAACTGTGGGGCGACGATGCT
GTGGAATTTAAACCGGAACGTTTCGCGGAAGGTATTAGTAAAGCAGCTAAAAATCAGGTTTC
CTATTTTCCGTTCGCGCTGGGTCCGCGTATTTGCGTCGGTCAAAACTTTGCACTGGTGGAAG
CTAAAATGGCAACCGCTATGATCCTGCAAAATTATAGCTTTGAACTGTCACCGAGCTATGTT
CATGCGCCGACCGCCGTTCCGACGCTGCACCCGGAACTGGGCACGCAACTGATTCTGCGTAA
ACTGTGGTGTAAAAACAAT (SEQ ID NO: 30)

*FIG. 4A (Cont'd)*

>AaAO [Artemesia annua]
MKSILKAMALSLTTSIALATILLFVYKFATRSKSTKKSLPEPWRLPIIGHMHHLIGTTPHRG
VRDLARKYGSLMHLQLGEVPTIVVSSPKWAKEILTTYDITFANRPETLTGEIVLYHNTDVVL
APYGEYWRQLRKICTLELLSVKKVKSFQSLREEECWNLVQEIKASGSGRPVNLSENVFKLIA
TILSRAAFGKGIKDQKELTEIVKEILRQTGGFDVADIFPSKKFLHHLSGKRARLTSLRKKID
NLIDNLVAEHTVNTSSKTNETLLDVLLRLKDSAEFPLTSDNIKAIILDMFGAGTDTSSSTIE
WAISELIKCPKAMEKVQAELRKALNGKEKIHEEDIQELSYLNMVIKETLRLHPPLPLVLPRE
CRQPVNLAGYNIPNKTKLIVNVFAINRDPEYWKDAEAFIPERFENSSATVMGAEYEYLPFGA
GRRMCPGAALGLANVQLPLANILYHFNWKLPNGVSYDQIDMTESSGATMQRKTELLLVPSF
(SEQ ID NO: 31 | Wild Type)

MALLLAVFIALATILLFVYKFATRSKSTKKSLPEPWRLPIIGHMHHLIGTTPHRGVRDLARK
YGSLMHLQLGEVPTIVVSSPKWAKEILTTYDITFANRPETLTGEIVLYHNTDVVLAPYGEYW
RQLRKICTLELLSVKKVKSFQSLREEECWNLVQEIKASGSGRPVNLSENVFKLIATIL*SR*AA
FGKGIKDQKELTEIVKEILRQTGGFDVADIFPSKKFLHHLSGKRARLTSLRKKIDNLIDNLV
AEHTVNTSSKTNETLLDVLLRLKDSAEFPLTSDNIKAIILDMFGAGTDTSSSTIEWAISELI
KCPKAMEKVQAELRKALNGKEKIHEEDIQELSYLNMVIKETLRLHPPLPLVLPRECRQPVNL
AGYNIPNKTKLIVNVFAINRDPEYWKDAEAFIPERFENSSATVMGAEYEYLPFGAGRRMCPG
AALGLANVQLPLANILYHFNWKLPNGVSYDQIDMTESSGATMQRKTELLLVPSF (SEQ ID
NO: 32)

ATGGCTCTGTTATTAGCAGTTTTCATCGCACTGGCAACCATTCTGCTGTTTGTGTATAAATT
CGCTACCCGTTCCAAATCAACGAAAAAATCACTGCCGGAACCGTGGCGCCTGCCGATTATCG
GTCACATGCATCACCTGATCGGCACCACCCCGCATCGTGGCGTGCGTGATCTGGCACGCAAA
TATGGCTCGCTGATGCATCTGCAACTGGGTGAAGTCCCGACCATTGTGGTTAGCTCTCCGAA
ATGGGCGAAAGAAATCCTGACCACCTATGATATTACCTTTGCCAACCGCCCGGAAACCCTGA
CGGGCGAAATCGTGCTGTACCACAATACGGATGTGGTGCTGGCGCCGTATGGTGAATACTGG
CGTCAACTGCGTAAAATTTGCACCCTGGAACTGCTGAGTGTGAAAAAAGTTAAATCTTTCCA
GAGCCTGCGTGAAGAAGAATGTTGGAACCTGGTTCAAGAAATTAAAGCATCGGGCAGCGGTC
GCCCGGTTAACCTGAGTGAAAATGTCTTTAAACTGATTGCTACCATCCTGTCCCGTGCGGCC
TTCGGCAAAGGTATCAAAGATCAGAAAGAACTGACCGAAATTGTCAAAGAAATCCTGCGCCA
AACGGGCGGTTTTGATGTGGCGGACATTTTTCCGTCGAAAAAATTCCTGCATCACCTGAGCG
GTAAACGTGCCCGCCTGACCAGCCTGCGTAAGAAAATTGATAACCTGATCGACAATCTGGTC
GCGGAACATACCGTGAACACGAGTTCCAAAACCAATGAAACGCTGCTGGATGTGCTGCTGCG
CCTGAAAGACTCCGCCGAATTTCCGCTGACCTCAGATAATATCAAAGCGATTATCCTGGATA
TGTTCGGTGCAGGCACCGATACCAGCAGCAGCACCATTGAATGGGCAATCTCAGAACTGATT
AAATGCCCGAAAGCTATGGAAAAAGTCCAGGCAGAACTGCGCAAAGCTCTGAACGGCAAAGA
AAAAATCCATGAAGAAGATATTCAAGAACTGTCTTACCTGAACATGGTTATCAAAGAAACCC
TGCGTCTGCACCCGCCGCTGCCGCTGGTGCTGCCGCGTGAATGTCGCCAGCCGGTTAACCTG
GCAGGCTATAACATCCCGAATAAAACGAAACTGATCGTTAACGTCTTTGCTATTAACCGTGA
CCCGGAATACTGGAAAGACGCGGAAGCCTTTATCCCGGAACGCTTTGAAAACAGCAGCGCGA
CCGTGATGGGTGCCGAATATGAATACCTGCCGTTTGGCGCGGGTCGTCGCATGTGTCCGGGC
GCAGCTCTGGGTCTGGCAAACGTGCAACTGCCGCTGGCTAATATCCTGTATCACTTCAACTG
GAAACTGCCGAATGGCGTTAGCTACGATCAAATTGACATGACCGAAAGCTCAGGTGCCACGA
TGCAACGCAAAACCGAACTGCTGCTGGTGCCGTCCTTC (SEQ ID NO: 33)

*FIG. 4A (Cont'd)*

>AtKO [Arabidopsis thaliana]
MAFFSMISILLGFVISSFIFIFFFKKLLSFSRKNMSEVSTLPSVPVVPGFPVIGNLLQLKEK
KPHKTFTRWSEIYGPIYSIKMGSSSLIVLNSTETAKEAMVTRFSSISTRKLSNALTVLTCDK
SMVATSDYDDFHKLVKRCLLNGLLGANAQKRKRHYRDALIENVSSKLHAHARDHPQEPVNFR
AIFEHELFGVALKQAFGKDVESIYVKELGVTLSKDEIFKVLVHDMMEGAIDVDWRDFFPYLK
WIPNKSFEARIQQKHKRRLAVMNALIQDRLKQNGSESDDDCYLNFLMSEAKTLTKEQIAILV
WETIIETADTTLVTTEWAIYELAKHPSVQDRLCKEIQNVCGGEKFKEEQLSQVPYLNGVFHE
TLRKYSPAPLVPIRYAHEDTQIGGYHVPAGSEIAINIYGCNMDKKRWERPEDWWPERFLDDG
KYETSDLHKTMAFGAGKRVCAGALQASLMAGIAIGRLVQEFEWKLRDGEEENVDTYGLTSQK
LYPLMAIINPRRS (SEQ ID NO: 34 | Wild Type)

MALLLAVFSMISILLGFVISSFIFIFFFKKLLSF*SR*KNMSEVSTLPSVPVVPGFPVIGNLL
QLKEKKPHKTFTRWSEIYGPIYSIKMGSSSLIVLNSTETAKEAMVTRFSSISTRKLSNALT
VLTCDKSMVATSDYDDFHKLVKRCLLNGLLGANAQKRKRHYRDALIENVSSKLHAHARDHP
QEPVNFRAIFEHELFGVALKQAFGKDVESIYVKELGVTLSKDEIFKVLVHDMMEGAIDVDW
RDFFPYLKWIPNKSFEARIQQKHKRRLAVMNALIQDRLKQNGSESDDDCYLNFLMSEAKTL
TKEQIAILVWETIIETADTTLVTTEWAIYELAKHPSVQDRLCKEIQNVCGGEKFKEEQLSQ
VPYLNGVFHETLRKYSPAPLVPIRYAHEDTQIGGYHVPAGSEIAINIYGCNMDKKRWERPE
DWWPERFLDDGKYETSDLHKTMAFGAGKRVCAGALQASLMAGIAIGRLVQEFEWKLRDGEE
ENVDTYGLTSQKLYPLMAIINPRRS (SEQ ID NO: 35)

ATGGCTCTGTTATTAGCAGTTTTTTCGATGATTTCTATCCTGCTGGGCTTTGTTATCTCGTC
CTTTATCTTTATCTTCTTCTTCAAAAAACTGCTGTCGTTTTCTCGTAAAAACATGTCCGAAG
TTTCAACCCTGCCGAGTGTCCCGGTGGTTCCGGGTTTTCCGGTTATCGGTAATCTGCTGCAG
CTGAAAGAAAAGAAACCGCATAAGACCTTCACGCGCTGGTCCGAAATCTATGGCCCGATCTA
CTCAATTAAAATGGGTAGCTCTAGTCTGATTGTGCTGAACTCTACCGAAACGGCAAAAGAAG
CTATGGTTACCCGTTTTTCCTCAATTTCGACGCGCAAGCTGAGCAATGCGCTGACCGTCCTG
ACGTGCGACAAATCTATGGTGGCCACCAGTGATTACGATGACTTCCATAAACTGGTTAAGCG
TTGTCTGCTGAACGGCCTGCTGGGTGCGAATGCCCAGAAGCGTAAGCGCCACTATCGCGACG
CCCTGATTGAAAACGTGTCGAGCAAACTGCATGCACACGCTCGTGATCATCCGCAGGAACCG
GTCAATTTTCGCGCAATCTTCGAACACGAACTGTTTGGCGTGGCGCTGAAACAAGCCTTCGG
CAAGGATGTTGAATCGATTTACGTCAAAGAACTGGGCGTGACCCTGAGCAAAGACGAAATCT
TTAAGGTCCTGGTGCATGATATGATGGAAGGTGCAATTGACGTTGATTGGCGTGATTTCTTT
CCGTATCTGAAATGGATTCCGAACAAGTCATTCGAAGCTCGCATTCAGCAAAAACACAAGCG
TCGCCTGGCAGTGATGAACGCTCTGATTCAGGATCGTCTGAAACAAAATGGCTCTGAAAGTG
ATGACGATTGCTATCTGAATTTTCTGATGTCCGAAGCAAAAACCCTGACGAAGGAACAGATT
GCTATCCTGGTTTGGGAAACCATTATCGAAACGGCGGACACCACGCTGGTCACCACGGAATG
GGCGATCTACGAACTGGCCAAGCATCCGAGCGTTCAGGATCGCCTGTGCAAAGAAATTCAAA
ACGTCTGTGGCGGTGAAAAATTTAAGGAAGAACAGCTGTCGCAAGTGCCGTATCTGAATGGT
GTTTTCCACGAAACCCTGCGTAAATATAGCCCGGCACCGCTGGTCCCGATCCGTTACGCCCA
TGAAGATACCCAGATTGGCGGTTATCACGTGCCGGCAGGCAGTGAAATTGCTATCAACATTT
ACGGTTGCAATATGGACAAAAAGCGTTGGGAACGCCCGGAAGATTGGTGGCCGGAACGTTTT
CTGGACGATGGCAAATATGAAACCTCTGATCTGCATAAGACGATGGCGTTCGGTGCAGGTAA
ACGTGTGTGTGCAGGTGCACTGCAAGCAAGTCTGATGGCAGGCATCGCTATTGGTCGTCTGG
TGCAAGAATTTGAATGGAAACTGCGCGACGGCGAAGAAGAAAACGTTGATACCTATGGTCTG
ACGTCCCAGAAACTGTACCCGCTGATGGCCATTATCAATCCGCGTCGCTCA (SEQ ID NO: 36)

*FIG. 4A (Cont'd)*

**>*Sr*KO [Stevia rebaudiana]**
MDAVTGLLTVPATAITIGGTAVALAVALIFWYLKSYTSARRSQSNHLPRVPEVPGVPLLGNL
LQLKEKKPYMTFTRWAATYGPIYSIKTGATSMVVVSSNEIAKEALVTRFQSISTRNLSKALK
VLTADKTMVAMSDYDDYHKTVKRHILTAVLGPNAQKKHRIHRDIMMDNISTQLHEFVKNNPE
QEEVDLRKIFQSELFGLAMRQALGKDVESLYVEDLKITMNRDEIFQVLVVDPMMGAIDVDWR
DFFPYLKWVPNKKFENTIQQMYIRREAVMKSLIKEHKKRIASGEKLNSYIDYLLSEAQTLTD
QQLLMSLWEPIIESSDTTMVTTEWAMYELAKNPKLQDRLYRDIKSVCGSEKITEEHLSQLPY
ITAIFHETLRRHSPVPIIPLRHVHEDTVLGGYHVPAGTELAVNIYGCNMDKNVWENPEEWNP
ERFMKENETIDFQKTMAFGGGKRVCAGSLQALLTASIGIGRMVQEFEWKLKDMTQEEVNTIG
LTTQMLRPLRAIIKPRI (SEQ ID NO: 37 | Wild Type)

MALLLAVFAVALAVALIFWYLKSYTSARRSQSNHLPRVPEVPGVPLLGNLLQLKEKKPYMT
FTRWAATYGPIYSIKTGATSMVVVSSNEIAKEALVTRFQSISTRNLSKALKVLTADKTMVA
MSDYDDYHKTVKRHILTAVLGPNAQKKHRIHRDIMMDNISTQLHEFVKNNPEQEEVDLRKI
FQSELFGLAMRQALGKDVESLYVEDLKITMNRDEIFQVLVVDPMMGAIDVDWRDFFPYLKW
VPNKKFENTIQQMYIRREAVMKSLIKEHKKRIASGEKLNSYIDYLLSEAQTLTDQQLLMSL
WEPIIESSDTTMVTTEWAMYELAKNPKLQDRLYRDIKSVCGSEKITEEHLSQLPYITAIFH
ETLRRHSPVPIIPLRHVHEDTVLGGYHVPAGTELAVNIYGCNMDKNVWENPEEWNPERFMK
ENETIDFQKTMAFGGGKRVCAGSLQALLTASIGIGRMVQEFEWKLKDMTQEEVNTIGLTTQ
MLRPLRAIIKPRI (SEQ ID NO: 38)

ATGGCTCTGTTATTAGCAGTTTTTGCCGTCGCTCTGGCGGTAGCACTGATCTTCTGGTATCT
GAAATCTTACACTAGCGCGCGCCGCTCTCAGTCCAACCACCTGCCGCGTGTGCCGGAAGTTC
CGGGTGTGCCACTGCTGGGCAACCTGCTGCAACTGAAAGAAAAGAAACCGTACATGACCTTT
ACCCGCTGGGCAGCGACTTATGGTCCTATCTACAGCATTAAAACCGGCGCTACGTCTATGGT
TGTGGTTTCTTCCAACGAAATCGCGAAAGAAGCCCTGGTGACTCGTTTCCAGTCCATTAGCA
CCCGCAACCTGTCCAAAGCGCTGAAGGTTCTGACGGCTGACAAGACTATGGTGGCTATGAGC
GACTATGATGACTACCACAAAACCGTTAAACGTCACATCCTGACCGCAGTACTGGGTCCGAA
CGCACAGAAAAAACATCGCATCCACCGCGACATTATGATGGATAACATCTCCACGCAGCTGC
ATGAGTTCGTTAAGAACAATCCAGAACAGGAAGAGGTAGATCTGCGTAAAATTTTTCAGTCC
GAACTGTTCGGTCTGGCTATGCGTCAGGCGCTGGGCAAAGACGTTGAAAGCCTGTATGTCGA
AGACCTGAAAATTACCATGAACCGTGATGAGATCTTCCAGGTTCTGGTTGTAGATCCGATGA
TGGGCGCCATCGACGTGGATTGGCGTGACTTCTTTCCGTACCTGAAATGGGTCCCGAACAAG
AAGTTCGAAAACACCATCCAGCAAATGTACATCCGTCGTGAAGCGGTGATGAAAAGCCTGAT
CAAAGAACACAAAAAGCGTATTGCTTCTGGTGAGAAACTGAACTCCTACATCGATTATCTGC
TGTCCGAAGCGCAGACCCTGACCGACCAACAGCTGCTGATGTCTCTGTGGGAACCGATTATC
GAAAGCAGCGACACCACTATGGTCACTACCGAATGGGCAATGTATGAGCTGGCCAAAAACCC
GAAACTGCAGGATCGTCTGTACCGTGACATCAAAAGCGTTTGCGGCTCCGAGAAAATCACTG
AAGAACACCTGTCTCAGCTGCCGTACATCACTGCTATTTTCCACGAAACCCTGCGTCGCCAT
TCTCCGGTTCCGATCATTCCGCTGCGTCACGTTCACGAAGATACTGTGCTGGGTGGTTACCA
TGTACCGGCAGGCACTGAACTGGCTGTCAACATCTACGGCTGTAACATGGATAAAAACGTTT
GGGAGAATCCTGAAGAATGGAACCCGGAACGCTTCATGAAAGAGAACGAAACCATCGACTTC
CAGAAAACGATGGCTTTCGGCGGTGGTAAACGTGTGTGCGCAGGTTCTCTGCAGGCGCTGCT
GACGGCGTCCATTGGTATCGGTCGCATGGTACAGGAATTTGAATGGAAGCTGAAAGACATGA
CCCAAGAAGAGGTGAATACCATTGGTCTGACTACCCAGATGCTGCGTCCACTGCGTGCAATC
ATCAAACCTCGTATT (SEQ ID NO: 39)

*FIG. 4A (Cont'd)*

>PpKO [Physcomitrella patens]

MAKHLATQLLQQWNEALKTMPPGFRTAGKILVWEELASNKVLITIALAWVLLFVARTCLRN
KKRLPPAIPGGLPVLGNLLQLTEKKPHRTFTAWSKEHGPIFTIKVGSVPQAVVNNSEIAKE
VLVTKFASISKRQMPMALRVLTRDKTMVAMSDYGEEHRMLKKLVMTNLLGPTTQNKNRSLR
DDALIGMIEGVLAELKASPTSPKVVNVRDYVQRSLFPFALQQVFGYIPDQVEVLELGTCVS
TWDMFDALVVAPLSAVINVDWRDFFPALRWIPNRSVEDLVRTVDFKRNSIMKALIRAQRMR
LANLKEPPRCYADIALTEATHLTEKQLEMSLWEPIIESADTTLVTSEWAMYEIAKNPDCQD
RLYREIVSVAGTERMVTEDDLPNMPYLGAIIKETLRKYTPVPLIP*SR*FVEEDITLGGYDIP
KGYQILVNLFAIANDPAVWSNPEKWDPERMLANKKVDMGFRDFSLMPFGAGKRMCAGITQA
MFIIPMNVAALVQHCEWRLSPQEISNINNKIEDVVYLTTHKLSPLSCEATPRISHRLP
(SEQ ID NO: 40 | Wild Type)

MALLLAVFTQLLQQWNEALKTMPPGFRTAGKILVWEELASNKVLITIALAWVLLFVARTCL
RNKKRLPPAIPGGLPVLGNLLQLTEKKPHRTFTAWSKEHGPIFTIKVGSVPQAVVNNSEIA
KEVLVTKFASISKRQMPMALRVLTRDKTMVAMSDYGEEHRMLKKLVMTNLLGPTTQNKNRS
LRDDALIGMIEGVLAELKASPTSPKVVNVRDYVQRSLFPFALQQVFGYIPDQVEVLELGTC
VSTWDMFDALVVAPLSAVINVDWRDFFPALRWIPNRSVEDLVRTVDFKRNSIMKALIRAQR
MRLANLKEPPRCYADIALTEATHLTEKQLEMSLWEPIIESADTTLVTSEWAMYEIAKNPDC
QDRLYREIVSVAGTERMVTEDDLPNMPYLGAIIKETLRKYTPVPLIP*SR*FVEEDITLGGYD
IPKGYQILVNLFAIANDPAVWSNPEKWDPERMLANKKVDMGFRDFSLMPFGAGKRMCAGIT
QAMFIIPMNVAALVQHCEWRLSPQEISNINNKIEDVVYLTTHKLSPLSCEATPRISHRLP
(SEQ ID NO: 41)

ATGGCTCTGTTATTAGCAGTTTTTACGCAACTGCTGCAACAATGGAATGAAGCTCTGAAGAC
GATGCCGCCGGGTTTTCGCACCGCTGGCAAAATTCTGGTGTGGGAAGAACTGGCAAGCAATA
AAGTTCTGATTACGATCGCACTGGCTTGGGTCCTGCTGTTTGTGGCTCGTACCTGCCTGCGC
AATAAAAAGCGTCTGCCGCCGGCAATCCCGGGCGGTCTGCCGGTGCTGGGCAACCTGCTGCA
GCTGACGGAAAAGAAACCGCATCGTACCTTTACGGCGTGGAGCAAGGAACACGGCCCGATTT
TCACCATCAAAGTCGGTTCGGTGCCGCAGGCTGTGGTTAACAATAGCGAAATTGCGAAAGAA
GTCCTGGTGACCAAGTTCGCCAGCATCTCTAAACGTCAAATGCCGATGGCACTGCGCGTCCT
GACGCGTGATAAAACGATGGTGGCTATGTCTGACTATGGCGAAGAACATCGCATGCTGAAAA
AGCTGGTGATGACGAATCTGCTGGGTCCGACCACGCAGAACAAAAATCGTAGTCTGCGCGAT
GACGCACTGATTGGCATGATCGAAGGTGTTCTGGCGGAACTGAAGGCCAGTCCGACCTCCCC
GAAAGTCGTGAACGTTCGCGATTATGTCCAGCGTTCTCTGTTTCCGTTCGCGCTGCAGCAAG
TGTTTGGCTACATTCCGGATCAAGTTGAAGTCCTGGAACTGGGCACGTGTGTTTCTACCTGG
GATATGTTCGACGCACTGGTTGTCGCTCCGCTGAGTGCGGTTATTAACGTCGATTGGCGTGA
CTTTTTCCCGGCCCTGCGCTGGATTCCGAATCGTTCCGTGGAAGATCTGGTGCGCACCGTTG
ACTTTAAGCGTAACTCAATTATGAAAGCCCTGATCCGTGCACAGCGTATGCGCCTGGCTAAC
CTGAAGGAACCGCCGCGCTGCTACGCAGATATTGCTCTGACCGAAGCGACGCACCTGACCGA
AAAACAACTGGAAATGAGTCTGTGGGAACCGATTATCGAATCCGCCGATACCACGCTGGTGA
CCTCAGAATGGGCTATGTATGAAATTGCGAAAAATCCGGATTGTCAGGACCGTCTGTACCGC
GAAATCGTGTCCGTTGCCGGCACGGAACGCATGGTTACCGAAGATGACCTGCCGAACATGCC
GTATCTGGGTGCAATTATCAAAGAAACGCTGCGCAAGTACACCCCGGTTCCGCTGATTCCGA
GTCGTTTTGTCGAAGAAGATATCACCCTGGGCGGTTATGACATTCCGAAAGGTTACCAGATC
CTGGTCAACCTGTTCGCGATTGCCAATGATCCGGCCGTTTGGTCGAACCCGGAAAAATGGGA
CCCGGAACGCATGCTGGCAAATAAAAAGGTGGATATGGGCTTTCGTGACTTCAGCCTGATGC
CGTTTGGCGCCGGTAAACGCATGTGCGCCGGTATCACCCAAGCAATGTTCATTATCCCGATG
AATGTGGCGGCCCTGGTTCAGCATTGTGAATGGCGCCTGAGCCCGCAAGAAATCTCTAACAT
CAACAACAAGATCGAAGATGTGGTTTACCTGACCACGCATAAACTGTCACCGCTGTCGTGCG
AAGCAACCCCGCGTATCAGCCACCGTCTGCCG (SEQ ID NO: 42)

*FIG. 4A (Cont'd)*

>BmVO [Bacillus megaterium]

MTIKEMPQPKTFGELKNLPLLNTDKPVQALMKIADELGEIFKFEAPGRVTRYLSSQRLIKEA
CDE*SR*FDKNLSQALKFVRDFAGDGLATSWTHEKNWKKAHNILLPSFSQQAMKGYHAMMVDIA
VQLVQKWERLNADEHIEVPEDMTRLTLDTIGLCGFNYRFNSFYRDQPHPFITSMVRALDEAM
NKLQRANPDDPAYDENKRQFQEDIKVMNDLVDKIIADRKASGEQSDDLLTHMLNGKDPETGE
PLDDENIRYQIITFLIAGHETTSGLLSFALYFLVKNPHVLQKAAEEAARVLVDPVPSYKQVK
QLKYVGMVLNEALRLWPTIPAFSLYAKEDTVLGGEYPLEKGDELMVLIPQLHRDKTIWGDDV
EEFRPERFENPSAIPQHAFKPFGNGQRACIGQQFALHEATLVLGMMLKHFDFEDHTNYELDI
KETLTLKPEGFVVKAKSKKIPLGGIPSPSTEQSAKKVRKKAENAHNTPLLVLYGSNMGTAEG
TARDLADIAMSKGFAPQVATLDSHAGNLPREGAVLIVTASYNGHPPDNAKQFVDWLDQASAD
EVKGVRYSVFGCGDKNWATTYQKVPAFIDETLAAKGAENIADRGEADASDDFEGTYEEWREH
MWSDVAAYFNLDIENSEDNKSTLSLQFVDSAADMPLAKMHGAFSTNVVASKELQQPGSARST
RHLEIELPKEASYQEGDHLGVIPRNYEGIVNRVTARFGLDASQQIRLEAEEEKLAHLPLAKT
VSVEELLQYVELQDPVTRTQLRAMAAKTVCPPHKVELEALLEKQAYKEQVLAKRLTMLELLE
KYPACEMKFSEFIALLPSIRPRYYSISSSPRVDEKQASITVSVVSGEAWSGYGEYKGIASNY
LAELQEGDTITCFISTPQSEFTLPKDPETPLIMVGPGTGVAPFRGFVQARKQLKEQGQSLGE
AHLYFGCRSPHEDYLYQEELENAQSEGIITLHTAF*SR*MPNQPKTYVQHVMEQDGKKLIELLD
QGAHFYICGDGSQMAPAVEATLMKSYADVHQVSEADARLWLQQLEEKGRYAKDVWAG (SEQ
ID NO: 43)

*FIG. 4A (Cont'd)*

ATGACGATTAAAGAAATGCCGCAACCGAAGACGTTTGGCGAACTGAAGAACCTGCCGCTGCT
GAACACGGATAAGCCGGTGCAAGCCCTGATGAAGATTGCTGATGAACTGGGCGAAATCTTTA
AATTCGAAGCGCCGGGTCGTGTGACCCGTTATCTGAGCAGCCAGCGTCTGATTAAAGAAGCC
TGCGATGAATCGCGCTTTGACAAGAACCTGAGCCAGGCACTGAAATTTGTTCGTGATTTCGC
AGGTGACGGTCTGGCCACCAGCTGGACGCATGAAAAGAACTGGAAAAAGGCCCACAATATTC
TGCTGCCGTCGTTCAGCCAGCAAGCAATGAAAGGCTACCATGCTATGATGGTCGATATCGCG
GTTCAGCTGGTCCAAAAATGGGAACGTCTGAATGCGGACGAACACATTGAAGTGCCGGAAGA
TATGACCCGCCTGACGCTGGACACCATCGGTCTGTGTGGCTTTAACTATCGTTTTAATTCGT
TCTACCGCGATCAGCCGCATCCGTTCATTACCAGCATGGTGCGTGCGCTGGACGAAGCCATG
AACAAACTGCAGCGTGCAAACCCGGATGACCCGGCGTATGATGAAAACAAGCGTCAGTTTCA
AGAAGACATCAAAGTGATGAATGATCTGGTTGACAAGATTATCGCAGATCGCAAAGCGAGCG
GCGAACAGTCAGATGACCTGCTGACGCACATGCTGAACGGCAAAGACCCGGAAACCGGTGAA
CCGCTGGATGACGAAAACATCCGTTATCAGATCATCACCTTTCTGATCGCAGGCCATGAAAC
CACGTCGGGTCTGCTGAGCTTTGCGCTGTACTTCCTGGTCAAGAACCCGCACGTGCTGCAGA
AAGCGGCCGAAGAAGCAGCTCGTGTGCTGGTTGATCCGGTTCCGTCGTATAAACAGGTCAAG
CAACTGAAATACGTGGGTATGGTTCTGAATGAAGCGCTGCGCCTGTGGCCGACGATTCCGGC
ATTTAGCCTGTATGCTAAGGAAGATACCGTTCTGGGCGGTGAATACCCGCTGGAAAAAGGCG
ATGAACTGATGGTCCTGATTCCGCAGCTGCATCGCGACAAAACCATCTGGGGTGATGACGTG
GAAGAATTTCGCCCGGAACGCTTCGAAAACCCGAGCGCGATTCCGCAGCATGCCTTTAAACC
GTTCGGCAATGGTCAACGTGCGTGCATCGGCCAGCAATTTGCGCTGCACGAAGCCACGCTGG
TTCTGGGTATGATGCTGAAACATTTTGATTTCGAAGACCACACCAACTATGAACTGGATATT
AAGGAAACCCTGACGCTGAAACCGGAAGGCTTCGTGGTTAAAGCGAAGTCTAAAAAGATTCC
GCTGGGCGGTATCCCGTCTCCGAGTACGGAACAGAGTGCCAAAAAGGTCCGTAAAAAGGCGG
AAAACGCCCATAATACCCCGCTGCTGGTGCTGTATGGTTCTAACATGGGCACGGCAGAAGGC
ACCGCTCGCGATCTGGCAGACATTGCTATGTCTAAAGGTTTTGCGCCGCAGGTGGCCACGCT
GGATAGTCATGCAGGCAATCTGCCGCGTGAAGGTGCTGTCCTGATCGTGACCGCAAGCTACA
ACGGTCACCCGCCGGATAATGCGAAGCAGTTCGTTGATTGGCTGGACCAAGCGTCGGCCGAT
GAAGTTAAAGGTGTCCGCTATAGCGTGTTTGGCTGTGGTGACAAGAACTGGGCTACCACGTA
CCAGAAAGTTCCGGCGTTCATTGATGAAACGCTGGCGGCCAAAGGCGCAGAAAATATCGCTG
ATCGTGGTGAAGCAGACGCTTCCGATGACTTTGAAGGCACCTATGAAGAATGGCGCGAACAC
ATGTGGTCGGATGTGGCAGCTTACTTCAACCTGGATATTGAAAACAGCGAAGACAATAAATC
CACCCTGTCACTGCAGTTTGTTGATAGTGCGGCCGACATGCCGCTGGCAAAGATGCACGGCG
CTTTCTCCACGAATGTCGTGGCTTCAAAAGAACTGCAGCAACCGGGTTCGGCACGTAGCACC
CGCCATCTGGAAATTGAACTGCCGAAAGAAGCCAGCTATCAGGAAGGCGATCACCTGGGTGT
GATTCCGCGTAACTACGAAGGCATCGTGAATCGTGTTACGGCCCGCTTTGGTCTGGATGCAT
CCCAGCAAATCCGCCTGGAAGCGGAAGAAGAAAAGCTGGCGCATCTGCCGCTGGCCAAAACC
GTCTCAGTGGAAGAACTGCTGCAGTATGTGGAACTGCAAGATCCGGTTACCCGTACGCAGCT
GCGTGCGATGGCGGCTAAGACCGTCTGCCCGCCGCACAAAGTGGAACTGGAAGCTCTGCTGG
AAAAGCAGGCGTATAAAGAACAAGTGCTGGCGAAACGCCTGACCATGCTGGAACTGCTGGAA
AAGTACCCGGCCTGTGAAATGAAGTTCTCTGAATTTATCGCACTGCTGCCGTCTATCCGTCC
GCGTTATTACAGTATTAGTTCCTCACCGCGTGTGGATGAAAAACAGGCCAGTATCACCGTTT
CTGTTGTCAGTGGCGAAGCATGGTCTGGCTATGGTGAATACAAGGGTATCGCAAGTAACTAC
CTGGCTGAACTGCAGGAAGGCGATACCATTACGTGCTTTATCTCTACGCCGCAAAGTGAATT
TACCCTGCCGAAAGACCCGGAAACGCCGCTGATCATGGTTGGCCCGGGCACCGGTGTCGCAC
CGTTTCGTGGTTTCGTGCAGGCACGCAAGCAACTGAAAGAACAGGGCCAATCCCTGGGTGAA
GCGCATCTGTATTTTGGCTGTCGCTCACCGCACGAAGATTATCTGTACCAGGAAGAACTGGA
AAACGCGCAATCCGAAGGTATTATCACGCTGCATACCGCCTTCTCACGTATGCCGAATCAGC
CGAAAACCTACGTCCAGCACGTGATGGAACAAGATGGCAAAAAGCTGATTGAACTGCTGGAC
CAGGGTGCGCATTTTTATATCTGCGGTGATGGCAGCCAAATGGCACCGGCAGTGGAAGCAAC
CCTGATGAAATCCTACGCAGATGTTCACCAGGTCTCAGAAGCAGACGCTCGTCTGTGGCTGC
AGCAACTGGAAGAAAAGGGCCGCTATGCGAAAGATGTTTGGGCCGGTTAA (SEQ ID NO:
44)

*FIG. 4A (Cont'd)*

>PsVO [Pleurotus sapidus]
MRYGCAAVALFYLTAMGKLHPLAIIPDYKGSMAASVTIFNKRTNPLDISVNQANDWPWRYAKT
CVLSSDWALHEMIIHLNNTHLVEEAVIVAAQRKLSPSHIVFRLLEPHWVVTLSLNALARSVLI
PEVIVPIAGFSAPHIFQFIRESFTNFDWKSLYVPADLE*SR*GFPVDQLNSPKFHNYAYARDIND
MWTTLKKFVSSVLQDAQYYPDDASVAGDTQIQAWCDEMRSGMGAGMTNFPESITTVDDLVNMV
TMCIHIAAPQHTAVNYLQQYYQTFVSNKPSALFSPLPTSIAQLQKYTESDLMAALPLNAKRQW
LLMAQIPYLLSMQVQEDENIVTYAANASTDKDPIIASAGRQLAADLKKLAAVFLVNSAQLDDQ
NTPYDVLAPEQLANAIVI (SEQ ID NO: 45)
ATGCGTTATGGCTGTGCTGCTGTGGCTCTGTTCTATCTGACCGCTATGGGCAAACTGCACCCG
CTGGCTATTATCCCGGACTACAAGGGTAGCATGGCGGCCTCTGTCACCATTTTTAACAAACGT
ACGAATCCGCTGGATATCAGCGTTAACCAGGCAAATGACTGGCCGTGGCGCTATGCTAAGACG
TGCGTGCTGAGCAGCGATTGGGCGCTGCATGAAATGATTATCCACCTGAACAATACCCATCTG
GTGGAAGAAGCCGTCATTGTGGCAGCTCAGCGTAAACTGTCACCGTCGCACATCGTTTTTCGC
CTGCTGGAACCGCATTGGGTGGTTACCCTGTCGCTGAACGCACTGGCTCGTAGCGTGCTGATC
CCGGAAGTTATTGTCCCGATCGCGGGTTTCTCTGCCCCGCACATTTTTCAGTTCATCCGCGAA
TCTTTTACCAATTTCGATTGGAAAAGTCTGTACGTCCCGGCGGACCTGGAATCGCGTGGCTTT
CCGGTGGATCAGCTGAACAGCCCGAAGTTCCATAATTATGCGTACGCCCGCGATATCAACGAC
ATGTGGACCACGCTGAAAAAGTTTGTGAGTTCCGTTCTGCAGGATGCCCAATATTACCCGGAT
GACGCAAGTGTGGCTGGTGATACGCAGATTCAAGCATGGTGCGACGAAATGCGTTCCGGCATG
GGTGCGGGCATGACCAACTTCCCGGAATCAATCACCACGGTTGATGACCTGGTCAATATGGTG
ACCATGTGTATTCACATCGCGGCCCCGCAGCATACGGCGGTTAACTATCTGCAGCAATACTAC
CAAACCTTCGTCAGTAACAAGCCGTCCGCACTGTTCTCACCGCTGCCGACCTCTATTGCTCAG
CTGCAAAAATACACGGAAAGTGATCTGATGGCAGCTCTGCCGCTGAACGCGAAGCGTCAGTGG
CTGCTGATGGCCCAAATTCCGTATCTGCTGTCGATGCAGGTGCAAGAAGATGAAAACATCGTT
ACCTACGCGGCCAATGCGTCCACGGATAAAGACCCGATTATCGCATCAGCTGGCCGCCAGCTG
GCAGCTGACCTGAAAAAGCTGGCGGCCGTTTTTCTGGTCAACTCAGCCCAGCTGGATGACCAA
AATACCCCGTATGATGTGCTGGCACCGGAACAGCTGGCGAATGCCATTGTTATCTAA (SEQ
ID NO: 46)

*FIG. 4A (Cont'd)*

>PoLO [Pleurotus ostreatus]

MAPTMSLSRSALKNVHLPYMVQHPEPTDCSTAMKHAAEGYDRARQMIAFLFDILDYESSVPQK
FTPEEKKEKYTWSHSDKFPPHLAIIPEDIDVPAYIIFSIVRLVQTLSIMSGIQCNERLAPGPE
QNTMEKLTKWNAERHKNQGWVKDMFNEPNIGLRNDWYTDAVFAQQFFTGPNPTTITLASDTWM
KAFTEEAASQGKRDLISLFRSAPPNSFYVQDFSDFRARMGAKPDEELCATSDGGVTRYGCAAV
ALFYLPPTGELHPLAIVPDYKGSMAASITLFNKRVDPSDASVDQANDWPWRYAKTCVLSADWV
LHEMIIHLNNTHLVQEAVIVAVQRTLPDSHIVFRLLKPHWVVTLSLNAQARSVLIPEVIVPIA
GFSELRIFQFVGHAFTNFDWKALYVPTDLEFRGFPLDRLDDDKFHNYAYAKDIKDMWMALRKF
VSSVLKDGKYYPDDSAVAADAQIQDWCDEMRSEKGAGMKKFPESISTLDDLIDMVTMCIHIAA
PQHTAVNYLQQYYQTFVPNKPSALFSPLPTLLSQLESYTESDLMAALPLGAKQEWLLMAQVPY
LLSKEVEQDGNIVTYAGTASNNEDPIIAAAGKELSADLVILAGVFLKNSEKLDDQNTAYNVLA
PDQLANAIVI (SEQ ID NO: 47)
ATGGCCCCGACGATGTCACTGTCTCGCTCCGCACTGAAGAATGTCCACCTGCCGTATATGGTC
CAACACCCGGAACCGACCGATTGCAGCACCGCGATGAAACACGCGGCCGAAGGTTATGATCGT
GCTCGCCAGATGATTGCGTTTCTGTTCGACATCCTGGATTACGAAAGCTCTGTTCCGCAAAAA
TTTACCCCGGAAGAAAAGAAAGAAAAATATACGTGGTCACACTCGGATAAGTTCCCGCCGCAT
CTGGCCATTATCCCGGAAGACATTGATGTGCCGGCATACATTATCTTTAGCATCGTTCGTCTG
GTCCAGACCCTGAGTATTATGTCCGGCATCCAATGCAACGAACGTCTGGCACCGGGGCCGGAA
CAGAATACGATGGAAAAACTGACGAAGTGGAACGCGGAACGTCATAAAAATCAAGGCTGGGTC
AAGGATATGTTTAACGAACCGAATATTGGTCTGCGCAACGACTGGTATACCGATGCTGTGTTC
GCGCAGCAATTTTTCACGGGTCCGAATCCGACCACGATTACCCTGGCCTCTGATACGTGGATG
AAAGCATTTACCGAAGAAGCAGCTAGTCAGGGCAAGCGTGACCTGATCAGCCTGTTTCGCTCT
GCCCCGCCGAACTCCTTCTACGTTCAGGACTTTTCAGATTTCCGTGCTCGCATGGGCGCGAAA
CCGGACGAAGAACTGTGCGCGACCTCTGATGGCGGTGTTACCCGTTATGGCTGTGCAGCAGTC
GCACTGTTTTACCTGCCGCCGACCGGTGAACTGCATCCGCTGGCCATTGTGCCGGATTATAAA
GGCAGTATGGCAGCTTCCATCACGCTGTTCAACAAGCGTGTGGACCCGTCAGATGCCTCGGTT
GACCAGGCAAATGATTGGCCGTGGCGCTACGCTAAAACCTGTGTTCTGTCCGCGGATTGGGTC
CTGCATGAAATGATTATCCACCTGAACAATACCCATCTGGTGCAGGAAGCCGTCATTGTGGCA
GTTCAACGTACGCTGCCGGATTCACACATCGTTTTTCGCCTGCTGAAACCGCATTGGGTGGTT
ACCCTGTCGCTGAATGCCCAGGCACGTAGCGTTCTGATCCCGGAAGTCATTGTGCCGATCGCG
GGCTTCAGTGAACTGCGCATCTTTCAGTTCGTTGGTCACGCCTTTACCAACTTCGACTGGAAA
GCACTGTATGTCCCGACGGATCTGGAATTTCGTGGTTTCCCGCTGGACCGCCTGGATGACGAT
AAGTTCCATAACTATGCTTACGCGAAGGACATTAAGGATATGTGGATGGCCCTGCGTAAGTTC
GTGAGTTCCGTTCTGAAAGATGGCAAGTATTACCCGGACGATTCGGCTGTTGCAGCAGACGCG
CAGATTCAAGACTGGTGCGATGAAATGCGCAGCGAAAAAGGCGCGGGTATGAAAAAGTTCCCG
GAAAGCATTTCTACCCTGGACGATCTGATCGATATGGTGACGATGTGTATTCACATCGCAGCT
CCGCAGCATACCGCCGTGAACTATCTGCAGCAATATTACCAAACGTTTGTTCCGAATAAACCG
TCAGCACTGTTCTCGCCGCTGCCGACCCTGCTGAGCCAGCTGGAATCTTACACGGAAAGTGAT
CTGATGGCGGCCCTGCCGCTGGGTGCTAAACAGGAATGGCTGCTGATGGCGCAAGTGCCGTAT
CTGCTGTCTAAGGAAGTCGAACAGGATGGCAACATTGTGACCTACGCCGGTACGGCAAGTAAC
AATGAAGATCCGATTATCGCAGCTGCGGGCAAAGAACTGTCCGCTGACCTGGTCATCCTGGCG
GGTGTGTTTCTGAAAAACTCAGAAAAGCTGGACGATCAGAACACCGCCTATAATGTCCTGGCA
CCGGATCAACTGGCCAATGCAATTGTGATCTAA (SEQ ID NO: 48)

*FIG. 4A (Cont'd)*

>CiVO [Cichorium intybus]
MEISIPTTLGLAVIIFIIFKLLTRTTSKKNLLPEPWRLPIIGHMHHLIGTMPHRGVMELARK
HGSLMHLQLGEVSTIVVSSPRWAKEVLTTYDITFANRPETLTGEIVAYHNTDIVLAPYGEYW
RQLRKLCTLELLSNKKVKSFQSLREEECWNLVKDIRSTGQGSPINLSENIFKMIATILSRAA
FGKGIKDQMKFTELVKEILRLTGGFDVADIFPSKKLLHHLSGKRAKLTNIHNKLDNLINNII
AEHPGNRTSSSQETLLDVLLRLKESAEFPLTADNVKAVILDMFGAGTDTSSATIEWAISELI
RCPRAMEKVQTELRQALNGKERIQEEDLQELNYLKLVIKETLRLHPPLPLVMPRECREPCVL
GGYDIPSKTKLIVNVFAINRDPEYWKDAETFMPERFENSPITVMGSEYEYLPFGAGRRMCPG
AALGLANVELPLAHILYFNWKLPNGKTFEDLDMTESFGATVQRKTELLLVPTDFQTLTAST
(SEQ ID NO: 49 | Wild Type)

MALLLAVFLAVIIFIIFKLLTRTTSKKNLLPEPWRLPIIGHMHHLIGTMPHRGVMELARKHG
SLMHLQLGEVSTIVVSSPRWAKEVLTTYDITFANRPETLTGEIVAYHNTDIVLAPYGEYWRQ
LRKLCTLELLSNKKVKSFQSLREEECWNLVKDIRSTGQGSPINLSENIFKMIATIL*SR*AAFG
KGIKDQMKFTELVKEILRLTGGFDVADIFPSKKLLHHLSGKRAKLTNIHNKLDNLINNIIAE
HPGNRTSSSQETLLDVLLRLKESAEFPLTADNVKAVILDMFGAGTDTSSATIEWAISELIRC
PRAMEKVQTELRQALNGKERIQEEDLQELNYLKLVIKETLRLHPPLPLVMPRECREPCVLGG
YDIPSKTKLIVNVFAINRDPEYWKDAETFMPERFENSPITVMGSEYEYLPFGAGRRMCPGAA
LGLANVELPLAHILYFNWKLPNGKTFEDLDMTESFGATVQRKTELLLVPTDFQTLTAST
(SEQ ID NO: 50)

ATGGCTCTGTTATTAGCAGTTTTTCTGGCTGTCATTATCTTTATCATCTTCAAACTGCTGAC
CCGCACCACCTCGAAGAAAAACCTGCTGCCGGAACCGTGGCGTCTGCCGATTATCGGCCACA
TGCATCACCTGATTGGCACCATGCCGCACCGTGGTGTGATGGAACTGGCGCGCAAACATGGC
TCACTGATGCACCTGCAGCTGGGTGAAGTGAGCACCATCGTGGTTAGCTCTCCGCGTTGGGC
GAAAGAAGTTCTGACCACGTATGATATTACCTTTGCCAACCGCCCGGAAACCCTGACGGGCG
AAATCGTGGCATACCATAATACGGACATTGTTCTGGCTCCGTATGGTGAATACTGGCGTCAG
CTGCGCAAACTGTGCACCCTGGAACTGCTGAGTAACAAAAAAGTCAAATCTTTTCAAAGTCT
GCGTGAAGAAGAATGTTGGAATCTGGTGAAAGATATCCGCTCCACCGGCCAGGGTTCACCGA
TCAACCTGTCGGAAAACATCTTCAAAATGATCGCGACGATCCTGTCTCGTGCGGCCTTTGGC
AAAGGTATTAAAGACCAAATGAAATTCACCGAACTGGTTAAAGAAATCCTGCGCCTGACGGG
CGGTTTTGATGTCGCAGACATTTTCCCGAGTAAAAAACTGCTGCATCACCTGTCCGGCAAAC
GTGCTAAACTGACCAACATCCATAACAAACTGGATAACCTGATCAACAACATTATCGCCGAA
CACCCGGGTAATCGTACCAGTTCCTCACAGGAAACGCTGCTGGATGTTCTGCTGCGCCTGAA
AGAAAGCGCAGAATTTCCGCTGACCGCGGACAATGTTAAAGCCGTCATTCTGGATATGTTCG
GTGCAGGCACCGACACGTCGAGCGCAACCATTGAATGGGCTATCTCTGAACTGATTCGTTGC
CCGCGCGCGATGGAAAAAGTGCAGACGGAACTGCGTCAAGCCCTGAACGGCAAAGAACGCAT
CCAGGAAGAAGATCTGCAAGAACTGAACTACCTGAAACTGGTTATCAAAGAAACCCTGCGCC
TGCATCCGCCGCTGCCGCTGGTCATGCCGCGTGAATGCCGCGAACCGTGTGTGCTGGGCGGT
TATGATATCCCGAGCAAAACCAAACTGATCGTCAACGTGTTTGCAATTAATCGTGACCCGGA
ATACTGGAAAGACGCTGAAACCTTTATGCCGGAACGCTTCGAAAACAGCCCGATTACGGTTA
TGGGTTCTGAATATGAATACCTGCCGTTTGGTGCAGGTCGTCGCATGTGTCCGGGTGCAGCT
CTGGGTCTGGCGAATGTCGAACTGCCGCTGGCCCACATCCTGTATTACTTCAACTGGAAACT
GCCGAATGGCAAAACCTTTGAAGATCTGGACATGACCGAATCCTTCGGTGCAACGGTGCAAC
GCAAAACCGAACTGCTGCTGGTGCCGACGGATTTCCAAACGCTGACCGCATCAACG (SEQ
ID NO: 51)

*FIG. 4A (Cont'd)*

>HaGAO [Helianthus annuus]
MEVSLTTSIALATIVFFLYKLLTRPTSSKNRLPEPWRLPIIGHMHHLIGTMPHRGVMDLARKY
GSLMHLQLGEVSAIVVSSPKWAKEILTTYDIPFANRPETLTGEIIAYHNTDIVLAPYGEYWRQ
LRKLCTLELLSVKKVKSFQSLREEECWNLVQEIKASGSGTPFNLSEGIFKVIATVLSRAAFGK
GIKDQKQFTEIVKEILRETGGFDVADIFPSKKFLHHLSGKRGRLTSIHNKLDSLINNLVAEHT
VSKSSKVNETLLDVLLRLKNSEEFPLTADNVKAIILDMFGAGTDTSSATVEWAISELIRCPRA
MEKVQAELRQALNGKERIKEEEIQDLPYLNLVIRETLRLHPPLPLVMPRECRQAMNLAGYDVA
NKTKLIVNVFAINRDPEYWKDAESFNPERFENSNTTIMGADYEYLPFGAGRRMCPGSALGLAN
VQLPLANILYYFKWKLPNGASHDQLDMTESFGATVQRKTELMLVPSF (SEQ ID NO: 52 | Wild Type)

MALLLAVFIALATIVFFLYKLLTRPTSSKNRLPEPWRLPIIGHMHHLIGTMPHRGVMDLARKY
GSLMHLQLGEVSAIVVSSPKWAKEILTTYDIPFANRPETLTGEIIAYHNTDIVLAPYGEYWRQ
LRKLCTLELLSVKKVKSFQSLREEECWNLVQEIKASGSGTPFNLSEGIFKVIATVLSRAAFGK
GIKDQKQFTEIVKEILRETGGFDVADIFPSKKFLHHLSGKRGRLTSIHNKLDSLINNLVAEHT
VSKSSKVNETLLDVLLRLKNSEEFPLTADNVKAIILDMFGAGTDTSSATVEWAISELIRCPRA
MEKVQAELRQALNGKERIKEEEIQDLPYLNLVIRETLRLHPPLPLVMPRECRQAMNLAGYDVA
NKTKLIVNVFAINRDPEYWKDAESFNPERFENSNTTIMGADYEYLPFGAGRRMCPGSALGLAN
VQLPLANILYYFKWKLPNGASHDQLDMTESFGATVQRKTELMLVPSF (SEQ ID NO: 53)

ATGGCTCTGTTATTAGCAGTTTTCATCGCCCTGGCAACCATTGTCTTTTTCCTGTATAAACTG
CTGACCCGTCCGACCTCATCTAAAAACCGTCTGCCGGAACCGTGGCGCCTGCCGATTATCGGC
CACATGCATCACCTGATTGGCACCATGCCGCACCGTGGTGTCATGGATCTGGCACGCAAATAT
GGCAGCCTGATGCATCTGCAACTGGGTGAAGTTTCTGCGATTGTGGTTAGCTCTCCGAAATGG
GCCAAAGAAATTCTGACCACCTATGATATTCCGTTTGCGAACCGCCCGGAAACCCTGACGGGC
GAAATTATCGCATACCACAATACCGACATTGTGCTGGCTCCGTATGGTGAATACTGGCGTCAA
CTGCGTAAACTGTGCACGCTGGAACTGCTGAGTGTTAAAAAAGTCAAAAGTTTCCAGAGCCTG
CGTGAAGAAGAATGTTGGAACCTGGTTCAAGAAATTAAAGCGAGCGGCAGCGGCACCCCGTTT
AATCTGAGTGAAGGTATTTTCAAAGTGATTGCGACCGTGCTGAGCCGTGCGGCATTTGGTAAA
GGTATCAAAGATCAGAAACAATTCACCGAAATTGTCAAAGAAATCCTGCGCGAAACGGGCGGT
TTTGATGTGGCGGACATCTTTCCGAGCAAAAAATTCCTGCATCACCTGTCTGGCAAACGTGGT
CGCCTGACCTCAATTCATAACAAACTGGATTCGCTGATCAACAATCTGGTCGCCGAACATACC
GTGAGCAAAAGCAGCAAAGTGAATGAAACGCTGCTGGATGTCCTGCTGCGTCTGAAAAACTCG
GAAGAATTTCCGCTGACCGCAGACAATGTGAAAGCTATTATCCTGGATATGTTCGGTGCAGGC
ACCGATACCAGCAGCGCAACGGTGGAATGGGCCATTAGCGAACTGATCCGTTGCCCGCGCGCA
ATGGAAAAAGTTCAGGCAGAACTGCGTCAAGCTCTGAACGGCAAAGAACGCATTAAAGAAGAA
GAAATCCAGGATCTGCCGTATCTGAATCTGGTTATTCGTGAAACCCTGCGTCTGCATCCGCCG
CTGCCGCTGGTCATGCCGCGTGAATGTCGCCAAGCAATGAACCTGGCTGGCTATGACGTGGCA
AATAAAACCAAACTGATCGTCAATGTGTTTGCGATTAACCGTGACCCGGAATACTGGAAAGAC
GCGGAAAGTTTTAACCCGGAACGCTTTGAAAACAGCAACACCACGATTATGGGTGCGGATTAT
GAATACCTGCCGTTTGGCGCCGGTCGTCGCATGTGTCCGGGCAGCGCGCTGGGTCTGGCCAAC
GTTCAACTGCCGCTGGCCAATATCCTGTATTACTTCAAATGGAAACTGCCGAATGGCGCCTCA
CACGATCAACTGGACATGACCGAATCGTTTGGTGCAACCGTGCAACGCAAAACGGAACTGATG
CTGGTTCCGTCTTTC (SEQ ID NO: 54)

*FIG. 4A (Cont'd)*

>n20yhcB-t29SrKO
MAWEYALIGLVVGIIIGAVAAWYLKSYTSARRSQSNHLPRVPEVPGVPLLGNLLQLKEKKPYM
TFTRWAATYGPIYSIKTGATSMVVVSSNEIAKEALVTRFQSISTRNLSKALKVLTADKTMVAM
SDYDDYHKTVKRHILTAVLGPNAQKKHRIHRDIMMDNISTQLHEFVKNNPEQEEVDLRKIFQS
ELFGLAMRQALGKDVESLYVEDLKITMNRDEIFQVLVVDPMMGAIDVDWRDFFPYLKWVPNKK
FENTIQQMYIRREAVMKSLIKEHKKRIASGEKLNSYIDYLLSEAQTLTDQQLLMSLWEPIIES
SDTTMVTTEWAMYELAKNPKLQDRLYRDIKSVCGSEKITEEHLSQLPYITAIFHETLRRHSPV
PIIPLRHVHEDTVLGGYHVPAGTELAVNIYGCNMDKNVWENPEEWNPERFMKENETIDFQKTM
AFGGGKRVCAGSLQALLTASIGIGRMVQEFEWKLKDMTQEEVNTIGLTTQMLRPLRAIIKPRI
(SEQ ID NO: 55)

>n22yhcB-t30VO1c9
MAWEYALIGLVVGIIIGAVAMRWYLKSYTSARRSQSNHLPRVPEVPGVPLLGNLLQLKEKKPY
MTFTRWAATYGPIYSIKTGATSVVVVSSNEIAKEAMVTRFQSISTRNLSKALKVLTADKTMVA
MSDYDDYHKTVKRHILTAVLGPNAQKKHRIHRDIMMDNISTQLHEFVKNNPEQEEVDLRKIFQ
SELFGLAMRQALGKDVESLYVEDLKITMNRDEILQVLVVDPMMGAIDVDWRDFFPYLKWVPNK
KFENTIQQMYIRREAVMKSLIKEHKKRIASGEKLNSYIDYLLSEAQTLTDQQLLMSLWEPIIE
SSDTTMVTTEWAMYELAKNPKLQDRLYRDIKSVCGSEKITEEHLSQLPYITAIFHETLRKHSP
VPILPLRHVHEDTVLGGYHVPAGTELAVNIYGCNMDKNVWENPEEWNPERFMKENETIDFQKT
MAFGGGKRVCAGSLQALLIASIGIGRMVQEFEWKLKDMTQEEVNTIGLTNQMLRPLRAIIKPR
I (SEQ ID NO: 56)

>n22yhcB-t30VO1c12
MAWEYALIGLVVGIIIGAVAMRWYLKSYTSARRSQSNHLPRVPEVPGVPLLGNLLQLKEKKPY
MTFTKWAATYGPIYSIKTGATSMVVVSSNEIAKEAMVTRFQSISTRNLSKALKVLTADKQMVA
MSDYDDYHKTVKRHILTAVLGPNAQKKHRIHRDIMMDNISTQLHEFVKNNPEQEEVDLRKIFQ
SELFGLAMRQALGKDVESLYVEDLKITMNRDEILQVLVVDPMMGAIDVDWRDFFPYLKWVPNK
KFENTIQQMYIRREAVMKSLIKEHKKRIASGEKLNSYIDYLLSEAQTLTDQQLLMSLWEPIIE
SSDTTMVTTEWAMYELAKNPKLQDRLYRDIKSVCGSEKITEEHLSQLPYITAIFHETLRKHSP
VPILPLRHVHEDTVLGGYHVPAGTELAVNIYGCNMDKNVWENPEEWNPERFMKENETIDFQKT
MAFGGGKRVCAGSLQALLIASIGIGRMVQEFEWKLKDMTQEEVNTIGLTNQMLRPLRAIIKPR
I (SEQ ID NO: 57)

>n22yhcB-t30VO1b4
MAWEYALIGLVVGIIIGAVAMRWYLKSYTSARRSQSNHLPRVPEVPGVPLLGNLLQLKEKKPY
MTFTRWAATYGPIYSIKTGATSVVVVSSNEIAKEAMVTRFQSISTRNLSKALKVLTADKQMVA
MSDYDDYHKTVKRHILTAVLGPNAQKKHRIHRDIMMDNISTQLHEFVKNNPEQEEVDLRKIFQ
SELFGLAMRQALGKDVESLYVEDLKITMNRDEILQVLVVDPMMGAIDVDWRDFFPYLKWVPNK
KFENTIQQMYIRREAVMKSLIKEHKKRIASGEKLNSYIDYLLSEAQTLTDQQLLMSLWEPIIE
SSDTTMVTTEWAMYELAKNPKLQDRLYRDIKSVCGSEKITEEHLSQLPYITAIFHETLRKHSP
VPILPLRHVHEDTVLGGYHVPAGTELAVNIYGCNMDKNVWENPEEWNPERFMKENETIDFQKT
MAFGGGKRVCAGSLQALLIASIGIGRMVQEFEWKLKDMTQEEVNTIGLTNQMLRPLRAIIKPR
I (SEQ ID NO: 58)

FIG. 4B

>n20yhcB-t29VO1c11
MAWEYALIGLVVGIIIGAVAAWYLKSYTSARRSQSNHLPRVPEVPGVPLLGNLLQLKEKKPYM
TFTKWAATYGPIYSIKTGATSMVVVSSNEIAKEAMVTRFQSISTRNLSKALKVLTADKQMVAM
SDYDDYHKTVKRHILTAVLGPNAQKKHRIHRDIMMDNISTQLHEFVKNNPEQEEVDLRKIFQS
ELFGLAMRQALGKDVESLYVEDLKITMNRDEILQVLVVDPMMGAIDVDWRDFFPYLKWVPNKK
FENTIQQMYIRREAVMKSLIKEHKKRIASGEKLNSYIDYLLSEAQTLTDQQLLMSLWEPIIES
SDTTMVTTEWAMYELAKNPKLQDRLYRDIKSVCGSEKITEEHLSQLPYITAIFHETLRKHSPV
PILPLRHVHEDTVLGGYHVPAGTELAVNIYGCNMDKNVWENPEEWNPERFMKENETIDFQKTM
AFGGGKRVCAGSLQALLIASIGIGRMVQEFEWKLKDMTQEEVNTIGLTNQMLRPLRAIIKPRI
(SEQ ID NO: 59)

>n22yhcB-t30VO1b6
MAWEYALIGLVVGIIIGAVAMRWYLKSYTSARRSQSNHLPRVPEVPGVPLLGNLLQLKEKKPY
MTFTKWAATYGPIYSIKTGATSVVVVSSNEIAKEAMVTRFQSISTRNLSKALKVLTADKTMVA
MSDYDDYHKTVKRHILTAVLGPNAQKKHRIHRDIMMDNISTQLHEFVKNNPEQEEVDLRKIFQ
SELFGLAMRQALGKDVESLYVEDLKITMNRDEILQVLVVDPMMGAIDVDWRDFFPYLKWVPNK
KFENTIQQMYIRREAVMKSLIKEHKKRIASGEKLNSYIDYLLSEAQTLTDQQLLMSLWEPIIE
SSDTTMVTTEWAMYELAKNPKLQDRLYRDIKSVCGSEKITEEHLSQLPYITAIFHETLRKHSP
VPIIPLRHVHEDTVLGGYHVPAGTELAVNIYGCNMDKNVWENPEEWNPERFMKENETIDFQKT
MAFGGGKRVCAGSLQALLIASIGIGRMVQEFEWKLKDMTQEEVNTIGLTNQMLRPLRAIIKPR
I (SEQ ID NO: 60)

>n22yhcB-t30VO1c6 (VO2)

MAWEYALIGLVVGIIIGAVAMRWYLKSYTSARRSQSNHLPRVPEVPGVPLLGNLLQLKEKKPY
MTFTKWAATYGPIYSIKTGATSVVVVSSNEIAKEALVTRFQSISTRNLSKALKVLTADKQMVA
MSDYDDYHKTVKRHILTAVLGPNAQKKHRIHRDIMMDNISTQLHEFVKNNPEQEEVDLRKIFQ
SELFGLAMRQALGKDVESLYVEDLKITMNRDEILQVLVVDPMMGAIDVDWRDFFPYLKWVPNK
KFENTIQQMYIRREAVMKSLIKEQKKRIASGEKLNSYIDYLLSEAQTLTDQQLLMSLWEPIIE
SSDTTMVTTEWAMYELAKNPKLQDRLYRDIKSVCGSEKITEEHLSQLPYITAIFHETLRKHSP
VPILPLRHVHEDTVLGGYHVPAGTELAVNIYGCNMDKNVWENPEEWNPERFMKENETIDFQKT
MAFGGGKRVCAGSLQALLIASIGIGRMVQEFEWKLKDMTQEEVNTIGLTNQMLRPLRAIIKPR
I (SEQ ID NO: 61)

*FIG. 4B (Cont'd)*

**>*Sr*CPR [Stevia rebaudiana]**

MQSDSVKVSPFDLVSAAMNGKAMEKLNASESEDPTTLPALKMLVENRELLTLFTTSFAVLIGC
LVFLMWRRSSSKKLVQDPVPQVIVVKKKEKESEVDDGKKKVSIFYGTQTGTAEGFAKALVEEA
KVRYEKTSFKVIDLDDYAADDDEYEEKLKKESLAFFFLATYGDGEPTDNAANFYKWFTEGDDK
GEWLKKLQYGVFGLGNRQYEHFNKIAIVVDDKLTEMGAKRLVPVGLGDDDQCIEDDFTAWKEL
VWPELDQLLRDEDDTSVTTPYTAAVLEYRVVYHDKPADSYAEDQTHTNGHVVHDAQHP*S*RSNV
AFKKELHTSQSDRSCTHLEFDISHTGLSYETGDHVGVYSENLSEVVDEALKLLGLSPDTYFSV
HADKEDGTPIGGASLPPPFPPCTLRDALTRYADVLSSPKKVALLALAAHASDPSEADRLKFLA
SPAGKDEYAQWIVANQRSLLEVMQSFPSAKPPLGVFFAAVAPRLQPRYYSISSSPKMSPNRIH
VTCALVYETTPAGRIHRGLCSTWMKNAVPLTESPDCSQASIFVRTSNFRLPVDPKVPVIMIGP
GTGLAPFRGFLQERLALKESGTELGSSIFFFGCRNRKVDFIYEDELNNFVETGALSELIVAF*S*
*R*EGTAKEYVQHKMSQKASDIWKLLSEGAYLYVCGDAKGMAKDVHRTLHTIVQEQGSLDSSKAE
LYVKNLQMSGRYLRDVW (SEQ ID NO: 62)

ATGCAGAGCGATTCTGTTAAAGTATCCCCGTTCGACCTGGTCTCTGCGGCTATGAACGGCAAA
GCAATGGAGAAACTGAACGCGAGCGAATCTGAAGATCCAACCACCCTGCCGGCACTGAAAATG
CTGGTAGAAAACCGTGAACTGCTGACTCTGTTCACCACCTCCTTCGCCGTTCTGATTGGTTGC
CTGGTCTTCCTGATGTGGCGCCGTTCCTCTTCCAAGAAGCTGGTACAGGACCCGGTTCCTCAG
GTGATCGTCGTTAAAAAGAAAGAGAAGGAAAGCGAAGTCGATGACGGCAAAAAGAAGGTTTCC
ATTTTCTACGGTACTCAGACCGGCACCGCTGAGGGTTTTGCCAAAGCACTGGTTGAAGAGGCA
AAAGTGCGTTACGAAAAAACTTCCTTCAAAGTGATTGACCTGGACGACTATGCTGCGGATGAT
GATGAATACGAGGAAAAACTGAAAAAAGAAAGCCTGGCCTTCTTCTTCCTGGCAACCTATGGC
GATGGTGAACCGACCGACAACGCGGCGAACTTCTACAAATGGTTTACCGAAGGCGACGACAAA
GGTGAATGGCTGAAGAAACTGCAGTATGGTGTTTTCGGTCTGGGCAATCGCCAGTACGAACAT
TTTAACAAAATCGCAATCGTTGTTGATGACAAACTGACTGAAATGGGTGCGAAACGTCTGGTG
CCGGTTGGCCTGGGTGACGATGATCAATGCATCGAAGATGACTTCACCGCATGGAAAGAACTG
GTTTGGCCGGAACTGGATCAGCTGCTGCGCGACGAAGACGACACTTCCGTGACCACCCCGTAT
ACCGCTGCAGTGCTGGAGTACCGTGTTGTTTACCACGATAAACCGGCGGACTCTTACGCCGAA
GATCAGACTCACACTAACGGTCACGTCGTACATGACGCACAGCACCCGTCTCGTAGCAATGTT
GCGTTTAAGAAAGAGCTGCACACGAGCCAGTCCGACCGCTCTTGTACGCACCTGGAGTTCGAT
ATCTCCCACACCGGTCTGTCCTATGAAACCGGTGACCATGTTGGCGTTTACAGCGAAAACCTG
AGCGAGGTAGTTGATGAAGCGCTGAAACTGCTGGGCCTGTCTCCAGACACCTACTTTAGCGTG
CATGCTGACAAGGAAGATGGTACTCCGATTGGCGGCGCTTCCCTGCCGCCACCGTTTCCACCT
TGCACTCTGCGTGATGCTCTGACTCGTTACGCTGATGTTCTGTCTAGCCCGAAAAAGGTTGCG
CTGCTGGCGCTGGCCGCACATGCTTCTGACCCGTCTGAAGCTGACCGTCTGAAATTCCTGGCG
TCTCCGGCCGGCAAAGACGAATACGCGCAGTGGATTGTCGCTAACCAGCGCTCTCTGCTGGAA
GTGATGCAGTCCTTCCCGTCTGCCAAACCGCCACTGGGCGTGTTTTTCGCAGCTGTGGCTCCG
CGCCTGCAGCCGCGCTACTATTCTATCTCTAGCTCCCCGAAAATGAGCCCGAACCGCATCCAC
GTTACTTGTGCTCTGGTTTACGAAACCACCCCTGCGGGCCGTATCCACCGTGGTCTGTGCTCT
ACGTGGATGAAAAATGCCGTGCCGCTGACCGAATCCCCGGACTGCTCTCAGGCGTCCATCTTC
GTGCGTACCTCTAACTTCCGTCTGCCGGTGGACCCGAAAGTTCCTGTTATCATGATCGGTCCT
GGCACGGGTCTGGCCCCGTTTCGTGGTTTTCTGCAGGAGCGTCTGGCTCTGAAAGAATCCGGT
ACTGAGCTGGGCTCTTCCATCTTTTTCTTCGGTTGTCGTAACCGCAAAGTCGATTTCATCTAT
GAAGACGAACTGAACAACTTCGTAGAGACTGGTGCACTGTCCGAACTGATTGTGGCATTCTCT
CGTGAAGGCACGGCGAAAGAATACGTTCAACACAAAATGTCTCAGAAAGCGAGCGATATCTGG
AAACTGCTGTCCGAGGGTGCGTATCTGTATGTTTGTGGCGACGCGAAAGGCATGGCTAAAGAT
GTACACCGCACCCTGCACACCATTGTACAAGAACAAGGCTCTCTGGATAGCTCCAAGGCAGAA
CTGTACGTGAAAAACCTGCAGATGTCTGGCCGTTACCTGCGTGATGTATGGTAA (SEQ ID
NO: 63)

FIG. 6A

>AtCPR [Arabidopsis thaliana]
MTSALYASDLFKQLKSIMGTDSLSDDVVLVIATTSLALVAGFVVLLWKKTTADRSGELKPLMI
PKSLMAKDEDDDLDLGSGKTRVSIFFGTQTGTAEGFAKALSEEIKARYEKAAVKVIDLDDYAA
DDDQYEEKLKKETLAFFCVATYGDGEPTDNAARFSKWFTEENERDIKLQQLAYGVFALGNRQY
EHFNKIGIVLDEELCKKGAKRLIEVGLGDDDQSIEDDFNAWKESLWSELDKLLKDEDDKSVAT
PYTAVIPEYRVVTHDPRFTTQKSMESNVANGNTTIDIHHPCRVDVAVQKELHTHESDRSCIHL
EFDI*SR*TGITYETGDHVGVYAENHVEIVEEAGKLLGHSLDLVFSIHADKEDGSPLESAVPPPF
PGPCTLGTGLARYADLLNPPRKSALVALAAYATEPSEAEKLKHLTSPDGKDEYSQWIVASQRS
LLEVMAAFPSAKPPLGVFFAAIAPRLQPRYYSISSCQDWAP*SR*VHVTSALVYGPTPTGRIHKG
VCSTWMKNAVPAEKSHECSGAPIFIRASNFKLPSNPSTPIVMVGPGTGLAPFRGFLQERMALK
EDGEELGSSLLFFGCRNRQMDFIYEDELNNFVDQGVISELIMAF*SR*EGAQKEYVQHKMMEKAA
QVWDLIKEEGYLYVCGDAKGMARDVHRTLHTIVQEQEGVSSSEAEAIVKKLQTEGRYLRDVW
(SEQ ID NO: 64)

ATGACCAGCGCACTGTACGCAAGCGACCTGTTTAAGCAACTGAAGAGCATTATGGGCACCGAT
AGCCTGAGCGATGATGTTGTCCTGGTCATTGCGACCACGAGCCTGGCACTGGTGGCTGGTTTT
GTGGTTCTGCTGTGGAAAAAGACCACGGCCGATCGTTCTGGCGAACTGAAACCGCTGATGATT
CCGAAAAGTCTGATGGCAAAGGACGAAGATGACGATCTGGATCTGGGCTCCGGTAAAACCCGT
GTGTCAATCTTTTTCGGTACCCAGACGGGCACCGCAGAAGGTTTCGCAAAAGCTCTGTCTGAA
GAAATTAAGGCGCGCTATGAAAAAGCGGCCGTTAAGGTCATCGATCTGGACGATTATGCAGCT
GACGATGACCAGTACGAAGAAAAACTGAAAAAGGAAACCCTGGCGTTTTTCTGCGTTGCCACC
TACGGCGACGGTGAACCGACGGATAACGCGGCCCGTTTTAGTAAATGGTTCACCGAAGAAAAT
GAACGCGACATTAAGCTGCAGCAACTGGCGTATGGCGTGTTTGCTCTGGGTAACCGTCAGTAC
GAACATTTCAACAAGATCGGTATCGTCCTGGATGAAGAACTGTGTAAAAAGGGCGCGAAGCGC
CTGATTGAAGTGGGCCTGGGTGATGACGATCAATCCATCGAAGACGATTTTAACGCCTGGAAA
GAATCTCTGTGGAGTGAACTGGACAAACTGCTGAAGGATGAAGACGATAAGAGCGTGGCGACG
CCGTATACCGCCGTTATTCCGGAATACCGTGTCGTGACCCATGATCCGCGCTTCACCACGCAG
AAAAGCATGGAATCAAATGTTGCGAACGGTAATACCACGATTGACATCCATCACCCGTGCCGT
GTGGATGTTGCCGTCCAAAAAGAACTGCATACCCACGAATCGGACCGTAGCTGTATCCACCTG
GAATTTGATATTAGCCGCACGGGCATCACCTATGAAACGGGCGACCATGTGGGTGTTTACGCA
GAAAACCACGTGGAAATTGTTGAAGAAGCTGGCAAACTGCTGGGTCATTCGCTGGATCTGGTT
TTTAGCATCCACGCGGACAAGGAAGATGGTTCGCCGCTGGAAAGCGCAGTGCCGCCGCCGTTC
CCGGGTCCGTGCACCCTGGGTACGGGTCTGGCACGTTATGCAGATCTGCTGAATCCGCCGCGC
AAATCCGCACTGGTGGCTCTGGCAGCTTACGCAACCGAACCGTCAGAAGCTGAAAAACTGAAG
CATCTGACGTCGCCGGACGGTAAAGATGAATATAGCCAGTGGATTGTTGCGTCTCAACGCAGT
CTGCTGGAAGTCATGGCAGCATTTCCGTCGGCAAAACCGCCGCTGGGCGTGTTTTTCGCAGCT
ATTGCACCGCGTCTGCAGCCGCGCTATTACAGCATCAGCTCTTGTCAAGATTGGGCGCCGTCT
CGTGTCCATGTGACCAGTGCACTGGTGTATGGTCCGACGCCGACCGGTCGCATTCACAAAGGC
GTGTGCTCTACCTGGATGAAAAACGCGGTTCCGGCCGAAAAGTCTCACGAATGTAGTGGTGCG
CCGATTTTTATCCGTGCCAGTAACTTCAAACTGCCGTCCAATCCGTCAACCCCGATCGTTATG
GTCGGTCCGGGTACGGGTCTGGCACCGTTTCGTGGTTTCCTGCAGGAACGCATGGCTCTGAAA
GAAGATGGCGAAGAACTGGGTAGTTCCCTGCTGTTTTTCGGCTGCCGTAATCGCCAGATGGAC
TTCATCTACGAAGATGAACTGAACAACTTCGTCGATCAAGGTGTGATTTCCGAACTGATCATG
GCATTTTCACGCGAAGGCGCTCAGAAAGAATACGTCCAACATAAAATGATGGAAAAGGCGGCC
CAAGTGTGGGATCTGATCAAAGAAGAAGGCTATCTGTACGTTTGTGGCGACGCAAAGGGTATG
GCTCGTGATGTCCATCGCACCCTGCACACGATTGTTCAGGAACAAGAAGGTGTCTCATCGAGC
GAAGCGGAAGCCATCGTGAAAAAGCTGCAGACCGAAGGCCGTTATCTGCGCGATGTTTGGTAA
(SEQ ID NO: 65)

*FIG. 6A (Cont'd)*

>TcCPR [Taxus cuspidata]

MQANSNTVEGASQGKSLLDI*SR*LDHIFALLLNGKGGDLGAMTGSALILTENSQNLMILTTALA
VLVACVFFFVWRRGGSDTQKPAVRPTPLVKEEDEEEEDDSAKKKVTIFFGTQTGTAEGFAKAL
AEEAKARYEKAVFKVVDLDNYAADDEQYEEKLKKEKLAFFMLATYGDGEPTDNAARFYKWFLE
GKEREPWLSDLTYGVFGLGNRQYEHFNKVAKAVDEVLIEQGAKRLVPVGLGDDDQCIEDDFTA
WREQVWPELDQLLRDEDDEPTSATPYTAAIPEYRVEIYDSVVSVYEETHALKQNGQAVYDIHH
PCRSNVAVRRELHTPLSDRSCIHLEFDISDTGLIYETGDHVGVHTENSIETVEEAAKLLGYQL
DTIFSVHGDKEDGTPLGGSSLPPPFPGPCTLRTALARYADLLNPPRKAAFLALAAHASDPAEA
ERLKFLSSPAGKDEYSQWVTASQRSLLEIMAEFPSAKPPLGVFFAAIAPRLQPRYYSISSSPR
FAP*SR*IHVTCALVYGPSPTGRIHKGVCSNWMKNSLPSEETHDCSWAPVFVRQSNFKLPADSTT
PIVMVGPGTGFAPFRGFLQERAKLQEAGEKLGPAVLFFGCRNRQMDYIYEDELKGYVEKGILT
NLIVAF*SR*EGATKEYVQHKMLEKASDTWSLIAQGGYLYVCGDAKGMARDVHRTLHTIVQEQES
VDSSKAEFLVKKLQMDGRYLRDIW (SEQ ID NO: 66)

ATGCAGGCTAATTCCAACACGGTGGAAGGTGCCTCCCAGGGGAAGAGCCTGCTGGACATATCT
CGGCTGGACCATATTTTTGCGCTGCTGTTGAACGGCAAGGGAGGAGATCTGGGAGCCATGACC
GGCTCGGCTTTGATTTTGACAGAGAATTCGCAGAATTTGATGATTTTGACCACGGCTTTGGCT
GTTTTGGTCGCGTGTGTTTTCTTCTTCGTTTGGAGGAGGGGAGGATCGGATACGCAGAAGCCG
GCGGTGAGACCGACGCCTCTGGTGAAGGAGGAAGATGAGGAGGAAGAAGACGATTCTGCAAAG
AAGAAAGTCACGATTTTCTTTGGGACACAGACTGGGACGGCCGAGGGATTTGCCAAGGCTCTA
GCAGAAGAGGCAAAGGCAAGATATGAGAAAGCTGTGTTTAAAGTCGTAGATTTGGACAACTAT
GCAGCAGATGATGAGCAGTATGAAGAAAAATTGAAAAAGGAAAAATTAGCATTTTTTATGCTA
GCAACGTATGGAGATGGGGAGCCCACTGACAATGCAGCAAGATTTTATAAGTGGTTTCTTGAG
GGCAAGGAGAGGGAGCCATGGCTTTCTGATCTCACTTATGGGGTGTTTGGATTAGGCAACAGA
CAATATGAACATTTTAATAAGGTGGCTAAAGCAGTAGATGAAGTCTTAATTGAACAAGGTGCA
AAGCGACTTGTTCCAGTGGGCCTTGGTGATGATGACCAATGCATTGAAGATGACTTTACTGCT
TGGCGAGAGCAGGTTTGGCCTGAACTGGATCAGTTACTCCGGGATGAAGATGATGAGCCCACA
AGTGCTACACCTTATACAGCTGCCATACCTGAGTATAGGGTTGAAATTTATGATTCCGTGGTT
TCAGTGTACGAGGAAACTCATGCTCTCAAGCAAAATGGCCAAGCTGTTTATGATATCCATCAC
CCCTGCAGATCTAATGTGGCAGTGAGAAGAGAGCTTCATACACCTTTGTCTGACCGCTCTTGC
ATCCATTTGGAATTTGATATATCAGACACTGGCCTTATATATGAGACAGGAGATCATGTTGGT
GTCCATACAGAAAACAGCATTGAAACTGTGGAGGAAGCAGCAAAGCTACTAGGCTACCAATTG
GACACTATATTCTCAGTCCACGGTGACAAAGAAGATGGCACGCCACTTGGAGGGTCTTCTTTG
CCACCACCTTTCCCTGGTCCATGCACCCTACGAACTGCTCTTGCTCGTTATGCTGATTTGCTG
AATCCTCCTCGGAAGGCCGCCTTTCTTGCATTGGCAGCTCATGCATCTGATCCAGCAGAGGCA
GAGCGGTTGAAGTTCCTCTCATCACCAGCTGGAAAGGATGAATATTCTCAATGGGTCACTGCA
AGTCAGAGAAGTCTTTTAGAAATAATGGCAGAATTTCCATCAGCAAAACCACCCCTTGGTGTT
TTCTTTGCAGCAATAGCCCCTCGTCTGCAACCCCGATATTATTCTATTTCTTCCTCTCCCAGG
TTTGCACCCTCAAGAATACATGTGACATGTGCTCTTGTTTACGGGCCCAGTCCAACCGGTAGA
ATTCACAAAGGTGTTTGTTCTAACTGGATGAAGAATTCGCTACCCTCAGAAGAAACCCATGAC
TGTAGCTGGGCTCCAGTCTTTGTCAGGCAATCAAATTTTAAATTGCCAGCAGATTCTACTACT
CCTATTGTCATGGTGGGTCCTGGAACTGGTTTTGCACCTTTTAGAGGTTTTTTGCAGGAAAGA
GCAAAACTTCAAGAAGCTGGTGAGAAGCTCGGTCCGGCTGTTTTATTTTTTGGGTGCAGGAAT
CGCCAAATGGACTACATTTATGAAGATGAGCTGAAGGGCTATGTGGAGAAAGGAATACTGACC
AATCTCATTGTTGCTTTCTCTCGTGAAGGAGCAACCAAAGAGTATGTCCAGCACAAGATGCTG
GAAAAGGCATCCGATACCTGGAGTCTCATTGCTCAGGGTGGGTATCTTTATGTATGTGGTGAT
GCCAAGGGTATGGCTAGGGATGTACACAGGACACTGCACACTATTGTCCAAGAGCAGGAATCT
GTGGATAGCAGCAAAGCAGAGTTTCTAGTGAAGAAATTACAGATGGATGGAAGATACTTACGA
GATATATGGTGA (SEQ ID NO: 67)

*FIG. 6A (Cont'd)*

>AaCPR [Artemisia annua]

MAQSTTSVKLSPFDLMTALLNGKVSFDTSNTSDTNIPLAVFMENRELLMILTTSVAVLIGCVV
VLVWRRSSSAAKKAAESPVIVVPKKVTEDEVDDGRKKVTVFFGTQTGTAEGFAKALVEEAKAR
YEKAVFKVIDLDDYAAEDDEYEEKLKKESLAFFFLATYGDGEPTDNAARFYKWFTEGEEKGEW
LDKLQYAVFGLGNRQYEHFNKIAKVVDEKLVEQGAKRLVPVGMGDDDQCIEDDFTAWKELVWP
ELDQLLRDEDDTSVATPYTAAVAEYRVVFHDKPETYDQDQLTNGHAVHDAQHPCRSNVAVKKE
LHSPLSDRSCTHLEFDISNTGLSYETGDHVGVYVENLSEVVDEAEKLIGLPPHTYFSVHADNE
DGTPLGGASLPPPFPPCTLRKALASYADVLSSPKKSALLALAAHATDSTEADRLKFLASPAGK
DEYAQWIVASHRSLLEVMEAFPSAKPPLGVFFASVAPRLQPRYYSISSSPRFAPNRIHVTCAL
VYEQTPSGRVHKGVCSTWMKNAVPMTESQDCSWAPIYVRTSNFRLPSDPKVPVIMIGPGTGLA
PFRGFLQERLAQKEAGTELGTAILFFGCRNRKVDFIYEDELNNFVETGALSELVTAFSREGAT
KEYVQHKMTQKASDIWNLLSEGAYLYVCGDAKGMAKDVHRTLHTIVQEQGSLDSSKAELYVKN
LQMAGRYLRDVW (SEQ ID NO: 68)

ATGGCGCAGTCTACCACCAGCGTGAAATTGTCCCCTTTTGATCTCATGACCGCTCTGCTGAAT
GGGAAAGTCTCATTCGATACAAGCAACACAAGTGATACCAACATCCCTTTGGCGGTTTTTATG
GAGAATAGAGAGTTACTCATGATTTTAACGACTTCCGTGGCCGTGCTCATTGGGTGCGTCGTC
GTACTTGTCTGGCGCCGGTCAAGTAGCGCAGCAAAGAAGGCGGCGGAGTCCCCGGTTATCGTC
GTCCCAAAGAAGGTTACAGAGGACGAGGTGGACGACGGACGCAAAAAAGTGACGGTATTCTTT
GGTACACAGACCGGAACCGCGGAAGGATTTGCTAAAGCGCTGGTGGAAGAAGCTAAAGCCCGT
TACGAAAAAGCGGTATTCAAAGTGATAGACCTGGATGACTATGCGGCAGAGGACGACGAGTAC
GAGGAAAAATTGAAAAAAGAATCTCTTGCGTTCTTTTTTCTCGCCACTTACGGCGATGGAGAA
CCTACTGATAATGCGGCTCGGTTTTATAAGTGGTTCACTGAGGGTGAAGAAAAAGGTGAATGG
CTGGACAAATTGCAGTACGCAGTATTTGGACTCGGGAATCGTCAATATGAACATTTTAACAAA
ATTGCTAAGGTCGTCGATGAAAAACTGGTTGAGCAGGGTGCGAAACGTCTGGTCCCGGTTGGA
ATGGGCGATGACGACCAGTGCATTGAAGACGACTTTACAGCATGGAAGGAACTGGTGTGGCCG
GAACTGGACCAACTTTTGCGTGACGAGGATGACACATCTGTAGCTACGCCGTACACTGCTGCG
GTAGCCGAGTATAGGGTCGTTTTTCACGATAAACCGGAAACCTACGACCAAGACCAGCTCACA
AATGGTCATGCAGTACATGATGCGCAACATCCTTGCAGGTCAAATGTGGCGGTGAAGAAAGAG
CTGCACAGTCCTCTGTCAGATCGTTCTTGCACCCACCTGGAATTTGACATATCCAATACGGGC
CTTTCGTATGAAACCGGAGATCACGTTGGTGTCTATGTTGAAAATCTGTCGGAAGTGGTTGAT
GAGGCGGAAAAACTTATCGGTCTGCCGCCTCATACGTACTTTTCAGTCCACGCTGATAATGAA
GACGGAACCCCGCTGGGTGGCGCATCGTTACCCCCACCCTTTCCACCATGCACTCTGCGTAAG
GCGCTTGCCAGTTATGCTGATGTTTTGTCTAGTCCCAAAAAGAGTGCACTTCTCGCACTGGCG
GCCCATGCCACTGATAGTACAGAGGCCGACAGGCTGAAATTTCTGGCGTCACCAGCGGGAAAA
GACGAATACGCCCAATGGATCGTTGCCAGTCATCGGTCTTTACTGGAAGTGATGGAAGCGTTC
CCTTCCGCTAAGCCACCTCTGGGGGTCTTTTTCGCTAGTGTGGCACCCCGTCTACAGCCCCGG
TATTACTCAATATCTAGCTCACCCAGATTTGCTCCGAATAGAATACACGTAACATGCGCGCTG
GTCTATGAGCAGACCCCAAGTGGACGGGTGCATAAAGGGGTTTGTTCTACCTGGATGAAGAAC
GCCGTCCCAATGACCGAGTCTCAGGATTGTTCCTGGGCACCTATATATGTTAGAACATCAAAC
TTTCGACTGCCAAGTGACCCGAAAGTTCCGGTAATTATGATAGGTCCAGGAACAGGGCTGGCT
CCCTTTCGCGGGTTCCTCCAGGAACGTCTGGCGCAGAAGGAGGCGGGAACTGAACTGGGGACG
GCGATTTTATTTTTCGGGTGTAGAAATCGTAAAGTCGATTTTATATATGAAGATGAGTTGAAC
AATTTCGTGGAAACCGGGGCATTATCGGAATTAGTTACGGCTTTTAGCAGGGAGGGGGCGACT
AAAGAGTATGTCCAGCACAAGATGACTCAGAAAGCCTCAGATATATGGAACCTGCTGTCGGAG
GGAGCCTATCTTTATGTTTGCGGTGATGCAAAAGGAATGGCCAAAGATGTCCACCGGACCCTC
CACACTATTGTGCAGGAACAGGGTTCATTAGACTCAAGTAAAGCCGAACTTTACGTAAAAAAT
CTACAGATGGCGGGCCGTTACCTCCGTGACGTTTGGTAA (SEQ ID NO: 69)

FIG. 6A (Cont'd)

>AtCPR1 [Arabidopsis thaliana]

MATSALYASDLFKQLKSIMGTDSLSDDVVLVIATTSLALVAGFVVLLWKKTTADRSGELKPLM
IPKSLMAKDEDDDLDLGSGKTRVSIFFGTQTGTAEGFAKALSEEIKARYEKAAVKVIDLDDYA
ADDDQYEEKLKKETLAFFCVATYGDGEPTDNAARFYKWFTEENERDIKLQQLAYGVFALGNRQ
YEHFNKIGIVLDEELCKKGAKRLIEVGLGDDDQSIEDDFNAWKESLWSELDKLLKDEDDKSVA
TPYTAVIPEYRVVTHDPRFTTQKSMESNVANGNTTIDIHHPCRVDVAVQKELHTHESDRSCIH
LEFDISRTGITYETGDHVGVYAENHVEIVEEAGKLLGHSLDLVFSIHADKEDGSPLESAVPPP
FPGPCTLGTGLARYADLLNPPRKSALVALAAYATEPSEAEKLKHLTSPDGKDEYSQWIVASQR
SLLEVMAAFPSAKPPLGVFFAAIAPRLQPRYYSISSSPRLAPSRVHVTSALVYGPTPTGRIHK
GVCSTWMKNAVPAEKSHECSGAPIFIRASNFKLPSNPSTPIVMVGPGTGLAPFRGFLQERMAL
KEDGEELGSSLLFFGCRNRQMDFIYEDELNNFVDQGVISELIMAFSREGAQKEYVQHKMMEKA
AQVWDLIKEEGYLYVCGDAKGMARDVHRTLHTIVQEQEGVSSSEAEAIVKKLQTEGRYLRDVW
(SEQ ID NO: 70)

ATGGCGACCAGCGCTCTGTATGCTAGTGACCTTTTTAAACAGCTCAAAAGCATCATGGGCACT
GATAGCCTGTCCGACGATGTTGTCCTGGTAATCGCAACCACTTCCCTTGCGCTTGTTGCGGGC
TTTGTGGTGTTACTGTGGAAGAAGACTACCGCAGATAGGAGTGGTGAATTGAAACCGCTGATG
ATCCCAAAAAGTCTGATGGCCAAAGATGAGGATGATGATCTGGATCTTGGATCAGGGAAGACG
CGAGTCAGTATTTTTTTCGGGACCCAGACGGGCACCGCGGAGGGCTTCGCCAAAGCTCTGTCC
GAGGAAATAAAGGCCAGATACGAGAAAGCCGCCGTAAAGGTTATAGACCTAGATGATTACGCC
GCTGATGACGATCAGTATGAGGAGAAACTTAAAAAGGAGACTCTGGCGTTTTTTGCGTGGCA
ACTTACGGAGACGGCGAGCCCACCGATAATGCAGCTAGGTTTTACAAGTGGTTTACCGAGGAG
AACGAACGAGATATAAAGTTACAGCAGTTGGCCTATGGCGTGTTTGCCCTGGGTAATCGGCAA
TATGAGCATTTCAACAAAATTGGCATCGTTCTGGATGAGGAATTGTGCAAAAAGGGTGCAAAA
CGGCTGATAGAGGTGGGTCTAGGTGACGATGATCAATCTATAGAAGACGATTTTAATGCGTGG
AAAGAGAGCTTATGGAGTGAACTGGATAAGCTCTTGAAAGATGAAGACGACAAGTCAGTGGCG
ACCCCTTATACCGCGGTAATCCCGGAATACCGCGTCGTGACACACGATCCGAGGTTTACAACC
CAAAAATCTATGGAGTCTAATGTCGCCAATGGCAACACAACGATTGATATTCACCACCCCTGT
CGTGTTGACGTGGCTGTTCAAAAAGAACTTCATACACACGAAAGTGACCGAAGTTGCATACAC
TTGGAATTTGACATTAGTCGCACCGGAATTACGTATGAAACTGGTGATCACGTGGGTGTATAC
GCAGAAAATCATGTCGAAATAGTAGAAGAAGCTGGCAAACTGCTGGGACATTCACTCGATCTA
GTGTTTAGTATACATGCCGATAAAGAGGATGGCAGCCCATTGGAAAGTGCCGTCCCTCCGCCG
TTTCCTGGACCGTGTACTCTGGGGACGGGACTCGCCCGCTATGCTGACCTGTTAAACCCCCCT
CGTAAAAGCGCCCTTGTGGCCCTGGCGGCATACGCAACTGAACCGAGCGAAGCGGAGAAGCTG
AAACATCTGACATCACCGGATGGCAAAGACGAGTATAGTCAGTGGATAGTAGCCTCTCAGCGC
TCTCTGCTGGAAGTGATGGCCGCATTTCCGTCCGCCAAACCACCTTTGGGAGTATTTTTCGCT
GCTATCGCACCTCGGCTCCAGCCGCGCTATTACAGCATATCTTCAAGTCCCCGCTTAGCACCG
TCTCGTGTCCATGTCACTTCTGCGTTGGTTTATGGTCCGACTCCAACAGGTCGCATCCACAAA
GGTGTCTGTTCAACCTGGATGAAAAACGCGGTGCCCGCGGAGAAATCTCATGAGTGCAGTGGT
GCACCTATTTTTATCCGCGCAAGTAACTTCAAACTCCCTTCTAATCCGAGCACGCCCATTGTG
ATGGTTGGCCCAGGCACTGGCCTTGCTCCGTTTCGCGGTTTTCTACAGGAGCGGATGGCCCTT
AAAGAAGATGGGGAAGAATTGGGATCATCGTTGCTCTTTTTTGGCTGCCGAAATCGCCAGATG
GATTTTATCTACGAAGACGAGTTGAATAACTTTGTCGATCAAGGAGTAATTTCGGAGTTGATT
ATGGCATTTTCACGCGAAGGGGCTCAGAAAGAGTATGTCCAACACAAGATGATGGAAAAAGCG
GCACAAGTGTGGGATCTTATTAAAGAAGAAGGCTATCTTTATGTATGTGGGGATGCGAAAGGT
ATGGCCCGTGATGTCCATCGCACCCTGCACACGATTGTACAGGAACAGGAAGGTGTGTCCTCG
TCCGAAGCAGAAGCAATCGTTAAAAAACTGCAAACAGAGGGTCGTTACCTTCGCGACGTGTGG
TAA (SEQ ID NO: 71)

FIG. 6A (Cont'd)

>AtCPR2 [Arabidopsis thaliana]

MASSSSSSSTSMIDLMAAIIKGEPVIVSDPANASAYESVAAELSSMLIENRQFAMIVTTSIAV
LIGCIVMLVWRRSGSGNSKRVEPLKPLVIKPREEEIDDGRKKVTIFFGTQTGTAEGFAKALGE
EAKARYEKTRFKIVDLDDYAADDDEYEEKLKKEDVAFFFLATYGDGEPTDNAARFYKWFTEGN
DRGEWLKNLKYGVFGLGNRQYEHFNKVAKVVDDILVEQGAQRLVQVGLGDDDQCIEDDFTAWR
EALWPELDTILREEGDTAVATPYTAAVLEYRVSIHDSEDAKFNDINMANGNGYTVFDAQHPYK
ANVAVKRELHTPESDRSCIHLEFDIAGSGLTYETGDHVGVLCDNLSETVDEALRLLDMSPDTY
FSLHAEKEDGTPISSSLPPPFPPCNLRTALTRYACLLSSPKKSALVALAAHASDPTEAERLKH
LASPAGKDEYSKWVVESQRSLLEVMAEFPSAKPPLGVFFAGVAPRLQPRFYSISSSPKIAETR
IHVTCALVYEKMPTGRIHKGVCSTWMKNAVPYEKSENCSSAPIFVRQSNFKLPSDSKVPIIMI
GPGTGLAPFRGFLQERLALVESGVELGPSVLFFGCRNRRMDFIYEEELQRFVESGALAELSVA
FSREGPTKEYVQHKMMDKASDIWNMISQGAYLYVCGDAKGMARDVHRSLHTIAQEQGSMDSTK
AEGFVKNLQTSGRYLRDVW (SEQ ID NO: 72)

ATGGCGTCCAGCAGTTCATCGAGTTCTACAAGCATGATCGATCTGATGGCCGCTATTATCAAA
GGGGAACCCGTAATTGTCTCTGATCCAGCAAATGCCTCGGCATACGAGTCGGTGGCTGCCGAA
TTATCATCTATGTTAATTGAAAATAGACAATTTGCCATGATTGTGACAACTTCTATTGCTGTG
CTGATAGGTTGCATCGTCATGCTCGTGTGGCGCCGTAGCGGATCAGGCAACTCAAAGCGCGTC
GAGCCTTTGAAACCCCTGGTTATCAAACCGCGAGAGGAGGAAATCGATGATGGCAGAAAAAAG
GTTACTATCTTTTTTGGCACACAGACGGGGACAGCGGAAGGTTTCGCGAAAGCACTCGGAGAG
GAAGCGAAAGCCCGATACGAGAAAACACGGTTCAAAATTGTGGATCTGGATGACTATGCGGCT
GATGATGATGAGTATGAAGAAAAACTGAAAAAAGAAGATGTGGCGTTTTTTTTCTTGCCACT
TATGGCGACGGAGAGCCCACCGATAATGCAGCGCGGTTTTACAAGTGGTTCACCGAAGGAAAT
GATCGGGGAGAATGGTTAAAAAATCTGAAATACGGTGTGTTCGGTCTTGGCAATCGCCAATAT
GAGCATTTTAATAAAGTCGCGAAAGTGGTCGATGATATATTGGTAGAACAGGGCGCTCAGCGC
CTCGTCCAGGTGGGGCTTGGCGACGATGATCAGTGCATAGAAGATGATTTTACTGCATGGCGT
GAAGCGCTGTGGCCGGAGCTGGACACCATTTTACGTGAAGAGGGCGATACAGCAGTGGCAACC
CCGTACACGGCTGCCGTCTTAGAGTATCGTGTGTCCATTCATGATAGCGAGGATGCCAAATTC
AATGACATCAATATGGCGAATGGAAATGGGTACACCGTGTTTGACGCGCAGCACCCGTATAAG
GCAAACGTTGCAGTCAAGAGGGAACTGCATACTCCTGAAAGTGATCGCAGTTGCATCCACCTG
GAGTTCGATATTGCGGGATCAGGTTTAACGTACGAAACGGGCGACCACGTAGGTGTGCTGTGC
GACAATCTTTCAGAGACAGTGGACGAAGCTCTGCGCCTGCTGGATATGAGCCCGGATACCTAT
TTTAGCTTGCACGCTGAGAAAGAAGATGGGACTCCAATTAGCAGTAGCTTACCTCCACCCTTT
CCGCCGTGTAATTTGCGTACCGCCCTTACGCGCTATGCGTGTCTGCTGAGTTCGCCAAAGAAG
TCGGCCCTTGTGGCACTGGCGGCACATGCAAGTGACCCGACCGAGGCGGAGAGGCTGAAACAT
CTGGCTTCTCCAGCGGGCAAAGATGAATACAGCAAATGGGTGGTAGAATCACAGCGTTCCCTA
CTAGAAGTAATGGCCGAATTTCCCTCAGCTAAACCACCGCTGGGAGTGTTCTTTGCGGGCGTT
GCTCCCCGCTTGCAACCACGCTTTTATTCAATTAGCTCAAGTCCTAAGATAGCGGAAACACGG
ATACATGTAACTTGCGCATTGGTTTATGAAAAAATGCCAACCGGGAGGATACATAAAGGCGTA
TGTTCAACCTGGATGAAAAATGCTGTGCCATACGAAAAGTCGGAGAATTGCTCCTCTGCCCCA
ATTTTCGTGCGTCAAAGCAACTTTAAACTGCCGAGTGATTCAAAGGTGCCTATTATTATGATA
GGCCCTGGTACAGGACTCGCCCCGTTTCGTGGTTTTCTTCAAGAAAGACTGGCTCTGGTCGAA
TCAGGCGTGGAATTAGGACCCTCCGTGTTATTTTTTGGCTGCCGCAACCGTCGAATGGACTTC
ATCTATGAAGAAGAATTGCAACGTTTTGTGGAGTCAGGCGCTCTGGCGGAACTATCCGTCGCC
TTTAGTAGAGAAGGCCCAACCAAAGAATACGTACAGCATAAGATGATGGATAAAGCGAGCGAC
ATTTGGAATATGATCTCACAAGGGGCGTACCTGTACGTATGTGGAGATGCCAAAGGAATGGCA
CGAGACGTACATAGATCGTTGCATACTATTGCTCAAGAACAGGGAAGCATGGATTCGACTAAA
GCAGAAGGCTTTGTTAAAAATCTACAGACATCTGGTCGCTATCTGCGTGACGTGTGGTAA
(SEQ ID NO: 73)

*FIG. 6A (Cont'd)*

>ATR2 [Arabidopsis thaliana]

MASSSSSSSTSMIDLMAAIIKGEPVIVSDPANASAYESVAAELSSMLIENRQFAMIVTTSIAV
LIGCIVMLVWRRSGSGNSKRVEPLKPLVIKPREEEIDDGRKKVTIFFGTQTGTAEGFAKALGE
EAKARYEKTRFKIVDLDDYAADDDEYEEKLKKEDVAFFFLATYGDGEPTDNAARFYKWFTEGN
DRGEWLKNLKYGVFGLGNRQYEHFNKVAKVVDDILVEQGAQRLVQVGLGDDDQCIEDDFTAWR
EALWPELDTILREEGDTAVATPYTAAVLEYRVSIHDSEDAKFNDITLANGNGYTVFDAQHPYK
ANVAVKRELHTPESDRSCIHLEFDIAGSGLTMKLGDHVGVLCDNLSETVDEALRLLDMSPDTY
FSLHAEKEDGTPISSSLPPPFPPCNLRTALTRYACLLSSPKKSALVALAAHASDPTEAERLKH
LASPAGKDEYSKWVVESQRSLLEVMAEFPSAKPPLGVFFAGVAPRLQPRFYSISSSPKIAETR
IHVTCALVYEKMPTGRIHKGVCSTWMKNAVPYEKSEKLFLGRPIFVRQSNFKLPSDSKVPIIM
IGPGTGLAPFRGFLQERLALVESGVELGPSVLFFGCRNRRMDFIYEEELQRFVESGALAELSV
AFSREGPTKEYVQHKMMDKASDIWNMISQGAYLYVCGDAKGMARDVHRSLHTIAQEQGSMDST
KAEGFVKNLQTSGRYLRDVW (SEQ ID NO: 74)

ATGGCGAGCAGTTCGTCCTCCTCTTCTACCAGTATGATCGATCTGATGGCCGCTATTATAAAA
GGAGAACCAGTCATTGTGTCTGATCCTGCAAACGCATCAGCCTACGAATCTGTGGCTGCTGAA
CTGTCCTCGATGCTGATCGAAAATCGCCAATTTGCAATGATTGTTACAACCAGCATCGCTGTT
CTTATCGGGTGTATTGTCATGCTGGTTTGGCGGCGGAGTGGCAGCGGCAATTCTAAAAGAGTG
GAGCCACTGAAGCCTCTGGTAATCAAACCCCGCGAAGAAGAAATCGATGATGGACGTAAGAAA
GTTACAATTTTTTTTGGTACACAGACAGGTACAGCAGAGGGCTTTGCCAAAGCTCTTGGAGAA
GAAGCAAAAGCTCGATATGAGAAAACACGCTTCAAGATCGTCGATCTGGATGACTACGCGGCA
GACGACGATGAGTACGAAGAAAAACTCAAAAAAGAGGATGTGGCTTTTTTTTTCCTGGCAACT
TATGGGGACGGCGAGCCTACCGACAATGCAGCGCGGTTTTACAAATGGTTTACCGAAGGCAAT
GATAGAGGGGAGTGGCTCAAAAATCTCAAATACGGAGTTTTCGGATTGGGGAATAGACAATAC
GAACACTTTAATAAGGTTGCGAAAGTGGTAGATGATATTCTGGTCGAGCAGGGCGCGCAACGT
TTAGTACAGGTCGGCCTGGGTGATGACGACCAGTGCATCGAAGATGACTTTACGGCCTGGCGA
GAAGCGCTCTGGCCGGAATTAGATACAATCCTTCGGGAAGAGGGGGACACTGCTGTCGCTACC
CCGTACACTGCCGCAGTGCTGGAATATCGTGTTTCAATACATGATTCGGAAGATGCCAAGTTT
AATGACATCACCCTGGCAAACGGCAACGGATATACCGTATTTGACGCTCAACATCCGTATAAG
GCCAATGTAGCAGTAAAGCGGGAACTCCATACTCCCGAAAGTGACAGAAGTTGCATCCATCTG
GAGTTCGATATAGCGGGAAGCGGACTGACTATGAAACTGGGAGATCATGTAGGGGTCCTGTGC
GATAATTTGAGCGAAACCGTTGACGAAGCGCTCCGGCTTTTAGATATGTCCCCTGATACTTAT
TTCTCTTTGCACGCCGAGAAGGAAGATGGTACACCTATATCCTCCTCGCTGCCGCCGCCTTTT
CCACCATGTAATCTGCGTACGGCCTTGACTAGGTATGCATGTCTTCTTAGCTCCCCGAAAAAG
TCCGCACTGGTAGCGTTGGCAGCTCATGCCAGCGATCCCACGGAGGCAGAGCGTTTAAAACAC
CTGGCGAGTCCTGCTGGCAAAGATGAATACAGCAAATGGGTGGTTGAGTCGCAGAGGTCCCTG
CTGGAAGTCATGGCTGAATTTCCGTCTGCGAAACCGCCTCTGGGAGTTTTCTTCGCAGGAGTA
GCCCCACGTTTACAACCGCGTTTCTATTCTATTTCTTCCTCCCCCAAGATCGCGGAAACTCGA
ATACACGTAACGTGCGCATTGGTGTATGAAAAGATGCCAACTGGTCGTATCCACAAGGGAGTG
TGCTCAACCTGGATGAAAAACGCCGTTCCGTATGAAAAATCGGAAAAATTGTTTTTGGGTAGA
CCCATATTCGTTCGGCAGTCAAACTTTAAACTACCTTCTGATAGCAAGGTTCCGATTATTATG
ATTGGACCGGGTACTGGCCTGGCGCCGTTCCGTGGTTTCCTGCAAGAACGGTTGGCGCTGGTG
GAATCCGGCGTGGAACTTGGGCCATCGGTTTTGTTTTTCGGGTGCCGCAATCGTCGCATGGAC
TTCATCTACGAGGAAGAACTCCAGCGTTTTGTCGAAAGCGGTGCCCTTGCTGAATTGTCCGTT
GCATTCAGCCGCGAAGGTCCAACTAAGGAGTATGTGCAGCACAAAATGATGGACAAAGCGAGC
GATATTTGGAATATGATTAGCCAGGGCGCATACCTTTATGTGTGCGGTGATGCTAAGGGAATG
GCGCGCGATGTCCATAGATCTTTACATACCATTGCACAGGAGCAGGGCTCTATGGATTCAACA
AAAGCTGAAGGTTTTGTGAAAAACCTTCAGACCAGCGGGCGGTATCTTCGCGATGTTTGGTAA
(SEQ ID NO: 75)

FIG. 6A (Cont'd)

>SrCPR1 [Stevia rebaudiana]
MAQSDSVKVSPFDLVSAAMNGKAMEKLNASESEDPTTLPALKMLVENRELLTLFTTSFAVLIG
CLVFLMWRRSSSKKLVQDPVPQVIVVKKKEKESEVDDGKKKVSIFYGTQTGTAEGFAKALVEE
AKVRYEKTSFKVIDLDDYAADDDEYEEKLKKESLAFFFLATYGDGEPTDNAANFYKWFTEGDD
KGELLKKLQYGVFGLGNRQYEHFNKIAIVVDDKLTEMGAKRLVPVGLGDDDQCIEDDFTAWKE
LVWPELDQLLRDEDDTSVTTPYTAAVLEYRVVYHDKPADSYAEDQTHTNGHVVHDAQHPSRSN
VAFKKELHTSQSDRSCTHLEFDISHTGLSYETGDHVGVYSENLSEVVDEALKLLGLSPDTYFS
VHADKEDGTPIGGASLPPPFPPCTLRDALTRYADVLSSPKKVALLALAAHASDPSEADRLKFL
ASPAGKDEYAQWIVANQRSLLEVMQSFPSAKPPLGVFFAAVAPRLQPRYYSISSSPKMSPNRI
HVTCALVYETTPAGRIHRGLCSTWMKNAVPLTESPDCSQASIFVRTSNFRLPVDPKVPVIMIG
PGTGLAPFRGFLQERLALKESGTELGSSIFFFGCRNRKVDFIYEDELNNFVETGALSELIVAF
SREGTAKEYVQHKMSQKASDIWKLLSEGAYLYVCGDAKGMAKDVHRTLHTIVQEQGSLDSSKA
ELYVKNLQMSGRYLRDVW (SEQ ID NO: 76)

ATGGCTCAGAGCGATTCTGTTAAAGTATCCCCGTTCGACCTGGTCTCTGCGGCTATGAACGGC
AAAGCAATGGAGAAACTGAACGCGAGCGAATCTGAAGATCCAACCACCCTGCCGGCACTGAAA
ATGCTGGTAGAAAACCGTGAACTGCTGACTCTGTTCACCACCTCCTTCGCCGTTCTGATTGGT
TGCCTGGTCTTCCTGATGTGGCGCCGTTCCTCTTCCAAGAAGCTGGTACAGGACCCGGTTCCT
CAGGTGATCGTCGTTAAAAAGAAAGAGAAGGAAAGCGAAGTCGATGACGGCAAAAAGAAGGTT
TCCATTTTCTACGGTACTCAGACCGGCACCGCTGAGGGTTTTGCCAAAGCACTGGTTGAAGAG
GCAAAAGTGCGTTACGAAAAAACTTCCTTCAAAGTGATTGACCTGGACGACTATGCTGCGGAT
GATGATGAATACGAGGAAAAACTGAAAAAAGAAAGCCTGGCCTTCTTCTTCCTGGCAACCTAT
GGCGATGGTGAACCGACCGACAACGCGGCGAACTTCTACAAATGGTTTACCGAAGGCGACGAC
AAAGGTGAATTGCTGAAGAAACTGCAGTATGGTGTTTTCGGTCTGGGCAATCGCCAGTACGAA
CATTTTAACAAAATCGCAATCGTTGTTGATGACAAACTGACTGAAATGGGTGCGAAACGTCTG
GTGCCGGTTGGCCTGGGTGACGATGATCAATGCATCGAAGATGACTTCACCGCATGGAAAGAA
CTGGTTTGGCCGGAACTGGATCAGCTGCTGCGCGACGAAGACGACACTTCCGTGACCACCCCG
TATACCGCTGCAGTGCTGGAGTACCGTGTTGTTTACCACGATAAACCGGCGGACTCTTACGCC
GAAGATCAGACTCACACTAACGGTCACGTCGTACATGACGCACAGCACCCGTCTCGTAGCAAT
GTTGCGTTTAAGAAAGAGCTGCACACGAGCCAGTCCGACCGCTCTTGTACGCACCTGGAGTTC
GATATCTCCCACACCGGTCTGTCCTATGAAACCGGTGACCATGTTGGCGTTTACAGCGAAAAC
CTGAGCGAGGTAGTTGATGAAGCGCTGAAACTGCTGGGCCTGTCTCCAGACACCTACTTTAGC
GTGCATGCTGACAAGGAAGATGGTACTCCGATTGGCGGCGCTTCCCTGCCGCCACCGTTTCCA
CCTTGCACTCTGCGTGATGCTCTGACTCGTTACGCTGATGTTCTGTCTAGCCCGAAAAAGGTT
GCGCTGCTGGCGCTGGCCGCACATGCTTCTGACCCGTCTGAAGCTGACCGTCTGAAATTCCTG
GCGTCTCCGGCCGGCAAAGACGAATACGCGCAGTGGATTGTCGCTAACCAGCGCTCTCTGCTG
GAAGTGATGCAGTCCTTCCCGTCTGCCAAACCGCCACTGGGCGTGTTTTTCGCAGCTGTGGCT
CCGCGCCTGCAGCCGCGCTACTATTCTATCTCTAGCTCCCCGAAAATGAGCCCGAACCGCATC
CACGTTACTTGTGCTCTGGTTTACGAAACCACCCCTGCGGGCCGTATCCACCGTGGTCTGTGC
TCTACGTGGATGAAAAATGCCGTGCCGCTGACCGAATCCCCGGACTGCTCTCAGGCGTCCATC
TTCGTGCGTACCTCTAACTTCCGTCTGCCGGTGGACCCGAAAGTTCCTGTTATCATGATCGGT
CCTGGCACGGGTCTGGCCCCGTTTCGTGGTTTTCTGCAGGAGCGTCTGGCTCTGAAAGAATCC
GGTACTGAGCTGGGCTCTTCCATCTTTTTCTTCGGTTGTCGTAACCGCAAAGTCGATTTCATC
TATGAAGACGAACTGAACAACTTCGTAGAGACTGGTGCACTGTCCGAACTGATTGTGGCATTC
TCTCGTGAAGGCACGGCGAAAGAATACGTTCAACACAAAATGTCTCAGAAAGCGAGCGATATC
TGGAAACTGCTGTCCGAGGGTGCGTATCTGTATGTTTGTGGCGACGCGAAAGGCATGGCTAAA
GATGTACACCGCACCCTGCACACCATTGTACAAGAACAAGGCTCTCTGGATAGCTCCAAGGCA
GAACTGTACGTGAAAAACCTGCAGATGTCTGGCCGTTACCTGCGTGATGTATGGTAA (SEQ
ID NO: 77)

*FIG. 6A (Cont'd)*

>SrCPR2 [Stevia rebaudiana]

MAQSESVEASTIDLMTAVLKDTVIDTANASDNGDSKMPPALAMMFEIRDLLLILTTSVAVLVG
CFVVLVWKRSSGKKSGKELEPPKIVVPKRRLEQEVDDGKKKVTIFFGTQTGTAEGFAKALFEE
AKARYEKAAFKVIDLDDYAADLDEYAEKLKKETYAFFFLATYGDGEPTDNAAKFYKWFTEGDE
KGVWLQKLQYGVFGLGNRQYEHFNKIGIVVDDGLTEQGAKRIVPVGLGDDDQSIEDDFSAWKE
LVWPELDLLLRDEDDKAAATPYTAAIPEYRVVFHDKPDAFSDDHTQTNGHAVHDAQHPCRSNV
AVKKELHTPESDRSCTHLEFDISHTGLSYETGDHVGVYCENLIEVVEEAGKLLGLSTDTYFSL
HIDNEDGSPLGGPSLQPPFPPCTLRKALTNYADLLSSPKKSTLLALAAHASDPTEADRLRFLA
SREGKDEYAEWVVANQRSLLEVMEAFPSARPPLGVFFAAVAPRLQPRYYSISSSPKMEPNRIH
VTCALVYEKTPAGRIHKGICSTWMKNAVPLTESQDCSWAPIFVRTSNFRLPIDPKVPVIMIGP
GTGLAPFRGFLQERLALKESGTELGSSILFFGCRNRKVDYIYENELNNFVENGALSELDVAFS
RDGPTKEYVQHKMTQKASEIWNMLSEGAYLYVCGDAKGMAKDVHRTLHTIVQEQGSLDSSKAE
LYVKNLQMSGRYLRDVW (SEQ ID NO: 78)

ATGGCGCAATCTGAAAGTGTTGAGGCCAGTACCATCGACCTTATGACGGCAGTGTTGAAGGAT
ACAGTTATTGACACTGCAAATGCTTCAGATAACGGCGATTCTAAAATGCCTCCTGCGCTTGCG
ATGATGTTCGAGATCCGCGATCTTCTGCTGATCCTTACCACATCAGTAGCGGTGCTGGTGGGA
TGCTTTGTGGTACTCGTGTGGAAACGTTCGTCGGGCAAAAAATCAGGTAAGGAGCTGGAACCG
CCTAAGATTGTCGTACCGAAACGCCGACTGGAACAAGAAGTTGATGATGGCAAAAAAAAAGTG
ACTATATTTTTTGGGACACAGACAGGCACAGCGGAGGGATTTGCGAAAGCCTTATTCGAGGAG
GCGAAGGCACGTTACGAGAAAGCAGCTTTTAAAGTCATTGATCTGGATGACTATGCAGCAGAC
CTAGATGAATACGCAGAGAAACTGAAAAAAGAAACTTATGCGTTTTTCTTCCTGGCCACATAC
GGAGACGGTGAACCGACGGACAATGCCGCCAAGTTTTATAAGTGGTTCACTGAAGGGGATGAG
AAAGGTGTATGGCTTCAGAAATTGCAATACGGAGTGTTCGGACTAGGAAATCGGCAATATGAG
CACTTTAATAAAATAGGCATAGTAGTAGACGATGGGCTAACCGAGCAGGGGGCCAAACGGATT
GTACCCGTGGGCCTGGGGGACGATGATCAGTCTATTGAGGATGATTTTAGTGCTTGGAAAGAG
CTTGTTTGGCCTGAACTGGACTTACTCCTGCGTGATGAAGACGATAAAGCGGCAGCGACTCCA
TACACGGCAGCAATCCCCGAGTATAGAGTCGTATTCCATGATAAACCGGATGCTTTCTCTGAT
GACCATACCCAAACTAATGGTCATGCGGTCCATGATGCACAACATCCCTGCCGCAGCAATGTA
GCGGTGAAAAAGGAGCTGCATACGCCTGAAAGTGATCGCTCATGTACGCATCTGGAGTTTGAT
ATTTCACACACAGGTCTTAGCTACGAGACTGGAGATCACGTCGGAGTCTATTGCGAAAATCTG
ATCGAAGTGGTTGAAGAGGCCGGGAAACTGTTGGGACTAAGTACAGATACTTATTTTTCTTTA
CATATAGATAACGAGGATGGTTCCCCACTTGGCGGTCCATCTCTTCAGCCTCCATTCCCACCA
TGTACCTTACGCAAAGCGCTGACTAACTACGCAGATCTGCTGTCTAGCCCAAAGAAATCAACG
CTTCTGGCGTTGGCTGCTCATGCCTCAGATCCGACCGAAGCTGATCGCCTTCGTTTTCTGGCA
TCCCGAGAAGGTAAAGATGAATATGCAGAATGGGTGGTAGCGAATCAGCGTTCTTTGCTGGAA
GTCATGGAGGCATTCCCCAGCGCGCGCCCTCCGCTGGGTGTTTTCTTCGCAGCGGTGGCCCCG
CGGCTCCAGCCGCGTTATTATTCAATTAGCAGTTCTCCTAAGATGGAACCTAATCGAATCCAT
GTAACATGTGCATTGGTCTATGAGAAAACGCCGGCTGGCCGCATCCATAAAGGTATATGTAGC
ACATGGATGAAAAATGCAGTACCCCTCACGGAGTCCCAGGATTGTAGTTGGGCGCCGATATTT
GTTCGGACGAGCAATTTTAGACTTCCTATAGACCCAAAGGTTCCAGTTATTATGATTGGTCCT
GGCACCGGACTTGCGCCATTCCGGGGGTTTCTGCAAGAAAGACTGGCTCTGAAAGAAAGCGGT
ACAGAACTCGGCTCCAGTATATTGTTTTTCGGCTGTCGCAACCGGAAAGTAGATTATATATAT
GAAAACGAGCTGAATAACTTCGTTGAAAATGGTGCCCTGTCTGAACTCGATGTCGCTTTTTCG
CGAGATGGCCCGACAAAAGAATACGTGCAGCATAAAATGACCCAGAAAGCAAGTGAAATCTGG
AATATGCTGTCAGAAGGGGCATATCTGTATGTGTGCGGAGATGCAAAGGGCATGGCCAAAGAC
GTTCACAGAACCTTGCATACCATAGTACAAGAGCAGGGCTCTCTGGATAGCTCAAAAGCCGAG
CTGTACGTGAAAAATCTCCAGATGAGTGGACGCTACCTGAGGGATGTTTGGTAA (SEQ ID
NO: 79)

FIG. 6A (Cont'd)

>SrCPR3 [Stevia rebaudiana]

MAQSNSVKISPLDLVTALFSGKVLDTSNASESGESAMLPTIAMIMENRELLMILTTSVAVLI
GCVVVLVWRRSSTKKSALEPPVIVVPKRVQEEEVDDGKKKVTVFFGTQTGTAEGFAKALVEE
AKARYEKAVFKVIDLDDYAADDDEYEEKLKKESLAFFFLATYGDGEPTDNAARFYKWFTEGD
AKGEWLNKLQYGVFGLGNRQYEHFNKIAKVVDDGLVEQGAKRLVPVGLGDDDQCIEDDFTAW
KELVWPELDQLLRDEDDTTVATPYTAAVAEYRVVFHEKPDALSEDYSYTNGHAVHDAQHPCR
SNVAVKKELHSPESDRSCTHLEFDISNTGLSYETGDHVGVYCENLSEVVNDAERLVGLPPDT
YFSIHTDSEDGSPLGGASLPPPFPPCTLRKALTCYADVLSSPKKSALLALAAHATDPSEADR
LKFLASPAGKDEYSQWIVASQRSLLEVMEAFPSAKPSLGVFFASVAPRLQPRYYSISSSPKM
APDRIHVTCALVYEKTPAGRIHKGVCSTWMKNAVPMTESQDCSWAPIYVRTSNFRLPSDPKV
PVIMIGPGTGLAPFRGFLQERLALKEAGTDLGLSILFFGCRNRKVDFIYENELNNFVETGAL
SELIVAFSREGPTKEYVQHKMSEKASDIWNLLSEGAYLYVCGDAKGMAKDVHRTLHTIVQEQ
GSLDSSKAELYVKNLQMSGRYLRDVW (SEQ ID NO: 80)

ATGGCGCAATCTAATTCTGTGAAAATCTCTCCATTGGATCTGGTTACAGCACTCTTTAGCGG
GAAGGTACTGGATACAAGTAACGCCAGTGAAAGCGGGGAATCCGCGATGCTGCCAACAATCG
CGATGATCATGGAAAATCGGGAACTGCTAATGATTCTGACAACGTCTGTAGCAGTTTTAATC
GGTTGCGTTGTGGTTCTGGTGTGGCGTCGATCATCCACGAAAAAGAGCGCATTAGAACCGCC
TGTTATCGTAGTACCAAAAAGAGTTCAGGAGGAAGAGGTGGATGATGGGAAAAAAAAAGTCA
CCGTTTTCTTCGGGACCCAAACTGGTACGGCAGAAGGTTTTGCGAAAGCACTGGTCGAAGAG
GCGAAAGCCCGCTATGAGAAGGCGGTTTTTAAGGTTATTGACCTTGATGACTATGCGGCGGA
CGATGATGAATACGAAGAAAAATTAAAGAAAGAATCACTTGCCTTTTTTTTTTTGGCAACAT
ACGGTGATGGCGAGCCGACTGATAACGCGGCACGGTTTTACAAATGGTTTACCGAAGGCGAC
GCGAAGGGGGAGTGGTTGAACAAGTTACAGTACGGTGTGTTCGGCTTGGGGAACCGCCAGTA
CGAGCACTTTAACAAGATAGCTAAAGTTGTCGATGATGGTCTGGTAGAACAGGGAGCGAAGC
GTCTCGTGCCAGTAGGGCTGGGCGATGATGATCAGTGTATAGAAGATGATTTTACGGCTTGG
AAGGAGTTAGTTTGGCCGGAACTGGACCAACTGCTGCGCGATGAGGATGATACAACTGTCGC
TACCCCGTATACAGCAGCGGTAGCTGAATACAGGGTGGTTTTTCACGAGAAACCTGATGCGC
TGAGTGAGGACTATTCGTATACTAACGGCCATGCCGTTCACGATGCACAGCACCCGTGCCGT
TCTAATGTCGCCGTAAAAAAGGAACTGCATAGCCCGGAGTCGGACCGCAGTTGTACCCATCT
GGAGTTTGATATTTCAAATACCGGGCTGAGTTACGAAACGGGCGATCACGTTGGCGTGTACT
GTGAGAATCTAAGCGAGGTTGTTAACGATGCAGAACGACTGGTCGGTTTGCCTCCAGATACT
TATTTCTCGATCCACACTGATAGCGAAGATGGCTCTCCACTCGGGGGGGCGAGTCTGCCGCC
CCCGTTTCCCCCGTGTACGCTGAGAAAGGCCCTTACATGTTATGCAGATGTACTCTCTTCCC
CCAAAAAAAGTGCCTTGCTCGCATTAGCAGCCCACGCTACCGATCCCTCGGAAGCAGATCGT
CTGAAATTCTTGGCATCGCCGGCGGGCAAAGATGAATACAGCCAATGGATAGTTGCAAGTCA
GCGCAGTCTCTTAGAAGTGATGGAAGCGTTTCCGTCCGCAAAGCCGTCCTTAGGTGTGTTTT
TCGCGTCCGTGGCACCGCGTCTTCAGCCTAGATATTACAGCATTAGTTCCTCTCCAAAAATG
GCCCCGGACCGTATTCACGTGACTTGTGCTCTTGTATATGAGAAAACCCCGGCAGGTCGTAT
TCACAAAGGCGTGTGCAGCACCTGGATGAAGAATGCAGTGCCGATGACCGAAAGCCAGGATT
GTTCATGGGCGCCAATCTATGTCAGGACAAGTAATTTCAGACTTCCGTCTGATCCTAAAGTT
CCAGTCATAATGATTGGCCCCGGCACGGGACTGGCTCCTTTTCGTGGTTTCCTGCAAGAGCG
CTTGGCACTGAAAGAAGCAGGCACTGACCTGGGACTGTCCATCCTGTTCTTTGGGTGCCGTA
ATCGTAAGGTCGATTTTATATATGAAAATGAATTGAACAACTTTGTAGAAACAGGCGCATTA
TCCGAACTGATCGTAGCTTTTAGTAGAGAGGGGCCGACGAAAGAATATGTACAACACAAGAT
GTCTGAGAAGGCTTCGGATATATGGAACCTGCTCTCTGAGGGTGCCTATCTGTACGTTTGCG
GTGATGCCAAAGGAATGGCCAAAGATGTGCACCGCACTTTACATACAATCGTCCAAGAGCAG
GGTAGCTTGGACTCATCTAAAGCTGAACTGTATGTGAAGAACTTACAGATGAGCGGGCGCTA
TTTGCGAGATGTTTGGTAA (SEQ ID NO: 81)

FIG. 6A (Cont'd)

>PgCPR [Pelargonium graveolens]

MAQSSSGSMSPFDFMTAIIKGKMEPSNASLGAAGEVTAMILDNRELVMILTTSIAVLIGCVV
VFIWRRSSSQTPTAVQPLKPLLAKETESEVDDGKQKVTIFFGTQTGTAEGFAKALADEAKAR
YDKVTFKVVDLDDYAADDEEYEEKLKKETLAFFFLATYGDGEPTDNAARFYKWFLEGKERGE
WLQNLKFGVFGLGNRQYEHFNKIAIVVDEILAEQGGKRLISVGLGDDDQCIEDDFTAWRESL
WPELDQLLRDEDDTTVSTPYTAAVLEYRVVFHDPADAPTLEKSYSNANGHSVVDAQHPLRAN
VAVRRELHTPASDRSCTHLEFDISGTGIAYETGDHVGVYCENLAETVEEALELLGLSPDTYF
SVHADKEDGTPLSGSSLPPPFPPCTLRTALTLHADLLSSPKKSALLALAAHASDPTEADRLR
HLASPAGKDEYAQWIVASQRSLLEVMAEFPSAKPPLGVFFASVAPRLQPRYYSISSSPRIAP
SRIHVTCALVYEKTPTGRVHKGVCSTWMKNSVPSEKSDECSWAPIFVRQSNFKLPADAKVPI
IMIGPGTGLAPFRGFLQERLALKEAGTELGPSILFFGCRNSKMDYIYEDELDNFVQNGALSE
LVLAFSREGPTKEYVQHKMMEKASDIWNLISQGAYLYVCGDAKGMARDVHRTLHTIAQEQGS
LDSSKAESMVKNLQMSGRYLRDVW (SEQ ID NO: 82)

ATGGCGCAGTCAAGCAGTGGATCAATGAGCCCTTTCGATTTTATGACCGCTATAATAAAAGG
TAAAATGGAGCCAAGTAATGCGTCTTTAGGAGCGGCAGGTGAAGTCACAGCAATGATACTTG
ATAATAGGGAGCTGGTTATGATTCTGACGACCAGCATTGCAGTGCTGATCGGTTGCGTTGTA
GTGTTCATTTGGCGTCGTTCATCATCCCAGACCCCTACCGCGGTGCAGCCATTAAAACCACT
TTTAGCGAAGGAAACAGAGAGCGAAGTAGACGATGGCAAACAGAAAGTAACTATCTTTTTTG
GTACTCAAACTGGAACCGCTGAAGGTTTCGCGAAAGCGCTCGCAGACGAGGCCAAAGCACGG
TATGATAAAGTCACTTTTAAAGTGGTTGATCTGGACGATTATGCCGCAGATGACGAAGAATA
TGAAGAAAAGCTGAAGAAGGAAACGTTAGCATTCTTTTTTCTTGCGACGTATGGAGATGGTG
AACCTACTGACAATGCTGCAAGGTTTTATAAGTGGTTTCTGGAAGGTAAAGAACGCGGAGAA
TGGCTTCAGAATCTAAAATTTGGTGTGTTTGGTTTAGGCAACCGTCAGTATGAGCATTTCAA
TAAAATTGCCATTGTGGTTGATGAAATCCTTGCAGAACAAGGTGGTAAGCGTCTCATTTCAG
TTGGCCTGGGCGATGATGATCAGTGTATTGAGGATGACTTTACTGCCTGGAGGGAATCGCTG
TGGCCGGAGCTAGATCAGTTATTACGCGATGAGGATGATACTACGGTTTCTACGCCGTATAC
CGCCGCGGTGCTGGAATACAGAGTCGTTTTTCATGATCCGGCAGATGCCCCAACTCTCGAAA
AAAGCTACAGCAACGCTAACGGGCATAGCGTGGTTGATGCGCAACATCCGTTACGGGCAAAT
GTTGCCGTCAGACGGGAGTTGCATACTCCTGCGTCTGACCGCTCATGTACCCATCTGGAATT
TGATATATCTGGTACTGGCATCGCATACGAGACGGGTGATCATGTTGGCGTGTATTGCGAGA
ATCTTGCAGAGACGGTAGAAGAAGCGTTGGAACTTTTAGGTCTTTCCCCGGATACATACTTC
TCCGTACACGCAGATAAAGAGGACGGTACGCCTCTCTCAGGCTCATCTCTCCCGCCGCCATT
TCCACCGTGCACTTTACGTACAGCCCTGACGTTACATGCTGACTTACTGTCTTCCCCAAAGA
AATCTGCATTGCTCGCGCTTGCAGCTCATGCATCAGACCCCACTGAAGCTGATCGATTGCGG
CACCTAGCAAGCCCTGCGGGCAAGGACGAATACGCTCAGTGGATAGTTGCTAGTCAGCGTTC
CTTGCTGGAAGTGATGGCGGAGTTCCCCAGTGCCAAGCCCCCGCTGGGAGTATTCTTCGCAT
CGGTTGCTCCAAGATTGCAGCCCCGGTACTACTCTATTTCTTCTTCCCCAAGAATAGCGCCG
TCTCGCATACACGTGACCTGCGCGTTAGTTTACGAGAAAACACCTACGGGCAGAGTACACAA
AGGAGTTTGCTCCACTTGGATGAAAAACTCAGTGCCCTCTGAAAAGAGTGATGAATGTTCAT
GGGCACCAATTTTCGTACGACAGAGCAACTTTAAACTGCCCGCCGATGCGAAAGTACCCATA
ATTATGATTGGTCCAGGAACGGGTCTGGCACCATTTCGCGGCTTCCTCCAGGAGCGGCTTGC
ATTGAAAGAAGCAGGGACAGAACTGGGACCTTCCATATTATTTTTGGGTGCCGCAACAGCA
AAATGGACTATATATACGAGGATGAACTGGATAATTTTGTACAGAATGGGGCACTCTCTGAA
CTCGTGTTGGCGTTCTCACGTGAAGGTCCTACCAAAGAGTATGTGCAACATAAGATGATGGA
GAAAGCCTCAGATATATGGAACCTTATTTCACAGGGAGCTTATTTGTATGTGTGCGGGGACG
CAAAAGGCATGGCGCGTGATGTGCACCGCACGTTACATACCATCGCTCAGGAGCAGGGGTCA
TTAGATAGCTCAAAAGCAGAGAGTATGGTGAAGAATCTTCAGATGTCAGGCAGATACCTGCG
CGATGTCTGGTAA (SEQ ID NO: 83)

*FIG. 6A (Cont'd)*

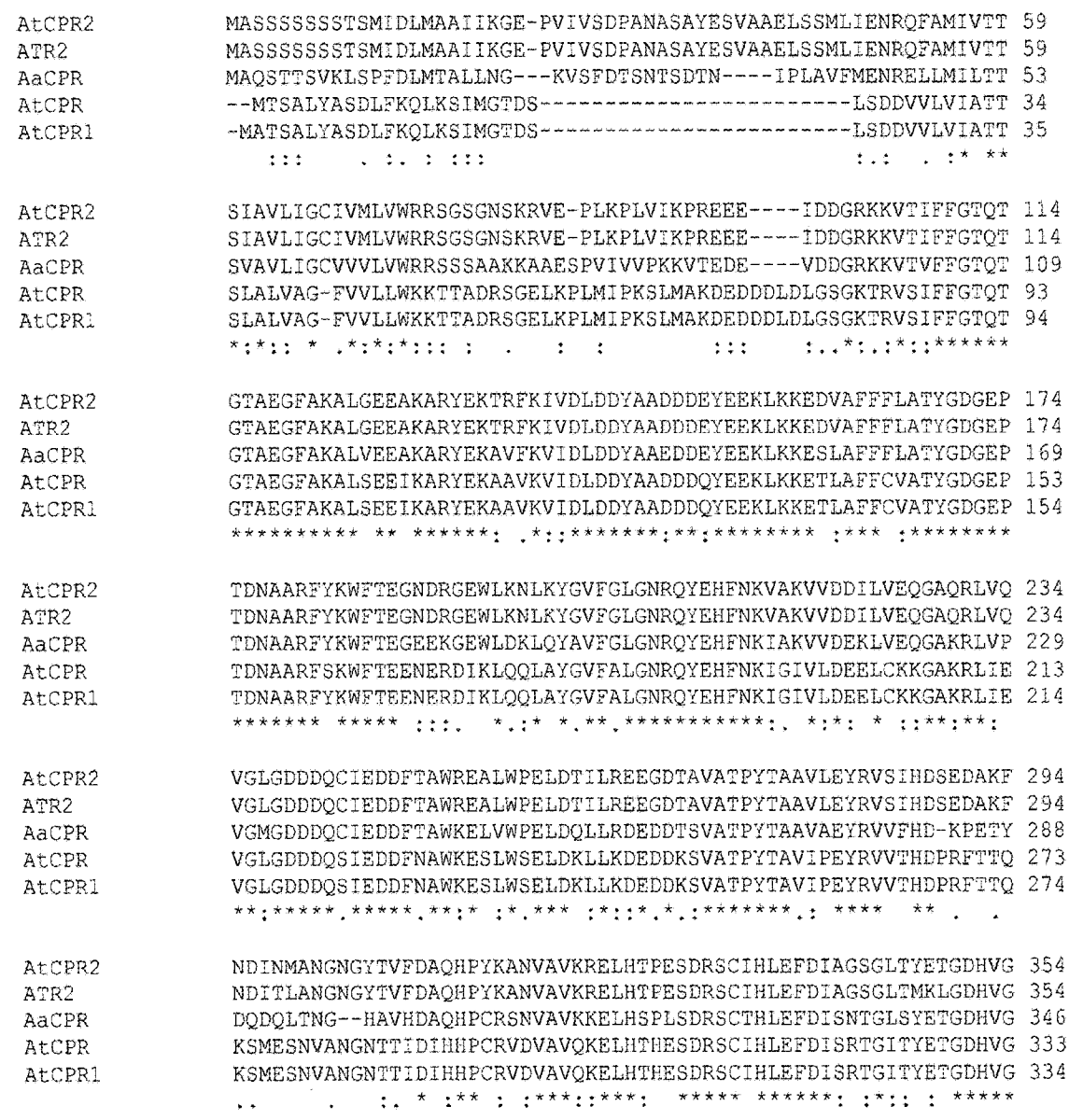

```
AtCPR2    MASSSSSSSTSMIDLMAAIIKGE-PVIVSDPANASAYESVAAELSSMLIENRQFAMIVTT 59
ATR2      MASSSSSSSTSMIDLMAAIIKGE-PVIVSDPANASAYESVAAELSSMLIENRQFAMIVTT 59
AaCPR     MAQSTTSVKLSPFDLMTALLNG---KVSFDTSNTSDTN----IPLAVFMENRELLMILTT 53
AtCPR     --MTSALYASDLFKQLKSIMGTDS-----------------------LSDDVVLVIATT 34
AtCPR1    -MATSALYASDLFKQLKSIMGTDS-----------------------LSDDVVLVIATT 35
             :::    . :. : :::                           :.:  . :* **

AtCPR2    SIAVLIGCIVMLVWRRSGSGNSKRVE-PLKPLVIKPREEE----IDDGRKKVTIFFGTQT 114
ATR2      SIAVLIGCIVMLVWRRSGSGNSKRVE-PLKPLVIKPREEE----IDDGRKKVTIFFGTQT 114
AaCPR     SVAVLIGCVVVLVWRRSSSAAKKAAESPVIVVPKKVTEDE----VDDGRKKVTVFFGTQT 109
AtCPR     SLALVAG-FVVLLWKKTTADRSGELKPLMIPKSLMAKDEDDDLDLGSGKTRVSIFFGTQT 93
AtCPR1    SLALVAG-FVVLLWKKTTADRSGELKPLMIPKSLMAKDEDDDLDLGSGKTRVSIFFGTQT 94
          *:*:: *  .*:*:*::: :   .   :  :         :::    :..*:.:*::******

AtCPR2    GTAEGFAKALGEEAKARYEKTRFKIVDLDDYAADDDEYEEKLKKEDVAFFFLATYGDGEP 174
ATR2      GTAEGFAKALGEEAKARYEKTRFKIVDLDDYAADDDEYEEKLKKEDVAFFFLATYGDGEP 174
AaCPR     GTAEGFAKALVEEAKARYEKAVFKVIDLDDYAAEDDEYEEKLKKESLAFFFLATYGDGEP 169
AtCPR     GTAEGFAKALSEEIKARYEKAAVKVIDLDDYAADDDQYEEKLKKETLAFFCVATYGDGEP 153
AtCPR1    GTAEGFAKALSEEIKARYEKAAVKVIDLDDYAADDDQYEEKLKKETLAFFCVATYGDGEP 154
          ********** ** ******: .*::*******:**:******** :*** :********

AtCPR2    TDNAARFYKWFTEGNDRGEWLKNLKYGVFGLGNRQYEHFNKVAKVVDDILVEQGAQRLVQ 234
ATR2      TDNAARFYKWFTEGNDRGEWLKNLKYGVFGLGNRQYEHFNKVAKVVDDILVEQGAQRLVQ 234
AaCPR     TDNAARFYKWFTEGEEKGEWLDKLQYAVFGLGNRQYEHFNKIAKVVDEKLVEQGAKRLVP 229
AtCPR     TDNAARFSKWFTEENERDIKLQQLAYGVFALGNRQYEHFNKIGIVLDEELCKKGAKRLIE 213
AtCPR1    TDNAARFYKWFTEENERDIKLQQLAYGVFALGNRQYEHFNKIGIVLDEELCKKGAKRLIE 214
          ******* ***** :::.   *.:* *.**.***********:. *:*: * ::**:**:

AtCPR2    VGLGDDDQCIEDDFTAWREALWPELDTILREEGDTAVATPYTAAVLEYRVSIHDSEDAKF 294
ATR2      VGLGDDDQCIEDDFTAWREALWPELDTILREEGDTAVATPYTAAVLEYRVSIHDSEDAKF 294
AaCPR     VGMGDDDQCIEDDFTAWKELVWPELDQLLRDEDDTSVATPYTAAVAEYRVVFHD-KPETY 288
AtCPR     VGLGDDDQSIEDDFNAWKESLWSELDKLLKDEDDKSVATPYTAVIPEYRVVTHDPRFTTQ 273
AtCPR1    VGLGDDDQSIEDDFNAWKESLWSELDKLLKDEDDKSVATPYTAVIPEYRVVTHDPRFTTQ 274
          **:*****.*****.**:*:* :*.*** :*::*.*.:*******.: ****  **  .  .

AtCPR2    NDINMANGNGYTVFDAQHPYKANVAVKRELHTPESDRSCIHLEFDIAGSGLTYETGDHVG 354
ATR2      NDITLANGNGYTVFDAQHPYKANVAVKRELHTPESDRSCIHLEFDIAGSGLTMKLGDHVG 354
AaCPR     DQDQLTNG--HAVHDAQHPCRSNVAVKKELHSPLSDRSCTHLEFDISNTGLSYETGDHVG 346
AtCPR     KSMESNVANGNTTIDIHHPCRVDVAVQKELHTHESDRSCIHLEFDISRTGITYETGDHVG 333
AtCPR1    KSMESNVANGNTTIDIHHPCRVDVAVQKELHTHESDRSCIHLEFDISRTGITYETGDHVG 334
          ..     .    :. * :** : :***::***:  ***** ******: :*:: : *****
```

FIG. 6B

```
AtCPR2    VLCDNLSETVDEALRLLDMSPDTYFSLHAEKEDGTPIS-SSLPPPFP-PCNLRTALTRYA 412
ATR2      VLCDNLSETVDEALRLLDMSPDTYFSLHAEKEDGTPIS-SSLPPPFP-PCNLRTALTRYA 412
AaCPR     VYVENLSEVVDEAEKLIGLPPHTYFSVHADNEDGTPLGGASLPPPFP-PCTLRKALASYA 405
AtCPR     VYAENHVEIVEEAGKLLGHSLDLVFSIHADKEDGSPLE-SAVPPPFPGPCTLGTGLARYA 392
AtCPR1    VYAENHVEIVEEAGKLLGHSLDLVFSIHADKEDGSPLE-SAVPPPFPGPCTLGTGLARYA 393
          *  :*   *  *:** :*:. .  .  **:**::***:*:  :::***** **.*  ..*: **

AtCPR2    CLLSSPKKSALVALAAHASDPTEAERLKHLASPAGKDEYSKWVVESQRSLLEVMAEFPSA 472
ATR2      CLLSSPKKSALVALAAHASDPTEAERLKHLASPAGKDEYSKWVVESQRSLLEVMAEFPSA 472
AaCPR     DVLSSPKKSALLALAAHATDSTEADRLKFLASPAGKDEYAQWIVASHRSLLEVMEAFPSA 465
AtCPR     DLLNPPRKSALVALAAYATEPSEAEKLKHLTSPDGKDEYSQWIVASQRSLLEVMAAFPSA 452
AtCPR1    DLLNPPRKSALVALAAYATEPSEAEKLKHLTSPDGKDEYSQWIVASQRSLLEVMAAFPSA 453
           :*..*:****:****:*::.:**::**.*:** *****::*:* *:*******  ****

AtCPR2    KPPLGVFFAGVAPRLQPRFYSISSSPKIAETRIHVTCALVYEKMPTGRIHKGVCSTWMKN 532
ATR2      KPPLGVFFAGVAPRLQPRFYSISSSPKIAETRIHVTCALVYEKMPTGRIHKGVCSTWMKN 532
AaCPR     KPPLGVFFASVAPRLQPRYYSISSSPRFAPNRIHVTCALVYEQTPSGRVHKGVCSTWMKN 525
AtCPR     KPPLGVFFAAIAPRLQPRYYSISSCQDWAPSRVHVTSALVYGPTPTGRIHKGVCSTWMKN 512
AtCPR1    KPPLGVFFAAIAPRLQPRYYSISSSPRLAPSRVHVTSALVYGPTPTGRIHKGVCSTWMKN 513
          *********.:*******:*****.    *  .*:***.****   *:**:***********

AtCPR2    AVPYEKSENCSS-APIFVRQSNFKLPSDSKVPIIMIGPGTGLAPFRGFLQERLALVESGV 591
ATR2      AVPYEKSEKLFLGRPIFVRQSNFKLPSDSKVPIIMIGPGTGLAPFRGFLQERLALVESGV 592
AaCPR     AVPMTESQDCSW-APIYVRTSNFRLPSDPKVPVIMIGPGTGLAPFRGFLQERLAQKEAGT 584
AtCPR     AVPAEKSHECSG-APIFIRASNFKLPSNPSTPIVMVGPGTGLAPFRGFLQERMALKEDGE 571
AtCPR1    AVPAEKSHECSG-APIFIRASNFKLPSNPSTPIVMVGPGTGLAPFRGFLQERMALKEDGE 572
          ***  :*..      **::* ***:***:...*::*:****************:*  * *

AtCPR2    ELGPSVLFFGCRNRRMDFIYEEELQRFVESGALAELSVAFSREGPTKEYVQHKMMDKASD 651
ATR2      ELGPSVLFFGCRNRRMDFIYEEELQRFVESGALAELSVAFSREGPTKEYVQHKMMDKASD 652
AaCPR     ELGTAILFFGCRNRKVDFIYEDELNNFVETGALSELVTAFSREGATKEYVQHKMTQKASD 644
AtCPR     ELGSSLLFFGCRNRQMDFIYEDELNNFVDQGVISELIMAFSREGAQKEYVQHKMMEKAAQ 631
AtCPR1    ELGSSLLFFGCRNRQMDFIYEDELNNFVDQGVISELIMAFSREGAQKEYVQHKMMEKAAQ 632
          ***.::********::*****:**:.**: *.::**  ******. ******** :**::

AtCPR2    IWNMISQGAYLYVCGDAKGMARDVHRSLHTIAQEQGSMDSTKAEGFVKNLQTSGRYLRDVW 712
ATR2      IWNMISQGAYLYVCGDAKGMARDVHRSLHTIAQEQGSMDSTKAEGFVKNLQTSGRYLRDVW 713
AaCPR     IWNLLSEGAYLYVCGDAKGMAKDVHRTLHTIVQEQGSLDSSKAELYVKNLQMAGRYLRDVW 705
AtCPR     VWDLIKEEGYLYVCGDAKGMARDVHRTLHTIVQEQEGVSSSEAEAIVKKLQTEGRYLRDVW 692
AtCPR1    VWDLIKEEGYLYVCGDAKGMARDVHRTLHTIVQEQEGVSSSEAEAIVKKLQTEGRYLRDVW 693
          :*:::.: .***********:****:****.*** .:.*::**  **:**  *******
```

FIG. 6B (Cont'd)

```
SrCPR2      MAQSESVEASTIDLMTAVLKDTVIDTANASDNGDSKMPPALAMMFEIRDLLLILTTSVAV 60
SrCPR3      MAQSNSVKISPLDLVTALFSGKVLDTSNASESGESAMLPTIAMIMENRELLMILTTSVAV 60
SrCPR       -MQSDSVKVSPFDLVSAAMNGKAMEKLNASESEDPTTLPALKMLVENRELLTLFTTSFAV 59
SrCPR1      MAQSDSVKVSPFDLVSAAMNGKAMEKLNASESEDPTTLPALKMLVENRELLTLFTTSFAV 60
              **:**: *.:**::* :....::. ***:. :.   *:: *:.* *:** ::***.**

SrCPR2      LVGCFVVLVWKRSSGKKSGKELEPPKIVVPKRRLEQEVDDGKKKVTIFFGTQTGTAEGFA 120
SrCPR3      LIGCVVVLVWRRSSTKKS--ALEPPVIVVPKRVQEEEVDDGKKKVTVFFGTQTGTAEGFA 118
SrCPR       LIGCLVFLMWRRSSSKKLVQDPVPQVIVVKKKEKESEVDDGKKKVSIFYGTQTGTAEGFA 119
SrCPR1      LIGCLVFLMWRRSSSKKLVQDPVPQVIVVKKKEKESEVDDGKKKVSIFYGTQTGTAEGFA 120
            *:**.*.*:*:*** **       *  *** *:  *.*********::*:**********

SrCPR2      KALFEEAKARYEKAAFKVIDLDDYAADLDEYAEKLKKETYAFFFLATYGDGEPTDNAAKF 180
SrCPR3      KALVEEAKARYEKAVFKVIDLDDYAADDDEYEEKLKKESLAFFFLATYGDGEPTDNAARF 178
SrCPR       KALVEEAKVRYEKTSFKVIDLDDYAADDDEYEEKLKKESLAFFFLATYGDGEPTDNAANF 179
SrCPR1      KALVEEAKVRYEKTSFKVIDLDDYAADDDEYEEKLKKESLAFFFLATYGDGEPTDNAANF 180
            ***.****.****: *********** *** ******: ****************.*

SrCPR2      YKWFTEGDEKGVWLQKLQYGVFGLGNRQYEHFNKIGIVVDDGLTEQGAKRIVPVGLGDDD 240
SrCPR3      YKWFTEGDAKGEWLNKLQYGVFGLGNRQYEHFNKIAKVVDDGLVEQGAKRLVPVGLGDDD 238
SrCPR       YKWFTEGDDKGEWLKKLQYGVFGLGNRQYEHFNKIAIVVDDKLTEMGAKRLVPVGLGDDD 239
SrCPR1      YKWFTEGDDKGELLKKLQYGVFGLGNRQYEHFNKIAIVVDDKLTEMGAKRLVPVGLGDDD 240
            ******** **  *:*******************. **** *.* ****:*********

SrCPR2      QSIEDDFSAWKELVWPELDLLLRDEDDKAAATPYTAAIPEYRVVFHDKP-DAFSDDHTQT 299
SrCPR3      QCIEDDFTAWKELVWPELDQLLRDEDDTTVATPYTAAVAEYRVVFHEKP-DALSEDYSYT 297
SrCPR       QCIEDDFTAWKELVWPELDQLLRDEDDTSVTTPYTAAVLEYRVVYHDKPADSYAEDQTHT 299
SrCPR1      QCIEDDFTAWKELVWPELDQLLRDEDDTSVTTPYTAAVLEYRVVYHDKPADSYAEDQTHT 300
            *.*****:*********** *******.:.:******: *****:*:** *: ::* : *

SrCPR2      NGHAVHDAQHPCRSNVAVKKELHTPESDRSCTHLEFDISHTGLSYETGDHVGVYCENLIE 359
SrCPR3      NGHAVHDAQHPCRSNVAVKKELHSPESDRSCTHLEFDISNTGLSYETGDHVGVYCENLSE 357
SrCPR       NGHVVHDAQHPSRSNVAFKKELHTSQSDRSCTHLEFDISHTGLSYETGDHVGVYSENLSE 359
SrCPR1      NGHVVHDAQHPSRSNVAFKKELHTSQSDRSCTHLEFDISHTGLSYETGDHVGVYSENLSE 360
            ***.*******.*****.*****:.:*************:*************.*** *

SrCPR2      VVEEAGKLLGLSTDTYFSLHIDNEDGSPLGGPSLQPPFPPCTLRKALTNYADLLSSPKKS 419
SrCPR3      VVNDAERLVGLPPDTYFSIHTDSEDGSPLGGASLPPPFPPCTLRKALTCYADVLSSPKKS 417
SrCPR       VVDEALKLLGLSPDTYFSVHADKEDGTPIGGASLPPPFPPCTLRDALTRYADVLSSPKKV 419
SrCPR1      VVDEALKLLGLSPDTYFSVHADKEDGTPIGGASLPPPFPPCTLRDALTRYADVLSSPKKV 420
            **::* :*:**..*****:* *.***:*:**.** *********.*** ***:******
```

FIG. 6C

```
SrCPR2      TLLALAAHASDPTEADRLRFLASREGKDEYAEWVVANQRSLLEVMEAFPSARPPLGVFFA 479
SrCPR3      ALLALAAHATDPSEADRLKFLASPAGKDEYSQWIVASQRSLLEVMEAFPSAKPSLGVFFA 477
SrCPR       ALLALAAHASDPSEADRLKFLASPAGKDEYAQWIVANQRSLLEVMQSFPSAKPPLGVFFA 479
SrCPR1      ALLALAAHASDPSEADRLKFLASPAGKDEYAQWIVANQRSLLEVMQSFPSAKPPLGVFFA 480
            :********:**:*****:****   ****::*:**.********::****:*.******

SrCPR2      AVAPRLQPRYYSISSSPKMEPNRIHVTCALVYEKTPAGRIHKGICSTWMKNAVPLTESQD 539
SrCPR3      SVAPRLQPRYYSISSSPKMAPDRIHVTCALVYEKTPAGRIHKGVCSTWMKNAVPMTESQD 537
SrCPR       AVAPRLQPRYYSISSSPKMSPNRIHVTCALVYETTPAGRIHRGLCSTWMKNAVPLTESPD 539
SrCPR1      AVAPRLQPRYYSISSSPKMSPNRIHVTCALVYETTPAGRIHRGLCSTWMKNAVPLTESPD 540
            :****************** *:***********.*******:*:**********:*** *

SrCPR2      CSWAPIFVRTSNFRLPIDPKVPVIMIGPGTGLAPFRGFLQERLALKESGTELGSSILFFG 599
SrCPR3      CSWAPIYVRTSNFRLPSDPKVPVIMIGPGTGLAPFRGFLQERLALKEAGTDLGLSILFFG 597
SrCPR       CSQASIFVRTSNFRLPVDPKVPVIMIGPGTGLAPFRGFLQERLALKESGTELGSSIFFFG 599
SrCPR1      CSQASIFVRTSNFRLPVDPKVPVIMIGPGTGLAPFRGFLQERLALKESGTELGSSIFFFG 600
            ** *.*:********* ******************************:**:** **:***

SrCPR2      CRNRKVDYIYENELNNFVENGALSELDVAFSRDGPTKEYVQHKMTQKASEIWNMLSEGAY 659
SrCPR3      CRNRKVDFIYENELNNFVETGALSELIVAFSREGPTKEYVQHKMSEKASDIWNLLSEGAY 657
SrCPR       CRNRKVDFIYEDELNNFVETGALSELIVAFSREGTAKEYVQHKMSQKASDIWKLLSEGAY 659
SrCPR1      CRNRKVDFIYEDELNNFVETGALSELIVAFSREGTAKEYVQHKMSQKASDIWKLLSEGAY 660
            *******:***:*******.****** *****:*.:*********::***:**::******

SrCPR2      LYVCGDAKGMAKDVHRTLHTIVQEQGSLDSSKAELYVKNLQMSGRYLRDVW 710
SrCPR3      LYVCGDAKGMAKDVHRTLHTIVQEQGSLDSSKAELYVKNLQMSGRYLRDVW 708
SrCPR       LYVCGDAKGMAKDVHRTLHTIVQEQGSLDSSKAELYVKNLQMSGRYLRDVW 710
SrCPR1      LYVCGDAKGMAKDVHRTLHTIVQEQGSLDSSKAELYVKNLQMSGRYLRDVW 711
            ***************************************************
```

FIG. 6C
(Cont'd)

```
ATR2      MASSSSSSSTSMIDLMAAIIKGEPVIVSDPANASAYESVAAELSSMLIENRQFAMIVTTS 60
AtCPR2    MASSSSSSSTSMIDLMAAIIKGEPVIVSDPANASAYESVAAELSSMLIENRQFAMIVTTS 60
PgCPR     MAQSSSGS-MSPFDFMTAIIKG----KMEPSNAS--LGAAGEVTAMILDNRELVMILTTS 53
AaCPR     MAQSTTSVKLSPFDLMTALLNGKVS-FDTSNTSDTN-----IP-LAVFMENRELLMILTTS 54
SrCPR3    MAQSN-SVKISPLDLVTALFSGKV--LDTSNASESGESAMLPTIAMIMENRELLMILTTS 57
SrCPR     MAQSD-SVKVSPFDLVSAAMNGKA--MEKLNASESEDPTTLPALKMLVENRELLTLFTTS 57
SrCPR2    MAQSE-SVEASTIDLMTAVLKDTV--IDTANASDNGDSKMPPALAMMFEIRDLLLILTTS 57
AtCPR1    MATSALYASDLFKQLKSIMGTDS-------------------------LSDDVVLVIATTS 36
          ** *         :: :   ..                         ..    .  :***

ATR2      IAVLIGCIVMLVWRRSGSGNSKRVEPLKP--LVIKPR---EEEIDDGRKKVTIFFGTQTG 115
AtCPR2    IAVLIGCIVMLVWRRSGSGNSKRVEPLKP--LVIKPR---EEEIDDGRKKVTIFFGTQTG 115
PgCPR     IAVLIGCVVVFIWRRSSSQTPTAVQPLKP--LLAKET---ESEVDDGKQKVTIFFGTQTG 108
AaCPR     VAVLIGCVVVLVWRRSSSAAKKAAESP-----VIVVPKKVTEDEVDDGRKKVTVFFGTQTG 110
SrCPR3    VAVLIGCVVVLVWRRSS-TKKSALEPP----VIVVPKRVQEEEVDDGKKKVTVFFGTQTG 112
SrCPR     FAVLIGCLVFLMWRRSS-SKKLVQDPVPQ--VIVVKKKEKESEVDDGKKKVSIFYGTQTG 114
SrCPR2    VAVLVGCFVVLVWKRSS-GKKSGKELEPP--KIVVPKRRLEQEVDDGKKKVTIFFGTQTG 114
AtCPR1    LALVAG-FVVLLWKKTTADRSGELKPLMIPKSLMAKDEDDDLDLGSGKTRVSIFFGTQTG 95
          .*:: * .*.::*:::        .       :       : ::..*: :*::*:*****

ATR2      TAEGFAKALGEEAKARYEKTRFKIVDLDDYAADDDEYEEKLKKEDVAFFFLATYGDGEPT 175
AtCPR2    TAEGFAKALGEEAKARYEKTRFKIVDLDDYAADDDEYEEKLKKEDVAFFFLATYGDGEPT 175
PgCPR     TAEGFAKALADEAKARYDKVTFKVVDLDDYAADDEEYEEKLKKETLAFFFLATYGDGEPT 168
AaCPR     TAEGFAKALVEEAKARYEKAVFKVIDLDDYAAEDDEYEEKLKKESLAFFFLATYGDGEPT 170
SrCPR3    TAEGFAKALVEEAKARYEKAVFKVIDLDDYAADDDEYEEKLKKESLAFFFLATYGDGEPT 172
SrCPR     TAEGFAKALVEEAKVRYEKTSFKVIDLDDYAADDDEYEEKLKKESLAFFFLATYGDGEPT 174
SrCPR2    TAEGFAKALFEEAKARYEKAAFKVIDLDDYAADLDEYAEKLKKETYAFFFLATYGDGEPT 174
AtCPR1    TAEGFAKALSEEIKARYEKAAVKVIDLDDYAADDDQYEEKLKKETLAFFCVATYGDGEPT 155
          ********* :* *.**:*. .*::*******:  ::*******  *** :*********

ATR2      DNAARFYKWFTEGNDRGEWLKNLKYGVFGLGNRQYEHFNKVAKVVDDILVEQGAQRLVQV 235
AtCPR2    DNAARFYKWFTEGNDRGEWLKNLKYGVFGLGNRQYEHFNKVAKVVDDILVEQGAQRLVQV 235
PgCPR     DNAARFYKWFLEGKERGEWLQNLKFGVFGLGNRQYEHFNKIAIVVDEILAEQGGKRLISV 228
AaCPR     DNAARFYKWFTEGEEKGEWLDKLQYAVFGLGNRQYEHFNKIAKVVDEKLVEQGAKRLVPV 230
SrCPR3    DNAARFYKWFTEGDAKGEWLNKLQYGVFGLGNRQYEHFNKIAKVVDDGLVEQGAKRLVPV 232
SrCPR     DNAANFYKWFTEGDDKGELLKKLQYGVFGLGNRQYEHFNKIAIVVDDKLTEMGAKRLVPV 234
SrCPR2    DNAAKFYKWFTEGDEKGVWLQKLQYGVFGLGNRQYEHFNKIGIVVDDGLTEQGAKRIVPV 234
AtCPR1    DNAARFYKWFTEENERDIKLQQLAYGVFALGNRQYEHFNKIGIVLDEELCKKGAKRLIEV 215
          ****.***** * . :.  *.:* :.**.***********:. *:*: * : *.:*:: *

ATR2      GLGDDDQCIEDDFTAWREALWPELDTILREEGDTAVATPYTAAVLEYRVSIHDSE--DAK 293
AtCPR2    GLGDDDQCIEDDFTAWREALWPELDTILREEGDTAVATPYTAAVLEYRVSIHDSE--DAK 293
PgCPR     GLGDDDQCIEDDFTAWRESLWPELDQLLRDEDDTTVSTPYTAAVLEYRVVFHDPA--DAP 286
AaCPR     GMGDDDQCIEDDFTAWKELVWPELDQLLRDEDDTSVATPYTAAVAEYRVVFHDKP--ETY 288
SrCPR3    GLGDDDQCIEDDFTAWKELVWPELDQLLRDEDDTTVATPYTAAVAEYRVVFHEKP--DAL 290
SrCPR     GLGDDDQCIEDDFTAWKELVWPELDQLLRDEDDTSVTTPYTAAVLEYRVVYHDKPA-DSY 293
SrCPR2    GLGDDDQSIEDDFSAWKELVWPELDLLLRDEDDKAAATPYTAAIPEYRVVFHDKP--DAF 292
AtCPR1    GLGDDDQSIEDDFNAWKESLWSELDKLLKDEDDKSVATPYTAVIPEYRVVTHDPRFTTQK 275
          *:*****.*****.**:* :*.*** :*::*.*.:.:*****.: ****  *:

ATR2      FNDITLANGNGYTVFDAQHPYKANVAVKRELHTPESDRSCIHLEFDIAGSGLTMKLGDHV 353
AtCPR2    FNDINMANGNGYTVFDAQHPYKANVAVKRELHTPESDRSCIHLEFDIAGSGLTYETGDHV 353
PgCPR     TLEKSYSNANGHSVVDAQHPLRANVAVRRELHTPASDRSCTHLEFDISGTGIAYETGDHV 346
AaCPR     DQDQ-LTN---GHAVHDAQHPCRSNVAVKKELHSPLSDRSCTHLEFDISNTGLSYETGDHV 345
SrCPR3    SEDYSYTN--GHAVHDAQHPCRSNVAVKKELHSPESDRSCTHLEFDISNTGLSYETGDHV 348
SrCPR     AEDQTHTN--GHVVHDAQHPSRSNVAFKKELHTSQSDRSCTHLEFDISHTGLSYETGDHV 351
SrCPR2    SDDHTQTN--GHAVHDAQHPCRSNVAVKKELHTPESDRSCTHLEFDISHTGLSYETGDHV 350
AtCPR1    SMESNVAN--GNTTIDIHHPCRVDVAVQKELHTHESDRSCIHLEFDISRTGITYETGDHV 333
            :   :*   *  . * :** : :**.::***:  ***** ******: :*:: : ****
```

FIG. 6D

```
ATR2      GVLCDNLSETVDEALRLLDMSPDTYFSLHAEKEDGTPIS-SSLPPPFP-PCNLRTALTRY 411
AtCPR2    GVLCDNLSETVDEALRLLDMSPDTYFSLHAEKEDGTPIS-SSLPPPFP-PCNLRTALTRY 411
PgCPR     GVYCENLAETVEEALELLGLSPDTYFSVHADKEDGTPLSGSSLPPPFP-PCTLRTALTLH 405
AaCPR     GVYVENLSEVVDEAEKLIGLPPHTYFSVHADNEDGTPLGGASLPPPFP-PCTLRKALASY 404
SrCPR3    GVYCENLSEVVNDAERLVGLPPDTYFSIHTDSEDGSPLGGASLPPPFP-PCTLRKALTCY 407
SrCPR     GVYSENLSEVVDEALKLLGLSPDTYFSVHADKEDGTPIGGASLPPPFP-PCTLRDALTRY 410
SrCPR2    GVYCENLIEVVEEAGKLLGLSTDTYFSLHIDNEDGSPLGGPSLQPPFP-PCTLRKALTNY 409
AtCPR1    GVYAENHVEIVEEAGKLLGHSLDLVFSIHADKEDGSPLE-SAVPPPFPGPCTLGTGLARY 392
          **   :*   *  *::* .*:.  .  .   **:*  :.***:*:   .:: **** **.*   .*: :

ATR2      ACLLSSPKKSALVALAAHASDPTEAERLKHLASPAGKDEYSKWVVESQRSLLEVMAEFPS 471
AtCPR2    ACLLSSPKKSALVALAAHASDPTEAERLKHLASPAGKDEYSKWVVESQRSLLEVMAEFPS 471
PgCPR     ADLLSSPKKSALLALAAHASDPTEADRLRHLASPAGKDEYAQWIVASQRSLLEVMAEFPS 465
AaCPR     ADVLSSPKKSALLALAAHATDSTEADRLKFLASPAGKDEYAQWIVASHRSLLEVMEAFPS 464
SrCPR3    ADVLSSPKKSALLALAAHATDPSEADRLKFLASPAGKDEYSQWIVASQRSLLEVMEAFPS 467
SrCPR     ADVLSSPKKVALLALAAHASDPSEADRLKFLASPAGKDEYAQWIVANQRSLLEVMQSFPS 470
SrCPR2    ADLLSSPKKSTLLALAAHASDPTEADRLRFLASREGKDEYAEWVVANQRSLLEVMEAFPS 469
AtCPR1    ADLLNPPRKSALVALAAYATEPSEAEKLKHLTSPDGKDEYSQWIVASQRSLLEVMAAFPS 452
          *  :*..*:*  :*:****:*::.:**::*:.*:*   *****::*:* .:*******   ***

ATR2      AKPPLGVFFAGVAPRLQPRFYSISSSPKIAETRIHVTCALVYEKMPTGRIHKGVCSTWMK 531
AtCPR2    AKPPLGVFFAGVAPRLQPRFYSISSSPKIAETRIHVTCALVYEKMPTGRIHKGVCSTWMK 531
PgCPR     AKPPLGVFFASVAPRLQPRYYSISSSPRIAPSRIHVTCALVYEKTPTGRVHKGVCSTWMK 525
AaCPR     AKPPLGVFFASVAPRLQPRYYSISSSPRFAPNRIHVTCALVYEQTPSGRVHKGVCSTWMK 524
SrCPR3    AKPSLGVFFASVAPRLQPRYYSISSSPKMAPDRIHVTCALVYEKTPAGRIHKGVCSTWMK 527
SrCPR     AKPPLGVFFAAVAPRLQPRYYSISSSPKMSPNRIHVTCALVYETTPAGRIHRGLCSTWMK 530
SrCPR2    ARPPLGVFFAAVAPRLQPRYYSISSSPKMEPNRIHVTCALVYEKTPAGRIHKGICSTWMK 529
AtCPR1    AKPPLGVFFAAIAPRLQPRYYSISSSPRLAPSRVHVTSALVYGPTPTGRIHKGVCSTWMK 512
          *:*.******.:*******:*******::     *:***.****     *:**:*:*:******

ATR2      NAVPYEKSEKLFLGRPIFVRQSNFKLPSDSKVPIIMIGPGTGLAPFRGFLQERLALVESG 591
AtCPR2    NAVPYEKSENCSS-APIFVRQSNFKLPSDSKVPIIMIGPGTGLAPFRGFLQERLALVESG 590
PgCPR     NSVPSEKSDECSW-APIFVRQSNFKLPADAKVPIIMIGPGTGLAPFRGFLQERLALKEAG 584
AaCPR     NAVPMTESQDCSW-APIYVRTSNFRLPSDPKVPVIMIGPGTGLAPFRGFLQERLAQKEAG 583
SrCPR3    NAVPMTESQDCSW-APIYVRTSNFRLPSDPKVPVIMIGPGTGLAPFRGFLQERLALKEAG 586
SrCPR     NAVPLTESPDCSQ-ASIFVRTSNFRLPVDPKVPVIMIGPGTGLAPFRGFLQERLALKESG 589
SrCPR2    NAVPLTESQDCSW-APIFVRTSNFRLPIDPKVPVIMIGPGTGLAPFRGFLQERLALKESG 588
AtCPR1    NAVPAEKSHECSG-APIFIRASNFKLPSNPSTPIVMVGPGTGLAPFRGFLQERMALKEDG 571
          *:**   :*  .       .*::*  ***:**  :...*::*:****************:*   *  *

ATR2      VELGPSVLFFGCRNRRMDFIYEEELQRFVESGALAELSVAFSREGPTKEYVQHKMMDKAS 651
AtCPR2    VELGPSVLFFGCRNRRMDFIYEEELQRFVESGALAELSVAFSREGPTKEYVQHKMMDKAS 650
PgCPR     TELGPSILFFGCRNSKMDYIYEDELDNFVQNGALSELVLAFSREGPTKEYVQHKMMEKAS 644
AaCPR     TELGTAILFFGCRNRKVDFIYEDELNNFVETGALSELVTAFSREGATKEYVQHKMTQKAS 643
SrCPR3    TDLGLSILFFGCRNRKVDFIYENELNNFVETGALSELIVAFSREGPTKEYVQHKMSEKAS 646
SrCPR     TELGSSIFFFGCRNRKVDFIYEDELNNFVETGALSELIVAFSREGTAKEYVQHKMSQKAS 649
SrCPR2    TELGSSILFFGCRNRKVDYIYENELNNFVENGALSELDVAFSRDGPTKEYVQHKMTQKAS 648
AtCPR1    EELGSSLLFFGCRNRQMDFIYEDELNNFVDQGVISELIMAFSREGAQKEYVQHKMMEKAA 631
           :**  :::******  ::*:***:**:.**: *.::**   ****:*.  ********  :**:

ATR2      DIWNMISQGAYLYVCGDAKGMARDVHRSLHTIAQEQGSMDSTKAEGFVKNLQTSGRYLRDVW 713
AtCPR2    DIWNMISQGAYLYVCGDAKGMARDVHRSLHTIAQEQGSMDSTKAEGFVKNLQTSGRYLRDVW 712
PgCPR     DIWNLISQGAYLYVCGDAKGMARDVHRTLHTIAQEQGSLDSSKAESMVKNLQMSGRYLRDVW 706
AaCPR     DIWNLLSEGAYLYVCGDAKGMAKDVHRTLHTIVQEQGSLDSSKAELYVKNLQMAGRYLRDVW 705
SrCPR3    DIWNLLSEGAYLYVCGDAKGMAKDVHRTLHTIVQEQGSLDSSKAELYVKNLQMSGRYLRDVW 708
SrCPR     DIWKLLSEGAYLYVCGDAKGMAKDVHRTLHTIVQEQGSLDSSKAELYVKNLQMSGRYLRDVW 711
SrCPR2    EIWNMLSEGAYLYVCGDAKGMAKDVHRTLHTIVQEQGSLDSSKAELYVKNLQMSGRYLRDVW 710
AtCPR1    QVWDLIKEEGYLYVCGDAKGMARDVHRTLHTIVQEQEGVSSSEAEAIVKKLQTEGRYLRDVW 693
          ::*.::.:  .***********:****:****.***   .:.*::**   **:**   ********
```

FIG. 6D (Cont'd)

| | n20yhcB | n21yhcB | n22yhcB | n23yhcB | n24yhcB |
|---|---|---|---|---|---|
| t28VO1 | n20yhcB_t28VO1 | n21yhcB_t28VO1 | n22yhcB_t28VO1 | n23yhcB_t28VO1 | n24yhcB_t28VO1 |
| t29VO1 | n20yhcB_t29VO1 | n21yhcB_t29VO1 | n22yhcB_t29VO1 | n23yhcB_t29VO1 | n24yhcB_t29VO1 |
| t30VO1 | n20yhcB_t30VO1 | n21yhcB_t30VO1 | Current | n23yhcB_t30VO1 | n24yhcB_t30VO1 |
| t31VO1 | n20yhcB_t31VO1 | n21yhcB_t31VO1 | n22yhcB_t31VO1 | n23yhcB_t31VO1 | n24yhcB_t31VO1 |
| t32VO1 | n20yhcB_t32VO1 | n21yhcB_t32VO1 | n22yhcB_t32VO1 | n23yhcB_t32VO1 | n24yhcB_t32VO1 |

| # | (+)-nootkatone Downstream Pathway Enzymes |
|---|---|
| 1 | Valencene synthase (VS) |
| 2 | Valencene oxygenase (VO) |
| 3 | P450 reductase (CPR) |
| 4 | Alcohol dehydrogenase (ADH) |

>ReCDH [Rhodococcus erythropolis]

MARVEGQVALITGAARGQGRSHAIKLAEEGADVILVDVPNDVVDIGYPLGTADELDQTAKDVENLG
RKAIVIHADVRDLESLTAEVDRAVSTLGRLDIVSANAGIASVPFLSHDIPDNTWRQMIDINLTGVW
HTAKVAVPHILAGERGGSIVLTSSAAGLKGYAQISHYSAAKHGVVGLMRSLALELAPHRVRVNSLH
PTQVNTPMIQNEGTYRIFSPDLENPTREDFEIASTTTNALPIPWVESVDVSNALLFLVSEDARYIT
GAAIPVDAGTTLK (SEQ ID NO: 84)

ATGGCCCGTGTGGAAGGTCAAGTGGCTCTGATTACCGGCGCTGCTCGTGGTCAAGGTCGTAGTCAT
GCGATTAAACTGGCGGAAGAAGGCGCGGATGTGATTCTGGTTGACGTCCCGAATGATGTGGTTGAC
ATCGGCTATCCGCTGGGTACGGCAGATGAACTGGACCAGACCGCTAAAGATGTTGAAAACCTGGGT
CGTAAGGCGATTGTCATCCATGCCGATGTGCGCGACCTGGAATCACTGACGGCAGAAGTGGATCGT
GCTGTTAGTACCCTGGGCCGCCTGGACATTGTTTCCGCAAATGCTGGTATCGCCAGCGTCCCGTTT
CTGTCTCACGATATTCCGGACAACACCTGGCGTCAGATGATTGATATCAATCTGACGGGCGTCTGG
CATACCGCGAAAGTGGCCGTTCCGCACATTCTGGCCGGTGAACGCGGCGGTTCCATCGTTCTGACC
AGCTCTGCGGCCGGCCTGAAAGGTTATGCACAAATTAGTCATTACTCCGCAGCTAAGCACGGCGTC
GTGGGTCTGATGCGTTCACTGGCACTGGAACTGGCTCCGCATCGTGTCCGCGTGAACTCGCTGCAC
CCGACGCAGGTGAACACCCCGATGATTCAAAATGAAGGCACGTATCGTATCTTTAGCCCGGATCTG
GAAAACCCGACCCGCGAAGACTTCGAAATTGCGTCTACCACGACCAATGCCCTGCCGATCCCGTGG
GTGGAATCAGTTGATGTCTCGAACGCACTGCTGTTCCTGGTTAGCGAAGACGCACGTTACATTACC
GGTGCAGCAATCCCGGTGGATGCCGGTACGACCCTGAAGTAA (SEQ ID NO: 85)

>CsDH [Citrus sinensis]

MATPPISSLISQRLLGKVALVTGGASGIGEGIVRLFHRHGAKVCFVDVQDELGYRLQESLVGDKDS
NIFYSHCDVTVEDDVRRAVDLTVTKFGTLDIMVNNAGISGTPSSDIRNVDVSEFEKVFDINVKGVF
MGMKYAASVMIPRKQGSIISLGSVGSVIGGIGPHHYISSKHAVVGLTRSIAAELGQHGIRVNCVSP
YAVPTNLAVAHLPEDERTEDMFTGFREFAKKNANLQGVELTVEDVANAVLFLASEDARYISGDNLI
VDGGFTRVNHSFRVFR (SEQ ID NO: 86)

ATGGCAACGCCGCCGATTTCATCCCTGATTTCACAACGCCTGCTGGGTAAAGTCGCCCTGGTCACG
GGTGGTGCTTCTGGTATTGGTGAAGGCATCGTGCGTCTGTTTCACCGTCATGGCGCGAAAGTGTGC
TTTGTTGATGTGCAGGATGAACTGGGCTACCGTCTGCAAGAATCTCTGGTGGGCGACAAAGATTCA
AACATCTTTTATAGCCACTGTGATGTCACCGTGGAAGACGATGTGCGCCGCGCTGTGGATCTGACC
GTGACGAAATTCGGTACGCTGGATATTATGGTCAATAACGCGGGTATTAGTGGCACCCCGTCCAGC
GATATTCGTAATGTTGATGTGAGCGAATTTGAAAAAGTGTTTGATATTAACGTCAAAGGCGTGTTT
ATGGGCATGAAATATGCCGCGAGCGTGATGATCCCGCGCAAACAGGGTAGCATCATCTCCCTGGGT
TCTGTTGGCAGCGTGATCGGTGGCATTGGCCCGCACCATTATATCAGCTCGAAACATGCGGTTGTG
GGCCTGACCCGCAGCATTGCAGCGGAACTGGGTCAGCATGGCATTCGTGTGAACTGTGTGTCTCCG
TATGCGGTTCCGACCAATCTGGCGGTTGCACACCTGCCGGAAGATGAACGTACCGAAGATATGTTT
ACGGGCTTCCGTGAATTTGCGAAAAAGAATGCCAACCTGCAAGGTGTTGAACTGACCGTCGAAGAT
GTGGCCAATGCGGTGCTGTTTCTGGCCAGCGAAGATGCACGCTACATTAGCGGTGATAATCTGATC
GTTGATGGCGGCTTTACCCGTGTGAACCACTCATTTCGTGTTTTCCGTTAA (SEQ ID NO: 87)

*FIG. 22A*

>CsDH1 [Citrus sinensis]

MSKPRLQGKVAIIMGAASGIGEATAKLFAEHGAFVIIADIQDELGNQVVSSIGPEKASYRHCDVRD
EKQVEETVAYAIEKYGSLDIMYSNAGVAGPVGTILDLDMAQFDRTIATNLAGSVMAVKYAARVMVA
NKIRGSIICTTSTASTVGGSGPHAYTISKHGLLGLVRSAASELGKHGIRVNCVSPFGVATPFSAGT
INDVEGFVCKVANLKGIVLKAKHVAEAALFLASDESAYVSGHDLVVDGGFTAVTNVMSMLEGHG
(SEQ ID NO: 88)

ATGTCAAAACCGCGTCTGCAAGGCAAAGTGGCTATTATTATGGGTGCTGCGTCTGGCATCGGTGAA
GCTACGGCTAAACTGTTCGCTGAACATGGCGCATTTGTGATTATCGCTGATATTCAGGACGAACTG
GGCAACCAGGTGGTTAGCTCTATCGGCCCGGAAAAAGCGTCTTATCGTCACTGCGATGTGCGTGAT
GAAAAACAGGTTGAAGAAACCGTCGCGTATGCGATTGAAAAATACGGCAGCCTGGATATTATGTAC
TCCAATGCGGGCGTGGCCGGTCCGGTTGGCACGATTCTGGATCTGGACATGGCCCAATTCGACCGT
ACCATCGCAACGAACCTGGCTGGTAGTGTTATGGCAGTCAAATATGCGGCCCGTGTCATGGTGGCG
AATAAAATTCGCGGTAGCATTATCTGTACCACGAGTACCGCCTCCACGGTGGGCGGCAGCGGCCCG
CACGCCTATACCATTAGCAAACACGGTCTGCTGGGCCTGGTTCGTTCAGCAGCTTCGGAACTGGGT
AAACATGGCATCCGCGTGAACTGCGTTAGCCCGTTTGGTGTTGCGACCCCGTTCTCTGCCGGTACG
ATTAACGATGTCGAAGGCTTTGTCTGTAAAGTGGCGAATCTGAAAGGCATCGTCCTGAAAGCGAAG
CATGTGGCCGAAGCGGCCCTGTTCCTGGCAAGCGATGAATCTGCTTATGTGAGCGGTCACGACCTG
GTGGTGGATGGTGGCTTTACGGCAGTTACGAATGTCATGTCAATGCTGGAAGGTCACGGCTAA
(SEQ ID NO: 89)

>CsDH2 [Citrus sinensis]

MSNPRMEGKVALITGAASGIGEAAVRLFAEHGAFVVAADVQDELGHQVAASVGTDQVCYHHCDVRD
EKQVEETVRYTLEKYGKLDVLFSNAGIMGPLTGILELDLTGFGNTMATNVCGVAATIKHAARAMVD
KNIRGSIICTTSVASSLGGTAPHAYTTSKHALVGLVRTACSELGAYGIRVNCISPFGVATPLSCTA
YNLRPDEVEANSCALANLKGIVLKAKHIAEAALFLASDESAYISGHNLAVDGGFTVVNHSSSSAT
(SEQ ID NO: 90)

ATGTCAAACCCGCGTATGGAAGGCAAAGTCGCACTGATTACGGGCGCAGCATCTGGTATCGGTGAA
GCAGCAGTCCGTCTGTTCGCTGAACATGGTGCGTTTGTCGTGGCGGCAGATGTGCAAGACGAACTG
GGTCATCAGGTGGCGGCATCTGTGGGTACGGACCAGGTGTGCTACCATCACTGCGATGTGCGCGAT
GAAAAACAAGTGGAAGAAACCGTGCGTTATACCCTGGAAAAATACGGCAAACTGGATGTCCTGTTT
TCAAACGCGGGCATCATGGGTCCGCTGACCGGCATTCTGGAACTGGATCTGACCGGCTTCGGTAAC
ACGATGGCAACCAATGTGTGCGGTGTTGCCGCGACCATTAAACACGCGGCACGCGCAATGGTGGAC
AAAAACATTCGCGGTAGCATTATCTGCACCACCAGCGTGGCTTCATCGCTGGGTGGCACCGCGCCG
CACGCATACACCACGAGCAAACACGCACTGGTGGGCCTGGTTCGTACGGCATGTTCGGAACTGGGT
GCGTATGGCATTCGTGTGAACTGTATCAGCCCGTTTGGTGTTGCAACGCCGCTGTCTTGCACGGCC
TATAACCTGCGCCCGGATGAAGTGGAAGCAAACTCATGCGCACTGGCGAACCTGAAAGGTATTGTG
CTGAAAGCGAAACACATTGCGGAAGCAGCGCTGTTCCTGGCGAGCGATGAAAGCGCGTATATTAGC
GGTCATAATCTGGCGGTGGATGGTGGTTTCACGGTGGTTAATCATTCAAGTTCGTCGGCGACGTAA
(SEQ ID NO: 91)

*FIG. 22A (Cont'd)*

>CsDH3 [Citrus sinensis]

MTTAGSRDSPLVAQRLLGKVALVTGGATGIGESIVRLFHKHGAKVCVVDINDDLGQHLCQTLGPTT
RFIHGDVAIEDDVSRAVDFTVANFGTLDIMVNNAGMGGPPCPDIREFPISTFEKVFDINTKGTFIG
MKHAARVMIPSKKGSIVSISSVTSAIGGAGPHAYTASKHAVLGLTKSVAAELGQHGIRVNCVSPYA
ILTNLALAHLHEDERTDDARAGFRAFIGKNANLQGVDLVEDDVANAVLFLASDDARYISGDNLFVD
GGFTCTNHSLRVFR (SEQ ID NO: 92)

ATGACGACGGCTGGTTCGCGTGACAGTCCGCTGGTCGCTCAACGCCTGCTGGGCAAAGTGGCCCTG
GTTACGGGTGGTGCTACCGGCATTGGTGAAAGTATCGTGCGTCTGTTTCATAAACACGGCGCGAAA
GTTTGCGTGGTTGATATTAACGATGACCTGGGCCAGCATCTGTGTCAAACCCTGGGTCCGACCACC
CGTTTCATTCACGGCGATGTTGCAATCGAAGATGATGTGAGCCGTGCGGTTGATTTTACCGTCGCC
AACTTCGGTACGCTGGACATTATGGTGAACAATGCCGGTATGGGCGGTCCGCCGTGCCCGGATATT
CGTGAATTTCCGATCTCGACCTTTGAAAAAGTCTTCGACATTAACACCAAAGGCACGTTCATCGGT
ATGAAACATGCGGCCCGCGTGATGATTCCGAGTAAAAAAGGTAGTATTGTCAGCATTAGCAGCGTG
ACCAGCGCGATTGGCGGCGCGGGTCCGCACGCCTATACCGCGAGCAAACATGCGGTGCTGGGCCTG
ACGAAATCTGTCGCGGCGGAACTGGGCCAGCACGGTATTCGTGTCAACTGTGTGTCTCCGTACGCC
ATCCTGACCAATCTGGCGCTGGCCCATCTGCACGAAGATGAACGTACGGATGACGCGCGTGCGGGT
TTTCGTGCATTCATTGGTAAAAACGCTAATCTGCAAGGTGTTGATCTGGTCGAAGATGACGTGGCG
AATGCCGTTCTGTTTCTGGCATCAGATGACGCTCGCTATATCTCGGGCGATAACCTGTTCGTGGAT
GGCGGCTTCACCTGTACCAATCACTCCCTGCGTGTGTTCCGTTAA (SEQ ID NO: 93)

>VvDH [Vitis vinifera]

MAATSIDNSPLPSQRLLGKVALVTGGATGIGESIVRLFLKQGAKVCIVDVQDDLGQKLCDTLGGDP
NVSFFHCDVTIEDDVCHAVDFTVTKFGTLDIMVNNAGMAGPPCSDIRNVEVSMFEKVFDVNVKGVF
LGMKHAARIMIPLKKGTIISLCSVSSAIAGVGPHAYTGSKCAVAGLTQSVAAEMGGHGIRVNCISP
YAIATGLALAHLPEDERTEDAMAGFRAFVGKNANLQGVELTVDDVAHAAVFLASDEARYISGLNLM
LDGGFSCTNHSLRVFR (SEQ ID NO: 94)

ATGGCCGCAACGAGCATTGATAATTCTCCGCTGCCGAGTCAACGTCTGCTGGGTAAAGTCGCACTG
GTCACGGGTGGCGCTACGGGTATTGGCGAAAGCATCGTGCGTCTGTTTCTGAAACAGGGTGCTAAA
GTGTGCATTGTGGACGTGCAAGATGACCTGGGCCAGAAACTGTGCGATACCCTGGGTGGCGATCCG
AACGTTAGCTTTTTCCATTGCGATGTGACCATCGAAGATGATGTGTGCCATGCAGTTGATTTTACC
GTCACGAAATTCGGCACCCTGGATATTATGGTGAACAATGCGGGTATGGCAGGTCCGCCGTGCTCG
GACATCCGCAACGTGGAAGTCAGCATGTTTGAAAAAGTGTTTGATGTGAATGTGAAAGGTGTTTTC
CTGGGCATGAAACATGCAGCCCGCATTATGATTCCGCTGAAAAAAGGCACCATTATCAGCCTGTGT
TCAGTTTCCAGCGCTATCGCGGGCGTTGGTCCGCACGCATATACGGGTAGCAAATGCGCAGTGGCG
GGTCTGACGCAATCGGTCGCAGCAGAAATGGGTGGTCATGGCATTCGCGTGAACTGTATCAGCCCG
TATGCAATCGCAACGGGTCTGGCGCTGGCACATCTGCCGGAAGATGAACGCACGGAAGATGCAATG
GCGGGTTTCCGTGCGTTTGTGGGTAAAAATGCGAATCTGCAAGGTGTTGAACTGACCGTGGATGAT
GTGGCGCACGCAGCGGTGTTTCTGGCAAGCGATGAAGCACGTTACATCTCTGGTCTGAATCTGATG
CTGGACGGCGGCTTTTCGTGTACCAACCACTCGCTGCGTGTCTTTCGCTAA (SEQ ID NO: 95)

*FIG. 22A (Cont'd)*

>VvDH1 [Vitis vinifera]

MSTASSGDVSLLSQRLVGKVALITGGATGIGESIARLFYRHGAKVCIVDIQDNPGQNLCRELGTDD
ACFFHCDVSIEIDVIRAVDFVVNRFGKLDIMVNNAGIADPPCPDIRNTDLSIFEKVFDVNVKGTFQ
CMKHAARVMVPQKKGSIISLTSVASVIGGAGPHAYTGSKHAVLGLTKSVAAELGLHGIRVNCVSPY
AVPTGMPLAHLPESEKTEDAMMGMRAFVGRNANLQGIELTVDDVANSVVFLASDEARYVSGLNLML
DGGFSCVNHSLRVFR (SEQ ID NO: 96)

ATGTCAACGGCTTCCTCGGGTGATGTGTCGCTGCTGTCGCAACGCCTGGTCGGTAAAGTCGCTCTG
ATTACGGGTGGTGCAACGGGCATTGGTGAATCGATTGCGCGTCTGTTTTACCGTCATGGTGCGAAA
GTGTGCATCGTTGACATTCAGGATAATCCGGGTCAAAACCTGTGCCGTGAACTGGGCACCGACGAT
GCGTGCTTCTTTCACTGCGATGTGAGCATTGAAATCGATGTGATTCGTGCTGTTGACTTTGTGGTT
AACCGCTTTGGTAAACTGGACATTATGGTTAATAACGCGGGCATCGCAGATCCGCCGTGCCCGGAT
ATTCGCAACACCGATCTGAGCATTTTTGAAAAAGTGTTCGATGTGAACGTGAAAGGCACCTTTCAG
TGTATGAAACACGCAGCGCGCGTTATGGTGCCGCAGAAAAAAGGTAGCATTATCAGCCTGACCTCG
GTGGCGAGCGTGATTGGTGGCGCGGGTCCGCACGCCTATACGGGTAGCAAACACGCGGTTCTGGGT
CTGACGAAAAGCGTTGCGGCAGAACTGGGTCTGCATGGTATTCGCGTGAACTGTGTGAGTCCGTAT
GCAGTTCCGACGGGTATGCCGCTGGCACATCTGCCGGAATCGGAAAAAACCGAAGATGCGATGATG
GGTATGCGTGCATTTGTGGGTCGTAATGCCAACCTGCAAGGTATTGAACTGACCGTGGACGATGTC
GCAAATAGCGTCGTGTTTCTGGCGTCGGATGAAGCGCGTTATGTTAGCGGTCTGAACCTGATGCTG
GACGGCGGCTTCTCGTGTGTCAACCACTCGCTGCGTGTGTTTCGCTAA (SEQ ID NO: 97)

>CsABA2 [Citrus sinensis]

MSNSNSTDSSPAVQRLVGRVALITGGATGIGESTVRLFHKHGAKVCIADVQDNLGQQVCQSLGGEP
DTFFCHCDVTKEEDVCSAVDLTVEKFGTLDIMVNNAGISGAPCPDIREADLSEFEKVFDINVKGVF
HGMKHAARIMIPQTKGTIISICSVAGAIGGLGPHAYTGSKHAVLGLNKNVAAELGKYGIRVNCVSP
YAVATGLALAHLPEEERTEDAMVGFRNFVARNANMQGTELTANDVANAVLFLASDEARYISGTNLM
VDGGFTSVNHSLRVFR (SEQ ID NO: 98)

ATGTCCAATAGCAACTCTACGGATTCGTCGCCGGCAGTCCAACGCCTGGTCGGTCGTGTCGCCCTG
ATTACGGGTGGTGCAACGGGTATTGGCGAAAGCACGGTGCGCCTGTTTCATAAACATGGCGCGAAA
GTGTGTATTGCCGACGTTCAGGATAACCTGGGTCAGCAAGTGTGTCAGAGTCTGGGTGGCGAACCG
GATACCTTTTTCTGCCATTGTGATGTGACGAAAGAAGAAGATGTGTGTAGCGCAGTTGATCTGACC
GTGGAAAAATTTGGCACCCTGGACATTATGGTGAACAATGCGGGTATTAGCGGCGCACCGTGCCCG
GACATTCGTGAAGCCGATCTGAGCGAATTTGAAAAAGTTTTCGACATCAACGTGAAAGGCGTGTTT
CACGGCATGAAACATGCAGCGCGTATTATGATCCCGCAAACCAAAGGCACCATTATCAGCATTTGC
TCCGTGGCTGGTGCGATTGGTGGCCTGGGTCCGCACGCATATACCGGCTCCAAACATGCAGTCCTG
GGCCTGAACAAAAACGTGGCCGCGGAACTGGGCAAATACGGTATCCGTGTGAATTGCGTCAGCCCG
TATGCTGTTGCCACCGGCCTGGCTCTGGCACACCTGCCGGAAGAAGAACGTACCGAAGATGCAATG
GTGGGCTTTCGTAATTTTGTGGCACGCAACGCGAATATGCAAGGCACCGAACTGACGGCGAATGAT
GTGGCAAACGCGGTCCTGTTTCTGGCCTCTGATGAAGCCCGTTATATCAGCGGCACGAATCTGATG
GTGGATGGCGGTTTTACCTCGGTCAATCACTCGCTGCGTGTCTTCCGTTAA (SEQ ID NO: 99)

FIG. 22A (Cont'd)

>BdDH [Brachypodium distachyon]

MSAAAAVSSSSSPRLEGKVALVTGGASGIGEAIVRLFRQHGAKVCIADVQDEAGQQVRDSLGDDAG
TDVLFVHCDVTVEEDVSRAVDAAAEKFGTLDIMVNNAGITGDKVTDIRNLDFAEVRKVFDINVHGM
LLGMKHAARVMIPGKKGSIVSLASVASVMGGMGPHAYTASKHAVVGLTKSVALELGKHGIRVNCVS
PYAVPTALSMPHLPQGEHKGDAVRDFLAFVGGEANLKGVDLLPKDVAQAVLYLASDEARYISALNL
VVDGGFTSVNPNLKAFED (SEQ ID NO: 100)

ATGTCCGCTGCTGCCGCCGTGTCCTCCTCATCGTCGCCGCGTCTGGAAGGCAAAGTCGCTCTGGTT
ACGGGTGGTGCGTCAGGTATCGGCGAAGCCATTGTGCGCCTGTTCCGTCAACATGGTGCCAAAGTG
TGTATCGCGGATGTCCAAGACGAAGCGGGCCAACAGGTCCGTGATAGCCTGGGTGACGATGCCGGT
ACGGATGTGCTGTTTGTGCATTGCGACGTTACCGTGGAAGAAGATGTGTCACGCGCGGTGGATGCC
GCTGCGGAAAAATTCGGCACCCTGGACATTATGGTGAACAACGCAGGTATTACGGGCGACAAAGTG
ACGGACATTCGCAACCTGGATTTCGCTGAAGTCCGTAAAGTGTTCGACATCAATGTGCACGGTATG
CTGCTGGGCATGAAACATGCGGCCCGCGTGATGATTCCGGGTAAAAAAGGCTCGATTGTGAGCCTG
GCATCGGTCGCAAGCGTTATGGGTGGTATGGGTCCGCACGCATATACCGCAAGCAAACACGCGGTT
GTGGGTCTGACGAAAAGCGTTGCACTGGAACTGGGCAAACATGGTATTCGTGTCAACTGTGTGAGC
CCGTATGCAGTTCCGACCGCACTGTCAATGCCGCACCTGCCGCAGGGCGAACATAAAGGTGATGCG
GTGCGTGATTTCCTGGCGTTTGTTGGCGGTGAAGCGAATCTGAAAGGTGTCGATCTGCTGCCGAAA
GATGTTGCACAGGCGGTTCTGTATCTGGCAAGCGACGAAGCGCGCTATATTTCTGCGCTGAATCTG
GTGGTTGATGGCGGTTTTACGAGCGTGAATCCGAATCTGAAAGCATTTGAAGACTAA (SEQ ID NO: 101)

>ZzSDR [Zingiber zerumbet]

MRLEGKVALVTGGASGIGESIARLFIEHGAKICIVDVQDELGQQVSQRLGGDPHACYFHCDVTVED
DVRRAVDFTAEKYGTIDIMVNNAGITGDKVIDIRDADFNEFKKVFDINVNGVFLGMKHAARIMIPK
MKGSIVSLASVSSVIAGAGPHGYTGAKHAVVGLTKSVAAELGRHGIRVNCVSPYAVPTRLSMPYLP
ESEMQEDALRGFLTFVRSNANLKGVDLMPNDVAEAVLYLATEESKYVSGLNLVIDGGFSIANHTLQ
VFE (SEQ ID NO: 102)

ATGCGTCTGGAAGGCAAAGTGGCTCTGGTCACGGGCGGTGCGTCGGGTATTGGCGAATCTATTGCT
CGTCTGTTTATTGAACACGGTGCAAAAATTTGCATCGTGGATGTCCAGGATGAACTGGGTCAACAG
GTCTCTCAGCGTCTGGGTGGCGATCCGCACGCCTGTTATTTCCACTGTGATGTGACCGTGGAAGAT
GACGTTCGTCGCGCGGTGGATTTTACGGCGGAAAAATATGGCACCATTGACATTATGGTTAACAAT
GCGGGCATTACGGGCGATAAAGTGATCGATATTCGTGATGCGGATTTCAACGAATTTAAAAAAGTG
TTCGACATTAACGTGAATGGTGTCTTTCTGGGCATGAAACACGCAGCGCGTATTATGATCCCGAAA
ATGAAAGGCTCCATCGTTTCGCTGGCGTCCGTTAGCTCGGTGATTGCTGGTGCAGGTCCGCATGGC
TATACCGGCGCAAAACATGCGGTTGTGGGTCTGACCAAAAGCGTTGCAGCCGAACTGGGTCGTCAT
GGTATTCGCGTGAACTGCGTTTCGCCGTATGCGGTGCCGACGCGCCTGTCAATGCCGTATCTGCCG
GAATCGGAAATGCAGGAAGATGCACTGCGCGGCTTTCTGACCTTTGTGCGTAGCAATGCGAACCTG
AAAGGCGTTGATCTGATGCCGAATGATGTGGCGGAAGCTGTTCTGTATCTGGCGACCGAAGAAAGC
AAATATGTTTCAGGTCTGAATCTGGTTATTGACGGCGGCTTCTCCATCGCTAATCATACCCTGCAA
GTGTTTGAATAA (SEQ ID NO: 103)

*FIG. 22A (Cont'd)*

```
CsDH3     MTTAGSRDSPLVAQRLLGKVALVTGGATGIGESIVRLFHKHGAKVCVVDIN--------- 51
VvDH      MAATSIDNSPLPSQRLLGKVALVTGGATGIGESIVRLFLKQGAKVCIVDVQ--------- 51
VvDH1     MSTASSGDVSLLSQRLVGKVALITGGATGIGESIARLFYRHGAKVCIVDIQ--------- 51
CsABA2    MSNSNSTDSSPAVQRLVGRVALITGGATGIGESTVRLFHKHGAKVCIADVQ--------- 51
CsDH      MATPPIS--SLISQRLLGKVALVTGGASGIGEGIVRLFHRHGAKVCFVDVQ--------- 49
BdDH      -MSAAAAVSSSSSPRLEGKVALVTGGASGIGEAIVRLFRQHGAKVCIADVQ--------- 50
ZzSDR     -------------MRLEGKVALVTGGASGIGESIARLFIEHGAKICIVDVQ--------- 38
CsDH1     ----------MSKPRLQGKVAIIMGAASGIGEATAKLFAEHGAFVIIADIQ--------- 41
CsDH2     ----------MSNPRMEGKVALITGAASGIGEAAVRLFAEHGAFVVAADVQ--------- 41
ReCDH     ------------MARVEGQVALITGAARGQGRSHAIKLAEEGADVILVDVPNDVVDIGYP 48
                        *: *:**:: *.* * *.. .  : ..** :  .*:

CsDH3     ----DDLGQHLCQTLG----PTTRFIHGDVAIEDDVSRAVDFTVANFGTLDIMVNNAGMG 103
VvDH      ----DDLGQKLCDTLGG--DPNVSFFHCDVTIEDDVCHAVDFTVTKFGTLDIMVNNAGMA 105
VvDH1     ----DNPGQNLCRELG---TDDACFFHCDVSIEIDVIRAVDFVVNRFGKLDIMVNNAGIA 104
CsABA2    ----DNLGQQVCQSLGG--EPDTFFCHCDVTKEEDVCSAVDLTVEKFGTLDIMVNNAGIS 105
CsDH      ----DELGYRLQESLVGDKDSNIFYSHCDVTVEDDVRRAVDLTVTKFGTLDIMVNNAGIS 105
BdDH      ----DEAGQQVRDSLGDDAGTDVLFVHCDVTVEEDVSRAVDAAAEKFGTLDIMVNNAGIT 106
ZzSDR     ----DELGQQVSQRLGGDP--HACYFHCDVTVEDDVRRAVDFTAEKYGTIDIMVNNAGIT 92
CsDH1     ----DELGNQVVSSIGP---EKASYRHCDVRDEKQVEETVAYAIEKYGSLDIMYSNAGVA 94
CsDH2     ----DELGHQVAASVGT---DQVCYHHCDVRDEKQVEETVRYTLEKYGKLDVLFSNAGIM 94
ReCDH     LGTADELDQTAKDVENLG--RKAIVIHADVRDLESLTAEVDRAVSTLGRLDIVSANAGIA 106
              *: .                 * **    .:   *   .    * :*::  ***:

CsDH3     GPPCPDIREFPISTFEKVFDINTKGTFIGMKHAARVMIPS-KKGSIVSISSVTSAIGGAG 162
VvDH      GPPCSDIRNVEVSMFEKVFDVNVKGVFLGMKHAARIMIPL-KKGTIISLCSVSSAIAGVG 164
VvDH1     DPPCPDIRNTDLSIFEKVFDVNVKGTFQCMKHAARVMVPQ-KKGSIISLTSVASVIGGAG 163
CsABA2    GAPCPDIREADLSEFEKVFDINVKGVFHGMKHAARIMIPQ-TKGTIISICSVAGAIGGLG 164
CsDH      GTPSSDIRNVDVSEFEKVFDINVKGVFMGMKYAASVMIPR-KQGSIISLGSVGSVIGGIG 164
BdDH      GDKVTDIRNLDFAEVRKVFDINVHGMLLGMKHAARVMIPG-KKGSIVSLASVASVMGGMG 165
ZzSDR     GDKVIDIRDADFNEFKKVFDINVNGVFLGMKHAARIMIPK-MKGSIVSLASVSSVIAGAG 151
CsDH1     G-PVGTILDLDMAQFDRTIATNLAGSVMAVKYAARVMVANKIRGSIICTTSTASTVGGSG 153
CsDH2     G-PLTGILELDLTGFGNTMATNVCGVAATIKHAARAMVDKNIRGSIICTTSVASSLGGTA 153
ReCDH     SVPFLSH-DIPDNTWRQMIDINLTGVWHTAKVAVPHILAGERGGSIVLTSSAAGLKGYAQ 165
          .       :       . :  *  *      * *.  ::      *:*:  .*.  .
```

FIG. 22B

| | | |
|---|---|---|
| CsDH3 | PHAYTASKHAVLGLTKSVAAELGQHGIRVNCVSPYAILTNLA----LAHLHEDERTDDAR | 218 |
| VvDH | PHAYTGSKCAVAGLTQSVAAEMGGHGIRVNCISPYAIATGLA----LAHLPEDERTEDAM | 220 |
| VvDH1 | PHAYTGSKHAVLGLTKSVAAELGLHGIRVNCVSPYAVPTGMP----LAHLPESEKTEDAM | 219 |
| CsABA2 | PHAYTGSKHAVLGLNKNVAAELGKYGIRVNCVSPYAVATGLA----LAHLPEERTEDAM | 220 |
| CsDH | PHHYISSKHAVVGLTRSIAAELGQHGIRVNCVSPYAVPTNLA----VAHLPEDERTEDMF | 220 |
| BdDH | PHAYTASKHAVVGLTKSVALELGKHGIRVNCVSPYAVPTALS----MPHLPQGEHKGDAV | 221 |
| ZzSDR | PHGYTGAKHAVVGLTRHGIRVNCVSPYAVPTRLS----MPYLPESEMQEDAL | 207 |
| CsDH1 | PHAYTISKHGLLGLVRSAASELGKHGIRVNCVSPFGVATPFS----AGTIN------ | 200 |
| CsDH2 | PHAYTTSKHALVGLVRTACSELGAYGIRVNCISPFGVATPLS----CTAYNLRP------ | 203 |
| ReCDH | ISHYSAAKHGVVGLMRSLALELAPHRVRVNSLHPTQVNTPMIQNEGTYRIFSPDLENPTR | 225 |
| | * :* ** :: . : :****:: : * . : | |
| | | |
| CsDH3 | AGFRAFIGKNANLQGVDLVEDDVANAVLFLASDDARYISGDNLFVDGGFTCTNHSLRVFR---- | 278 |
| VvDH | AGFRAFVGKNANLQGVKNANLQGVELTVDDVAHAAVFLASDEARYISGLNLMLDGGFSCTNHSLRVFR---- | 280 |
| VvDH1 | MGMRAFVGRNANLQGIELTVDDVANSVVFLASDEARYVSGLNLMLDGGFSCVNHSLRVFR---- | 279 |
| CsABA2 | VGFRNFVARNANMQGTELTANDVANAVLFLASDEARYISGTNLMVDGGFTSVNHSLRVFR---- | 280 |
| CsDH | TGFREFAKKNANLQGVELTVEDVANAVLFLASEDARYISGDNLIVDGGFTRVNHSFRVFR---- | 280 |
| BdDH | RDFLAFVGGEANLKGVDLLPKDVAQAVLYLASDEARYISALNLVVDGGFTSVNPNLKAFED-- | 282 |
| ZzSDR | RGFLTFVRSNANLKGVDLMPNDVAEAVLYLATEESKYVSGLNLVIDGGFSIANHTLQVFE--- | 267 |
| CsDH1 | -DVEGFVCKVANLKGIVLKAKHVAEAALFLASDESAYVSGHDLVVDGGFTAVTNVMSMLEGHG | 262 |
| CsDH2 | DEVEANSCALANLKGIVLKAKHIAEAALFLASDESAYISGHNLAVDGGFTVVNHSSSSAT--- | 263 |
| ReCDH | EDFEIASTTNALPIPWVESVDVSNALLFLVSEDARYITGAAIPVDAGTTLK---------- | 277 |
| | .: .:::: :*:::::: ***.: : :.**.: | |

FIG. 22B (Cont'd)

```
8rp-t20SrKO          ----MALLLAVFAVALAVALIFWYLKSYTSARRSQSNHLPRVPEVPGVPLLGNLLQLKEK
8rp-t20VO0           ----MALLLAVFAVALAVALIFWYLKSYTSARRSQSNHLPRVPEVPGVPLLGNLLQLKEK
n22yhcB-t30VO1       MAWEYALIGLVVGIIIGAVAMRWYLKSYTSARRSQSNRLPRVPEVPGVPLLGNLLQLKEK
n22yhcB-t30VO2       MAWEYALIGLVVGIIIGAVAMRWYLKSYTSARRSQSNHLPRVPEVPGVPLLGNLLQLKEK
                          **:  *..: :... : ***************:**********************

8rp-t20SrKO          KPYMTFTRWAATYGPIYSIKTGATSMVVVSSNEIAKEALVTRFQSISTRNLSKALKVLTA
8rp-t20VO0           KPYMTFTRWAATYGPIYSIKTGATSMVVVSSNEIAKEALVTRFQSISTRNLSKALKVLTA
n22yhcB-t30VO1       KPYMTFTRWAATYGPIYSIKTGATSMVVVSSNEIAKEALVTRFQSISTRNLSKALKVLTA
n22yhcB-t30VO2       KPYMTFTKWAATYGPIYSIKTGATSVVVVSSNEIAKEALVTRFQSISTRNLSKALKVLTA
                     *******:*****************:**********************************

8rp-t20SrKO          DKTMVAMSDYDDYHKTVKRHILTAVLGPNAQKKHRIHRDIMMDNISTQLHEFVKNNPEQE
8rp-t20VO0           DKTMVAMSDYDDYHKTVKRHILTAVLGPNAQKKHRIHRDIMMDNISTQLHEFVKNNPEQE
n22yhcB-t30VO1       DKTMVAMSDYDDYHKTVKRHILTAVLGPNAQKKHRIHRDIMMDNISTQLHEFVKNNPEQE
n22yhcB-t30VO2       DKQMVAMSDYDDYHKTVKRHILTAVLGPNAQKKHRIHRDIMMDNISTQLHEFVKNNPEQE
                     ** *********************************************************

8rp-t20SrKO          EVDLRKIFQSELFGLAMRQALGKDVESLYVEDLKITMNRDEIFQVLVVDPMMGAIDVDWR
8rp-t20VO0           EVDLRKIFQSELFGLAMRQALGKDVESLYVEDLKITMNRDEIFQVLVVDPMMGAIDVDWR
n22yhcB-t30VO1       EVDLRKIFQSELFGLAMRQALGKDVESLYVEDLKITMNRDEILQVLVVDPMMGAIDVDWR
n22yhcB-t30VO2       EVDLRKIFQSELFGLAMRQALGKDVESLYVEDLKITMNRDEILQVLVVDPMMGAIDVDWR
                     ******************************************:*****************

8rp-t20SrKO          DFFPYLKWVPNK   NTIQQMYIRREAVMKSLIKEHKKRIASGEKLNSYIDYLLSEAQTL
8rp-t20VO0           DFFPYLKWVPNKKFENTIQQMYIRREAVMKSLIKEHKKRIASGEKLNSYIDYLLSEAQTL
n22yhcB-t30VO1       DFFPYLKWVPNKKFENTIQQMYIRREAVMKSLIKEQKKRIASGEKLNSYIDYLLSEAQTL
n22yhcB-t30VO2       DFFPYLKWVPNKKFENTIQQMYIRREAVMKSLIKEQKKRIASGEKLNSYIDYLLSEAQTL
                     ***********************************:************************

8rp-t20SrKO          TDQQLLMSLWEPIIESSDTTMVTTEWAMYELAKNPKLQDRLYRDIKSVCGSEKITEEHLS
8rp-t20VO0           TDQQLLMSLWEPIIESSDTTMVTTEWAMYELAKNPKLQDRLYRDIKSVCGSEKITEEHLS
n22yhcB-t30VO1       TDQQLLMSLWEPIIESSDTTMVTTEWAMYELAKNPKLQDRLYRDIKSVCGSEKITEEHLS
n22yhcB-t30VO2       TDQQLLMSLWEPIIESSDTTMVTTEWAMYELAKNPKLQDRLYRDIKSVCGSEKITEEHLS
                     ************************************************************
```

FIG. 23A

```
8rp-t20SrKO          QLPYITAIFHETLRRHSPVPIIPLRHVHEDTVLGGYHVPAGTELAVNIYGCNMDKNVWEN
8rp-t20VO0           QLPYITAIFHETLRRHSPVPIIPLRHVHEDTVLGGYHVPAGTELAVNIYGCNMDKNVWEN
n22yhcB-t30VO1       QLPYITAIFHETLRKHSPVPIIPLRHVHEDTQLGGYHVPAGTELAVNIYGCNMDKNVWEN
n22yhcB-t30VO2       QLPYITAIFHETLRKHSPVPILPLRHVHEDTVLGGYHVPAGTELAVNIYGCNMDKNVWEN
                     **************:******:********* ****************************

8rp-t20SrKO          PEEWNPERFMKENETIDFQKTMAFGGGKRVCAGSLQALLTASIGIGRMVQEFEWKLKDMT
8rp-t20VO0           PEEWNPERFMKENETIDFQKTMAFGGGKRVCAGSLQALLTASIGIGRMVQEFEWKLKDMT
n22yhcB-t30VO1       PEEWNPERFMKENETADFQKTMAFGGGKRVCAGSLQALLTASIGIGRMVQEFEWKLKDMD
n22yhcB-t30VO2       PEEWNPERFMKENETIDFQKTMAFGGGKRVCAGSLQALLIASIGIGRMVQEFEWKLKDMT
                     *************** *********************** *******************

8rp-t20SrKO          QEEVNTIGLTTQMLRPLRAIIKPRI (SEQ ID NO: 106)
8rp-t20VO0           QEEVNTIGLTNQMLRPLRAIIKPRI (SEQ ID NO: 107)
n22yhcB-t30VO1       QEEVNTIGLTNQMLRPLRAIIKPRI (SEQ ID NO: 104)
n22yhcB-t30VO2       QEEVNTIGLTNQMLRPLRAIIKPRI (SEQ ID NO: 105)
                     ********** **************
```

FIG. 23A (Cont'd)

```
VO2     MDAVTGLLTVPATAITIGGTAVALAVALIFWYLKSYTSARRSQSNHLPRVPEVPGVPLLG
VO1     MDAVTGLLTVPATAITIGGTAVALAVALIFWYLKSYTSARRSQSNRLPRVPEVPGVPLLG
SrKO    MDAVTGLLTVPATAITIGGTAVALAVALIFWYLKSYTSARRSQSNHLPRVPEVPGVPLLG
VO0     MDAVTGLLTVPATAITIGGTAVALAVALIFWYLKSYTSARRSQSNHLPRVPEVPGVPLLG
        *********************************************:**************

VO2     NLLQLKEKKPYMTFTKWAATYGPIYSIKTGATSVVVVSSNEIAKEALVTRFQSISTRNLS
VO1     NLLQLKEKKPYMTFTRWAATYGPIYSIKTGATSMVVVSSNEIAKEALVTRFQSISTRNLS
SrKO    NLLQLKEKKPYMTFTRWAATYGPIYSIKTGATSMVVVSSNEIAKEALVTRFQSISTRNLS
VO0     NLLQLKEKKPYMTFTRWAATYGPIYSIKTGATSMVVVSSNEIAKEALVTRFQSISTRNLS
        ***************:*****************:**************************

VO2     KALKVLTADKQMVAMSDYDDYHKTVKRHILTAVLGPNAQKKHRIHRDIMMDNISTQLHEF
VO1     KALKVLTADKTMVAMSDYDDYHKTVKRHILTAVLGPNAQKKHRIHRDIMMDNISTQLHEF
SrKO    KALKVLTADKTMVAMSDYDDYHKTVKRHILTAVLGPNAQKKHRIHRDIMMDNISTQLHEF
VO0     KALKVLTADKTMVAMSDYDDYHKTVKRHILTAVLGPNAQKKHRIHRDIMMDNISTQLHEF
        ********** *************************************************

VO2     VKNNPEQEEVDLRKIFQSELFGLAMRQALGKDVESLYVEDLKITMNRDEILQVLVVDPMM
VO1     VKNNPEQEEVDLRKIFQSELFGLAMRQALGKDVESLYVEDLKITMNRDEILQVLVVDPMM
SrKO    VKNNPEQEEVDLRKIFQSELFGLAMRQALGKDVESLYVEDLKITMNRDEIFQVLVVDPMM
VO0     VKNNPEQEEVDLRKIFQSELFGLAMRQALGKDVESLYVEDLKITMNRDEIFQVLVVDPMM
        **************************************************:*********

VO2     GAIDVDWRDFFPYLKWVPNKKFENTIQQMYIRREAVMKSLIKEQKKRIASGEKLNSYIDY
VO1     GAIDVDWRDFFPYLKWVPNKKFENTIQQMYIRREAVMKSLIKEQKKRIASGEKLNSYIDY
SrKO    GAIDVDWRDFFPYLKWVPNKKFENTIQQMYIRREAVMKSLIKEHKKRIASGEKLNSYIDY
VO0     GAIDVDWRDFFPYLKWVPNKKFENTIQQMYIRREAVMKSLIKEHKKRIASGEKLNSYIDY
        *******************************************.****************
```

FIG. 23B

```
VO2     LLSEAQTLTDQQLLMSLWEPIIESSDTTMVTTEWAMYELAKNPKLQDRLYRDIKSVCGSE
VO1     LLSEAQTLTDQQLLMSLWEPIIESSDTTMVTTEWAMYELAKNPKLQDRLYRDIKSVCGSE
SrKO    LLSEAQTLTDQQLLMSLWEPIIESSDTTMVTTEWAMYELAKNPKLQDRLYRDIKSVCGSE
VO0     LLSEAQTLTDQQLLMSLWEPIIESSDTTMVTTEWAMYELAKNPKLQDRLYRDIKSVCGSE
        ************************************************************

VO2     KITEEHLSQLPYITAIFHETLRKHSPVPILPLRHVHEDTVLGGYHVPAGTELAVNIYGCN
VO1     KITEEHLSQLPYITAIFHETLRKHSPVPIIPLRHVHEDTQLGGYHVPAGTELAVNIYGCN
SrKO    KITEEHLSQLPYITAIFHETLRRHSPVPIIPLRHVHEDTVLGGYHVPAGTELAVNIYGCN
VO0     KITEEHLSQLPYITAIFHETLRRHSPVPIIPLRHVHEDTVLGGYHVPAGTELAVNIYGCN
        *********************:******:********* *********************

VO2     MDKNVWENPEEWNPERFMKENETIDFQKTMAFGGGKRVCAGSLQALLIASIGIGRMVQEF
VO1     MDKNVWENPEEWNPERFMKENETADFQKTMAFGGGKRVCAGSLQALLTASIGIGRMVQEF
SrKO    MDKNVWENPEEWNPERFMKENETIDFQKTMAFGGGKRVCAGSLQALLTASIGIGRMVQEF
VO0     MDKNVWENPEEWNPERFMKENETIDFQKTMAFGGGKRVCAGSLQALLTASIGIGRMVQEF
        *********************** *********************** ************

VO2     EWKLKDMTQEEVNTIGLTNQMLRPLRAIIKPRI (SEQ ID NO: 111)
VO1     EWKLKDMDQEEVNTIGLTNQMLRPLRAIIKPRI (SEQ ID NO: 110)
SrKO    EWKLKDMTQEEVNTIGLTTQMLRPLRAIIKPRI (SEQ ID NO: 108)
VO0     EWKLKDMTQEEVNTIGLTNQMLRPLRAIIKPRI (SEQ ID NO: 109)
        ******* **********.**************
```

FIG. 23B (Cont'd)

SEQUENCE LISTING

```
<160> NUMBER OF SEQ ID NOS: 132

<210> SEQ ID NO 1
<211> LENGTH: 556
<212> TYPE: PRT
<213> ORGANISM: Vitis vinifera

<400> SEQUENCE: 1

Met Ser Thr Gln Val Ser Ala Ser Ser Leu Ala Gln Ile Pro Gln Pro
1               5                   10                  15

Lys Asn Arg Pro Val Ala Asn Phe His Pro Asn Ile Trp Gly Asp Gln
            20                  25                  30

Phe Ile Thr Tyr Thr Pro Glu Asp Lys Val Thr Arg Ala Cys Lys Glu
        35                  40                  45

Glu Gln Ile Glu Asp Leu Lys Lys Glu Val Lys Arg Lys Leu Thr Ala
    50                  55                  60

Ala Ala Val Ala Asn Pro Ser Gln Leu Leu Asn Phe Ile Asp Ala Val
65                  70                  75                  80

Gln Arg Leu Gly Val Ala Tyr His Phe Glu Gln Glu Ile Glu Glu Ala
                85                  90                  95

Leu Gln His Ile Cys Asn Ser Phe His Asp Cys Asn Asp Met Asp Gly
            100                 105                 110

Asp Leu Tyr Asn Ile Ala Leu Gly Phe Arg Leu Leu Arg Gln Gln Gly
        115                 120                 125

Tyr Thr Ile Ser Cys Asp Ile Phe Asn Lys Phe Thr Asp Glu Arg Gly
    130                 135                 140

Arg Phe Lys Glu Ala Leu Ile Ser Asp Val Arg Gly Met Leu Gly Leu
145                 150                 155                 160

Tyr Glu Ala Ala His Leu Arg Val His Gly Glu Asp Ile Leu Ala Lys
                165                 170                 175

Ala Leu Ala Phe Thr Thr Thr His Leu Lys Ala Met Val Glu Ser Leu
            180                 185                 190

Gly Tyr His Leu Ala Glu Gln Val Ala His Ala Leu Asn Arg Pro Ile
        195                 200                 205
```

```
Arg Lys Gly Leu Glu Arg Leu Glu Ala Arg Trp Tyr Ile Ser Val Tyr
    210                 215                 220

Gln Asp Glu Ala Phe His Asp Lys Thr Leu Leu Glu Leu Ala Lys Leu
225                 230                 235                 240

Asp Phe Asn Leu Val Gln Ser Leu His Lys Glu Glu Leu Ser Asn Leu
                245                 250                 255

Ala Arg Trp Trp Lys Glu Leu Asp Phe Ala Thr Lys Leu Pro Phe Ala
            260                 265                 270

Arg Asp Arg Leu Val Glu Gly Tyr Phe Trp Met His Gly Val Tyr Phe
        275                 280                 285

Glu Pro Gln Tyr Leu Arg Gly Arg Arg Ile Leu Thr Lys Val Ile Ala
    290                 295                 300

Met Thr Ser Ile Leu Asp Asp Ile His Asp Ala Tyr Gly Thr Pro Glu
305                 310                 315                 320

Glu Leu Lys Leu Phe Ile Glu Ala Ile Glu Arg Trp Asp Ile Asn Ser
                325                 330                 335

Ile Asn Gln Leu Pro Glu Tyr Met Lys Leu Cys Tyr Val Ala Leu Leu
            340                 345                 350

Asp Val Tyr Lys Glu Ile Glu Glu Glu Met Glu Lys Glu Gly Asn Gln
        355                 360                 365

Tyr Arg Val His Tyr Ala Lys Glu Val Met Lys Asn Gln Val Arg Ala
    370                 375                 380

Tyr Phe Ala Glu Ala Lys Trp Leu His Glu Glu His Val Pro Ala Phe
385                 390                 395                 400

Glu Glu Tyr Met Arg Val Ala Leu Ala Ser Ser Gly Tyr Cys Leu Leu
                405                 410                 415

Ala Thr Thr Ser Phe Val Gly Met Gly Glu Ile Ala Thr Lys Glu Ala
            420                 425                 430

Phe Asp Trp Val Thr Ser Asp Pro Lys Ile Met Ser Ser Ser Asn Phe
        435                 440                 445

Ile Thr Arg Leu Met Asp Asp Ile Lys Ser His Lys Phe Glu Gln Lys
    450                 455                 460

Arg Gly His Val Thr Ser Ala Val Glu Cys Tyr Met Lys Gln Tyr Gly
465                 470                 475                 480

Val Ser Glu Glu Gln Val Tyr Ser Glu Phe Gln Lys Gln Ile Glu Asn
                485                 490                 495

Ala Trp Leu Asp Ile Asn Gln Glu Cys Leu Lys Pro Thr Ala Val Ser
            500                 505                 510

Met Pro Leu Leu Ala Arg Leu Leu Asn Phe Thr Arg Thr Met Asp Val
        515                 520                 525

Ile Tyr Lys Glu Gln Asp Ser Tyr Thr His Val Gly Lys Val Met Arg
    530                 535                 540

Asp Asn Ile Ala Ser Val Phe Ile Asn Ala Val Ile
545                 550                 555
```

<210> SEQ ID NO 2
<211> LENGTH: 1671
<212> TYPE: DNA
<213> ORGANISM: Vitis vinifera

<400> SEQUENCE: 2

```
atggctacgc aggtctcagc ctcgtcactg gcacaaatcc cgcagccgaa aaatcgtccg      60

gtggcgaact tccatccgaa tatctggggt gaccagttta tcacgtatac cccggaagat     120

aaagtgaccc gtgcgtgcaa ggaagaacaa attgaagacc tgaaaaagga agtcaaacgc     180
```

-continued

```
aagctgaccg cagcagcagt ggcaaacccg tctcagctgc tgaattttat cgatgcggtt    240
caacgtctgg gcgtcgccta tcatttcgaa caggaaattg aagaagcact gcaacatatc    300
tgcaacagct ttcacgattg taatgatatg gacggcgatc tgtataacat tgctctgggt    360
ttccgtctgc tgcgccagca aggctacacg atttcctgtg acatctttaa taaattcacc    420
gatgaacgtg gtcgctttaa ggaagcgctg atctcagacg ttcgtggcat gctgggtctg    480
tatgaagctg cgcatctgcg cgtccacggc gaagatattc tggccaaagc actggctttc    540
accacgaccc acctgaaggc gatggtcgaa tctctgggtt accatctggc agaacaggtg    600
gcacacgccc tgaaccgtcc gatccgcaaa ggcctggaac gtctggaagc gcgctggtat    660
attagtgtgt accaggacga agcatttcat gataaaaccc tgctggaact ggctaagctg    720
gatttcaacc tggttcaatc tctgcacaaa gaagaactga gtaatctggc ccgttggtgg    780
aaagaactgg actttgcgac caagctgccg ttcgcccgtg atcgcctggt tgaaggctat    840
ttttggatgc atggtgtcta tttcgaaccg cagtacctgc gcggtcgtcg cattctgacg    900
aaagtgatcg caatgacctc gattctggat gacatccacg acgcttacgg caccccggaa    960
gaactgaaac tgtttattga agcgatcgaa cgttgggata ttaacagcat caatcagctg   1020
ccggaatata tgaaactgtg ctacgtggcc ctgctggatg tttacaagga aatcgaagaa   1080
gaaatggaaa aggaaggtaa ccagtatcgt gttcattacg cgaaagaagt catgaagaat   1140
caagtgcgcg cctactttgc agaagctaaa tggctgcatg aagaacacgt gccggcgttc   1200
gaagaatata tgcgcgttgc gctggccagc tctggctact gtctgctggc cacgacctct   1260
tttgtgggca tgggtgaaat tgcaacgaaa gaagcgtttg actgggttac cagtgatccg   1320
aagattatga gttcctcaaa ctttatcacc cgtctgatgg atgacattaa atcccataag   1380
ttcgaacaga aacgcggtca cgtcacctca gccgtggaat gctatatgaa acagtacggc   1440
gtttcggaag aacaagtcta tagcgaattt cagaaacaaa tcgaaaacgc atggctggat   1500
attaatcagg aatgtctgaa accgacggca gtctccatgc cgctgctggc tcgtctgctg   1560
aattttacgc gcacgatgga tgtgatctat aaagaacagg attcgtacac ccatgtgggc   1620
aaggttatgc gcgataacat tgcaagcgtg ttcattaatg ctgttatcta a             1671
```

<210> SEQ ID NO 3
<211> LENGTH: 556
<212> TYPE: PRT
<213> ORGANISM: Artificial Sequence
<220> FEATURE:
<223> OTHER INFORMATION: Synthetic - Engineered valencene synthase

<400> SEQUENCE: 3

```
Met Ala Thr Gln Val Ser Ala Ser Ser Leu Ala Gln Ile Pro Gln Pro
1               5                   10                  15

Lys Asn Arg Pro Val Ala Asn Phe His Pro Asn Ile Trp Gly Asp Gln
            20                  25                  30

Phe Ile Thr Tyr Thr Pro Glu Asp Lys Val Thr Arg Ala Cys Lys Glu
        35                  40                  45

Glu Gln Ile Glu Asp Leu Lys Lys Glu Val Lys Arg Lys Leu Thr Ala
    50                  55                  60

Ala Ala Val Ala Asn Pro Ser Gln Leu Leu Asn Phe Ile Asp Ala Val
65                  70                  75                  80

Gln Arg Leu Gly Val Ala Tyr His Phe Glu Gln Glu Ile Glu Glu Ala
                85                  90                  95
```

```
Leu Gln His Ile Cys Asn Ser Phe His Asp Cys Asn Asp Met Asp Gly
            100                 105                 110

Asp Leu Tyr Asn Ile Ala Leu Gly Phe Arg Leu Leu Arg Gln Gln Gly
        115                 120                 125

Tyr Thr Ile Ser Cys Asp Ile Phe Asn Lys Phe Thr Asp Glu Arg Gly
    130                 135                 140

Arg Phe Lys Glu Ala Leu Ile Ser Asp Val Arg Gly Met Leu Gly Leu
145                 150                 155                 160

Tyr Glu Ala Ala His Leu Arg Val His Gly Glu Asp Ile Leu Ala Lys
                165                 170                 175

Ala Leu Ala Phe Thr Thr Thr His Leu Lys Ala Met Val Glu Ser Leu
            180                 185                 190

Gly Tyr His Leu Ala Glu Gln Val Ala His Ala Leu Asn Arg Pro Ile
        195                 200                 205

Arg Lys Gly Leu Glu Arg Leu Glu Ala Arg Trp Tyr Ile Ser Val Tyr
    210                 215                 220

Gln Asp Glu Ala Phe His Asp Lys Thr Leu Leu Glu Leu Ala Lys Leu
225                 230                 235                 240

Asp Phe Asn Leu Val Gln Ser Leu His Lys Glu Glu Leu Ser Asn Leu
                245                 250                 255

Ala Arg Trp Trp Lys Glu Leu Asp Phe Ala Thr Lys Leu Pro Phe Ala
            260                 265                 270

Arg Asp Arg Leu Val Glu Gly Tyr Phe Trp Met His Gly Val Tyr Phe
        275                 280                 285

Glu Pro Gln Tyr Leu Arg Gly Arg Arg Ile Leu Thr Lys Val Ile Ala
    290                 295                 300

Met Thr Ser Ile Leu Asp Asp Ile His Asp Ala Tyr Gly Ser Pro Glu
305                 310                 315                 320

Glu Leu Lys Leu Phe Ile Glu Ala Ile Glu Lys Trp Asp Glu Ser Ser
                325                 330                 335

Ile Asn Gln Leu Pro Glu Tyr Met Lys Leu Cys Phe Val Ala Leu Ile
            340                 345                 350

Asp Val Tyr Asn Glu Ile Glu Glu Glu Met Glu Lys Glu Gly Asn Gln
        355                 360                 365

Tyr Arg Ile His Tyr Leu Lys Glu Val Met Lys Asn Gln Val Arg Ala
    370                 375                 380

Tyr Phe Ala Glu Ala Lys Trp Leu His Asp Glu His Val Pro Ala Phe
385                 390                 395                 400

Glu Glu Tyr Met Arg Val Ala Leu Ala Ser Ser Gly Tyr Cys Leu Leu
                405                 410                 415

Ala Val Thr Ser Phe Val Gly Met Gly Glu Ile Val Thr Lys Glu Ala
            420                 425                 430

Phe Asp Trp Val Thr Ser Asp Pro Lys Leu Met Ser Ser Ser Asn Phe
        435                 440                 445

Ile Thr Arg Leu Met Asp Asp Ile Lys Ser His Lys Phe Glu Gln Lys
    450                 455                 460

Arg Gly His Val Thr Ser Ala Val Glu Cys Tyr Met Lys Gln Tyr Gly
465                 470                 475                 480

Val Thr Glu Glu Gln Val Tyr Ser Glu Phe Lys Lys Gln Ile Glu Asn
                485                 490                 495

Ala Trp Leu Asp Ile Asn Gln Glu Cys Leu Lys Pro Thr Ala Val Pro
            500                 505                 510

Met Pro Leu Leu Ala Arg Leu Leu Asn Phe Thr Arg Thr Met Asp Val
```

-continued 515 520 525

Ile Tyr Lys Glu Gln Asp Ser Tyr Thr His Val Gly Lys Val Met Arg
530 535 540

Asp Asn Ile Ala Ser Val Phe Ile Asn Pro Val Ile
545 550 555

<210> SEQ ID NO 4
<211> LENGTH: 1671
<212> TYPE: DNA
<213> ORGANISM: Artificial Sequence
<220> FEATURE:
<223> OTHER INFORMATION: Synthetic - Engineered valencene synthase

<400> SEQUENCE: 4
atggcaaccc aggtgagtgc aagcagcctg gcccaaatcc ctcagccgaa aaaccgcccg 60
gttgcaaact tccaccctaa tatctggggc gatcagttca tcacctatac cccggaagat 120
aaagtgacaa gggcctgcaa agaggagcag atcgaggacc tgaaaaaaga ggtgaagcgc 180
aagctgaccg cagccgcagt ggcaaacccg agccaactgt taaacttcat cgatgccgtg 240
cagcgcctgg gcgttgccta tcacttcgag caggaaatcg aagaagccct acagcacatc 300
tgtaacagct tccacgattg taacgacatg gatggcgact tatacaacat agcattaggt 360
ttccgcttac tgcgtcagca gggctacacc ataagctgcg acatctttaa caagtttacc 420
gacgagcgcg gtcgttttaa agaggcgctg attagcgacg ttcgcggcat gttaggtctg 480
tacgaagccg cacatctgcg cgtgcacggc gaagacattc tggcgaaggc gctggcattc 540
acaaccacac acctgaaggc aatggtggaa agtctgggct accacttagc cgagcaggtt 600
gcccatgcac tgaatcgccc gattcgtaag ggcctggaac gcctggaagc ccgctggtac 660
atcagtgttt atcaggatga agcctttcat gataagaccc tgctggagct ggcaaagctg 720
gatttcaacc tggttcagag cctgcataag gaagagctga gcaacctggc ccgttggtgg 780
aaggagctgg atttcgcaac caagctgccg ttcgccaggg acaggttagt tgaaggctac 840
ttctggatgc acggcgttta cttcgagccg caatacctgc gtggccgccg catcctgacg 900
aaggtgatcg ccatgaccag cattctggac gacatccacg atgcgtacgg gagccctgag 960
gagttaaagc tgttcatcga ggcaatcgag aagtgggatg agagtagcat caaccaactg 1020
ccggagtata tgaaactgtg cttcgtggcc ctgattgatg tttacaatga gattgaagag 1080
gagatggaga aagaggggaa ccagtaccgc atccactacc tgaaagaggt gatgaagaat 1140
caggtgcgcg catacttcgc agaggccaaa tggctgcatg atgagcatgt tcctgccttc 1200
gaggagtaca tgcgcgtggc attagccagc agtggttact gtctgttagc cgttacgagc 1260
ttcgtgggta tgggcgagat cgtgaccaaa gaggcattcg actgggtgac gagcgacccg 1320
aagctgatga gcagcagcaa cttcatcacc cgtctgatgg acgacatcaa gagccacaag 1380
ttcgagcaga aacgcggtca cgttaccagc gccgtggagt gctacatgaa gcagtacggc 1440
gtgacagagg agcaagtgta cagcgagttc aagaaacaaa tcgagaacgc ctggctggac 1500
atcaaccaag agtgcctgaa accgaccgca gtgccgatgc ctctgttagc ccgtctgctg 1560
aatttcacac gcacgatgga cgttatctac aaggagcagg atagctacac ccacgttggt 1620
aaggtgatgc gcgacaacat cgccagtgtg ttcatcaacc cggtgatcta a 1671

<210> SEQ ID NO 5
<211> LENGTH: 556
<212> TYPE: PRT
<213> ORGANISM: Artificial Sequence -continued
<220> FEATURE:
<223> OTHER INFORMATION: Synthetic - Engineered valencene synthase

<400> SEQUENCE: 5

Met Ala Thr Gln Val Ser Ala Ser Ser Leu Ala Gln Ile Pro Gln Pro
1 5 10 15

Lys Asn Arg Pro Val Ala Asn Phe His Pro Asn Ile Trp Gly Asp Gln
20 25 30

Phe Ile Thr Tyr Thr Pro Glu Asp Lys Val Thr Arg Ala Cys Lys Glu
35 40 45

Glu Gln Ile Glu Asp Leu Lys Lys Glu Val Lys Arg Lys Leu Thr Ala
50 55 60

Ala Ala Val Ala Asn Pro Ser Gln Leu Leu Asn Phe Ile Asp Ala Val
65 70 75 80

Gln Arg Leu Gly Val Ala Tyr His Phe Glu Gln Glu Ile Glu Glu Ala
85 90 95

Leu Gln His Ile Cys Asn Ser Phe His Asp Cys Asn Asp Met Asp Gly
100 105 110

Asp Leu Tyr Asn Ile Ala Leu Gly Phe Arg Leu Leu Arg Gln Gln Gly
115 120 125

Tyr Thr Ile Ser Cys Asp Ile Phe Asn Lys Phe Thr Asp Glu Arg Gly
130 135 140

Arg Phe Lys Glu Ala Leu Ile Ser Asp Val Arg Gly Met Leu Gly Leu
145 150 155 160

Tyr Glu Ala Ala His Leu Arg Val His Gly Glu Asp Ile Leu Ala Lys
165 170 175

Ala Leu Ala Phe Thr Thr Thr His Leu Lys Ala Met Val Glu Ser Leu
180 185 190

Gly Tyr His Leu Ala Glu Gln Val Ala His Ala Leu Asn Arg Pro Ile
195 200 205

Arg Lys Gly Leu Glu Arg Leu Glu Ala Arg Trp Tyr Ile Ser Val Tyr
210 215 220

Gln Asp Glu Ala Phe His Asp Lys Thr Leu Leu Glu Leu Ala Lys Leu
225 230 235 240

Asp Phe Asn Leu Val Gln Ser Leu His Lys Glu Glu Leu Ser Asn Leu
245 250 255

Ala Arg Trp Trp Lys Glu Leu Asp Phe Ala Thr Lys Leu Pro Phe Ala
260 265 270

Arg Asp Arg Leu Val Glu Gly Tyr Phe Trp Met His Gly Val Tyr Phe
275 280 285

Glu Pro Gln Tyr Leu Arg Gly Arg Arg Ile Leu Thr Lys Val Ile Ala
290 295 300

Leu Thr Ser Ile Leu Asp Asp Ile His Asp Ala Tyr Gly Thr Pro Glu
305 310 315 320

Glu Leu Lys Leu Phe Ile Glu Ala Ile Glu Lys Trp Asp Glu Ser Ser
325 330 335

Ile Asn Gln Leu Pro Glu Tyr Met Lys Leu Cys Tyr Val Ala Leu Leu
340 345 350

Asp Val Tyr Asn Glu Ile Glu Glu Glu Met Glu Lys Glu Gly Asn Gln
355 360 365

Tyr Arg Ile His Tyr Leu Lys Glu Val Met Lys Asn Gln Val Arg Ala
370 375 380

Tyr Phe Ala Glu Ala Lys Trp Leu His Asp Glu His Val Pro Ala Phe
385 390 395 400

```
Glu Glu Tyr Met Arg Val Ala Leu Ala Ser Ser Gly Tyr Cys Leu Leu
                405                 410                 415

Ala Val Thr Ser Phe Val Gly Met Gly Glu Ile Val Thr Lys Glu Ala
            420                 425                 430

Phe Asp Trp Val Thr Ser Asp Pro Arg Ile Met Ser Ser Ser Asn Phe
        435                 440                 445

Ile Thr Arg Leu Met Asp Asp Ile Lys Ser His Lys Phe Glu Gln Lys
    450                 455                 460

Arg Gly His Val Thr Ser Ala Val Glu Cys Tyr Met Lys Gln Tyr Ala
465                 470                 475                 480

Val Thr Glu Glu Gln Val Tyr Ser Glu Phe Lys Lys Gln Ile Glu Asn
                485                 490                 495

Ala Trp Leu Asp Ile Asn Gln Glu Cys Leu Lys Pro Thr Ala Val Pro
            500                 505                 510

Met Pro Leu Leu Ala Arg Leu Leu Asn Phe Thr Arg Thr Met Asp Val
        515                 520                 525

Ile Tyr Lys Glu Gln Asp Ser Tyr Thr His Val Gly Lys Thr Met Arg
    530                 535                 540

Asp Asn Ile Ala Ser Val Phe Ile Asn Pro Val Ile
545                 550                 555
```

<210> SEQ ID NO 6
<211> LENGTH: 1671
<212> TYPE: DNA
<213> ORGANISM: Artificial Sequence
<220> FEATURE:
<223> OTHER INFORMATION: Synthetic - Engineered valencene synthase

<400> SEQUENCE: 6

```
atggcaaccc aggtgagtgc aagcagcctg gcccaaatcc ctcagccgaa aaaccgcccg      60

gttgcaaact tccaccctaa tatctggggc gatcagttca tcacctatac cccggaagat     120

aaagtgacaa gggcctgcaa agaggagcag atcgaggacc tgaaaaaaga ggtgaagcgc     180

aagctgaccg cagccgcagt ggcaaacccg agccaactgt taaacttcat cgatgccgtg     240

cagcgcctgg gcgttgccta tcacttcgag caggaaatcg aagaagccct acagcacatc     300

tgtaacagct tccacgattg taacgacatg gatggcgact tatacaacat agcattaggt     360

ttccgcttac tgcgtcagca gggctacacc ataagctgcg acatctttaa caagtttacc     420

gacgagcgcg gtcgttttaa agaggcgctg attagcgacg ttcgcggcat gttaggtctg     480

tacgaagccg cacatctgcg cgtgcacggc gaagacattc tggcgaaggc gctggcattc     540

acaaccacac acctgaaggc aatggtggaa agtctgggct accacttagc cgagcaggtt     600

gcccatgcac tgaatcgccc gattcgtaag ggcctggaac gcctggaagc ccgctggtac     660

atcagtgttt atcaggatga agcctttcat gataagaccc tgctggagct ggcaaagctg     720

gatttcaacc tggttcagag cctgcataag gaagagctga gcaacctggc ccgttggtgg     780

aaggagctgg atttcgcaac caagctgccg ttcgccaggg acaggttagt tgaaggctac     840

ttctggatgc acggcgttta cttcgagccg caatacctgc gtggccgccg catcctgacg     900

aaggtgatcg ccctgaccag cattctggac gacatccacg atgcgtacgg gacccctgag     960

gagttaaagc tgttcatcga ggcaatcgag aagtgggatg agagtagcat caaccaactg    1020

ccggagtata tgaaactgtg ctatgtggcc ctgctggatg tttacaatga gattgaagag    1080

gagatggaga aagaggggaa ccagtaccgc atccactacc tgaaagaggt gatgaagaat    1140
```

```
caggtgcgcg catacttcgc agaggccaaa tggctgcatg atgagcatgt tcctgccttc   1200

gaggagtaca tgcgcgtggc attagccagc agtggttact gtctgttagc cgttacgagc   1260

ttcgtgggta tgggcgagat cgtgaccaaa gaggcattcg actgggtgac gagcgacccg   1320

cgtattatga gcagcagcaa cttcatcacc cgtctgatgg acgacatcaa gagccacaag   1380

ttcgagcaga aacgcggtca cgttaccagc gccgtggagt gctacatgaa gcagtacgca   1440

gtgacagagg agcaagtgta cagcgagttc aagaaacaaa tcgagaacgc ctggctggac   1500

atcaaccaag agtgcctgaa accgaccgca gtgccgatgc ctctgttagc ccgtctgctg   1560

aatttcacac gcacgatgga cgttatctac aaggagcagg atagctacac ccacgttggt   1620

aagaccatgc gcgacaacat cgccagtgtg ttcatcaacc cggtgatcta a            1671


<210> SEQ ID NO 7
<211> LENGTH: 556
<212> TYPE: PRT
<213> ORGANISM: Artificial Sequence
<220> FEATURE:
<223> OTHER INFORMATION: Synthetic - Engineered valencene synthase

<400> SEQUENCE: 7

Met Ala Thr Gln Val Ser Ala Ser Ser Leu Ala Gln Ile Pro Gln Pro
1               5                   10                  15

Lys Asn Arg Pro Val Ala Asn Phe His Pro Asn Ile Trp Gly Asp Gln
            20                  25                  30

Phe Ile Thr Tyr Thr Pro Glu Asp Lys Val Thr Arg Ala Lys Lys Glu
        35                  40                  45

Glu Gln Ile Glu Asp Leu Lys Lys Glu Val Lys Arg Lys Leu Thr Ala
    50                  55                  60

Ala Ala Val Ala Asn Pro Ser Gln Leu Leu Asn Phe Ile Asp Ala Val
65                  70                  75                  80

Gln Arg Leu Gly Val Ala Tyr His Phe Glu Gln Glu Ile Glu Glu Ala
                85                  90                  95

Leu Gln His Ile Cys Asn Ser Phe His Asp Cys Asn Asp Met Asp Gly
            100                 105                 110

Asp Leu Tyr Asn Ile Ala Leu Gly Phe Arg Leu Leu Arg Gln Gln Gly
        115                 120                 125

Tyr Thr Ile Ser Cys Asp Ile Phe Asn Lys Phe Thr Asp Glu Arg Gly
    130                 135                 140

Arg Phe Lys Glu Ala Leu Ile Ser Asp Val Arg Gly Met Leu Gly Leu
145                 150                 155                 160

Tyr Glu Ala Ala His Leu Arg Val His Gly Glu Asp Ile Leu Ala Lys
                165                 170                 175

Ala Leu Ala Phe Thr Thr Thr His Leu Lys Ala Met Val Glu Ser Leu
            180                 185                 190

Gly Tyr His Leu Ala Glu Gln Val Ala His Ala Leu Asn Arg Pro Ile
        195                 200                 205

Arg Lys Gly Leu Glu Arg Leu Glu Ala Arg Trp Tyr Ile Ser Val Tyr
    210                 215                 220

Gln Asp Glu Ala Phe His Asp Lys Thr Leu Leu Glu Leu Ala Lys Leu
225                 230                 235                 240

Asp Phe Asn Leu Val Gln Ser Leu His Lys Glu Glu Leu Ser Asn Leu
                245                 250                 255

Ala Arg Trp Trp Lys Glu Leu Asp Phe Ala Thr Lys Leu Pro Phe Ala
            260                 265                 270
```

-continued

```
Arg Asp Arg Leu Val Glu Gly Tyr Phe Trp Met Met Gly Val Tyr Phe
        275                 280                 285

Glu Pro Gln Tyr Leu Arg Gly Arg Arg Ile Leu Thr Lys Val Ile Ala
    290                 295                 300

Met Thr Ser Ile Leu Asp Asp Ile His Asp Ala Tyr Gly Ser Pro Glu
305                 310                 315                 320

Glu Leu Lys Leu Phe Ile Glu Ala Ile Glu Lys Trp Asp Glu Ser Ser
                325                 330                 335

Ile Asn Gln Leu Pro Glu Tyr Met Lys Leu Cys Phe Val Ala Leu Ile
            340                 345                 350

Asp Val Tyr Asn Glu Ile Glu Glu Glu Met Glu Lys Glu Gly Asn Gln
        355                 360                 365

Tyr Arg Ile His Tyr Leu Lys Glu Val Met Lys Asn Gln Val Arg Ala
    370                 375                 380

Tyr Phe Ala Glu Ala Lys Trp Leu His Asp Glu His Val Pro Ala Phe
385                 390                 395                 400

Glu Glu Tyr Met Arg Val Ala Leu Ala Ser Ser Gly Tyr Cys Leu Leu
                405                 410                 415

Ala Val Thr Ser Phe Val Gly Met Gly Glu Ile Val Thr Lys Glu Ala
            420                 425                 430

Phe Asp Trp Val Thr Ser Asp Pro Lys Leu Met Ser Ser Ser Asn Thr
        435                 440                 445

Ile Thr Arg Leu Met Asp Asp Ile Lys Ser His Lys Phe Glu Gln Lys
    450                 455                 460

Arg Gly His Val Thr Ser Ala Val Glu Cys Tyr Met Lys Gln Tyr Gly
465                 470                 475                 480

Val Thr Glu Glu Gln Val Tyr Ser Glu Phe Lys Lys Gln Ile Glu Asn
                485                 490                 495

Ala Trp Leu Asp Ile Asn Gln Glu Cys Leu Lys Pro Thr Ala Val Pro
            500                 505                 510

Met Pro Leu Leu Ala Arg Leu Leu Asn Phe Thr Arg Thr Met Asp Val
        515                 520                 525

Ile Tyr Lys Glu Glu Asp Ser Tyr Thr His Val Gly Lys Val Met Arg
    530                 535                 540

Asp Asn Ile Ala Ser Val Phe Ile Asn Pro Val Ile
545                 550                 555
```

<210> SEQ ID NO 8
<211> LENGTH: 1671
<212> TYPE: DNA
<213> ORGANISM: Artificial Sequence
<220> FEATURE:
<223> OTHER INFORMATION: Synthetic - Engineered valencene synthase

<400> SEQUENCE: 8

```
atggcaaccc aggtgagtgc aagcagcctg gcccaaatcc ctcagccgaa aaaccgcccg      60

gttgcaaact tccaccctaa tatctggggc gatcagttca tcacctatac cccggaagat     120

aaagtgacaa gggccaaaaa agaggagcag atcgaggacc tgaaaaaaga ggtgaagcgc     180

aagctgaccg cagccgcagt ggcaaacccg agccaactgt taaacttcat cgatgccgtg     240

cagcgcctgg gcgttgccta tcacttcgag caggaaatcg aagaagccct acagcacatc     300

tgtaacagct tccacgattg taacgacatg gatggcgact tatacaacat agcattaggt     360

ttccgcttac tgcgtcagca gggctacacc ataagctgcg acatctttaa caagtttacc     420

gacgagcgcg gtcgttttaa agaggcgctg attagcgacg ttcgcggcat gttaggtctg     480
```

```
tacgaagccg cacatctgcg cgtgcacggc gaagacattc tggcgaaggc gctggcattc    540

acaaccacac acctgaaggc aatggtggaa agtctgggct accacttagc cgagcaggtt    600

gcccatgcac tgaatcgccc gattcgtaag ggcctggaac gcctggaagc ccgctggtac    660

atcagtgttt atcaggatga agcctttcat gataagaccc tgctggagct ggcaaagctg    720

gatttcaacc tggttcagag cctgcataag gaagagctga gcaacctggc ccgttggtgg    780

aaggagctgg atttcgcaac caagctgccg ttcgccaggg acaggttagt tgaaggctac    840

ttctggatga tgggcgttta cttcgagccg caatacctgc gtggccgccg catcctgacg    900

aaggtgatcg ccatgaccag cattctggac gacatccacg atgcgtacgg gagccctgag    960

gagttaaagc tgttcatcga ggcaatcgag aagtgggatg agagtagcat caaccaactg   1020

ccggagtata tgaaactgtg cttcgtggcc ctgattgatg tttacaatga gattgaagag   1080

gagatggaga aagaggggaa ccagtaccgc atccactacc tgaaagaggt gatgaagaat   1140

caggtgcgcg catacttcgc agaggccaaa tggctgcatg atgagcatgt tcctgccttc   1200

gaggagtaca tgcgcgtggc attagccagc agtggttact gtctgttagc cgttacgagc   1260

ttcgtgggta tgggcgagat cgtgaccaaa gaggcattcg actgggtgac gagcgacccg   1320

aagctgatga gcagcagcaa caccatcacc cgtctgatgg acgacatcaa gagccacaag   1380

ttcgagcaga aacgcggtca cgttaccagc gccgtggagt gctacatgaa gcagtacggc   1440

gtgacagagg agcaagtgta cagcgagttc aagaaacaaa tcgagaacgc ctggctggac   1500

atcaaccaag agtgcctgaa accgaccgca gtgccgatgc ctctgttagc ccgtctgctg   1560

aatttcacac gcacgatgga cgttatctac aaggaggaag atagctacac ccacgttggt   1620

aaggtgatgc gcgacaacat cgccagtgtg ttcatcaacc cggtgatcta a            1671
```

<210> SEQ ID NO 9
<211> LENGTH: 556
<212> TYPE: PRT
<213> ORGANISM: Artificial Sequence
<220> FEATURE:
<223> OTHER INFORMATION: Synthetic - Engineered valencene synthase

<400> SEQUENCE: 9

```
Met Ala Thr Gln Val Ser Ala Ser Ser Leu Ala Gln Ile Pro Gln Pro
1               5                   10                  15

Lys Asn Arg Pro Val Ala Asn Phe His Pro Asn Ile Trp Gly Asp Gln
            20                  25                  30

Phe Ile Thr Tyr Thr Pro Glu Asp Lys Val Thr Arg Ala Lys Lys Glu
        35                  40                  45

Glu Gln Ile Glu Asp Leu Lys Lys Glu Val Lys Arg Lys Leu Thr Ala
    50                  55                  60

Ala Ala Val Ala Asn Pro Ser Gln Leu Leu Asn Phe Ile Asp Ala Val
65                  70                  75                  80

Gln Arg Leu Gly Val Ala Tyr His Phe Glu Gln Glu Ile Glu Glu Ala
                85                  90                  95

Leu Gln His Ile Cys Asn Ser Phe His Asp Cys Asn Asp Met Asp Gly
            100                 105                 110

Asp Leu Tyr Asn Ile Ala Leu Gly Phe Arg Leu Leu Arg Gln Gln Gly
        115                 120                 125

Tyr Thr Ile Ser Cys Asp Ile Phe Asn Lys Phe Thr Asp Glu Arg Gly
    130                 135                 140

Arg Phe Lys Glu Ala Leu Ile Ser Asp Val Arg Gly Met Leu Gly Leu
```

-continued

```
145                 150                 155                 160

Tyr Glu Ala Ala His Leu Arg Val His Gly Glu Asp Ile Leu Ala Lys
                165                 170                 175

Ala Leu Ala Phe Thr Thr Thr His Leu Lys Ala Met Val Glu Ser Leu
            180                 185                 190

Gly Tyr His Leu Ala Glu Gln Val Ala His Ala Leu Asn Arg Pro Ile
        195                 200                 205

Arg Lys Gly Leu Glu Arg Leu Glu Ala Arg Trp Tyr Ile Ser Val Tyr
    210                 215                 220

Gln Asp Glu Ala Phe His Asp Lys Thr Leu Leu Glu Leu Ala Lys Leu
225                 230                 235                 240

Asp Phe Asn Leu Val Gln Ser Leu His Lys Glu Glu Leu Ser Asn Leu
                245                 250                 255

Ala Arg Trp Trp Lys Glu Leu Asp Phe Ala Thr Lys Leu Pro Phe Ala
            260                 265                 270

Arg Asp Arg Leu Val Glu Gly Tyr Phe Trp Met Met Gly Val Tyr Phe
        275                 280                 285

Glu Pro Gln Tyr Leu Arg Gly Arg Arg Ile Leu Thr Lys Val Ile Ala
    290                 295                 300

Leu Thr Ser Ile Leu Asp Asp Ile His Asp Ala Tyr Gly Thr Pro Glu
305                 310                 315                 320

Glu Leu Lys Leu Phe Ile Glu Ala Ile Glu Lys Trp Asp Glu Ser Ser
                325                 330                 335

Ile Asn Gln Leu Pro Glu Tyr Met Lys Leu Cys Tyr Val Ala Leu Leu
            340                 345                 350

Asp Val Tyr Asn Glu Ile Glu Glu Glu Met Glu Lys Glu Gly Asn Gln
        355                 360                 365

Tyr Arg Ile His Tyr Leu Lys Glu Val Met Lys Asn Gln Val Arg Ala
    370                 375                 380

Tyr Phe Ala Glu Ala Lys Trp Leu His Asp Glu His Val Pro Ala Phe
385                 390                 395                 400

Glu Glu Tyr Met Arg Val Ala Leu Ala Ser Ser Gly Tyr Cys Leu Leu
                405                 410                 415

Ala Val Thr Ser Phe Val Gly Met Gly Glu Ile Val Thr Lys Glu Ala
            420                 425                 430

Phe Asp Trp Val Thr Ser Asp Pro Arg Ile Met Ser Ser Ser Asn Thr
        435                 440                 445

Ile Thr Arg Leu Met Asp Asp Ile Lys Ser His Lys Phe Glu Gln Lys
    450                 455                 460

Arg Gly His Val Thr Ser Ala Val Glu Cys Tyr Met Lys Gln Tyr Ala
465                 470                 475                 480

Val Thr Glu Glu Gln Val Tyr Ser Glu Phe Lys Lys Gln Ile Glu Asn
                485                 490                 495

Ala Trp Leu Asp Ile Asn Gln Glu Cys Leu Lys Pro Thr Ala Val Pro
            500                 505                 510

Met Pro Leu Leu Ala Arg Leu Leu Asn Phe Thr Arg Thr Met Asp Val
        515                 520                 525

Ile Tyr Lys Glu Glu Asp Ser Tyr Thr His Val Gly Lys Thr Met Arg
    530                 535                 540

Asp Asn Ile Ala Ser Val Phe Ile Asn Pro Val Ile
545                 550                 555
```

<210> SEQ ID NO 10

-continued

<211> LENGTH: 1671
<212> TYPE: DNA
<213> ORGANISM: Artificial Sequence
<220> FEATURE:
<223> OTHER INFORMATION: Synthetic - Engineered valencene synthase

<400> SEQUENCE: 10

```
atggcaaccc aggtgagtgc aagcagcctg gcccaaatcc ctcagccgaa aaaccgcccg     60

gttgcaaact tccaccctaa tatctggggc gatcagttca tcacctatac cccggaagat    120

aaagtgacaa gggccaaaaa agaggagcag atcgaggacc tgaaaaaaga ggtgaagcgc    180

aagctgaccg cagccgcagt ggcaaacccg agccaactgt taaacttcat cgatgccgtg    240

cagcgcctgg gcgttgccta tcacttcgag caggaaatcg aagaagccct acagcacatc    300

tgtaacagct tccacgattg taacgacatg gatggcgact tatacaacat agcattaggt    360

ttccgcttac tgcgtcagca gggctacacc ataagctgcg acatctttaa caagtttacc    420

gacgagcgcg gtcgttttaa agaggcgctg attagcgacg ttcgcggcat gttaggtctg    480

tacgaagccg cacatctgcg cgtgcacggc gaagacattc tggcgaaggc gctggcattc    540

acaaccacac acctgaaggc aatggtggaa agtctgggct accacttagc cgagcaggtt    600

gcccatgcac tgaatcgccc gattcgtaag ggcctggaac gcctggaagc ccgctggtac    660

atcagtgttt atcaggatga agcctttcat gataagaccc tgctggagct ggcaaagctg    720

gatttcaacc tggttcagag cctgcataag gaagagctga gcaacctggc ccgttggtgg    780

aaggagctgg atttcgcaac caagctgccg ttcgccaggg acaggttagt tgaaggctac    840

ttctggatga tgggcgttta cttcgagccg caatacctgc gtggccgccg catcctgacg    900

aaggtgatcg ccctgaccag cattctggac gacatccacg atgcgtacgg gacccctgag    960

gagttaaagc tgttcatcga ggcaatcgag aagtgggatg agagtagcat caaccaactg   1020

ccggagtata tgaaactgtg ctatgtggcc ctgctggatg tttacaatga gattgaagag   1080

gagatggaga aagaggggaa ccagtaccgc atccactacc tgaaagaggt gatgaagaat   1140

caggtgcgcg catacttcgc agaggccaaa tggctgcatg atgagcatgt tcctgccttc   1200

gaggagtaca tgcgcgtggc attagccagc agtggttact gtctgttagc cgttacgagc   1260

ttcgtgggta tgggcgagat cgtgaccaaa gaggcattcg actgggtgac gagcgacccg   1320

cgtattatga gcagcagcaa caccatcacc cgtctgatgg acgacatcaa gagccacaag   1380

ttcgagcaga aacgcggtca cgttaccagc gccgtggagt gctacatgaa gcagtacgca   1440

gtgacagagg agcaagtgta cagcgagttc aagaaacaaa tcgagaacgc ctggctggac   1500

atcaaccaag agtgcctgaa accgaccgca gtgccgatgc ctctgttagc ccgtctgctg   1560

aatttcacac gcacgatgga cgttatctac aaggaggaag atagctacac ccacgttggt   1620

aagaccatgc gcgacaacat cgccagtgtg ttcatcaacc cggtgatcta a            1671
```

<210> SEQ ID NO 11
<211> LENGTH: 556
<212> TYPE: PRT
<213> ORGANISM: Artificial Sequence
<220> FEATURE:
<223> OTHER INFORMATION: Synthetic - Engineered valencene synthase

<400> SEQUENCE: 11

```
Met Ala Thr Gln Val Ser Ala Ser Ser Leu Ala Gln Ile Pro Gln Pro
1               5                   10                  15

Lys Asn Arg Pro Val Ala Asn Phe His Pro Asn Ile Trp Gly Asp Gln
            20                  25                  30
```

```
Phe Ile Thr Tyr Thr Pro Glu Asp Lys Val Thr Arg Ala Lys Lys Glu
        35                  40                  45

Glu Gln Ile Glu Asp Leu Lys Lys Glu Val Lys Arg Lys Leu Thr Ala
    50                  55                  60

Ala Ala Val Ala Asn Pro Ser Gln Leu Leu Asn Phe Ile Asp Ala Val
65                  70                  75                  80

Gln Arg Leu Gly Val Ala Tyr His Phe Glu Gln Glu Ile Glu Glu Ala
                85                  90                  95

Leu Gln His Ile Cys Asn Ser Phe His Asp Cys Asn Asp Met Asp Gly
            100                 105                 110

Asp Leu Tyr Asn Ile Ala Leu Gly Phe Arg Leu Leu Arg Gln Gln Gly
        115                 120                 125

Tyr Thr Ile Ser Cys Asp Ile Phe Asn Lys Phe Thr Asp Glu Arg Gly
    130                 135                 140

Arg Phe Lys Glu Ala Leu Ile Ser Asp Val Arg Gly Met Leu Gly Leu
145                 150                 155                 160

Tyr Glu Ala Ala His Leu Arg Val His Gly Glu Asp Ile Leu Ala Lys
                165                 170                 175

Ala Leu Ala Phe Thr Thr Thr His Leu Lys Ala Met Val Glu Ser Leu
            180                 185                 190

Gly Tyr His Leu Ala Glu Gln Val Ala His Ala Leu Asn Arg Pro Ile
        195                 200                 205

Arg Lys Gly Leu Glu Arg Leu Glu Ala Arg Trp Tyr Ile Ser Val Tyr
    210                 215                 220

Gln Asp Glu Ala Phe His Asp Lys Thr Leu Leu Glu Leu Ala Lys Leu
225                 230                 235                 240

Asp Phe Asn Leu Val Gln Ser Leu His Lys Glu Glu Leu Ser Asn Leu
                245                 250                 255

Ala Arg Trp Trp Lys Glu Leu Asp Phe Ala Thr Lys Leu Pro Phe Ala
            260                 265                 270

Arg Asp Arg Leu Val Glu Gly Tyr Phe Trp Met Met Gly Val Tyr Phe
        275                 280                 285

Glu Pro Gln Tyr Leu Arg Gly Arg Arg Ile Leu Thr Lys Val Ile Ala
    290                 295                 300

Leu Thr Ser Ile Leu Asp Asp Ile His Asp Ala Tyr Gly Thr Pro Glu
305                 310                 315                 320

Glu Leu Lys Leu Phe Ile Glu Ala Ile Glu Lys Trp Asp Glu Ser Ser
                325                 330                 335

Ile Asn Gln Leu Pro Glu Tyr Met Lys Leu Cys Tyr Val Ala Leu Leu
            340                 345                 350

Asp Val Tyr Asn Glu Ile Glu Glu Glu Met Glu Lys Glu Gly Asn Gln
        355                 360                 365

Tyr Arg Ile His Tyr Leu Lys Glu Val Met Lys Asn Gln Val Arg Ala
    370                 375                 380

Tyr Phe Ala Glu Ala Lys Trp Leu His Asp Glu His Val Pro Ala Phe
385                 390                 395                 400

Glu Glu Tyr Met Arg Val Ala Leu Ala Ser Ser Gly Tyr Cys Leu Leu
                405                 410                 415

Ala Val Thr Ser Phe Val Gly Met Gly Glu Ile Val Thr Lys Glu Ala
            420                 425                 430

Phe Asp Trp Val Thr Ser Asp Pro Arg Ile Met Ser Ser Ser Asn Thr
        435                 440                 445
```

-continued

```
Ile Thr Arg Leu Met Asp Asp Ile Lys Ser His Lys Phe Glu Gln Lys
    450                 455                 460

Arg Gly His Val Thr Ser Ala Val Glu Cys Tyr Met Lys Gln Tyr Ala
465                 470                 475                 480

Val Thr Glu Glu Gln Val Tyr Ser Glu Phe Lys Lys Gln Ile Glu Asn
                485                 490                 495

Ala Trp Leu Asp Ile Asn Gln Glu Cys Leu Lys Pro Thr Ala Val Pro
            500                 505                 510

Met Pro Leu Leu Ala Arg Leu Leu Asn Phe Thr Arg Thr Met Asp Val
        515                 520                 525

Ile Tyr Lys Glu Glu Asp Ser Tyr Thr His Val Gly Lys Thr Met Arg
    530                 535                 540

Asp Asn Ile Ala Ser Val Phe Ile Asn Pro Val Ile
545                 550                 555


<210> SEQ ID NO 12
<211> LENGTH: 548
<212> TYPE: PRT
<213> ORGANISM: Citrus sinensis

<400> SEQUENCE: 12

Met Ala Ser Gly Glu Thr Phe Arg Pro Thr Ala Asp Phe His Pro Ser
1               5                   10                  15

Leu Trp Arg Asn His Phe Leu Lys Gly Ala Ser Asp Phe Lys Thr Val
            20                  25                  30

Asp His Thr Ala Thr Gln Glu Arg His Glu Ala Leu Lys Glu Glu Val
        35                  40                  45

Arg Arg Met Ile Thr Asp Ala Glu Asp Lys Pro Val Gln Lys Leu Arg
    50                  55                  60

Leu Ile Asp Glu Val Gln Arg Leu Gly Val Ala Tyr His Phe Glu Lys
65                  70                  75                  80

Glu Ile Gly Asp Ala Ile Gln Lys Leu Cys Pro Ile Tyr Ile Asp Ser
                85                  90                  95

Asn Arg Ala Asp Leu His Thr Val Ser Leu His Phe Arg Leu Leu Arg
            100                 105                 110

Gln Gln Gly Ile Lys Ile Ser Cys Asp Val Phe Glu Lys Phe Lys Asp
        115                 120                 125

Asp Glu Gly Arg Phe Lys Ser Ser Leu Ile Asn Asp Val Gln Gly Met
    130                 135                 140

Leu Ser Leu Tyr Glu Ala Ala Tyr Met Ala Val Arg Gly Glu His Ile
145                 150                 155                 160

Leu Asp Glu Ala Ile Ala Phe Thr Thr Thr His Leu Lys Ser Leu Val
                165                 170                 175

Ala Gln Asp His Val Thr Pro Lys Leu Ala Glu Gln Ile Asn His Ala
            180                 185                 190

Leu Tyr Arg Pro Leu Arg Lys Thr Leu Pro Arg Leu Glu Ala Arg Tyr
        195                 200                 205

Phe Met Ser Met Ile Asn Ser Thr Ser Asp His Leu Cys Asn Lys Thr
    210                 215                 220

Leu Leu Asn Phe Ala Lys Leu Asp Phe Asn Ile Leu Leu Glu Leu His
225                 230                 235                 240

Lys Glu Glu Leu Asn Glu Leu Thr Lys Trp Trp Lys Asp Leu Asp Phe
                245                 250                 255

Thr Thr Lys Leu Pro Tyr Ala Arg Asp Arg Leu Val Glu Leu Tyr Phe
            260                 265                 270
```

Trp Asp Leu Gly Thr Tyr Phe Glu Pro Gln Tyr Ala Phe Gly Arg Lys
275 280 285

Ile Met Thr Gln Leu Asn Tyr Ile Leu Ser Ile Ile Asp Asp Thr Tyr
290 295 300

Asp Ala Tyr Gly Thr Leu Glu Glu Leu Ser Leu Phe Thr Glu Ala Val
305 310 315 320

Gln Arg Trp Asn Ile Glu Ala Val Asp Met Leu Pro Glu Tyr Met Lys
325 330 335

Leu Ile Tyr Arg Thr Leu Leu Asp Ala Phe Asn Glu Ile Glu Glu Asp
340 345 350

Met Ala Lys Gln Gly Arg Ser His Cys Val Arg Tyr Ala Lys Glu Glu
355 360 365

Asn Gln Lys Val Ile Gly Ala Tyr Ser Val Gln Ala Lys Trp Phe Ser
370 375 380

Glu Gly Tyr Val Pro Thr Ile Glu Glu Tyr Met Pro Ile Ala Leu Thr
385 390 395 400

Ser Cys Ala Tyr Thr Phe Val Ile Thr Asn Ser Phe Leu Gly Met Gly
405 410 415

Asp Phe Ala Thr Lys Glu Val Phe Glu Trp Ile Ser Asn Asn Pro Lys
420 425 430

Val Val Lys Ala Ala Ser Val Ile Cys Arg Leu Met Asp Asp Met Gln
435 440 445

Gly His Glu Phe Glu Gln Lys Arg Gly His Val Ala Ser Ala Ile Glu
450 455 460

Cys Tyr Thr Lys Gln His Gly Val Ser Lys Glu Glu Ala Ile Lys Met
465 470 475 480

Phe Glu Glu Glu Val Ala Asn Ala Trp Lys Asp Ile Asn Glu Glu Leu
485 490 495

Met Met Lys Pro Thr Val Val Ala Arg Pro Leu Leu Gly Thr Ile Leu
500 505 510

Asn Leu Ala Arg Ala Ile Asp Phe Ile Tyr Lys Glu Asp Asp Gly Tyr
515 520 525

Thr His Ser Tyr Leu Ile Lys Asp Gln Ile Ala Ser Val Leu Gly Asp
530 535 540

His Val Pro Phe
545

<210> SEQ ID NO 13
<211> LENGTH: 513
<212> TYPE: PRT
<213> ORGANISM: Zingiber zerumbet

<400> SEQUENCE: 13

Met Glu Ala Ile Ser Leu Phe Ser Pro Phe Phe Phe Ile Thr Leu Phe
1 5 10 15

Leu Gly Phe Phe Ile Thr Leu Leu Ile Lys Arg Ser Ser Arg Ser Ser
20 25 30

Val His Lys Gln Gln Val Leu Leu Ala Ser Leu Pro Pro Ser Pro Pro
35 40 45

Arg Leu Pro Leu Ile Gly Asn Ile His Gln Leu Val Gly Gly Asn Pro
50 55 60

His Arg Ile Leu Leu Gln Leu Ala Arg Thr His Gly Pro Leu Ile Cys
65 70 75 80

Leu Arg Leu Gly Gln Val Asp Gln Val Val Ala Ser Ser Val Glu Ala

-continued

```
                85                  90                  95

Val Glu Glu Ile Ile Lys Arg His Asp Leu Lys Phe Ala Asp Arg Pro
            100                 105                 110

Arg Asp Leu Thr Phe Ser Arg Ile Phe Phe Tyr Asp Gly Asn Ala Val
        115                 120                 125

Val Met Thr Pro Tyr Gly Gly Glu Trp Lys Gln Met Arg Lys Ile Tyr
    130                 135                 140

Ala Met Glu Leu Leu Asn Ser Arg Arg Val Lys Ser Phe Ala Ala Ile
145                 150                 155                 160

Arg Glu Asp Val Ala Arg Lys Leu Thr Gly Glu Ile Ala His Lys Ala
                165                 170                 175

Phe Ala Gln Thr Pro Val Ile Asn Leu Ser Glu Met Val Met Ser Met
            180                 185                 190

Ile Asn Ala Ile Val Ile Arg Val Ala Phe Gly Asp Lys Cys Lys Gln
        195                 200                 205

Gln Ala Tyr Phe Leu His Leu Val Lys Glu Ala Met Ser Tyr Val Ser
    210                 215                 220

Ser Phe Ser Val Ala Asp Met Tyr Pro Ser Leu Lys Phe Leu Asp Thr
225                 230                 235                 240

Leu Thr Gly Leu Lys Ser Lys Leu Glu Gly Val His Gly Lys Leu Asp
                245                 250                 255

Lys Val Phe Asp Glu Ile Ile Ala Gln Arg Gln Ala Ala Leu Ala Ala
            260                 265                 270

Glu Gln Ala Glu Glu Asp Leu Ile Ile Asp Val Leu Leu Lys Leu Lys
        275                 280                 285

Asp Glu Gly Asn Gln Glu Phe Pro Ile Thr Tyr Thr Ser Val Lys Ala
    290                 295                 300

Ile Val Met Glu Ile Phe Leu Ala Gly Thr Glu Thr Ser Ser Ser Val
305                 310                 315                 320

Ile Asp Trp Val Met Ser Glu Leu Ile Lys Asn Pro Lys Ala Met Glu
                325                 330                 335

Lys Val Gln Lys Glu Met Arg Glu Ala Met Gln Gly Lys Thr Lys Leu
            340                 345                 350

Glu Glu Ser Asp Ile Pro Lys Phe Ser Tyr Leu Asn Leu Val Ile Lys
        355                 360                 365

Glu Thr Leu Arg Leu His Pro Pro Gly Pro Leu Leu Phe Pro Arg Glu
    370                 375                 380

Cys Arg Glu Thr Cys Glu Val Met Gly Tyr Arg Val Pro Ala Gly Ala
385                 390                 395                 400

Arg Leu Leu Ile Asn Ala Phe Ala Leu Ser Arg Asp Glu Lys Tyr Trp
                405                 410                 415

Gly Ser Asp Ala Glu Ser Phe Lys Pro Glu Arg Phe Glu Gly Ile Ser
            420                 425                 430

Val Asp Phe Lys Gly Ser Asn Phe Glu Phe Met Pro Phe Gly Ala Gly
        435                 440                 445

Arg Arg Ile Cys Pro Gly Met Thr Phe Gly Ile Ser Ser Val Glu Val
    450                 455                 460

Ala Leu Ala His Leu Leu Phe His Phe Asp Trp Gln Leu Pro Gln Gly
465                 470                 475                 480

Met Lys Ile Glu Asp Leu Asp Met Met Glu Val Ser Gly Met Ser Ala
                485                 490                 495

Thr Arg Arg Ser Pro Leu Leu Val Leu Ala Lys Leu Ile Ile Pro Leu
            500                 505                 510
```

Pro

<210> SEQ ID NO 14
<211> LENGTH: 512
<212> TYPE: PRT
<213> ORGANISM: Zingiber zerumbet

<400> SEQUENCE: 14

```
Met Ala Leu Leu Leu Ala Val Phe Phe Phe Phe Ile Thr Leu Phe Leu
1               5                   10                  15

Gly Phe Phe Ile Thr Leu Leu Ile Lys Arg Ser Ser Arg Ser Ser Val
            20                  25                  30

His Lys Gln Gln Val Leu Leu Ala Ser Leu Pro Pro Ser Pro Pro Arg
        35                  40                  45

Leu Pro Leu Ile Gly Asn Ile His Gln Leu Val Gly Gly Asn Pro His
    50                  55                  60

Arg Ile Leu Leu Gln Leu Ala Arg Thr His Gly Pro Leu Ile Cys Leu
65                  70                  75                  80

Arg Leu Gly Gln Val Asp Gln Val Val Ala Ser Ser Val Glu Ala Val
                85                  90                  95

Glu Glu Ile Ile Lys Arg His Asp Leu Lys Phe Ala Asp Arg Pro Arg
            100                 105                 110

Asp Leu Thr Phe Ser Arg Ile Phe Phe Tyr Asp Gly Asn Ala Val Val
        115                 120                 125

Met Thr Pro Tyr Gly Gly Glu Trp Lys Gln Met Arg Lys Ile Tyr Ala
    130                 135                 140

Met Glu Leu Leu Asn Ser Arg Arg Val Lys Ser Phe Ala Ala Ile Arg
145                 150                 155                 160

Glu Asp Val Ala Arg Lys Leu Thr Gly Glu Ile Ala His Lys Ala Phe
                165                 170                 175

Ala Gln Thr Pro Val Ile Asn Leu Ser Glu Met Val Met Ser Met Ile
            180                 185                 190

Asn Ala Ile Val Ile Arg Val Ala Phe Gly Asp Lys Cys Lys Gln Gln
        195                 200                 205

Ala Tyr Phe Leu His Leu Val Lys Glu Ala Met Ser Tyr Val Ser Ser
    210                 215                 220

Phe Ser Val Ala Asp Met Tyr Pro Ser Leu Lys Phe Leu Asp Thr Leu
225                 230                 235                 240

Thr Gly Leu Lys Ser Lys Leu Glu Gly Val His Gly Lys Leu Asp Lys
                245                 250                 255

Val Phe Asp Glu Ile Ile Ala Gln Arg Gln Ala Ala Leu Ala Ala Glu
            260                 265                 270

Gln Ala Glu Glu Asp Leu Ile Ile Asp Val Leu Leu Lys Leu Lys Asp
        275                 280                 285

Glu Gly Asn Gln Glu Phe Pro Ile Thr Tyr Thr Ser Val Lys Ala Ile
    290                 295                 300

Val Met Glu Ile Phe Leu Ala Gly Thr Glu Thr Ser Ser Ser Val Ile
305                 310                 315                 320

Asp Trp Val Met Ser Glu Leu Ile Lys Asn Pro Lys Ala Met Glu Lys
                325                 330                 335

Val Gln Lys Glu Met Arg Glu Ala Met Gln Gly Lys Thr Lys Leu Glu
            340                 345                 350

Glu Ser Asp Ile Pro Lys Phe Ser Tyr Leu Asn Leu Val Ile Lys Glu
        355                 360                 365
```

```
Thr Leu Arg Leu His Pro Pro Gly Pro Leu Leu Phe Pro Arg Glu Cys
    370                 375                 380

Arg Glu Thr Cys Glu Val Met Gly Tyr Arg Val Pro Ala Gly Ala Arg
385                 390                 395                 400

Leu Leu Ile Asn Ala Phe Ala Leu Ser Arg Asp Glu Lys Tyr Trp Gly
                405                 410                 415

Ser Asp Ala Glu Ser Phe Lys Pro Glu Arg Phe Glu Gly Ile Ser Val
            420                 425                 430

Asp Phe Lys Gly Ser Asn Phe Glu Phe Met Pro Phe Gly Ala Gly Arg
        435                 440                 445

Arg Ile Cys Pro Gly Met Thr Phe Gly Ile Ser Ser Val Glu Val Ala
    450                 455                 460

Leu Ala His Leu Leu Phe His Phe Asp Trp Gln Leu Pro Gln Gly Met
465                 470                 475                 480

Lys Ile Glu Asp Leu Asp Met Met Glu Val Ser Gly Met Ser Ala Thr
                485                 490                 495

Arg Arg Ser Pro Leu Leu Val Leu Ala Lys Leu Ile Ile Pro Leu Pro
            500                 505                 510


<210> SEQ ID NO 15
<211> LENGTH: 1536
<212> TYPE: DNA
<213> ORGANISM: Zingiber zerumbet

<400> SEQUENCE: 15

atggctctgt tattagcagt gttcttcttt ttcattacgc tgtttctggg tttctttatt      60

acgctgctga ttaaacgctc gtcccgtagc tctgtccata aacagcaagt gctgctggcc     120

tctctgccgc cgagtccgcc gcgcctgccg ctgattggca acatccatca actggtgggc     180

ggcaacccgc atcgtattct gctgcaactg gcgcgtaccc acggcccgct gatctgcctg     240

cgtctgggtc aggttgatca agtggttgca agttccgtgg aagctgttga agaaattatc     300

aaacgtcacg acctgaaatt tgcagatcgt ccgcgcgacc tgacctttag ccgtattttc     360

ttttatgatg gtaacgctgt cgtgatgacg ccgtacggcg gtgaatggaa acagatgcgt     420

aaaatctatg caatggaact gctgaacagc cgtcgtgtga aatcttttgc ggccattcgt     480

gaagacgttg cacgcaaact gaccggcgaa atcgctcaca aagcattcgc tcagacgccg     540

gtcattaacc tgtctgaaat ggtgatgagt atgatcaatg cgattgtcat ccgcgtggcc     600

tttggtgata aatgtaaaca gcaagcatac ttcctgcatc tggtgaaaga agctatgtcc     660

tatgtttcat cgttttcagt cgcggatatg tacccgtccc tgaaattcct ggacaccctg     720

acgggcctga aaagcaaact ggaaggcgtt cacggtaaac tggataaagt cttcgacgaa     780

atcatcgcac agcgtcaagc agcgctggcg gcggaacagg ctgaagaaga tctgattatc     840

gacgtgctgc tgaaactgaa agatgaaggc aaccaggaat ttccgattac ctatacgtca     900

gttaaagcga ttgtcatgga aatcttcctg gccggcaccg aaaccagcag cagcgtgatt     960

gactgggtta tgagtgaact gatcaaaaac ccgaaagcga tggaaaaagt gcagaaagaa    1020

atgcgtgaag ccatgcaagg caaaaccaaa ctggaagaat cggatattcc gaaatttagc    1080

tacctgaatc tggttatcaa agaaaccctg cgtctgcatc cgccgggtcc gctgctgttc    1140

ccgcgtgaat gccgcgaaac ctgcgaagtg atgggctatc gtgttccggc gggtgcccgc    1200

ctgctgatta acgcatttgc tctgtctcgt gatgaaaaat actggggttc cgacgccgaa    1260

tcatttaaac cggaacgctt tgaaggcatc tctgtggatt tcaaaggtag taattttgaa    1320
```

tttatgccgt tcggcgcggg ccgtcgtatt tgtccgggca tgacctttgg tatctcctca 1380
gttgaagtcg cgctggccca tctgctgttt cacttcgatt ggcaactgcc gcaaggcatg 1440
aaaattgaag atctggacat gatggaagtc tcgggtatga gcgcaacccg tcgtagcccg 1500
ctgctggttc tggccaaact gattatcccg ctgccg 1536

<210> SEQ ID NO 16
<211> LENGTH: 496
<212> TYPE: PRT
<213> ORGANISM: Barnadesia spinosa

<400> SEQUENCE: 16

Met Glu Leu Thr Leu Thr Thr Ser Leu Gly Leu Ala Val Phe Val Phe
1 5 10 15

Ile Leu Phe Lys Leu Leu Thr Gly Ser Lys Ser Thr Lys Asn Ser Leu
20 25 30

Pro Glu Ala Trp Arg Leu Pro Ile Ile Gly His Met His His Leu Val
35 40 45

Gly Thr Leu Pro His Arg Gly Val Thr Asp Met Ala Arg Lys Tyr Gly
50 55 60

Ser Leu Met His Leu Gln Leu Gly Glu Val Ser Thr Ile Val Val Ser
65 70 75 80

Ser Pro Arg Trp Ala Lys Glu Val Leu Thr Thr Tyr Asp Ile Thr Phe
85 90 95

Ala Asn Arg Pro Glu Thr Leu Thr Gly Glu Ile Val Ala Tyr His Asn
100 105 110

Thr Asp Ile Val Leu Ser Pro Tyr Gly Glu Tyr Trp Arg Gln Leu Arg
115 120 125

Lys Leu Cys Thr Leu Glu Leu Leu Ser Ala Lys Lys Val Lys Ser Phe
130 135 140

Gln Ser Leu Arg Glu Glu Glu Cys Trp Asn Leu Val Lys Glu Val Arg
145 150 155 160

Ser Ser Gly Ser Gly Ser Pro Val Asp Leu Ser Glu Ser Ile Phe Lys
165 170 175

Leu Ile Ala Thr Ile Leu Ser Arg Ala Ala Phe Gly Lys Gly Ile Lys
180 185 190

Asp Gln Arg Glu Phe Thr Glu Ile Val Lys Glu Ile Leu Arg Leu Thr
195 200 205

Gly Gly Phe Asp Val Ala Asp Ile Phe Pro Ser Lys Lys Ile Leu His
210 215 220

His Leu Ser Gly Lys Arg Ala Lys Leu Thr Asn Ile His Asn Lys Leu
225 230 235 240

Asp Ser Leu Ile Asn Asn Ile Val Ser Glu His Pro Gly Ser Arg Thr
245 250 255

Ser Ser Ser Gln Glu Ser Leu Leu Asp Val Leu Leu Arg Leu Lys Asp
260 265 270

Ser Ala Glu Leu Pro Leu Thr Ser Asp Asn Val Lys Ala Val Ile Leu
275 280 285

Asp Met Phe Gly Ala Gly Thr Asp Thr Ser Ser Ala Thr Ile Glu Trp
290 295 300

Ala Ile Ser Glu Leu Ile Arg Cys Pro Arg Ala Met Glu Lys Val Gln
305 310 315 320

Thr Glu Leu Arg Gln Ala Leu Asn Gly Lys Glu Arg Ile Gln Glu Glu
325 330 335

```
Asp Ile Gln Glu Leu Ser Tyr Leu Lys Leu Val Ile Lys Glu Thr Leu
            340                 345                 350

Arg Leu His Pro Pro Leu Pro Leu Val Met Pro Arg Glu Cys Arg Glu
        355                 360                 365

Pro Cys Val Leu Ala Gly Tyr Glu Ile Pro Thr Lys Thr Lys Leu Ile
    370                 375                 380

Val Asn Val Phe Ala Ile Asn Arg Asp Pro Glu Tyr Trp Lys Asp Ala
385                 390                 395                 400

Glu Thr Phe Met Pro Glu Arg Phe Glu Asn Ser Pro Ile Asn Ile Met
                405                 410                 415

Gly Ser Glu Tyr Glu Tyr Leu Pro Phe Gly Ala Gly Arg Arg Met Cys
            420                 425                 430

Pro Gly Ala Ala Leu Gly Leu Ala Asn Val Glu Leu Pro Leu Ala His
        435                 440                 445

Ile Leu Tyr Tyr Phe Asn Trp Lys Leu Pro Asn Gly Ala Arg Leu Asp
    450                 455                 460

Glu Leu Asp Met Ser Glu Cys Phe Gly Ala Thr Val Gln Arg Lys Ser
465                 470                 475                 480

Glu Leu Leu Leu Val Pro Thr Ala Tyr Lys Thr Ala Asn Asn Ser Ala
                485                 490                 495


<210> SEQ ID NO 17
<211> LENGTH: 496
<212> TYPE: PRT
<213> ORGANISM: Barnadesia spinosa

<400> SEQUENCE: 17

Met Ala Leu Leu Leu Ala Val Phe Leu Gly Leu Ala Val Phe Val Phe
1               5                   10                  15

Ile Leu Phe Lys Leu Leu Thr Gly Ser Lys Ser Thr Lys Asn Ser Leu
            20                  25                  30

Pro Glu Ala Trp Arg Leu Pro Ile Ile Gly His Met His His Leu Val
        35                  40                  45

Gly Thr Leu Pro His Arg Gly Val Thr Asp Met Ala Arg Lys Tyr Gly
    50                  55                  60

Ser Leu Met His Leu Gln Leu Gly Glu Val Ser Thr Ile Val Val Ser
65                  70                  75                  80

Ser Pro Arg Trp Ala Lys Glu Val Leu Thr Thr Tyr Asp Ile Thr Phe
                85                  90                  95

Ala Asn Arg Pro Glu Thr Leu Thr Gly Glu Ile Val Ala Tyr His Asn
            100                 105                 110

Thr Asp Ile Val Leu Ser Pro Tyr Gly Glu Tyr Trp Arg Gln Leu Arg
        115                 120                 125

Lys Leu Cys Thr Leu Glu Leu Leu Ser Ala Lys Lys Val Lys Ser Phe
    130                 135                 140

Gln Ser Leu Arg Glu Glu Glu Cys Trp Asn Leu Val Lys Glu Val Arg
145                 150                 155                 160

Ser Ser Gly Ser Gly Ser Pro Val Asp Leu Ser Glu Ser Ile Phe Lys
                165                 170                 175

Leu Ile Ala Thr Ile Leu Ser Arg Ala Ala Phe Gly Lys Gly Ile Lys
            180                 185                 190

Asp Gln Arg Glu Phe Thr Glu Ile Val Lys Glu Ile Leu Arg Leu Thr
        195                 200                 205

Gly Gly Phe Asp Val Ala Asp Ile Phe Pro Ser Lys Lys Ile Leu His
```

-continued

```
    210                 215                 220

His Leu Ser Gly Lys Arg Ala Lys Leu Thr Asn Ile His Asn Lys Leu
225                 230                 235                 240

Asp Ser Leu Ile Asn Asn Ile Val Ser Glu His Pro Gly Ser Arg Thr
                245                 250                 255

Ser Ser Ser Gln Glu Ser Leu Leu Asp Val Leu Leu Arg Leu Lys Asp
            260                 265                 270

Ser Ala Glu Leu Pro Leu Thr Ser Asp Asn Val Lys Ala Val Ile Leu
        275                 280                 285

Asp Met Phe Gly Ala Gly Thr Asp Thr Ser Ser Ala Thr Ile Glu Trp
    290                 295                 300

Ala Ile Ser Glu Leu Ile Arg Cys Pro Arg Ala Met Glu Lys Val Gln
305                 310                 315                 320

Thr Glu Leu Arg Gln Ala Leu Asn Gly Lys Glu Arg Ile Gln Glu Glu
                325                 330                 335

Asp Ile Gln Glu Leu Ser Tyr Leu Lys Leu Val Ile Lys Glu Thr Leu
            340                 345                 350

Arg Leu His Pro Pro Leu Pro Leu Val Met Pro Arg Glu Cys Arg Glu
        355                 360                 365

Pro Cys Val Leu Ala Gly Tyr Glu Ile Pro Thr Lys Thr Lys Leu Ile
    370                 375                 380

Val Asn Val Phe Ala Ile Asn Arg Asp Pro Glu Tyr Trp Lys Asp Ala
385                 390                 395                 400

Glu Thr Phe Met Pro Glu Arg Phe Glu Asn Ser Pro Ile Asn Ile Met
                405                 410                 415

Gly Ser Glu Tyr Glu Tyr Leu Pro Phe Gly Ala Gly Arg Arg Met Cys
            420                 425                 430

Pro Gly Ala Ala Leu Gly Leu Ala Asn Val Glu Leu Pro Leu Ala His
        435                 440                 445

Ile Leu Tyr Tyr Phe Asn Trp Lys Leu Pro Asn Gly Ala Arg Leu Asp
    450                 455                 460

Glu Leu Asp Met Ser Glu Cys Phe Gly Ala Thr Val Gln Arg Lys Ser
465                 470                 475                 480

Glu Leu Leu Leu Val Pro Thr Ala Tyr Lys Thr Ala Asn Asn Ser Ala
                485                 490                 495


<210> SEQ ID NO 18
<211> LENGTH: 1488
<212> TYPE: DNA
<213> ORGANISM: Barnadesia spinosa

<400> SEQUENCE: 18

atggctctgt tattagcagt tttcctgggc ctggctgtct tcgtctttat cctgttcaaa      60

ctgctgaccg gctcaaaatc aaccaaaaat tcactgccgg aagcatggcg tctgccgatc     120

attggccaca tgcatcacct ggttggcacg ctgccgcatc gcggtgtgac cgacatggcg     180

cgtaaatacg gcagcctgat gcatctgcaa ctgggcgaag tgagcaccat tgtcgtctca     240

tcgccgcgtt gggcaaaaga agtgctgacg acgtatgata ttacctttgc gaatcgcccg     300

gaaaccctga ccggcgaaat tgttgcgtac cacaacacgg atattgtgct gtcaccgtat     360

ggcgaatact ggcgccaact gcgtaaactg tgcacgctgg aactgctgag cgccaaaaaa     420

gtgaaaagtt ttcagtcgct gcgtgaagaa gaatgctgga atctggtgaa agaagtgcgt     480

tcgagcggct caggttcccc ggtcgatctg tcggaatcca tctttaaact gattgcaacc     540
```

```
attctgagcc gcgcagcgtt tggcaaaggt atcaaagatc agcgtgaatt taccgaaatt    600

gtgaaagaaa tcctgcgcct gacgggcggt tttgatgtgg cggatatttt cccgtccaaa    660

aagatcctgc accacctgag cggcaaacgt gcgaaactga ccaacatcca caacaaactg    720

gattccctga ttaataacat tgtttctgaa catccgggtt cgcgtacctc gtcgagccag    780

gaaagcctgc tggatgtgct gctgcgcctg aaagattccg cggaactgcc gctgacctcg    840

gacaatgtta aagccgtgat cctggatatg ttcggtgcgg gcacggatac gtcgagcgcc    900

acgattgaat gggcgatcag cgaactgatc cgctgcccgc gtgcaatgga aaaagtgcaa    960

acggaactgc gtcaagcgct gaatggtaaa gaacgcattc aggaagaaga tattcaggaa   1020

ctgtcctatc tgaaactggt cattaaagaa accctgcgcc tgcatccgcc gctgccgctg   1080

gtgatgccgc gtgaatgtcg tgaaccgtgt gtcctggcgg gttacgaaat cccgaccaaa   1140

acgaaactga ttgtgaatgt ctttgccatc aatcgtgacc cggaatactg gaaagatgca   1200

gaaaccttca tgccggaacg ctttgaaaac agcccgatta acatcatggg tagtgaatat   1260

gaatacctgc cgtttggcgc aggccgccgt atgtgtccgg gtgcagctct gggtctggcg   1320

aatgtggaac tgccgctggc gcacatcctg tattatttta actggaaact gccgaatggc   1380

gctcgcctgg atgaactgga tatgtcggaa tgctttggcg cgacggtcca acgcaaaagc   1440

gaactgctgc tggtcccgac ggcatacaaa acggcaaaca actccgca                1488
```

```
<210> SEQ ID NO 19
<211> LENGTH: 502
<212> TYPE: PRT
<213> ORGANISM: Hyoscyamus muticus

<400> SEQUENCE: 19

Met Gln Phe Phe Ser Leu Val Ser Ile Phe Leu Phe Leu Ser Phe Leu
1               5                   10                  15

Phe Leu Leu Arg Lys Trp Lys Asn Ser Asn Ser Gln Ser Lys Lys Leu
            20                  25                  30

Pro Pro Gly Pro Trp Lys Leu Pro Leu Leu Gly Ser Met Leu His Met
        35                  40                  45

Val Gly Gly Leu Pro His His Val Leu Arg Asp Leu Ala Lys Lys Tyr
    50                  55                  60

Gly Pro Leu Met His Leu Gln Leu Gly Glu Val Ser Ala Val Val Val
65                  70                  75                  80

Thr Ser Pro Asp Met Ala Lys Glu Val Leu Lys Thr His Asp Ile Ala
                85                  90                  95

Phe Ala Ser Arg Pro Lys Leu Leu Ala Pro Glu Ile Val Cys Tyr Asn
            100                 105                 110

Arg Ser Asp Ile Ala Phe Cys Pro Tyr Gly Asp Tyr Trp Arg Gln Met
        115                 120                 125

Arg Lys Ile Cys Val Leu Glu Val Leu Ser Ala Lys Asn Val Arg Ser
    130                 135                 140

Phe Ser Ser Ile Arg Arg Asp Glu Val Leu Arg Leu Val Asn Phe Val
145                 150                 155                 160

Arg Ser Ser Thr Ser Glu Pro Val Asn Phe Thr Glu Arg Leu Phe Leu
                165                 170                 175

Phe Thr Ser Ser Met Thr Cys Arg Ser Ala Phe Gly Lys Val Phe Lys
            180                 185                 190

Glu Gln Glu Thr Phe Ile Gln Leu Ile Lys Glu Val Ile Gly Leu Ala
        195                 200                 205
```

```
Gly Gly Phe Asp Val Ala Asp Ile Phe Pro Ser Leu Lys Phe Leu His
    210                 215                 220

Val Leu Thr Gly Met Glu Gly Lys Ile Met Lys Ala His His Lys Val
225                 230                 235                 240

Asp Ala Ile Val Glu Asp Val Ile Asn Glu His Lys Lys Asn Leu Ala
                245                 250                 255

Met Gly Lys Thr Asn Gly Ala Leu Gly Gly Glu Asp Leu Ile Asp Val
            260                 265                 270

Leu Leu Arg Leu Met Asn Asp Gly Gly Leu Gln Phe Pro Ile Thr Asn
        275                 280                 285

Asp Asn Ile Lys Ala Ile Ile Phe Asp Met Phe Ala Ala Gly Thr Glu
    290                 295                 300

Thr Ser Ser Ser Thr Leu Val Trp Ala Met Val Gln Met Met Arg Asn
305                 310                 315                 320

Pro Thr Ile Leu Ala Lys Ala Gln Ala Glu Val Arg Glu Ala Phe Lys
                325                 330                 335

Gly Lys Glu Thr Phe Asp Glu Asn Asp Val Glu Glu Leu Lys Tyr Leu
            340                 345                 350

Lys Leu Val Ile Lys Glu Thr Leu Arg Leu His Pro Pro Val Pro Leu
        355                 360                 365

Leu Val Pro Arg Glu Cys Arg Glu Glu Thr Glu Ile Asn Gly Tyr Thr
    370                 375                 380

Ile Pro Val Lys Thr Lys Val Met Val Asn Val Trp Ala Leu Gly Arg
385                 390                 395                 400

Asp Pro Lys Tyr Trp Asp Asp Ala Asp Asn Phe Lys Pro Glu Arg Phe
                405                 410                 415

Glu Gln Cys Ser Val Asp Phe Ile Gly Asn Asn Phe Glu Tyr Leu Pro
            420                 425                 430

Phe Gly Gly Gly Arg Arg Ile Cys Pro Gly Ile Ser Phe Gly Leu Ala
        435                 440                 445

Asn Val Tyr Leu Pro Leu Ala Gln Leu Leu Tyr His Phe Asp Trp Lys
    450                 455                 460

Leu Pro Thr Gly Met Glu Pro Lys Asp Leu Asp Leu Thr Glu Leu Val
465                 470                 475                 480

Gly Val Thr Ala Ala Arg Lys Ser Asp Leu Met Leu Val Ala Thr Pro
                485                 490                 495

Tyr Gln Pro Ser Arg Glu
            500
```

<210> SEQ ID NO 20
<211> LENGTH: 508
<212> TYPE: PRT
<213> ORGANISM: Hyoscyamus muticus

<400> SEQUENCE: 20

```
Met Ala Leu Leu Leu Ala Val Phe Phe Phe Ser Leu Val Ser Ile Phe
1               5                   10                  15

Leu Phe Leu Ser Phe Leu Phe Leu Leu Arg Lys Trp Lys Asn Ser Asn
            20                  25                  30

Ser Gln Ser Lys Lys Leu Pro Pro Gly Pro Trp Lys Leu Pro Leu Leu
        35                  40                  45

Gly Ser Met Leu His Met Val Gly Gly Leu Pro His His Val Leu Arg
    50                  55                  60

Asp Leu Ala Lys Lys Tyr Gly Pro Leu Met His Leu Gln Leu Gly Glu
65                  70                  75                  80
```

```
Val Ser Ala Val Val Val Thr Ser Pro Asp Met Ala Lys Glu Val Leu
                85                  90                  95

Lys Thr His Asp Ile Ala Phe Ala Ser Arg Pro Lys Leu Leu Ala Pro
            100                 105                 110

Glu Ile Val Cys Tyr Asn Arg Ser Asp Ile Ala Phe Cys Pro Tyr Gly
        115                 120                 125

Asp Tyr Trp Arg Gln Met Arg Lys Ile Cys Val Leu Glu Val Leu Ser
    130                 135                 140

Ala Lys Asn Val Arg Ser Phe Ser Ser Ile Arg Arg Asp Glu Val Leu
145                 150                 155                 160

Arg Leu Val Asn Phe Val Arg Ser Ser Thr Ser Glu Pro Val Asn Phe
                165                 170                 175

Thr Glu Arg Leu Phe Leu Phe Thr Ser Ser Met Thr Cys Arg Ser Ala
            180                 185                 190

Phe Gly Lys Val Phe Lys Glu Gln Glu Thr Phe Ile Gln Leu Ile Lys
        195                 200                 205

Glu Val Ile Gly Leu Ala Gly Gly Phe Asp Val Ala Asp Ile Phe Pro
    210                 215                 220

Ser Leu Lys Phe Leu His Val Leu Thr Gly Met Glu Gly Lys Ile Met
225                 230                 235                 240

Lys Ala His His Lys Val Asp Ala Ile Val Glu Asp Val Ile Asn Glu
                245                 250                 255

His Lys Lys Asn Leu Ala Met Gly Lys Thr Asn Gly Ala Leu Gly Gly
            260                 265                 270

Glu Asp Leu Ile Asp Val Leu Leu Arg Leu Met Asn Asp Gly Gly Leu
        275                 280                 285

Gln Phe Pro Ile Thr Asn Asp Asn Ile Lys Ala Ile Ile Phe Asp Met
    290                 295                 300

Phe Ala Ala Gly Thr Glu Thr Ser Ser Ser Thr Leu Val Trp Ala Met
305                 310                 315                 320

Val Gln Met Met Arg Asn Pro Thr Ile Leu Ala Lys Ala Gln Ala Glu
                325                 330                 335

Val Arg Glu Ala Phe Lys Gly Lys Glu Thr Phe Asp Glu Asn Asp Val
            340                 345                 350

Glu Glu Leu Lys Tyr Leu Lys Leu Val Ile Lys Glu Thr Leu Arg Leu
        355                 360                 365

His Pro Pro Val Pro Leu Leu Val Pro Arg Glu Cys Arg Glu Glu Thr
    370                 375                 380

Glu Ile Asn Gly Tyr Thr Ile Pro Val Lys Thr Lys Val Met Val Asn
385                 390                 395                 400

Val Trp Ala Leu Gly Arg Asp Pro Lys Tyr Trp Asp Asp Ala Asp Asn
                405                 410                 415

Phe Lys Pro Glu Arg Phe Glu Gln Cys Ser Val Asp Phe Ile Gly Asn
            420                 425                 430

Asn Phe Glu Tyr Leu Pro Phe Gly Gly Gly Arg Arg Ile Cys Pro Gly
        435                 440                 445

Ile Ser Phe Gly Leu Ala Asn Val Tyr Leu Pro Leu Ala Gln Leu Leu
    450                 455                 460

Tyr His Phe Asp Trp Lys Leu Pro Thr Gly Met Glu Pro Lys Asp Leu
465                 470                 475                 480

Asp Leu Thr Glu Leu Val Gly Val Thr Ala Ala Arg Lys Ser Asp Leu
                485                 490                 495
```

-continued

```
Met Leu Val Ala Thr Pro Tyr Gln Pro Ser Arg Glu
            500                 505


<210> SEQ ID NO 21
<211> LENGTH: 1524
<212> TYPE: DNA
<213> ORGANISM: Hyoscyamus muticus

<400> SEQUENCE: 21

atggctctgt tattagcagt tttcttcttc tccctggtct caatctttct gttcctgtcc     60

tttctgttcc tgctgcgtaa atggaaaaac tcaaactccc aatcgaaaaa actgccgccg    120

ggtccgtgga aactgccgct gctgggctct atgctgcaca tggttggcgg cctgccgcat    180

cacgttctgc gtgatctggc gaaaaaatat ggtccgctga tgcatctgca actgggcgaa    240

gtctccgccg tggttgtcac ctcaccggat atggcaaaag aagtgctgaa aacgcatgac    300

attgcgttcg cctcccgtcc gaaactgctg gccccggaaa ttgtgtgcta caaccgctca    360

gatattgcat tttgtccgta tggtgactac tggcgtcaaa tgcgcaaaat ttgcgtcctg    420

gaagtgctgt cggccaaaaa tgtgcgcagc tttagctcta ttcgtcgtga tgaagttctg    480

cgtctggtta acttcgtccg cagttccacc tcggagccgg tgaattttac ggaacgtctg    540

tttctgttca cctcatcgat gacctgccgt agcgcatttg gtaaagtttt caaagaacag    600

gaaaccttca ttcaactgat caaagaagtc attggcctgg ccggcggttt tgatgtggca    660

gacatctttc cgagtctgaa attcctgcat gttctgaccg gcatggaagg caaaattatg    720

aaagctcatc acaaagtcga tgcgattgtg gaagacgtta tcaacgaaca caagaaaaac    780

ctggcgatgg gcaaaacgaa cggcgcactg ggcggtgaag atctgatcga cgttctgctg    840

cgtctgatga atgatggcgg cctgcaattt ccgatcacca acgataatat caaagctatt    900

atctttgata tgtttgcggc gggcaccgaa accagcagca gcaccctggt gtgggcgatg    960

gtgcagatga tgcgtaaccc gacgattctg gcaaaagctc aagcggaagt gcgcgaagcc   1020

ttcaaaggca aagaaacctt tgatgaaaat gacgttgaag aactgaaata tctgaaactg   1080

gtcatcaaag aaacgctgcg tctgcatccg ccggttccgc tgctggtccc gcgtgaatgc   1140

cgcgaagaaa ccgaaattaa cggttatacc atcccggtta aaacgaaagt gatggttaat   1200

gtctgggctc tgggccgtga tccgaaatac tgggatgacg cggacaactt taaaccggaa   1260

cgctttgaac agtgctctgt ggatttcatc ggcaacaact ttgaatatct gccgtttggc   1320

ggtggccgtc gcatttgtcc gggtatcagc ttcggcctgg ctaatgttta tctgccgctg   1380

gcgcaactgc tgtaccactt tgattggaaa ctgccgaccg gcatggaacc gaaagatctg   1440

gacctgaccg aactggtggg cgttacggca gctcgtaaat ctgatctgat gctggttgcg   1500

accccgtacc agccgagccg tgaa                                          1524


<210> SEQ ID NO 22
<211> LENGTH: 488
<212> TYPE: PRT
<213> ORGANISM: Lactuca sativa

<400> SEQUENCE: 22

Met Glu Leu Ser Ile Thr Thr Ser Ile Ala Leu Ala Thr Ile Val Phe
1               5                   10                  15

Phe Leu Tyr Lys Leu Ala Thr Arg Pro Lys Ser Thr Lys Lys Gln Leu
            20                  25                  30

Pro Glu Ala Ser Arg Leu Pro Ile Ile Gly His Met His His Leu Ile
        35                  40                  45
```

-continued

```
Gly Thr Met Pro His Arg Gly Val Met Asp Leu Ala Arg Lys His Gly
    50                  55                  60

Ser Leu Met His Leu Gln Leu Gly Glu Val Ser Thr Ile Val Val Ser
65                  70                  75                  80

Ser Pro Lys Trp Ala Lys Glu Ile Leu Thr Thr Tyr Asp Ile Thr Phe
                85                  90                  95

Ala Asn Arg Pro Glu Thr Leu Thr Gly Glu Ile Ile Ala Tyr His Asn
            100                 105                 110

Thr Asp Ile Val Leu Ala Pro Tyr Gly Glu Tyr Trp Arg Gln Leu Arg
        115                 120                 125

Lys Leu Cys Thr Leu Glu Leu Leu Ser Val Lys Lys Val Lys Ser Phe
    130                 135                 140

Gln Ser Ile Arg Glu Glu Glu Cys Trp Asn Leu Val Lys Glu Val Lys
145                 150                 155                 160

Glu Ser Gly Ser Gly Lys Pro Ile Asn Leu Ser Glu Ser Ile Phe Thr
                165                 170                 175

Met Ile Ala Thr Ile Leu Ser Arg Ala Ala Phe Gly Lys Gly Ile Lys
            180                 185                 190

Asp Gln Arg Glu Phe Thr Glu Ile Val Lys Glu Ile Leu Arg Gln Thr
        195                 200                 205

Gly Gly Phe Asp Val Ala Asp Ile Phe Pro Ser Lys Lys Phe Leu His
    210                 215                 220

His Leu Ser Gly Lys Arg Ala Arg Leu Thr Ser Ile His Lys Lys Leu
225                 230                 235                 240

Asp Asn Leu Ile Asn Asn Ile Val Ala Glu His His Val Ser Thr Ser
                245                 250                 255

Ser Lys Ala Asn Glu Thr Leu Leu Asp Val Leu Leu Arg Leu Lys Asp
            260                 265                 270

Ser Ala Glu Phe Pro Leu Thr Ala Asp Asn Val Lys Ala Ile Ile Leu
        275                 280                 285

Asp Met Phe Gly Ala Gly Thr Asp Thr Ser Ser Ala Thr Val Glu Trp
    290                 295                 300

Ala Ile Ser Glu Leu Ile Arg Cys Pro Arg Ala Met Glu Lys Val Gln
305                 310                 315                 320

Ala Glu Leu Arg Gln Ala Leu Asn Gly Lys Glu Lys Ile Gln Glu Glu
                325                 330                 335

Asp Ile Gln Asp Leu Ala Tyr Leu Asn Leu Val Ile Arg Glu Thr Leu
            340                 345                 350

Arg Leu His Pro Pro Leu Pro Leu Val Met Pro Arg Glu Cys Arg Glu
        355                 360                 365

Pro Val Asn Leu Ala Gly Tyr Glu Ile Ala Asn Lys Thr Lys Leu Ile
    370                 375                 380

Val Asn Val Phe Ala Ile Asn Arg Asp Pro Glu Tyr Trp Lys Asp Ala
385                 390                 395                 400

Glu Ala Phe Ile Pro Glu Arg Phe Glu Asn Asn Pro Asn Asn Ile Met
                405                 410                 415

Gly Ala Asp Tyr Glu Tyr Leu Pro Phe Gly Ala Gly Arg Arg Met Cys
            420                 425                 430

Pro Gly Ala Ala Leu Gly Leu Ala Asn Val Gln Leu Pro Leu Ala Asn
        435                 440                 445

Ile Leu Tyr His Phe Asn Trp Lys Leu Pro Asn Gly Ala Ser His Asp
    450                 455                 460
```

Gln Leu Asp Met Thr Glu Ser Phe Gly Ala Thr Val Gln Arg Lys Thr
465 470 475 480

Glu Leu Leu Leu Val Pro Ser Phe
485

<210> SEQ ID NO 23
<211> LENGTH: 488
<212> TYPE: PRT
<213> ORGANISM: Lactuca sativa

<400> SEQUENCE: 23

Met Ala Leu Leu Leu Ala Val Phe Ile Ala Leu Ala Thr Ile Val Phe
1 5 10 15

Phe Leu Tyr Lys Leu Ala Thr Arg Pro Lys Ser Thr Lys Lys Gln Leu
20 25 30

Pro Glu Ala Ser Arg Leu Pro Ile Ile Gly His Met His His Leu Ile
35 40 45

Gly Thr Met Pro His Arg Gly Val Met Asp Leu Ala Arg Lys His Gly
50 55 60

Ser Leu Met His Leu Gln Leu Gly Glu Val Ser Thr Ile Val Val Ser
65 70 75 80

Ser Pro Lys Trp Ala Lys Glu Ile Leu Thr Thr Tyr Asp Ile Thr Phe
85 90 95

Ala Asn Arg Pro Glu Thr Leu Thr Gly Glu Ile Ile Ala Tyr His Asn
100 105 110

Thr Asp Ile Val Leu Ala Pro Tyr Gly Glu Tyr Trp Arg Gln Leu Arg
115 120 125

Lys Leu Cys Thr Leu Glu Leu Leu Ser Val Lys Lys Val Lys Ser Phe
130 135 140

Gln Ser Ile Arg Glu Glu Glu Cys Trp Asn Leu Val Lys Glu Val Lys
145 150 155 160

Glu Ser Gly Ser Gly Lys Pro Ile Asn Leu Ser Glu Ser Ile Phe Thr
165 170 175

Met Ile Ala Thr Ile Leu Ser Arg Ala Ala Phe Gly Lys Gly Ile Lys
180 185 190

Asp Gln Arg Glu Phe Thr Glu Ile Val Lys Glu Ile Leu Arg Gln Thr
195 200 205

Gly Gly Phe Asp Val Ala Asp Ile Phe Pro Ser Lys Lys Phe Leu His
210 215 220

His Leu Ser Gly Lys Arg Ala Arg Leu Thr Ser Ile His Lys Lys Leu
225 230 235 240

Asp Asn Leu Ile Asn Asn Ile Val Ala Glu His His Val Ser Thr Ser
245 250 255

Ser Lys Ala Asn Glu Thr Leu Leu Asp Val Leu Leu Arg Leu Lys Asp
260 265 270

Ser Ala Glu Phe Pro Leu Thr Ala Asp Asn Val Lys Ala Ile Ile Leu
275 280 285

Asp Met Phe Gly Ala Gly Thr Asp Thr Ser Ser Ala Thr Val Glu Trp
290 295 300

Ala Ile Ser Glu Leu Ile Arg Cys Pro Arg Ala Met Glu Lys Val Gln
305 310 315 320

Ala Glu Leu Arg Gln Ala Leu Asn Gly Lys Glu Lys Ile Gln Glu Glu
325 330 335

Asp Ile Gln Asp Leu Ala Tyr Leu Asn Leu Val Ile Arg Glu Thr Leu
340 345 350

```
Arg Leu His Pro Pro Leu Pro Leu Val Met Pro Arg Glu Cys Arg Glu
        355                 360                 365

Pro Val Asn Leu Ala Gly Tyr Glu Ile Ala Asn Lys Thr Lys Leu Ile
    370                 375                 380

Val Asn Val Phe Ala Ile Asn Arg Asp Pro Glu Tyr Trp Lys Asp Ala
385                 390                 395                 400

Glu Ala Phe Ile Pro Glu Arg Phe Glu Asn Asn Pro Asn Asn Ile Met
                405                 410                 415

Gly Ala Asp Tyr Glu Tyr Leu Pro Phe Gly Ala Gly Arg Arg Met Cys
            420                 425                 430

Pro Gly Ala Ala Leu Gly Leu Ala Asn Val Gln Leu Pro Leu Ala Asn
        435                 440                 445

Ile Leu Tyr His Phe Asn Trp Lys Leu Pro Asn Gly Ala Ser His Asp
    450                 455                 460

Gln Leu Asp Met Thr Glu Ser Phe Gly Ala Thr Val Gln Arg Lys Thr
465                 470                 475                 480

Glu Leu Leu Leu Val Pro Ser Phe
                485


<210> SEQ ID NO 24
<211> LENGTH: 1464
<212> TYPE: DNA
<213> ORGANISM: Lactuca sativa

<400> SEQUENCE: 24

atggctctgt tattagcagt tttcatcgca ctggctacca tcgtcttctt cctgtataaa      60

ctggcaacgc gcccgaaatc taccaaaaaa caactgccgg aagcgagccg tctgccgatt     120

atcggccaca tgcatcacct gattggcacc atgccgcacc gtggtgtcat ggatctggcc     180

cgcaaacatg gctcgctgat gcatctgcaa ctgggcgaag tgagcaccat tgtggttagc     240

tctccgaaat gggcaaaaga aattctgacc acctatgata ttacctttgc taaccgcccg     300

gaaaccctga cgggcgaaat tatcgcgtac cataatacgg acattgtgct ggccccgtat     360

ggtgaatact ggcgtcaact gcgtaaactg tgcaccctgg aactgctgtc cgttaaaaaa     420

gtcaaatcat ttcaatcgat tcgtgaagaa gaatgttgga acctggtgaa agaagttaaa     480

gaaagcggct ctggtaaacc gattaatctg agtgaatcca tcttcaccat gattgcgacg     540

atcctgagtc gtgcggcctt tggcaaaggt attaaagatc agcgcgaatt taccgaaatt     600

gtcaaagaaa tcctgcgtca aacgggcggt ttcgatgtgg cagacatttt tccgagcaaa     660

aaattcctgc atcacctgtc tggcaaacgt gctcgcctga ccagtatcca taaaaaactg     720

gataacctga tcaacaatat cgtcgcggaa catcatgtga gcaccagcag caaagcgaat     780

gaaacgctgc tggatgttct gctgcgcctg aaagacagtg ccgaatttcc gctgaccgca     840

gacaacgtca aagctattat cctggatatg ttcggtgcag gcaccgatac cagcagcgca     900

acggtggaat gggccattag cgaactgatc cgttgcccgc gcgcaatgga aaaagttcag     960

gcagaactgc gtcaagctct gaacggtaaa gaaaaaatcc aggaagaaga tattcaagac    1020

ctggcctatc tgaatctggt gattcgtgaa accctgcgtc tgcacccgcc gctgccgctg    1080

gttatgccgc gtgaatgccg tgagccggtg aacctggcgg gctatgaaat cgccaataaa    1140

accaaactga tcgtcaatgt gtttgcgatt aaccgtgacc cggaatactg gaaagacgcg    1200

gaagccttta tcccggaacg ttttgaaaac aatccgaaca atatcatggg tgcagattat    1260

gaatacctgc cgtttggcgc tggtcgtcgc atgtgtccgg gcgcagctct gggtctggca    1320
```

aacgttcaac tgccgctggc gaacattctg taccatttca actggaaact gccgaatggc 1380
gcgtcccacg atcaactgga catgaccgaa tcatttggtg ccaccgtgca acgtaaaacg 1440
gaactgctgc tggttccgag cttc 1464

<210> SEQ ID NO 25
<211> LENGTH: 504
<212> TYPE: PRT
<213> ORGANISM: Nicotiani tabacum

<400> SEQUENCE: 25

Met Gln Phe Phe Ser Leu Val Ser Ile Phe Leu Phe Leu Ser Phe Leu
1 5 10 15

Phe Leu Leu Arg Lys Trp Lys Asn Ser Asn Ser Gln Ser Lys Lys Leu
20 25 30

Pro Pro Gly Pro Trp Lys Ile Pro Ile Leu Gly Ser Met Leu His Met
35 40 45

Ile Gly Gly Glu Pro His His Val Leu Arg Asp Leu Ala Lys Lys Tyr
50 55 60

Gly Pro Leu Met His Leu Gln Leu Gly Glu Ile Ser Ala Val Val Val
65 70 75 80

Thr Ser Arg Asp Met Ala Lys Glu Val Leu Lys Thr His Asp Val Val
85 90 95

Phe Ala Ser Arg Pro Lys Ile Val Ala Met Asp Ile Ile Cys Tyr Asn
100 105 110

Gln Ser Asp Ile Ala Phe Ser Pro Tyr Gly Asp His Trp Arg Gln Met
115 120 125

Arg Lys Ile Cys Val Met Glu Leu Leu Asn Ala Lys Asn Val Arg Ser
130 135 140

Phe Ser Ser Ile Arg Arg Asp Glu Val Val Arg Leu Ile Asp Ser Ile
145 150 155 160

Arg Ser Asp Ser Ser Ser Gly Glu Leu Val Asn Phe Thr Gln Arg Ile
165 170 175

Ile Trp Phe Ala Ser Ser Met Thr Cys Arg Ser Ala Phe Gly Gln Val
180 185 190

Leu Lys Gly Gln Asp Ile Phe Ala Lys Lys Ile Arg Glu Val Ile Gly
195 200 205

Leu Ala Glu Gly Phe Asp Val Val Asp Ile Phe Pro Thr Tyr Lys Phe
210 215 220

Leu His Val Leu Ser Gly Met Lys Arg Lys Leu Leu Asn Ala His Leu
225 230 235 240

Lys Val Asp Ala Ile Val Glu Asp Val Ile Asn Glu His Lys Lys Asn
245 250 255

Leu Ala Ala Gly Lys Ser Asn Gly Ala Leu Gly Gly Glu Asp Leu Ile
260 265 270

Asp Val Leu Leu Arg Leu Met Asn Asp Thr Ser Leu Gln Phe Pro Ile
275 280 285

Thr Asn Asp Asn Ile Lys Ala Val Ile Val Asp Met Phe Ala Ala Gly
290 295 300

Thr Glu Thr Ser Ser Thr Thr Thr Val Trp Ala Met Ala Glu Met Met
305 310 315 320

Lys Asn Pro Ser Val Phe Thr Lys Ala Gln Ala Glu Val Arg Glu Ala
325 330 335

Phe Arg Asp Lys Val Ser Phe Asp Glu Asn Asp Val Glu Glu Leu Lys

```
            340                 345                 350

Tyr Leu Lys Leu Val Ile Lys Glu Thr Leu Arg Leu His Pro Pro Ser
        355                 360                 365

Pro Leu Leu Val Pro Arg Glu Cys Arg Glu Asp Thr Asp Ile Asn Gly
    370                 375                 380

Tyr Thr Ile Pro Ala Lys Thr Lys Val Met Val Asn Val Trp Ala Leu
385                 390                 395                 400

Gly Arg Asp Pro Lys Tyr Trp Asp Asp Ala Glu Ser Phe Lys Pro Glu
                405                 410                 415

Arg Phe Glu Gln Cys Ser Val Asp Phe Phe Gly Asn Asn Phe Glu Phe
            420                 425                 430

Leu Pro Phe Gly Gly Gly Arg Arg Ile Cys Pro Gly Met Ser Phe Gly
        435                 440                 445

Leu Ala Asn Leu Tyr Leu Pro Leu Ala Gln Leu Leu Tyr His Phe Asp
    450                 455                 460

Trp Lys Leu Pro Thr Gly Ile Met Pro Arg Asp Leu Asp Leu Thr Glu
465                 470                 475                 480

Leu Ser Gly Ile Thr Ile Ala Arg Lys Gly Gly Leu Tyr Leu Asn Ala
                485                 490                 495

Thr Pro Tyr Gln Pro Ser Arg Glu
            500


<210> SEQ ID NO 26
<211> LENGTH: 510
<212> TYPE: PRT
<213> ORGANISM: Nicotiani tabacum

<400> SEQUENCE: 26

Met Ala Leu Leu Leu Ala Val Phe Phe Phe Ser Leu Val Ser Ile Phe
1               5                   10                  15

Leu Phe Leu Ser Phe Leu Phe Leu Leu Arg Lys Trp Lys Asn Ser Asn
            20                  25                  30

Ser Gln Ser Lys Lys Leu Pro Pro Gly Pro Trp Lys Ile Pro Ile Leu
        35                  40                  45

Gly Ser Met Leu His Met Ile Gly Gly Glu Pro His His Val Leu Arg
    50                  55                  60

Asp Leu Ala Lys Lys Tyr Gly Pro Leu Met His Leu Gln Leu Gly Glu
65                  70                  75                  80

Ile Ser Ala Val Val Val Thr Ser Arg Asp Met Ala Lys Glu Val Leu
                85                  90                  95

Lys Thr His Asp Val Val Phe Ala Ser Arg Pro Lys Ile Val Ala Met
            100                 105                 110

Asp Ile Ile Cys Tyr Asn Gln Ser Asp Ile Ala Phe Ser Pro Tyr Gly
        115                 120                 125

Asp His Trp Arg Gln Met Arg Lys Ile Cys Val Met Glu Leu Leu Asn
    130                 135                 140

Ala Lys Asn Val Arg Ser Phe Ser Ser Ile Arg Arg Asp Glu Val Val
145                 150                 155                 160

Arg Leu Ile Asp Ser Ile Arg Ser Asp Ser Ser Ser Gly Glu Leu Val
                165                 170                 175

Asn Phe Thr Gln Arg Ile Ile Trp Phe Ala Ser Ser Met Thr Cys Arg
            180                 185                 190

Ser Ala Phe Gly Gln Val Leu Lys Gly Gln Asp Ile Phe Ala Lys Lys
        195                 200                 205
```

```
Ile Arg Glu Val Ile Gly Leu Ala Glu Gly Phe Asp Val Val Asp Ile
    210                 215                 220

Phe Pro Thr Tyr Lys Phe Leu His Val Leu Ser Gly Met Lys Arg Lys
225                 230                 235                 240

Leu Leu Asn Ala His Leu Lys Val Asp Ala Ile Val Glu Asp Val Ile
                245                 250                 255

Asn Glu His Lys Lys Asn Leu Ala Ala Gly Lys Ser Asn Gly Ala Leu
            260                 265                 270

Gly Gly Glu Asp Leu Ile Asp Val Leu Leu Arg Leu Met Asn Asp Thr
        275                 280                 285

Ser Leu Gln Phe Pro Ile Thr Asn Asp Asn Ile Lys Ala Val Ile Val
    290                 295                 300

Asp Met Phe Ala Ala Gly Thr Glu Thr Ser Ser Thr Thr Thr Val Trp
305                 310                 315                 320

Ala Met Ala Glu Met Met Lys Asn Pro Ser Val Phe Thr Lys Ala Gln
                325                 330                 335

Ala Glu Val Arg Glu Ala Phe Arg Asp Lys Val Ser Phe Asp Glu Asn
            340                 345                 350

Asp Val Glu Glu Leu Lys Tyr Leu Lys Leu Val Ile Lys Glu Thr Leu
        355                 360                 365

Arg Leu His Pro Pro Ser Pro Leu Leu Val Pro Arg Glu Cys Arg Glu
    370                 375                 380

Asp Thr Asp Ile Asn Gly Tyr Thr Ile Pro Ala Lys Thr Lys Val Met
385                 390                 395                 400

Val Asn Val Trp Ala Leu Gly Arg Asp Pro Lys Tyr Trp Asp Asp Ala
                405                 410                 415

Glu Ser Phe Lys Pro Glu Arg Phe Glu Gln Cys Ser Val Asp Phe Phe
            420                 425                 430

Gly Asn Asn Phe Glu Phe Leu Pro Phe Gly Gly Gly Arg Arg Ile Cys
        435                 440                 445

Pro Gly Met Ser Phe Gly Leu Ala Asn Leu Tyr Leu Pro Leu Ala Gln
    450                 455                 460

Leu Leu Tyr His Phe Asp Trp Lys Leu Pro Thr Gly Ile Met Pro Arg
465                 470                 475                 480

Asp Leu Asp Leu Thr Glu Leu Ser Gly Ile Thr Ile Ala Arg Lys Gly
                485                 490                 495

Gly Leu Tyr Leu Asn Ala Thr Pro Tyr Gln Pro Ser Arg Glu
            500                 505                 510


<210> SEQ ID NO 27
<211> LENGTH: 1530
<212> TYPE: DNA
<213> ORGANISM: Nicotiani tabacum

<400> SEQUENCE: 27

atggctctgt tattagcagt tttcttcttc tccctggtct caatcttcct gttcctgtcc      60

tttctgttcc tgctgcgtaa atggaaaaac tctaatagcc aatccaaaaa actgccgccg     120

ggtccgtgga aaattccgat cctgggctct atgctgcaca tgattggcgg tgaaccgcat     180

catgtgctgc gtgatctggc gaaaaaatat ggtccgctga tgcatctgca actgggcgaa     240

atctctgcgg tggttgtcac gagtcgtgac atggccaaag aagtgctgaa aacccatgat     300

gtggtttttg catctcgccc gaaaatcgtt gctatggata ttatctgcta taaccagtcg     360

gacatcgcgt tcagcccgta cggtgatcac tggcgtcaaa tgcgcaaaat ttgtgtcatg     420
```

```
gaactgctga acgccaaaaa tgtgcgcagt tttagctcta ttcgtcgtga tgaagtcgtg    480

cgtctgattg attccatccg ctcagacagt tcctcaggcg aactggtgaa ttttacgcag    540

cgtattatct ggttcgcatc gagcatgacc tgccgctcgg cttttggtca ggttctgaaa    600

ggccaagata tttttgcgaa gaaaattcgt gaagtgatcg gtctggccga aggcttcgat    660

gttgtggata tttttccgac ctataaattc ctgcatgtcc tgagcggtat gaaacgcaaa    720

ctgctgaacg cgcacctgaa agttgatgcc attgtcgaag acgtgatcaa cgaacataag    780

aaaaacctgg cggcgggtaa atccaacggc gcactgggcg gtgaagatct gattgacgtg    840

ctgctgcgtc tgatgaatga taccagcctg caatttccga tcaccaacga caacattaaa    900

gcggtgatcg ttgatatgtt cgcggcgggc accgaaacct ctagtaccac gaccgtttgg    960

gcgatggccg aaatgatgaa aaacccgtcg gtgtttacca aagcacaagc ggaagtgcgt   1020

gaagcgtttc gtgataaagt tagcttcgat gaaaatgatg tggaagaact gaaatacctg   1080

aaactggtga ttaaagaaac gctgcgtctg catccgccga gcccgctgct ggttccgcgt   1140

gaatgccgtg aagataccga cattaacggt tatacgatcc cggcaaaaac caaagtcatg   1200

gtgaatgttt gggctctggg ccgtgacccg aaatactggg atgacgcaga atcctttaaa   1260

ccggaacgct ttgaacagtg ctcagtggat ttctttggta acaactttga atttctgccg   1320

tttggcggtg gccgtcgcat ttgtccgggt atgtccttcg gcctggcgaa cctgtatctg   1380

ccgctggccc aactgctgta ccactttgat tggaaactgc cgacgggtat tatgccgcgt   1440

gatctggacc tgacggaact gtctggcatt accatcgcac gcaaaggtgg cctgtatctg   1500

aatgctaccc cgtaccagcc gagtcgtgaa                                    1530
```

```
<210> SEQ ID NO 28
<211> LENGTH: 522
<212> TYPE: PRT
<213> ORGANISM: Citrus x paradisi

<400> SEQUENCE: 28

Met Glu Leu Pro Leu Lys Ser Ile Ala Leu Thr Ile Val Ile Val Thr
1               5                   10                  15

Val Leu Thr Trp Ala Trp Arg Val Leu Asn Trp Val Trp Leu Arg Pro
            20                  25                  30

Lys Lys Leu Glu Lys Phe Leu Arg Gln Gln Gly Leu Lys Gly Asn Ser
        35                  40                  45

Tyr Arg Leu Leu Phe Gly Asp Leu Lys Glu Asn Ser Ile Glu Leu Lys
    50                  55                  60

Glu Ala Lys Ala Arg Pro Leu Ser Leu Asp Asp Ile Ala Ile Arg
65                  70                  75                  80

Val Asn Pro Phe Leu His Lys Leu Val Asn Asp Tyr Gly Lys Asn Ser
                85                  90                  95

Phe Met Trp Phe Gly Pro Thr Pro Arg Val Asn Ile Met Asn Pro Asp
            100                 105                 110

Gln Ile Lys Ala Ile Phe Thr Lys Ile Asn Asp Phe Gln Lys Val Asn
        115                 120                 125

Ser Ile Pro Leu Ala Arg Leu Leu Ile Val Gly Leu Ala Thr Leu Glu
    130                 135                 140

Gly Glu Lys Trp Ala Lys His Arg Lys Leu Ile Asn Pro Ala Phe His
145                 150                 155                 160

Gln Glu Lys Leu Lys Leu Met Leu Pro Ala Phe Tyr Leu Ser Cys Ile
                165                 170                 175
```

```
Glu Ile Ile Thr Lys Trp Glu Lys Gln Met Ser Val Glu Gly Ser Ser
            180                 185                 190

Glu Leu Asp Val Trp Pro Tyr Leu Ala Asn Leu Thr Ser Asp Val Ile
        195                 200                 205

Ser Arg Thr Ala Phe Gly Ser Ser Tyr Glu Glu Gly Arg Arg Ile Phe
    210                 215                 220

Gln Leu Gln Ala Glu Leu Ala Glu Leu Thr Met Gln Val Phe Arg Ser
225                 230                 235                 240

Val His Ile Pro Gly Trp Arg Phe Leu Pro Thr Lys Arg Asn Arg Arg
                245                 250                 255

Met Lys Glu Ile Asp Lys Glu Ile Arg Ala Ser Leu Met Gly Ile Ile
            260                 265                 270

Lys Asn Arg Glu Lys Ala Met Arg Ala Gly Glu Ala Ala Asn Asn Asp
        275                 280                 285

Leu Leu Gly Ile Leu Met Glu Thr Ser Phe Arg Glu Ile Glu Glu His
    290                 295                 300

Gly Asn Asn Lys Asn Val Gly Phe Ser Met Asn Asp Val Ile Glu Glu
305                 310                 315                 320

Cys Lys Leu Phe Tyr Phe Ala Gly Gln Glu Thr Thr Ser Val Leu Leu
                325                 330                 335

Asn Trp Thr Met Val Leu Leu Ser Lys His Gln Asp Trp Gln Glu Arg
            340                 345                 350

Ala Arg Gln Glu Val Leu Gln Val Phe Gly Asn Asn Lys Pro Asp Tyr
        355                 360                 365

Asp Gly Leu Asn His Leu Lys Ile Val Gln Met Ile Leu Tyr Glu Val
    370                 375                 380

Leu Arg Leu Tyr Pro Pro Val Thr Val Leu Ser Arg Ala Val Phe Lys
385                 390                 395                 400

Glu Thr Lys Leu Gly Asn Leu Thr Leu Pro Ala Gly Val Gln Ile Gly
                405                 410                 415

Leu Pro Met Ile Leu Val His Gln Asp Pro Glu Leu Trp Gly Asp Asp
            420                 425                 430

Ala Val Glu Phe Lys Pro Glu Arg Phe Ala Glu Gly Ile Ser Lys Ala
        435                 440                 445

Ala Lys Asn Gln Val Ser Tyr Phe Pro Phe Ala Leu Gly Pro Arg Ile
    450                 455                 460

Cys Val Gly Gln Asn Phe Ala Leu Val Glu Ala Lys Met Ala Thr Ala
465                 470                 475                 480

Met Ile Leu Gln Asn Tyr Ser Phe Glu Leu Ser Pro Ser Tyr Val His
                485                 490                 495

Ala Pro Thr Ala Val Pro Thr Leu His Pro Glu Leu Gly Thr Gln Leu
            500                 505                 510

Ile Leu Arg Lys Leu Trp Cys Lys Asn Asn
        515                 520
```

<210> SEQ ID NO 29
<211> LENGTH: 523
<212> TYPE: PRT
<213> ORGANISM: Citrus x paradisi

<400> SEQUENCE: 29

```
Met Ala Leu Leu Leu Ala Val Phe Ile Ala Leu Thr Ile Val Ile Val
1               5                   10                  15

Thr Val Leu Thr Trp Ala Trp Arg Val Leu Asn Trp Val Trp Leu Arg
            20                  25                  30
```

```
Pro Lys Lys Leu Glu Lys Phe Leu Arg Gln Gln Gly Leu Lys Gly Asn
        35                  40                  45

Ser Tyr Arg Leu Leu Phe Gly Asp Leu Lys Glu Asn Ser Ile Glu Leu
    50                  55                  60

Lys Glu Ala Lys Ala Arg Pro Leu Ser Leu Asp Asp Asp Ile Ala Ile
65                  70                  75                  80

Arg Val Asn Pro Phe Leu His Lys Leu Val Asn Asp Tyr Gly Lys Asn
                85                  90                  95

Ser Phe Met Trp Phe Gly Pro Thr Pro Arg Val Asn Ile Met Asn Pro
            100                 105                 110

Asp Gln Ile Lys Ala Ile Phe Thr Lys Ile Asn Asp Phe Gln Lys Val
        115                 120                 125

Asn Ser Ile Pro Leu Ala Arg Leu Leu Ile Val Gly Leu Ala Thr Leu
    130                 135                 140

Glu Gly Glu Lys Trp Ala Lys His Arg Lys Leu Ile Asn Pro Ala Phe
145                 150                 155                 160

His Gln Glu Lys Leu Lys Leu Met Leu Pro Ala Phe Tyr Leu Ser Cys
                165                 170                 175

Ile Glu Ile Ile Thr Lys Trp Glu Lys Gln Met Ser Val Glu Gly Ser
            180                 185                 190

Ser Glu Leu Asp Val Trp Pro Tyr Leu Ala Asn Leu Thr Ser Asp Val
        195                 200                 205

Ile Ser Arg Thr Ala Phe Gly Ser Ser Tyr Glu Glu Gly Arg Arg Ile
    210                 215                 220

Phe Gln Leu Gln Ala Glu Leu Ala Glu Leu Thr Met Gln Val Phe Arg
225                 230                 235                 240

Ser Val His Ile Pro Gly Trp Arg Phe Leu Pro Thr Lys Arg Asn Arg
                245                 250                 255

Arg Met Lys Glu Ile Asp Lys Glu Ile Arg Ala Ser Leu Met Gly Ile
            260                 265                 270

Ile Lys Asn Arg Glu Lys Ala Met Arg Ala Gly Glu Ala Ala Asn Asn
        275                 280                 285

Asp Leu Leu Gly Ile Leu Met Glu Thr Ser Phe Arg Glu Ile Glu Glu
    290                 295                 300

His Gly Asn Asn Lys Asn Val Gly Phe Ser Met Asn Asp Val Ile Glu
305                 310                 315                 320

Glu Cys Lys Leu Phe Tyr Phe Ala Gly Gln Glu Thr Thr Ser Val Leu
                325                 330                 335

Leu Asn Trp Thr Met Val Leu Leu Ser Lys His Gln Asp Trp Gln Glu
            340                 345                 350

Arg Ala Arg Gln Glu Val Leu Gln Val Phe Gly Asn Asn Lys Pro Asp
        355                 360                 365

Tyr Asp Gly Leu Asn His Leu Lys Ile Val Gln Met Ile Leu Tyr Glu
    370                 375                 380

Val Leu Arg Leu Tyr Pro Pro Val Thr Val Leu Ser Arg Ala Val Phe
385                 390                 395                 400

Lys Glu Thr Lys Leu Gly Asn Leu Thr Leu Pro Ala Gly Val Gln Ile
                405                 410                 415

Gly Leu Pro Met Ile Leu Val His Gln Asp Pro Glu Leu Trp Gly Asp
            420                 425                 430

Asp Ala Val Glu Phe Lys Pro Glu Arg Phe Ala Glu Gly Ile Ser Lys
        435                 440                 445
```

```
Ala Ala Lys Asn Gln Val Ser Tyr Phe Pro Phe Ala Leu Gly Pro Arg
    450                 455                 460

Ile Cys Val Gly Gln Asn Phe Ala Leu Val Glu Ala Lys Met Ala Thr
465                 470                 475                 480

Ala Met Ile Leu Gln Asn Tyr Ser Phe Glu Leu Ser Pro Ser Tyr Val
                485                 490                 495

His Ala Pro Thr Ala Val Pro Thr Leu His Pro Glu Leu Gly Thr Gln
            500                 505                 510

Leu Ile Leu Arg Lys Leu Trp Cys Lys Asn Asn
        515                 520
```

<210> SEQ ID NO 30
<211> LENGTH: 1569
<212> TYPE: DNA
<213> ORGANISM: Citrus x paradisi

<400> SEQUENCE: 30

```
atggctctgt tattagcagt tttcattgct ctgacgattg ttattgttac ggtgctgacc     60

tgggcgtggc gtgtgctgaa ctgggtttgg ctgcgtccga aaaaactgga aaaatttctg    120

cgccagcaag gcctgaaggg taacagctat cgtctgctgt tcggcgatct gaaagaaaat    180

tctattgaac tgaaagaagc gaaagcccgt ccgctgagtc tggatgacga tattgcaatc    240

cgcgttaacc cgtttctgca taaactggtc aacgattacg gcaaaaattc ttttatgtgg    300

ttcggtccga ccccgcgcgt gaacattatg aacccggatc agattaaagc gatctttacg    360

aaaatcaacg atttccaaaa agttaatagc attccgctgg cgcgtctgct gatcgtcggc    420

ctggccaccc tggaaggtga aaaatgggca aaacatcgca aactgattaa cccggctttt    480

caccaagaaa aactgaaact gatgctgccg gcgttctatc tgtcctgcat cgaaattatc    540

acgaaatggg aaaaacagat gtcagtggaa ggtagctctg aactggacgt ttggccgtat    600

ctggccaatc tgaccagcga tgttatttct cgtacggcat ttggcagttc ctacgaagaa    660

ggtcgtcgca tcttccagtt acaggcggaa ctggccgaac tgaccatgca ggtttttcgt    720

tctgtccata ttccgggctg gcgtttcctg ccgacgaaac gcaaccgtcg catgaaagaa    780

attgacaaag aaatccgcgc cagtctgatg ggtattatca aaaatcgtga aaaagcaatg    840

cgcgctggcg aagcggccaa caatgatctg ctgggtattc tgatggaaac cagctttcgt    900

gaaatcgaag aacacggcaa caataaaaac gtcggtttca gcatgaatga cgtgatcgaa    960

gaatgtaaac tgttttattt cgctggccag gaaaccacgt cagttctgct gaactggacg   1020

atggtgctgc tgtcgaaaca tcaggattgg caagaacgtg cccgccagga agtcctgcaa   1080

gtgtttggca acaataaacc ggactacgat ggtctgaacc acctgaaaat tgtgcagatg   1140

atcctgtatg aagttctgcg tctgtatccg ccggtgacgg tgctgagccg tgcggtgttt   1200

aaagaaacca aactgggtaa tctgacgctg ccggcaggcg tccagattgg tctgccgatg   1260

atcctggtgc accaggaccc ggaactgtgg ggcgacgatg ctgtggaatt taaaccggaa   1320

cgtttcgcgg aaggtattag taaagcagct aaaaatcagg tttcctattt tccgttcgcg   1380

ctgggtccgc gtatttgcgt cggtcaaaac tttgcactgg tggaagctaa aatggcaacc   1440

gctatgatcc tgcaaaatta tagctttgaa ctgtcaccga gctatgttca tgcgccgacc   1500

gccgttccga cgctgcaccc ggaactgggc acgcaactga ttctgcgtaa actgtggtgt   1560

aaaaacaat                                                           1569
```

<210> SEQ ID NO 31

<211> LENGTH: 495
<212> TYPE: PRT
<213> ORGANISM: Artemesia annua

<400> SEQUENCE: 31

```
Met Lys Ser Ile Leu Lys Ala Met Ala Leu Ser Leu Thr Thr Ser Ile
1               5                   10                  15

Ala Leu Ala Thr Ile Leu Leu Phe Val Tyr Lys Phe Ala Thr Arg Ser
            20                  25                  30

Lys Ser Thr Lys Lys Ser Leu Pro Glu Pro Trp Arg Leu Pro Ile Ile
        35                  40                  45

Gly His Met His His Leu Ile Gly Thr Thr Pro His Arg Gly Val Arg
    50                  55                  60

Asp Leu Ala Arg Lys Tyr Gly Ser Leu Met His Leu Gln Leu Gly Glu
65                  70                  75                  80

Val Pro Thr Ile Val Val Ser Ser Pro Lys Trp Ala Lys Glu Ile Leu
                85                  90                  95

Thr Thr Tyr Asp Ile Thr Phe Ala Asn Arg Pro Glu Thr Leu Thr Gly
            100                 105                 110

Glu Ile Val Leu Tyr His Asn Thr Asp Val Val Leu Ala Pro Tyr Gly
        115                 120                 125

Glu Tyr Trp Arg Gln Leu Arg Lys Ile Cys Thr Leu Glu Leu Leu Ser
    130                 135                 140

Val Lys Lys Val Lys Ser Phe Gln Ser Leu Arg Glu Glu Glu Cys Trp
145                 150                 155                 160

Asn Leu Val Gln Glu Ile Lys Ala Ser Gly Ser Gly Arg Pro Val Asn
                165                 170                 175

Leu Ser Glu Asn Val Phe Lys Leu Ile Ala Thr Ile Leu Ser Arg Ala
            180                 185                 190

Ala Phe Gly Lys Gly Ile Lys Asp Gln Lys Glu Leu Thr Glu Ile Val
        195                 200                 205

Lys Glu Ile Leu Arg Gln Thr Gly Gly Phe Asp Val Ala Asp Ile Phe
    210                 215                 220

Pro Ser Lys Lys Phe Leu His His Leu Ser Gly Lys Arg Ala Arg Leu
225                 230                 235                 240

Thr Ser Leu Arg Lys Lys Ile Asp Asn Leu Ile Asp Asn Leu Val Ala
                245                 250                 255

Glu His Thr Val Asn Thr Ser Ser Lys Thr Asn Glu Thr Leu Leu Asp
            260                 265                 270

Val Leu Leu Arg Leu Lys Asp Ser Ala Glu Phe Pro Leu Thr Ser Asp
        275                 280                 285

Asn Ile Lys Ala Ile Ile Leu Asp Met Phe Gly Ala Gly Thr Asp Thr
    290                 295                 300

Ser Ser Ser Thr Ile Glu Trp Ala Ile Ser Glu Leu Ile Lys Cys Pro
305                 310                 315                 320

Lys Ala Met Glu Lys Val Gln Ala Glu Leu Arg Lys Ala Leu Asn Gly
                325                 330                 335

Lys Glu Lys Ile His Glu Glu Asp Ile Gln Glu Leu Ser Tyr Leu Asn
            340                 345                 350

Met Val Ile Lys Glu Thr Leu Arg Leu His Pro Pro Leu Pro Leu Val
        355                 360                 365

Leu Pro Arg Glu Cys Arg Gln Pro Val Asn Leu Ala Gly Tyr Asn Ile
    370                 375                 380

Pro Asn Lys Thr Lys Leu Ile Val Asn Val Phe Ala Ile Asn Arg Asp
```

-continued

```
385                 390                 395                 400

Pro Glu Tyr Trp Lys Asp Ala Glu Ala Phe Ile Pro Glu Arg Phe Glu
                405                 410                 415

Asn Ser Ser Ala Thr Val Met Gly Ala Glu Tyr Glu Tyr Leu Pro Phe
            420                 425                 430

Gly Ala Gly Arg Arg Met Cys Pro Gly Ala Ala Leu Gly Leu Ala Asn
        435                 440                 445

Val Gln Leu Pro Leu Ala Asn Ile Leu Tyr His Phe Asn Trp Lys Leu
    450                 455                 460

Pro Asn Gly Val Ser Tyr Asp Gln Ile Asp Met Thr Glu Ser Ser Gly
465                 470                 475                 480

Ala Thr Met Gln Arg Lys Thr Glu Leu Leu Leu Val Pro Ser Phe
                485                 490                 495


<210> SEQ ID NO 32
<211> LENGTH: 488
<212> TYPE: PRT
<213> ORGANISM: Artemesia annua

<400> SEQUENCE: 32

Met Ala Leu Leu Leu Ala Val Phe Ile Ala Leu Ala Thr Ile Leu Leu
1               5                   10                  15

Phe Val Tyr Lys Phe Ala Thr Arg Ser Lys Ser Thr Lys Lys Ser Leu
            20                  25                  30

Pro Glu Pro Trp Arg Leu Pro Ile Ile Gly His Met His His Leu Ile
        35                  40                  45

Gly Thr Thr Pro His Arg Gly Val Arg Asp Leu Ala Arg Lys Tyr Gly
    50                  55                  60

Ser Leu Met His Leu Gln Leu Gly Glu Val Pro Thr Ile Val Val Ser
65                  70                  75                  80

Ser Pro Lys Trp Ala Lys Glu Ile Leu Thr Thr Tyr Asp Ile Thr Phe
                85                  90                  95

Ala Asn Arg Pro Glu Thr Leu Thr Gly Glu Ile Val Leu Tyr His Asn
            100                 105                 110

Thr Asp Val Val Leu Ala Pro Tyr Gly Glu Tyr Trp Arg Gln Leu Arg
        115                 120                 125

Lys Ile Cys Thr Leu Glu Leu Leu Ser Val Lys Lys Val Lys Ser Phe
    130                 135                 140

Gln Ser Leu Arg Glu Glu Glu Cys Trp Asn Leu Val Gln Glu Ile Lys
145                 150                 155                 160

Ala Ser Gly Ser Gly Arg Pro Val Asn Leu Ser Glu Asn Val Phe Lys
                165                 170                 175

Leu Ile Ala Thr Ile Leu Ser Arg Ala Ala Phe Gly Lys Gly Ile Lys
            180                 185                 190

Asp Gln Lys Glu Leu Thr Glu Ile Val Lys Glu Ile Leu Arg Gln Thr
        195                 200                 205

Gly Gly Phe Asp Val Ala Asp Ile Phe Pro Ser Lys Lys Phe Leu His
    210                 215                 220

His Leu Ser Gly Lys Arg Ala Arg Leu Thr Ser Leu Arg Lys Lys Ile
225                 230                 235                 240

Asp Asn Leu Ile Asp Asn Leu Val Ala Glu His Thr Val Asn Thr Ser
                245                 250                 255

Ser Lys Thr Asn Glu Thr Leu Leu Asp Val Leu Leu Arg Leu Lys Asp
            260                 265                 270
```

```
Ser Ala Glu Phe Pro Leu Thr Ser Asp Asn Ile Lys Ala Ile Ile Leu
        275                 280                 285

Asp Met Phe Gly Ala Gly Thr Asp Thr Ser Ser Ser Thr Ile Glu Trp
    290                 295                 300

Ala Ile Ser Glu Leu Ile Lys Cys Pro Lys Ala Met Glu Lys Val Gln
305                 310                 315                 320

Ala Glu Leu Arg Lys Ala Leu Asn Gly Lys Glu Lys Ile His Glu Glu
                325                 330                 335

Asp Ile Gln Glu Leu Ser Tyr Leu Asn Met Val Ile Lys Glu Thr Leu
            340                 345                 350

Arg Leu His Pro Pro Leu Pro Leu Val Leu Pro Arg Glu Cys Arg Gln
        355                 360                 365

Pro Val Asn Leu Ala Gly Tyr Asn Ile Pro Asn Lys Thr Lys Leu Ile
    370                 375                 380

Val Asn Val Phe Ala Ile Asn Arg Asp Pro Glu Tyr Trp Lys Asp Ala
385                 390                 395                 400

Glu Ala Phe Ile Pro Glu Arg Phe Glu Asn Ser Ser Ala Thr Val Met
                405                 410                 415

Gly Ala Glu Tyr Glu Tyr Leu Pro Phe Gly Ala Gly Arg Arg Met Cys
            420                 425                 430

Pro Gly Ala Ala Leu Gly Leu Ala Asn Val Gln Leu Pro Leu Ala Asn
        435                 440                 445

Ile Leu Tyr His Phe Asn Trp Lys Leu Pro Asn Gly Val Ser Tyr Asp
    450                 455                 460

Gln Ile Asp Met Thr Glu Ser Ser Gly Ala Thr Met Gln Arg Lys Thr
465                 470                 475                 480

Glu Leu Leu Leu Val Pro Ser Phe
                485
```

<210> SEQ ID NO 33
<211> LENGTH: 1464
<212> TYPE: DNA
<213> ORGANISM: Artemesia annua

<400> SEQUENCE: 33

```
atggctctgt tattagcagt tttcatcgca ctggcaacca ttctgctgtt tgtgtataaa      60

ttcgctaccc gttccaaatc aacgaaaaaa tcactgccgg aaccgtggcg cctgccgatt     120

atcggtcaca tgcatcacct gatcggcacc accccgcatc gtggcgtgcg tgatctggca     180

cgcaaatatg gctcgctgat gcatctgcaa ctgggtgaag tcccgaccat tgtggttagc     240

tctccgaaat gggcgaaaga aatcctgacc acctatgata ttacctttgc caaccgcccg     300

gaaaccctga cgggcgaaat cgtgctgtac cacaatacgg atgtggtgct ggcgccgtat     360

ggtgaatact ggcgtcaact gcgtaaaatt tgcaccctgg aactgctgag tgtgaaaaaa     420

gttaaatctt tccagagcct gcgtgaagaa gaatgttgga acctggttca agaaattaaa     480

gcatcgggca gcggtcgccc ggttaacctg agtgaaaatg tctttaaact gattgctacc     540

atcctgtccc gtgcggcctt cggcaaaggt atcaaagatc agaaagaact gaccgaaatt     600

gtcaaagaaa tcctgcgcca aacgggcggt tttgatgtgg cggacatttt tccgtcgaaa     660

aaattcctgc atcacctgag cggtaaacgt gcccgcctga ccagcctgcg taagaaaatt     720

gataacctga tcgacaatct ggtcgcggaa cataccgtga acacgagttc caaaaccaat     780

gaaacgctgc tggatgtgct gctgcgcctg aaagactccg ccgaatttcc gctgacctca     840

gataatatca aagcgattat cctggatatg ttcggtgcag gcaccgatac cagcagcagc     900
```

```
accattgaat gggcaatctc agaactgatt aaatgcccga aagctatgga aaaagtccag    960

gcagaactgc gcaaagctct gaacggcaaa gaaaaaatcc atgaagaaga tattcaagaa   1020

ctgtcttacc tgaacatggt tatcaaagaa accctgcgtc tgcacccgcc gctgccgctg   1080

gtgctgccgc gtgaatgtcg ccagccggtt aacctggcag gctataacat cccgaataaa   1140

acgaaactga tcgttaacgt ctttgctatt aaccgtgacc cggaatactg gaaagacgcg   1200

gaagccttta tcccggaacg ctttgaaaac agcagcgcga ccgtgatggg tgccgaatat   1260

gaatacctgc cgtttggcgc gggtcgtcgc atgtgtccgg gcgcagctct gggtctggca   1320

aacgtgcaac tgccgctggc taatatcctg tatcacttca actggaaact gccgaatggc   1380

gttagctacg atcaaattga catgaccgaa agctcaggtg ccacgatgca acgcaaaacc   1440

gaactgctgc tggtgccgtc cttc                                          1464


<210> SEQ ID NO 34
<211> LENGTH: 509
<212> TYPE: PRT
<213> ORGANISM: Arabidopsis thaliana

<400> SEQUENCE: 34

Met Ala Phe Phe Ser Met Ile Ser Ile Leu Leu Gly Phe Val Ile Ser
1               5                   10                  15

Ser Phe Ile Phe Ile Phe Phe Phe Lys Lys Leu Leu Ser Phe Ser Arg
            20                  25                  30

Lys Asn Met Ser Glu Val Ser Thr Leu Pro Ser Val Pro Val Val Pro
        35                  40                  45

Gly Phe Pro Val Ile Gly Asn Leu Leu Gln Leu Lys Glu Lys Lys Pro
    50                  55                  60

His Lys Thr Phe Thr Arg Trp Ser Glu Ile Tyr Gly Pro Ile Tyr Ser
65                  70                  75                  80

Ile Lys Met Gly Ser Ser Ser Leu Ile Val Leu Asn Ser Thr Glu Thr
                85                  90                  95

Ala Lys Glu Ala Met Val Thr Arg Phe Ser Ser Ile Ser Thr Arg Lys
            100                 105                 110

Leu Ser Asn Ala Leu Thr Val Leu Thr Cys Asp Lys Ser Met Val Ala
        115                 120                 125

Thr Ser Asp Tyr Asp Asp Phe His Lys Leu Val Lys Arg Cys Leu Leu
    130                 135                 140

Asn Gly Leu Leu Gly Ala Asn Ala Gln Lys Arg Lys Arg His Tyr Arg
145                 150                 155                 160

Asp Ala Leu Ile Glu Asn Val Ser Ser Lys Leu His Ala His Ala Arg
                165                 170                 175

Asp His Pro Gln Glu Pro Val Asn Phe Arg Ala Ile Phe Glu His Glu
            180                 185                 190

Leu Phe Gly Val Ala Leu Lys Gln Ala Phe Gly Lys Asp Val Glu Ser
        195                 200                 205

Ile Tyr Val Lys Glu Leu Gly Val Thr Leu Ser Lys Asp Glu Ile Phe
    210                 215                 220

Lys Val Leu Val His Asp Met Met Glu Gly Ala Ile Asp Val Asp Trp
225                 230                 235                 240

Arg Asp Phe Phe Pro Tyr Leu Lys Trp Ile Pro Asn Lys Ser Phe Glu
                245                 250                 255

Ala Arg Ile Gln Gln Lys His Lys Arg Arg Leu Ala Val Met Asn Ala
            260                 265                 270
```

Leu Ile Gln Asp Arg Leu Lys Gln Asn Gly Ser Glu Ser Asp Asp Asp
275 280 285

Cys Tyr Leu Asn Phe Leu Met Ser Glu Ala Lys Thr Leu Thr Lys Glu
290 295 300

Gln Ile Ala Ile Leu Val Trp Glu Thr Ile Ile Glu Thr Ala Asp Thr
305 310 315 320

Thr Leu Val Thr Thr Glu Trp Ala Ile Tyr Glu Leu Ala Lys His Pro
325 330 335

Ser Val Gln Asp Arg Leu Cys Lys Glu Ile Gln Asn Val Cys Gly Gly
340 345 350

Glu Lys Phe Lys Glu Glu Gln Leu Ser Gln Val Pro Tyr Leu Asn Gly
355 360 365

Val Phe His Glu Thr Leu Arg Lys Tyr Ser Pro Ala Pro Leu Val Pro
370 375 380

Ile Arg Tyr Ala His Glu Asp Thr Gln Ile Gly Gly Tyr His Val Pro
385 390 395 400

Ala Gly Ser Glu Ile Ala Ile Asn Ile Tyr Gly Cys Asn Met Asp Lys
405 410 415

Lys Arg Trp Glu Arg Pro Glu Asp Trp Trp Pro Glu Arg Phe Leu Asp
420 425 430

Asp Gly Lys Tyr Glu Thr Ser Asp Leu His Lys Thr Met Ala Phe Gly
435 440 445

Ala Gly Lys Arg Val Cys Ala Gly Ala Leu Gln Ala Ser Leu Met Ala
450 455 460

Gly Ile Ala Ile Gly Arg Leu Val Gln Glu Phe Glu Trp Lys Leu Arg
465 470 475 480

Asp Gly Glu Glu Glu Asn Val Asp Thr Tyr Gly Leu Thr Ser Gln Lys
485 490 495

Leu Tyr Pro Leu Met Ala Ile Ile Asn Pro Arg Arg Ser
500 505

<210> SEQ ID NO 35
<211> LENGTH: 513
<212> TYPE: PRT
<213> ORGANISM: Arabidopsis thaliana

<400> SEQUENCE: 35

Met Ala Leu Leu Leu Ala Val Phe Ser Met Ile Ser Ile Leu Leu Gly
1 5 10 15

Phe Val Ile Ser Ser Phe Ile Phe Ile Phe Phe Phe Lys Lys Leu Leu
20 25 30

Ser Phe Ser Arg Lys Asn Met Ser Glu Val Ser Thr Leu Pro Ser Val
35 40 45

Pro Val Val Pro Gly Phe Pro Val Ile Gly Asn Leu Leu Gln Leu Lys
50 55 60

Glu Lys Lys Pro His Lys Thr Phe Thr Arg Trp Ser Glu Ile Tyr Gly
65 70 75 80

Pro Ile Tyr Ser Ile Lys Met Gly Ser Ser Ser Leu Ile Val Leu Asn
85 90 95

Ser Thr Glu Thr Ala Lys Glu Ala Met Val Thr Arg Phe Ser Ser Ile
100 105 110

Ser Thr Arg Lys Leu Ser Asn Ala Leu Thr Val Leu Thr Cys Asp Lys
115 120 125

Ser Met Val Ala Thr Ser Asp Tyr Asp Asp Phe His Lys Leu Val Lys

-continued

```
    130                 135                 140

Arg Cys Leu Leu Asn Gly Leu Leu Gly Ala Asn Ala Gln Lys Arg Lys
145                 150                 155                 160

Arg His Tyr Arg Asp Ala Leu Ile Glu Asn Val Ser Ser Lys Leu His
                165                 170                 175

Ala His Ala Arg Asp His Pro Gln Glu Pro Val Asn Phe Arg Ala Ile
            180                 185                 190

Phe Glu His Glu Leu Phe Gly Val Ala Leu Lys Gln Ala Phe Gly Lys
        195                 200                 205

Asp Val Glu Ser Ile Tyr Val Lys Glu Leu Gly Val Thr Leu Ser Lys
    210                 215                 220

Asp Glu Ile Phe Lys Val Leu Val His Asp Met Met Glu Gly Ala Ile
225                 230                 235                 240

Asp Val Asp Trp Arg Asp Phe Phe Pro Tyr Leu Lys Trp Ile Pro Asn
                245                 250                 255

Lys Ser Phe Glu Ala Arg Ile Gln Gln Lys His Lys Arg Arg Leu Ala
            260                 265                 270

Val Met Asn Ala Leu Ile Gln Asp Arg Leu Lys Gln Asn Gly Ser Glu
        275                 280                 285

Ser Asp Asp Asp Cys Tyr Leu Asn Phe Leu Met Ser Glu Ala Lys Thr
    290                 295                 300

Leu Thr Lys Glu Gln Ile Ala Ile Leu Val Trp Glu Thr Ile Ile Glu
305                 310                 315                 320

Thr Ala Asp Thr Thr Leu Val Thr Thr Glu Trp Ala Ile Tyr Glu Leu
                325                 330                 335

Ala Lys His Pro Ser Val Gln Asp Arg Leu Cys Lys Glu Ile Gln Asn
            340                 345                 350

Val Cys Gly Gly Glu Lys Phe Lys Glu Glu Gln Leu Ser Gln Val Pro
        355                 360                 365

Tyr Leu Asn Gly Val Phe His Glu Thr Leu Arg Lys Tyr Ser Pro Ala
    370                 375                 380

Pro Leu Val Pro Ile Arg Tyr Ala His Glu Asp Thr Gln Ile Gly Gly
385                 390                 395                 400

Tyr His Val Pro Ala Gly Ser Glu Ile Ala Ile Asn Ile Tyr Gly Cys
                405                 410                 415

Asn Met Asp Lys Lys Arg Trp Glu Arg Pro Glu Asp Trp Trp Pro Glu
            420                 425                 430

Arg Phe Leu Asp Asp Gly Lys Tyr Glu Thr Ser Asp Leu His Lys Thr
        435                 440                 445

Met Ala Phe Gly Ala Gly Lys Arg Val Cys Ala Gly Ala Leu Gln Ala
    450                 455                 460

Ser Leu Met Ala Gly Ile Ala Ile Gly Arg Leu Val Gln Glu Phe Glu
465                 470                 475                 480

Trp Lys Leu Arg Asp Gly Glu Glu Glu Asn Val Asp Thr Tyr Gly Leu
                485                 490                 495

Thr Ser Gln Lys Leu Tyr Pro Leu Met Ala Ile Ile Asn Pro Arg Arg
            500                 505                 510

Ser
```

<210> SEQ ID NO 36
<211> LENGTH: 1539
<212> TYPE: DNA
<213> ORGANISM: Arabidopsis thaliana -continued

<400> SEQUENCE: 36

```
atggctctgt tattagcagt tttttcgatg atttctatcc tgctgggctt tgttatctcg     60
tcctttatct ttatcttctt cttcaaaaaa ctgctgtcgt tttctcgtaa aaacatgtcc    120
gaagtttcaa ccctgccgag tgtcccggtg gttccgggtt ttccggttat cggtaatctg    180
ctgcagctga aagaaaagaa accgcataag accttcacgc gctggtccga aatctatggc    240
ccgatctact caattaaaat gggtagctct agtctgattg tgctgaactc taccgaaacg    300
gcaaaagaag ctatggttac ccgtttttcc tcaatttcga cgcgcaagct gagcaatgcg    360
ctgaccgtcc tgacgtgcga caaatctatg gtggccacca gtgattacga tgacttccat    420
aaactggtta agcgttgtct gctgaacggc ctgctgggtg cgaatgccca gaagcgtaag    480
cgccactatc gcgacgccct gattgaaaac gtgtcgagca aactgcatgc acacgctcgt    540
gatcatccgc aggaaccggt caattttcgc gcaatcttcg aacacgaact gtttggcgtg    600
gcgctgaaac aagccttcgg caaggatgtt gaatcgattt acgtcaaaga actgggcgtg    660
accctgagca aagacgaaat ctttaaggtc ctggtgcatg atatgatgga aggtgcaatt    720
gacgttgatt ggcgtgattt ctttccgtat ctgaaatgga ttccgaacaa gtcattcgaa    780
gctcgcattc agcaaaaaca caagcgtcgc ctggcagtga tgaacgctct gattcaggat    840
cgtctgaaac aaaatggctc tgaaagtgat gacgattgct atctgaattt tctgatgtcc    900
gaagcaaaaa ccctgacgaa ggaacagatt gctatcctgg tttgggaaac cattatcgaa    960
acggcggaca ccacgctggt caccacggaa tgggcgatct acgaactggc caagcatccg   1020
agcgttcagg atcgcctgtg caaagaaatt caaaacgtct gtggcggtga aaaatttaag   1080
gaagaacagc tgtcgcaagt gccgtatctg aatggtgttt tccacgaaac cctgcgtaaa   1140
tatagcccgg caccgctggt cccgatccgt tacgcccatg aagataccca gattggcggt   1200
tatcacgtgc cggcaggcag tgaaattgct atcaacattt acggttgcaa tatggacaaa   1260
aagcgttggg aacgcccgga agattggtgg ccggaacgtt ttctggacga tggcaaatat   1320
gaaacctctg atctgcataa gacgatggcg ttcggtgcag gtaaacgtgt gtgtgcaggt   1380
gcactgcaag caagtctgat ggcaggcatc gctattggtc gtctggtgca agaatttgaa   1440
tggaaactgc gcgacggcga agaagaaaac gttgatacct atggtctgac gtcccagaaa   1500
ctgtacccgc tgatggccat tatcaatccg cgtcgctca                          1539
```

<210> SEQ ID NO 37
<211> LENGTH: 513
<212> TYPE: PRT
<213> ORGANISM: Stevia rebaudiana

<400> SEQUENCE: 37

```
Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
            20                  25                  30

Leu Lys Ser Tyr Thr Ser Ala Arg Arg Ser Gln Ser Asn His Leu Pro
        35                  40                  45

Arg Val Pro Glu Val Pro Gly Val Pro Leu Leu Gly Asn Leu Leu Gln
    50                  55                  60

Leu Lys Glu Lys Lys Pro Tyr Met Thr Phe Thr Arg Trp Ala Ala Thr
65                  70                  75                  80

Tyr Gly Pro Ile Tyr Ser Ile Lys Thr Gly Ala Thr Ser Met Val Val
                85                  90                  95
```

-continued

```
Val Ser Ser Asn Glu Ile Ala Lys Glu Ala Leu Val Thr Arg Phe Gln
            100                 105                 110

Ser Ile Ser Thr Arg Asn Leu Ser Lys Ala Leu Lys Val Leu Thr Ala
        115                 120                 125

Asp Lys Thr Met Val Ala Met Ser Asp Tyr Asp Asp Tyr His Lys Thr
    130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                165                 170                 175

Leu His Glu Phe Val Lys Asn Asn Pro Glu Gln Glu Glu Val Asp Leu
            180                 185                 190

Arg Lys Ile Phe Gln Ser Glu Leu Phe Gly Leu Ala Met Arg Gln Ala
        195                 200                 205

Leu Gly Lys Asp Val Glu Ser Leu Tyr Val Glu Asp Leu Lys Ile Thr
    210                 215                 220

Met Asn Arg Asp Glu Ile Phe Gln Val Leu Val Val Asp Pro Met Met
225                 230                 235                 240

Gly Ala Ile Asp Val Asp Trp Arg Asp Phe Phe Pro Tyr Leu Lys Trp
                245                 250                 255

Val Pro Asn Lys Lys Phe Glu Asn Thr Ile Gln Gln Met Tyr Ile Arg
            260                 265                 270

Arg Glu Ala Val Met Lys Ser Leu Ile Lys Glu His Lys Lys Arg Ile
        275                 280                 285

Ala Ser Gly Glu Lys Leu Asn Ser Tyr Ile Asp Tyr Leu Leu Ser Glu
    290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
                325                 330                 335

Tyr Glu Leu Ala Lys Asn Pro Lys Leu Gln Asp Arg Leu Tyr Arg Asp
            340                 345                 350

Ile Lys Ser Val Cys Gly Ser Glu Lys Ile Thr Glu Glu His Leu Ser
        355                 360                 365

Gln Leu Pro Tyr Ile Thr Ala Ile Phe His Glu Thr Leu Arg Arg His
    370                 375                 380

Ser Pro Val Pro Ile Ile Pro Leu Arg His Val His Glu Asp Thr Val
385                 390                 395                 400

Leu Gly Gly Tyr His Val Pro Ala Gly Thr Glu Leu Ala Val Asn Ile
                405                 410                 415

Tyr Gly Cys Asn Met Asp Lys Asn Val Trp Glu Asn Pro Glu Glu Trp
            420                 425                 430

Asn Pro Glu Arg Phe Met Lys Glu Asn Glu Thr Ile Asp Phe Gln Lys
        435                 440                 445

Thr Met Ala Phe Gly Gly Gly Lys Arg Val Cys Ala Gly Ser Leu Gln
    450                 455                 460

Ala Leu Leu Thr Ala Ser Ile Gly Ile Gly Arg Met Val Gln Glu Phe
465                 470                 475                 480

Glu Trp Lys Leu Lys Asp Met Thr Gln Glu Glu Val Asn Thr Ile Gly
                485                 490                 495

Leu Thr Thr Gln Met Leu Arg Pro Leu Arg Ala Ile Ile Lys Pro Arg
            500                 505                 510
```

Ile

<210> SEQ ID NO 38
<211> LENGTH: 501
<212> TYPE: PRT
<213> ORGANISM: Stevia rebaudiana

<400> SEQUENCE: 38

```
Met Ala Leu Leu Leu Ala Val Phe Ala Val Ala Leu Ala Val Ala Leu
1               5                   10                  15

Ile Phe Trp Tyr Leu Lys Ser Tyr Thr Ser Ala Arg Arg Ser Gln Ser
            20                  25                  30

Asn His Leu Pro Arg Val Pro Glu Val Pro Gly Val Pro Leu Leu Gly
        35                  40                  45

Asn Leu Leu Gln Leu Lys Glu Lys Lys Pro Tyr Met Thr Phe Thr Arg
    50                  55                  60

Trp Ala Ala Thr Tyr Gly Pro Ile Tyr Ser Ile Lys Thr Gly Ala Thr
65                  70                  75                  80

Ser Met Val Val Val Ser Ser Asn Glu Ile Ala Lys Glu Ala Leu Val
                85                  90                  95

Thr Arg Phe Gln Ser Ile Ser Thr Arg Asn Leu Ser Lys Ala Leu Lys
            100                 105                 110

Val Leu Thr Ala Asp Lys Thr Met Val Ala Met Ser Asp Tyr Asp Asp
        115                 120                 125

Tyr His Lys Thr Val Lys Arg His Ile Leu Thr Ala Val Leu Gly Pro
    130                 135                 140

Asn Ala Gln Lys Lys His Arg Ile His Arg Asp Ile Met Met Asp Asn
145                 150                 155                 160

Ile Ser Thr Gln Leu His Glu Phe Val Lys Asn Asn Pro Glu Gln Glu
                165                 170                 175

Glu Val Asp Leu Arg Lys Ile Phe Gln Ser Glu Leu Phe Gly Leu Ala
            180                 185                 190

Met Arg Gln Ala Leu Gly Lys Asp Val Glu Ser Leu Tyr Val Glu Asp
        195                 200                 205

Leu Lys Ile Thr Met Asn Arg Asp Glu Ile Phe Gln Val Leu Val Val
    210                 215                 220

Asp Pro Met Met Gly Ala Ile Asp Val Asp Trp Arg Asp Phe Phe Pro
225                 230                 235                 240

Tyr Leu Lys Trp Val Pro Asn Lys Lys Phe Glu Asn Thr Ile Gln Gln
                245                 250                 255

Met Tyr Ile Arg Arg Glu Ala Val Met Lys Ser Leu Ile Lys Glu His
            260                 265                 270

Lys Lys Arg Ile Ala Ser Gly Glu Lys Leu Asn Ser Tyr Ile Asp Tyr
        275                 280                 285

Leu Leu Ser Glu Ala Gln Thr Leu Thr Asp Gln Gln Leu Leu Met Ser
    290                 295                 300

Leu Trp Glu Pro Ile Ile Glu Ser Ser Asp Thr Thr Met Val Thr Thr
305                 310                 315                 320

Glu Trp Ala Met Tyr Glu Leu Ala Lys Asn Pro Lys Leu Gln Asp Arg
                325                 330                 335

Leu Tyr Arg Asp Ile Lys Ser Val Cys Gly Ser Glu Lys Ile Thr Glu
            340                 345                 350

Glu His Leu Ser Gln Leu Pro Tyr Ile Thr Ala Ile Phe His Glu Thr
        355                 360                 365
```

```
Leu Arg Arg His Ser Pro Val Pro Ile Ile Pro Leu Arg His Val His
    370                 375                 380

Glu Asp Thr Val Leu Gly Gly Tyr His Val Pro Ala Gly Thr Glu Leu
385                 390                 395                 400

Ala Val Asn Ile Tyr Gly Cys Asn Met Asp Lys Asn Val Trp Glu Asn
                405                 410                 415

Pro Glu Glu Trp Asn Pro Glu Arg Phe Met Lys Glu Asn Glu Thr Ile
            420                 425                 430

Asp Phe Gln Lys Thr Met Ala Phe Gly Gly Gly Lys Arg Val Cys Ala
        435                 440                 445

Gly Ser Leu Gln Ala Leu Leu Thr Ala Ser Ile Gly Ile Gly Arg Met
    450                 455                 460

Val Gln Glu Phe Glu Trp Lys Leu Lys Asp Met Thr Gln Glu Glu Val
465                 470                 475                 480

Asn Thr Ile Gly Leu Thr Thr Gln Met Leu Arg Pro Leu Arg Ala Ile
                485                 490                 495

Ile Lys Pro Arg Ile
            500


<210> SEQ ID NO 39
<211> LENGTH: 1503
<212> TYPE: DNA
<213> ORGANISM: Stevia rebaudiana

<400> SEQUENCE: 39

atggctctgt tattagcagt ttttgccgtc gctctggcgg tagcactgat cttctggtat      60

ctgaaatctt acactagcgc gcgccgctct cagtccaacc acctgccgcg tgtgccggaa     120

gttccgggtg tgccactgct gggcaacctg ctgcaactga aagaaaagaa accgtacatg     180

acctttaccc gctgggcagc gacttatggt cctatctaca gcattaaaac cggcgctacg     240

tctatggttg tggtttcttc caacgaaatc gcgaaagaag ccctggtgac tcgtttccag     300

tccattagca cccgcaacct gtccaaagcg ctgaaggttc tgacggctga caagactatg     360

gtggctatga gcgactatga tgactaccac aaaaccgtta aacgtcacat cctgaccgca     420

gtactgggtc cgaacgcaca gaaaaaacat cgcatccacc gcgacattat gatggataac     480

atctccacgc agctgcatga gttcgttaag aacaatccag aacaggaaga ggtagatctg     540

cgtaaaattt ttcagtccga actgttcggt ctggctatgc gtcaggcgct gggcaaagac     600

gttgaaagcc tgtatgtcga agacctgaaa attaccatga accgtgatga gatcttccag     660

gttctggttg tagatccgat gatgggcgcc atcgacgtgg attggcgtga cttctttccg     720

tacctgaaat gggtcccgaa caagaagttc gaaaacacca tccagcaaat gtacatccgt     780

cgtgaagcgg tgatgaaaag cctgatcaaa gaacacaaaa agcgtattgc ttctggtgag     840

aaactgaact cctacatcga ttatctgctg tccgaagcgc agaccctgac cgaccaacag     900

ctgctgatgt ctctgtggga accgattatc gaaagcagcg acaccactat ggtcactacc     960

gaatgggcaa tgtatgagct ggccaaaaac ccgaaactgc aggatcgtct gtaccgtgac    1020

atcaaaagcg tttgcggctc cgagaaaatc actgaagaac acctgtctca gctgccgtac    1080

atcactgcta ttttccacga aaccctgcgt cgccattctc cggttccgat cattccgctg    1140

cgtcacgttc acgaagatac tgtgctgggt ggttaccatg taccggcagg cactgaactg    1200

gctgtcaaca tctacggctg taacatggat aaaaacgttt gggagaatcc tgaagaatgg    1260

aacccggaac gcttcatgaa agagaacgaa accatcgact tccagaaaac gatggctttc    1320
```

```
ggcggtggta aacgtgtgtg cgcaggttct ctgcaggcgc tgctgacggc gtccattggt   1380

atcggtcgca tggtacagga atttgaatgg aagctgaaag acatgaccca agaagaggtg   1440

aataccattg gtctgactac ccagatgctg cgtccactgc gtgcaatcat caaacctcgt   1500

att                                                                 1503


<210> SEQ ID NO 40
<211> LENGTH: 546
<212> TYPE: PRT
<213> ORGANISM: Physcomitrella patens

<400> SEQUENCE: 40

Met Ala Lys His Leu Ala Thr Gln Leu Leu Gln Gln Trp Asn Glu Ala
1               5                   10                  15

Leu Lys Thr Met Pro Pro Gly Phe Arg Thr Ala Gly Lys Ile Leu Val
            20                  25                  30

Trp Glu Glu Leu Ala Ser Asn Lys Val Leu Ile Thr Ile Ala Leu Ala
        35                  40                  45

Trp Val Leu Leu Phe Val Ala Arg Thr Cys Leu Arg Asn Lys Lys Arg
    50                  55                  60

Leu Pro Pro Ala Ile Pro Gly Gly Leu Pro Val Leu Gly Asn Leu Leu
65                  70                  75                  80

Gln Leu Thr Glu Lys Lys Pro His Arg Thr Phe Thr Ala Trp Ser Lys
                85                  90                  95

Glu His Gly Pro Ile Phe Thr Ile Lys Val Gly Ser Val Pro Gln Ala
            100                 105                 110

Val Val Asn Asn Ser Glu Ile Ala Lys Glu Val Leu Val Thr Lys Phe
        115                 120                 125

Ala Ser Ile Ser Lys Arg Gln Met Pro Met Ala Leu Arg Val Leu Thr
    130                 135                 140

Arg Asp Lys Thr Met Val Ala Met Ser Asp Tyr Gly Glu Glu His Arg
145                 150                 155                 160

Met Leu Lys Lys Leu Val Met Thr Asn Leu Leu Gly Pro Thr Thr Gln
                165                 170                 175

Asn Lys Asn Arg Ser Leu Arg Asp Asp Ala Leu Ile Gly Met Ile Glu
            180                 185                 190

Gly Val Leu Ala Glu Leu Lys Ala Ser Pro Thr Ser Pro Lys Val Val
        195                 200                 205

Asn Val Arg Asp Tyr Val Gln Arg Ser Leu Phe Pro Phe Ala Leu Gln
    210                 215                 220

Gln Val Phe Gly Tyr Ile Pro Asp Gln Val Glu Val Leu Glu Leu Gly
225                 230                 235                 240

Thr Cys Val Ser Thr Trp Asp Met Phe Asp Ala Leu Val Val Ala Pro
                245                 250                 255

Leu Ser Ala Val Ile Asn Val Asp Trp Arg Asp Phe Phe Pro Ala Leu
            260                 265                 270

Arg Trp Ile Pro Asn Arg Ser Val Glu Asp Leu Val Arg Thr Val Asp
        275                 280                 285

Phe Lys Arg Asn Ser Ile Met Lys Ala Leu Ile Arg Ala Gln Arg Met
    290                 295                 300

Arg Leu Ala Asn Leu Lys Glu Pro Pro Arg Cys Tyr Ala Asp Ile Ala
305                 310                 315                 320

Leu Thr Glu Ala Thr His Leu Thr Glu Lys Gln Leu Glu Met Ser Leu
                325                 330                 335
```

Trp Glu Pro Ile Ile Glu Ser Ala Asp Thr Thr Leu Val Thr Ser Glu
            340                 345                 350

Trp Ala Met Tyr Glu Ile Ala Lys Asn Pro Asp Cys Gln Asp Arg Leu
        355                 360                 365

Tyr Arg Glu Ile Val Ser Val Ala Gly Thr Glu Arg Met Val Thr Glu
    370                 375                 380

Asp Asp Leu Pro Asn Met Pro Tyr Leu Gly Ala Ile Ile Lys Glu Thr
385                 390                 395                 400

Leu Arg Lys Tyr Thr Pro Val Pro Leu Ile Pro Ser Arg Phe Val Glu
                405                 410                 415

Glu Asp Ile Thr Leu Gly Gly Tyr Asp Ile Pro Lys Gly Tyr Gln Ile
            420                 425                 430

Leu Val Asn Leu Phe Ala Ile Ala Asn Asp Pro Ala Val Trp Ser Asn
        435                 440                 445

Pro Glu Lys Trp Asp Pro Glu Arg Met Leu Ala Asn Lys Lys Val Asp
    450                 455                 460

Met Gly Phe Arg Asp Phe Ser Leu Met Pro Phe Gly Ala Gly Lys Arg
465                 470                 475                 480

Met Cys Ala Gly Ile Thr Gln Ala Met Phe Ile Ile Pro Met Asn Val
                485                 490                 495

Ala Ala Leu Val Gln His Cys Glu Trp Arg Leu Ser Pro Gln Glu Ile
            500                 505                 510

Ser Asn Ile Asn Asn Lys Ile Glu Asp Val Val Tyr Leu Thr Thr His
        515                 520                 525

Lys Leu Ser Pro Leu Ser Cys Glu Ala Thr Pro Arg Ile Ser His Arg
    530                 535                 540

Leu Pro
545

<210> SEQ ID NO 41
<211> LENGTH: 548
<212> TYPE: PRT
<213> ORGANISM: Physcomitrella patens

<400> SEQUENCE: 41

Met Ala Leu Leu Leu Ala Val Phe Thr Gln Leu Leu Gln Gln Trp Asn
1               5                   10                  15

Glu Ala Leu Lys Thr Met Pro Pro Gly Phe Arg Thr Ala Gly Lys Ile
            20                  25                  30

Leu Val Trp Glu Glu Leu Ala Ser Asn Lys Val Leu Ile Thr Ile Ala
        35                  40                  45

Leu Ala Trp Val Leu Leu Phe Val Ala Arg Thr Cys Leu Arg Asn Lys
    50                  55                  60

Lys Arg Leu Pro Pro Ala Ile Pro Gly Gly Leu Pro Val Leu Gly Asn
65                  70                  75                  80

Leu Leu Gln Leu Thr Glu Lys Lys Pro His Arg Thr Phe Thr Ala Trp
                85                  90                  95

Ser Lys Glu His Gly Pro Ile Phe Thr Ile Lys Val Gly Ser Val Pro
            100                 105                 110

Gln Ala Val Val Asn Asn Ser Glu Ile Ala Lys Glu Val Leu Val Thr
        115                 120                 125

Lys Phe Ala Ser Ile Ser Lys Arg Gln Met Pro Met Ala Leu Arg Val
    130                 135                 140

Leu Thr Arg Asp Lys Thr Met Val Ala Met Ser Asp Tyr Gly Glu Glu
145                 150                 155                 160

```
His Arg Met Leu Lys Lys Leu Val Met Thr Asn Leu Leu Gly Pro Thr
                165                 170                 175

Thr Gln Asn Lys Asn Arg Ser Leu Arg Asp Asp Ala Leu Ile Gly Met
            180                 185                 190

Ile Glu Gly Val Leu Ala Glu Leu Lys Ala Ser Pro Thr Ser Pro Lys
        195                 200                 205

Val Val Asn Val Arg Asp Tyr Val Gln Arg Ser Leu Phe Pro Phe Ala
    210                 215                 220

Leu Gln Gln Val Phe Gly Tyr Ile Pro Asp Gln Val Glu Val Leu Glu
225                 230                 235                 240

Leu Gly Thr Cys Val Ser Thr Trp Asp Met Phe Asp Ala Leu Val Val
                245                 250                 255

Ala Pro Leu Ser Ala Val Ile Asn Val Asp Trp Arg Asp Phe Phe Pro
            260                 265                 270

Ala Leu Arg Trp Ile Pro Asn Arg Ser Val Glu Asp Leu Val Arg Thr
        275                 280                 285

Val Asp Phe Lys Arg Asn Ser Ile Met Lys Ala Leu Ile Arg Ala Gln
    290                 295                 300

Arg Met Arg Leu Ala Asn Leu Lys Glu Pro Pro Arg Cys Tyr Ala Asp
305                 310                 315                 320

Ile Ala Leu Thr Glu Ala Thr His Leu Thr Glu Lys Gln Leu Glu Met
                325                 330                 335

Ser Leu Trp Glu Pro Ile Ile Glu Ser Ala Asp Thr Thr Leu Val Thr
            340                 345                 350

Ser Glu Trp Ala Met Tyr Glu Ile Ala Lys Asn Pro Asp Cys Gln Asp
        355                 360                 365

Arg Leu Tyr Arg Glu Ile Val Ser Val Ala Gly Thr Glu Arg Met Val
    370                 375                 380

Thr Glu Asp Asp Leu Pro Asn Met Pro Tyr Leu Gly Ala Ile Ile Lys
385                 390                 395                 400

Glu Thr Leu Arg Lys Tyr Thr Pro Val Pro Leu Ile Pro Ser Arg Phe
                405                 410                 415

Val Glu Glu Asp Ile Thr Leu Gly Gly Tyr Asp Ile Pro Lys Gly Tyr
            420                 425                 430

Gln Ile Leu Val Asn Leu Phe Ala Ile Ala Asn Asp Pro Ala Val Trp
        435                 440                 445

Ser Asn Pro Glu Lys Trp Asp Pro Glu Arg Met Leu Ala Asn Lys Lys
    450                 455                 460

Val Asp Met Gly Phe Arg Asp Phe Ser Leu Met Pro Phe Gly Ala Gly
465                 470                 475                 480

Lys Arg Met Cys Ala Gly Ile Thr Gln Ala Met Phe Ile Ile Pro Met
                485                 490                 495

Asn Val Ala Ala Leu Val Gln His Cys Glu Trp Arg Leu Ser Pro Gln
            500                 505                 510

Glu Ile Ser Asn Ile Asn Asn Lys Ile Glu Asp Val Val Tyr Leu Thr
        515                 520                 525

Thr His Lys Leu Ser Pro Leu Ser Cys Glu Ala Thr Pro Arg Ile Ser
    530                 535                 540

His Arg Leu Pro
545
```

<210> SEQ ID NO 42
<211> LENGTH: 1644

<212> TYPE: DNA
<213> ORGANISM: Physcomitrella patens

<400> SEQUENCE: 42
atggctctgt tattagcagt ttttacgcaa ctgctgcaac aatggaatga agctctgaag 60
acgatgccgc cgggttttcg caccgctggc aaaattctgg tgtgggaaga actggcaagc 120
aataaagttc tgattacgat cgcactggct tgggtcctgc tgtttgtggc tcgtacctgc 180
ctgcgcaata aaaagcgtct gccgccggca atcccgggcg gtctgccggt gctgggcaac 240
ctgctgcagc tgacggaaaa gaaaccgcat cgtaccttta cggcgtggag caaggaacac 300
ggcccgattt tcaccatcaa agtcggttcg gtgccgcagg ctgtggttaa caatagcgaa 360
attgcgaaag aagtcctggt gaccaagttc gccagcatct ctaaacgtca aatgccgatg 420
gcactgcgcg tcctgacgcg tgataaaacg atggtggcta tgtctgacta tggcgaagaa 480
catcgcatgc tgaaaaagct ggtgatgacg aatctgctgg gtccgaccac gcagaacaaa 540
aatcgtagtc tgcgcgatga cgcactgatt ggcatgatcg aaggtgttct ggcggaactg 600
aaggccagtc cgacctcccc gaaagtcgtg aacgttcgcg attatgtcca gcgttctctg 660
tttccgttcg cgctgcagca agtgtttggc tacattccgg atcaagttga agtcctggaa 720
ctgggcacgt gtgtttctac ctgggatatg ttcgacgcac tggttgtcgc tccgctgagt 780
gcggttatta acgtcgattg gcgtgacttt ttcccggccc tgcgctggat tccgaatcgt 840
tccgtggaag atctggtgcg caccgttgac tttaagcgta actcaattat gaaagccctg 900
atccgtgcac agcgtatgcg cctggctaac ctgaaggaac cgccgcgctg ctacgcagat 960
attgctctga ccgaagcgac gcacctgacc gaaaaacaac tggaaatgag tctgtgggaa 1020
ccgattatcg aatccgccga taccacgctg gtgacctcag aatgggctat gtatgaaatt 1080
gcgaaaaatc cggattgtca ggaccgtctg taccgcgaaa tcgtgtccgt tgccggcacg 1140
gaacgcatgg ttaccgaaga tgacctgccg aacatgccgt atctgggtgc aattatcaaa 1200
gaaacgctgc gcaagtacac cccggttccg ctgattccga gtcgttttgt cgaagaagat 1260
atcaccctgg gcggttatga cattccgaaa ggttaccaga tcctggtcaa cctgttcgcg 1320
attgccaatg atccggccgt ttggtcgaac ccggaaaaat gggacccgga acgcatgctg 1380
gcaaataaaa aggtggatat gggctttcgt gacttcagcc tgatgccgtt tggcgccggt 1440
aaacgcatgt gcgccggtat cacccaagca atgttcatta tcccgatgaa tgtggcggcc 1500
ctggttcagc attgtgaatg gcgcctgagc ccgcaagaaa tctctaacat caacaacaag 1560
atcgaagatg tggtttacct gaccacgcat aaactgtcac cgctgtcgtg cgaagcaacc 1620
ccgcgtatca gccaccgtct gccg 1644

<210> SEQ ID NO 43
<211> LENGTH: 1049
<212> TYPE: PRT
<213> ORGANISM: Bacillus megaterium

<400> SEQUENCE: 43

Met Thr Ile Lys Glu Met Pro Gln Pro Lys Thr Phe Gly Glu Leu Lys
1 5 10 15

Asn Leu Pro Leu Leu Asn Thr Asp Lys Pro Val Gln Ala Leu Met Lys
20 25 30

Ile Ala Asp Glu Leu Gly Glu Ile Phe Lys Phe Glu Ala Pro Gly Arg
35 40 45

Val Thr Arg Tyr Leu Ser Ser Gln Arg Leu Ile Lys Glu Ala Cys Asp

-continued

```
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Ala Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
            180                 185                 190

Asn Pro Asp Asp Pro Ala Tyr Asp Glu Asn Lys Arg Gln Phe Gln Glu
        195                 200                 205

Asp Ile Lys Val Met Asn Asp Leu Val Asp Lys Ile Ile Ala Asp Arg
    210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
            260                 265                 270

Leu Leu Ser Phe Ala Leu Tyr Phe Leu Val Lys Asn Pro His Val Leu
        275                 280                 285

Gln Lys Ala Ala Glu Glu Ala Ala Arg Val Leu Val Asp Pro Val Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ile Pro Ala Phe Ser Leu Tyr Ala
                325                 330                 335

Lys Glu Asp Thr Val Leu Gly Gly Glu Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln Ser Ala Lys Lys Val Arg Lys Lys Ala Glu Asn Ala His Asn
465                 470                 475                 480
```

-continued

```
Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
705                 710                 715                 720

Leu Asp Ala Ser Gln Gln Ile Arg Leu Glu Ala Glu Glu Glu Lys Leu
                725                 730                 735

Ala His Leu Pro Leu Ala Lys Thr Val Ser Val Glu Glu Leu Leu Gln
            740                 745                 750

Tyr Val Glu Leu Gln Asp Pro Val Thr Arg Thr Gln Leu Arg Ala Met
        755                 760                 765

Ala Ala Lys Thr Val Cys Pro Pro His Lys Val Glu Leu Glu Ala Leu
    770                 775                 780

Leu Glu Lys Gln Ala Tyr Lys Glu Gln Val Leu Ala Lys Arg Leu Thr
785                 790                 795                 800

Met Leu Glu Leu Leu Glu Lys Tyr Pro Ala Cys Glu Met Lys Phe Ser
                805                 810                 815

Glu Phe Ile Ala Leu Leu Pro Ser Ile Arg Pro Arg Tyr Tyr Ser Ile
            820                 825                 830

Ser Ser Ser Pro Arg Val Asp Glu Lys Gln Ala Ser Ile Thr Val Ser
        835                 840                 845

Val Val Ser Gly Glu Ala Trp Ser Gly Tyr Gly Glu Tyr Lys Gly Ile
    850                 855                 860

Ala Ser Asn Tyr Leu Ala Glu Leu Gln Glu Gly Asp Thr Ile Thr Cys
865                 870                 875                 880

Phe Ile Ser Thr Pro Gln Ser Glu Phe Thr Leu Pro Lys Asp Pro Glu
                885                 890                 895
```

```
Thr Pro Leu Ile Met Val Gly Pro Gly Thr Gly Val Ala Pro Phe Arg
            900                 905                 910

Gly Phe Val Gln Ala Arg Lys Gln Leu Lys Glu Gln Gly Gln Ser Leu
        915                 920                 925

Gly Glu Ala His Leu Tyr Phe Gly Cys Arg Ser Pro His Glu Asp Tyr
    930                 935                 940

Leu Tyr Gln Glu Glu Leu Glu Asn Ala Gln Ser Glu Gly Ile Ile Thr
945                 950                 955                 960

Leu His Thr Ala Phe Ser Arg Met Pro Asn Gln Pro Lys Thr Tyr Val
                965                 970                 975

Gln His Val Met Glu Gln Asp Gly Lys Lys Leu Ile Glu Leu Leu Asp
            980                 985                 990

Gln Gly Ala His Phe Tyr Ile Cys  Gly Asp Gly Ser Gln  Met Ala Pro
        995                 1000                 1005

Ala Val  Glu Ala Thr Leu Met  Lys Ser Tyr Ala Asp  Val His Gln
    1010                 1015                 1020

Val Ser  Glu Ala Asp Ala Arg  Leu Trp Leu Gln Gln  Leu Glu Glu
    1025                 1030                 1035

Lys Gly  Arg Tyr Ala Lys Asp  Val Trp Ala Gly
    1040                 1045


<210> SEQ ID NO 44
<211> LENGTH: 3150
<212> TYPE: DNA
<213> ORGANISM: Bacillus megaterium

<400> SEQUENCE: 44

atgacgatta aagaaatgcc gcaaccgaag acgtttggcg aactgaagaa cctgccgctg     60

ctgaacacgg ataagccggt gcaagccctg atgaagattg ctgatgaact gggcgaaatc    120

tttaaattcg aagcgccggg tcgtgtgacc cgttatctga gcagccagcg tctgattaaa    180

gaagcctgcg atgaatcgcg ctttgacaag aacctgagcc aggcactgaa atttgttcgt    240

gatttcgcag gtgacggtct ggccaccagc tggacgcatg aaaagaactg gaaaaaggcc    300

cacaatattc tgctgccgtc gttcagccag caagcaatga aaggctacca tgctatgatg    360

gtcgatatcg cggttcagct ggtccaaaaa tgggaacgtc tgaatgcgga cgaacacatt    420

gaagtgccgg aagatatgac ccgcctgacg ctggacacca tcggtctgtg tggctttaac    480

tatcgtttta attcgttcta ccgcgatcag ccgcatccgt tcattaccag catggtgcgt    540

gcgctggacg aagccatgaa caaactgcag cgtgcaaacc cggatgaccc ggcgtatgat    600

gaaaacaagc gtcagtttca agaagacatc aaagtgatga atgatctggt tgacaagatt    660

atcgcagatc gcaaagcgag cggcgaacag tcagatgacc tgctgacgca catgctgaac    720

ggcaaagacc cggaaaccgg tgaaccgctg gatgacgaaa acatccgtta tcagatcatc    780

acctttctga tcgcaggcca tgaaaccacg tcgggtctgc tgagctttgc gctgtacttc    840

ctggtcaaga acccgcacgt gctgcagaaa gcggccgaag aagcagctcg tgtgctggtt    900

gatccggttc cgtcgtataa acaggtcaag caactgaaat acgtgggtat ggttctgaat    960

gaagcgctgc gcctgtggcc gacgattccg gcatttagcc tgtatgctaa ggaagatacc   1020

gttctgggcg gtgaataccc gctggaaaaa ggcgatgaac tgatggtcct gattccgcag   1080

ctgcatcgcg acaaaaccat ctggggtgat gacgtggaag aatttcgccc ggaacgcttc   1140

gaaaacccga gcgcgattcc gcagcatgcc tttaaaccgt tcggcaatgg tcaacgtgcg   1200

tgcatcggcc agcaatttgc gctgcacgaa gccacgctgg ttctgggtat gatgctgaaa   1260
```

```
cattttgatt tcgaagacca caccaactat gaactggata ttaaggaaac cctgacgctg   1320

aaaccggaag gcttcgtggt taaagcgaag tctaaaaaga ttccgctggg cggtatcccg   1380

tctccgagta cggaacagag tgccaaaaag gtccgtaaaa aggcggaaaa cgcccataat   1440

accccgctgc tggtgctgta tggttctaac atgggcacgg cagaaggcac cgctcgcgat   1500

ctggcagaca ttgctatgtc taaaggtttt gcgccgcagg tggccacgct ggatagtcat   1560

gcaggcaatc tgccgcgtga aggtgctgtc ctgatcgtga ccgcaagcta caacggtcac   1620

ccgccggata atgcgaagca gttcgttgat tggctggacc aagcgtcggc cgatgaagtt   1680

aaaggtgtcc gctatagcgt gtttggctgt ggtgacaaga actgggctac cacgtaccag   1740

aaagttccgg cgttcattga tgaaacgctg gcggccaaag gcgcagaaaa tatcgctgat   1800

cgtggtgaag cagacgcttc cgatgacttt gaaggcacct atgaagaatg gcgcgaacac   1860

atgtggtcgg atgtggcagc ttacttcaac ctggatattg aaaacagcga agacaataaa   1920

tccaccctgt cactgcagtt tgttgatagt gcggccgaca tgccgctggc aaagatgcac   1980

ggcgctttct ccacgaatgt cgtggcttca aaagaactgc agcaaccggg ttcggcacgt   2040

agcacccgcc atctggaaat tgaactgccg aaagaagcca gctatcagga aggcgatcac   2100

ctgggtgtga ttccgcgtaa ctacgaaggc atcgtgaatc gtgttacggc ccgctttggt   2160

ctggatgcat cccagcaaat ccgcctggaa gcggaagaag aaaagctggc gcatctgccg   2220

ctggccaaaa ccgtctcagt ggaagaactg ctgcagtatg tggaactgca agatccggtt   2280

acccgtacgc agctgcgtgc gatggcggct aagaccgtct gcccgccgca caaagtggaa   2340

ctggaagctc tgctggaaaa gcaggcgtat aaagaacaag tgctggcgaa acgcctgacc   2400

atgctggaac tgctggaaaa gtacccggcc tgtgaaatga agttctctga atttatcgca   2460

ctgctgccgt ctatccgtcc gcgttattac agtattagtt cctcaccgcg tgtggatgaa   2520

aaacaggcca gtatcaccgt ttctgttgtc agtggcgaag catggtctgg ctatggtgaa   2580

tacaagggta tcgcaagtaa ctacctggct gaactgcagg aaggcgatac cattacgtgc   2640

tttatctcta cgccgcaaag tgaatttacc ctgccgaaag acccggaaac gccgctgatc   2700

atggttggcc cgggcaccgg tgtcgcaccg tttcgtggtt tcgtgcaggc acgcaagcaa   2760

ctgaaagaac agggccaatc cctgggtgaa gcgcatctgt attttggctg tcgctcaccg   2820

cacgaagatt atctgtacca ggaagaactg gaaaacgcgc aatccgaagg tattatcacg   2880

ctgcataccg ccttctcacg tatgccgaat cagccgaaaa cctacgtcca gcacgtgatg   2940

gaacaagatg gcaaaaagct gattgaactg ctggaccagg gtgcgcattt ttatatctgc   3000

ggtgatggca gccaaatggc accggcagtg gaagcaaccc tgatgaaatc ctacgcagat   3060

gttcaccagg tctcagaagc agacgctcgt ctgtggctgc agcaactgga agaaaagggc   3120

cgctatgcga aagatgtttg ggccggttaa                                    3150
```

<210> SEQ ID NO 45
<211> LENGTH: 396
<212> TYPE: PRT
<213> ORGANISM: Pleurotus sapidus

<400> SEQUENCE: 45

```
Met Arg Tyr Gly Cys Ala Ala Val Ala Leu Phe Tyr Leu Thr Ala Met
1               5                   10                  15

Gly Lys Leu His Pro Leu Ala Ile Ile Pro Asp Tyr Lys Gly Ser Met
            20                  25                  30
```

-continued

```
Ala Ala Ser Val Thr Ile Phe Asn Lys Arg Thr Asn Pro Leu Asp Ile
        35                  40                  45

Ser Val Asn Gln Ala Asn Asp Trp Pro Trp Arg Tyr Ala Lys Thr Cys
    50                  55                  60

Val Leu Ser Ser Asp Trp Ala Leu His Glu Met Ile Ile His Leu Asn
65                  70                  75                  80

Asn Thr His Leu Val Glu Glu Ala Val Ile Val Ala Ala Gln Arg Lys
                85                  90                  95

Leu Ser Pro Ser His Ile Val Phe Arg Leu Leu Glu Pro His Trp Val
            100                 105                 110

Val Thr Leu Ser Leu Asn Ala Leu Ala Arg Ser Val Leu Ile Pro Glu
        115                 120                 125

Val Ile Val Pro Ile Ala Gly Phe Ser Ala Pro His Ile Phe Gln Phe
    130                 135                 140

Ile Arg Glu Ser Phe Thr Asn Phe Asp Trp Lys Ser Leu Tyr Val Pro
145                 150                 155                 160

Ala Asp Leu Glu Ser Arg Gly Phe Pro Val Asp Gln Leu Asn Ser Pro
                165                 170                 175

Lys Phe His Asn Tyr Ala Tyr Ala Arg Asp Ile Asn Asp Met Trp Thr
            180                 185                 190

Thr Leu Lys Lys Phe Val Ser Ser Val Leu Gln Asp Ala Gln Tyr Tyr
        195                 200                 205

Pro Asp Asp Ala Ser Val Ala Gly Asp Thr Gln Ile Gln Ala Trp Cys
    210                 215                 220

Asp Glu Met Arg Ser Gly Met Gly Ala Gly Met Thr Asn Phe Pro Glu
225                 230                 235                 240

Ser Ile Thr Thr Val Asp Asp Leu Val Asn Met Val Thr Met Cys Ile
                245                 250                 255

His Ile Ala Ala Pro Gln His Thr Ala Val Asn Tyr Leu Gln Gln Tyr
            260                 265                 270

Tyr Gln Thr Phe Val Ser Asn Lys Pro Ser Ala Leu Phe Ser Pro Leu
        275                 280                 285

Pro Thr Ser Ile Ala Gln Leu Gln Lys Tyr Thr Glu Ser Asp Leu Met
    290                 295                 300

Ala Ala Leu Pro Leu Asn Ala Lys Arg Gln Trp Leu Leu Met Ala Gln
305                 310                 315                 320

Ile Pro Tyr Leu Leu Ser Met Gln Val Gln Glu Asp Glu Asn Ile Val
                325                 330                 335

Thr Tyr Ala Ala Asn Ala Ser Thr Asp Lys Asp Pro Ile Ile Ala Ser
            340                 345                 350

Ala Gly Arg Gln Leu Ala Ala Asp Leu Lys Lys Leu Ala Ala Val Phe
        355                 360                 365

Leu Val Asn Ser Ala Gln Leu Asp Asp Gln Asn Thr Pro Tyr Asp Val
    370                 375                 380

Leu Ala Pro Glu Gln Leu Ala Asn Ala Ile Val Ile
385                 390                 395


<210> SEQ ID NO 46
<211> LENGTH: 1191
<212> TYPE: DNA
<213> ORGANISM: Pleurotus sapidus

<400> SEQUENCE: 46

atgcgttatg gctgtgctgc tgtggctctg ttctatctga ccgctatggg caaactgcac      60
```

-continued

```
ccgctggcta ttatcccgga ctacaagggt agcatggcgg cctctgtcac catttttaac    120

aaacgtacga atccgctgga tatcagcgtt aaccaggcaa atgactggcc gtggcgctat    180

gctaagacgt gcgtgctgag cagcgattgg gcgctgcatg aaatgattat ccacctgaac    240

aatacccatc tggtggaaga agccgtcatt gtggcagctc agcgtaaact gtcaccgtcg    300

cacatcgttt ttcgcctgct ggaaccgcat tgggtggtta ccctgtcgct gaacgcactg    360

gctcgtagcg tgctgatccc ggaagttatt gtcccgatcg cgggtttctc tgccccgcac    420

atttttcagt tcatccgcga atcttttacc aatttcgatt ggaaaagtct gtacgtcccg    480

gcggacctgg aatcgcgtgg ctttccggtg gatcagctga acagcccgaa gttccataat    540

tatgcgtacg cccgcgatat caacgacatg tggaccacgc tgaaaaagtt tgtgagttcc    600

gttctgcagg atgcccaata ttacccggat gacgcaagtg tggctggtga tacgcagatt    660

caagcatggt gcgacgaaat gcgttccggc atgggtgcgg gcatgaccaa cttcccggaa    720

tcaatcacca cggttgatga cctggtcaat atggtgacca tgtgtattca catcgcggcc    780

ccgcagcata cggcggttaa ctatctgcag caatactacc aaaccttcgt cagtaacaag    840

ccgtccgcac tgttctcacc gctgccgacc tctattgctc agctgcaaaa atacacggaa    900

agtgatctga tggcagctct gccgctgaac gcgaagcgtc agtggctgct gatggcccaa    960

attccgtatc tgctgtcgat gcaggtgcaa gaagatgaaa acatcgttac ctacgcggcc   1020

aatgcgtcca cggataaaga cccgattatc gcatcagctg gccgccagct ggcagctgac   1080

ctgaaaaagc tggcggccgt tttctggtc aactcagccc agctggatga ccaaaatacc   1140

ccgtatgatg tgctggcacc ggaacagctg gcgaatgcca ttgttatcta a            1191
```

<210> SEQ ID NO 47
<211> LENGTH: 640
<212> TYPE: PRT
<213> ORGANISM: Pleurotus ostreatus

<400> SEQUENCE: 47

```
Met Ala Pro Thr Met Ser Leu Ser Arg Ser Ala Leu Lys Asn Val His
1               5                   10                  15

Leu Pro Tyr Met Val Gln His Pro Glu Pro Thr Asp Cys Ser Thr Ala
            20                  25                  30

Met Lys His Ala Ala Glu Gly Tyr Asp Arg Ala Arg Gln Met Ile Ala
        35                  40                  45

Phe Leu Phe Asp Ile Leu Asp Tyr Glu Ser Ser Val Pro Gln Lys Phe
    50                  55                  60

Thr Pro Glu Glu Lys Lys Glu Lys Tyr Thr Trp Ser His Ser Asp Lys
65                  70                  75                  80

Phe Pro Pro His Leu Ala Ile Ile Pro Glu Asp Ile Asp Val Pro Ala
                85                  90                  95

Tyr Ile Ile Phe Ser Ile Val Arg Leu Val Gln Thr Leu Ser Ile Met
            100                 105                 110

Ser Gly Ile Gln Cys Asn Glu Arg Leu Ala Pro Gly Pro Glu Gln Asn
        115                 120                 125

Thr Met Glu Lys Leu Thr Lys Trp Asn Ala Glu Arg His Lys Asn Gln
    130                 135                 140

Gly Trp Val Lys Asp Met Phe Asn Glu Pro Asn Ile Gly Leu Arg Asn
145                 150                 155                 160

Asp Trp Tyr Thr Asp Ala Val Phe Ala Gln Gln Phe Phe Thr Gly Pro
                165                 170                 175
```

-continued

```
Asn Pro Thr Thr Ile Thr Leu Ala Ser Asp Thr Trp Met Lys Ala Phe
            180                 185                 190

Thr Glu Glu Ala Ala Ser Gln Gly Lys Arg Asp Leu Ile Ser Leu Phe
        195                 200                 205

Arg Ser Ala Pro Pro Asn Ser Phe Tyr Val Gln Asp Phe Ser Asp Phe
    210                 215                 220

Arg Ala Arg Met Gly Ala Lys Pro Asp Glu Glu Leu Cys Ala Thr Ser
225                 230                 235                 240

Asp Gly Gly Val Thr Arg Tyr Gly Cys Ala Ala Val Ala Leu Phe Tyr
                245                 250                 255

Leu Pro Pro Thr Gly Glu Leu His Pro Leu Ala Ile Val Pro Asp Tyr
            260                 265                 270

Lys Gly Ser Met Ala Ala Ser Ile Thr Leu Phe Asn Lys Arg Val Asp
        275                 280                 285

Pro Ser Asp Ala Ser Val Asp Gln Ala Asn Asp Trp Pro Trp Arg Tyr
    290                 295                 300

Ala Lys Thr Cys Val Leu Ser Ala Asp Trp Val Leu His Glu Met Ile
305                 310                 315                 320

Ile His Leu Asn Asn Thr His Leu Val Gln Glu Ala Val Ile Val Ala
                325                 330                 335

Val Gln Arg Thr Leu Pro Asp Ser His Ile Val Phe Arg Leu Leu Lys
            340                 345                 350

Pro His Trp Val Val Thr Leu Ser Leu Asn Ala Gln Ala Arg Ser Val
        355                 360                 365

Leu Ile Pro Glu Val Ile Val Pro Ile Ala Gly Phe Ser Glu Leu Arg
    370                 375                 380

Ile Phe Gln Phe Val Gly His Ala Phe Thr Asn Phe Asp Trp Lys Ala
385                 390                 395                 400

Leu Tyr Val Pro Thr Asp Leu Glu Phe Arg Gly Phe Pro Leu Asp Arg
                405                 410                 415

Leu Asp Asp Asp Lys Phe His Asn Tyr Ala Tyr Ala Lys Asp Ile Lys
            420                 425                 430

Asp Met Trp Met Ala Leu Arg Lys Phe Val Ser Ser Val Leu Lys Asp
        435                 440                 445

Gly Lys Tyr Tyr Pro Asp Asp Ser Ala Val Ala Ala Asp Ala Gln Ile
    450                 455                 460

Gln Asp Trp Cys Asp Glu Met Arg Ser Glu Lys Gly Ala Gly Met Lys
465                 470                 475                 480

Lys Phe Pro Glu Ser Ile Ser Thr Leu Asp Asp Leu Ile Asp Met Val
                485                 490                 495

Thr Met Cys Ile His Ile Ala Ala Pro Gln His Thr Ala Val Asn Tyr
            500                 505                 510

Leu Gln Gln Tyr Tyr Gln Thr Phe Val Pro Asn Lys Pro Ser Ala Leu
        515                 520                 525

Phe Ser Pro Leu Pro Thr Leu Leu Ser Gln Leu Glu Ser Tyr Thr Glu
    530                 535                 540

Ser Asp Leu Met Ala Ala Leu Pro Leu Gly Ala Lys Gln Glu Trp Leu
545                 550                 555                 560

Leu Met Ala Gln Val Pro Tyr Leu Leu Ser Lys Glu Val Glu Gln Asp
                565                 570                 575

Gly Asn Ile Val Thr Tyr Ala Gly Thr Ala Ser Asn Asn Glu Asp Pro
            580                 585                 590

Ile Ile Ala Ala Ala Gly Lys Glu Leu Ser Ala Asp Leu Val Ile Leu
```

-continued

```
        595                 600                 605

Ala Gly Val Phe Leu Lys Asn Ser Glu Lys Leu Asp Asp Gln Asn Thr
    610                 615                 620

Ala Tyr Asn Val Leu Ala Pro Asp Gln Leu Ala Asn Ala Ile Val Ile
625                 630                 635                 640


<210> SEQ ID NO 48
<211> LENGTH: 1923
<212> TYPE: DNA
<213> ORGANISM: Pleurotus ostreatus

<400> SEQUENCE: 48

atggccccga cgatgtcact gtctcgctcc gcactgaaga atgtccacct gccgtatatg      60

gtccaacacc cggaaccgac cgattgcagc accgcgatga aacacgcggc cgaaggttat     120

gatcgtgctc gccagatgat tgcgtttctg ttcgacatcc tggattacga aagctctgtt     180

ccgcaaaaat ttaccccgga agaaaagaaa gaaaaatata cgtggtcaca ctcggataag     240

ttcccgccgc atctggccat tatcccggaa gacattgatg tgccggcata cattatcttt     300

agcatcgttc gtctggtcca gaccctgagt attatgtccg gcatccaatg caacgaacgt     360

ctggcaccgg ggccggaaca gaatacgatg gaaaaactga cgaagtggaa cgcggaacgt     420

cataaaaatc aaggctgggt caaggatatg tttaacgaac cgaatattgg tctgcgcaac     480

gactggtata ccgatgctgt gttcgcgcag caatttttca cgggtccgaa tccgaccacg     540

attaccctgg cctctgatac gtggatgaaa gcatttaccg aagaagcagc tagtcagggc     600

aagcgtgacc tgatcagcct gtttcgctct gccccgccga actccttcta cgttcaggac     660

ttttcagatt tccgtgctcg catgggcgcg aaaccggacg aagaactgtg cgcgacctct     720

gatggcggtg ttacccgtta tggctgtgca gcagtcgcac tgttttacct gccgccgacc     780

ggtgaactgc atccgctggc cattgtgccg gattataaag gcagtatggc agcttccatc     840

acgctgttca acaagcgtgt ggacccgtca gatgcctcgg ttgaccaggc aaatgattgg     900

ccgtggcgct acgctaaaac ctgtgttctg tccgcggatt gggtcctgca tgaaatgatt     960

atccacctga acaataccca tctggtgcag gaagccgtca ttgtggcagt tcaacgtacg    1020

ctgccggatt cacacatcgt ttttcgcctg ctgaaaccgc attgggtggt taccctgtcg    1080

ctgaatgccc aggcacgtag cgttctgatc ccggaagtca ttgtgccgat cgcgggcttc    1140

agtgaactgc gcatctttca gttcgttggt cacgccttta ccaacttcga ctggaaagca    1200

ctgtatgtcc cgacggatct ggaatttcgt ggtttcccgc tggaccgcct ggatgacgat    1260

aagttccata actatgctta cgcgaaggac attaaggata tgtggatggc cctgcgtaag    1320

ttcgtgagtt ccgttctgaa agatggcaag tattacccgg acgattcggc tgttgcagca    1380

gacgcgcaga ttcaagactg gtgcgatgaa atgcgcagcg aaaaaggcgc gggtatgaaa    1440

aagttcccgg aaagcatttc taccctggac gatctgatcg atatggtgac gatgtgtatt    1500

cacatcgcag ctccgcagca taccgccgtg aactatctgc agcaatatta ccaaacgttt    1560

gttccgaata aaccgtcagc actgttctcg ccgctgccga ccctgctgag ccagctggaa    1620

tcttacacgg aaagtgatct gatggcggcc ctgccgctgg gtgctaaaca ggaatggctg    1680

ctgatggcgc aagtgccgta tctgctgtct aaggaagtcg aacaggatgg caacattgtg    1740

acctacgccg gtacggcaag taacaatgaa gatccgatta tcgcagctgc gggcaaagaa    1800

ctgtccgctg acctggtcat cctggcgggt gtgtttctga aaaactcaga aaagctggac    1860

gatcagaaca ccgcctataa tgtcctggca ccggatcaac tggccaatgc aattgtgatc    1920
```

taa 1923

<210> SEQ ID NO 49
<211> LENGTH: 495
<212> TYPE: PRT
<213> ORGANISM: Cichorium intybus

<400> SEQUENCE: 49

```
Met Glu Ile Ser Ile Pro Thr Thr Leu Gly Leu Ala Val Ile Ile Phe
1               5                   10                  15

Ile Ile Phe Lys Leu Leu Thr Arg Thr Thr Ser Lys Lys Asn Leu Leu
            20                  25                  30

Pro Glu Pro Trp Arg Leu Pro Ile Ile Gly His Met His His Leu Ile
        35                  40                  45

Gly Thr Met Pro His Arg Gly Val Met Glu Leu Ala Arg Lys His Gly
    50                  55                  60

Ser Leu Met His Leu Gln Leu Gly Glu Val Ser Thr Ile Val Val Ser
65                  70                  75                  80

Ser Pro Arg Trp Ala Lys Glu Val Leu Thr Thr Tyr Asp Ile Thr Phe
                85                  90                  95

Ala Asn Arg Pro Glu Thr Leu Thr Gly Glu Ile Val Ala Tyr His Asn
            100                 105                 110

Thr Asp Ile Val Leu Ala Pro Tyr Gly Glu Tyr Trp Arg Gln Leu Arg
        115                 120                 125

Lys Leu Cys Thr Leu Glu Leu Leu Ser Asn Lys Lys Val Lys Ser Phe
    130                 135                 140

Gln Ser Leu Arg Glu Glu Glu Cys Trp Asn Leu Val Lys Asp Ile Arg
145                 150                 155                 160

Ser Thr Gly Gln Gly Ser Pro Ile Asn Leu Ser Glu Asn Ile Phe Lys
                165                 170                 175

Met Ile Ala Thr Ile Leu Ser Arg Ala Ala Phe Gly Lys Gly Ile Lys
            180                 185                 190

Asp Gln Met Lys Phe Thr Glu Leu Val Lys Glu Ile Leu Arg Leu Thr
        195                 200                 205

Gly Gly Phe Asp Val Ala Asp Ile Phe Pro Ser Lys Lys Leu Leu His
    210                 215                 220

His Leu Ser Gly Lys Arg Ala Lys Leu Thr Asn Ile His Asn Lys Leu
225                 230                 235                 240

Asp Asn Leu Ile Asn Asn Ile Ile Ala Glu His Pro Gly Asn Arg Thr
                245                 250                 255

Ser Ser Ser Gln Glu Thr Leu Leu Asp Val Leu Leu Arg Leu Lys Glu
            260                 265                 270

Ser Ala Glu Phe Pro Leu Thr Ala Asp Asn Val Lys Ala Val Ile Leu
        275                 280                 285

Asp Met Phe Gly Ala Gly Thr Asp Thr Ser Ser Ala Thr Ile Glu Trp
    290                 295                 300

Ala Ile Ser Glu Leu Ile Arg Cys Pro Arg Ala Met Glu Lys Val Gln
305                 310                 315                 320

Thr Glu Leu Arg Gln Ala Leu Asn Gly Lys Glu Arg Ile Gln Glu Glu
                325                 330                 335

Asp Leu Gln Glu Leu Asn Tyr Leu Lys Leu Val Ile Lys Glu Thr Leu
            340                 345                 350

Arg Leu His Pro Pro Leu Pro Leu Val Met Pro Arg Glu Cys Arg Glu
        355                 360                 365
```

```
Pro Cys Val Leu Gly Gly Tyr Asp Ile Pro Ser Lys Thr Lys Leu Ile
    370                 375                 380

Val Asn Val Phe Ala Ile Asn Arg Asp Pro Glu Tyr Trp Lys Asp Ala
385                 390                 395                 400

Glu Thr Phe Met Pro Glu Arg Phe Glu Asn Ser Pro Ile Thr Val Met
                405                 410                 415

Gly Ser Glu Tyr Glu Tyr Leu Pro Phe Gly Ala Gly Arg Arg Met Cys
            420                 425                 430

Pro Gly Ala Ala Leu Gly Leu Ala Asn Val Glu Leu Pro Leu Ala His
        435                 440                 445

Ile Leu Tyr Phe Asn Trp Lys Leu Pro Asn Gly Lys Thr Phe Glu Asp
    450                 455                 460

Leu Asp Met Thr Glu Ser Phe Gly Ala Thr Val Gln Arg Lys Thr Glu
465                 470                 475                 480

Leu Leu Leu Val Pro Thr Asp Phe Gln Thr Leu Thr Ala Ser Thr
                485                 490                 495
```

<210> SEQ ID NO 50
<211> LENGTH: 493
<212> TYPE: PRT
<213> ORGANISM: Cichorium intybus

<400> SEQUENCE: 50

```
Met Ala Leu Leu Leu Ala Val Phe Leu Ala Val Ile Ile Phe Ile Ile
1               5                   10                  15

Phe Lys Leu Leu Thr Arg Thr Thr Ser Lys Lys Asn Leu Leu Pro Glu
            20                  25                  30

Pro Trp Arg Leu Pro Ile Ile Gly His Met His His Leu Ile Gly Thr
        35                  40                  45

Met Pro His Arg Gly Val Met Glu Leu Ala Arg Lys His Gly Ser Leu
    50                  55                  60

Met His Leu Gln Leu Gly Glu Val Ser Thr Ile Val Val Ser Ser Pro
65                  70                  75                  80

Arg Trp Ala Lys Glu Val Leu Thr Thr Tyr Asp Ile Thr Phe Ala Asn
                85                  90                  95

Arg Pro Glu Thr Leu Thr Gly Glu Ile Val Ala Tyr His Asn Thr Asp
            100                 105                 110

Ile Val Leu Ala Pro Tyr Gly Glu Tyr Trp Arg Gln Leu Arg Lys Leu
        115                 120                 125

Cys Thr Leu Glu Leu Leu Ser Asn Lys Lys Val Lys Ser Phe Gln Ser
    130                 135                 140

Leu Arg Glu Glu Glu Cys Trp Asn Leu Val Lys Asp Ile Arg Ser Thr
145                 150                 155                 160

Gly Gln Gly Ser Pro Ile Asn Leu Ser Glu Asn Ile Phe Lys Met Ile
                165                 170                 175

Ala Thr Ile Leu Ser Arg Ala Ala Phe Gly Lys Gly Ile Lys Asp Gln
            180                 185                 190

Met Lys Phe Thr Glu Leu Val Lys Glu Ile Leu Arg Leu Thr Gly Gly
        195                 200                 205

Phe Asp Val Ala Asp Ile Phe Pro Ser Lys Lys Leu Leu His His Leu
    210                 215                 220

Ser Gly Lys Arg Ala Lys Leu Thr Asn Ile His Asn Lys Leu Asp Asn
225                 230                 235                 240

Leu Ile Asn Asn Ile Ile Ala Glu His Pro Gly Asn Arg Thr Ser Ser
```

```
                245                 250                 255

Ser Gln Glu Thr Leu Leu Asp Val Leu Leu Arg Leu Lys Glu Ser Ala
            260                 265                 270

Glu Phe Pro Leu Thr Ala Asp Asn Val Lys Ala Val Ile Leu Asp Met
        275                 280                 285

Phe Gly Ala Gly Thr Asp Thr Ser Ser Ala Thr Ile Glu Trp Ala Ile
    290                 295                 300

Ser Glu Leu Ile Arg Cys Pro Arg Ala Met Glu Lys Val Gln Thr Glu
305                 310                 315                 320

Leu Arg Gln Ala Leu Asn Gly Lys Glu Arg Ile Gln Glu Glu Asp Leu
                325                 330                 335

Gln Glu Leu Asn Tyr Leu Lys Leu Val Ile Lys Glu Thr Leu Arg Leu
            340                 345                 350

His Pro Pro Leu Pro Leu Val Met Pro Arg Glu Cys Arg Glu Pro Cys
        355                 360                 365

Val Leu Gly Gly Tyr Asp Ile Pro Ser Lys Thr Lys Leu Ile Val Asn
    370                 375                 380

Val Phe Ala Ile Asn Arg Asp Pro Glu Tyr Trp Lys Asp Ala Glu Thr
385                 390                 395                 400

Phe Met Pro Glu Arg Phe Glu Asn Ser Pro Ile Thr Val Met Gly Ser
                405                 410                 415

Glu Tyr Glu Tyr Leu Pro Phe Gly Ala Gly Arg Arg Met Cys Pro Gly
            420                 425                 430

Ala Ala Leu Gly Leu Ala Asn Val Glu Leu Pro Leu Ala His Ile Leu
        435                 440                 445

Tyr Phe Asn Trp Lys Leu Pro Asn Gly Lys Thr Phe Glu Asp Leu Asp
    450                 455                 460

Met Thr Glu Ser Phe Gly Ala Thr Val Gln Arg Lys Thr Glu Leu Leu
465                 470                 475                 480

Leu Val Pro Thr Asp Phe Gln Thr Leu Thr Ala Ser Thr
                485                 490
```

<210> SEQ ID NO 51
<211> LENGTH: 1482
<212> TYPE: DNA
<213> ORGANISM: Cichorium intybus

<400> SEQUENCE: 51

```
atggctctgt tattagcagt ttttctggct gtcattatct ttatcatctt caaactgctg      60

acccgcacca cctcgaagaa aaacctgctg ccggaaccgt ggcgtctgcc gattatcggc     120

cacatgcatc acctgattgg caccatgccg caccgtggtg tgatggaact ggcgcgcaaa     180

catggctcac tgatgcacct gcagctgggt gaagtgagca ccatcgtggt tagctctccg     240

cgttgggcga aagaagttct gaccacgtat gatattacct ttgccaaccg cccggaaacc     300

ctgacgggcg aaatcgtggc ataccataat acggacattg ttctggctcc gtatggtgaa     360

tactggcgtc agctgcgcaa actgtgcacc ctggaactgc tgagtaacaa aaaagtcaaa     420

tcttttcaaa gtctgcgtga agaagaatgt tggaatctgg tgaaagatat ccgctccacc     480

ggccagggtt caccgatcaa cctgtcggaa aacatcttca aaatgatcgc gacgatcctg     540

tctcgtgcgg cctttggcaa aggtattaaa gaccaaatga aattcaccga actggttaaa     600

gaaatcctgc gcctgacggg cggttttgat gtcgcagaca ttttcccgag taaaaaactg     660

ctgcatcacc tgtccggcaa acgtgctaaa ctgaccaaca tccataacaa actggataac     720
```

```
ctgatcaaca acattatcgc cgaacacccg ggtaatcgta ccagttcctc acaggaaacg    780

ctgctggatg ttctgctgcg cctgaaagaa agcgcagaat ttccgctgac cgcggacaat    840

gttaaagccg tcattctgga tatgttcggt gcaggcaccg acacgtcgag cgcaaccatt    900

gaatgggcta tctctgaact gattcgttgc ccgcgcgcga tggaaaaagt gcagacggaa    960

ctgcgtcaag ccctgaacgg caaagaacgc atccaggaag aagatctgca agaactgaac   1020

tacctgaaac tggttatcaa agaaaccctg cgcctgcatc cgccgctgcc gctggtcatg   1080

ccgcgtgaat gccgcgaacc gtgtgtgctg ggcggttatg atatcccgag caaaaccaaa   1140

ctgatcgtca acgtgtttgc aattaatcgt gacccggaat actggaaaga cgctgaaacc   1200

tttatgccgg aacgcttcga aaacagcccg attacggtta tgggttctga atatgaatac   1260

ctgccgtttg gtgcaggtcg tcgcatgtgt ccgggtgcag ctctgggtct ggcgaatgtc   1320

gaactgccgc tggcccacat cctgtattac ttcaactgga aactgccgaa tggcaaaacc   1380

tttgaagatc tggacatgac cgaatccttc ggtgcaacgg tgcaacgcaa aaccgaactg   1440

ctgctggtgc cgacggattt ccaaacgctg accgcatcaa cg                      1482
```

<210> SEQ ID NO 52
<211> LENGTH: 488
<212> TYPE: PRT
<213> ORGANISM: Helianthus annuus

<400> SEQUENCE: 52

```
Met Glu Val Ser Leu Thr Thr Ser Ile Ala Leu Ala Thr Ile Val Phe
1               5                   10                  15

Phe Leu Tyr Lys Leu Leu Thr Arg Pro Thr Ser Ser Lys Asn Arg Leu
            20                  25                  30

Pro Glu Pro Trp Arg Leu Pro Ile Ile Gly His Met His His Leu Ile
        35                  40                  45

Gly Thr Met Pro His Arg Gly Val Met Asp Leu Ala Arg Lys Tyr Gly
    50                  55                  60

Ser Leu Met His Leu Gln Leu Gly Glu Val Ser Ala Ile Val Val Ser
65                  70                  75                  80

Ser Pro Lys Trp Ala Lys Glu Ile Leu Thr Thr Tyr Asp Ile Pro Phe
                85                  90                  95

Ala Asn Arg Pro Glu Thr Leu Thr Gly Glu Ile Ile Ala Tyr His Asn
            100                 105                 110

Thr Asp Ile Val Leu Ala Pro Tyr Gly Glu Tyr Trp Arg Gln Leu Arg
        115                 120                 125

Lys Leu Cys Thr Leu Glu Leu Leu Ser Val Lys Lys Val Lys Ser Phe
    130                 135                 140

Gln Ser Leu Arg Glu Glu Glu Cys Trp Asn Leu Val Gln Glu Ile Lys
145                 150                 155                 160

Ala Ser Gly Ser Gly Thr Pro Phe Asn Leu Ser Glu Gly Ile Phe Lys
                165                 170                 175

Val Ile Ala Thr Val Leu Ser Arg Ala Ala Phe Gly Lys Gly Ile Lys
            180                 185                 190

Asp Gln Lys Gln Phe Thr Glu Ile Val Lys Glu Ile Leu Arg Glu Thr
        195                 200                 205

Gly Gly Phe Asp Val Ala Asp Ile Phe Pro Ser Lys Lys Phe Leu His
    210                 215                 220

His Leu Ser Gly Lys Arg Gly Arg Leu Thr Ser Ile His Asn Lys Leu
225                 230                 235                 240
```

-continued

Asp Ser Leu Ile Asn Asn Leu Val Ala Glu His Thr Val Ser Lys Ser
245 250 255

Ser Lys Val Asn Glu Thr Leu Leu Asp Val Leu Leu Arg Leu Lys Asn
260 265 270

Ser Glu Glu Phe Pro Leu Thr Ala Asp Asn Val Lys Ala Ile Ile Leu
275 280 285

Asp Met Phe Gly Ala Gly Thr Asp Thr Ser Ser Ala Thr Val Glu Trp
290 295 300

Ala Ile Ser Glu Leu Ile Arg Cys Pro Arg Ala Met Glu Lys Val Gln
305 310 315 320

Ala Glu Leu Arg Gln Ala Leu Asn Gly Lys Glu Arg Ile Lys Glu Glu
325 330 335

Glu Ile Gln Asp Leu Pro Tyr Leu Asn Leu Val Ile Arg Glu Thr Leu
340 345 350

Arg Leu His Pro Pro Leu Pro Leu Val Met Pro Arg Glu Cys Arg Gln
355 360 365

Ala Met Asn Leu Ala Gly Tyr Asp Val Ala Asn Lys Thr Lys Leu Ile
370 375 380

Val Asn Val Phe Ala Ile Asn Arg Asp Pro Glu Tyr Trp Lys Asp Ala
385 390 395 400

Glu Ser Phe Asn Pro Glu Arg Phe Glu Asn Ser Asn Thr Thr Ile Met
405 410 415

Gly Ala Asp Tyr Glu Tyr Leu Pro Phe Gly Ala Gly Arg Arg Met Cys
420 425 430

Pro Gly Ser Ala Leu Gly Leu Ala Asn Val Gln Leu Pro Leu Ala Asn
435 440 445

Ile Leu Tyr Tyr Phe Lys Trp Lys Leu Pro Asn Gly Ala Ser His Asp
450 455 460

Gln Leu Asp Met Thr Glu Ser Phe Gly Ala Thr Val Gln Arg Lys Thr
465 470 475 480

Glu Leu Met Leu Val Pro Ser Phe
485

<210> SEQ ID NO 53
<211> LENGTH: 488
<212> TYPE: PRT
<213> ORGANISM: Helianthus annuus

<400> SEQUENCE: 53

Met Ala Leu Leu Leu Ala Val Phe Ile Ala Leu Ala Thr Ile Val Phe
1 5 10 15

Phe Leu Tyr Lys Leu Leu Thr Arg Pro Thr Ser Ser Lys Asn Arg Leu
20 25 30

Pro Glu Pro Trp Arg Leu Pro Ile Ile Gly His Met His His Leu Ile
35 40 45

Gly Thr Met Pro His Arg Gly Val Met Asp Leu Ala Arg Lys Tyr Gly
50 55 60

Ser Leu Met His Leu Gln Leu Gly Glu Val Ser Ala Ile Val Val Ser
65 70 75 80

Ser Pro Lys Trp Ala Lys Glu Ile Leu Thr Thr Tyr Asp Ile Pro Phe
85 90 95

Ala Asn Arg Pro Glu Thr Leu Thr Gly Glu Ile Ile Ala Tyr His Asn
100 105 110

Thr Asp Ile Val Leu Ala Pro Tyr Gly Glu Tyr Trp Arg Gln Leu Arg
115 120 125

Lys Leu Cys Thr Leu Glu Leu Leu Ser Val Lys Lys Val Lys Ser Phe
130 135 140

Gln Ser Leu Arg Glu Glu Glu Cys Trp Asn Leu Val Gln Glu Ile Lys
145 150 155 160

Ala Ser Gly Ser Gly Thr Pro Phe Asn Leu Ser Glu Gly Ile Phe Lys
165 170 175

Val Ile Ala Thr Val Leu Ser Arg Ala Ala Phe Gly Lys Gly Ile Lys
180 185 190

Asp Gln Lys Gln Phe Thr Glu Ile Val Lys Glu Ile Leu Arg Glu Thr
195 200 205

Gly Gly Phe Asp Val Ala Asp Ile Phe Pro Ser Lys Lys Phe Leu His
210 215 220

His Leu Ser Gly Lys Arg Gly Arg Leu Thr Ser Ile His Asn Lys Leu
225 230 235 240

Asp Ser Leu Ile Asn Asn Leu Val Ala Glu His Thr Val Ser Lys Ser
245 250 255

Ser Lys Val Asn Glu Thr Leu Leu Asp Val Leu Leu Arg Leu Lys Asn
260 265 270

Ser Glu Glu Phe Pro Leu Thr Ala Asp Asn Val Lys Ala Ile Ile Leu
275 280 285

Asp Met Phe Gly Ala Gly Thr Asp Thr Ser Ser Ala Thr Val Glu Trp
290 295 300

Ala Ile Ser Glu Leu Ile Arg Cys Pro Arg Ala Met Glu Lys Val Gln
305 310 315 320

Ala Glu Leu Arg Gln Ala Leu Asn Gly Lys Glu Arg Ile Lys Glu Glu
325 330 335

Glu Ile Gln Asp Leu Pro Tyr Leu Asn Leu Val Ile Arg Glu Thr Leu
340 345 350

Arg Leu His Pro Pro Leu Pro Leu Val Met Pro Arg Glu Cys Arg Gln
355 360 365

Ala Met Asn Leu Ala Gly Tyr Asp Val Ala Asn Lys Thr Lys Leu Ile
370 375 380

Val Asn Val Phe Ala Ile Asn Arg Asp Pro Glu Tyr Trp Lys Asp Ala
385 390 395 400

Glu Ser Phe Asn Pro Glu Arg Phe Glu Asn Ser Asn Thr Thr Ile Met
405 410 415

Gly Ala Asp Tyr Glu Tyr Leu Pro Phe Gly Ala Gly Arg Arg Met Cys
420 425 430

Pro Gly Ser Ala Leu Gly Leu Ala Asn Val Gln Leu Pro Leu Ala Asn
435 440 445

Ile Leu Tyr Tyr Phe Lys Trp Lys Leu Pro Asn Gly Ala Ser His Asp
450 455 460

Gln Leu Asp Met Thr Glu Ser Phe Gly Ala Thr Val Gln Arg Lys Thr
465 470 475 480

Glu Leu Met Leu Val Pro Ser Phe
485

<210> SEQ ID NO 54
<211> LENGTH: 1464
<212> TYPE: DNA
<213> ORGANISM: Helianthus annuus

<400> SEQUENCE: 54
atggctctgt tattagcagt tttcatcgcc ctggcaacca ttgtcttttt cctgtataaa 60

```
ctgctgaccc gtccgacctc atctaaaaac cgtctgccgg aaccgtggcg cctgccgatt    120

atcggccaca tgcatcacct gattggcacc atgccgcacc gtggtgtcat ggatctggca    180

cgcaaatatg gcagcctgat gcatctgcaa ctgggtgaag tttctgcgat tgtggttagc    240

tctccgaaat gggccaaaga aattctgacc acctatgata ttccgtttgc gaaccgcccg    300

gaaaccctga cgggcgaaat tatcgcatac cacaataccg acattgtgct ggctccgtat    360

ggtgaatact ggcgtcaact gcgtaaactg tgcacgctgg aactgctgag tgttaaaaaa    420

gtcaaaagtt tccagagcct gcgtgaagaa gaatgttgga acctggttca agaaattaaa    480

gcgagcggca gcggcacccc gtttaatctg agtgaaggta ttttcaaagt gattgcgacc    540

gtgctgagcc gtgcggcatt tggtaaaggt atcaaagatc agaaacaatt caccgaaatt    600

gtcaaagaaa tcctgcgcga aacgggcggt tttgatgtgg cggacatctt tccgagcaaa    660

aaattcctgc atcacctgtc tggcaaacgt ggtcgcctga cctcaattca taacaaactg    720

gattcgctga tcaacaatct ggtcgccgaa cataccgtga gcaaaagcag caaagtgaat    780

gaaacgctgc tggatgtcct gctgcgtctg aaaaactcgg aagaatttcc gctgaccgca    840

gacaatgtga aagctattat cctggatatg ttcggtgcag gcaccgatac cagcagcgca    900

acggtggaat gggccattag cgaactgatc cgttgcccgc gcgcaatgga aaaagttcag    960

gcagaactgc gtcaagctct gaacggcaaa gaacgcatta aagaagaaga aatccaggat   1020

ctgccgtatc tgaatctggt tattcgtgaa accctgcgtc tgcatccgcc gctgccgctg   1080

gtcatgccgc gtgaatgtcg ccaagcaatg aacctggctg gctatgacgt ggcaaataaa   1140

accaaactga tcgtcaatgt gtttgcgatt aaccgtgacc cggaatactg gaaagacgcg   1200

gaaagtttta acccggaacg ctttgaaaac agcaacacca cgattatggg tgcggattat   1260

gaatacctgc cgtttggcgc cggtcgtcgc atgtgtccgg gcagcgcgct gggtctggcc   1320

aacgttcaac tgccgctggc caatatcctg tattacttca aatggaaact gccgaatggc   1380

gcctcacacg atcaactgga catgaccgaa tcgtttggtg caaccgtgca acgcaaaacg   1440

gaactgatgc tggttccgtc tttc                                          1464
```

<210> SEQ ID NO 55
<211> LENGTH: 504
<212> TYPE: PRT
<213> ORGANISM: Artificial Sequence
<220> FEATURE:
<223> OTHER INFORMATION: Synthetic - Engineered valencene oxidase

<400> SEQUENCE: 55

```
Met Ala Trp Glu Tyr Ala Leu Ile Gly Leu Val Val Gly Ile Ile Ile
1               5                   10                  15

Gly Ala Val Ala Ala Trp Tyr Leu Lys Ser Tyr Thr Ser Ala Arg Arg
            20                  25                  30

Ser Gln Ser Asn His Leu Pro Arg Val Pro Glu Val Pro Gly Val Pro
        35                  40                  45

Leu Leu Gly Asn Leu Leu Gln Leu Lys Glu Lys Lys Pro Tyr Met Thr
    50                  55                  60

Phe Thr Arg Trp Ala Ala Thr Tyr Gly Pro Ile Tyr Ser Ile Lys Thr
65                  70                  75                  80

Gly Ala Thr Ser Met Val Val Val Ser Ser Asn Glu Ile Ala Lys Glu
                85                  90                  95

Ala Leu Val Thr Arg Phe Gln Ser Ile Ser Thr Arg Asn Leu Ser Lys
            100                 105                 110
```

```
Ala Leu Lys Val Leu Thr Ala Asp Lys Thr Met Val Ala Met Ser Asp
        115                 120                 125

Tyr Asp Asp Tyr His Lys Thr Val Lys Arg His Ile Leu Thr Ala Val
    130                 135                 140

Leu Gly Pro Asn Ala Gln Lys Lys His Arg Ile His Arg Asp Ile Met
145                 150                 155                 160

Met Asp Asn Ile Ser Thr Gln Leu His Glu Phe Val Lys Asn Asn Pro
                165                 170                 175

Glu Gln Glu Glu Val Asp Leu Arg Lys Ile Phe Gln Ser Glu Leu Phe
            180                 185                 190

Gly Leu Ala Met Arg Gln Ala Leu Gly Lys Asp Val Glu Ser Leu Tyr
        195                 200                 205

Val Glu Asp Leu Lys Ile Thr Met Asn Arg Asp Glu Ile Phe Gln Val
    210                 215                 220

Leu Val Val Asp Pro Met Met Gly Ala Ile Asp Val Asp Trp Arg Asp
225                 230                 235                 240

Phe Phe Pro Tyr Leu Lys Trp Val Pro Asn Lys Lys Phe Glu Asn Thr
                245                 250                 255

Ile Gln Gln Met Tyr Ile Arg Arg Glu Ala Val Met Lys Ser Leu Ile
            260                 265                 270

Lys Glu His Lys Lys Arg Ile Ala Ser Gly Glu Lys Leu Asn Ser Tyr
        275                 280                 285

Ile Asp Tyr Leu Leu Ser Glu Ala Gln Thr Leu Thr Asp Gln Gln Leu
    290                 295                 300

Leu Met Ser Leu Trp Glu Pro Ile Ile Glu Ser Ser Asp Thr Thr Met
305                 310                 315                 320

Val Thr Thr Glu Trp Ala Met Tyr Glu Leu Ala Lys Asn Pro Lys Leu
                325                 330                 335

Gln Asp Arg Leu Tyr Arg Asp Ile Lys Ser Val Cys Gly Ser Glu Lys
            340                 345                 350

Ile Thr Glu Glu His Leu Ser Gln Leu Pro Tyr Ile Thr Ala Ile Phe
        355                 360                 365

His Glu Thr Leu Arg Arg His Ser Pro Val Pro Ile Ile Pro Leu Arg
    370                 375                 380

His Val His Glu Asp Thr Val Leu Gly Gly Tyr His Val Pro Ala Gly
385                 390                 395                 400

Thr Glu Leu Ala Val Asn Ile Tyr Gly Cys Asn Met Asp Lys Asn Val
                405                 410                 415

Trp Glu Asn Pro Glu Glu Trp Asn Pro Glu Arg Phe Met Lys Glu Asn
            420                 425                 430

Glu Thr Ile Asp Phe Gln Lys Thr Met Ala Phe Gly Gly Gly Lys Arg
        435                 440                 445

Val Cys Ala Gly Ser Leu Gln Ala Leu Leu Thr Ala Ser Ile Gly Ile
    450                 455                 460

Gly Arg Met Val Gln Glu Phe Glu Trp Lys Leu Lys Asp Met Thr Gln
465                 470                 475                 480

Glu Glu Val Asn Thr Ile Gly Leu Thr Thr Gln Met Leu Arg Pro Leu
                485                 490                 495

Arg Ala Ile Ile Lys Pro Arg Ile
            500
```

<210> SEQ ID NO 56
<211> LENGTH: 505

<212> TYPE: PRT
<213> ORGANISM: Artificial Sequence
<220> FEATURE:
<223> OTHER INFORMATION: Synthetic - Engineered valencene oxidase

<400> SEQUENCE: 56

```
Met Ala Trp Glu Tyr Ala Leu Ile Gly Leu Val Val Gly Ile Ile Ile
1               5                   10                  15

Gly Ala Val Ala Met Arg Trp Tyr Leu Lys Ser Tyr Thr Ser Ala Arg
            20                  25                  30

Arg Ser Gln Ser Asn His Leu Pro Arg Val Pro Glu Val Pro Gly Val
        35                  40                  45

Pro Leu Leu Gly Asn Leu Leu Gln Leu Lys Glu Lys Lys Pro Tyr Met
    50                  55                  60

Thr Phe Thr Arg Trp Ala Ala Thr Tyr Gly Pro Ile Tyr Ser Ile Lys
65                  70                  75                  80

Thr Gly Ala Thr Ser Val Val Val Val Ser Ser Asn Glu Ile Ala Lys
                85                  90                  95

Glu Ala Met Val Thr Arg Phe Gln Ser Ile Ser Thr Arg Asn Leu Ser
            100                 105                 110

Lys Ala Leu Lys Val Leu Thr Ala Asp Lys Thr Met Val Ala Met Ser
        115                 120                 125

Asp Tyr Asp Asp Tyr His Lys Thr Val Lys Arg His Ile Leu Thr Ala
    130                 135                 140

Val Leu Gly Pro Asn Ala Gln Lys Lys His Arg Ile His Arg Asp Ile
145                 150                 155                 160

Met Met Asp Asn Ile Ser Thr Gln Leu His Glu Phe Val Lys Asn Asn
                165                 170                 175

Pro Glu Gln Glu Glu Val Asp Leu Arg Lys Ile Phe Gln Ser Glu Leu
            180                 185                 190

Phe Gly Leu Ala Met Arg Gln Ala Leu Gly Lys Asp Val Glu Ser Leu
        195                 200                 205

Tyr Val Glu Asp Leu Lys Ile Thr Met Asn Arg Asp Glu Ile Leu Gln
    210                 215                 220

Val Leu Val Val Asp Pro Met Met Gly Ala Ile Asp Val Asp Trp Arg
225                 230                 235                 240

Asp Phe Phe Pro Tyr Leu Lys Trp Val Pro Asn Lys Lys Phe Glu Asn
                245                 250                 255

Thr Ile Gln Gln Met Tyr Ile Arg Arg Glu Ala Val Met Lys Ser Leu
            260                 265                 270

Ile Lys Glu His Lys Lys Arg Ile Ala Ser Gly Glu Lys Leu Asn Ser
        275                 280                 285

Tyr Ile Asp Tyr Leu Leu Ser Glu Ala Gln Thr Leu Thr Asp Gln Gln
    290                 295                 300

Leu Leu Met Ser Leu Trp Glu Pro Ile Ile Glu Ser Ser Asp Thr Thr
305                 310                 315                 320

Met Val Thr Thr Glu Trp Ala Met Tyr Glu Leu Ala Lys Asn Pro Lys
                325                 330                 335

Leu Gln Asp Arg Leu Tyr Arg Asp Ile Lys Ser Val Cys Gly Ser Glu
            340                 345                 350

Lys Ile Thr Glu Glu His Leu Ser Gln Leu Pro Tyr Ile Thr Ala Ile
        355                 360                 365

Phe His Glu Thr Leu Arg Lys His Ser Pro Val Pro Ile Leu Pro Leu
    370                 375                 380
```

```
Arg His Val His Glu Asp Thr Val Leu Gly Gly Tyr His Val Pro Ala
385                 390                 395                 400

Gly Thr Glu Leu Ala Val Asn Ile Tyr Gly Cys Asn Met Asp Lys Asn
                405                 410                 415

Val Trp Glu Asn Pro Glu Glu Trp Asn Pro Glu Arg Phe Met Lys Glu
            420                 425                 430

Asn Glu Thr Ile Asp Phe Gln Lys Thr Met Ala Phe Gly Gly Gly Lys
        435                 440                 445

Arg Val Cys Ala Gly Ser Leu Gln Ala Leu Leu Ile Ala Ser Ile Gly
    450                 455                 460

Ile Gly Arg Met Val Gln Glu Phe Glu Trp Lys Leu Lys Asp Met Thr
465                 470                 475                 480

Gln Glu Glu Val Asn Thr Ile Gly Leu Thr Asn Gln Met Leu Arg Pro
                485                 490                 495

Leu Arg Ala Ile Ile Lys Pro Arg Ile
            500                 505


<210> SEQ ID NO 57
<211> LENGTH: 505
<212> TYPE: PRT
<213> ORGANISM: Artificial Sequence
<220> FEATURE:
<223> OTHER INFORMATION: Synthetic - Engineered valencene oxidase

<400> SEQUENCE: 57

Met Ala Trp Glu Tyr Ala Leu Ile Gly Leu Val Val Gly Ile Ile Ile
1               5                   10                  15

Gly Ala Val Ala Met Arg Trp Tyr Leu Lys Ser Tyr Thr Ser Ala Arg
            20                  25                  30

Arg Ser Gln Ser Asn His Leu Pro Arg Val Pro Glu Val Pro Gly Val
        35                  40                  45

Pro Leu Leu Gly Asn Leu Leu Gln Leu Lys Glu Lys Lys Pro Tyr Met
    50                  55                  60

Thr Phe Thr Lys Trp Ala Ala Thr Tyr Gly Pro Ile Tyr Ser Ile Lys
65                  70                  75                  80

Thr Gly Ala Thr Ser Met Val Val Val Ser Ser Asn Glu Ile Ala Lys
                85                  90                  95

Glu Ala Met Val Thr Arg Phe Gln Ser Ile Ser Thr Arg Asn Leu Ser
            100                 105                 110

Lys Ala Leu Lys Val Leu Thr Ala Asp Lys Gln Met Val Ala Met Ser
        115                 120                 125

Asp Tyr Asp Asp Tyr His Lys Thr Val Lys Arg His Ile Leu Thr Ala
    130                 135                 140

Val Leu Gly Pro Asn Ala Gln Lys Lys His Arg Ile His Arg Asp Ile
145                 150                 155                 160

Met Met Asp Asn Ile Ser Thr Gln Leu His Glu Phe Val Lys Asn Asn
                165                 170                 175

Pro Glu Gln Glu Glu Val Asp Leu Arg Lys Ile Phe Gln Ser Glu Leu
            180                 185                 190

Phe Gly Leu Ala Met Arg Gln Ala Leu Gly Lys Asp Val Glu Ser Leu
        195                 200                 205

Tyr Val Glu Asp Leu Lys Ile Thr Met Asn Arg Asp Glu Ile Leu Gln
    210                 215                 220

Val Leu Val Val Asp Pro Met Met Gly Ala Ile Asp Val Asp Trp Arg
225                 230                 235                 240
```

```
Asp Phe Phe Pro Tyr Leu Lys Trp Val Pro Asn Lys Lys Phe Glu Asn
                245                 250                 255

Thr Ile Gln Gln Met Tyr Ile Arg Arg Glu Ala Val Met Lys Ser Leu
            260                 265                 270

Ile Lys Glu His Lys Lys Arg Ile Ala Ser Gly Glu Lys Leu Asn Ser
        275                 280                 285

Tyr Ile Asp Tyr Leu Leu Ser Glu Ala Gln Thr Leu Thr Asp Gln Gln
    290                 295                 300

Leu Leu Met Ser Leu Trp Glu Pro Ile Ile Glu Ser Ser Asp Thr Thr
305                 310                 315                 320

Met Val Thr Thr Glu Trp Ala Met Tyr Glu Leu Ala Lys Asn Pro Lys
                325                 330                 335

Leu Gln Asp Arg Leu Tyr Arg Asp Ile Lys Ser Val Cys Gly Ser Glu
            340                 345                 350

Lys Ile Thr Glu Glu His Leu Ser Gln Leu Pro Tyr Ile Thr Ala Ile
        355                 360                 365

Phe His Glu Thr Leu Arg Lys His Ser Pro Val Pro Ile Leu Pro Leu
    370                 375                 380

Arg His Val His Glu Asp Thr Val Leu Gly Gly Tyr His Val Pro Ala
385                 390                 395                 400

Gly Thr Glu Leu Ala Val Asn Ile Tyr Gly Cys Asn Met Asp Lys Asn
                405                 410                 415

Val Trp Glu Asn Pro Glu Glu Trp Asn Pro Glu Arg Phe Met Lys Glu
            420                 425                 430

Asn Glu Thr Ile Asp Phe Gln Lys Thr Met Ala Phe Gly Gly Gly Lys
        435                 440                 445

Arg Val Cys Ala Gly Ser Leu Gln Ala Leu Leu Ile Ala Ser Ile Gly
    450                 455                 460

Ile Gly Arg Met Val Gln Glu Phe Glu Trp Lys Leu Lys Asp Met Thr
465                 470                 475                 480

Gln Glu Glu Val Asn Thr Ile Gly Leu Thr Asn Gln Met Leu Arg Pro
                485                 490                 495

Leu Arg Ala Ile Ile Lys Pro Arg Ile
            500                 505
```

<210> SEQ ID NO 58
<211> LENGTH: 505
<212> TYPE: PRT
<213> ORGANISM: Artificial Sequence
<220> FEATURE:
<223> OTHER INFORMATION: Synthetic - Engineered valencene oxidase

<400> SEQUENCE: 58

```
Met Ala Trp Glu Tyr Ala Leu Ile Gly Leu Val Val Gly Ile Ile Ile
1               5                   10                  15

Gly Ala Val Ala Met Arg Trp Tyr Leu Lys Ser Tyr Thr Ser Ala Arg
            20                  25                  30

Arg Ser Gln Ser Asn His Leu Pro Arg Val Pro Glu Val Pro Gly Val
        35                  40                  45

Pro Leu Leu Gly Asn Leu Leu Gln Leu Lys Glu Lys Lys Pro Tyr Met
    50                  55                  60

Thr Phe Thr Arg Trp Ala Ala Thr Tyr Gly Pro Ile Tyr Ser Ile Lys
65                  70                  75                  80

Thr Gly Ala Thr Ser Val Val Val Val Ser Ser Asn Glu Ile Ala Lys
                85                  90                  95
```

-continued

```
Glu Ala Met Val Thr Arg Phe Gln Ser Ile Ser Thr Arg Asn Leu Ser
            100                 105                 110

Lys Ala Leu Lys Val Leu Thr Ala Asp Lys Gln Met Val Ala Met Ser
        115                 120                 125

Asp Tyr Asp Asp Tyr His Lys Thr Val Lys Arg His Ile Leu Thr Ala
    130                 135                 140

Val Leu Gly Pro Asn Ala Gln Lys Lys His Arg Ile His Arg Asp Ile
145                 150                 155                 160

Met Met Asp Asn Ile Ser Thr Gln Leu His Glu Phe Val Lys Asn Asn
                165                 170                 175

Pro Glu Gln Glu Glu Val Asp Leu Arg Lys Ile Phe Gln Ser Glu Leu
            180                 185                 190

Phe Gly Leu Ala Met Arg Gln Ala Leu Gly Lys Asp Val Glu Ser Leu
        195                 200                 205

Tyr Val Glu Asp Leu Lys Ile Thr Met Asn Arg Asp Glu Ile Leu Gln
    210                 215                 220

Val Leu Val Val Asp Pro Met Met Gly Ala Ile Asp Val Asp Trp Arg
225                 230                 235                 240

Asp Phe Phe Pro Tyr Leu Lys Trp Val Pro Asn Lys Lys Phe Glu Asn
                245                 250                 255

Thr Ile Gln Gln Met Tyr Ile Arg Arg Glu Ala Val Met Lys Ser Leu
            260                 265                 270

Ile Lys Glu His Lys Lys Arg Ile Ala Ser Gly Glu Lys Leu Asn Ser
        275                 280                 285

Tyr Ile Asp Tyr Leu Leu Ser Glu Ala Gln Thr Leu Thr Asp Gln Gln
    290                 295                 300

Leu Leu Met Ser Leu Trp Glu Pro Ile Ile Glu Ser Ser Asp Thr Thr
305                 310                 315                 320

Met Val Thr Thr Glu Trp Ala Met Tyr Glu Leu Ala Lys Asn Pro Lys
                325                 330                 335

Leu Gln Asp Arg Leu Tyr Arg Asp Ile Lys Ser Val Cys Gly Ser Glu
            340                 345                 350

Lys Ile Thr Glu Glu His Leu Ser Gln Leu Pro Tyr Ile Thr Ala Ile
        355                 360                 365

Phe His Glu Thr Leu Arg Lys His Ser Pro Val Pro Ile Leu Pro Leu
    370                 375                 380

Arg His Val His Glu Asp Thr Val Leu Gly Gly Tyr His Val Pro Ala
385                 390                 395                 400

Gly Thr Glu Leu Ala Val Asn Ile Tyr Gly Cys Asn Met Asp Lys Asn
                405                 410                 415

Val Trp Glu Asn Pro Glu Glu Trp Asn Pro Glu Arg Phe Met Lys Glu
            420                 425                 430

Asn Glu Thr Ile Asp Phe Gln Lys Thr Met Ala Phe Gly Gly Gly Lys
        435                 440                 445

Arg Val Cys Ala Gly Ser Leu Gln Ala Leu Leu Ile Ala Ser Ile Gly
    450                 455                 460

Ile Gly Arg Met Val Gln Glu Phe Glu Trp Lys Leu Lys Asp Met Thr
465                 470                 475                 480

Gln Glu Glu Val Asn Thr Ile Gly Leu Thr Asn Gln Met Leu Arg Pro
                485                 490                 495

Leu Arg Ala Ile Ile Lys Pro Arg Ile
            500                 505
```

<210> SEQ ID NO 59
<211> LENGTH: 504
<212> TYPE: PRT
<213> ORGANISM: Artificial Sequence
<220> FEATURE:
<223> OTHER INFORMATION: Synthetic - Engineered valencene oxidase

<400> SEQUENCE: 59

```
Met Ala Trp Glu Tyr Ala Leu Ile Gly Leu Val Val Gly Ile Ile Ile
1               5                   10                  15

Gly Ala Val Ala Ala Trp Tyr Leu Lys Ser Tyr Thr Ser Ala Arg Arg
            20                  25                  30

Ser Gln Ser Asn His Leu Pro Arg Val Pro Glu Val Pro Gly Val Pro
        35                  40                  45

Leu Leu Gly Asn Leu Leu Gln Leu Lys Glu Lys Lys Pro Tyr Met Thr
    50                  55                  60

Phe Thr Lys Trp Ala Ala Thr Tyr Gly Pro Ile Tyr Ser Ile Lys Thr
65                  70                  75                  80

Gly Ala Thr Ser Met Val Val Val Ser Ser Asn Glu Ile Ala Lys Glu
                85                  90                  95

Ala Met Val Thr Arg Phe Gln Ser Ile Ser Thr Arg Asn Leu Ser Lys
            100                 105                 110

Ala Leu Lys Val Leu Thr Ala Asp Lys Gln Met Val Ala Met Ser Asp
        115                 120                 125

Tyr Asp Asp Tyr His Lys Thr Val Lys Arg His Ile Leu Thr Ala Val
    130                 135                 140

Leu Gly Pro Asn Ala Gln Lys Lys His Arg Ile His Arg Asp Ile Met
145                 150                 155                 160

Met Asp Asn Ile Ser Thr Gln Leu His Glu Phe Val Lys Asn Asn Pro
                165                 170                 175

Glu Gln Glu Glu Val Asp Leu Arg Lys Ile Phe Gln Ser Glu Leu Phe
            180                 185                 190

Gly Leu Ala Met Arg Gln Ala Leu Gly Lys Asp Val Glu Ser Leu Tyr
        195                 200                 205

Val Glu Asp Leu Lys Ile Thr Met Asn Arg Asp Glu Ile Leu Gln Val
    210                 215                 220

Leu Val Val Asp Pro Met Met Gly Ala Ile Asp Val Asp Trp Arg Asp
225                 230                 235                 240

Phe Phe Pro Tyr Leu Lys Trp Val Pro Asn Lys Lys Phe Glu Asn Thr
                245                 250                 255

Ile Gln Gln Met Tyr Ile Arg Arg Glu Ala Val Met Lys Ser Leu Ile
            260                 265                 270

Lys Glu His Lys Lys Arg Ile Ala Ser Gly Glu Lys Leu Asn Ser Tyr
        275                 280                 285

Ile Asp Tyr Leu Leu Ser Glu Ala Gln Thr Leu Thr Asp Gln Gln Leu
    290                 295                 300

Leu Met Ser Leu Trp Glu Pro Ile Ile Glu Ser Ser Asp Thr Thr Met
305                 310                 315                 320

Val Thr Thr Glu Trp Ala Met Tyr Glu Leu Ala Lys Asn Pro Lys Leu
                325                 330                 335

Gln Asp Arg Leu Tyr Arg Asp Ile Lys Ser Val Cys Gly Ser Glu Lys
            340                 345                 350

Ile Thr Glu Glu His Leu Ser Gln Leu Pro Tyr Ile Thr Ala Ile Phe
        355                 360                 365

His Glu Thr Leu Arg Lys His Ser Pro Val Pro Ile Leu Pro Leu Arg
```

370 375 380

His Val His Glu Asp Thr Val Leu Gly Gly Tyr His Val Pro Ala Gly
385 390 395 400

Thr Glu Leu Ala Val Asn Ile Tyr Gly Cys Asn Met Asp Lys Asn Val
405 410 415

Trp Glu Asn Pro Glu Glu Trp Asn Pro Glu Arg Phe Met Lys Glu Asn
420 425 430

Glu Thr Ile Asp Phe Gln Lys Thr Met Ala Phe Gly Gly Gly Lys Arg
435 440 445

Val Cys Ala Gly Ser Leu Gln Ala Leu Leu Ile Ala Ser Ile Gly Ile
450 455 460

Gly Arg Met Val Gln Glu Phe Glu Trp Lys Leu Lys Asp Met Thr Gln
465 470 475 480

Glu Glu Val Asn Thr Ile Gly Leu Thr Asn Gln Met Leu Arg Pro Leu
485 490 495

Arg Ala Ile Ile Lys Pro Arg Ile
500

<210> SEQ ID NO 60
<211> LENGTH: 505
<212> TYPE: PRT
<213> ORGANISM: Artificial Sequence
<220> FEATURE:
<223> OTHER INFORMATION: Synthetic - Engineered valencene oxidase

<400> SEQUENCE: 60

Met Ala Trp Glu Tyr Ala Leu Ile Gly Leu Val Val Gly Ile Ile Ile
1 5 10 15

Gly Ala Val Ala Met Arg Trp Tyr Leu Lys Ser Tyr Thr Ser Ala Arg
20 25 30

Arg Ser Gln Ser Asn His Leu Pro Arg Val Pro Glu Val Pro Gly Val
35 40 45

Pro Leu Leu Gly Asn Leu Leu Gln Leu Lys Glu Lys Lys Pro Tyr Met
50 55 60

Thr Phe Thr Lys Trp Ala Ala Thr Tyr Gly Pro Ile Tyr Ser Ile Lys
65 70 75 80

Thr Gly Ala Thr Ser Val Val Val Val Ser Ser Asn Glu Ile Ala Lys
85 90 95

Glu Ala Met Val Thr Arg Phe Gln Ser Ile Ser Thr Arg Asn Leu Ser
100 105 110

Lys Ala Leu Lys Val Leu Thr Ala Asp Lys Thr Met Val Ala Met Ser
115 120 125

Asp Tyr Asp Asp Tyr His Lys Thr Val Lys Arg His Ile Leu Thr Ala
130 135 140

Val Leu Gly Pro Asn Ala Gln Lys Lys His Arg Ile His Arg Asp Ile
145 150 155 160

Met Met Asp Asn Ile Ser Thr Gln Leu His Glu Phe Val Lys Asn Asn
165 170 175

Pro Glu Gln Glu Glu Val Asp Leu Arg Lys Ile Phe Gln Ser Glu Leu
180 185 190

Phe Gly Leu Ala Met Arg Gln Ala Leu Gly Lys Asp Val Glu Ser Leu
195 200 205

Tyr Val Glu Asp Leu Lys Ile Thr Met Asn Arg Asp Glu Ile Leu Gln
210 215 220

Val Leu Val Val Asp Pro Met Met Gly Ala Ile Asp Val Asp Trp Arg

```
225                 230                 235                 240

Asp Phe Phe Pro Tyr Leu Lys Trp Val Pro Asn Lys Lys Phe Glu Asn
                245                 250                 255

Thr Ile Gln Gln Met Tyr Ile Arg Arg Glu Ala Val Met Lys Ser Leu
            260                 265                 270

Ile Lys Glu His Lys Lys Arg Ile Ala Ser Gly Glu Lys Leu Asn Ser
        275                 280                 285

Tyr Ile Asp Tyr Leu Leu Ser Glu Ala Gln Thr Leu Thr Asp Gln Gln
    290                 295                 300

Leu Leu Met Ser Leu Trp Glu Pro Ile Ile Glu Ser Ser Asp Thr Thr
305                 310                 315                 320

Met Val Thr Thr Glu Trp Ala Met Tyr Glu Leu Ala Lys Asn Pro Lys
                325                 330                 335

Leu Gln Asp Arg Leu Tyr Arg Asp Ile Lys Ser Val Cys Gly Ser Glu
            340                 345                 350

Lys Ile Thr Glu Glu His Leu Ser Gln Leu Pro Tyr Ile Thr Ala Ile
        355                 360                 365

Phe His Glu Thr Leu Arg Lys His Ser Pro Val Pro Ile Ile Pro Leu
    370                 375                 380

Arg His Val His Glu Asp Thr Val Leu Gly Gly Tyr His Val Pro Ala
385                 390                 395                 400

Gly Thr Glu Leu Ala Val Asn Ile Tyr Gly Cys Asn Met Asp Lys Asn
                405                 410                 415

Val Trp Glu Asn Pro Glu Glu Trp Asn Pro Glu Arg Phe Met Lys Glu
            420                 425                 430

Asn Glu Thr Ile Asp Phe Gln Lys Thr Met Ala Phe Gly Gly Gly Lys
        435                 440                 445

Arg Val Cys Ala Gly Ser Leu Gln Ala Leu Leu Ile Ala Ser Ile Gly
    450                 455                 460

Ile Gly Arg Met Val Gln Glu Phe Glu Trp Lys Leu Lys Asp Met Thr
465                 470                 475                 480

Gln Glu Glu Val Asn Thr Ile Gly Leu Thr Asn Gln Met Leu Arg Pro
                485                 490                 495

Leu Arg Ala Ile Ile Lys Pro Arg Ile
            500                 505


<210> SEQ ID NO 61
<211> LENGTH: 505
<212> TYPE: PRT
<213> ORGANISM: Artificial Sequence
<220> FEATURE:
<223> OTHER INFORMATION: Synthetic - Engineered valencene oxidase

<400> SEQUENCE: 61

Met Ala Trp Glu Tyr Ala Leu Ile Gly Leu Val Val Gly Ile Ile Ile
1               5                   10                  15

Gly Ala Val Ala Met Arg Trp Tyr Leu Lys Ser Tyr Thr Ser Ala Arg
            20                  25                  30

Arg Ser Gln Ser Asn His Leu Pro Arg Val Pro Glu Val Pro Gly Val
        35                  40                  45

Pro Leu Leu Gly Asn Leu Leu Gln Leu Lys Glu Lys Lys Pro Tyr Met
    50                  55                  60

Thr Phe Thr Lys Trp Ala Ala Thr Tyr Gly Pro Ile Tyr Ser Ile Lys
65                  70                  75                  80

Thr Gly Ala Thr Ser Val Val Val Val Ser Ser Asn Glu Ile Ala Lys
```

-continued

```
                85                  90                  95

Glu Ala Leu Val Thr Arg Phe Gln Ser Ile Ser Thr Arg Asn Leu Ser
            100                 105                 110

Lys Ala Leu Lys Val Leu Thr Ala Asp Lys Gln Met Val Ala Met Ser
        115                 120                 125

Asp Tyr Asp Asp Tyr His Lys Thr Val Lys Arg His Ile Leu Thr Ala
    130                 135                 140

Val Leu Gly Pro Asn Ala Gln Lys Lys His Arg Ile His Arg Asp Ile
145                 150                 155                 160

Met Met Asp Asn Ile Ser Thr Gln Leu His Glu Phe Val Lys Asn Asn
                165                 170                 175

Pro Glu Gln Glu Glu Val Asp Leu Arg Lys Ile Phe Gln Ser Glu Leu
            180                 185                 190

Phe Gly Leu Ala Met Arg Gln Ala Leu Gly Lys Asp Val Glu Ser Leu
        195                 200                 205

Tyr Val Glu Asp Leu Lys Ile Thr Met Asn Arg Asp Glu Ile Leu Gln
    210                 215                 220

Val Leu Val Val Asp Pro Met Met Gly Ala Ile Asp Val Asp Trp Arg
225                 230                 235                 240

Asp Phe Phe Pro Tyr Leu Lys Trp Val Pro Asn Lys Lys Phe Glu Asn
                245                 250                 255

Thr Ile Gln Gln Met Tyr Ile Arg Arg Glu Ala Val Met Lys Ser Leu
            260                 265                 270

Ile Lys Glu Gln Lys Lys Arg Ile Ala Ser Gly Glu Lys Leu Asn Ser
        275                 280                 285

Tyr Ile Asp Tyr Leu Leu Ser Glu Ala Gln Thr Leu Thr Asp Gln Gln
    290                 295                 300

Leu Leu Met Ser Leu Trp Glu Pro Ile Ile Glu Ser Ser Asp Thr Thr
305                 310                 315                 320

Met Val Thr Thr Glu Trp Ala Met Tyr Glu Leu Ala Lys Asn Pro Lys
                325                 330                 335

Leu Gln Asp Arg Leu Tyr Arg Asp Ile Lys Ser Val Cys Gly Ser Glu
            340                 345                 350

Lys Ile Thr Glu Glu His Leu Ser Gln Leu Pro Tyr Ile Thr Ala Ile
        355                 360                 365

Phe His Glu Thr Leu Arg Lys His Ser Pro Val Pro Ile Leu Pro Leu
    370                 375                 380

Arg His Val His Glu Asp Thr Val Leu Gly Gly Tyr His Val Pro Ala
385                 390                 395                 400

Gly Thr Glu Leu Ala Val Asn Ile Tyr Gly Cys Asn Met Asp Lys Asn
                405                 410                 415

Val Trp Glu Asn Pro Glu Glu Trp Asn Pro Glu Arg Phe Met Lys Glu
            420                 425                 430

Asn Glu Thr Ile Asp Phe Gln Lys Thr Met Ala Phe Gly Gly Gly Lys
        435                 440                 445

Arg Val Cys Ala Gly Ser Leu Gln Ala Leu Leu Ile Ala Ser Ile Gly
    450                 455                 460

Ile Gly Arg Met Val Gln Glu Phe Glu Trp Lys Leu Lys Asp Met Thr
465                 470                 475                 480

Gln Glu Glu Val Asn Thr Ile Gly Leu Thr Asn Gln Met Leu Arg Pro
                485                 490                 495

Leu Arg Ala Ile Ile Lys Pro Arg Ile
            500                 505
```

<210> SEQ ID NO 62
<211> LENGTH: 710
<212> TYPE: PRT
<213> ORGANISM: Stevia rebaudiana

<400> SEQUENCE: 62

Met Gln Ser Asp Ser Val Lys Val Ser Pro Phe Asp Leu Val Ser Ala
1               5                   10                  15

Ala Met Asn Gly Lys Ala Met Glu Lys Leu Asn Ala Ser Glu Ser Glu
            20                  25                  30

Asp Pro Thr Thr Leu Pro Ala Leu Lys Met Leu Val Glu Asn Arg Glu
        35                  40                  45

Leu Leu Thr Leu Phe Thr Thr Ser Phe Ala Val Leu Ile Gly Cys Leu
    50                  55                  60

Val Phe Leu Met Trp Arg Arg Ser Ser Ser Lys Lys Leu Val Gln Asp
65                  70                  75                  80

Pro Val Pro Gln Val Ile Val Val Lys Lys Lys Glu Lys Glu Ser Glu
                85                  90                  95

Val Asp Asp Gly Lys Lys Lys Val Ser Ile Phe Tyr Gly Thr Gln Thr
            100                 105                 110

Gly Thr Ala Glu Gly Phe Ala Lys Ala Leu Val Glu Glu Ala Lys Val
        115                 120                 125

Arg Tyr Glu Lys Thr Ser Phe Lys Val Ile Asp Leu Asp Asp Tyr Ala
    130                 135                 140

Ala Asp Asp Asp Glu Tyr Glu Glu Lys Leu Lys Lys Glu Ser Leu Ala
145                 150                 155                 160

Phe Phe Phe Leu Ala Thr Tyr Gly Asp Gly Glu Pro Thr Asp Asn Ala
                165                 170                 175

Ala Asn Phe Tyr Lys Trp Phe Thr Glu Gly Asp Asp Lys Gly Glu Trp
            180                 185                 190

Leu Lys Lys Leu Gln Tyr Gly Val Phe Gly Leu Gly Asn Arg Gln Tyr
        195                 200                 205

Glu His Phe Asn Lys Ile Ala Ile Val Val Asp Asp Lys Leu Thr Glu
    210                 215                 220

Met Gly Ala Lys Arg Leu Val Pro Val Gly Leu Gly Asp Asp Asp Gln
225                 230                 235                 240

Cys Ile Glu Asp Asp Phe Thr Ala Trp Lys Glu Leu Val Trp Pro Glu
                245                 250                 255

Leu Asp Gln Leu Leu Arg Asp Glu Asp Asp Thr Ser Val Thr Thr Pro
            260                 265                 270

Tyr Thr Ala Ala Val Leu Glu Tyr Arg Val Val Tyr His Asp Lys Pro
        275                 280                 285

Ala Asp Ser Tyr Ala Glu Asp Gln Thr His Thr Asn Gly His Val Val
    290                 295                 300

His Asp Ala Gln His Pro Ser Arg Ser Asn Val Ala Phe Lys Lys Glu
305                 310                 315                 320

Leu His Thr Ser Gln Ser Asp Arg Ser Cys Thr His Leu Glu Phe Asp
                325                 330                 335

Ile Ser His Thr Gly Leu Ser Tyr Glu Thr Gly Asp His Val Gly Val
            340                 345                 350

Tyr Ser Glu Asn Leu Ser Glu Val Val Asp Glu Ala Leu Lys Leu Leu
        355                 360                 365

Gly Leu Ser Pro Asp Thr Tyr Phe Ser Val His Ala Asp Lys Glu Asp

```
    370                 375                 380

Gly Thr Pro Ile Gly Gly Ala Ser Leu Pro Pro Pro Phe Pro Pro Cys
385                 390                 395                 400

Thr Leu Arg Asp Ala Leu Thr Arg Tyr Ala Asp Val Leu Ser Ser Pro
                405                 410                 415

Lys Lys Val Ala Leu Leu Ala Leu Ala Ala His Ala Ser Asp Pro Ser
            420                 425                 430

Glu Ala Asp Arg Leu Lys Phe Leu Ala Ser Pro Ala Gly Lys Asp Glu
        435                 440                 445

Tyr Ala Gln Trp Ile Val Ala Asn Gln Arg Ser Leu Leu Glu Val Met
    450                 455                 460

Gln Ser Phe Pro Ser Ala Lys Pro Pro Leu Gly Val Phe Phe Ala Ala
465                 470                 475                 480

Val Ala Pro Arg Leu Gln Pro Arg Tyr Tyr Ser Ile Ser Ser Ser Pro
                485                 490                 495

Lys Met Ser Pro Asn Arg Ile His Val Thr Cys Ala Leu Val Tyr Glu
            500                 505                 510

Thr Thr Pro Ala Gly Arg Ile His Arg Gly Leu Cys Ser Thr Trp Met
        515                 520                 525

Lys Asn Ala Val Pro Leu Thr Glu Ser Pro Asp Cys Ser Gln Ala Ser
    530                 535                 540

Ile Phe Val Arg Thr Ser Asn Phe Arg Leu Pro Val Asp Pro Lys Val
545                 550                 555                 560

Pro Val Ile Met Ile Gly Pro Gly Thr Gly Leu Ala Pro Phe Arg Gly
                565                 570                 575

Phe Leu Gln Glu Arg Leu Ala Leu Lys Glu Ser Gly Thr Glu Leu Gly
            580                 585                 590

Ser Ser Ile Phe Phe Phe Gly Cys Arg Asn Arg Lys Val Asp Phe Ile
        595                 600                 605

Tyr Glu Asp Glu Leu Asn Asn Phe Val Glu Thr Gly Ala Leu Ser Glu
    610                 615                 620

Leu Ile Val Ala Phe Ser Arg Glu Gly Thr Ala Lys Glu Tyr Val Gln
625                 630                 635                 640

His Lys Met Ser Gln Lys Ala Ser Asp Ile Trp Lys Leu Leu Ser Glu
                645                 650                 655

Gly Ala Tyr Leu Tyr Val Cys Gly Asp Ala Lys Gly Met Ala Lys Asp
            660                 665                 670

Val His Arg Thr Leu His Thr Ile Val Gln Glu Gln Gly Ser Leu Asp
        675                 680                 685

Ser Ser Lys Ala Glu Leu Tyr Val Lys Asn Leu Gln Met Ser Gly Arg
    690                 695                 700

Tyr Leu Arg Asp Val Trp
705                 710
```

<210> SEQ ID NO 63
<211> LENGTH: 2133
<212> TYPE: DNA
<213> ORGANISM: Stevia rebaudiana

<400> SEQUENCE: 63

```
atgcagagcg attctgttaa agtatccccg ttcgacctgg tctctgcggc tatgaacggc      60

aaagcaatgg agaaactgaa cgcgagcgaa tctgaagatc caaccaccct gccggcactg     120

aaaatgctgg tagaaaaccg tgaactgctg actctgttca ccacctcctt cgccgttctg     180
```

-continued

```
attggttgcc tggtcttcct gatgtggcgc cgttcctctt ccaagaagct ggtacaggac    240
ccggttcctc aggtgatcgt cgttaaaaag aaagagaagg aaagcgaagt cgatgacggc    300
aaaaagaagg tttccatttt ctacggtact cagaccggca ccgctgaggg ttttgccaaa    360
gcactggttg aagaggcaaa agtgcgttac gaaaaaactt ccttcaaagt gattgacctg    420
gacgactatg ctgcggatga tgatgaatac gaggaaaaac tgaaaaaaga aagcctggcc    480
ttcttcttcc tggcaaccta tggcgatggt gaaccgaccg acaacgcggc gaacttctac    540
aaatggttta ccgaaggcga cgacaaaggt gaatggctga agaaactgca gtatggtgtt    600
ttcggtctgg gcaatcgcca gtacgaacat tttaacaaaa tcgcaatcgt tgttgatgac    660
aaactgactg aaatgggtgc gaaacgtctg gtgccggttg gcctgggtga cgatgatcaa    720
tgcatcgaag atgacttcac cgcatggaaa gaactggttt ggccggaact ggatcagctg    780
ctgcgcgacg aagacgacac ttccgtgacc accccgtata ccgctgcagt gctggagtac    840
cgtgttgttt accacgataa accggcggac tcttacgccg aagatcagac tcacactaac    900
ggtcacgtcg tacatgacgc acagcacccg tctcgtagca atgttgcgtt taagaaagag    960
ctgcacacga gccagtccga ccgctcttgt acgcacctgg agttcgatat ctcccacacc   1020
ggtctgtcct atgaaaccgg tgaccatgtt ggcgtttaca gcgaaaacct gagcgaggta   1080
gttgatgaag cgctgaaact gctgggcctg tctccagaca cctactttag cgtgcatgct   1140
gacaaggaag atggtactcc gattggcggc gcttccctgc cgccaccgtt tccaccttgc   1200
actctgcgtg atgctctgac tcgttacgct gatgttctgt ctagcccgaa aaaggttgcg   1260
ctgctggcgc tggccgcaca tgcttctgac ccgtctgaag ctgaccgtct gaaattcctg   1320
gcgtctccgg ccggcaaaga cgaatacgcg cagtggattg tcgctaacca gcgctctctg   1380
ctggaagtga tgcagtcctt cccgtctgcc aaaccgccac tgggcgtgtt tttcgcagct   1440
gtggctccgc gcctgcagcc gcgctactat tctatctcta gctccccgaa aatgagcccg   1500
aaccgcatcc acgttacttg tgctctggtt tacgaaacca cccctgcggg ccgtatccac   1560
cgtggtctgt gctctacgtg gatgaaaaat gccgtgccgc tgaccgaatc cccggactgc   1620
tctcaggcgt ccatcttcgt gcgtacctct aacttccgtc tgccggtgga cccgaaagtt   1680
cctgttatca tgatcggtcc tggcacgggt ctggccccgt ttcgtggttt tctgcaggag   1740
cgtctggctc tgaaagaatc cggtactgag ctgggctctt ccatcttttt cttcggttgt   1800
cgtaaccgca aagtcgattt catctatgaa gacgaactga acaacttcgt agagactggt   1860
gcactgtccg aactgattgt ggcattctct cgtgaaggca cggcgaaaga atacgttcaa   1920
cacaaaatgt ctcagaaagc gagcgatatc tggaaactgc tgtccgaggg tgcgtatctg   1980
tatgtttgtg gcgacgcgaa aggcatggct aaagatgtac accgcaccct gcacaccatt   2040
gtacaagaac aaggctctct ggatagctcc aaggcagaac tgtacgtgaa aaacctgcag   2100
atgtctggcc gttacctgcg tgatgtatgg taa                                2133
```

<210> SEQ ID NO 64
<211> LENGTH: 692
<212> TYPE: PRT
<213> ORGANISM: Arabidopsis thaliana

<400> SEQUENCE: 64

```
Met Thr Ser Ala Leu Tyr Ala Ser Asp Leu Phe Lys Gln Leu Lys Ser
1               5                   10                  15

Ile Met Gly Thr Asp Ser Leu Ser Asp Asp Val Val Leu Val Ile Ala
            20                  25                  30
```

-continued

```
Thr Thr Ser Leu Ala Leu Val Ala Gly Phe Val Val Leu Leu Trp Lys
        35                  40                  45

Lys Thr Thr Ala Asp Arg Ser Gly Glu Leu Lys Pro Leu Met Ile Pro
    50                  55                  60

Lys Ser Leu Met Ala Lys Asp Glu Asp Asp Asp Leu Asp Leu Gly Ser
65                  70                  75                  80

Gly Lys Thr Arg Val Ser Ile Phe Phe Gly Thr Gln Thr Gly Thr Ala
                85                  90                  95

Glu Gly Phe Ala Lys Ala Leu Ser Glu Glu Ile Lys Ala Arg Tyr Glu
            100                 105                 110

Lys Ala Ala Val Lys Val Ile Asp Leu Asp Asp Tyr Ala Ala Asp Asp
        115                 120                 125

Asp Gln Tyr Glu Glu Lys Leu Lys Lys Glu Thr Leu Ala Phe Phe Cys
    130                 135                 140

Val Ala Thr Tyr Gly Asp Gly Glu Pro Thr Asp Asn Ala Ala Arg Phe
145                 150                 155                 160

Ser Lys Trp Phe Thr Glu Glu Asn Glu Arg Asp Ile Lys Leu Gln Gln
                165                 170                 175

Leu Ala Tyr Gly Val Phe Ala Leu Gly Asn Arg Gln Tyr Glu His Phe
            180                 185                 190

Asn Lys Ile Gly Ile Val Leu Asp Glu Glu Leu Cys Lys Lys Gly Ala
        195                 200                 205

Lys Arg Leu Ile Glu Val Gly Leu Gly Asp Asp Asp Gln Ser Ile Glu
    210                 215                 220

Asp Asp Phe Asn Ala Trp Lys Glu Ser Leu Trp Ser Glu Leu Asp Lys
225                 230                 235                 240

Leu Leu Lys Asp Glu Asp Asp Lys Ser Val Ala Thr Pro Tyr Thr Ala
                245                 250                 255

Val Ile Pro Glu Tyr Arg Val Val Thr His Asp Pro Arg Phe Thr Thr
            260                 265                 270

Gln Lys Ser Met Glu Ser Asn Val Ala Asn Gly Asn Thr Thr Ile Asp
        275                 280                 285

Ile His His Pro Cys Arg Val Asp Val Ala Val Gln Lys Glu Leu His
    290                 295                 300

Thr His Glu Ser Asp Arg Ser Cys Ile His Leu Glu Phe Asp Ile Ser
305                 310                 315                 320

Arg Thr Gly Ile Thr Tyr Glu Thr Gly Asp His Val Gly Val Tyr Ala
                325                 330                 335

Glu Asn His Val Glu Ile Val Glu Glu Ala Gly Lys Leu Leu Gly His
            340                 345                 350

Ser Leu Asp Leu Val Phe Ser Ile His Ala Asp Lys Glu Asp Gly Ser
        355                 360                 365

Pro Leu Glu Ser Ala Val Pro Pro Pro Phe Pro Gly Pro Cys Thr Leu
    370                 375                 380

Gly Thr Gly Leu Ala Arg Tyr Ala Asp Leu Leu Asn Pro Pro Arg Lys
385                 390                 395                 400

Ser Ala Leu Val Ala Leu Ala Ala Tyr Ala Thr Glu Pro Ser Glu Ala
                405                 410                 415

Glu Lys Leu Lys His Leu Thr Ser Pro Asp Gly Lys Asp Glu Tyr Ser
            420                 425                 430

Gln Trp Ile Val Ala Ser Gln Arg Ser Leu Leu Glu Val Met Ala Ala
        435                 440                 445
```

-continued

```
Phe Pro Ser Ala Lys Pro Pro Leu Gly Val Phe Phe Ala Ala Ile Ala
    450                 455                 460

Pro Arg Leu Gln Pro Arg Tyr Tyr Ser Ile Ser Ser Cys Gln Asp Trp
465                 470                 475                 480

Ala Pro Ser Arg Val His Val Thr Ser Ala Leu Val Tyr Gly Pro Thr
                485                 490                 495

Pro Thr Gly Arg Ile His Lys Gly Val Cys Ser Thr Trp Met Lys Asn
            500                 505                 510

Ala Val Pro Ala Glu Lys Ser His Glu Cys Ser Gly Ala Pro Ile Phe
        515                 520                 525

Ile Arg Ala Ser Asn Phe Lys Leu Pro Ser Asn Pro Ser Thr Pro Ile
    530                 535                 540

Val Met Val Gly Pro Gly Thr Gly Leu Ala Pro Phe Arg Gly Phe Leu
545                 550                 555                 560

Gln Glu Arg Met Ala Leu Lys Glu Asp Gly Glu Glu Leu Gly Ser Ser
                565                 570                 575

Leu Leu Phe Phe Gly Cys Arg Asn Arg Gln Met Asp Phe Ile Tyr Glu
            580                 585                 590

Asp Glu Leu Asn Asn Phe Val Asp Gln Gly Val Ile Ser Glu Leu Ile
        595                 600                 605

Met Ala Phe Ser Arg Glu Gly Ala Gln Lys Glu Tyr Val Gln His Lys
    610                 615                 620

Met Met Glu Lys Ala Ala Gln Val Trp Asp Leu Ile Lys Glu Glu Gly
625                 630                 635                 640

Tyr Leu Tyr Val Cys Gly Asp Ala Lys Gly Met Ala Arg Asp Val His
                645                 650                 655

Arg Thr Leu His Thr Ile Val Gln Glu Gln Glu Gly Val Ser Ser Ser
            660                 665                 670

Glu Ala Glu Ala Ile Val Lys Lys Leu Gln Thr Glu Gly Arg Tyr Leu
        675                 680                 685

Arg Asp Val Trp
    690
```

<210> SEQ ID NO 65
<211> LENGTH: 2079
<212> TYPE: DNA
<213> ORGANISM: Arabidopsis thaliana

<400> SEQUENCE: 65

```
atgaccagcg cactgtacgc aagcgacctg tttaagcaac tgaagagcat tatgggcacc      60

gatagcctga gcgatgatgt tgtcctggtc attgcgacca cgagcctggc actggtggct     120

ggttttgtgg ttctgctgtg gaaaaagacc acggccgatc gttctggcga actgaaaccg     180

ctgatgattc cgaaaagtct gatggcaaag gacgaagatg acgatctgga tctgggctcc     240

ggtaaaaccc gtgtgtcaat ctttttcggt acccagacgg gcaccgcaga aggtttcgca     300

aaagctctgt ctgaagaaat taaggcgcgc tatgaaaaag cggccgttaa ggtcatcgat     360

ctggacgatt atgcagctga cgatgaccag tacgaagaaa aactgaaaaa ggaaaccctg     420

gcgtttttct gcgttgccac ctacggcgac ggtgaaccga cggataacgc ggcccgtttt     480

agtaaatggt tcaccgaaga aaatgaacgc gacattaagc tgcagcaact ggcgtatggc     540

gtgtttgctc tgggtaaccg tcagtacgaa catttcaaca agatcggtat cgtcctggat     600

gaagaactgt gtaaaaaggg cgcgaagcgc ctgattgaag tgggcctggg tgatgacgat     660

caatccatcg aagacgattt taacgcctgg aaagaatctc tgtggagtga actggacaaa     720
```

ctgctgaagg atgaagacga taagagcgtg gcgacgccgt ataccgccgt tattccggaa 780
taccgtgtcg tgacccatga tccgcgcttc accacgcaga aaagcatgga atcaaatgtt 840
gcgaacggta ataccacgat tgacatccat cacccgtgcc gtgtggatgt tgccgtccaa 900
aaagaactgc atacccacga atcggaccgt agctgtatcc acctggaatt tgatattagc 960
cgcacgggca tcacctatga aacgggcgac catgtgggtg tttacgcaga aaaccacgtg 1020
gaaattgttg aagaagctgg caaactgctg ggtcattcgc tggatctggt ttttagcatc 1080
cacgcggaca aggaagatgg ttcgccgctg gaaagcgcag tgccgccgcc gttcccgggt 1140
ccgtgcaccc tgggtacggg tctggcacgt tatgcagatc tgctgaatcc gccgcgcaaa 1200
tccgcactgg tggctctggc agcttacgca accgaaccgt cagaagctga aaaactgaag 1260
catctgacgt cgccggacgg taaagatgaa tatagccagt ggattgttgc gtctcaacgc 1320
agtctgctgg aagtcatggc agcatttccg tcggcaaaac cgccgctggg cgtgtttttc 1380
gcagctattg caccgcgtct gcagccgcgc tattacagca tcagctcttg tcaagattgg 1440
gcgccgtctc gtgtccatgt gaccagtgca ctggtgtatg gtccgacgcc gaccggtcgc 1500
attcacaaag gcgtgtgctc tacctggatg aaaaacgcgg ttccggccga aaagtctcac 1560
gaatgtagtg gtgcgccgat ttttatccgt gccagtaact tcaaactgcc gtccaatccg 1620
tcaaccccga tcgttatggt cggtccgggt acgggtctgg caccgtttcg tggtttcctg 1680
caggaacgca tggctctgaa agaagatggc gaagaactgg gtagttccct gctgtttttc 1740
ggctgccgta atcgccagat ggacttcatc tacgaagatg aactgaacaa cttcgtcgat 1800
caaggtgtga tttccgaact gatcatggca ttttcacgcg aaggcgctca gaaagaatac 1860
gtccaacata aaatgatgga aaaggcggcc caagtgtggg atctgatcaa agaagaaggc 1920
tatctgtacg tttgtggcga cgcaaagggt atggctcgtg atgtccatcg caccctgcac 1980
acgattgttc aggaacaaga aggtgtctca tcgagcgaag cggaagccat cgtgaaaaag 2040
ctgcagaccg aaggccgtta tctgcgcgat gtttggtaa 2079

<210> SEQ ID NO 66
<211> LENGTH: 717
<212> TYPE: PRT
<213> ORGANISM: Taxus cuspidata

<400> SEQUENCE: 66

Met Gln Ala Asn Ser Asn Thr Val Glu Gly Ala Ser Gln Gly Lys Ser
1 5 10 15

Leu Leu Asp Ile Ser Arg Leu Asp His Ile Phe Ala Leu Leu Leu Asn
20 25 30

Gly Lys Gly Gly Asp Leu Gly Ala Met Thr Gly Ser Ala Leu Ile Leu
35 40 45

Thr Glu Asn Ser Gln Asn Leu Met Ile Leu Thr Thr Ala Leu Ala Val
50 55 60

Leu Val Ala Cys Val Phe Phe Phe Val Trp Arg Arg Gly Gly Ser Asp
65 70 75 80

Thr Gln Lys Pro Ala Val Arg Pro Thr Pro Leu Val Lys Glu Glu Asp
85 90 95

Glu Glu Glu Glu Asp Asp Ser Ala Lys Lys Lys Val Thr Ile Phe Phe
100 105 110

Gly Thr Gln Thr Gly Thr Ala Glu Gly Phe Ala Lys Ala Leu Ala Glu
115 120 125

```
Glu Ala Lys Ala Arg Tyr Glu Lys Ala Val Phe Lys Val Val Asp Leu
    130                 135                 140

Asp Asn Tyr Ala Ala Asp Asp Glu Gln Tyr Glu Glu Lys Leu Lys Lys
145                 150                 155                 160

Glu Lys Leu Ala Phe Phe Met Leu Ala Thr Tyr Gly Asp Gly Glu Pro
                165                 170                 175

Thr Asp Asn Ala Ala Arg Phe Tyr Lys Trp Phe Leu Glu Gly Lys Glu
            180                 185                 190

Arg Glu Pro Trp Leu Ser Asp Leu Thr Tyr Gly Val Phe Gly Leu Gly
        195                 200                 205

Asn Arg Gln Tyr Glu His Phe Asn Lys Val Ala Lys Ala Val Asp Glu
    210                 215                 220

Val Leu Ile Glu Gln Gly Ala Lys Arg Leu Val Pro Val Gly Leu Gly
225                 230                 235                 240

Asp Asp Asp Gln Cys Ile Glu Asp Asp Phe Thr Ala Trp Arg Glu Gln
                245                 250                 255

Val Trp Pro Glu Leu Asp Gln Leu Leu Arg Asp Glu Asp Asp Glu Pro
            260                 265                 270

Thr Ser Ala Thr Pro Tyr Thr Ala Ala Ile Pro Glu Tyr Arg Val Glu
        275                 280                 285

Ile Tyr Asp Ser Val Val Ser Val Tyr Glu Glu Thr His Ala Leu Lys
    290                 295                 300

Gln Asn Gly Gln Ala Val Tyr Asp Ile His His Pro Cys Arg Ser Asn
305                 310                 315                 320

Val Ala Val Arg Arg Glu Leu His Thr Pro Leu Ser Asp Arg Ser Cys
                325                 330                 335

Ile His Leu Glu Phe Asp Ile Ser Asp Thr Gly Leu Ile Tyr Glu Thr
            340                 345                 350

Gly Asp His Val Gly Val His Thr Glu Asn Ser Ile Glu Thr Val Glu
        355                 360                 365

Glu Ala Ala Lys Leu Leu Gly Tyr Gln Leu Asp Thr Ile Phe Ser Val
    370                 375                 380

His Gly Asp Lys Glu Asp Gly Thr Pro Leu Gly Gly Ser Ser Leu Pro
385                 390                 395                 400

Pro Pro Phe Pro Gly Pro Cys Thr Leu Arg Thr Ala Leu Ala Arg Tyr
                405                 410                 415

Ala Asp Leu Leu Asn Pro Pro Arg Lys Ala Ala Phe Leu Ala Leu Ala
            420                 425                 430

Ala His Ala Ser Asp Pro Ala Glu Ala Glu Arg Leu Lys Phe Leu Ser
        435                 440                 445

Ser Pro Ala Gly Lys Asp Glu Tyr Ser Gln Trp Val Thr Ala Ser Gln
    450                 455                 460

Arg Ser Leu Leu Glu Ile Met Ala Glu Phe Pro Ser Ala Lys Pro Pro
465                 470                 475                 480

Leu Gly Val Phe Phe Ala Ala Ile Ala Pro Arg Leu Gln Pro Arg Tyr
                485                 490                 495

Tyr Ser Ile Ser Ser Ser Pro Arg Phe Ala Pro Ser Arg Ile His Val
            500                 505                 510

Thr Cys Ala Leu Val Tyr Gly Pro Ser Pro Thr Gly Arg Ile His Lys
        515                 520                 525

Gly Val Cys Ser Asn Trp Met Lys Asn Ser Leu Pro Ser Glu Glu Thr
    530                 535                 540

His Asp Cys Ser Trp Ala Pro Val Phe Val Arg Gln Ser Asn Phe Lys
```

```
545                 550                 555                 560

Leu Pro Ala Asp Ser Thr Thr Pro Ile Val Met Val Gly Pro Gly Thr
                565                 570                 575

Gly Phe Ala Pro Phe Arg Gly Phe Leu Gln Glu Arg Ala Lys Leu Gln
            580                 585                 590

Glu Ala Gly Glu Lys Leu Gly Pro Ala Val Leu Phe Phe Gly Cys Arg
        595                 600                 605

Asn Arg Gln Met Asp Tyr Ile Tyr Glu Asp Glu Leu Lys Gly Tyr Val
    610                 615                 620

Glu Lys Gly Ile Leu Thr Asn Leu Ile Val Ala Phe Ser Arg Glu Gly
625                 630                 635                 640

Ala Thr Lys Glu Tyr Val Gln His Lys Met Leu Glu Lys Ala Ser Asp
                645                 650                 655

Thr Trp Ser Leu Ile Ala Gln Gly Gly Tyr Leu Tyr Val Cys Gly Asp
            660                 665                 670

Ala Lys Gly Met Ala Arg Asp Val His Arg Thr Leu His Thr Ile Val
        675                 680                 685

Gln Glu Gln Glu Ser Val Asp Ser Ser Lys Ala Glu Phe Leu Val Lys
    690                 695                 700

Lys Leu Gln Met Asp Gly Arg Tyr Leu Arg Asp Ile Trp
705                 710                 715


<210> SEQ ID NO 67
<211> LENGTH: 2154
<212> TYPE: DNA
<213> ORGANISM: Taxus cuspidata

<400> SEQUENCE: 67

atgcaggcta attccaacac ggtggaaggt gcctcccagg ggaagagcct gctggacata     60

tctcggctgg accatatttt tgcgctgctg ttgaacggca agggaggaga tctgggagcc    120

atgaccggct cggctttgat tttgacagag aattcgcaga atttgatgat tttgaccacg    180

gctttggctg ttttggtcgc gtgtgttttc ttcttcgttt ggaggagggg aggatcggat    240

acgcagaagc cggcggtgag accgacgcct ctggtgaagg aggaagatga ggaggaagaa    300

gacgattctg caaagaagaa agtcacgatt ttctttggga cacagactgg gacggccgag    360

ggatttgcca aggctctagc agaagaggca aaggcaagat atgagaaagc tgtgtttaaa    420

gtcgtagatt tggacaacta tgcagcagat gatgagcagt atgaagaaaa attgaaaaag    480

gaaaaattag catttttat gctagcaacg tatggagatg gggagcccac tgacaatgca    540

gcaagatttt ataagtggtt tcttgagggc aaggagaggg agccatggct ttctgatctc    600

acttatgggg tgtttggatt aggcaacaga caatatgaac attttaataa ggtggctaaa    660

gcagtagatg aagtcttaat tgaacaaggt gcaaagcgac ttgttccagt gggccttggt    720

gatgatgacc aatgcattga agatgacttt actgcttggc gagagcaggt ttggcctgaa    780

ctggatcagt tactccggga tgaagatgat gagcccacaa gtgctacacc ttatacagct    840

gccatacctg agtatagggt tgaaatttat gattccgtgg tttcagtgta cgaggaaact    900

catgctctca agcaaaatgg ccaagctgtt tatgatatcc atcacccctg cagatctaat    960

gtggcagtga gaagagagct tcatacacct ttgtctgacc gctcttgcat ccatttggaa   1020

tttgatatat cagacactgg ccttatatat gagacaggag atcatgttgg tgtccataca   1080

gaaaacagca ttgaaactgt ggaggaagca gcaaagctac taggctacca attggacact   1140

atattctcag tccacggtga caaagaagat ggcacgccac ttggagggtc ttctttgcca   1200
```

```
ccacctttcc ctggtccatg caccctacga actgctcttg ctcgttatgc tgatttgctg   1260

aatcctcctc ggaaggccgc ctttcttgca ttggcagctc atgcatctga tccagcagag   1320

gcagagcggt tgaagttcct ctcatcacca gctggaaagg atgaatattc tcaatgggtc   1380

actgcaagtc agagaagtct tttagaaata atggcagaat ttccatcagc aaaaccaccc   1440

cttggtgttt tctttgcagc aatagcccct cgtctgcaac cccgatatta ttctatttct   1500

tcctctccca ggtttgcacc ctcaagaata catgtgacat gtgctcttgt ttacgggccc   1560

agtccaaccg gtagaattca caaaggtgtt tgttctaact ggatgaagaa ttcgctaccc   1620

tcagaagaaa cccatgactg tagctgggct ccagtctttg tcaggcaatc aaattttaaa   1680

ttgccagcag attctactac tcctattgtc atggtgggtc ctggaactgg ttttgcacct   1740

tttagaggtt ttttgcagga aagagcaaaa cttcaagaag ctggtgagaa gctcggtccg   1800

gctgttttat tttttgggtg caggaatcgc caaatggact acatttatga agatgagctg   1860

aagggctatg tggagaaagg aatactgacc aatctcattg ttgctttctc tcgtgaagga   1920

gcaaccaaag agtatgtcca gcacaagatg ctggaaaagg catccgatac ctggagtctc   1980

attgctcagg gtgggtatct ttatgtatgt ggtgatgcca agggtatggc tagggatgta   2040

cacaggacac tgcacactat tgtccaagag caggaatctg tggatagcag caaagcagag   2100

tttctagtga agaaattaca gatggatgga agatacttac gagatatatg gtga         2154
```

<210> SEQ ID NO 68
<211> LENGTH: 705
<212> TYPE: PRT
<213> ORGANISM: Artemisia annua

<400> SEQUENCE: 68

```
Met Ala Gln Ser Thr Thr Ser Val Lys Leu Ser Pro Phe Asp Leu Met
1               5                   10                  15

Thr Ala Leu Leu Asn Gly Lys Val Ser Phe Asp Thr Ser Asn Thr Ser
            20                  25                  30

Asp Thr Asn Ile Pro Leu Ala Val Phe Met Glu Asn Arg Glu Leu Leu
        35                  40                  45

Met Ile Leu Thr Thr Ser Val Ala Val Leu Ile Gly Cys Val Val Val
    50                  55                  60

Leu Val Trp Arg Arg Ser Ser Ser Ala Ala Lys Lys Ala Ala Glu Ser
65                  70                  75                  80

Pro Val Ile Val Val Pro Lys Lys Val Thr Glu Asp Glu Val Asp Asp
                85                  90                  95

Gly Arg Lys Lys Val Thr Val Phe Phe Gly Thr Gln Thr Gly Thr Ala
            100                 105                 110

Glu Gly Phe Ala Lys Ala Leu Val Glu Glu Ala Lys Ala Arg Tyr Glu
        115                 120                 125

Lys Ala Val Phe Lys Val Ile Asp Leu Asp Asp Tyr Ala Ala Glu Asp
    130                 135                 140

Asp Glu Tyr Glu Glu Lys Leu Lys Lys Glu Ser Leu Ala Phe Phe Phe
145                 150                 155                 160

Leu Ala Thr Tyr Gly Asp Gly Glu Pro Thr Asp Asn Ala Ala Arg Phe
                165                 170                 175

Tyr Lys Trp Phe Thr Glu Gly Glu Glu Lys Gly Glu Trp Leu Asp Lys
            180                 185                 190

Leu Gln Tyr Ala Val Phe Gly Leu Gly Asn Arg Gln Tyr Glu His Phe
        195                 200                 205
```

```
Asn Lys Ile Ala Lys Val Val Asp Glu Lys Leu Val Glu Gln Gly Ala
    210                 215                 220

Lys Arg Leu Val Pro Val Gly Met Gly Asp Asp Asp Gln Cys Ile Glu
225                 230                 235                 240

Asp Asp Phe Thr Ala Trp Lys Glu Leu Val Trp Pro Glu Leu Asp Gln
                245                 250                 255

Leu Leu Arg Asp Glu Asp Asp Thr Ser Val Ala Thr Pro Tyr Thr Ala
            260                 265                 270

Ala Val Ala Glu Tyr Arg Val Val Phe His Asp Lys Pro Glu Thr Tyr
        275                 280                 285

Asp Gln Asp Gln Leu Thr Asn Gly His Ala Val His Asp Ala Gln His
    290                 295                 300

Pro Cys Arg Ser Asn Val Ala Val Lys Lys Glu Leu His Ser Pro Leu
305                 310                 315                 320

Ser Asp Arg Ser Cys Thr His Leu Glu Phe Asp Ile Ser Asn Thr Gly
                325                 330                 335

Leu Ser Tyr Glu Thr Gly Asp His Val Gly Val Tyr Val Glu Asn Leu
            340                 345                 350

Ser Glu Val Val Asp Glu Ala Glu Lys Leu Ile Gly Leu Pro Pro His
        355                 360                 365

Thr Tyr Phe Ser Val His Ala Asp Asn Glu Asp Gly Thr Pro Leu Gly
    370                 375                 380

Gly Ala Ser Leu Pro Pro Pro Phe Pro Pro Cys Thr Leu Arg Lys Ala
385                 390                 395                 400

Leu Ala Ser Tyr Ala Asp Val Leu Ser Ser Pro Lys Lys Ser Ala Leu
                405                 410                 415

Leu Ala Leu Ala Ala His Ala Thr Asp Ser Thr Glu Ala Asp Arg Leu
            420                 425                 430

Lys Phe Leu Ala Ser Pro Ala Gly Lys Asp Glu Tyr Ala Gln Trp Ile
        435                 440                 445

Val Ala Ser His Arg Ser Leu Leu Glu Val Met Glu Ala Phe Pro Ser
    450                 455                 460

Ala Lys Pro Pro Leu Gly Val Phe Phe Ala Ser Val Ala Pro Arg Leu
465                 470                 475                 480

Gln Pro Arg Tyr Tyr Ser Ile Ser Ser Ser Pro Arg Phe Ala Pro Asn
                485                 490                 495

Arg Ile His Val Thr Cys Ala Leu Val Tyr Glu Gln Thr Pro Ser Gly
            500                 505                 510

Arg Val His Lys Gly Val Cys Ser Thr Trp Met Lys Asn Ala Val Pro
        515                 520                 525

Met Thr Glu Ser Gln Asp Cys Ser Trp Ala Pro Ile Tyr Val Arg Thr
    530                 535                 540

Ser Asn Phe Arg Leu Pro Ser Asp Pro Lys Val Pro Val Ile Met Ile
545                 550                 555                 560

Gly Pro Gly Thr Gly Leu Ala Pro Phe Arg Gly Phe Leu Gln Glu Arg
                565                 570                 575

Leu Ala Gln Lys Glu Ala Gly Thr Glu Leu Gly Thr Ala Ile Leu Phe
            580                 585                 590

Phe Gly Cys Arg Asn Arg Lys Val Asp Phe Ile Tyr Glu Asp Glu Leu
        595                 600                 605

Asn Asn Phe Val Glu Thr Gly Ala Leu Ser Glu Leu Val Thr Ala Phe
    610                 615                 620
```

```
Ser Arg Glu Gly Ala Thr Lys Glu Tyr Val Gln His Lys Met Thr Gln
625                 630                 635                 640

Lys Ala Ser Asp Ile Trp Asn Leu Leu Ser Glu Gly Ala Tyr Leu Tyr
                645                 650                 655

Val Cys Gly Asp Ala Lys Gly Met Ala Lys Asp Val His Arg Thr Leu
            660                 665                 670

His Thr Ile Val Gln Glu Gln Gly Ser Leu Asp Ser Ser Lys Ala Glu
        675                 680                 685

Leu Tyr Val Lys Asn Leu Gln Met Ala Gly Arg Tyr Leu Arg Asp Val
    690                 695                 700

Trp
705


<210> SEQ ID NO 69
<211> LENGTH: 2118
<212> TYPE: DNA
<213> ORGANISM: Artemisia annua

<400> SEQUENCE: 69

atggcgcagt ctaccaccag cgtgaaattg tccccttttg atctcatgac cgctctgctg     60

aatgggaaag tctcattcga tacaagcaac acaagtgata ccaacatccc tttggcggtt    120

tttatggaga atagagagtt actcatgatt ttaacgactt ccgtggccgt gctcattggg    180

tgcgtcgtcg tacttgtctg gcgccggtca agtagcgcag caaagaaggc ggcggagtcc    240

ccggttatcg tcgtcccaaa gaaggttaca gaggacgagg tggacgacgg acgcaaaaaa    300

gtgacggtat tctttggtac acagaccgga accgcggaag gatttgctaa agcgctggtg    360

gaagaagcta aagcccgtta cgaaaaagcg gtattcaaag tgatagacct ggatgactat    420

gcggcagagg acgacgagta cgaggaaaaa ttgaaaaaag aatctcttgc gttctttttt    480

ctcgccactt acggcgatgg agaacctact gataatgcgg ctcggtttta taagtggttc    540

actgagggtg aagaaaaagg tgaatggctg gacaaattgc agtacgcagt atttggactc    600

gggaatcgtc aatatgaaca ttttaacaaa attgctaagg tcgtcgatga aaaactggtt    660

gagcagggtg cgaaacgtct ggtcccggtt ggaatgggcg atgacgacca gtgcattgaa    720

gacgacttta cagcatggaa ggaactggtg tggccggaac tggaccaact tttgcgtgac    780

gaggatgaca catctgtagc tacgccgtac actgctgcgg tagccgagta tagggtcgtt    840

tttcacgata aaccggaaac ctacgaccaa gaccagctca caaatggtca tgcagtacat    900

gatgcgcaac atccttgcag gtcaaatgtg gcggtgaaga aagagctgca cagtcctctg    960

tcagatcgtt cttgcaccca cctggaattt gacatatcca atacgggcct ttcgtatgaa   1020

accggagatc acgttggtgt ctatgttgaa aatctgtcgg aagtggttga tgaggcggaa   1080

aaacttatcg gtctgccgcc tcatacgtac ttttcagtcc acgctgataa tgaagacgga   1140

accccgctgg gtggcgcatc gttacccccca cccctttccac catgcactct gcgtaaggcg   1200

cttgccagtt atgctgatgt tttgtctagt cccaaaaaga gtgcacttct cgcactggcg   1260

gcccatgcca ctgatagtac agaggccgac aggctgaaat ttctggcgtc accagcggga   1320

aaagacgaat acgcccaatg gatcgttgcc agtcatcggt ctttactgga agtgatggaa   1380

gcgttccctt ccgctaagcc acctctgggg gtctttttcg ctagtgtggc accccgtcta   1440

cagccccggt attactcaat atctagctca cccagatttg ctccgaatag aatacacgta   1500

acatgcgcgc tggtctatga gcagacccca agtggacggg tgcataaagg ggtttgttct   1560

acctggatga agaacgccgt cccaatgacc gagtctcagg attgttcctg ggcacctata   1620
```

```
tatgttagaa catcaaactt tcgactgcca agtgacccga aagttccggt aattatgata   1680

ggtccaggaa cagggctggc tccctttcgc gggttcctcc aggaacgtct ggcgcagaag   1740

gaggcgggaa ctgaactggg gacggcgatt ttatttttcg ggtgtagaaa tcgtaaagtc   1800

gattttatat atgaagatga gttgaacaat ttcgtggaaa ccggggcatt atcggaatta   1860

gttacggctt ttagcaggga gggggcgact aaagagtatg tccagcacaa gatgactcag   1920

aaagcctcag atatatggaa cctgctgtcg gagggagcct atctttatgt ttgcggtgat   1980

gcaaaaggaa tggccaaaga tgtccaccgg accctccaca ctattgtgca ggaacagggt   2040

tcattagact caagtaaagc cgaactttac gtaaaaaatc tacagatggc gggccgttac   2100

ctccgtgacg tttggtaa                                                 2118


<210> SEQ ID NO 70
<211> LENGTH: 693
<212> TYPE: PRT
<213> ORGANISM: Arabidopsis thaliana

<400> SEQUENCE: 70

Met Ala Thr Ser Ala Leu Tyr Ala Ser Asp Leu Phe Lys Gln Leu Lys
1               5                   10                  15

Ser Ile Met Gly Thr Asp Ser Leu Ser Asp Asp Val Val Leu Val Ile
            20                  25                  30

Ala Thr Thr Ser Leu Ala Leu Val Ala Gly Phe Val Val Leu Leu Trp
        35                  40                  45

Lys Lys Thr Thr Ala Asp Arg Ser Gly Glu Leu Lys Pro Leu Met Ile
    50                  55                  60

Pro Lys Ser Leu Met Ala Lys Asp Glu Asp Asp Asp Leu Asp Leu Gly
65                  70                  75                  80

Ser Gly Lys Thr Arg Val Ser Ile Phe Phe Gly Thr Gln Thr Gly Thr
                85                  90                  95

Ala Glu Gly Phe Ala Lys Ala Leu Ser Glu Glu Ile Lys Ala Arg Tyr
            100                 105                 110

Glu Lys Ala Ala Val Lys Val Ile Asp Leu Asp Asp Tyr Ala Ala Asp
        115                 120                 125

Asp Asp Gln Tyr Glu Glu Lys Leu Lys Lys Glu Thr Leu Ala Phe Phe
    130                 135                 140

Cys Val Ala Thr Tyr Gly Asp Gly Glu Pro Thr Asp Asn Ala Ala Arg
145                 150                 155                 160

Phe Tyr Lys Trp Phe Thr Glu Glu Asn Glu Arg Asp Ile Lys Leu Gln
                165                 170                 175

Gln Leu Ala Tyr Gly Val Phe Ala Leu Gly Asn Arg Gln Tyr Glu His
            180                 185                 190

Phe Asn Lys Ile Gly Ile Val Leu Asp Glu Glu Leu Cys Lys Lys Gly
        195                 200                 205

Ala Lys Arg Leu Ile Glu Val Gly Leu Gly Asp Asp Asp Gln Ser Ile
    210                 215                 220

Glu Asp Asp Phe Asn Ala Trp Lys Glu Ser Leu Trp Ser Glu Leu Asp
225                 230                 235                 240

Lys Leu Leu Lys Asp Glu Asp Asp Lys Ser Val Ala Thr Pro Tyr Thr
                245                 250                 255

Ala Val Ile Pro Glu Tyr Arg Val Val Thr His Asp Pro Arg Phe Thr
            260                 265                 270

Thr Gln Lys Ser Met Glu Ser Asn Val Ala Asn Gly Asn Thr Thr Ile
```

-continued

```
        275                 280                 285

Asp Ile His His Pro Cys Arg Val Asp Val Ala Val Gln Lys Glu Leu
    290                 295                 300

His Thr His Glu Ser Asp Arg Ser Cys Ile His Leu Glu Phe Asp Ile
305                 310                 315                 320

Ser Arg Thr Gly Ile Thr Tyr Glu Thr Gly Asp His Val Gly Val Tyr
                325                 330                 335

Ala Glu Asn His Val Glu Ile Val Glu Glu Ala Gly Lys Leu Leu Gly
            340                 345                 350

His Ser Leu Asp Leu Val Phe Ser Ile His Ala Asp Lys Glu Asp Gly
        355                 360                 365

Ser Pro Leu Glu Ser Ala Val Pro Pro Pro Phe Pro Gly Pro Cys Thr
    370                 375                 380

Leu Gly Thr Gly Leu Ala Arg Tyr Ala Asp Leu Leu Asn Pro Pro Arg
385                 390                 395                 400

Lys Ser Ala Leu Val Ala Leu Ala Ala Tyr Ala Thr Glu Pro Ser Glu
                405                 410                 415

Ala Glu Lys Leu Lys His Leu Thr Ser Pro Asp Gly Lys Asp Glu Tyr
            420                 425                 430

Ser Gln Trp Ile Val Ala Ser Gln Arg Ser Leu Leu Glu Val Met Ala
        435                 440                 445

Ala Phe Pro Ser Ala Lys Pro Pro Leu Gly Val Phe Phe Ala Ala Ile
    450                 455                 460

Ala Pro Arg Leu Gln Pro Arg Tyr Tyr Ser Ile Ser Ser Ser Pro Arg
465                 470                 475                 480

Leu Ala Pro Ser Arg Val His Val Thr Ser Ala Leu Val Tyr Gly Pro
                485                 490                 495

Thr Pro Thr Gly Arg Ile His Lys Gly Val Cys Ser Thr Trp Met Lys
            500                 505                 510

Asn Ala Val Pro Ala Glu Lys Ser His Glu Cys Ser Gly Ala Pro Ile
        515                 520                 525

Phe Ile Arg Ala Ser Asn Phe Lys Leu Pro Ser Asn Pro Ser Thr Pro
    530                 535                 540

Ile Val Met Val Gly Pro Gly Thr Gly Leu Ala Pro Phe Arg Gly Phe
545                 550                 555                 560

Leu Gln Glu Arg Met Ala Leu Lys Glu Asp Gly Glu Glu Leu Gly Ser
                565                 570                 575

Ser Leu Leu Phe Phe Gly Cys Arg Asn Arg Gln Met Asp Phe Ile Tyr
            580                 585                 590

Glu Asp Glu Leu Asn Asn Phe Val Asp Gln Gly Val Ile Ser Glu Leu
        595                 600                 605

Ile Met Ala Phe Ser Arg Glu Gly Ala Gln Lys Glu Tyr Val Gln His
    610                 615                 620

Lys Met Met Glu Lys Ala Ala Gln Val Trp Asp Leu Ile Lys Glu Glu
625                 630                 635                 640

Gly Tyr Leu Tyr Val Cys Gly Asp Ala Lys Gly Met Ala Arg Asp Val
                645                 650                 655

His Arg Thr Leu His Thr Ile Val Gln Glu Gln Glu Gly Val Ser Ser
            660                 665                 670

Ser Glu Ala Glu Ala Ile Val Lys Lys Leu Gln Thr Glu Gly Arg Tyr
        675                 680                 685

Leu Arg Asp Val Trp
    690
```

<210> SEQ ID NO 71
<211> LENGTH: 2082
<212> TYPE: DNA
<213> ORGANISM: Arabidopsis thaliana

<400> SEQUENCE: 71

```
atggcgacca gcgctctgta tgctagtgac ctttttaaac agctcaaaag catcatgggc      60
actgatagcc tgtccgacga tgttgtcctg gtaatcgcaa ccacttccct tgcgcttgtt     120
gcgggctttg tggtgttact gtggaagaag actaccgcag ataggagtgg tgaattgaaa     180
ccgctgatga tcccaaaaag tctgatggcc aaagatgagg atgatgatct ggatcttgga     240
tcagggaaga cgcgagtcag tattttttc gggacccaga cgggcaccgc ggagggcttc     300
gccaaagctc tgtccgagga aataaaggcc agatacgaga aagccgccgt aaaggttata     360
gacctagatg attacgccgc tgatgacgat cagtatgagg agaaacttaa aaaggagact     420
ctggcgtttt tttgcgtggc aacttacgga gacggcgagc ccaccgataa tgcagctagg     480
ttttacaagt ggtttaccga ggagaacgaa cgagatataa agttacagca gttggcctat     540
ggcgtgtttg ccctgggtaa tcggcaatat gagcatttca acaaaattgg catcgttctg     600
gatgaggaat tgtgcaaaaa gggtgcaaaa cggctgatag aggtgggtct aggtgacgat     660
gatcaatcta tagaagacga ttttaatgcg tggaaagaga gcttatggag tgaactggat     720
aagctcttga aagatgaaga cgacaagtca gtggcgaccc cttataccgc ggtaatcccg     780
gaataccgcg tcgtgacaca cgatccgagg tttacaaccc aaaaatctat ggagtctaat     840
gtcgccaatg gcaacacaac gattgatatt caccacccct gtcgtgttga cgtggctgtt     900
caaaaagaac ttcatacaca cgaaagtgac cgaagttgca tacacttgga atttgacatt     960
agtcgcaccg gaattacgta tgaaactggt gatcacgtgg gtgtatacgc agaaaatcat    1020
gtcgaaatag tagaagaagc tggcaaactg ctgggacatt cactcgatct agtgtttagt    1080
atacatgccg ataaagagga tggcagccca ttggaaagtg ccgtccctcc gccgtttcct    1140
ggaccgtgta ctctggggac gggactcgcc cgctatgctg acctgttaaa cccccctcgt    1200
aaaagcgccc ttgtggccct ggcggcatac gcaactgaac cgagcgaagc ggagaagctg    1260
aaacatctga catcaccgga tggcaaagac gagtatagtc agtggatagt agcctctcag    1320
cgctctctgc tggaagtgat ggccgcattt ccgtccgcca aaccaccttt gggagtattt    1380
ttcgctgcta tcgcacctcg gctccagccg cgctattaca gcatatcttc aagtccccgc    1440
ttagcaccgt ctcgtgtcca tgtcacttct gcgttggttt atggtccgac tccaacaggt    1500
cgcatccaca aaggtgtctg ttcaacctgg atgaaaaacg cggtgcccgc ggagaaatct    1560
catgagtgca gtggtgcacc tatttttatc cgcgcaagta acttcaaact cccttctaat    1620
ccgagcacgc ccattgtgat ggttggccca ggcactggcc ttgctccgtt tcgcggtttt    1680
ctacaggagc ggatggccct taaagaagat ggggaagaat tgggatcatc gttgctcttt    1740
tttggctgcc gaaatcgcca gatggatttt atctacgaag acgagttgaa taactttgtc    1800
gatcaaggag taatttcgga gttgattatg gcattttcac gcgaaggggc tcagaaagag    1860
tatgtccaac acaagatgat ggaaaaagcg gcacaagtgt gggatcttat taaagaagaa    1920
ggctatcttt atgtatgtgg ggatgcgaaa ggtatggccc gtgatgtcca tcgcaccctg    1980
cacacgattg tacaggaaca ggaaggtgtg tcctcgtccg aagcagaagc aatcgttaaa    2040
aaactgcaaa cagagggtcg ttaccttcgc gacgtgtggt aa                       2082
```

<210> SEQ ID NO 72
<211> LENGTH: 712
<212> TYPE: PRT
<213> ORGANISM: Arabidopsis thaliana

<400> SEQUENCE: 72

Met Ala Ser Ser Ser Ser Ser Ser Ser Thr Ser Met Ile Asp Leu Met
1               5                   10                  15

Ala Ala Ile Ile Lys Gly Glu Pro Val Ile Val Ser Asp Pro Ala Asn
            20                  25                  30

Ala Ser Ala Tyr Glu Ser Val Ala Ala Glu Leu Ser Ser Met Leu Ile
        35                  40                  45

Glu Asn Arg Gln Phe Ala Met Ile Val Thr Thr Ser Ile Ala Val Leu
    50                  55                  60

Ile Gly Cys Ile Val Met Leu Val Trp Arg Arg Ser Gly Ser Gly Asn
65                  70                  75                  80

Ser Lys Arg Val Glu Pro Leu Lys Pro Leu Val Ile Lys Pro Arg Glu
                85                  90                  95

Glu Glu Ile Asp Asp Gly Arg Lys Lys Val Thr Ile Phe Phe Gly Thr
            100                 105                 110

Gln Thr Gly Thr Ala Glu Gly Phe Ala Lys Ala Leu Gly Glu Glu Ala
        115                 120                 125

Lys Ala Arg Tyr Glu Lys Thr Arg Phe Lys Ile Val Asp Leu Asp Asp
    130                 135                 140

Tyr Ala Ala Asp Asp Asp Glu Tyr Glu Glu Lys Leu Lys Lys Glu Asp
145                 150                 155                 160

Val Ala Phe Phe Phe Leu Ala Thr Tyr Gly Asp Gly Glu Pro Thr Asp
                165                 170                 175

Asn Ala Ala Arg Phe Tyr Lys Trp Phe Thr Glu Gly Asn Asp Arg Gly
            180                 185                 190

Glu Trp Leu Lys Asn Leu Lys Tyr Gly Val Phe Gly Leu Gly Asn Arg
        195                 200                 205

Gln Tyr Glu His Phe Asn Lys Val Ala Lys Val Val Asp Asp Ile Leu
    210                 215                 220

Val Glu Gln Gly Ala Gln Arg Leu Val Gln Val Gly Leu Gly Asp Asp
225                 230                 235                 240

Asp Gln Cys Ile Glu Asp Asp Phe Thr Ala Trp Arg Glu Ala Leu Trp
                245                 250                 255

Pro Glu Leu Asp Thr Ile Leu Arg Glu Glu Gly Asp Thr Ala Val Ala
            260                 265                 270

Thr Pro Tyr Thr Ala Ala Val Leu Glu Tyr Arg Val Ser Ile His Asp
        275                 280                 285

Ser Glu Asp Ala Lys Phe Asn Asp Ile Asn Met Ala Asn Gly Asn Gly
    290                 295                 300

Tyr Thr Val Phe Asp Ala Gln His Pro Tyr Lys Ala Asn Val Ala Val
305                 310                 315                 320

Lys Arg Glu Leu His Thr Pro Glu Ser Asp Arg Ser Cys Ile His Leu
                325                 330                 335

Glu Phe Asp Ile Ala Gly Ser Gly Leu Thr Tyr Glu Thr Gly Asp His
            340                 345                 350

Val Gly Val Leu Cys Asp Asn Leu Ser Glu Thr Val Asp Glu Ala Leu
        355                 360                 365

Arg Leu Leu Asp Met Ser Pro Asp Thr Tyr Phe Ser Leu His Ala Glu
    370                 375                 380

Lys Glu Asp Gly Thr Pro Ile Ser Ser Ser Leu Pro Pro Pro Phe Pro
385 390 395 400

Pro Cys Asn Leu Arg Thr Ala Leu Thr Arg Tyr Ala Cys Leu Leu Ser
405 410 415

Ser Pro Lys Lys Ser Ala Leu Val Ala Leu Ala Ala His Ala Ser Asp
420 425 430

Pro Thr Glu Ala Glu Arg Leu Lys His Leu Ala Ser Pro Ala Gly Lys
435 440 445

Asp Glu Tyr Ser Lys Trp Val Val Glu Ser Gln Arg Ser Leu Leu Glu
450 455 460

Val Met Ala Glu Phe Pro Ser Ala Lys Pro Pro Leu Gly Val Phe Phe
465 470 475 480

Ala Gly Val Ala Pro Arg Leu Gln Pro Arg Phe Tyr Ser Ile Ser Ser
485 490 495

Ser Pro Lys Ile Ala Glu Thr Arg Ile His Val Thr Cys Ala Leu Val
500 505 510

Tyr Glu Lys Met Pro Thr Gly Arg Ile His Lys Gly Val Cys Ser Thr
515 520 525

Trp Met Lys Asn Ala Val Pro Tyr Glu Lys Ser Glu Asn Cys Ser Ser
530 535 540

Ala Pro Ile Phe Val Arg Gln Ser Asn Phe Lys Leu Pro Ser Asp Ser
545 550 555 560

Lys Val Pro Ile Ile Met Ile Gly Pro Gly Thr Gly Leu Ala Pro Phe
565 570 575

Arg Gly Phe Leu Gln Glu Arg Leu Ala Leu Val Glu Ser Gly Val Glu
580 585 590

Leu Gly Pro Ser Val Leu Phe Phe Gly Cys Arg Asn Arg Arg Met Asp
595 600 605

Phe Ile Tyr Glu Glu Glu Leu Gln Arg Phe Val Glu Ser Gly Ala Leu
610 615 620

Ala Glu Leu Ser Val Ala Phe Ser Arg Glu Gly Pro Thr Lys Glu Tyr
625 630 635 640

Val Gln His Lys Met Met Asp Lys Ala Ser Asp Ile Trp Asn Met Ile
645 650 655

Ser Gln Gly Ala Tyr Leu Tyr Val Cys Gly Asp Ala Lys Gly Met Ala
660 665 670

Arg Asp Val His Arg Ser Leu His Thr Ile Ala Gln Glu Gln Gly Ser
675 680 685

Met Asp Ser Thr Lys Ala Glu Gly Phe Val Lys Asn Leu Gln Thr Ser
690 695 700

Gly Arg Tyr Leu Arg Asp Val Trp
705 710

<210> SEQ ID NO 73
<211> LENGTH: 2139
<212> TYPE: DNA
<213> ORGANISM: Arabidopsis thaliana

<400> SEQUENCE: 73
atggcgtcca gcagttcatc gagttctaca agcatgatcg atctgatggc cgctattatc 60
aaaggggaac ccgtaattgt ctctgatcca gcaaatgcct cggcatacga gtcggtggct 120
gccgaattat catctatgtt aattgaaaat agacaatttg ccatgattgt gacaacttct 180
attgctgtgc tgataggttg catcgtcatg ctcgtgtggc gccgtagcgg atcaggcaac 240

```
tcaaagcgcg tcgagccttt gaaacccctg gttatcaaac cgcgagagga ggaaatcgat    300

gatggcagaa aaaaggttac tatctttttt ggcacacaga cggggacagc ggaaggtttc    360

gcgaaagcac tcggagagga agcgaaagcc cgatacgaga aaacacggtt caaaattgtg    420

gatctggatg actatgcggc tgatgatgat gagtatgaag aaaaactgaa aaaagaagat    480

gtggcgtttt tttttcttgc cacttatggc gacggagagc ccaccgataa tgcagcgcgg    540

ttttacaagt ggttcaccga aggaaatgat cggggagaat ggttaaaaaa tctgaaatac    600

ggtgtgttcg gtcttggcaa tcgccaatat gagcatttta ataaagtcgc gaaagtggtc    660

gatgatatat tggtagaaca gggcgctcag cgcctcgtcc aggtggggct tggcgacgat    720

gatcagtgca tagaagatga ttttactgca tggcgtgaag cgctgtggcc ggagctggac    780

accattttac gtgaagaggg cgatacagca gtggcaaccc cgtacacggc tgccgtctta    840

gagtatcgtg tgtccattca tgatagcgag gatgccaaat tcaatgacat caatatggcg    900

aatggaaatg ggtacaccgt gtttgacgcg cagcacccgt ataaggcaaa cgttgcagtc    960

aagagggaac tgcatactcc tgaaagtgat cgcagttgca tccacctgga gttcgatatt   1020

gcgggatcag gtttaacgta cgaaacgggc gaccacgtag gtgtgctgtg cgacaatctt   1080

tcagagacag tggacgaagc tctgcgcctg ctggatatga gcccggatac ctattttagc   1140

ttgcacgctg agaaagaaga tgggactcca attagcagta gcttacctcc accctttccg   1200

ccgtgtaatt tgcgtaccgc ccttacgcgc tatgcgtgtc tgctgagttc gccaaagaag   1260

tcggcccttg tggcactggc ggcacatgca agtgacccga ccgaggcgga gaggctgaaa   1320

catctggctt ctccagcggg caaagatgaa tacagcaaat gggtggtaga atcacagcgt   1380

tccctactag aagtaatggc cgaatttccc tcagctaaac caccgctggg agtgttcttt   1440

gcgggcgttg ctccccgctt gcaaccacgc ttttattcaa ttagctcaag tcctaagata   1500

gcggaaacac ggatacatgt aacttgcgca ttggtttatg aaaaaatgcc aaccgggagg   1560

atacataaag gcgtatgttc aacctggatg aaaaatgctg tgccatacga aaagtcggag   1620

aattgctcct ctgccccaat tttcgtgcgt caaagcaact ttaaactgcc gagtgattca   1680

aaggtgccta ttattatgat aggccctggt acaggactcg ccccgtttcg tggttttctt   1740

caagaaagac tggctctggt cgaatcaggc gtggaattag gaccctccgt gttatttttt   1800

ggctgccgca accgtcgaat ggacttcatc tatgaagaag aattgcaacg ttttgtggag   1860

tcaggcgctc tggcggaact atccgtcgcc tttagtagag aaggcccaac caaagaatac   1920

gtacagcata agatgatgga taaagcgagc gacatttgga atatgatctc acaaggggcg   1980

tacctgtacg tatgtggaga tgccaaagga atggcacgag acgtacatag atcgttgcat   2040

actattgctc aagaacaggg aagcatggat tcgactaaag cagaaggctt tgttaaaaat   2100

ctacagacat ctggtcgcta tctgcgtgac gtgtggtaa                          2139
```

<210> SEQ ID NO 74
<211> LENGTH: 713
<212> TYPE: PRT
<213> ORGANISM: Arabidopsis thaliana

<400> SEQUENCE: 74

```
Met Ala Ser Ser Ser Ser Ser Ser Ser Thr Ser Met Ile Asp Leu Met
1               5                   10                  15

Ala Ala Ile Ile Lys Gly Glu Pro Val Ile Val Ser Asp Pro Ala Asn
            20                  25                  30
```

-continued

Ala Ser Ala Tyr Glu Ser Val Ala Ala Glu Leu Ser Ser Met Leu Ile
35 40 45

Glu Asn Arg Gln Phe Ala Met Ile Val Thr Thr Ser Ile Ala Val Leu
50 55 60

Ile Gly Cys Ile Val Met Leu Val Trp Arg Arg Ser Gly Ser Gly Asn
65 70 75 80

Ser Lys Arg Val Glu Pro Leu Lys Pro Leu Val Ile Lys Pro Arg Glu
85 90 95

Glu Glu Ile Asp Asp Gly Arg Lys Lys Val Thr Ile Phe Phe Gly Thr
100 105 110

Gln Thr Gly Thr Ala Glu Gly Phe Ala Lys Ala Leu Gly Glu Glu Ala
115 120 125

Lys Ala Arg Tyr Glu Lys Thr Arg Phe Lys Ile Val Asp Leu Asp Asp
130 135 140

Tyr Ala Ala Asp Asp Asp Glu Tyr Glu Glu Lys Leu Lys Lys Glu Asp
145 150 155 160

Val Ala Phe Phe Phe Leu Ala Thr Tyr Gly Asp Gly Glu Pro Thr Asp
165 170 175

Asn Ala Ala Arg Phe Tyr Lys Trp Phe Thr Glu Gly Asn Asp Arg Gly
180 185 190

Glu Trp Leu Lys Asn Leu Lys Tyr Gly Val Phe Gly Leu Gly Asn Arg
195 200 205

Gln Tyr Glu His Phe Asn Lys Val Ala Lys Val Val Asp Asp Ile Leu
210 215 220

Val Glu Gln Gly Ala Gln Arg Leu Val Gln Val Gly Leu Gly Asp Asp
225 230 235 240

Asp Gln Cys Ile Glu Asp Asp Phe Thr Ala Trp Arg Glu Ala Leu Trp
245 250 255

Pro Glu Leu Asp Thr Ile Leu Arg Glu Glu Gly Asp Thr Ala Val Ala
260 265 270

Thr Pro Tyr Thr Ala Ala Val Leu Glu Tyr Arg Val Ser Ile His Asp
275 280 285

Ser Glu Asp Ala Lys Phe Asn Asp Ile Thr Leu Ala Asn Gly Asn Gly
290 295 300

Tyr Thr Val Phe Asp Ala Gln His Pro Tyr Lys Ala Asn Val Ala Val
305 310 315 320

Lys Arg Glu Leu His Thr Pro Glu Ser Asp Arg Ser Cys Ile His Leu
325 330 335

Glu Phe Asp Ile Ala Gly Ser Gly Leu Thr Met Lys Leu Gly Asp His
340 345 350

Val Gly Val Leu Cys Asp Asn Leu Ser Glu Thr Val Asp Glu Ala Leu
355 360 365

Arg Leu Leu Asp Met Ser Pro Asp Thr Tyr Phe Ser Leu His Ala Glu
370 375 380

Lys Glu Asp Gly Thr Pro Ile Ser Ser Ser Leu Pro Pro Pro Phe Pro
385 390 395 400

Pro Cys Asn Leu Arg Thr Ala Leu Thr Arg Tyr Ala Cys Leu Leu Ser
405 410 415

Ser Pro Lys Lys Ser Ala Leu Val Ala Leu Ala Ala His Ala Ser Asp
420 425 430

Pro Thr Glu Ala Glu Arg Leu Lys His Leu Ala Ser Pro Ala Gly Lys
435 440 445

Asp Glu Tyr Ser Lys Trp Val Val Glu Ser Gln Arg Ser Leu Leu Glu

```
    450                 455                 460

Val Met Ala Glu Phe Pro Ser Ala Lys Pro Pro Leu Gly Val Phe Phe
465                 470                 475                 480

Ala Gly Val Ala Pro Arg Leu Gln Pro Arg Phe Tyr Ser Ile Ser Ser
                485                 490                 495

Ser Pro Lys Ile Ala Glu Thr Arg Ile His Val Thr Cys Ala Leu Val
            500                 505                 510

Tyr Glu Lys Met Pro Thr Gly Arg Ile His Lys Gly Val Cys Ser Thr
        515                 520                 525

Trp Met Lys Asn Ala Val Pro Tyr Glu Lys Ser Glu Lys Leu Phe Leu
    530                 535                 540

Gly Arg Pro Ile Phe Val Arg Gln Ser Asn Phe Lys Leu Pro Ser Asp
545                 550                 555                 560

Ser Lys Val Pro Ile Ile Met Ile Gly Pro Gly Thr Gly Leu Ala Pro
                565                 570                 575

Phe Arg Gly Phe Leu Gln Glu Arg Leu Ala Leu Val Glu Ser Gly Val
            580                 585                 590

Glu Leu Gly Pro Ser Val Leu Phe Phe Gly Cys Arg Asn Arg Arg Met
        595                 600                 605

Asp Phe Ile Tyr Glu Glu Glu Leu Gln Arg Phe Val Glu Ser Gly Ala
    610                 615                 620

Leu Ala Glu Leu Ser Val Ala Phe Ser Arg Glu Gly Pro Thr Lys Glu
625                 630                 635                 640

Tyr Val Gln His Lys Met Met Asp Lys Ala Ser Asp Ile Trp Asn Met
                645                 650                 655

Ile Ser Gln Gly Ala Tyr Leu Tyr Val Cys Gly Asp Ala Lys Gly Met
            660                 665                 670

Ala Arg Asp Val His Arg Ser Leu His Thr Ile Ala Gln Glu Gln Gly
        675                 680                 685

Ser Met Asp Ser Thr Lys Ala Glu Gly Phe Val Lys Asn Leu Gln Thr
    690                 695                 700

Ser Gly Arg Tyr Leu Arg Asp Val Trp
705                 710
```

<210> SEQ ID NO 75
<211> LENGTH: 2142
<212> TYPE: DNA
<213> ORGANISM: Arabidopsis thaliana

<400> SEQUENCE: 75

```
atggcgagca gttcgtcctc ctcttctacc agtatgatcg atctgatggc cgctattata     60

aaaggagaac cagtcattgt gtctgatcct gcaaacgcat cagcctacga atctgtggct    120

gctgaactgt cctcgatgct gatcgaaaat cgccaatttg caatgattgt tacaaccagc    180

atcgctgttc ttatcgggtg tattgtcatg ctggtttggc ggcggagtgg cagcggcaat    240

tctaaaagag tggagccact gaagcctctg gtaatcaaac cccgcgaaga agaaatcgat    300

gatggacgta agaaagttac aatttttttt ggtacacaga caggtacagc agagggcttt    360

gccaaagctc ttggagaaga agcaaaagct cgatatgaga aaacacgctt caagatcgtc    420

gatctggatg actacgcggc agacgacgat gagtacgaag aaaaactcaa aaaagaggat    480

gtggcttttt ttttcctggc aacttatggg gacggcgagc ctaccgacaa tgcagcgcgg    540

ttttacaaat ggtttaccga aggcaatgat agaggggagt ggctcaaaaa tctcaaatac    600

ggagttttcg gattggggaa tagacaatac gaacacttta ataaggttgc gaaagtggta    660
```

```
gatgatattc tggtcgagca gggcgcgcaa cgtttagtac aggtcggcct gggtgatgac    720
gaccagtgca tcgaagatga ctttacggcc tggcgagaag cgctctggcc ggaattagat    780
acaatccttc gggaagaggg ggacactgct gtcgctaccc cgtacactgc cgcagtgctg    840
gaatatcgtg tttcaataca tgattcggaa gatgccaagt ttaatgacat caccctggca    900
aacggcaacg gatataccgt atttgacgct caacatccgt ataaggccaa tgtagcagta    960
aagcgggaac tccatactcc cgaaagtgac agaagttgca tccatctgga gttcgatata   1020
gcgggaagcg gactgactat gaaactggga gatcatgtag ggtcctgtg cgataatttg   1080
agcgaaaccg ttgacgaagc gctccggctt ttagatatgt cccctgatac ttatttctct   1140
ttgcacgccg agaaggaaga tggtacacct atatcctcct cgctgccgcc gccttttcca   1200
ccatgtaatc tgcgtacggc cttgactagg tatgcatgtc ttcttagctc cccgaaaaag   1260
tccgcactgg tagcgttggc agctcatgcc agcgatccca cggaggcaga gcgtttaaaa   1320
cacctggcga gtcctgctgg caaagatgaa tacagcaaat gggtggttga gtcgcagagg   1380
tccctgctgg aagtcatggc tgaatttccg tctgcgaaac cgcctctggg agttttcttc   1440
gcaggagtag ccccacgttt acaaccgcgt ttctattcta tttcttcctc ccccaagatc   1500
gcggaaactc gaatacacgt aacgtgcgca ttggtgtatg aaaagatgcc aactggtcgt   1560
atccacaagg gagtgtgctc aacctggatg aaaaacgccg ttccgtatga aaaatcggaa   1620
aaattgtttt tgggtagacc catattcgtt cggcagtcaa actttaaact accttctgat   1680
agcaaggttc cgattattat gattggaccg ggtactggcc tggcgccgtt ccgtggtttc   1740
ctgcaagaac ggttggcgct ggtggaatcc ggcgtggaac ttgggccatc ggttttgttt   1800
ttcgggtgcc gcaatcgtcg catggacttc atctacgagg aagaactcca gcgttttgtc   1860
gaaagcggtg cccttgctga attgtccgtt gcattcagcc gcgaaggtcc aactaaggag   1920
tatgtgcagc acaaaatgat ggacaaagcg agcgatattt ggaatatgat tagccagggc   1980
gcatatcttt atgtgtgcgg tgatgctaag ggaatggcgc gcgatgtcca tagatcttta   2040
cataccattg cacaggagca gggctctatg gattcaacaa aagctgaagg ttttgtgaaa   2100
aaccttcaga ccagcgggcg gtatcttcgc gatgtttggt aa                      2142
```

<210> SEQ ID NO 76
<211> LENGTH: 711
<212> TYPE: PRT
<213> ORGANISM: Stevia rebaudiana

<400> SEQUENCE: 76

```
Met Ala Gln Ser Asp Ser Val Lys Val Ser Pro Phe Asp Leu Val Ser
1               5                   10                  15

Ala Ala Met Asn Gly Lys Ala Met Glu Lys Leu Asn Ala Ser Glu Ser
            20                  25                  30

Glu Asp Pro Thr Thr Leu Pro Ala Leu Lys Met Leu Val Glu Asn Arg
        35                  40                  45

Glu Leu Leu Thr Leu Phe Thr Thr Ser Phe Ala Val Leu Ile Gly Cys
    50                  55                  60

Leu Val Phe Leu Met Trp Arg Arg Ser Ser Ser Lys Lys Leu Val Gln
65                  70                  75                  80

Asp Pro Val Pro Gln Val Ile Val Val Lys Lys Lys Glu Lys Glu Ser
                85                  90                  95

Glu Val Asp Asp Gly Lys Lys Lys Val Ser Ile Phe Tyr Gly Thr Gln
            100                 105                 110
```

```
Thr Gly Thr Ala Glu Gly Phe Ala Lys Ala Leu Val Glu Glu Ala Lys
        115                 120                 125

Val Arg Tyr Glu Lys Thr Ser Phe Lys Val Ile Asp Leu Asp Asp Tyr
    130                 135                 140

Ala Ala Asp Asp Asp Glu Tyr Glu Glu Lys Leu Lys Lys Glu Ser Leu
145                 150                 155                 160

Ala Phe Phe Phe Leu Ala Thr Tyr Gly Asp Gly Glu Pro Thr Asp Asn
                165                 170                 175

Ala Ala Asn Phe Tyr Lys Trp Phe Thr Glu Gly Asp Asp Lys Gly Glu
            180                 185                 190

Leu Leu Lys Lys Leu Gln Tyr Gly Val Phe Gly Leu Gly Asn Arg Gln
        195                 200                 205

Tyr Glu His Phe Asn Lys Ile Ala Ile Val Val Asp Asp Lys Leu Thr
    210                 215                 220

Glu Met Gly Ala Lys Arg Leu Val Pro Val Gly Leu Gly Asp Asp Asp
225                 230                 235                 240

Gln Cys Ile Glu Asp Asp Phe Thr Ala Trp Lys Glu Leu Val Trp Pro
                245                 250                 255

Glu Leu Asp Gln Leu Leu Arg Asp Glu Asp Asp Thr Ser Val Thr Thr
            260                 265                 270

Pro Tyr Thr Ala Ala Val Leu Glu Tyr Arg Val Val Tyr His Asp Lys
        275                 280                 285

Pro Ala Asp Ser Tyr Ala Glu Asp Gln Thr His Thr Asn Gly His Val
    290                 295                 300

Val His Asp Ala Gln His Pro Ser Arg Ser Asn Val Ala Phe Lys Lys
305                 310                 315                 320

Glu Leu His Thr Ser Gln Ser Asp Arg Ser Cys Thr His Leu Glu Phe
                325                 330                 335

Asp Ile Ser His Thr Gly Leu Ser Tyr Glu Thr Gly Asp His Val Gly
            340                 345                 350

Val Tyr Ser Glu Asn Leu Ser Glu Val Val Asp Glu Ala Leu Lys Leu
        355                 360                 365

Leu Gly Leu Ser Pro Asp Thr Tyr Phe Ser Val His Ala Asp Lys Glu
    370                 375                 380

Asp Gly Thr Pro Ile Gly Gly Ala Ser Leu Pro Pro Pro Phe Pro Pro
385                 390                 395                 400

Cys Thr Leu Arg Asp Ala Leu Thr Arg Tyr Ala Asp Val Leu Ser Ser
                405                 410                 415

Pro Lys Lys Val Ala Leu Leu Ala Leu Ala Ala His Ala Ser Asp Pro
            420                 425                 430

Ser Glu Ala Asp Arg Leu Lys Phe Leu Ala Ser Pro Ala Gly Lys Asp
        435                 440                 445

Glu Tyr Ala Gln Trp Ile Val Ala Asn Gln Arg Ser Leu Leu Glu Val
    450                 455                 460

Met Gln Ser Phe Pro Ser Ala Lys Pro Pro Leu Gly Val Phe Phe Ala
465                 470                 475                 480

Ala Val Ala Pro Arg Leu Gln Pro Arg Tyr Tyr Ser Ile Ser Ser Ser
                485                 490                 495

Pro Lys Met Ser Pro Asn Arg Ile His Val Thr Cys Ala Leu Val Tyr
            500                 505                 510

Glu Thr Thr Pro Ala Gly Arg Ile His Arg Gly Leu Cys Ser Thr Trp
        515                 520                 525
```

-continued

```
Met Lys Asn Ala Val Pro Leu Thr Glu Ser Pro Asp Cys Ser Gln Ala
    530                 535                 540

Ser Ile Phe Val Arg Thr Ser Asn Phe Arg Leu Pro Val Asp Pro Lys
545                 550                 555                 560

Val Pro Val Ile Met Ile Gly Pro Gly Thr Gly Leu Ala Pro Phe Arg
                565                 570                 575

Gly Phe Leu Gln Glu Arg Leu Ala Leu Lys Glu Ser Gly Thr Glu Leu
            580                 585                 590

Gly Ser Ser Ile Phe Phe Phe Gly Cys Arg Asn Arg Lys Val Asp Phe
        595                 600                 605

Ile Tyr Glu Asp Glu Leu Asn Asn Phe Val Glu Thr Gly Ala Leu Ser
    610                 615                 620

Glu Leu Ile Val Ala Phe Ser Arg Glu Gly Thr Ala Lys Glu Tyr Val
625                 630                 635                 640

Gln His Lys Met Ser Gln Lys Ala Ser Asp Ile Trp Lys Leu Leu Ser
                645                 650                 655

Glu Gly Ala Tyr Leu Tyr Val Cys Gly Asp Ala Lys Gly Met Ala Lys
            660                 665                 670

Asp Val His Arg Thr Leu His Thr Ile Val Gln Glu Gln Gly Ser Leu
        675                 680                 685

Asp Ser Ser Lys Ala Glu Leu Tyr Val Lys Asn Leu Gln Met Ser Gly
    690                 695                 700

Arg Tyr Leu Arg Asp Val Trp
705                 710
```

<210> SEQ ID NO 77
<211> LENGTH: 2136
<212> TYPE: DNA
<213> ORGANISM: Stevia rebaudiana

<400> SEQUENCE: 77

```
atggctcaga gcgattctgt taaagtatcc ccgttcgacc tggtctctgc ggctatgaac     60

ggcaaagcaa tggagaaact gaacgcgagc gaatctgaag atccaaccac cctgccggca    120

ctgaaaatgc tggtagaaaa ccgtgaactg ctgactctgt tcaccacctc cttcgccgtt    180

ctgattggtt gcctggtctt cctgatgtgg cgccgttcct cttccaagaa gctggtacag    240

gacccggttc ctcaggtgat cgtcgttaaa aagaaagaga aggaaagcga agtcgatgac    300

ggcaaaaaga aggtttccat tttctacggt actcagaccg gcaccgctga gggttttgcc    360

aaagcactgg ttgaagaggc aaaagtgcgt tacgaaaaaa cttccttcaa agtgattgac    420

ctggacgact atgctgcgga tgatgatgaa tacgaggaaa aactgaaaaa agaaagcctg    480

gccttcttct tcctggcaac ctatggcgat ggtgaaccga ccgacaacgc ggcgaacttc    540

tacaaatggt ttaccgaagg cgacgacaaa ggtgaattgc tgaagaaact gcagtatggt    600

gttttcggtc tgggcaatcg ccagtacgaa cattttaaca aaatcgcaat cgttgttgat    660

gacaaactga ctgaaatggg tgcgaaacgt ctggtgccgg ttggcctggg tgacgatgat    720

caatgcatcg aagatgactt caccgcatgg aaagaactgg tttggccgga actggatcag    780

ctgctgcgcg acgaagacga cacttccgtg accaccccgt ataccgctgc agtgctggag    840

taccgtgttg tttaccacga taaaccggcg gactcttacg ccgaagatca gactcacact    900

aacggtcacg tcgtacatga cgcacagcac ccgtctcgta gcaatgttgc gtttaagaaa    960

gagctgcaca cgagccagtc cgaccgctct tgtacgcacc tggagttcga tatctcccac   1020

accggtctgt cctatgaaac cggtgaccat gttggcgttt acagcgaaaa cctgagcgag   1080
```

gtagttgatg aagcgctgaa actgctgggc ctgtctccag acacctactt tagcgtgcat 1140
gctgacaagg aagatggtac tccgattggc ggcgcttccc tgccgccacc gtttccacct 1200
tgcactctgc gtgatgctct gactcgttac gctgatgttc tgtctagccc gaaaaaggtt 1260
gcgctgctgg cgctggccgc acatgcttct gacccgtctg aagctgaccg tctgaaattc 1320
ctggcgtctc cggccggcaa agacgaatac gcgcagtgga ttgtcgctaa ccagcgctct 1380
ctgctggaag tgatgcagtc cttcccgtct gccaaaccgc cactgggcgt gtttttcgca 1440
gctgtggctc cgcgcctgca gccgcgctac tattctatct ctagctcccc gaaaatgagc 1500
ccgaaccgca tccacgttac ttgtgctctg gtttacgaaa ccacccctgc gggccgtatc 1560
caccgtggtc tgtgctctac gtggatgaaa aatgccgtgc cgctgaccga atccccggac 1620
tgctctcagg cgtccatctt cgtgcgtacc tctaacttcc gtctgccggt ggacccgaaa 1680
gttcctgtta tcatgatcgg tcctggcacg ggtctggccc cgtttcgtgg ttttctgcag 1740
gagcgtctgg ctctgaaaga atccggtact gagctgggct cttccatctt tttcttcggt 1800
tgtcgtaacc gcaaagtcga tttcatctat gaagacgaac tgaacaactt cgtagagact 1860
ggtgcactgt ccgaactgat tgtggcattc tctcgtgaag gcacggcgaa agaatacgtt 1920
caacacaaaa tgtctcagaa agcgagcgat atctggaaac tgctgtccga gggtgcgtat 1980
ctgtatgttt gtggcgacgc gaaaggcatg gctaaagatg tacaccgcac cctgcacacc 2040
attgtacaag aacaaggctc tctggatagc tccaaggcag aactgtacgt gaaaaacctg 2100
cagatgtctg gccgttacct gcgtgatgta tggtaa 2136

<210> SEQ ID NO 78
<211> LENGTH: 710
<212> TYPE: PRT
<213> ORGANISM: Stevia rebaudiana

<400> SEQUENCE: 78

Met Ala Gln Ser Glu Ser Val Glu Ala Ser Thr Ile Asp Leu Met Thr
1               5                   10                  15

Ala Val Leu Lys Asp Thr Val Ile Asp Thr Ala Asn Ala Ser Asp Asn
            20                  25                  30

Gly Asp Ser Lys Met Pro Pro Ala Leu Ala Met Met Phe Glu Ile Arg
        35                  40                  45

Asp Leu Leu Leu Ile Leu Thr Thr Ser Val Ala Val Leu Val Gly Cys
    50                  55                  60

Phe Val Val Leu Val Trp Lys Arg Ser Ser Gly Lys Lys Ser Gly Lys
65                  70                  75                  80

Glu Leu Glu Pro Pro Lys Ile Val Val Pro Lys Arg Arg Leu Glu Gln
                85                  90                  95

Glu Val Asp Asp Gly Lys Lys Lys Val Thr Ile Phe Phe Gly Thr Gln
            100                 105                 110

Thr Gly Thr Ala Glu Gly Phe Ala Lys Ala Leu Phe Glu Glu Ala Lys
        115                 120                 125

Ala Arg Tyr Glu Lys Ala Ala Phe Lys Val Ile Asp Leu Asp Asp Tyr
    130                 135                 140

Ala Ala Asp Leu Asp Glu Tyr Ala Glu Lys Leu Lys Lys Glu Thr Tyr
145                 150                 155                 160

Ala Phe Phe Phe Leu Ala Thr Tyr Gly Asp Gly Glu Pro Thr Asp Asn
                165                 170                 175

Ala Ala Lys Phe Tyr Lys Trp Phe Thr Glu Gly Asp Glu Lys Gly Val

```
            180                 185                 190

Trp Leu Gln Lys Leu Gln Tyr Gly Val Phe Gly Leu Gly Asn Arg Gln
        195                 200                 205

Tyr Glu His Phe Asn Lys Ile Gly Ile Val Val Asp Asp Gly Leu Thr
    210                 215                 220

Glu Gln Gly Ala Lys Arg Ile Val Pro Val Gly Leu Gly Asp Asp Asp
225                 230                 235                 240

Gln Ser Ile Glu Asp Asp Phe Ser Ala Trp Lys Glu Leu Val Trp Pro
                245                 250                 255

Glu Leu Asp Leu Leu Leu Arg Asp Glu Asp Asp Lys Ala Ala Ala Thr
            260                 265                 270

Pro Tyr Thr Ala Ala Ile Pro Glu Tyr Arg Val Val Phe His Asp Lys
        275                 280                 285

Pro Asp Ala Phe Ser Asp Asp His Thr Gln Thr Asn Gly His Ala Val
    290                 295                 300

His Asp Ala Gln His Pro Cys Arg Ser Asn Val Ala Val Lys Lys Glu
305                 310                 315                 320

Leu His Thr Pro Glu Ser Asp Arg Ser Cys Thr His Leu Glu Phe Asp
                325                 330                 335

Ile Ser His Thr Gly Leu Ser Tyr Glu Thr Gly Asp His Val Gly Val
            340                 345                 350

Tyr Cys Glu Asn Leu Ile Glu Val Val Glu Glu Ala Gly Lys Leu Leu
        355                 360                 365

Gly Leu Ser Thr Asp Thr Tyr Phe Ser Leu His Ile Asp Asn Glu Asp
    370                 375                 380

Gly Ser Pro Leu Gly Gly Pro Ser Leu Gln Pro Pro Phe Pro Pro Cys
385                 390                 395                 400

Thr Leu Arg Lys Ala Leu Thr Asn Tyr Ala Asp Leu Leu Ser Ser Pro
                405                 410                 415

Lys Lys Ser Thr Leu Leu Ala Leu Ala Ala His Ala Ser Asp Pro Thr
            420                 425                 430

Glu Ala Asp Arg Leu Arg Phe Leu Ala Ser Arg Glu Gly Lys Asp Glu
        435                 440                 445

Tyr Ala Glu Trp Val Val Ala Asn Gln Arg Ser Leu Leu Glu Val Met
    450                 455                 460

Glu Ala Phe Pro Ser Ala Arg Pro Pro Leu Gly Val Phe Phe Ala Ala
465                 470                 475                 480

Val Ala Pro Arg Leu Gln Pro Arg Tyr Tyr Ser Ile Ser Ser Ser Pro
                485                 490                 495

Lys Met Glu Pro Asn Arg Ile His Val Thr Cys Ala Leu Val Tyr Glu
            500                 505                 510

Lys Thr Pro Ala Gly Arg Ile His Lys Gly Ile Cys Ser Thr Trp Met
        515                 520                 525

Lys Asn Ala Val Pro Leu Thr Glu Ser Gln Asp Cys Ser Trp Ala Pro
    530                 535                 540

Ile Phe Val Arg Thr Ser Asn Phe Arg Leu Pro Ile Asp Pro Lys Val
545                 550                 555                 560

Pro Val Ile Met Ile Gly Pro Gly Thr Gly Leu Ala Pro Phe Arg Gly
                565                 570                 575

Phe Leu Gln Glu Arg Leu Ala Leu Lys Glu Ser Gly Thr Glu Leu Gly
            580                 585                 590

Ser Ser Ile Leu Phe Phe Gly Cys Arg Asn Arg Lys Val Asp Tyr Ile
        595                 600                 605
```

```
Tyr Glu Asn Glu Leu Asn Asn Phe Val Glu Asn Gly Ala Leu Ser Glu
    610                 615                 620

Leu Asp Val Ala Phe Ser Arg Asp Gly Pro Thr Lys Glu Tyr Val Gln
625                 630                 635                 640

His Lys Met Thr Gln Lys Ala Ser Glu Ile Trp Asn Met Leu Ser Glu
                645                 650                 655

Gly Ala Tyr Leu Tyr Val Cys Gly Asp Ala Lys Gly Met Ala Lys Asp
            660                 665                 670

Val His Arg Thr Leu His Thr Ile Val Gln Glu Gln Gly Ser Leu Asp
        675                 680                 685

Ser Ser Lys Ala Glu Leu Tyr Val Lys Asn Leu Gln Met Ser Gly Arg
    690                 695                 700

Tyr Leu Arg Asp Val Trp
705                 710


<210> SEQ ID NO 79
<211> LENGTH: 2133
<212> TYPE: DNA
<213> ORGANISM: Stevia rebaudiana

<400> SEQUENCE: 79

atggcgcaat ctgaaagtgt tgaggccagt accatcgacc ttatgacggc agtgttgaag     60

gatacagtta ttgacactgc aaatgcttca gataacggcg attctaaaat gcctcctgcg    120

cttgcgatga tgttcgagat ccgcgatctt ctgctgatcc ttaccacatc agtagcggtg    180

ctggtgggat gctttgtggt actcgtgtgg aaacgttcgt cgggcaaaaa atcaggtaag    240

gagctggaac cgcctaagat tgtcgtaccg aaacgccgac tggaacaaga agttgatgat    300

ggcaaaaaaa aagtgactat attttttggg acacagacag gcacagcgga gggatttgcg    360

aaagccttat tcgaggaggc gaaggcacgt tacgagaaag cagcttttaa agtcattgat    420

ctggatgact atgcagcaga cctagatgaa tacgcagaga aactgaaaaa agaaacttat    480

gcgtttttct tcctggccac atacggagac ggtgaaccga cggacaatgc cgccaagttt    540

tataagtggt tcactgaagg ggatgagaaa ggtgtatggc ttcagaaatt gcaatacgga    600

gtgttcggac taggaaatcg gcaatatgag cactttaata aaataggcat agtagtagac    660

gatgggctaa ccgagcaggg ggccaaacgg attgtacccg tgggcctggg ggacgatgat    720

cagtctattg aggatgattt tagtgcttgg aaagagcttg tttggcctga actggactta    780

ctcctgcgtg atgaagacga taaagcggca gcgactccat acacggcagc aatccccgag    840

tatagagtcg tattccatga taaaccggat gctttctctg atgaccatac ccaaactaat    900

ggtcatgcgg tccatgatgc acaacatccc tgccgcagca atgtagcggt gaaaaaggag    960

ctgcatacgc ctgaaagtga tcgctcatgt acgcatctgg agtttgatat ttcacacaca   1020

ggtcttagct acgagactgg agatcacgtc ggagtctatt gcgaaaatct gatcgaagtg   1080

gttgaagagg ccgggaaact gttgggacta agtacagata cttatttttc tttacatata   1140

gataacgagg atggttcccc acttggcggt ccatctcttc agcctccatt cccaccatgt   1200

accttacgca aagcgctgac taactacgca gatctgctgt ctagcccaaa gaaatcaacg   1260

cttctggcgt tggctgctca tgcctcagat ccgaccgaag ctgatcgcct tcgttttctg   1320

gcatcccgag aaggtaaaga tgaatatgca gaatgggtgg tagcgaatca gcgttctttg   1380

ctggaagtca tggaggcatt ccccagcgcg cgccctccgc tgggtgtttt cttcgcagcg   1440

gtggccccgc ggctccagcc gcgttattat tcaattagca gttctcctaa gatggaacct   1500
```

```
aatcgaatcc atgtaacatg tgcattggtc tatgagaaaa cgccggctgg ccgcatccat   1560

aaaggtatat gtagcacatg gatgaaaaat gcagtacccc tcacggagtc ccaggattgt   1620

agttgggcgc cgatatttgt tcggacgagc aattttagac ttcctataga cccaaaggtt   1680

ccagttatta tgattggtcc tggcaccgga cttgcgccat tccgggggtt tctgcaagaa   1740

agactggctc tgaaagaaag cggtacagaa ctcggctcca gtatattgtt tttcggctgt   1800

cgcaaccgga aagtagatta tatatatgaa aacgagctga ataacttcgt tgaaaatggt   1860

gccctgtctg aactcgatgt cgctttttcg cgagatggcc cgacaaaaga atacgtgcag   1920

cataaaatga cccagaaagc aagtgaaatc tggaatatgc tgtcagaagg ggcatatctg   1980

tatgtgtgcg gagatgcaaa gggcatggcc aaagacgttc acagaacctt gcataccata   2040

gtacaagagc agggctctct ggatagctca aaagccgagc tgtacgtgaa aaatctccag   2100

atgagtggac gctacctgag ggatgtttgg taa                                2133


<210> SEQ ID NO 80
<211> LENGTH: 708
<212> TYPE: PRT
<213> ORGANISM: Stevia rebaudiana

<400> SEQUENCE: 80

Met Ala Gln Ser Asn Ser Val Lys Ile Ser Pro Leu Asp Leu Val Thr
1               5                   10                  15

Ala Leu Phe Ser Gly Lys Val Leu Asp Thr Ser Asn Ala Ser Glu Ser
            20                  25                  30

Gly Glu Ser Ala Met Leu Pro Thr Ile Ala Met Ile Met Glu Asn Arg
        35                  40                  45

Glu Leu Leu Met Ile Leu Thr Thr Ser Val Ala Val Leu Ile Gly Cys
    50                  55                  60

Val Val Val Leu Val Trp Arg Arg Ser Ser Thr Lys Lys Ser Ala Leu
65                  70                  75                  80

Glu Pro Pro Val Ile Val Val Pro Lys Arg Val Gln Glu Glu Glu Val
                85                  90                  95

Asp Asp Gly Lys Lys Lys Val Thr Val Phe Phe Gly Thr Gln Thr Gly
            100                 105                 110

Thr Ala Glu Gly Phe Ala Lys Ala Leu Val Glu Glu Ala Lys Ala Arg
        115                 120                 125

Tyr Glu Lys Ala Val Phe Lys Val Ile Asp Leu Asp Asp Tyr Ala Ala
    130                 135                 140

Asp Asp Asp Glu Tyr Glu Glu Lys Leu Lys Lys Glu Ser Leu Ala Phe
145                 150                 155                 160

Phe Phe Leu Ala Thr Tyr Gly Asp Gly Glu Pro Thr Asp Asn Ala Ala
                165                 170                 175

Arg Phe Tyr Lys Trp Phe Thr Glu Gly Asp Ala Lys Gly Glu Trp Leu
            180                 185                 190

Asn Lys Leu Gln Tyr Gly Val Phe Gly Leu Gly Asn Arg Gln Tyr Glu
        195                 200                 205

His Phe Asn Lys Ile Ala Lys Val Val Asp Asp Gly Leu Val Glu Gln
    210                 215                 220

Gly Ala Lys Arg Leu Val Pro Val Gly Leu Gly Asp Asp Asp Gln Cys
225                 230                 235                 240

Ile Glu Asp Asp Phe Thr Ala Trp Lys Glu Leu Val Trp Pro Glu Leu
                245                 250                 255
```

-continued

```
Asp Gln Leu Leu Arg Asp Glu Asp Asp Thr Thr Val Ala Thr Pro Tyr
            260                 265                 270

Thr Ala Ala Val Ala Glu Tyr Arg Val Val Phe His Glu Lys Pro Asp
        275                 280                 285

Ala Leu Ser Glu Asp Tyr Ser Tyr Thr Asn Gly His Ala Val His Asp
    290                 295                 300

Ala Gln His Pro Cys Arg Ser Asn Val Ala Val Lys Lys Glu Leu His
305                 310                 315                 320

Ser Pro Glu Ser Asp Arg Ser Cys Thr His Leu Glu Phe Asp Ile Ser
                325                 330                 335

Asn Thr Gly Leu Ser Tyr Glu Thr Gly Asp His Val Gly Val Tyr Cys
            340                 345                 350

Glu Asn Leu Ser Glu Val Val Asn Asp Ala Glu Arg Leu Val Gly Leu
        355                 360                 365

Pro Pro Asp Thr Tyr Phe Ser Ile His Thr Asp Ser Glu Asp Gly Ser
    370                 375                 380

Pro Leu Gly Gly Ala Ser Leu Pro Pro Pro Phe Pro Pro Cys Thr Leu
385                 390                 395                 400

Arg Lys Ala Leu Thr Cys Tyr Ala Asp Val Leu Ser Ser Pro Lys Lys
                405                 410                 415

Ser Ala Leu Leu Ala Leu Ala Ala His Ala Thr Asp Pro Ser Glu Ala
            420                 425                 430

Asp Arg Leu Lys Phe Leu Ala Ser Pro Ala Gly Lys Asp Glu Tyr Ser
        435                 440                 445

Gln Trp Ile Val Ala Ser Gln Arg Ser Leu Leu Glu Val Met Glu Ala
    450                 455                 460

Phe Pro Ser Ala Lys Pro Ser Leu Gly Val Phe Phe Ala Ser Val Ala
465                 470                 475                 480

Pro Arg Leu Gln Pro Arg Tyr Tyr Ser Ile Ser Ser Ser Pro Lys Met
                485                 490                 495

Ala Pro Asp Arg Ile His Val Thr Cys Ala Leu Val Tyr Glu Lys Thr
            500                 505                 510

Pro Ala Gly Arg Ile His Lys Gly Val Cys Ser Thr Trp Met Lys Asn
        515                 520                 525

Ala Val Pro Met Thr Glu Ser Gln Asp Cys Ser Trp Ala Pro Ile Tyr
    530                 535                 540

Val Arg Thr Ser Asn Phe Arg Leu Pro Ser Asp Pro Lys Val Pro Val
545                 550                 555                 560

Ile Met Ile Gly Pro Gly Thr Gly Leu Ala Pro Phe Arg Gly Phe Leu
                565                 570                 575

Gln Glu Arg Leu Ala Leu Lys Glu Ala Gly Thr Asp Leu Gly Leu Ser
            580                 585                 590

Ile Leu Phe Phe Gly Cys Arg Asn Arg Lys Val Asp Phe Ile Tyr Glu
        595                 600                 605

Asn Glu Leu Asn Asn Phe Val Glu Thr Gly Ala Leu Ser Glu Leu Ile
    610                 615                 620

Val Ala Phe Ser Arg Glu Gly Pro Thr Lys Glu Tyr Val Gln His Lys
625                 630                 635                 640

Met Ser Glu Lys Ala Ser Asp Ile Trp Asn Leu Leu Ser Glu Gly Ala
                645                 650                 655

Tyr Leu Tyr Val Cys Gly Asp Ala Lys Gly Met Ala Lys Asp Val His
            660                 665                 670

Arg Thr Leu His Thr Ile Val Gln Glu Gln Gly Ser Leu Asp Ser Ser
```

```
        675                 680                 685

Lys Ala Glu Leu Tyr Val Lys Asn Leu Gln Met Ser Gly Arg Tyr Leu
    690                 695                 700

Arg Asp Val Trp
705


<210> SEQ ID NO 81
<211> LENGTH: 2127
<212> TYPE: DNA
<213> ORGANISM: Stevia rebaudiana

<400> SEQUENCE: 81

atggcgcaat ctaattctgt gaaaatctct ccattggatc tggttacagc actctttagc     60

gggaaggtac tggatacaag taacgccagt gaaagcgggg aatccgcgat gctgccaaca    120

atcgcgatga tcatggaaaa tcgggaactg ctaatgattc tgacaacgtc tgtagcagtt    180

ttaatcggtt gcgttgtggt tctggtgtgg cgtcgatcat ccacgaaaaa gagcgcatta    240

gaaccgcctg ttatcgtagt accaaaaaga gttcaggagg aagaggtgga tgatgggaaa    300

aaaaaagtca ccgttttctt cgggacccaa actggtacgg cagaaggttt tgcgaaagca    360

ctggtcgaag aggcgaaagc ccgctatgag aaggcggttt ttaaggttat tgaccttgat    420

gactatgcgg cggacgatga tgaatacgaa gaaaaattaa agaaagaatc acttgccttt    480

ttttttttgg caacatacgg tgatggcgag ccgactgata acgcggcacg gttttacaaa    540

tggtttaccg aaggcgacgc gaagggggag tggttgaaca agttacagta cggtgtgttc    600

ggcttgggga accgccagta cgagcacttt aacaagatag ctaaagttgt cgatgatggt    660

ctggtagaac agggagcgaa gcgtctcgtg ccagtagggc tgggcgatga tgatcagtgt    720

atagaagatg attttacggc ttggaaggag ttagtttggc cggaactgga ccaactgctg    780

cgcgatgagg atgatacaac tgtcgctacc ccgtatacag cagcggtagc tgaatacagg    840

gtggtttttc acgagaaacc tgatgcgctg agtgaggact attcgtatac taacggccat    900

gccgttcacg atgcacagca cccgtgccgt tctaatgtcg ccgtaaaaaa ggaactgcat    960

agcccggagt cggaccgcag ttgtacccat ctggagtttg atatttcaaa taccgggctg   1020

agttacgaaa cgggcgatca cgttggcgtg tactgtgaga atctaagcga ggttgttaac   1080

gatgcagaac gactggtcgg tttgcctcca gatacttatt tctcgatcca cactgatagc   1140

gaagatggct ctccactcgg gggggcgagt ctgccgcccc cgtttccccc gtgtacgctg   1200

agaaaggccc ttacatgtta tgcagatgta ctctcttccc ccaaaaaaag tgccttgctc   1260

gcattagcag cccacgctac cgatccctcg gaagcagatc gtctgaaatt cttggcatcg   1320

ccggcgggca aagatgaata cagccaatgg atagttgcaa gtcagcgcag tctcttagaa   1380

gtgatggaag cgtttccgtc cgcaaagccg tccttaggtg tgtttttcgc gtccgtggca   1440

ccgcgtcttc agcctagata ttacagcatt agttcctctc caaaaatggc cccggaccgt   1500

attcacgtga cttgtgctct tgtatatgag aaaaccccgg caggtcgtat tcacaaaggc   1560

gtgtgcagca cctggatgaa gaatgcagtg ccgatgaccg aaagccagga ttgttcatgg   1620

gcgccaatct atgtcaggac aagtaatttc agacttccgt ctgatcctaa agttccagtc   1680

ataatgattg gccccggcac gggactggct ccttttcgtg gtttcctgca agagcgcttg   1740

gcactgaaag aagcaggcac tgacctggga ctgtccatcc tgttctttgg gtgccgtaat   1800

cgtaaggtcg attttatata tgaaaatgaa ttgaacaact ttgtagaaac aggcgcatta   1860

tccgaactga tcgtagcttt tagtagagag ggccgacga aagaatatgt acaacacaag   1920
```

atgtctgaga aggcttcgga tatatggaac ctgctctctg agggtgccta tctgtacgtt 1980
tgcggtgatg ccaaaggaat ggccaaagat gtgcaccgca ctttacatac aatcgtccaa 2040
gagcagggta gcttggactc atctaaagct gaactgtatg tgaagaactt acagatgagc 2100
gggcgctatt tgcgagatgt ttggtaa 2127

<210> SEQ ID NO 82
<211> LENGTH: 706
<212> TYPE: PRT
<213> ORGANISM: Pelargonium graveolens

<400> SEQUENCE: 82

Met Ala Gln Ser Ser Ser Gly Ser Met Ser Pro Phe Asp Phe Met Thr
1 5 10 15

Ala Ile Ile Lys Gly Lys Met Glu Pro Ser Asn Ala Ser Leu Gly Ala
20 25 30

Ala Gly Glu Val Thr Ala Met Ile Leu Asp Asn Arg Glu Leu Val Met
35 40 45

Ile Leu Thr Thr Ser Ile Ala Val Leu Ile Gly Cys Val Val Val Phe
50 55 60

Ile Trp Arg Arg Ser Ser Ser Gln Thr Pro Thr Ala Val Gln Pro Leu
65 70 75 80

Lys Pro Leu Leu Ala Lys Glu Thr Glu Ser Glu Val Asp Asp Gly Lys
85 90 95

Gln Lys Val Thr Ile Phe Phe Gly Thr Gln Thr Gly Thr Ala Glu Gly
100 105 110

Phe Ala Lys Ala Leu Ala Asp Glu Ala Lys Ala Arg Tyr Asp Lys Val
115 120 125

Thr Phe Lys Val Val Asp Leu Asp Asp Tyr Ala Ala Asp Asp Glu Glu
130 135 140

Tyr Glu Glu Lys Leu Lys Lys Glu Thr Leu Ala Phe Phe Phe Leu Ala
145 150 155 160

Thr Tyr Gly Asp Gly Glu Pro Thr Asp Asn Ala Ala Arg Phe Tyr Lys
165 170 175

Trp Phe Leu Glu Gly Lys Glu Arg Gly Glu Trp Leu Gln Asn Leu Lys
180 185 190

Phe Gly Val Phe Gly Leu Gly Asn Arg Gln Tyr Glu His Phe Asn Lys
195 200 205

Ile Ala Ile Val Val Asp Glu Ile Leu Ala Glu Gln Gly Gly Lys Arg
210 215 220

Leu Ile Ser Val Gly Leu Gly Asp Asp Asp Gln Cys Ile Glu Asp Asp
225 230 235 240

Phe Thr Ala Trp Arg Glu Ser Leu Trp Pro Glu Leu Asp Gln Leu Leu
245 250 255

Arg Asp Glu Asp Asp Thr Thr Val Ser Thr Pro Tyr Thr Ala Ala Val
260 265 270

Leu Glu Tyr Arg Val Val Phe His Asp Pro Ala Asp Ala Pro Thr Leu
275 280 285

Glu Lys Ser Tyr Ser Asn Ala Asn Gly His Ser Val Val Asp Ala Gln
290 295 300

His Pro Leu Arg Ala Asn Val Ala Val Arg Arg Glu Leu His Thr Pro
305 310 315 320

Ala Ser Asp Arg Ser Cys Thr His Leu Glu Phe Asp Ile Ser Gly Thr
325 330 335

```
Gly Ile Ala Tyr Glu Thr Gly Asp His Val Gly Val Tyr Cys Glu Asn
            340                 345                 350

Leu Ala Glu Thr Val Glu Glu Ala Leu Glu Leu Leu Gly Leu Ser Pro
        355                 360                 365

Asp Thr Tyr Phe Ser Val His Ala Asp Lys Glu Asp Gly Thr Pro Leu
    370                 375                 380

Ser Gly Ser Ser Leu Pro Pro Pro Phe Pro Pro Cys Thr Leu Arg Thr
385                 390                 395                 400

Ala Leu Thr Leu His Ala Asp Leu Leu Ser Ser Pro Lys Lys Ser Ala
                405                 410                 415

Leu Leu Ala Leu Ala Ala His Ala Ser Asp Pro Thr Glu Ala Asp Arg
            420                 425                 430

Leu Arg His Leu Ala Ser Pro Ala Gly Lys Asp Glu Tyr Ala Gln Trp
        435                 440                 445

Ile Val Ala Ser Gln Arg Ser Leu Leu Glu Val Met Ala Glu Phe Pro
    450                 455                 460

Ser Ala Lys Pro Pro Leu Gly Val Phe Phe Ala Ser Val Ala Pro Arg
465                 470                 475                 480

Leu Gln Pro Arg Tyr Tyr Ser Ile Ser Ser Ser Pro Arg Ile Ala Pro
                485                 490                 495

Ser Arg Ile His Val Thr Cys Ala Leu Val Tyr Glu Lys Thr Pro Thr
            500                 505                 510

Gly Arg Val His Lys Gly Val Cys Ser Thr Trp Met Lys Asn Ser Val
        515                 520                 525

Pro Ser Glu Lys Ser Asp Glu Cys Ser Trp Ala Pro Ile Phe Val Arg
    530                 535                 540

Gln Ser Asn Phe Lys Leu Pro Ala Asp Ala Lys Val Pro Ile Ile Met
545                 550                 555                 560

Ile Gly Pro Gly Thr Gly Leu Ala Pro Phe Arg Gly Phe Leu Gln Glu
                565                 570                 575

Arg Leu Ala Leu Lys Glu Ala Gly Thr Glu Leu Gly Pro Ser Ile Leu
            580                 585                 590

Phe Phe Gly Cys Arg Asn Ser Lys Met Asp Tyr Ile Tyr Glu Asp Glu
        595                 600                 605

Leu Asp Asn Phe Val Gln Asn Gly Ala Leu Ser Glu Leu Val Leu Ala
    610                 615                 620

Phe Ser Arg Glu Gly Pro Thr Lys Glu Tyr Val Gln His Lys Met Met
625                 630                 635                 640

Glu Lys Ala Ser Asp Ile Trp Asn Leu Ile Ser Gln Gly Ala Tyr Leu
                645                 650                 655

Tyr Val Cys Gly Asp Ala Lys Gly Met Ala Arg Asp Val His Arg Thr
            660                 665                 670

Leu His Thr Ile Ala Gln Glu Gln Gly Ser Leu Asp Ser Ser Lys Ala
        675                 680                 685

Glu Ser Met Val Lys Asn Leu Gln Met Ser Gly Arg Tyr Leu Arg Asp
    690                 695                 700

Val Trp
705
```

<210> SEQ ID NO 83
<211> LENGTH: 2121
<212> TYPE: DNA
<213> ORGANISM: Pelargonium graveolens

<400> SEQUENCE: 83

```
atggcgcagt caagcagtgg atcaatgagc cctttcgatt ttatgaccgc tataataaaa     60
ggtaaaatgg agccaagtaa tgcgtcttta ggagcggcag gtgaagtcac agcaatgata    120
cttgataata gggagctggt tatgattctg acgaccagca ttgcagtgct gatcggttgc    180
gttgtagtgt tcatttggcg tcgttcatca tcccagaccc ctaccgcggt gcagccatta    240
aaaccacttt tagcgaagga aacagagagc gaagtagacg atggcaaaca gaaagtaact    300
atctttttg gtactcaaac tggaaccgct gaaggtttcg cgaaagcgct cgcagacgag     360
gccaaagcac ggtatgataa agtcactttt aaagtggttg atctggacga ttatgccgca    420
gatgacgaag aatatgaaga aaagctgaag aaggaaacgt tagcattctt ttttcttgcg    480
acgtatggag atggtgaacc tactgacaat gctgcaaggt tttataagtg gtttctggaa    540
ggtaaagaac gcggagaatg gcttcagaat ctaaaatttg gtgtgtttgg tttaggcaac    600
cgtcagtatg agcatttcaa taaaattgcc attgtggttg atgaaatcct tgcagaacaa    660
ggtggtaagc gtctcatttc agttggcctg ggcgatgatg atcagtgtat tgaggatgac    720
tttactgcct ggagggaatc gctgtggccg gagctagatc agttattacg cgatgaggat    780
gatactacgg tttctacgcc gtataccgcc gcggtgctgg aatacagagt cgtttttcat    840
gatccggcag atgccccaac tctcgaaaaa agctacagca acgctaacgg gcatagcgtg    900
gttgatgcgc aacatccgtt acgggcaaat gttgccgtca gacgggagtt gcatactcct    960
gcgtctgacc gctcatgtac ccatctggaa tttgatatat ctggtactgg catcgcatac   1020
gagacgggtg atcatgttgg cgtgtattgc gagaatcttg cagagacggt agaagaagcg   1080
ttggaacttt taggtctttc ccccggataca tacttctccg tacacgcaga taaagaggac  1140
ggtacgcctc tctcaggctc atctctcccg ccgccatttc caccgtgcac tttacgtaca   1200
gccctgacgt tacatgctga cttactgtct tccccaaaga aatctgcatt gctcgcgctt   1260
gcagctcatg catcagaccc cactgaagct gatcgattgc ggcacctagc aagccctgcg   1320
ggcaaggacg aatacgctca gtggatagtt gctagtcagc gttccttgct ggaagtgatg   1380
gcggagttcc ccagtgccaa gcccccgctg ggagtattct tcgcatcggt tgctccaaga   1440
ttgcagcccc ggtactactc tatttcttct tccccaagaa tagcgccgtc tcgcatacac   1500
gtgacctgcg cgttagttta cgagaaaaca cctacgggca gagtacacaa aggagtttgc   1560
tccacttgga tgaaaaactc agtgccctct gaaaagagtg atgaatgttc atgggcacca   1620
attttcgtac gacagagcaa ctttaaactg cccgccgatg cgaaagtacc cataattatg   1680
attggtccag gaacgggtct ggcaccattt cgcggcttcc tccaggagcg gcttgcattg   1740
aaagaagcag ggacagaact gggaccttcc atattatttt ttgggtgccg caacagcaaa   1800
atggactata tatacgagga tgaactggat aattttgtac agaatggggc actctctgaa   1860
ctcgtgttgg cgttctcacg tgaaggtcct accaaagagt atgtgcaaca taagatgatg   1920
gagaaagcct cagatatatg gaaccttatt tcacagggag cttatttgta tgtgtgcggg   1980
gacgcaaaag gcatggcgcg tgatgtgcac cgcacgttac ataccatcgc tcaggagcag   2040
gggtcattag atagctcaaa agcagagagt atggtgaaga atcttcagat gtcaggcaga   2100
tacctgcgcg atgtctggta a                                             2121
```

<210> SEQ ID NO 84
<211> LENGTH: 277
<212> TYPE: PRT
<213> ORGANISM: Rhodococcus erythropolis

<400> SEQUENCE: 84

Met Ala Arg Val Glu Gly Gln Val Ala Leu Ile Thr Gly Ala Ala Arg
1 5 10 15

Gly Gln Gly Arg Ser His Ala Ile Lys Leu Ala Glu Glu Gly Ala Asp
20 25 30

Val Ile Leu Val Asp Val Pro Asn Asp Val Val Asp Ile Gly Tyr Pro
35 40 45

Leu Gly Thr Ala Asp Glu Leu Asp Gln Thr Ala Lys Asp Val Glu Asn
50 55 60

Leu Gly Arg Lys Ala Ile Val Ile His Ala Asp Val Arg Asp Leu Glu
65 70 75 80

Ser Leu Thr Ala Glu Val Asp Arg Ala Val Ser Thr Leu Gly Arg Leu
85 90 95

Asp Ile Val Ser Ala Asn Ala Gly Ile Ala Ser Val Pro Phe Leu Ser
100 105 110

His Asp Ile Pro Asp Asn Thr Trp Arg Gln Met Ile Asp Ile Asn Leu
115 120 125

Thr Gly Val Trp His Thr Ala Lys Val Ala Val Pro His Ile Leu Ala
130 135 140

Gly Glu Arg Gly Gly Ser Ile Val Leu Thr Ser Ser Ala Ala Gly Leu
145 150 155 160

Lys Gly Tyr Ala Gln Ile Ser His Tyr Ser Ala Ala Lys His Gly Val
165 170 175

Val Gly Leu Met Arg Ser Leu Ala Leu Glu Leu Ala Pro His Arg Val
180 185 190

Arg Val Asn Ser Leu His Pro Thr Gln Val Asn Thr Pro Met Ile Gln
195 200 205

Asn Glu Gly Thr Tyr Arg Ile Phe Ser Pro Asp Leu Glu Asn Pro Thr
210 215 220

Arg Glu Asp Phe Glu Ile Ala Ser Thr Thr Thr Asn Ala Leu Pro Ile
225 230 235 240

Pro Trp Val Glu Ser Val Asp Val Ser Asn Ala Leu Leu Phe Leu Val
245 250 255

Ser Glu Asp Ala Arg Tyr Ile Thr Gly Ala Ala Ile Pro Val Asp Ala
260 265 270

Gly Thr Thr Leu Lys
275

<210> SEQ ID NO 85
<211> LENGTH: 834
<212> TYPE: DNA
<213> ORGANISM: Rhodococcus erythropolis

<400> SEQUENCE: 85
atggcccgtg tggaaggtca agtggctctg attaccggcg ctgctcgtgg tcaaggtcgt 60
agtcatgcga ttaaactggc ggaagaaggc gcggatgtga ttctggttga cgtcccgaat 120
gatgtggttg acatcggcta tccgctgggt acggcagatg aactggacca gaccgctaaa 180
gatgttgaaa acctgggtcg taaggcgatt gtcatccatg ccgatgtgcg cgacctggaa 240
tcactgacgg cagaagtgga tcgtgctgtt agtaccctgg gccgcctgga cattgtttcc 300
gcaaatgctg gtatcgccag cgtcccgttt ctgtctcacg atattccgga caacacctgg 360
cgtcagatga ttgatatcaa tctgacgggc gtctggcata ccgcgaaagt ggccgttccg 420

-continued

```
cacattctgg ccggtgaacg cggcggttcc atcgttctga ccagctctgc ggccggcctg    480

aaaggttatg cacaaattag tcattactcc gcagctaagc acggcgtcgt gggtctgatg    540

cgttcactgg cactggaact ggctccgcat cgtgtccgcg tgaactcgct gcacccgacg    600

caggtgaaca ccccgatgat tcaaaatgaa ggcacgtatc gtatctttag cccggatctg    660

gaaaacccga cccgcgaaga cttcgaaatt gcgtctacca cgaccaatgc cctgccgatc    720

ccgtgggtgg aatcagttga tgtctcgaac gcactgctgt tcctggttag cgaagacgca    780

cgttacatta ccggtgcagc aatcccggtg gatgccggta cgaccctgaa gtaa          834
```

<210> SEQ ID NO 86
<211> LENGTH: 280
<212> TYPE: PRT
<213> ORGANISM: Citrus sinensis

<400> SEQUENCE: 86

```
Met Ala Thr Pro Pro Ile Ser Ser Leu Ile Ser Gln Arg Leu Leu Gly
1               5                   10                  15

Lys Val Ala Leu Val Thr Gly Gly Ala Ser Gly Ile Gly Glu Gly Ile
            20                  25                  30

Val Arg Leu Phe His Arg His Gly Ala Lys Val Cys Phe Val Asp Val
        35                  40                  45

Gln Asp Glu Leu Gly Tyr Arg Leu Gln Glu Ser Leu Val Gly Asp Lys
    50                  55                  60

Asp Ser Asn Ile Phe Tyr Ser His Cys Asp Val Thr Val Glu Asp Asp
65                  70                  75                  80

Val Arg Arg Ala Val Asp Leu Thr Val Thr Lys Phe Gly Thr Leu Asp
                85                  90                  95

Ile Met Val Asn Asn Ala Gly Ile Ser Gly Thr Pro Ser Ser Asp Ile
            100                 105                 110

Arg Asn Val Asp Val Ser Glu Phe Glu Lys Val Phe Asp Ile Asn Val
        115                 120                 125

Lys Gly Val Phe Met Gly Met Lys Tyr Ala Ala Ser Val Met Ile Pro
    130                 135                 140

Arg Lys Gln Gly Ser Ile Ile Ser Leu Gly Ser Val Gly Ser Val Ile
145                 150                 155                 160

Gly Gly Ile Gly Pro His His Tyr Ile Ser Ser Lys His Ala Val Val
                165                 170                 175

Gly Leu Thr Arg Ser Ile Ala Ala Glu Leu Gly Gln His Gly Ile Arg
            180                 185                 190

Val Asn Cys Val Ser Pro Tyr Ala Val Pro Thr Asn Leu Ala Val Ala
        195                 200                 205

His Leu Pro Glu Asp Glu Arg Thr Glu Asp Met Phe Thr Gly Phe Arg
    210                 215                 220

Glu Phe Ala Lys Lys Asn Ala Asn Leu Gln Gly Val Glu Leu Thr Val
225                 230                 235                 240

Glu Asp Val Ala Asn Ala Val Leu Phe Leu Ala Ser Glu Asp Ala Arg
                245                 250                 255

Tyr Ile Ser Gly Asp Asn Leu Ile Val Asp Gly Gly Phe Thr Arg Val
            260                 265                 270

Asn His Ser Phe Arg Val Phe Arg
        275                 280
```

<210> SEQ ID NO 87
<211> LENGTH: 843

<212> TYPE: DNA
<213> ORGANISM: Citrus sinensis

<400> SEQUENCE: 87
atggcaacgc cgccgatttc atccctgatt tcacaacgcc tgctgggtaa agtcgccctg 60
gtcacgggtg gtgcttctgg tattggtgaa ggcatcgtgc gtctgtttca ccgtcatggc 120
gcgaaagtgt gctttgttga tgtgcaggat gaactgggct accgtctgca agaatctctg 180
gtgggcgaca aagattcaaa catcttttat agccactgtg atgtcaccgt ggaagacgat 240
gtgcgccgcg ctgtggatct gaccgtgacg aaattcggta cgctggatat tatggtcaat 300
aacgcgggta ttagtggcac cccgtccagc gatattcgta atgttgatgt gagcgaattt 360
gaaaaagtgt ttgatattaa cgtcaaaggc gtgtttatgg gcatgaaata tgccgcgagc 420
gtgatgatcc cgcgcaaaca gggtagcatc atctccctgg gttctgttgg cagcgtgatc 480
ggtggcattg gcccgcacca ttatatcagc tcgaaacatg cggttgtggg cctgacccgc 540
agcattgcag cggaactggg tcagcatggc attcgtgtga actgtgtgtc tccgtatgcg 600
gttccgacca atctggcggt tgcacacctg ccggaagatg aacgtaccga agatatgttt 660
acgggcttcc gtgaatttgc gaaaaagaat gccaacctgc aaggtgttga actgaccgtc 720
gaagatgtgg ccaatgcggt gctgtttctg gccagcgaag atgcacgcta cattagcggt 780
gataatctga tcgttgatgg cggctttacc cgtgtgaacc actcatttcg tgttttccgt 840
taa 843

<210> SEQ ID NO 88
<211> LENGTH: 262
<212> TYPE: PRT
<213> ORGANISM: Citrus sinensis

<400> SEQUENCE: 88

Met Ser Lys Pro Arg Leu Gln Gly Lys Val Ala Ile Ile Met Gly Ala
1 5 10 15

Ala Ser Gly Ile Gly Glu Ala Thr Ala Lys Leu Phe Ala Glu His Gly
20 25 30

Ala Phe Val Ile Ile Ala Asp Ile Gln Asp Glu Leu Gly Asn Gln Val
35 40 45

Val Ser Ser Ile Gly Pro Glu Lys Ala Ser Tyr Arg His Cys Asp Val
50 55 60

Arg Asp Glu Lys Gln Val Glu Glu Thr Val Ala Tyr Ala Ile Glu Lys
65 70 75 80

Tyr Gly Ser Leu Asp Ile Met Tyr Ser Asn Ala Gly Val Ala Gly Pro
85 90 95

Val Gly Thr Ile Leu Asp Leu Asp Met Ala Gln Phe Asp Arg Thr Ile
100 105 110

Ala Thr Asn Leu Ala Gly Ser Val Met Ala Val Lys Tyr Ala Ala Arg
115 120 125

Val Met Val Ala Asn Lys Ile Arg Gly Ser Ile Ile Cys Thr Thr Ser
130 135 140

Thr Ala Ser Thr Val Gly Gly Ser Gly Pro His Ala Tyr Thr Ile Ser
145 150 155 160

Lys His Gly Leu Leu Gly Leu Val Arg Ser Ala Ala Ser Glu Leu Gly
165 170 175

Lys His Gly Ile Arg Val Asn Cys Val Ser Pro Phe Gly Val Ala Thr
180 185 190

-continued

Pro Phe Ser Ala Gly Thr Ile Asn Asp Val Glu Gly Phe Val Cys Lys
195 200 205

Val Ala Asn Leu Lys Gly Ile Val Leu Lys Ala Lys His Val Ala Glu
210 215 220

Ala Ala Leu Phe Leu Ala Ser Asp Glu Ser Ala Tyr Val Ser Gly His
225 230 235 240

Asp Leu Val Val Asp Gly Gly Phe Thr Ala Val Thr Asn Val Met Ser
245 250 255

Met Leu Glu Gly His Gly
260

<210> SEQ ID NO 89
<211> LENGTH: 789
<212> TYPE: DNA
<213> ORGANISM: Citrus sinensis

<400> SEQUENCE: 89
atgtcaaaac cgcgtctgca aggcaaagtg gctattatta tgggtgctgc gtctggcatc 60
ggtgaagcta cggctaaact gttcgctgaa catggcgcat ttgtgattat cgctgatatt 120
caggacgaac tgggcaacca ggtggttagc tctatcggcc cggaaaaagc gtcttatcgt 180
cactgcgatg tgcgtgatga aaaacaggtt gaagaaaccg tcgcgtatgc gattgaaaaa 240
tacggcagcc tggatattat gtactccaat gcgggcgtgg ccggtccggt tggcacgatt 300
ctggatctgg acatggccca attcgaccgt accatcgcaa cgaacctggc tggtagtgtt 360
atggcagtca aatatgcggc ccgtgtcatg gtggcgaata aaattcgcgg tagcattatc 420
tgtaccacga gtaccgcctc cacggtgggc ggcagcggcc cgcacgccta taccattagc 480
aaacacggtc tgctgggcct ggttcgttca gcagcttcgg aactgggtaa acatggcatc 540
cgcgtgaact gcgttagccc gtttggtgtt gcgaccccgt tctctgccgg tacgattaac 600
gatgtcgaag gctttgtctg taaagtggcg aatctgaaag gcatcgtcct gaaagcgaag 660
catgtggccg aagcggccct gttcctggca agcgatgaat ctgcttatgt gagcggtcac 720
gacctggtgg tggatggtgg ctttacggca gttacgaatg tcatgtcaat gctggaaggt 780
cacggctaa 789

<210> SEQ ID NO 90
<211> LENGTH: 263
<212> TYPE: PRT
<213> ORGANISM: Citrus sinensis

<400> SEQUENCE: 90

Met Ser Asn Pro Arg Met Glu Gly Lys Val Ala Leu Ile Thr Gly Ala
1 5 10 15

Ala Ser Gly Ile Gly Glu Ala Ala Val Arg Leu Phe Ala Glu His Gly
20 25 30

Ala Phe Val Val Ala Ala Asp Val Gln Asp Glu Leu Gly His Gln Val
35 40 45

Ala Ala Ser Val Gly Thr Asp Gln Val Cys Tyr His His Cys Asp Val
50 55 60

Arg Asp Glu Lys Gln Val Glu Glu Thr Val Arg Tyr Thr Leu Glu Lys
65 70 75 80

Tyr Gly Lys Leu Asp Val Leu Phe Ser Asn Ala Gly Ile Met Gly Pro
85 90 95

Leu Thr Gly Ile Leu Glu Leu Asp Leu Thr Gly Phe Gly Asn Thr Met
100 105 110

```
Ala Thr Asn Val Cys Gly Val Ala Ala Thr Ile Lys His Ala Ala Arg
        115                 120                 125

Ala Met Val Asp Lys Asn Ile Arg Gly Ser Ile Ile Cys Thr Thr Ser
    130                 135                 140

Val Ala Ser Ser Leu Gly Gly Thr Ala Pro His Ala Tyr Thr Thr Ser
145                 150                 155                 160

Lys His Ala Leu Val Gly Leu Val Arg Thr Ala Cys Ser Glu Leu Gly
                165                 170                 175

Ala Tyr Gly Ile Arg Val Asn Cys Ile Ser Pro Phe Gly Val Ala Thr
            180                 185                 190

Pro Leu Ser Cys Thr Ala Tyr Asn Leu Arg Pro Asp Glu Val Glu Ala
        195                 200                 205

Asn Ser Cys Ala Leu Ala Asn Leu Lys Gly Ile Val Leu Lys Ala Lys
    210                 215                 220

His Ile Ala Glu Ala Ala Leu Phe Leu Ala Ser Asp Glu Ser Ala Tyr
225                 230                 235                 240

Ile Ser Gly His Asn Leu Ala Val Asp Gly Gly Phe Thr Val Val Asn
                245                 250                 255

His Ser Ser Ser Ser Ala Thr
            260
```

<210> SEQ ID NO 91
<211> LENGTH: 792
<212> TYPE: DNA
<213> ORGANISM: Citrus sinensis

<400> SEQUENCE: 91

```
atgtcaaacc cgcgtatgga aggcaaagtc gcactgatta cgggcgcagc atctggtatc     60

ggtgaagcag cagtccgtct gttcgctgaa catggtgcgt ttgtcgtggc ggcagatgtg    120

caagacgaac tgggtcatca ggtggcggca tctgtgggta cggaccaggt gtgctaccat    180

cactgcgatg tgcgcgatga aaaacaagtg gaagaaaccg tgcgttatac cctggaaaaa    240

tacggcaaac tggatgtcct gttttcaaac gcgggcatca tgggtccgct gaccggcatt    300

ctggaactgg atctgaccgg cttcggtaac acgatggcaa ccaatgtgtg cggtgttgcc    360

gcgaccatta aacacgcggc acgcgcaatg gtggacaaaa acattcgcgg tagcattatc    420

tgcaccacca gcgtggcttc atcgctgggt ggcaccgcgc cgcacgcata caccacgagc    480

aaacacgcac tggtgggcct ggttcgtacg gcatgttcgg aactgggtgc gtatggcatt    540

cgtgtgaact gtatcagccc gtttggtgtt gcaacgccgc tgtcttgcac ggcctataac    600

ctgcgcccgg atgaagtgga agcaaactca tgcgcactgg cgaacctgaa aggtattgtg    660

ctgaaagcga aacacattgc ggaagcagcg ctgttcctgg cgagcgatga aagcgcgtat    720

attagcggtc ataatctggc ggtggatggt ggtttcacgg tggttaatca ttcaagttcg    780

tcggcgacgt aa                                                        792
```

<210> SEQ ID NO 92
<211> LENGTH: 278
<212> TYPE: PRT
<213> ORGANISM: Citrus sinensis

<400> SEQUENCE: 92

```
Met Thr Thr Ala Gly Ser Arg Asp Ser Pro Leu Val Ala Gln Arg Leu
1               5                   10                  15

Leu Gly Lys Val Ala Leu Val Thr Gly Gly Ala Thr Gly Ile Gly Glu
```

```
            20                  25                  30

Ser Ile Val Arg Leu Phe His Lys His Gly Ala Lys Val Cys Val Val
        35                  40                  45

Asp Ile Asn Asp Asp Leu Gly Gln His Leu Cys Gln Thr Leu Gly Pro
    50                  55                  60

Thr Thr Arg Phe Ile His Gly Asp Val Ala Ile Glu Asp Asp Val Ser
65                  70                  75                  80

Arg Ala Val Asp Phe Thr Val Ala Asn Phe Gly Thr Leu Asp Ile Met
                85                  90                  95

Val Asn Asn Ala Gly Met Gly Gly Pro Pro Cys Pro Asp Ile Arg Glu
            100                 105                 110

Phe Pro Ile Ser Thr Phe Glu Lys Val Phe Asp Ile Asn Thr Lys Gly
        115                 120                 125

Thr Phe Ile Gly Met Lys His Ala Ala Arg Val Met Ile Pro Ser Lys
    130                 135                 140

Lys Gly Ser Ile Val Ser Ile Ser Ser Val Thr Ser Ala Ile Gly Gly
145                 150                 155                 160

Ala Gly Pro His Ala Tyr Thr Ala Ser Lys His Ala Val Leu Gly Leu
                165                 170                 175

Thr Lys Ser Val Ala Ala Glu Leu Gly Gln His Gly Ile Arg Val Asn
            180                 185                 190

Cys Val Ser Pro Tyr Ala Ile Leu Thr Asn Leu Ala Leu Ala His Leu
        195                 200                 205

His Glu Asp Glu Arg Thr Asp Asp Ala Arg Ala Gly Phe Arg Ala Phe
    210                 215                 220

Ile Gly Lys Asn Ala Asn Leu Gln Gly Val Asp Leu Val Glu Asp Asp
225                 230                 235                 240

Val Ala Asn Ala Val Leu Phe Leu Ala Ser Asp Asp Ala Arg Tyr Ile
                245                 250                 255

Ser Gly Asp Asn Leu Phe Val Asp Gly Gly Phe Thr Cys Thr Asn His
            260                 265                 270

Ser Leu Arg Val Phe Arg
        275
```

<210> SEQ ID NO 93
<211> LENGTH: 837
<212> TYPE: DNA
<213> ORGANISM: Citrus sinensis

<400> SEQUENCE: 93

```
atgacgacgg ctggttcgcg tgacagtccg ctggtcgctc aacgcctgct gggcaaagtg      60

gccctggtta cgggtggtgc taccggcatt ggtgaaagta tcgtgcgtct gtttcataaa     120

cacggcgcga aagtttgcgt ggttgatatt aacgatgacc tgggccagca tctgtgtcaa     180

accctgggtc cgaccacccg tttcattcac ggcgatgttg caatcgaaga tgatgtgagc     240

cgtgcggttg attttaccgt cgccaacttc ggtacgctgg acattatggt gaacaatgcc     300

ggtatgggcg gtccgccgtg cccggatatt cgtgaatttc cgatctcgac ctttgaaaaa     360

gtcttcgaca ttaacaccaa aggcacgttc atcggtatga aacatgcggc ccgcgtgatg     420

attccgagta aaaaaggtag tattgtcagc attagcagcg tgaccagcgc gattggcggc     480

gcgggtccgc acgcctatac cgcgagcaaa catgcggtgc tgggcctgac gaaatctgtc     540

gcggcggaac tgggccagca cggtattcgt gtcaactgtg tgtctccgta cgccatcctg     600

accaatctgg cgctggccca tctgcacgaa gatgaacgta cggatgacgc gcgtgcgggt     660
```

tttcgtgcat tcattggtaa aaacgctaat ctgcaaggtg ttgatctggt cgaagatgac 720
gtggcgaatg ccgttctgtt tctggcatca gatgacgctc gctatatctc gggcgataac 780
ctgttcgtgg atggcggctt cacctgtacc aatcactccc tgcgtgtgtt ccgttaa 837

<210> SEQ ID NO 94
<211> LENGTH: 280
<212> TYPE: PRT
<213> ORGANISM: Vitis vinifera

<400> SEQUENCE: 94

Met Ala Ala Thr Ser Ile Asp Asn Ser Pro Leu Pro Ser Gln Arg Leu
1               5                   10                  15

Leu Gly Lys Val Ala Leu Val Thr Gly Gly Ala Thr Gly Ile Gly Glu
            20                  25                  30

Ser Ile Val Arg Leu Phe Leu Lys Gln Gly Ala Lys Val Cys Ile Val
        35                  40                  45

Asp Val Gln Asp Asp Leu Gly Gln Lys Leu Cys Asp Thr Leu Gly Gly
    50                  55                  60

Asp Pro Asn Val Ser Phe Phe His Cys Asp Val Thr Ile Glu Asp Asp
65                  70                  75                  80

Val Cys His Ala Val Asp Phe Thr Val Thr Lys Phe Gly Thr Leu Asp
                85                  90                  95

Ile Met Val Asn Asn Ala Gly Met Ala Gly Pro Pro Cys Ser Asp Ile
            100                 105                 110

Arg Asn Val Glu Val Ser Met Phe Glu Lys Val Phe Asp Val Asn Val
        115                 120                 125

Lys Gly Val Phe Leu Gly Met Lys His Ala Ala Arg Ile Met Ile Pro
    130                 135                 140

Leu Lys Lys Gly Thr Ile Ile Ser Leu Cys Ser Val Ser Ser Ala Ile
145                 150                 155                 160

Ala Gly Val Gly Pro His Ala Tyr Thr Gly Ser Lys Cys Ala Val Ala
                165                 170                 175

Gly Leu Thr Gln Ser Val Ala Ala Glu Met Gly Gly His Gly Ile Arg
            180                 185                 190

Val Asn Cys Ile Ser Pro Tyr Ala Ile Ala Thr Gly Leu Ala Leu Ala
        195                 200                 205

His Leu Pro Glu Asp Glu Arg Thr Glu Asp Ala Met Ala Gly Phe Arg
    210                 215                 220

Ala Phe Val Gly Lys Asn Ala Asn Leu Gln Gly Val Glu Leu Thr Val
225                 230                 235                 240

Asp Asp Val Ala His Ala Ala Val Phe Leu Ala Ser Asp Glu Ala Arg
                245                 250                 255

Tyr Ile Ser Gly Leu Asn Leu Met Leu Asp Gly Gly Phe Ser Cys Thr
            260                 265                 270

Asn His Ser Leu Arg Val Phe Arg
        275                 280

<210> SEQ ID NO 95
<211> LENGTH: 843
<212> TYPE: DNA
<213> ORGANISM: Vitis vinifera

<400> SEQUENCE: 95
atggccgcaa cgagcattga taattctccg ctgccgagtc aacgtctgct gggtaaagtc 60

```
gcactggtca cgggtggcgc tacgggtatt ggcgaaagca tcgtgcgtct gtttctgaaa    120

cagggtgcta aagtgtgcat tgtggacgtg caagatgacc tgggccagaa actgtgcgat    180

accctgggtg gcgatccgaa cgttagcttt ttccattgcg atgtgaccat cgaagatgat    240

gtgtgccatg cagttgattt taccgtcacg aaattcggca ccctggatat tatggtgaac    300

aatgcgggta tggcaggtcc gccgtgctcg gacatccgca acgtggaagt cagcatgttt    360

gaaaaagtgt ttgatgtgaa tgtgaaaggt gttttcctgg gcatgaaaca tgcagcccgc    420

attatgattc cgctgaaaaa aggcaccatt atcagcctgt gttcagtttc cagcgctatc    480

gcgggcgttg gtccgcacgc atatacgggt agcaaatgcg cagtggcggg tctgacgcaa    540

tcggtcgcag cagaaatggg tggtcatggc attcgcgtga actgtatcag cccgtatgca    600

atcgcaacgg gtctggcgct ggcacatctg ccggaagatg aacgcacgga agatgcaatg    660

gcgggtttcc gtgcgtttgt gggtaaaaat gcgaatctgc aaggtgttga actgaccgtg    720

gatgatgtgg cgcacgcagc ggtgtttctg gcaagcgatg aagcacgtta catctctggt    780

ctgaatctga tgctggacgg cggcttttcg tgtaccaacc actcgctgcg tgtctttcgc    840

taa                                                                  843
```

<210> SEQ ID NO 96
<211> LENGTH: 279
<212> TYPE: PRT
<213> ORGANISM: Vitis vinifera

<400> SEQUENCE: 96

```
Met Ser Thr Ala Ser Ser Gly Asp Val Ser Leu Leu Ser Gln Arg Leu
1               5                   10                  15

Val Gly Lys Val Ala Leu Ile Thr Gly Gly Ala Thr Gly Ile Gly Glu
            20                  25                  30

Ser Ile Ala Arg Leu Phe Tyr Arg His Gly Ala Lys Val Cys Ile Val
        35                  40                  45

Asp Ile Gln Asp Asn Pro Gly Gln Asn Leu Cys Arg Glu Leu Gly Thr
    50                  55                  60

Asp Asp Ala Cys Phe Phe His Cys Asp Val Ser Ile Glu Ile Asp Val
65                  70                  75                  80

Ile Arg Ala Val Asp Phe Val Val Asn Arg Phe Gly Lys Leu Asp Ile
                85                  90                  95

Met Val Asn Asn Ala Gly Ile Ala Asp Pro Pro Cys Pro Asp Ile Arg
            100                 105                 110

Asn Thr Asp Leu Ser Ile Phe Glu Lys Val Phe Asp Val Asn Val Lys
        115                 120                 125

Gly Thr Phe Gln Cys Met Lys His Ala Ala Arg Val Met Val Pro Gln
    130                 135                 140

Lys Lys Gly Ser Ile Ile Ser Leu Thr Ser Val Ala Ser Val Ile Gly
145                 150                 155                 160

Gly Ala Gly Pro His Ala Tyr Thr Gly Ser Lys His Ala Val Leu Gly
                165                 170                 175

Leu Thr Lys Ser Val Ala Ala Glu Leu Gly Leu His Gly Ile Arg Val
            180                 185                 190

Asn Cys Val Ser Pro Tyr Ala Val Pro Thr Gly Met Pro Leu Ala His
        195                 200                 205

Leu Pro Glu Ser Glu Lys Thr Glu Asp Ala Met Met Gly Met Arg Ala
    210                 215                 220

Phe Val Gly Arg Asn Ala Asn Leu Gln Gly Ile Glu Leu Thr Val Asp
```

```
225                 230                 235                 240

Asp Val Ala Asn Ser Val Val Phe Leu Ala Ser Asp Glu Ala Arg Tyr
                245                 250                 255

Val Ser Gly Leu Asn Leu Met Leu Asp Gly Gly Phe Ser Cys Val Asn
            260                 265                 270

His Ser Leu Arg Val Phe Arg
        275


<210> SEQ ID NO 97
<211> LENGTH: 840
<212> TYPE: DNA
<213> ORGANISM: Vitis vinifera

<400> SEQUENCE: 97

atgtcaacgg cttcctcggg tgatgtgtcg ctgctgtcgc aacgcctggt cggtaaagtc      60

gctctgatta cgggtggtgc aacgggcatt ggtgaatcga ttgcgcgtct gttttaccgt     120

catggtgcga aagtgtgcat cgttgacatt caggataatc cgggtcaaaa cctgtgccgt     180

gaactgggca ccgacgatgc gtgcttcttt cactgcgatg tgagcattga aatcgatgtg     240

attcgtgctg ttgactttgt ggttaaccgc tttggtaaac tggacattat ggttaataac     300

gcgggcatcg cagatccgcc gtgcccggat attcgcaaca ccgatctgag catttttgaa     360

aaagtgttcg atgtgaacgt gaaaggcacc tttcagtgta tgaaacacgc agcgcgcgtt     420

atggtgccgc agaaaaaagg tagcattatc agcctgacct cggtggcgag cgtgattggt     480

ggcgcgggtc cgcacgccta tacgggtagc aaacacgcgg ttctgggtct gacgaaaagc     540

gttgcggcag aactgggtct gcatggtatt cgcgtgaact gtgtgagtcc gtatgcagtt     600

ccgacgggta tgccgctggc acatctgccg gaatcggaaa aaaccgaaga tgcgatgatg     660

ggtatgcgtg catttgtggg tcgtaatgcc aacctgcaag gtattgaact gaccgtggac     720

gatgtcgcaa atagcgtcgt gtttctggcg tcggatgaag cgcgttatgt tagcggtctg     780

aacctgatgc tggacggcgg cttctcgtgt gtcaaccact cgctgcgtgt gtttcgctaa     840


<210> SEQ ID NO 98
<211> LENGTH: 280
<212> TYPE: PRT
<213> ORGANISM: Citrus sinensis

<400> SEQUENCE: 98

Met Ser Asn Ser Asn Ser Thr Asp Ser Ser Pro Ala Val Gln Arg Leu
1               5                   10                  15

Val Gly Arg Val Ala Leu Ile Thr Gly Gly Ala Thr Gly Ile Gly Glu
            20                  25                  30

Ser Thr Val Arg Leu Phe His Lys His Gly Ala Lys Val Cys Ile Ala
        35                  40                  45

Asp Val Gln Asp Asn Leu Gly Gln Gln Val Cys Gln Ser Leu Gly Gly
    50                  55                  60

Glu Pro Asp Thr Phe Phe Cys His Cys Asp Val Thr Lys Glu Glu Asp
65                  70                  75                  80

Val Cys Ser Ala Val Asp Leu Thr Val Glu Lys Phe Gly Thr Leu Asp
                85                  90                  95

Ile Met Val Asn Asn Ala Gly Ile Ser Gly Ala Pro Cys Pro Asp Ile
            100                 105                 110

Arg Glu Ala Asp Leu Ser Glu Phe Glu Lys Val Phe Asp Ile Asn Val
        115                 120                 125
```

```
Lys Gly Val Phe His Gly Met Lys His Ala Ala Arg Ile Met Ile Pro
    130                 135                 140

Gln Thr Lys Gly Thr Ile Ile Ser Ile Cys Ser Val Ala Gly Ala Ile
145                 150                 155                 160

Gly Gly Leu Gly Pro His Ala Tyr Thr Gly Ser Lys His Ala Val Leu
                165                 170                 175

Gly Leu Asn Lys Asn Val Ala Ala Glu Leu Gly Lys Tyr Gly Ile Arg
            180                 185                 190

Val Asn Cys Val Ser Pro Tyr Ala Val Ala Thr Gly Leu Ala Leu Ala
        195                 200                 205

His Leu Pro Glu Glu Glu Arg Thr Glu Asp Ala Met Val Gly Phe Arg
    210                 215                 220

Asn Phe Val Ala Arg Asn Ala Asn Met Gln Gly Thr Glu Leu Thr Ala
225                 230                 235                 240

Asn Asp Val Ala Asn Ala Val Leu Phe Leu Ala Ser Asp Glu Ala Arg
                245                 250                 255

Tyr Ile Ser Gly Thr Asn Leu Met Val Asp Gly Gly Phe Thr Ser Val
            260                 265                 270

Asn His Ser Leu Arg Val Phe Arg
        275                 280
```

<210> SEQ ID NO 99
<211> LENGTH: 843
<212> TYPE: DNA
<213> ORGANISM: Citrus sinensis

<400> SEQUENCE: 99

```
atgtccaata gcaactctac ggattcgtcg ccggcagtcc aacgcctggt cggtcgtgtc     60

gccctgatta cgggtggtgc aacgggtatt ggcgaaagca cggtgcgcct gtttcataaa    120

catggcgcga aagtgtgtat tgccgacgtt caggataacc tgggtcagca agtgtgtcag    180

agtctgggtg gcgaaccgga taccttttc tgccattgtg atgtgacgaa agaagaagat    240

gtgtgtagcg cagttgatct gaccgtggaa aaatttggca ccctggacat tatggtgaac    300

aatgcgggta ttagcggcgc accgtgcccg gacattcgtg aagccgatct gagcgaattt    360

gaaaaagttt tcgacatcaa cgtgaaaggc gtgtttcacg gcatgaaaca tgcagcgcgt    420

attatgatcc cgcaaaccaa aggcaccatt atcagcattt gctccgtggc tggtgcgatt    480

ggtggcctgg gtccgcacgc atataccggc tccaaacatg cagtcctggg cctgaacaaa    540

aacgtggccg cggaactggg caaatacggt atccgtgtga attgcgtcag cccgtatgct    600

gttgccaccg gcctggctct ggcacacctg ccggaagaag aacgtaccga agatgcaatg    660

gtgggctttc gtaattttgt ggcacgcaac gcgaatatgc aaggcaccga actgacggcg    720

aatgatgtgg caaacgcggt cctgtttctg gcctctgatg aagcccgtta tatcagcggc    780

acgaatctga tggtggatgg cggttttacc tcggtcaatc actcgctgcg tgtcttccgt    840

taa                                                                   843
```

<210> SEQ ID NO 100
<211> LENGTH: 282
<212> TYPE: PRT
<213> ORGANISM: Brachypodium distachyon

<400> SEQUENCE: 100

```
Met Ser Ala Ala Ala Ala Val Ser Ser Ser Ser Ser Pro Arg Leu Glu
1               5                   10                  15
```

```
Gly Lys Val Ala Leu Val Thr Gly Gly Ala Ser Gly Ile Gly Glu Ala
            20                  25                  30

Ile Val Arg Leu Phe Arg Gln His Gly Ala Lys Val Cys Ile Ala Asp
        35                  40                  45

Val Gln Asp Glu Ala Gly Gln Gln Val Arg Asp Ser Leu Gly Asp Asp
    50                  55                  60

Ala Gly Thr Asp Val Leu Phe Val His Cys Asp Val Thr Val Glu Glu
65                  70                  75                  80

Asp Val Ser Arg Ala Val Asp Ala Ala Ala Glu Lys Phe Gly Thr Leu
                85                  90                  95

Asp Ile Met Val Asn Asn Ala Gly Ile Thr Gly Asp Lys Val Thr Asp
            100                 105                 110

Ile Arg Asn Leu Asp Phe Ala Glu Val Arg Lys Val Phe Asp Ile Asn
        115                 120                 125

Val His Gly Met Leu Leu Gly Met Lys His Ala Ala Arg Val Met Ile
    130                 135                 140

Pro Gly Lys Lys Gly Ser Ile Val Ser Leu Ala Ser Val Ala Ser Val
145                 150                 155                 160

Met Gly Gly Met Gly Pro His Ala Tyr Thr Ala Ser Lys His Ala Val
                165                 170                 175

Val Gly Leu Thr Lys Ser Val Ala Leu Glu Leu Gly Lys His Gly Ile
            180                 185                 190

Arg Val Asn Cys Val Ser Pro Tyr Ala Val Pro Thr Ala Leu Ser Met
        195                 200                 205

Pro His Leu Pro Gln Gly Glu His Lys Gly Asp Ala Val Arg Asp Phe
    210                 215                 220

Leu Ala Phe Val Gly Gly Glu Ala Asn Leu Lys Gly Val Asp Leu Leu
225                 230                 235                 240

Pro Lys Asp Val Ala Gln Ala Val Leu Tyr Leu Ala Ser Asp Glu Ala
                245                 250                 255

Arg Tyr Ile Ser Ala Leu Asn Leu Val Val Asp Gly Gly Phe Thr Ser
            260                 265                 270

Val Asn Pro Asn Leu Lys Ala Phe Glu Asp
        275                 280
```

<210> SEQ ID NO 101
<211> LENGTH: 849
<212> TYPE: DNA
<213> ORGANISM: Brachypodium distachyon

<400> SEQUENCE: 101

```
atgtccgctg ctgccgccgt gtcctcctca tcgtcgccgc gtctggaagg caaagtcgct      60

ctggttacgg gtggtgcgtc aggtatcggc gaagccattg tgcgcctgtt ccgtcaacat     120

ggtgccaaag tgtgtatcgc ggatgtccaa gacgaagcgg gccaacaggt ccgtgatagc     180

ctgggtgacg atgccggtac ggatgtgctg tttgtgcatt gcgacgttac cgtggaagaa     240

gatgtgtcac gcgcggtgga tgccgctgcg gaaaaattcg gcaccctgga cattatggtg     300

aacaacgcag gtattacggg cgacaaagtg acggacattc gcaacctgga tttcgctgaa     360

gtccgtaaag tgttcgacat caatgtgcac ggtatgctgc tgggcatgaa acatgcggcc     420

cgcgtgatga ttccgggtaa aaaaggctcg attgtgagcc tggcatcggt cgcaagcgtt     480

atgggtggta tgggtccgca cgcatatacc gcaagcaaac acgcggttgt gggtctgacg     540

aaaagcgttg cactggaact gggcaaacat ggtattcgtg tcaactgtgt gagcccgtat     600
```

-continued gcagttccga ccgcactgtc aatgccgcac ctgccgcagg gcgaacataa aggtgatgcg 660
gtgcgtgatt tcctggcgtt tgttggcggt gaagcgaatc tgaaaggtgt cgatctgctg 720
ccgaaagatg ttgcacaggc ggttctgtat ctggcaagcg acgaagcgcg ctatatttct 780
gcgctgaatc tggtggttga tggcggtttt acgagcgtga atccgaatct gaaagcattt 840
gaagactaa 849

<210> SEQ ID NO 102
<211> LENGTH: 267
<212> TYPE: PRT
<213> ORGANISM: Zingiber zerumbet

<400> SEQUENCE: 102

Met Arg Leu Glu Gly Lys Val Ala Leu Val Thr Gly Gly Ala Ser Gly
1 5 10 15

Ile Gly Glu Ser Ile Ala Arg Leu Phe Ile Glu His Gly Ala Lys Ile
20 25 30

Cys Ile Val Asp Val Gln Asp Glu Leu Gly Gln Gln Val Ser Gln Arg
35 40 45

Leu Gly Gly Asp Pro His Ala Cys Tyr Phe His Cys Asp Val Thr Val
50 55 60

Glu Asp Asp Val Arg Arg Ala Val Asp Phe Thr Ala Glu Lys Tyr Gly
65 70 75 80

Thr Ile Asp Ile Met Val Asn Asn Ala Gly Ile Thr Gly Asp Lys Val
85 90 95

Ile Asp Ile Arg Asp Ala Asp Phe Asn Glu Phe Lys Lys Val Phe Asp
100 105 110

Ile Asn Val Asn Gly Val Phe Leu Gly Met Lys His Ala Ala Arg Ile
115 120 125

Met Ile Pro Lys Met Lys Gly Ser Ile Val Ser Leu Ala Ser Val Ser
130 135 140

Ser Val Ile Ala Gly Ala Gly Pro His Gly Tyr Thr Gly Ala Lys His
145 150 155 160

Ala Val Val Gly Leu Thr Lys Ser Val Ala Ala Glu Leu Gly Arg His
165 170 175

Gly Ile Arg Val Asn Cys Val Ser Pro Tyr Ala Val Pro Thr Arg Leu
180 185 190

Ser Met Pro Tyr Leu Pro Glu Ser Glu Met Gln Glu Asp Ala Leu Arg
195 200 205

Gly Phe Leu Thr Phe Val Arg Ser Asn Ala Asn Leu Lys Gly Val Asp
210 215 220

Leu Met Pro Asn Asp Val Ala Glu Ala Val Leu Tyr Leu Ala Thr Glu
225 230 235 240

Glu Ser Lys Tyr Val Ser Gly Leu Asn Leu Val Ile Asp Gly Gly Phe
245 250 255

Ser Ile Ala Asn His Thr Leu Gln Val Phe Glu
260 265

<210> SEQ ID NO 103
<211> LENGTH: 804
<212> TYPE: DNA
<213> ORGANISM: Zingiber zerumbet

<400> SEQUENCE: 103
atgcgtctgg aaggcaaagt ggctctggtc acgggcggtg cgtcgggtat tggcgaatct 60

```
attgctcgtc tgtttattga acacggtgca aaaatttgca tcgtggatgt ccaggatgaa    120

ctgggtcaac aggtctctca gcgtctgggt ggcgatccgc acgcctgtta tttccactgt    180

gatgtgaccg tggaagatga cgttcgtcgc gcggtggatt ttacggcgga aaaatatggc    240

accattgaca ttatggttaa caatgcgggc attacgggcg ataaagtgat cgatattcgt    300

gatgcggatt tcaacgaatt taaaaaagtg ttcgacatta acgtgaatgg tgtctttctg    360

ggcatgaaac acgcagcgcg tattatgatc ccgaaaatga aaggctccat cgtttcgctg    420

gcgtccgtta gctcggtgat tgctggtgca ggtccgcatg gctataccgg cgcaaaacat    480

gcggttgtgg gtctgaccaa aagcgttgca gccgaactgg gtcgtcatgg tattcgcgtg    540

aactgcgttt cgccgtatgc ggtgccgacg cgcctgtcaa tgccgtatct gccggaatcg    600

gaaatgcagg aagatgcact gcgcggcttt ctgacctttg tgcgtagcaa tgcgaacctg    660

aaaggcgttg atctgatgcc gaatgatgtg gcggaagctg ttctgtatct ggcgaccgaa    720

gaaagcaaat atgtttcagg tctgaatctg gttattgacg gcggcttctc catcgctaat    780

catacccctgc aagtgtttga ataa                                          804


<210> SEQ ID NO 104
<211> LENGTH: 505
<212> TYPE: PRT
<213> ORGANISM: Artificial Sequence
<220> FEATURE:
<223> OTHER INFORMATION: Synthetic - Engineered valencene oxidase
      variant

<400> SEQUENCE: 104

Met Ala Trp Glu Tyr Ala Leu Ile Gly Leu Val Val Gly Ile Ile Ile
1               5                   10                  15

Gly Ala Val Ala Met Arg Trp Tyr Leu Lys Ser Tyr Thr Ser Ala Arg
            20                  25                  30

Arg Ser Gln Ser Asn Arg Leu Pro Arg Val Pro Glu Val Pro Gly Val
        35                  40                  45

Pro Leu Leu Gly Asn Leu Leu Gln Leu Lys Glu Lys Lys Pro Tyr Met
    50                  55                  60

Thr Phe Thr Arg Trp Ala Ala Thr Tyr Gly Pro Ile Tyr Ser Ile Lys
65                  70                  75                  80

Thr Gly Ala Thr Ser Met Val Val Val Ser Ser Asn Glu Ile Ala Lys
                85                  90                  95

Glu Ala Leu Val Thr Arg Phe Gln Ser Ile Ser Thr Arg Asn Leu Ser
            100                 105                 110

Lys Ala Leu Lys Val Leu Thr Ala Asp Lys Thr Met Val Ala Met Ser
        115                 120                 125

Asp Tyr Asp Asp Tyr His Lys Thr Val Lys Arg His Ile Leu Thr Ala
    130                 135                 140

Val Leu Gly Pro Asn Ala Gln Lys Lys His Arg Ile His Arg Asp Ile
145                 150                 155                 160

Met Met Asp Asn Ile Ser Thr Gln Leu His Glu Phe Val Lys Asn Asn
                165                 170                 175

Pro Glu Gln Glu Glu Val Asp Leu Arg Lys Ile Phe Gln Ser Glu Leu
            180                 185                 190

Phe Gly Leu Ala Met Arg Gln Ala Leu Gly Lys Asp Val Glu Ser Leu
        195                 200                 205

Tyr Val Glu Asp Leu Lys Ile Thr Met Asn Arg Asp Glu Ile Leu Gln
    210                 215                 220
```

Val Leu Val Val Asp Pro Met Met Gly Ala Ile Asp Val Asp Trp Arg
225 230 235 240

Asp Phe Phe Pro Tyr Leu Lys Trp Val Pro Asn Lys Lys Phe Glu Asn
245 250 255

Thr Ile Gln Gln Met Tyr Ile Arg Arg Glu Ala Val Met Lys Ser Leu
260 265 270

Ile Lys Glu Gln Lys Lys Arg Ile Ala Ser Gly Glu Lys Leu Asn Ser
275 280 285

Tyr Ile Asp Tyr Leu Leu Ser Glu Ala Gln Thr Leu Thr Asp Gln Gln
290 295 300

Leu Leu Met Ser Leu Trp Glu Pro Ile Ile Glu Ser Ser Asp Thr Thr
305 310 315 320

Met Val Thr Thr Glu Trp Ala Met Tyr Glu Leu Ala Lys Asn Pro Lys
325 330 335

Leu Gln Asp Arg Leu Tyr Arg Asp Ile Lys Ser Val Cys Gly Ser Glu
340 345 350

Lys Ile Thr Glu Glu His Leu Ser Gln Leu Pro Tyr Ile Thr Ala Ile
355 360 365

Phe His Glu Thr Leu Arg Lys His Ser Pro Val Pro Ile Ile Pro Leu
370 375 380

Arg His Val His Glu Asp Thr Gln Leu Gly Gly Tyr His Val Pro Ala
385 390 395 400

Gly Thr Glu Leu Ala Val Asn Ile Tyr Gly Cys Asn Met Asp Lys Asn
405 410 415

Val Trp Glu Asn Pro Glu Glu Trp Asn Pro Glu Arg Phe Met Lys Glu
420 425 430

Asn Glu Thr Ala Asp Phe Gln Lys Thr Met Ala Phe Gly Gly Gly Lys
435 440 445

Arg Val Cys Ala Gly Ser Leu Gln Ala Leu Leu Thr Ala Ser Ile Gly
450 455 460

Ile Gly Arg Met Val Gln Glu Phe Glu Trp Lys Leu Lys Asp Met Asp
465 470 475 480

Gln Glu Glu Val Asn Thr Ile Gly Leu Thr Asn Gln Met Leu Arg Pro
485 490 495

Leu Arg Ala Ile Ile Lys Pro Arg Ile
500 505

<210> SEQ ID NO 105
<211> LENGTH: 505
<212> TYPE: PRT
<213> ORGANISM: Artificial Sequence
<220> FEATURE:
<223> OTHER INFORMATION: Synthetic - Engineered valencene oxidase variant

<400> SEQUENCE: 105

Met Ala Trp Glu Tyr Ala Leu Ile Gly Leu Val Val Gly Ile Ile Ile
1 5 10 15

Gly Ala Val Ala Met Arg Trp Tyr Leu Lys Ser Tyr Thr Ser Ala Arg
20 25 30

Arg Ser Gln Ser Asn His Leu Pro Arg Val Pro Glu Val Pro Gly Val
35 40 45

Pro Leu Leu Gly Asn Leu Leu Gln Leu Lys Glu Lys Lys Pro Tyr Met
50 55 60

Thr Phe Thr Lys Trp Ala Ala Thr Tyr Gly Pro Ile Tyr Ser Ile Lys
65 70 75 80

-continued

```
Thr Gly Ala Thr Ser Val Val Val Val Ser Ser Asn Glu Ile Ala Lys
                85                  90                  95

Glu Ala Leu Val Thr Arg Phe Gln Ser Ile Ser Thr Arg Asn Leu Ser
            100                 105                 110

Lys Ala Leu Lys Val Leu Thr Ala Asp Lys Gln Met Val Ala Met Ser
        115                 120                 125

Asp Tyr Asp Asp Tyr His Lys Thr Val Lys Arg His Ile Leu Thr Ala
    130                 135                 140

Val Leu Gly Pro Asn Ala Gln Lys Lys His Arg Ile His Arg Asp Ile
145                 150                 155                 160

Met Met Asp Asn Ile Ser Thr Gln Leu His Glu Phe Val Lys Asn Asn
                165                 170                 175

Pro Glu Gln Glu Glu Val Asp Leu Arg Lys Ile Phe Gln Ser Glu Leu
            180                 185                 190

Phe Gly Leu Ala Met Arg Gln Ala Leu Gly Lys Asp Val Glu Ser Leu
        195                 200                 205

Tyr Val Glu Asp Leu Lys Ile Thr Met Asn Arg Asp Glu Ile Leu Gln
    210                 215                 220

Val Leu Val Val Asp Pro Met Met Gly Ala Ile Asp Val Asp Trp Arg
225                 230                 235                 240

Asp Phe Phe Pro Tyr Leu Lys Trp Val Pro Asn Lys Lys Phe Glu Asn
                245                 250                 255

Thr Ile Gln Gln Met Tyr Ile Arg Arg Glu Ala Val Met Lys Ser Leu
            260                 265                 270

Ile Lys Glu Gln Lys Lys Arg Ile Ala Ser Gly Glu Lys Leu Asn Ser
        275                 280                 285

Tyr Ile Asp Tyr Leu Leu Ser Glu Ala Gln Thr Leu Thr Asp Gln Gln
    290                 295                 300

Leu Leu Met Ser Leu Trp Glu Pro Ile Ile Glu Ser Ser Asp Thr Thr
305                 310                 315                 320

Met Val Thr Thr Glu Trp Ala Met Tyr Glu Leu Ala Lys Asn Pro Lys
                325                 330                 335

Leu Gln Asp Arg Leu Tyr Arg Asp Ile Lys Ser Val Cys Gly Ser Glu
            340                 345                 350

Lys Ile Thr Glu Glu His Leu Ser Gln Leu Pro Tyr Ile Thr Ala Ile
        355                 360                 365

Phe His Glu Thr Leu Arg Lys His Ser Pro Val Pro Ile Leu Pro Leu
    370                 375                 380

Arg His Val His Glu Asp Thr Val Leu Gly Gly Tyr His Val Pro Ala
385                 390                 395                 400

Gly Thr Glu Leu Ala Val Asn Ile Tyr Gly Cys Asn Met Asp Lys Asn
                405                 410                 415

Val Trp Glu Asn Pro Glu Glu Trp Asn Pro Glu Arg Phe Met Lys Glu
            420                 425                 430

Asn Glu Thr Ile Asp Phe Gln Lys Thr Met Ala Phe Gly Gly Gly Lys
        435                 440                 445

Arg Val Cys Ala Gly Ser Leu Gln Ala Leu Leu Ile Ala Ser Ile Gly
    450                 455                 460

Ile Gly Arg Met Val Gln Glu Phe Glu Trp Lys Leu Lys Asp Met Thr
465                 470                 475                 480

Gln Glu Glu Val Asn Thr Ile Gly Leu Thr Asn Gln Met Leu Arg Pro
                485                 490                 495
```

```
Leu Arg Ala Ile Ile Lys Pro Arg Ile
            500                 505


<210> SEQ ID NO 106
<211> LENGTH: 501
<212> TYPE: PRT
<213> ORGANISM: Artificial Sequence
<220> FEATURE:
<223> OTHER INFORMATION: Synthetic - Engineered valencene oxidase
      variant

<400> SEQUENCE: 106

Met Ala Leu Leu Leu Ala Val Phe Ala Val Ala Leu Ala Val Ala Leu
1               5                   10                  15

Ile Phe Trp Tyr Leu Lys Ser Tyr Thr Ser Ala Arg Arg Ser Gln Ser
            20                  25                  30

Asn His Leu Pro Arg Val Pro Glu Val Pro Gly Val Pro Leu Leu Gly
        35                  40                  45

Asn Leu Leu Gln Leu Lys Glu Lys Lys Pro Tyr Met Thr Phe Thr Arg
    50                  55                  60

Trp Ala Ala Thr Tyr Gly Pro Ile Tyr Ser Ile Lys Thr Gly Ala Thr
65                  70                  75                  80

Ser Met Val Val Val Ser Ser Asn Glu Ile Ala Lys Glu Ala Leu Val
                85                  90                  95

Thr Arg Phe Gln Ser Ile Ser Thr Arg Asn Leu Ser Lys Ala Leu Lys
            100                 105                 110

Val Leu Thr Ala Asp Lys Thr Met Val Ala Met Ser Asp Tyr Asp Asp
        115                 120                 125

Tyr His Lys Thr Val Lys Arg His Ile Leu Thr Ala Val Leu Gly Pro
    130                 135                 140

Asn Ala Gln Lys Lys His Arg Ile His Arg Asp Ile Met Met Asp Asn
145                 150                 155                 160

Ile Ser Thr Gln Leu His Glu Phe Val Lys Asn Asn Pro Glu Gln Glu
                165                 170                 175

Glu Val Asp Leu Arg Lys Ile Phe Gln Ser Glu Leu Phe Gly Leu Ala
            180                 185                 190

Met Arg Gln Ala Leu Gly Lys Asp Val Glu Ser Leu Tyr Val Glu Asp
        195                 200                 205

Leu Lys Ile Thr Met Asn Arg Asp Glu Ile Phe Gln Val Leu Val Val
    210                 215                 220

Asp Pro Met Met Gly Ala Ile Asp Val Asp Trp Arg Asp Phe Phe Pro
225                 230                 235                 240

Tyr Leu Lys Trp Val Pro Asn Lys Lys Phe Glu Asn Thr Ile Gln Gln
                245                 250                 255

Met Tyr Ile Arg Arg Glu Ala Val Met Lys Ser Leu Ile Lys Glu His
            260                 265                 270

Lys Lys Arg Ile Ala Ser Gly Glu Lys Leu Asn Ser Tyr Ile Asp Tyr
        275                 280                 285

Leu Leu Ser Glu Ala Gln Thr Leu Thr Asp Gln Gln Leu Leu Met Ser
    290                 295                 300

Leu Trp Glu Pro Ile Ile Glu Ser Ser Asp Thr Thr Met Val Thr Thr
305                 310                 315                 320

Glu Trp Ala Met Tyr Glu Leu Ala Lys Asn Pro Lys Leu Gln Asp Arg
                325                 330                 335

Leu Tyr Arg Asp Ile Lys Ser Val Cys Gly Ser Glu Lys Ile Thr Glu
            340                 345                 350
```

```
Glu His Leu Ser Gln Leu Pro Tyr Ile Thr Ala Ile Phe His Glu Thr
        355                 360                 365

Leu Arg Arg His Ser Pro Val Pro Ile Ile Pro Leu Arg His Val His
    370                 375                 380

Glu Asp Thr Val Leu Gly Gly Tyr His Val Pro Ala Gly Thr Glu Leu
385                 390                 395                 400

Ala Val Asn Ile Tyr Gly Cys Asn Met Asp Lys Asn Val Trp Glu Asn
                405                 410                 415

Pro Glu Glu Trp Asn Pro Glu Arg Phe Met Lys Glu Asn Glu Thr Ile
            420                 425                 430

Asp Phe Gln Lys Thr Met Ala Phe Gly Gly Gly Lys Arg Val Cys Ala
        435                 440                 445

Gly Ser Leu Gln Ala Leu Leu Thr Ala Ser Ile Gly Ile Gly Arg Met
    450                 455                 460

Val Gln Glu Phe Glu Trp Lys Leu Lys Asp Met Thr Gln Glu Glu Val
465                 470                 475                 480

Asn Thr Ile Gly Leu Thr Thr Gln Met Leu Arg Pro Leu Arg Ala Ile
                485                 490                 495

Ile Lys Pro Arg Ile
            500


<210> SEQ ID NO 107
<211> LENGTH: 501
<212> TYPE: PRT
<213> ORGANISM: Artificial Sequence
<220> FEATURE:
<223> OTHER INFORMATION: Synthetic - Engineered valencene oxidase
      variant

<400> SEQUENCE: 107

Met Ala Leu Leu Leu Ala Val Phe Ala Val Ala Leu Ala Val Ala Leu
1               5                   10                  15

Ile Phe Trp Tyr Leu Lys Ser Tyr Thr Ser Ala Arg Arg Ser Gln Ser
            20                  25                  30

Asn His Leu Pro Arg Val Pro Glu Val Pro Gly Val Pro Leu Leu Gly
        35                  40                  45

Asn Leu Leu Gln Leu Lys Glu Lys Lys Pro Tyr Met Thr Phe Thr Arg
    50                  55                  60

Trp Ala Ala Thr Tyr Gly Pro Ile Tyr Ser Ile Lys Thr Gly Ala Thr
65                  70                  75                  80

Ser Met Val Val Val Ser Ser Asn Glu Ile Ala Lys Glu Ala Leu Val
                85                  90                  95

Thr Arg Phe Gln Ser Ile Ser Thr Arg Asn Leu Ser Lys Ala Leu Lys
            100                 105                 110

Val Leu Thr Ala Asp Lys Thr Met Val Ala Met Ser Asp Tyr Asp Asp
        115                 120                 125

Tyr His Lys Thr Val Lys Arg His Ile Leu Thr Ala Val Leu Gly Pro
    130                 135                 140

Asn Ala Gln Lys Lys His Arg Ile His Arg Asp Ile Met Met Asp Asn
145                 150                 155                 160

Ile Ser Thr Gln Leu His Glu Phe Val Lys Asn Asn Pro Glu Gln Glu
                165                 170                 175

Glu Val Asp Leu Arg Lys Ile Phe Gln Ser Glu Leu Phe Gly Leu Ala
            180                 185                 190

Met Arg Gln Ala Leu Gly Lys Asp Val Glu Ser Leu Tyr Val Glu Asp
```

```
        195                 200                 205

Leu Lys Ile Thr Met Asn Arg Asp Glu Ile Phe Gln Val Leu Val Val
    210                 215                 220

Asp Pro Met Met Gly Ala Ile Asp Val Asp Trp Arg Asp Phe Phe Pro
225                 230                 235                 240

Tyr Leu Lys Trp Val Pro Asn Lys Lys Phe Glu Asn Thr Ile Gln Gln
                245                 250                 255

Met Tyr Ile Arg Arg Glu Ala Val Met Lys Ser Leu Ile Lys Glu His
            260                 265                 270

Lys Lys Arg Ile Ala Ser Gly Glu Lys Leu Asn Ser Tyr Ile Asp Tyr
        275                 280                 285

Leu Leu Ser Glu Ala Gln Thr Leu Thr Asp Gln Gln Leu Leu Met Ser
    290                 295                 300

Leu Trp Glu Pro Ile Ile Glu Ser Ser Asp Thr Thr Met Val Thr Thr
305                 310                 315                 320

Glu Trp Ala Met Tyr Glu Leu Ala Lys Asn Pro Lys Leu Gln Asp Arg
                325                 330                 335

Leu Tyr Arg Asp Ile Lys Ser Val Cys Gly Ser Glu Lys Ile Thr Glu
            340                 345                 350

Glu His Leu Ser Gln Leu Pro Tyr Ile Thr Ala Ile Phe His Glu Thr
        355                 360                 365

Leu Arg Arg His Ser Pro Val Pro Ile Ile Pro Leu Arg His Val His
    370                 375                 380

Glu Asp Thr Val Leu Gly Gly Tyr His Val Pro Ala Gly Thr Glu Leu
385                 390                 395                 400

Ala Val Asn Ile Tyr Gly Cys Asn Met Asp Lys Asn Val Trp Glu Asn
                405                 410                 415

Pro Glu Glu Trp Asn Pro Glu Arg Phe Met Lys Glu Asn Glu Thr Ile
            420                 425                 430

Asp Phe Gln Lys Thr Met Ala Phe Gly Gly Gly Lys Arg Val Cys Ala
        435                 440                 445

Gly Ser Leu Gln Ala Leu Leu Thr Ala Ser Ile Gly Ile Gly Arg Met
    450                 455                 460

Val Gln Glu Phe Glu Trp Lys Leu Lys Asp Met Thr Gln Glu Glu Val
465                 470                 475                 480

Asn Thr Ile Gly Leu Thr Asn Gln Met Leu Arg Pro Leu Arg Ala Ile
                485                 490                 495

Ile Lys Pro Arg Ile
            500


<210> SEQ ID NO 108
<211> LENGTH: 513
<212> TYPE: PRT
<213> ORGANISM: Artificial Sequence
<220> FEATURE:
<223> OTHER INFORMATION: Synthetic - Engineered valencene oxidase
      variant

<400> SEQUENCE: 108

Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
            20                  25                  30

Leu Lys Ser Tyr Thr Ser Ala Arg Arg Ser Gln Ser Asn His Leu Pro
        35                  40                  45
```

-continued

```
Arg Val Pro Glu Val Pro Gly Val Pro Leu Leu Gly Asn Leu Leu Gln
    50                  55                  60

Leu Lys Glu Lys Lys Pro Tyr Met Thr Phe Thr Arg Trp Ala Ala Thr
65                  70                  75                  80

Tyr Gly Pro Ile Tyr Ser Ile Lys Thr Gly Ala Thr Ser Met Val Val
                85                  90                  95

Val Ser Ser Asn Glu Ile Ala Lys Glu Ala Leu Val Thr Arg Phe Gln
            100                 105                 110

Ser Ile Ser Thr Arg Asn Leu Ser Lys Ala Leu Lys Val Leu Thr Ala
        115                 120                 125

Asp Lys Thr Met Val Ala Met Ser Asp Tyr Asp Asp Tyr His Lys Thr
    130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                165                 170                 175

Leu His Glu Phe Val Lys Asn Asn Pro Glu Gln Glu Glu Val Asp Leu
            180                 185                 190

Arg Lys Ile Phe Gln Ser Glu Leu Phe Gly Leu Ala Met Arg Gln Ala
        195                 200                 205

Leu Gly Lys Asp Val Glu Ser Leu Tyr Val Glu Asp Leu Lys Ile Thr
    210                 215                 220

Met Asn Arg Asp Glu Ile Phe Gln Val Leu Val Val Asp Pro Met Met
225                 230                 235                 240

Gly Ala Ile Asp Val Asp Trp Arg Asp Phe Phe Pro Tyr Leu Lys Trp
                245                 250                 255

Val Pro Asn Lys Lys Phe Glu Asn Thr Ile Gln Gln Met Tyr Ile Arg
            260                 265                 270

Arg Glu Ala Val Met Lys Ser Leu Ile Lys Glu His Lys Lys Arg Ile
        275                 280                 285

Ala Ser Gly Glu Lys Leu Asn Ser Tyr Ile Asp Tyr Leu Leu Ser Glu
    290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
                325                 330                 335

Tyr Glu Leu Ala Lys Asn Pro Lys Leu Gln Asp Arg Leu Tyr Arg Asp
            340                 345                 350

Ile Lys Ser Val Cys Gly Ser Glu Lys Ile Thr Glu Glu His Leu Ser
        355                 360                 365

Gln Leu Pro Tyr Ile Thr Ala Ile Phe His Glu Thr Leu Arg Arg His
    370                 375                 380

Ser Pro Val Pro Ile Ile Pro Leu Arg His Val His Glu Asp Thr Val
385                 390                 395                 400

Leu Gly Gly Tyr His Val Pro Ala Gly Thr Glu Leu Ala Val Asn Ile
                405                 410                 415

Tyr Gly Cys Asn Met Asp Lys Asn Val Trp Glu Asn Pro Glu Glu Trp
            420                 425                 430

Asn Pro Glu Arg Phe Met Lys Glu Asn Glu Thr Ile Asp Phe Gln Lys
        435                 440                 445

Thr Met Ala Phe Gly Gly Gly Lys Arg Val Cys Ala Gly Ser Leu Gln
    450                 455                 460

Ala Leu Leu Thr Ala Ser Ile Gly Ile Gly Arg Met Val Gln Glu Phe
```

```
465                 470                 475                 480

Glu Trp Lys Leu Lys Asp Met Thr Gln Glu Glu Val Asn Thr Ile Gly
                485                 490                 495

Leu Thr Thr Gln Met Leu Arg Pro Leu Arg Ala Ile Ile Lys Pro Arg
            500                 505                 510

Ile


<210> SEQ ID NO 109
<211> LENGTH: 513
<212> TYPE: PRT
<213> ORGANISM: Artificial Sequence
<220> FEATURE:
<223> OTHER INFORMATION: Synthetic - Engineered valencene oxidase
      variant

<400> SEQUENCE: 109

Met Asp Ala Val Thr Gly Leu Leu Thr Val Pro Ala Thr Ala Ile Thr
1               5                   10                  15

Ile Gly Gly Thr Ala Val Ala Leu Ala Val Ala Leu Ile Phe Trp Tyr
            20                  25                  30

Leu Lys Ser Tyr Thr Ser Ala Arg Arg Ser Gln Ser Asn His Leu Pro
        35                  40                  45

Arg Val Pro Glu Val Pro Gly Val Pro Leu Leu Gly Asn Leu Leu Gln
    50                  55                  60

Leu Lys Glu Lys Lys Pro Tyr Met Thr Phe Thr Arg Trp Ala Ala Thr
65                  70                  75                  80

Tyr Gly Pro Ile Tyr Ser Ile Lys Thr Gly Ala Thr Ser Met Val Val
                85                  90                  95

Val Ser Ser Asn Glu Ile Ala Lys Glu Ala Leu Val Thr Arg Phe Gln
            100                 105                 110

Ser Ile Ser Thr Arg Asn Leu Ser Lys Ala Leu Lys Val Leu Thr Ala
        115                 120                 125

Asp Lys Thr Met Val Ala Met Ser Asp Tyr Asp Asp Tyr His Lys Thr
    130                 135                 140

Val Lys Arg His Ile Leu Thr Ala Val Leu Gly Pro Asn Ala Gln Lys
145                 150                 155                 160

Lys His Arg Ile His Arg Asp Ile Met Met Asp Asn Ile Ser Thr Gln
                165                 170                 175

Leu His Glu Phe Val Lys Asn Asn Pro Glu Gln Glu Glu Val Asp Leu
            180                 185                 190

Arg Lys Ile Phe Gln Ser Glu Leu Phe Gly Leu Ala Met Arg Gln Ala
        195                 200                 205

Leu Gly Lys Asp Val Glu Ser Leu Tyr Val Glu Asp Leu Lys Ile Thr
    210                 215                 220

Met Asn Arg Asp Glu Ile Phe Gln Val Leu Val Val Asp Pro Met Met
225                 230                 235                 240

Gly Ala Ile Asp Val Asp Trp Arg Asp Phe Phe Pro Tyr Leu Lys Trp
                245                 250                 255

Val Pro Asn Lys Lys Phe Glu Asn Thr Ile Gln Gln Met Tyr Ile Arg
            260                 265                 270

Arg Glu Ala Val Met Lys Ser Leu Ile Lys Glu His Lys Lys Arg Ile
        275                 280                 285

Ala Ser Gly Glu Lys Leu Asn Ser Tyr Ile Asp Tyr Leu Leu Ser Glu
    290                 295                 300

Ala Gln Thr Leu Thr Asp Gln Gln Leu Leu Met Ser Leu Trp Glu Pro
```

305 310 315 320

Ile Ile Glu Ser Ser Asp Thr Thr Met Val Thr Thr Glu Trp Ala Met
325 330 335

Tyr Glu Leu Ala Lys Asn Pro Lys Leu Gln Asp Arg Leu Tyr Arg Asp
340 345 350

Ile Lys Ser Val Cys Gly Ser Glu Lys Ile Thr Glu Glu His Leu Ser
355 360 365

Gln Leu Pro Tyr Ile Thr Ala Ile Phe His Glu Thr Leu Arg Arg His
370 375 380

Ser Pro Val Pro Ile Ile Pro Leu Arg His Val His Glu Asp Thr Val
385 390 395 400

Leu Gly Gly Tyr His Val Pro Ala Gly Thr Glu Leu Ala Val Asn Ile
405 410 415

Tyr Gly Cys Asn Met Asp Lys Asn Val Trp Glu Asn Pro Glu Glu Trp
420 425 430

Asn Pro Glu Arg Phe Met Lys Glu Asn Glu Thr Ile Asp Phe Gln Lys
435 440 445

Thr Met Ala Phe Gly Gly Gly Lys Arg Val Cys Ala Gly Ser Leu Gln
450 455 460

Ala Leu Leu Thr Ala Ser Ile Gly Ile Gly Arg Met Val Gln Glu Phe
465 470 475 480

Glu Trp Lys Leu Lys Asp Met Thr Gln Glu Glu Val Asn Thr Ile Gly
485 490 495

Leu Thr Asn Gln Met Leu Arg Pro Leu Arg Ala Ile Ile Lys Pro Arg
500 505 510

Ile

<210> SEQ ID NO 110
<211> LENGTH: 513
<212> TYPE: PRT
<213> ORGANISM: Artificial Sequence
<220> FEATURE:
<223> OTHER INFORMATION: Synthetic - Engineered valencene oxidase variant

<400> SEQUENCE: 110

Met Asp Ala Val Thr Gly Leu Leu Thr Val Pro Ala Thr Ala Ile Thr
1 5 10 15

Ile Gly Gly Thr Ala Val Ala Leu Ala Val Ala Leu Ile Phe Trp Tyr
20 25 30

Leu Lys Ser Tyr Thr Ser Ala Arg Arg Ser Gln Ser Asn Arg Leu Pro
35 40 45

Arg Val Pro Glu Val Pro Gly Val Pro Leu Leu Gly Asn Leu Leu Gln
50 55 60

Leu Lys Glu Lys Lys Pro Tyr Met Thr Phe Thr Arg Trp Ala Ala Thr
65 70 75 80

Tyr Gly Pro Ile Tyr Ser Ile Lys Thr Gly Ala Thr Ser Met Val Val
85 90 95

Val Ser Ser Asn Glu Ile Ala Lys Glu Ala Leu Val Thr Arg Phe Gln
100 105 110

Ser Ile Ser Thr Arg Asn Leu Ser Lys Ala Leu Lys Val Leu Thr Ala
115 120 125

Asp Lys Thr Met Val Ala Met Ser Asp Tyr Asp Asp Tyr His Lys Thr
130 135 140

Val Lys Arg His Ile Leu Thr Ala Val Leu Gly Pro Asn Ala Gln Lys

-continued

```
145                 150                 155                 160

Lys His Arg Ile His Arg Asp Ile Met Met Asp Asn Ile Ser Thr Gln
                165                 170                 175

Leu His Glu Phe Val Lys Asn Asn Pro Glu Gln Glu Glu Val Asp Leu
            180                 185                 190

Arg Lys Ile Phe Gln Ser Glu Leu Phe Gly Leu Ala Met Arg Gln Ala
        195                 200                 205

Leu Gly Lys Asp Val Glu Ser Leu Tyr Val Glu Asp Leu Lys Ile Thr
    210                 215                 220

Met Asn Arg Asp Glu Ile Leu Gln Val Leu Val Val Asp Pro Met Met
225                 230                 235                 240

Gly Ala Ile Asp Val Asp Trp Arg Asp Phe Phe Pro Tyr Leu Lys Trp
                245                 250                 255

Val Pro Asn Lys Lys Phe Glu Asn Thr Ile Gln Gln Met Tyr Ile Arg
            260                 265                 270

Arg Glu Ala Val Met Lys Ser Leu Ile Lys Glu Gln Lys Lys Arg Ile
        275                 280                 285

Ala Ser Gly Glu Lys Leu Asn Ser Tyr Ile Asp Tyr Leu Leu Ser Glu
    290                 295                 300

Ala Gln Thr Leu Thr Asp Gln Gln Leu Leu Met Ser Leu Trp Glu Pro
305                 310                 315                 320

Ile Ile Glu Ser Ser Asp Thr Thr Met Val Thr Thr Glu Trp Ala Met
                325                 330                 335

Tyr Glu Leu Ala Lys Asn Pro Lys Leu Gln Asp Arg Leu Tyr Arg Asp
            340                 345                 350

Ile Lys Ser Val Cys Gly Ser Glu Lys Ile Thr Glu Glu His Leu Ser
        355                 360                 365

Gln Leu Pro Tyr Ile Thr Ala Ile Phe His Glu Thr Leu Arg Lys His
    370                 375                 380

Ser Pro Val Pro Ile Ile Pro Leu Arg His Val His Glu Asp Thr Gln
385                 390                 395                 400

Leu Gly Gly Tyr His Val Pro Ala Gly Thr Glu Leu Ala Val Asn Ile
                405                 410                 415

Tyr Gly Cys Asn Met Asp Lys Asn Val Trp Glu Asn Pro Glu Glu Trp
            420                 425                 430

Asn Pro Glu Arg Phe Met Lys Glu Asn Glu Thr Ala Asp Phe Gln Lys
        435                 440                 445

Thr Met Ala Phe Gly Gly Gly Lys Arg Val Cys Ala Gly Ser Leu Gln
    450                 455                 460

Ala Leu Leu Thr Ala Ser Ile Gly Ile Gly Arg Met Val Gln Glu Phe
465                 470                 475                 480

Glu Trp Lys Leu Lys Asp Met Asp Gln Glu Glu Val Asn Thr Ile Gly
                485                 490                 495

Leu Thr Asn Gln Met Leu Arg Pro Leu Arg Ala Ile Ile Lys Pro Arg
            500                 505                 510

Ile


<210> SEQ ID NO 111
<211> LENGTH: 513
<212> TYPE: PRT
<213> ORGANISM: Artificial Sequence
<220> FEATURE:
<223> OTHER INFORMATION: Synthetic - Engineered valencene oxidase
      variant
```

<400> SEQUENCE: 111

Met Asp Ala Val Thr Gly Leu Leu Thr Val Pro Ala Thr Ala Ile Thr
1 5 10 15

Ile Gly Gly Thr Ala Val Ala Leu Ala Val Ala Leu Ile Phe Trp Tyr
20 25 30

Leu Lys Ser Tyr Thr Ser Ala Arg Arg Ser Gln Ser Asn His Leu Pro
35 40 45

Arg Val Pro Glu Val Pro Gly Val Pro Leu Leu Gly Asn Leu Leu Gln
50 55 60

Leu Lys Glu Lys Lys Pro Tyr Met Thr Phe Thr Lys Trp Ala Ala Thr
65 70 75 80

Tyr Gly Pro Ile Tyr Ser Ile Lys Thr Gly Ala Thr Ser Val Val Val
85 90 95

Val Ser Ser Asn Glu Ile Ala Lys Glu Ala Leu Val Thr Arg Phe Gln
100 105 110

Ser Ile Ser Thr Arg Asn Leu Ser Lys Ala Leu Lys Val Leu Thr Ala
115 120 125

Asp Lys Gln Met Val Ala Met Ser Asp Tyr Asp Asp Tyr His Lys Thr
130 135 140

Val Lys Arg His Ile Leu Thr Ala Val Leu Gly Pro Asn Ala Gln Lys
145 150 155 160

Lys His Arg Ile His Arg Asp Ile Met Met Asp Asn Ile Ser Thr Gln
165 170 175

Leu His Glu Phe Val Lys Asn Asn Pro Glu Gln Glu Glu Val Asp Leu
180 185 190

Arg Lys Ile Phe Gln Ser Glu Leu Phe Gly Leu Ala Met Arg Gln Ala
195 200 205

Leu Gly Lys Asp Val Glu Ser Leu Tyr Val Glu Asp Leu Lys Ile Thr
210 215 220

Met Asn Arg Asp Glu Ile Leu Gln Val Leu Val Val Asp Pro Met Met
225 230 235 240

Gly Ala Ile Asp Val Asp Trp Arg Asp Phe Phe Pro Tyr Leu Lys Trp
245 250 255

Val Pro Asn Lys Lys Phe Glu Asn Thr Ile Gln Gln Met Tyr Ile Arg
260 265 270

Arg Glu Ala Val Met Lys Ser Leu Ile Lys Glu Gln Lys Lys Arg Ile
275 280 285

Ala Ser Gly Glu Lys Leu Asn Ser Tyr Ile Asp Tyr Leu Leu Ser Glu
290 295 300

Ala Gln Thr Leu Thr Asp Gln Gln Leu Leu Met Ser Leu Trp Glu Pro
305 310 315 320

Ile Ile Glu Ser Ser Asp Thr Thr Met Val Thr Thr Glu Trp Ala Met
325 330 335

Tyr Glu Leu Ala Lys Asn Pro Lys Leu Gln Asp Arg Leu Tyr Arg Asp
340 345 350

Ile Lys Ser Val Cys Gly Ser Glu Lys Ile Thr Glu Glu His Leu Ser
355 360 365

Gln Leu Pro Tyr Ile Thr Ala Ile Phe His Glu Thr Leu Arg Lys His
370 375 380

Ser Pro Val Pro Ile Leu Pro Leu Arg His Val His Glu Asp Thr Val
385 390 395 400

Leu Gly Gly Tyr His Val Pro Ala Gly Thr Glu Leu Ala Val Asn Ile
405 410 415

-continued

Tyr Gly Cys Asn Met Asp Lys Asn Val Trp Glu Asn Pro Glu Glu Trp
420 425 430

Asn Pro Glu Arg Phe Met Lys Glu Asn Glu Thr Ile Asp Phe Gln Lys
435 440 445

Thr Met Ala Phe Gly Gly Gly Lys Arg Val Cys Ala Gly Ser Leu Gln
450 455 460

Ala Leu Leu Ile Ala Ser Ile Gly Ile Gly Arg Met Val Gln Glu Phe
465 470 475 480

Glu Trp Lys Leu Lys Asp Met Thr Gln Glu Glu Val Asn Thr Ile Gly
485 490 495

Leu Thr Asn Gln Met Leu Arg Pro Leu Arg Ala Ile Ile Lys Pro Arg
500 505 510

Ile

<210> SEQ ID NO 112
<211> LENGTH: 8
<212> TYPE: PRT
<213> ORGANISM: Artificial Sequence
<220> FEATURE:
<223> OTHER INFORMATION: Synthetic - Leader sequence

<400> SEQUENCE: 112

Met Ala Leu Leu Leu Ala Val Phe
1 5

<210> SEQ ID NO 113
<211> LENGTH: 7
<212> TYPE: PRT
<213> ORGANISM: Artificial Sequence
<220> FEATURE:
<223> OTHER INFORMATION: Synthetic - Linker sequence

<400> SEQUENCE: 113

Gly Ser Gly Gly Gly Gly Ser
1 5

<210> SEQ ID NO 114
<211> LENGTH: 8
<212> TYPE: PRT
<213> ORGANISM: Artificial Sequence
<220> FEATURE:
<223> OTHER INFORMATION: Synthetic - Linker sequence

<400> SEQUENCE: 114

Gly Ser Gly Glu Ala Ala Ala Lys
1 5

<210> SEQ ID NO 115
<211> LENGTH: 13
<212> TYPE: PRT
<213> ORGANISM: Artificial Sequence
<220> FEATURE:
<223> OTHER INFORMATION: Synthetic - Linker sequence

<400> SEQUENCE: 115

Gly Ser Gly Glu Ala Ala Ala Lys Glu Ala Ala Ala Lys
1 5 10

<210> SEQ ID NO 116
<211> LENGTH: 9
<212> TYPE: PRT
<213> ORGANISM: Artificial Sequence
<220> FEATURE:

<223> OTHER INFORMATION: Synthetic - Linker sequence

<400> SEQUENCE: 116

Gly Ser Gly Met Gly Ser Ser Ser Asn
1               5

<210> SEQ ID NO 117
<211> LENGTH: 5
<212> TYPE: PRT
<213> ORGANISM: Artificial Sequence
<220> FEATURE:
<223> OTHER INFORMATION: Synthetic - Linker sequence

<400> SEQUENCE: 117

Gly Ser Thr Gly Ser
1               5

<210> SEQ ID NO 118
<211> LENGTH: 20
<212> TYPE: PRT
<213> ORGANISM: Artificial Sequence
<220> FEATURE:
<223> OTHER INFORMATION: Synthetic - N-terminal fragment of yhcB

<400> SEQUENCE: 118

Met Ala Trp Glu Tyr Ala Leu Ile Gly Leu Val Val Gly Ile Ile Ile
1               5                   10                  15

Gly Ala Val Ala
            20

<210> SEQ ID NO 119
<211> LENGTH: 1647
<212> TYPE: DNA
<213> ORGANISM: Citrus sinensis

<400> SEQUENCE: 119
atggcctccg gcgaaacctt ccgtccgacc gcagacttcc atccgtcact gtggcgtaat 60
cacttcctga aaggcgcaag cgacttcaaa acggtggatc atacggcaac ccaggaacgt 120
cacgaagctc tgaaggaaga agtccgtcgc atgattaccg atgccgaaga caaaccggtg 180
cagaagctgc gtctgatcga tgaagttcaa cgcctgggcg tcgcgtatca ttttgaaaaa 240
gaaattggtg acgccatcca gaagctgtgc ccgatttaca tcgatagcaa ccgcgcagac 300
ctgcataccg tgtctctgca ctttcgtctg ctgcgccagc aaggcatcaa gatcagctgt 360
gatgttttcg aaaagttcaa ggatgacgaa ggccgtttca aaagctctct gattaatgat 420
gttcagggta tgctgtctct gtatgaagcg gcctacatgg cggtccgcgg tgaacatatt 480
ctggatgaag cgatcgcctt taccacgacc catctgaaaa gcctggtggc ccaggaccac 540
gttacgccga agctggcgga acaaattaac cacgccctgt atcgtccgct gcgcaaaacc 600
ctgccgcgtc tggaagcacg ctacttcatg agcatgatta atagtacgtc cgatcatctg 660
tgcaacaaaa ccctgctgaa ttttgctaag ctggacttca acatcctgct ggaactgcac 720
aaagaagaac tgaatgaact gaccaaatgg tggaaggatc tggactttac gaccaaactg 780
ccgtatgcac gtgatcgcct ggttgaactg tacttctggg acctgggcac gtattttgaa 840
ccgcagtacg ctttcggtcg taaaattatg acccaactga actatatcct gtcaattatc 900
gatgacacgt atgatgcgta cggcaccctg gaagaactgt cgctgtttac ggaagcggtg 960
cagcgttgga atattgaagc cgttgatatg ctgccggaat atatgaaact gatttaccgc 1020
accctgctgg atgcattcaa cgaaatcgaa gaagacatgg ctaaacaagg tcgtagtcat 1080
tgcgtgcgct atgcgaaaga agaaaatcag aaggttattg gcgcgtactc agtccaagcc 1140
aaatggtttt cggaaggtta tgttccgacg attgaagaat acatgccgat cgcactgacc 1200
tcatgtgctt atacgtttgt gatcaccaac tcgttcctgg gcatgggtga ttttgccacc 1260
aaagaagttt tcgaatggat tagcaacaat ccgaaagtgg ttaaggcagc ttctgtcatc 1320
tgccgtctga tggatgacat gcagggccat gaatttgaac aaaaacgcgg tcacgttgca 1380
agtgctattg aatgttatac caagcagcac ggcgtctcca aagaagaagc aattaagatg 1440
ttcgaagaag aagtggcgaa cgcctggaaa gatatcaatg aagaactgat gatgaagccg 1500
acggtcgtgg cacgtccgct gctgggcacc atcctgaatc tggcacgcgc tatcgatttc 1560
atctacaaag aagatgacgg ctacacccat agttacctga ttaaggatca gatcgcctcc 1620
gtcctgggtg accacgtgcc gttctaa 1647

<210> SEQ ID NO 120
<211> LENGTH: 1671
<212> TYPE: DNA
<213> ORGANISM: Artificial Sequence
<220> FEATURE:
<223> OTHER INFORMATION: Synthetic - Engineered valencene synthase

<400> SEQUENCE: 120
atggcaaccc aggtgagcgc cagtagcctg gcacaaatcc cgcagcctaa aaaccgccct 60
gttgccaatt tccatccgaa catctggggc gaccacttta tcacctacac cccggaagac 120
aaagtgaccc gcgccaaaaa agaagagagg attgaagatc tgaaggaaga agtgaaacgc 180
aaactgaccg cagccgccgt ggccaatccg agtcaactgc tgaacttcat tgatgcagtt 240
cagcgcctgg gcgttgccta tcactttgag caggagatcg aggaggcatt acagcatatt 300
tgtaatagct ttcacgactg caatgatatg gatggcgacc tgtataatat cgccctgcta 360
tttcgtctgc tgcgccaaca gggttacaca atcagttgcg acatctttaa caagttcacc 420
gatgaagagg gccgctttaa agaagccctg attagcgacg tgcgcggtat gttaggcctg 480
tatgaagcag cccacctgcg cgttcacggc gaagacatcc tggcagaggc actggccttt 540
acaaccaccc acctgaaagc aatggttgaa tcgctgggct accatctggc cgagcaagtg 600
aggcacgcct taaaccgtcc gatccgtaaa ggcatggaac gtctggaagc acgttggtac 660
atcagcatat accaggatga ggcctttcat gacaaaaccc tgctggagct ggccaaactg 720
gacttcaacc tggtgcagag cctgcacaaa gaagagctga gcaatctggc acgctggtgg 780
aaggagctgg attttgccac caaactgcct tttgcccgcg accgtttagt tgaaggctac 840
ttttggatga tgggtgtgta ttttgagccg cagtatctgc gtggccgtcg catcctgaca 900
aaggtgatcg ccctgaccag catcattgac gacatccacg atgcctatgg caccccggag 960
gaactgaaac tgtttatcga ggccatcgaa aaatgggacg agagcagcat caaccaactg 1020
cctgagtaca tgaagctgtg ctatgtggcc ctgctggacg tgtataatga aatcgaagag 1080
gagatggaaa aggagggcaa ccaataccgt atccactacc tgaaggaggt tatgaaaaac 1140
caggtgcgtg cctactttgc agaggcaaaa tggctgcacg atgagcatgt gccggccttt 1200
gaagaataca tgcgcgttgc cctggccagc agtggttatt gtctgctggc cgttacaagt 1260
tttgtgggca tgggcgagat cgtgacaaag gaagcctttg actgggttac aagcgacccg 1320
cgcatcataa gcagcagcaa cacaattaca cgcctgatgg acgacattaa aagccataaa 1380
tttgaacaga aacgcggtca tgtgaccagc gccgtggaat gctacatgaa acagtacgcc 1440

```
gtgaccgaag agcaggttta cgaggaattt aaaaaacaga ttgaaaacgc atggctggac   1500
attaatcagg agtgtctgaa gccgaccgca gtgccgatgc cgctgttagc acgcctgctg   1560
aatttcaccc gcacaatgga tgtgatttat aaagaagaag acagctatac ccatgtgggc   1620
aagaccatgc gcgacaacat cgccagcgtg tttatcaacc ctgtgatcta a            1671
```

<210> SEQ ID NO 121
<211> LENGTH: 1515
<212> TYPE: DNA
<213> ORGANISM: Artificial Sequence
<220> FEATURE:
<223> OTHER INFORMATION: Synthetic - Engineered valencene oxidase

<400> SEQUENCE: 121

```
atggcttggg aatatgcgct aattgggtta gtcgtcggca tcattattgg tgctgtggcc     60
ttctggtatc tgaaatctta cactagcgcg cgccgctctc agtccaacca cctgccgcgt    120
gtgccggaag ttccgggtgt gccactgctg ggcaacctgc tgcaactgaa agaaaagaaa    180
ccgtacatga cctttacccg ctgggcagcg acttatggtc ctatctacag cattaaaacc    240
ggcgctacgt ctatggttgt ggtttcttcc aacgaaatcg cgaaagaagc cctggtgact    300
cgtttccagt ccattagcac ccgcaacctg tccaaagcgc tgaaggttct gacggctgac    360
aagactatgg tggctatgag cgactatgat gactaccaca aaaccgttaa acgtcacatc    420
ctgaccgcag tactgggtcc gaacgcacag aaaaaacatc gcatccaccg cgacattatg    480
atggataaca tctccacgca gctgcatgag ttcgttaaga acaatccaga acaggaagag    540
gtagatctgc gtaaaatttt tcagtccgaa ctgttcggtc tggctatgcg tcaggcgctg    600
ggcaaagacg ttgaaagcct gtatgtcgaa gacctgaaaa ttaccatgaa ccgtgatgag    660
atcttccagg ttctggttgt agatccgatg atgggcgcca tcgacgtgga ttggcgtgac    720
ttctttccgt acctgaaatg ggtcccgaac aagaagttcg aaaacaccat ccagcaaatg    780
tacatccgtc gtgaagcggt gatgaaaagc ctgatcaaag aacacaaaaa gcgtattgct    840
tctggtgaga aactgaactc ctacatcgat tatctgctgt ccgaagcgca gaccctgacc    900
gaccaacagc tgctgatgtc tctgtgggaa ccgattatcg aaagcagcga caccactatg    960
gtcactaccg aatgggcaat gtatgagctg gccaaaaacc cgaaactgca ggatcgtctg   1020
taccgtgaca tcaaaagcgt ttgcggctcc gagaaaatca ctgaagaaca cctgtctcag   1080
ctgccgtaca tcactgctat tttccacgaa accctgcgtc gccattctcc ggttccgatc   1140
attccgctgc gtcacgttca cgaagatact gtgctgggtg gttaccatgt accggcaggc   1200
actgaactgg ctgtcaacat ctacggctgt aacatggata aaaacgtttg ggagaatcct   1260
gaagaatgga acccggaacg cttcatgaaa gagaacgaaa ccatcgactt ccagaaaacg   1320
atggctttcg gcggtggtaa acgtgtgtgc gcaggttctc tgcaggcgct gctgacggcg   1380
tccattggta tcggtcgcat ggtacaggaa tttgaatgga agctgaaaga catgacccaa   1440
gaagaggtga ataccattgg tctgactacc cagatgctgc gtccactgcg tgcaatcatc   1500
aaacctcgta tttaa                                                    1515
```

<210> SEQ ID NO 122
<211> LENGTH: 1518
<212> TYPE: DNA
<213> ORGANISM: Artificial Sequence
<220> FEATURE:
<223> OTHER INFORMATION: Synthetic - Engineered valencene oxidase

<400> SEQUENCE: 122

```
atggcttggg aatatgcgct aattgggtta gtcgtcggca tcattattgg tgctgtggcc     60

atgcgttggt atctgaaatc ttacactagc gcgcgccgct ctcagtccaa ccacctgccg    120

cgtgtgccgg aagttccggg tgtgccactg ctgggcaacc tgctgcaact gaaagaaaag    180

aaaccgtaca tgacctttac ccgctgggca gcgacttatg gtcctatcta cagcattaaa    240

accggcgcta cgtctgtggt tgtggtttct tccaacgaaa tcgcgaaaga agccctggtg    300

actcgtttcc agtccattag cacccgcaac ctgtccaaag cgctgaaggt tctgacggct    360

gacaagacta tggtggctat gagcgactat gatgactacc acaaaaccgt taaacgtcac    420

atcctgaccg cattactggg tccgaacgca cagaaaaaac atcgcatcca ccgcgacatt    480

atgatggata acatctccac gcagctgcat gagttcgtta agaacaatcc agaacaggaa    540

gaggtagatc tgcgtaaaat ttttcagtcc gaactgttcg gtctggctat gcgtcaggcg    600

ctgggcaaag acgttgaaag cctgtatgtc gaagacctga aaattaccat gaaccgtgat    660

gagatcctac aggttctggt tgtagatccg atgatgggcg ccatcgacgt ggattggcgt    720

gacttctttc cgtacctgaa atgggtcccg aacaagaagt tcgaaaacac catccagcaa    780

atgtacatcc gtcgtgaagc ggtgatgaaa agcctgatca aagaacaaaa aaagcgtatt    840

gcttctggtg agaaactgaa ctcctacatc gattatctgc tgtccgaagc gcagaccctg    900

accgaccaac agctgctgat gtctctgtgg gaaccgatta tcgaaagcag cgacaccact    960

atggtcacta ccgaatgggc aatgtatgag ctggccaaaa acccgaaact gcaggatcgt   1020

ctgtaccgtg acatcaaaag cgtttgcggc tccgagaaaa tcactgaaga acacctgtct   1080

cagctgccgt acatcactgc tattttccac gaaaccctgc gtaagcattc tccggttccg   1140

atcctgccgc tgcgtcacgt tcacgaagat actgtgctgg gtggttacca tgtaccggca   1200

ggcactgaac tggctgtcaa catctacggc tgtaacatgg ataaaaacgt ttgggagaat   1260

cctgaagaat ggaacccgga acgcttcatg aaagagaacg aaaccatcga cttccagaaa   1320

acgatggctt tcggcggtgg taaacgtgtg tgcgcaggtt ctctgcaggc gctgctgatt   1380

gcgtccattg gtatcggtcg catggtacag gaatttgaat ggaagctgaa agacatgacc   1440

caagaagagg tgaataccat tggtctgact aatcagatgc tgcgtccact gcgtgcaatc   1500

atcaaacctc gtatttaa                                                 1518


<210> SEQ ID NO 123
<211> LENGTH: 1518
<212> TYPE: DNA
<213> ORGANISM: Artificial Sequence
<220> FEATURE:
<223> OTHER INFORMATION: Synthetic - Engineered valencene oxidase

<400> SEQUENCE: 123

atggcttggg aatatgcgct aattgggtta gtcgtcggca tcattattgg tgctgtggcc     60

atgcgttggt atctgaaatc ttacactagc gcgcgccgct ctcagtccaa ccacctgccg    120

cgtgtgccgg aagttccggg tgtgccactg ctgggcaacc tgctgcaact gaaagaaaag    180

aaaccgtaca tgacctttac caaatgggca gcgacttatg gtcctatcta cagcattaaa    240

accggcgcta cgtctatggt tgtggtttct tccaacgaaa tcgcgaaaga agccctggtg    300

actcgtttcc agtccattag cacccgcaac ctgtccaaag cgctgaaggt tctgacggct    360

gacaagcaga tggtggctat gagcgactat gatgactacc acaaaaccgt taaacgtcac    420

atcctgaccg cagtactggg tccgaacgca cagaaaaaac atcgcatcca ccgcgacatt    480
```

-continued

```
atgatggata acatctccac gcagctgcat gagttcgtta agaacaatcc agaacaggaa    540

gaggtagatc tgcgtaaaat ttttcagtcc gaactgttcg gtctggctat gcgtcaggcg    600

ctgggcaaag acgttgaaag cctgtatgtc gaagacctga aaattaccat gaaccgtgat    660

gagatcctac aggttctggt tgtagatccg atgatgggcg ccatcgacgt ggattggcgt    720

gacttctttc cgtacctgaa atgggtcccg aacaagaagt tcgaaaacac catccagcaa    780

atgtacatcc gtcgtgaagc ggtgatgaaa agcctgatca aagaacaaaa aaagcgtatt    840

gcttctggtg agaaactgaa ctcctacatc gattatctgc tgtccgaagc gcagaccctg    900

accgaccaac agctgctgat gtctctgtgg gaaccgatta tcgaaagcag cgacaccact    960

atggtcacta ccgaatgggc aatgtatgag ctggccaaaa acccgaaact gcaggatcgt   1020

ctgtaccgtg acatcaaaag cgtttgcggc tccgagaaaa tcactgaaga acacctgtct   1080

cagctgccgt acatcactgc tattttccac gaaaccctgc gtaagcattc tccggttccg   1140

atcctgccgc tgcgtcacgt tcacgaagat actgtgctgg gtggttacca tgtaccggca   1200

ggcactgaac tggctgtcaa catctacggc tgtaacatgg ataaaaacgt ttgggagaat   1260

cctgaagaat ggaacccgga acgcttcatg aaagagaacg aaaccatcga cttccagaaa   1320

acgatggctt tcggcggtgg taaacgtgtg tgcgcaggtt ctctgcaggc gctgctgatt   1380

gcgtccattg gtatcggtcg catggtacag gaatttgaat ggaagctgaa agacatgacc   1440

caagaagagg tgaataccat tggtctgact aatcagatgc tgcgtccact gcgtgcaatc   1500

atcaaacctc gtatttaa                                                 1518
```

<210> SEQ ID NO 124
<211> LENGTH: 1518
<212> TYPE: DNA
<213> ORGANISM: Artificial Sequence
<220> FEATURE:
<223> OTHER INFORMATION: Synthetic - Engineered valencene oxidase

<400> SEQUENCE: 124

```
atggcttggg aatatgcgct aattgggtta gtcgtcggca tcattattgg tgctgtggcc     60

atgcgttggt atctgaaatc ttacactagc gcgcgccgct ctcagtccaa ccatctgccg    120

cgtgtgccgg aagttccggg tgtgccactg ctgggcaacc tgctgcaact gaaagaaaag    180

aaaccgtaca tgacctttac ccgctgggca gcgacttatg gtcctatcta cagcattaaa    240

accggcgcta cgtctgtggt tgtggtttct tccaacgaaa tcgcgaaaga agccctggtg    300

actcgtttcc agtccattag cacccgcaac ctgtccaaag cgctgaaggt tctgacggct    360

gacaagcaga tggtggctat gagcgactat gatgactacc acaaaaccgt taaacgtcac    420

atcctgaccg cagtactggg tccgaacgca cagaaaaaac atcgcatcca ccgcgacatt    480

atgatggata acatctccac gcagctgcat gagttcgtta agaacaatcc agaacaggaa    540

gaggtagatc tgcgtaaaat ttttcagtcc gaactgttcg gtctggctat gcgtcaggcg    600

ctgggcaaag acgttgaaag cctgtatgtc gaagacctga aaattaccat gaaccgtgat    660

gagatcctac aggttctggt tgtagatccg atgatgggcg ccatcgacgt ggattggcgt    720

gacttctttc cgtacctgaa atgggtcccg aacaagaagt tcgaaaacac catccagcaa    780

atgtacatcc gtcgtgaagc ggtgatgaaa agcctgatca aagaacaaaa aaagcgtatt    840

gcttctggtg agaaactgaa ctcctacatc gattatctgc tgtccgaagc gcagaccctg    900

accgaccaac agctgctgat gtctctgtgg gaaccgatta tcgaaagcag cgacaccact    960

atggtcacta ccgaatgggc aatgtatgag ctggccaaaa acccgaaact gcaggatcgt   1020
```

ctgtaccgtg acatcaaaag cgtttgcggc tccgagaaaa tcactgaaga acacctgtct 1080
cagctgccgt acatcactgc tattttccac gaaaccctgc gtaagcattc tccggttccg 1140
atcctgccgc tgcgtcacgt tcacgaagat actgtgctgg gtggttacca tgtaccggca 1200
ggcactgaac tggctgtcaa catctacggc tgtaacatgg ataaaaacgt ttgggagaat 1260
cctgaagaat ggaacccgga acgcttcatg aaagagaacg aaaccatcga cttccagaaa 1320
acgatggctt tcggcggtgg taaacgtgtg tgcgcaggtt ctctgcaggc gctgctgatt 1380
gcgtccattg gtatcggtcg catggtacag gaatttgaat ggaagctgaa agacatgacc 1440
caagaagagg tgaataccat tggtctgact aatcagatgc tgcgtccact gcgtgcaatc 1500
atcaaacctc gtatttaa 1518

<210> SEQ ID NO 125
<211> LENGTH: 1515
<212> TYPE: DNA
<213> ORGANISM: Artificial Sequence
<220> FEATURE:
<223> OTHER INFORMATION: Synthetic - Engineered valencene oxidase

<400> SEQUENCE: 125
atggcttggg aatatgcgct aattgggtta gtcgtcggca tcattattgg tgctgtggcc 60
gcttggtatc tgaaatctta cactagcgcg cgccgctctc agtccaacca tctgccgcgt 120
gtgccggaag ttccgggtgt gccactgctg ggcaacctgc tgcaactgaa agaaaagaaa 180
ccgtacatga cctttaccaa atgggcagcg acttatggtc ctatctacag cattaaaacc 240
ggcgctacgt ctatggttgt ggtttcttcc aacgaaatcg cgaaagaagc cctggtgact 300
cgtttccagt ccattagcac ccgcaacctg tccaaagcgc tgaaggttct gacggctgac 360
aagcagatgg tggctatgag cgactatgat gactaccaca aaccgttaa acgtcacatc 420 ctgaccgcag tactgggtcc gaacgcacag aaaaaacatc gcatccaccg cgacattatg 480
atggataaca tctccacgca gctgcatgag ttcgttaaga acaatccaga acaggaagag 540
gtagatctgc gtaaaatttt tcagtccgaa ctgttcggtc tggctatgcg tcaggcgctg 600
ggcaaagacg ttgaaagcct gtatgtcgaa gacctgaaaa ttaccatgaa ccgtgatgag 660
atcctacagg ttctggttgt agatccgatg atgggcgcca tcgacgtgga ttggcgtgac 720
ttctttccgt acctgaaatg ggtcccgaac aagaagttcg aaaacaccat ccagcaaatg 780
tacatccgtc gtgaagcggt gatgaaaagc ctgatcaaag aacaaaaaaa gcgtattgct 840
tctggtgaga aactgaactc ctacatcgat tatctgctgt ccgaagcgca gaccctgacc 900
gaccaacagc tgctgatgtc tctgtgggaa ccgattatcg aaagcagcga caccactatg 960
gtcactaccg aatgggcaat gtatgagctg gccaaaaacc cgaaactgca ggatcgtctg 1020
taccgtgaca tcaaaagcgt ttgcggctcc gagaaaatca ctgaagaaca cctgtctcag 1080
ctgccgtaca tcactgctat tttccacgaa accctgcgta agcattctcc ggttccgatc 1140
ctgccgctgc gtcacgttca cgaagatact gtgctgggtg gttaccatgt accggcaggc 1200
actgaactgg ctgtcaacat ctacggctgt aacatggata aaaacgtttg ggagaatcct 1260
gaagaatgga acccggaacg cttcatgaaa gagaacgaaa ccatcgactt ccagaaaacg 1320
atggctttcg gcggtggtaa acgtgtgtgc gcaggttctc tgcaggcgct gctgattgcg 1380
tccattggta tcggtcgcat ggtacaggaa tttgaatgga agctgaaaga catgacccaa 1440
gaagaggtga ataccattgg tctgactaat cagatgctgc gtccactgcg tgcaatcatc 1500
aaacctcgta tttaa 1515

<210> SEQ ID NO 126
<211> LENGTH: 1518
<212> TYPE: DNA
<213> ORGANISM: Artificial Sequence
<220> FEATURE:
<223> OTHER INFORMATION: Synthetic - Engineered valencene oxidase

<400> SEQUENCE: 126
atggcttggg aatatgcgct aattgggtta gtcgtcggca tcattattgg tgctgtggcc 60
atgcgttggt atctgaaatc ttacactagc gcgcgccgct ctcagtccaa ccacctgccg 120
cgtgtgccgg aagttccggg tgtgccactg ctgggcaacc tgctgcaact gaaagaaaag 180
aaaccgtaca tgacctttac caaatgggca gcgacttatg gtcctatcta cagcattaaa 240
accggcgcta cgtctgtggt tgtggtttct tccaacgaaa tcgcgaaaga agccctggtg 300
actcgtttcc agtccattag cacccgcaac ctgtccaaag cgctgaaggt tctgacggct 360
gacaagcaga tggtggctat gagcgactat gatgactacc acaaaaccgt taaacgtcac 420
atcctgaccg cagtactggg tccgaacgca cagaaaaaac atcgcatcca ccgcgacatt 480
atgatggata acatctccac gcagctgcat gagttcgtta agaacaatcc agaacaggaa 540
gaggtagatc tgcgtaaaat ttttcagtcc gaactgttcg gtctggctat gcgtcaggcg 600
ctgggcaaag acgttgaaag cctgtatgtc gaagacctga aattaccat gaaccgtgat 660 gagatcctac aggttctggt tgtagatccg atgatgggcg ccatcgacgt ggattggcgt 720
gacttctttc cgtacctgaa atgggtcccg aacaagaagt tcgaaaacac catccagcaa 780
atgtacatcc gtcgtgaagc ggtgatgaaa agcctgatca aagaacaaaa aaagcgtatt 840
gcttctggtg agaaactgaa ctcctacatc gattatctgc tgtccgaagc gcagaccctg 900
accgaccaac agctgctgat gtctctgtgg gaaccgatta tcgaaagcag cgacaccact 960
atggtcacta ccgaatgggc aatgtatgag ctggccaaaa acccgaaact gcaggatcgt 1020
ctgtaccgtg acatcaaaag cgtttgcggc tccgagaaaa tcactgaaga acacctgtct 1080
cagctgccgt acatcactgc tattttccac gaaaccctgc gtaagcattc tccggttccg 1140
atcctgccgc tgcgtcacgt tcacgaagat actgtgctgg gtggttacca tgtaccggca 1200
ggcactgaac tggctgtcaa catctacggc tgtaacatgg ataaaaacgt ttgggagaat 1260
cctgaagaat ggaacccgga acgcttcatg aaagagaacg aaaccatcga cttccagaaa 1320
acgatggctt tcggcggtgg taaacgtgtg tgcgcaggtt ctctgcaggc gctgctgatt 1380
gcgtccattg gtatcggtcg catggtacag gaatttgaat ggaagctgaa agacatgacc 1440
caagaagagg tgaataccat tggtctgact aatcagatgc tgcgtccact gcgtgcaatc 1500
atcaaacctc gtatttaa 1518

<210> SEQ ID NO 127
<211> LENGTH: 1518
<212> TYPE: DNA
<213> ORGANISM: Artificial Sequence
<220> FEATURE:
<223> OTHER INFORMATION: Synthetic - Engineered valencene oxidase

<400> SEQUENCE: 127
atggcttggg aatatgcgct aattgggtta gtcgtcggca tcattattgg tgctgtggcc 60
atgcgttggt atctgaaatc ttacactagc gcgcgccgct ctcagtccaa ccacctgccg 120
cgtgtgccgg aagttccggg tgtgccactg ctgggcaacc tgctgcaact gaaagaaaag 180
aaaccgtaca tgacctttac caaatgggca gcgacttatg gtcctatcta cagcattaaa 240
accggcgcta cgtctgtggt tgtggtttct tccaacgaaa tcgcgaaaga agccctggtg 300
actcgtttcc agtccattag cacccgcaac ctgtccaaag cgctgaaggt tctgacggct 360
gacaagacta tggtggctat gagcgactat gatgactacc acaaaaccgt taaacgtcac 420
atcctgaccg cagtactggg tccgaacgca cagaaaaaac atcgcatcca ccgcgacatt 480
atgatggata acatctccac gcagctgcat gagttcgtta agaacaatcc agaacaggaa 540
gaggtagatc tgcgtaaaat ttttcagtcc gaactgttcg gtctggctat gcgtcaggcg 600
ctgggcaaag acgttgaaag cctgtatgtc gaagacctga aaattaccat gaaccgtgat 660
gagatcctac aggttctggt tgtagatccg atgatgggcg ccatcgacgt ggattggcgt 720
gacttctttc cgtacctgaa atgggtcccg aacaagaagt tcgaaaacac catccagcaa 780
atgtacatcc gtcgtgaagc ggtgatgaaa agcctgatca aagaacaaaa aaagcgtatt 840
gcttctggtg agaaactgaa ctcctacatc gattatctgc tgtccgaagc gcagaccctg 900
accgaccaac agctgctgat gtctctgtgg gaaccgatta tcgaaagcag cgacaccact 960
atggtcacta ccgaatgggc aatgtatgag ctggccaaaa acccgaaact gcaggatcgt 1020
ctgtaccgtg acatcaaaag cgtttgcggc tccgagaaaa tcactgaaga acacctgtct 1080
cagctgccgt acatcactgc tattttccac gaaaccctgc gtaagcattc tccggttccg 1140
atcattccgc tgcgtcacgt tcacgaagat actgtgctgg gtggttacca tgtaccggca 1200
ggcactgaac tggctgtcaa catctacggc tgtaacatgg ataaaaacgt ttgggagaat 1260
cctgaagaat ggaacccgga acgcttcatg aaagagaacg aaaccatcga cttccagaaa 1320
acgatggctt tcggcggtgg taaacgtgtg tgcgcaggtt ctctgcaggc gctgctgatt 1380
gcgtccattg gtatcggtcg catggtacag gaatttgaat ggaagctgaa agacatgacc 1440
caagaagagg tgaataccat tggtctgact aatcagatgc tgcgtccact gcgtgcaatc 1500
atcaaacctc gtatttaa 1518

<210> SEQ ID NO 128
<211> LENGTH: 1671
<212> TYPE: DNA
<213> ORGANISM: Artificial Sequence
<220> FEATURE:
<223> OTHER INFORMATION: Synthetic - Engineered valencene synthase

<400> SEQUENCE: 128
atggcaaccc aggtgagcgc cagtagcctg gcacaaatcc cgcagcctaa aaaccgccct 60
gttgccaatt tccataaaaa catctggggc gaccacttta tcacctacac cccggaagac 120
aaagtgaccc gcgccaaaaa agaagagagg attgaagatc tgaaggaaga agtgaaacgc 180
aaactgaccg cagccgccgt ggccaatccg agtcaactgc tgaacttcat tgatgcagtt 240
cagcgcctgg gcgttgccta tcactttgag caggagatcg aggaggcatt acagcatatt 300
tgtaatagct ttcacgactg caatgatatg gatggcgacc tgtataatat cgccctgcta 360
tttcgtctgc tgcgccaaca gggttacaca atcagttgcg acatctttaa caagttcacc 420
gatgaagagg gccgctttaa agaagccctg attagcgacg tgcgcggtat gttaggcctg 480
tatgaagcag cctacctgcg cgttcacggc gaagacatcc tggcagaggc actggccttt 540
acaaccaccc acctgaaagc aatggttgaa tcgctgggct accatctggc cgagcaagtg 600
aggcacgcct taaaccgtcc gatccgtaaa ggcatggaac gtctggaagc acgttggtac 660

```
atcagcatat accaggatga ggcctttcat gacaaaaccc tgctggagct ggccaaactg    720

gacttcaacc tggtgcagag cctgcacaaa gaagagctga gcaatctggc acgctggtgg    780

aaggagctgg attttgccac caaactgcct tttgcccgcg accgtttagt tgaaggctac    840

ttttggatga tgggtgtgta ttttgagccg cagtatctgc gtggccgtcg catcctgaca    900

aaggtgatcg ccctgaccag catcattgac gacatccacg atgcctatgg caccccggag    960

gaactgaaac tgtttatcga ggccatcgaa aaatgggacg agagcagcat caaccaactg   1020

cctgagtaca tgaagctgtg ctataatgcc ctgctggacg tgtataatga aatcgaagag   1080

gagatggaaa aggagggcaa ccaataccgt atccactacc tgaaggaggt tatgaaaaac   1140

caggtgcgtg cctactttgc agaggcaaaa tggctgcacg atgagcatgt gccggccttt   1200

gaagaataca tgcgcgttgc cctggccagc agtggttatt gtctgctggc cgttacaagt   1260

tttgtgggca tgggcgagat cgtgacaaag gaagcctttg actgggttac aagcgacccg   1320

cgcatcataa gcagcagcaa cacaattaca cgcctgatgg acgacattaa aagccataaa   1380

tttgaacaga aacgcggtca tgtgtggagc gccgtggaat gctacatgaa acagtacgcc   1440

gtgaccgaag agcaggttta cgaggaattt aaaaaacaga ttgaaaacgc atggctggac   1500

attaatcagg agtgtctgaa gccgaccgca gtgccgatgc cgctgttagc acgcctgctg   1560

aatttcaccc gcacaatgga tgtgatttat aaagaagaag acagctatac ccatgtgggc   1620

aagaccatgc gcgacaacat cgccagcgtg tttatcaacc ctgtgatcta a            1671
```

<210> SEQ ID NO 129
<211> LENGTH: 556
<212> TYPE: PRT
<213> ORGANISM: Artificial Sequence
<220> FEATURE:
<223> OTHER INFORMATION: Synthetic - Engineered valencene synthase

<400> SEQUENCE: 129

```
Met Ala Thr Gln Val Ser Ala Ser Ser Leu Ala Gln Ile Pro Gln Pro
1               5                   10                  15

Lys Asn Arg Pro Val Ala Asn Phe His Lys Asn Ile Trp Gly Asp His
            20                  25                  30

Phe Ile Thr Tyr Thr Pro Glu Asp Lys Val Thr Arg Ala Lys Lys Glu
        35                  40                  45

Glu Arg Ile Glu Asp Leu Lys Glu Glu Val Lys Arg Lys Leu Thr Ala
    50                  55                  60

Ala Ala Val Ala Asn Pro Ser Gln Leu Leu Asn Phe Ile Asp Ala Val
65                  70                  75                  80

Gln Arg Leu Gly Val Ala Tyr His Phe Glu Gln Glu Ile Glu Glu Ala
                85                  90                  95

Leu Gln His Ile Cys Asn Ser Phe His Asp Cys Asn Asp Met Asp Gly
            100                 105                 110

Asp Leu Tyr Asn Ile Ala Leu Leu Phe Arg Leu Leu Arg Gln Gln Gly
        115                 120                 125

Tyr Thr Ile Ser Cys Asp Ile Phe Asn Lys Phe Thr Asp Glu Glu Gly
    130                 135                 140

Arg Phe Lys Glu Ala Leu Ile Ser Asp Val Arg Gly Met Leu Gly Leu
145                 150                 155                 160

Tyr Glu Ala Ala Tyr Leu Arg Val His Gly Glu Asp Ile Leu Ala Glu
                165                 170                 175

Ala Leu Ala Phe Thr Thr Thr His Leu Lys Ala Met Val Glu Ser Leu
            180                 185                 190
```

-continued

Gly Tyr His Leu Ala Glu Gln Val Arg His Ala Leu Asn Arg Pro Ile
195 200 205

Arg Lys Gly Met Glu Arg Leu Glu Ala Arg Trp Tyr Ile Ser Ile Tyr
210 215 220

Gln Asp Glu Ala Phe His Asp Lys Thr Leu Leu Glu Leu Ala Lys Leu
225 230 235 240

Asp Phe Asn Leu Val Gln Ser Leu His Lys Glu Glu Leu Ser Asn Leu
245 250 255

Ala Arg Trp Trp Lys Glu Leu Asp Phe Ala Thr Lys Leu Pro Phe Ala
260 265 270

Arg Asp Arg Leu Val Glu Gly Tyr Phe Trp Met Met Gly Val Tyr Phe
275 280 285

Glu Pro Gln Tyr Leu Arg Gly Arg Arg Ile Leu Thr Lys Val Ile Ala
290 295 300

Leu Thr Ser Ile Ile Asp Asp Ile His Asp Ala Tyr Gly Thr Pro Glu
305 310 315 320

Glu Leu Lys Leu Phe Ile Glu Ala Ile Glu Lys Trp Asp Glu Ser Ser
325 330 335

Ile Asn Gln Leu Pro Glu Tyr Met Lys Leu Cys Tyr Asn Ala Leu Leu
340 345 350

Asp Val Tyr Asn Glu Ile Glu Glu Glu Met Glu Lys Glu Gly Asn Gln
355 360 365

Tyr Arg Ile His Tyr Leu Lys Glu Val Met Lys Asn Gln Val Arg Ala
370 375 380

Tyr Phe Ala Glu Ala Lys Trp Leu His Asp Glu His Val Pro Ala Phe
385 390 395 400

Glu Glu Tyr Met Arg Val Ala Leu Ala Ser Ser Gly Tyr Cys Leu Leu
405 410 415

Ala Val Thr Ser Phe Val Gly Met Gly Glu Ile Val Thr Lys Glu Ala
420 425 430

Phe Asp Trp Val Thr Ser Asp Pro Arg Ile Ile Ser Ser Ser Asn Thr
435 440 445

Ile Thr Arg Leu Met Asp Asp Ile Lys Ser His Lys Phe Glu Gln Lys
450 455 460

Arg Gly His Val Trp Ser Ala Val Glu Cys Tyr Met Lys Gln Tyr Ala
465 470 475 480

Val Thr Glu Glu Gln Val Tyr Glu Glu Phe Lys Lys Gln Ile Glu Asn
485 490 495

Ala Trp Leu Asp Ile Asn Gln Glu Cys Leu Lys Pro Thr Ala Val Pro
500 505 510

Met Pro Leu Leu Ala Arg Leu Leu Asn Phe Thr Arg Thr Met Asp Val
515 520 525

Ile Tyr Lys Glu Glu Asp Ser Tyr Thr His Val Gly Lys Thr Met Arg
530 535 540

Asp Asn Ile Ala Ser Val Phe Ile Asn Pro Val Ile
545 550 555

<210> SEQ ID NO 130
<211> LENGTH: 132
<212> TYPE: PRT
<213> ORGANISM: Escherichia coli

<400> SEQUENCE: 130

Met Thr Trp Glu Tyr Ala Leu Ile Gly Leu Val Val Gly Ile Ile Ile

-continued

```
1               5                   10                  15

Gly Ala Val Ala Met Arg Phe Gly Asn Arg Lys Leu Arg Gln Gln Gln
            20                  25                  30

Ala Leu Gln Tyr Glu Leu Glu Lys Asn Lys Ala Glu Leu Asp Glu Tyr
        35                  40                  45

Arg Glu Glu Leu Val Ser His Phe Ala Arg Ser Ala Glu Leu Leu Asp
    50                  55                  60

Thr Met Ala His Asp Tyr Arg Gln Leu Tyr Gln His Met Ala Lys Ser
65                  70                  75                  80

Ser Ser Ser Leu Leu Pro Glu Leu Ser Ala Glu Ala Asn Pro Phe Arg
                85                  90                  95

Asn Arg Leu Ala Glu Ser Glu Ala Ser Asn Asp Gln Ala Pro Val Gln
            100                 105                 110

Met Pro Arg Asp Tyr Ser Glu Gly Ala Ser Gly Leu Leu Arg Thr Gly
        115                 120                 125

Ala Lys Arg Asp
    130
```

<210> SEQ ID NO 131
<211> LENGTH: 1542
<212> TYPE: DNA
<213> ORGANISM: Stevia rebaudiana

<400> SEQUENCE: 131

```
atggatgccg tcaccggttt gctgacagtt ccggcaaccg caataaccat cggcggtacg     60

gccgtcgcac tcgccgtcgc tctgatattc tggtacctca aaagctacac atctgcacgc    120

aggagccaat caaaccatct ccctcgggtt cccgaggtac ctggtgtgcc attattgggg    180

aatttattgc agttgaagga gaagaaacct tacatgactt ttacaagatg ggcggcaact    240

tatggtccga tttattcgat taaaaccgga gcaacttcta tggtggtcgt cagttcaaat    300

gaaattgcaa aggaggcatt ggttaccaga tttcaatcta tctcaaccag aaacctatca    360

aaggcattaa aggttctcac agcagataaa accatggtgg cgatgagtga ttatgatgat    420

tatcataaga ctgtcaaacg ccatatactg accgctgttt tgggaccaaa tgctcagaag    480

aaacaccgca tccataggga catcatgatg gataatatat caacccaact tcatgaattt    540

gttaaaaata atcctgaaca agaggaagtg gatctaagga aaatattcca atccgaactt    600

tttggattag ctatgagaca agcattggga aaggatgtgg agagcttata tgttgaggat    660

cttaaaatca ccatgaaccg agacgagata tttcaggtat tggttgttga cccgatgatg    720

ggtgcaattg acgtcgactg gagagatttc ttcccgtatc taaagtgggt cccgaataaa    780

aagtttgaaa acacgatcca acaaatgtat atccggagag aagctgtgat gaagtctctt    840

attaaagaac ataaaaaacg tattgcatcc ggagagaaat taaacagcta cattgattac    900

ttgctatcgg aagcacaaac gttaaccgat caacaactac ttatgtctct atgggaacct    960

attattgaat catcagacac cactatggtt acaactgaat gggctatgta tgaacttgca   1020

aaaaacccca aacttcagga tcgtttgtat cgggatatca aaagtgtttg cgggtcagag   1080

aagattacag aagaacactt gtctcaactg ccatacataa ctgccatttt tcatgaaacc   1140

ttgagaaggc atagtccagt tcctataatt ccattaagac acgtgcatga agacacagtg   1200

ttaggagggt accatgtgcc agctggaacc gagctagcgg taaacattta tggatgtaac   1260

atggataaga atgtgtggga gaatcctgaa gaatggaatc cagagagatt catgaaggaa   1320

aatgaaacga tagatttcca gaaaacaatg gcgtttggag gtggaaagcg cgtatgtgct   1380
```

-continued

```
ggttcgcttc aagcattgtt gactgcttcc attggaattg gaagaatggt gcaagagttt   1440

gagtggaaac tgaaagatat gacccaagaa gaagttaata cgattgggct tacgacccag   1500

atgcttcgtc cactgcgggc cataataaag cccaggatat ga                       1542
```

<210> SEQ ID NO 132
<211> LENGTH: 1518
<212> TYPE: DNA
<213> ORGANISM: Artificial Sequence
<220> FEATURE:
<223> OTHER INFORMATION: Synthetic - Engineered valencene oxidase variant

<400> SEQUENCE: 132

```
atggcttggg aatatgcgct aattgggtta gtcgtcggca tcattattgg tgctgtggcc     60

atgcgttggt atctgaaatc ttacactagc gcgcgccgct ctcagtccaa ccacctgccg    120

cgtgtgccgg aagttccggg tgtgccactg ctgggcaacc tgctgcaact gaaagaaaag    180

aaaccgtaca tgacctttac caaatgggca gcgacttatg gtcctatcta cagcattaaa    240

accggcgcta cgtctgtggt tgtggtttct tccaacgaaa tcgcgaaaga agccctggtg    300

actcgtttcc agtccattag cacccgcaac ctgtccaaag cgctgaaggt tctgacggct    360

gacaagcaga tggtggctat gagcgactat gatgactacc acaaaaccgt taaacgtcac    420

atcctgaccg cagtactggg tccgaacgca cagaaaaaac atcgcatcca ccgcgacatt    480

atgatggata acatctccac gcagctgcat gagttcgtta agaacaatcc agaacaggaa    540

gaggtagatc tgcgtaaaat ttttcagtcc gaactgttcg gtctggctat gcgtcaggcg    600

ctgggcaaag acgttgaaag cctgtatgtc gaagacctga aaattaccat gaaccgtgat    660

gagatcctac aggttctggt tgtagatccg atgatgggcg ccatcgacgt ggattggcgt    720

gacttctttc cgtacctgaa atgggtcccg aacaagaagt tcgaaaacac catccagcaa    780

atgtacatcc gtcgtgaagc ggtgatgaaa agcctgatca aagaacaaaa aaagcgtatt    840

gcttctggtg agaaactgaa ctcctacatc gattatctgc tgtccgaagc gcagaccctg    900

accgaccaac agctgctgat gtctctgtgg gaaccgatta tcgaaagcag cgacaccact    960

atggtcacta ccgaatgggc aatgtatgag ctggccaaaa acccgaaact gcaggatcgt   1020

ctgtaccgtg acatcaaaag cgtttgcggc tccgagaaaa tcactgaaga acacctgtct   1080

cagctgccgt acatcactgc tattttccac gaaaccctgc gtaagcattc tccggttccg   1140

atcctgccgc tgcgtcacgt tcacgaagat actgtgctgg gtggttacca tgtaccggca   1200

ggcactgaac tggctgtcaa catctacggc tgtaacatgg ataaaaacgt ttgggagaat   1260

cctgaagaat ggaacccgga acgcttcatg aaagagaacg aaaccatcga cttccagaaa   1320

acgatggctt tcggcggtgg taaacgtgtg tgcgcaggtt ctctgcaggc gctgctgatt   1380

gcgtccattg gtatcggtcg catggtacag gaatttgaat ggaagctgaa agacatgacc   1440

caagaagagg tgaataccat tggtctgact aatcagatgc tgcgtccact gcgtgcaatc   1500

atcaaacctc gtatttaa                                                  1518
```

METHODS FOR PRODUCTION OF OXYGENATED TERPENES

CROSS-REFERENCE TO RELATED APPLICATIONS

This application is a divisional of U.S. patent application Ser. No. 15/505,022, filed Feb. 17, 2017, which is a United States National Stage Application of International Application No. PCT/US/2015/046421, filed Aug. 21, 2015, which claims the benefit of, and priority to, United States Provisional Application No. 62/040,284, filed Aug. 21, 2014. The application hereby incorporates by reference these United States and international priority applications.

FIELD OF THE INVENTION

The present disclosure relates to oxygenated sesquiterpenes (e.g., nootkatone and/or nootkatol) and methods for their production and use. The disclosure also provides enzymes for the production of oxygenated sesquiterpenes (e.g., nootkatone and/or nootkatol) and methods for identifying, selecting, making and using these enzymes.

BACKGROUND OF THE INVENTION

The food and beverage industries as well as other industries such as the perfume, cosmetic and health care industries routinely use terpenes and/or terpenoid products as flavours and fragrances. By way of example, many sesquiterpene compounds are used in perfumery (e.g., patchoulol) and in the flavour industry (e.g., nootkatone) and many are extracted from plants. However, factors such as: (i) the availability and high price of the plant raw material; (ii) the relatively low terpene content in plant; and (iii) the tedious and inefficient extraction processes to produce sufficient quantities of terpene products on an industrial scale all have stimulated research on the biosynthesis of terpenes using plant-independent systems. Consequently, effort has been expended in developing technologies to engineer microorganisms for converting renewable resources such as glucose into terpenoid products. By comparison with traditional methods, microorganisms have the advantage of fast growth without the need for land to sustain development.

Many microorganisms use either the methylerythritol 4-phosphate (MEP) pathway or the melavonate (MVA) pathway to supply intermediates necessary to produce terpenoid products. These MEP or MVA pathways can include an endogenous or an engineered MEP or MVA pathway or both. A detailed understanding of isoprenoid pathway engineering and optimization is disclosed in WO 2011/060057, US 2011/0189717, US 2012/107893, U.S. Pat. No. 8,512,988 and Ajikumar et al (2010) *Science* 330 70-74, which discloses the production of various terpenoid compounds including sesquiterpene compounds such as nootkatone, which is an oxidised sesquiterpene produced from a valencene sesquiterpene substrate.

Nootkatone (4,4a,5,6,7,8-hexahydro-6-isopropenyl-4,4a-dimethyl-2(3II)-naphtalenone) is an important flavour constituent of grapefruit and is used commercially to flavour soft drinks and other beverages, as well as being used in perfumery. The conventional method for nootkatone preparation is by oxidation of valencene (see, e.g., U.S. Pat. Nos. 6,200,786 and 8,097,442). The starting material valencene is expensive and thus methods that consume valencene are less commercially acceptable. Because of these drawbacks, there is a need for commercially feasible and sustainable methods to prepare nootkatone and associated products.

SUMMARY OF THE INVENTION

An object of the present disclosure is to provide sustainable production of oxygenated sesquiterpene products. Specifically, the present disclosure provides enzyme catalysts for the ex vivo or in vivo production of certain oxygenated sesquiterpenes. In some embodiments, the disclosure provides host cells engineered for the biosynthesis of the oxygenated sesquiterpenes. Another object of the present disclosure is to provide engineered cytochrome P450 (CYP450) enzymes for synthesis of oxygenated sesquiterpenes, including in some embodiments functional expression alongside a reductase counterpart in *E. coli*, yeast, or other host cell. The disclosure thereby harnesses the unique capability of this class of enzymes to conduct oxidative chemistry.

In one aspect, the disclosure provides a method for making an oxygenated product of a sesquiterpene. The method comprises contacting the sesquiterpene with *Stevia rebaudiana* Kaurene Oxidase (SrKO) or a derivative thereof having sesquiterpene oxidizing activity. Surprisingly, the wild type SrKO enzyme was shown to have activity on a sesquiterpene substrate even though its natural activity is understood to act on a diterpene substrate. Further, SrKO enzyme showed unique activities, including oxygenation, by creating different stereoisomers of the hydroxylated product (alpha and beta nootkatol and further oxidizing to ketone, nootkatone), and produced different oxygenated terpene products including hydroxygermacra-1(10)5-diene, and murolan-3,9(11) diene-10-peroxy. This activity is distinct from other P450 enzymes tested, which produced only one of the stereoisomers of the hydroxylated product (e.g., β-nootkatol), as the major product and produced only minor amounts of nootkatone. This activity of SrKO provides a unique sesquiterpene oil for flavoring applications.

In some embodiments, the method takes place in an ex vivo (e.g., cell free) system. In other embodiments, the sesquiterpene substrate and the SrKO or derivative thereof are contacted in a cell expressing the SrKO, such as a bacterium (e.g., *E. coli*). The oxygenated product of a sesquiterpene may be recovered, or may be the substrate for further chemical transformation. Functional expression of wild type cytochrome P450 in *E. coli* has inherent limitations attributable to the bacterial platforms (such as the absence of electron transfer machinery and cytochrome P450 reductases, and translational incompatibility of the membrane signal modules of P450 enzymes due to the lack of an endoplasmic reticulum). Thus, in some embodiments the SrKO enzyme is modified for functional expression in an *E. coli* host cell, for example, by replacing a portion of the SrKO N-terminal transmembrane region with a short peptide sequence that stabilizes interactions with the *E. coli* inner membrane and/or reduces cell stress.

In some embodiments, the SrKO derivative has at least one mutation with respect to the wild type SrKO that increases valencene oxidase activity, or increases production of nootkatone, α-nootkatol, and/or β-nootkatol. For example, the SrKO may have from 1 to 50 mutations independently selected from substitutions, deletions, or insertions relative to wild type SrKO (SEQ ID NOS: 37 and 108) or an SrKO modified for expression and activity in *E. coli* (e.g., SEQ ID NOS: 38 and 106). For example, the SrKO derivative may have from 1 to 40 mutations, from 1 to 30 mutations, from 1 to 20 mutations, or from 1 to 10 mutations relative to SrKO (SEQ ID NOS: 37 or 38). In these or other embodiments, the SrKO derivative may comprise an amino acid sequence having at least 50% sequence identity, or at least 60% sequence identity, or at least 70% sequence identity, or at least 80% sequence identity, or at least 90% sequence identity to SrKO (SEQ ID NOS: 37 or 38), and has valencene oxidase activity. The SrKO in various embodiments maintains valencene oxidase activity, or has increased valencene oxidase activity as compared to the wild type enzyme in an ex vivo or bacterial system (e.g., *E coli*). Various mutations of SrKO which maintain or enhance valencene oxidase activity are listed in Tables 2.1, 2.2, 2.3 and 6. Thus, in various embodiments, the SrKO may have at least 2, at least 3, at least 4, at least 5, at least 6, at least 7, at least 8, at least 9, or at least 10 mutations selected from Tables 2.1, 2.2, 2.3 and/or 6. Exemplary derivatives of SrKO, also referred to herein as "valencene oxidase" or "VO" are represented by, for example, SEQ ID NOS: 104 and 105, which may further be derivatized for improvements in desired activity. Mutations may be selected empirically for increases in oxygenated sesquiterpene titer, or selected by in silico evaluation, or both.

In accordance with aspects of the disclosure, oxygenated sesquiterpene products are obtainable by contacting a sesquiterpene substrate with *Stevia rebaudiana* Kaurene Oxidase (SrKO) or derivative thereof having valencene oxidizing activity. Unlike other CYP450 enzymes, when a SrKO enzyme is used with valencene sesquiterpene substrate, it produces a different oxygenated terpene product profile that can include hydroxygermacra-1(10)5-diene, murolan-3,9 (11) diene-10-peroxy, alpha-nootkatol, beta-nootkatol, and nootkatone. By comparison, other CYP450's having the activity of hydroxylating valencene only produced one of the stereoisomers (beta nootkatol) and did not produce significant amounts of the ketone (nootkatone), which requires two oxygenation cycles. See Table 4 and FIG. 7.

In various embodiments, the sesquiterpene substrate is (or the predominant sesquiterpene substrate is) valencene, germacrene (A, B, C, D, or E), farnesene, farnesol, nootkatol, patchoulol, cadinene, cedrol, humulene, longifolene, and/or bergamotene, β-ylangene, β-santalol, β-santalene, α-santalene, α-santalol, β-vetivone, α-vetivone, khusimol, bisabolene, β-aryophyllene, longifolene; α-sinensal; α-bisabolol, (−)-β-copaene, (−)-α-copaene, 4(Z),7(Z)-ecadienal, cedrol, cedrene, cedrol, guaiol, (−)-6,9-guaiadiene, bulnesol, guaiol, ledene, ledol, lindestrene, and alpha-bergamotene. In some embodiments, the predominant sesquiterpene substrate is valencene, and the predominant oxygenated product is nootkatone and/or nootkatol, which in some embodiments comprises both α and β nootkatol.

The disclosure, when applied in vivo, is applicable to a wide array of host cells. In some embodiments, the host cell is a microbial host, such as a bacterium selected from *E. coli, Bacillus subtillus*, or *Pseuclomonas putida*; or a yeast, such as a species of *Saccharomyces, Pichia*, or *Yarrowia*, including *Saccharomyces cerevisiae, Pichia pastoris*, and *Yarrowia lipolytica.*

In some embodiments, the host cell produces isopentyl pyrophosphate (IPP), which acts as a substrate for the synthesis of the sesquiterpene. In some embodiments, the IPP is produced by metabolic flux through an endogenous or heterologous methylerythritol phosphate (MEP) or mevalonic acid (MVA) pathway. In some embodiments, the sesquiterpene is produced at least in part by metabolic flux through an MEP pathway, and wherein the host cell has at least one additional copy of a dxs, ispD, ispF, and/or idi gene.

In some embodiments, the host cell expresses a farnesyl pyrophosphate synthase (FPPS), which produces farnesyl pyrophosphate (FPP) from IPP or DMAPP. The host cell may further express a heterologous sesquiterpene synthase to produce the desired sesquiterpene scaffold. For example, in some embodiments the cell expresses a valencene synthase. Several valencene synthase enzymes are known including *Vitis vinifera* valencene synthase (VvVS) (SEQ ID NO: 1) or *Citrus sinensis* valencene synthase (CsVS) (SEQ ID NO: 12), which may be employed with the present disclosure, or alternatively a derivative of the VvVS or CsVS. Exemplary derivative VvVS enzymes are disclosed herein. In certain embodiments, the sesquiterpene synthase is a valencene synthase selected from Vv1M1 (SEQ ID NO: 3), Vv2M1 (SEQ ID NO: 5), Vv1M5 (SEQ ID NO: 7), Vv2M5 (SEQ ID NO: 9), VS2 (SEQ ID NO: 11), and VS3 (SEQ ID NO: 129), as disclosed herein.

The SrKO or derivative thereof acts on the sesquiterpene (e.g., valencene) to produce the oxygenated terpene product. In some embodiments the SrKO is a fusion protein with a cytochrome P450 reductase partner (e.g., SrCPR), allowing the cofactor to be efficiently regenerated. In other embodiments, a P450 reductase is provided (e.g., to in vitro system) or expressed in the host cell separately, and may be expressed in the same operon as the SrKO in some embodiments. In some embodiments, the CPR enzyme is expressed separately, and the gene may be integrated into the host cell genome in some embodiments. Various exemplary CPR enzymes are disclosed herein, and which may be derivatized to improve oxygenated sesquiterpenoid titer and/or to improve P450 efficiency.

In some embodiments, the host cell expresses one or more enzymes that further direct oxygenated product to nootkatone, such as the expression of one or more alcohol dehydrogenase (ADH) enzymes. Exemplary ADH enzymes are disclosed herein.

In other aspects, the disclosure provides a method for making a product containing an oxygenated sesquiterpene, which comprises incorporating the oxygenated sesquiterpene prepared and recovered according to the methods described herein into a consumer or industrial product. For example, the product may be a flavor product, a fragrance product, a cosmetic, a cleaning product, a detergent or soap, or a pest control product. In some embodiments, the oxygenated product recovered comprises nootkatol (e.g., α and/or β nootkatol) and/or nootkatone, and the product is a flavor product selected from a beverage, a chewing gum, a candy, or a flavor additive.

In other aspects, the disclosure provides engineered SrKO enzymes having enhanced valencene oxidase activity as compared to wild type, as well as host cells producing an oxygenated sesquiterpene as described herein, and which express all of the enzyme components for producing the desired oxygenated sesquiterpene from isopentyl pyrophosphate (IPP). For example, the host cell in various embodiments expresses a farnesyl pyrophosphate synthase, a sesquiterpene synthase, and the SrKO or derivative thereof. IPP may be produced through the MEP and/or MVA pathway, which may be endogenous to the host cell, and which may be enhanced through expression of heterologous enzymes or duplication of certain enzymes in the pathway. Host cells include various bacteria and yeast as described herein. The oxygenated sesquiterpene (e.g., nootkatone and/or nootkatol) may be recovered from the culture, and/or optionally may act as the substrate for further chemical transformation in the cell or ex vivo system.

In another aspect, the disclosure provides sesquiterpene-containing oil produced by the methods and host cells described herein. In some embodiments, the oil comprises hydroxygermacra-1(10)5-diene, murolan-3,9(11) diene-10-peroxy, alpha-nootkatol, beta-nootkatol, and nootkatone. In some embodiments, the predominant oxygenated products of valencene is nootkatone and nootkatol, and the oxygenated sesquiterpene product comprises both alpha and beta nootkatol.

In another aspect, there is provided an SrKO crystal model structure (CMS) based on the structural coordinates of P45017A1 (which catalyzes the biosynthesis of androgens). The CMS, including the terpene binding pocket domain (TBD) that comprises a terpene binding pocket (TBP) and a terpene (e.g., valencene) bound to the TBD, is illustrated in FIGS. 8A and 8B. This SrKO crystal model structure (CMS) facilitates in-silico testing of SrKO derivatives. In part aided by this homology model, the present disclosure illustrates the use of several mutational strategies to identify increases or improvements in sesquiterpene oxygenation activity, including back-to-consensus mutagenesis, site-saturation mutagenesis, and recombination library screening.

Additional aspects and embodiments of the invention will be apparent from the following detailed description.

DESCRIPTION OF THE DRAWINGS

FIG. 2 shows the number of VvVS mutants (y-axis) exhibiting certain levels of productivity (x-axis) versus the wild type.

FIG. 3 (A and B) provides the amino acid and nucleotide sequences of valencene synthases. FIG. 3A shows amino acid and nucleotide sequences from *Vitis vinifera* wild-type (WT) (VvVS) (SEQ ID NOS: 1 and 2) and derivatives Vv1M1 (SEQ ID NOS: 3 and 4), Vv2M1 (SEQ ID NOS: 5 and 6), Vv1M5 (SEQ ID NOS: 7 and 8), Vv2M5 (SEQ ID NOS: 9 and 10), and VS2 (SEQ ID NOS: 11 and 120); as well as amino acid sequence for *Citrus sinensis* wild-type (CsVS) (SEQ ID NOS: 12 and 119). FIG. 3B shows an alignment of wild-type VvVS and CsVS sequences, and the engineered Vv2M5 and VS2 sequences.

FIG. 4 (A and B) provides the amino acid and nucleotide sequences of various CYP450 (Cytochrome P450) enzymes having activity on sesquiterpene scaffolds. FIG. 4A shows sequences of wild type amino acid sequences and amino acid and nucleotide sequences engineered for bacterial expression: ZzHO (SEQ ID NO: 13, 14, and 15 respectively), BsGAO (SEQ ID NO: 16, 17, and 18, respectively), HmPO (SEQ ID NO: 19, 20, and 21 respectively), LsGAO (SEQ ID NO: 22, 23, and 24, respectively), NtEAO (SEQ ID NO: 25, 26, and 27, respectively), CpVO (SEQ ID NO: 28, 29, and 30, respectively), AaAO (SEQ ID NO: 31, 32, and 33, respectively), AtKO (SEQ ID NO: 34, 35, and 36 respectively), SrKO (SEQ ID NO: 37, 38, and 39 respectively), PpKO (SEQ ID NO: 40, 41, and 42, respectively), BmVO (SEQ ID NO: 43 and SEQ ID NO: 44, respectively), PsVO (SEQ ID NO: 45 and SEQ ID NO: 46, respectively), PoLO (SEQ ID NO: 47 and SEQ ID NO: 48, respectively), CiVO (SEQ ID NO: 49, 50, and 51 respectively), HaGAO (SEQ ID NO: 52, 53, and 54, respectively). FIG. 4B shows amino acid sequences of engineered Valencene Oxidase enzymes based on the SrKO scaffold (SEQ ID NOS: 55-61).

FIG. 5A shows strain configuration of upstream MEP pathway genes and the two plasmids harboring downstream pathway genes. FIG. 5B shows construction of P450 fusions, whereby N-terminal regions of both the P450 and CPR (Cytochrome P450 reductase) are truncated and an exemplary leader sequence (MALLLAVF—SEQ ID NO:112) (8RP) is added while the two are fused with a short linker peptide.

FIG. 6 (A-D) provides the amino acid and nucleotide sequences of various CPR (Cytochrome P450 reductase) enzymes with sequence alignments. In FIG. 6A: *Stevia rebaudiana* (Sr)CPR (SEQ ID NOS: 62 and 63, *Stevia rebaudiana* (Sr)CPR1 SEQ ID NOS: 76 and 77), *Arabidopsis thaliana* (At) CPR (SEQ ID NOS: 64 and 65), *Taxus cuspidata* (Tc) CPR (SEQ ID NOS: 66 and 67), *Arteinisia annua* (Aa)CPR)SEQ ID NOS: 68 and 69), *Arabidopsis thaliana* (At)CPR1 (SEQ ID NOS: 70 and 71), *Arabidopsis thaliana* (At)CPR2 (SEQ ID NOS: 72 and 73), *Arabidopsis thaliana* (At)R2 (SEQ ID NOS: 74 and 75); *Stevia rebaudiana* (Sr)CPR2 (SEQ ID NOS: 78 and 79); *Stevia rebaudiana* (Sr)CPR3 (SEQ ID NOS: 80 and 81); *Pelargonium graveolens* (Pg)CPR (SEQ ID NO: 82 and 83). FIG. 6B shows an alignment of amino acid sequences for *Arabidopsis thaliana* and *Artenzisia annua* CPR sequences (SEQ ID NOS:72, 74, 68, 64, and 70). FIG. 6C shows an alignment of *Stevia rebaudiana* CPR sequences (SEQ ID NOS: 78, 80, 62, and 76). FIG. 6D shows an alignment of eight CPR amino acid sequences (SEQ ID NO: 74, 72, 82, 68, 80, 62, 78, and 76).

FIG. 8B depicts a structural model of SrKO active site with valencene docked in its α-binding mode. Secondary structure motifs (B-C Loop and I-Helix) and amino acids targeted for mutagenesis are shown.

FIG. 22 (A and B) depicts alcohol dehydrogenase enzymes. FIG. 22A shows amino acid and nucleotide sequences including those for *Rhodococcus erythropolis* (Re)CDH (SEQ ID NOS: 84 and 85), *Citrus sinensis* (Cs) DH (SEQ ID NOS: 86 and 87), *Citrus sinensis* (Cs)DH1 (SEQ ID NOS: 88 and 89), *Citrus sinensis* (Cs)DH2 (SEQ ID NOS: 90 and 91), *Citrus sinensis* (Cs)DH3 (SEQ ID NOS: 92 and 93), *Vitis vinifera* (Vv)DH (SEQ ID NOS: 94 and 95), *Vitis vinifera* (Vv)DH1 (SEQ ID NOS: 96 and 97, *Citrus sinensis* (Cs)ABA2 (SEQ ID NOS: 98 and 99), *Brachypodium distachyon* (Bd)DH (SEQ ID NO: 100 and 101), *Zingiber zerumbet* (Zz)SDR (SEQ ID NOS: 102 and 103). FIG. 22B shows an alignment of the amino acid sequences.

FIG. 23 (A and B) shows alignments of several engineered valencene oxidase (VO) variants. In FIG. 23A: 8rp-t20SrKO (SEQ ID NO: 106) is the SrKO sequence with a 20-amino acid truncation at the N-terminus, and the addition of an 8-amino acid membrane anchor. 8rp-t20VO0 (SEQ ID NO: 107) has a truncation of 20 amino acids of the SrKO N-terminus, the addition of an 8-amino acid N-terminal anchor, and a single mutation at position 499 (numbered according to wild-type SrKO). n22yhcB-t30VO1 (SEQ ID NO: 104) has a 30-amino acid truncation of the SrKO N-terminus, a membrane anchor based on 22 amino acids from *E. coli* yhcB, and eight point mutations at positions 46, 231, 284, 383, 400, 444, 488, and 499 (with respect to SrKO wild-type). n22yhcB-t30VO2 (SEQ ID NO: 105) has a 30-amino acid truncation of the SrKO N-terminus, a membrane anchor based on 22 amino acids from *E. coli* yhcB, and nine point mutations at positions 76, 94, 131, 231, 284, 383, 390, 468, and 499 (with respect to SrKO wild-type). In FIG. 23B, point mutations in VO0 (SEQ ID NO: 109), VO1 (SEQ ID NO: 110), and VO2 (SEQ ID NO: 111) are shown against wild-type SrKO (SEQ ID NO: 108) (all shown with the wild-type SrKO N-terminus for convenience).

DETAILED DESCRIPTION OF THE INVENTION

Figure 1:
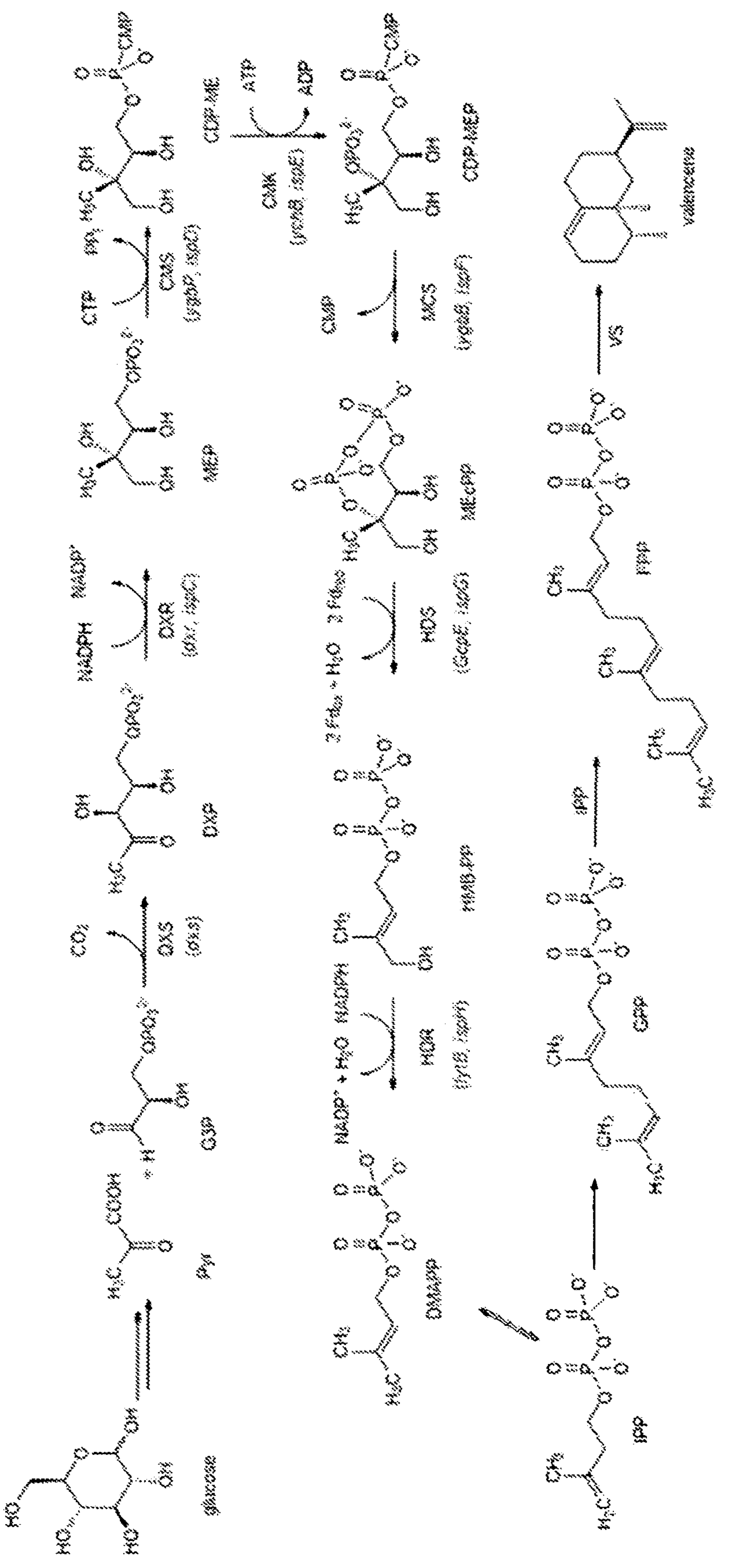
FIG. 1 shows a scheme for biosynthesis of valencene, which is a substrate for SrKO in accordance with the present disclosure.

The present disclosure in various aspects provides methods for making oxygenated terpenes or terpenoids in ex vivo or in cell systems. The disclosure further provides engineered or modified enzymes, polynucleotides, and host cells for use in such methods. The disclosure in various embodiments is directed to a method to produce nootkatone and/or nootkatol using an SrKO enzyme. Surprisingly, it was found that the SrKO enzyme can be used to catalyze sesquiterpene oxidation (e.g., valencene oxidation to nootkatol and nootkatone).

As used herein, SrKO refers to ent-kaurene oxidase CYP701A5 [*Stevia rebaudiana*] with Accession No AAQ63464.1 (SEQ ID NO: 37). SrKO and its activity on diterpenes (and kaurene in particular) are known and are described in, for example, US 2012/0164678, which is hereby incorporated by reference in its entirety. It is a member of the CYP70 family of cytochrome p450 enzymes (CYP450). An exemplary SrKO sequence modified for expression in *E. coli* is shown as SEQ ID NO: 38. As shown herein, SrKO is active on sesquiterpene substrates (e.g., valencene), producing nootkatol (both α and β) and nootkatone, which are valuable terpenoid compounds. Further, SrKO provides a unique product profile with unique sensory characteristics that is based on the oxygenation of valencene. These activities and product profiles can be further refined by mutagenesis of the SrKO using processes (and aided by in silico models) described in detail herein.

As used herein, the term "SrKO derivative," "modified SrKO polypeptide," "engineered SrKO," "SrKO variant," "engineered valencene oxidase," or "valencene oxidase variant" refers to an amino acid sequence that has substantial structural and/or sequence identity with SrKO, and catalyzes oxygenation of a sesquiterpene scaffold, such as valencene. SrKO enzymes engineered for the oxygentation of valencene are also referred to herein as "valencene oxidase" or "VO" enzymes. Generally, derivatives comprise mutated forms of SrKO having at least one mutation that increases the activity of the enzyme for the valencene substrate or for the production of nootkatone, nootkatol, and/or other products. Some SrKO mutations are provided in Tables 2.1, 2.2, and 2.3. Some such additional SrKO mutations are provided in Table 6.

The term "contacting" means that the components are physically brought together, whether in vivo through co-expression of relevant protein products (e.g., sesquiterpene synthase and CYP450) in a host cell, or by adding or feeding a substrate of interest to a host cell expressing an SrKO or derivative thereof, or in vitro (or "ex vivo") by adding sesquiterpene substrate to purified P450 enzyme or cellular extract or partially purified extract containing the same. The terms in vitro and ex vivo refer to a cell free system, and may be performed in a reaction tube or well.

As used herein, "terpenes" are a large and varied class of hydrocarbons that have a simple unifying feature, despite their structural diversity. According to the "isoprene rule", all terpenes consist of isoprene (C5) units. This fact is used for a rational classification depending on the number of such units. Monoterpenes comprise 2 isoprene units and are classified as (C10) terpenes, sesquiterpenes comprise 3 isoprene units and are classified as (C15) terpenes, diterpenes comprise 4 isoprene units and are classified as (C20) terpenes, sesterterpenes (C25), triterpenes (C30) and rubber (C5)n. They occur as acyclic or mono- to pentacyclic derivatives with alcohol, ether, ester, aldehyde, or ketone groups (the so called "terpenoids"), everywhere in organisms, particularly in higher plants, and are characteristic of the individual type of plants. Terpenes such as Monoterpenes (C10), Sesquiterpenes (C15) and Diterpenes (C20) are derived from the prenyl diphosphate substrates, geranyl diphosphate (GPP), farnesyl diphosphate (FPP) and geranylgeranyl diphosphate (GGPP) respectively through the action of a very large group of enzymes called the terpene (terpenoid) synthases. These enzymes are often referred to as terpene cyclases since the product of the reactions are cyclised to various monoterpene, sesquiterpene and diterpene carbon skeleton products. Many of the resulting carbon skeletons undergo subsequence oxygenation by cytochrome p450 hydrolysase enzymes to give rise to large families of derivatives. The technical syntheses of top-selling flavours and fragrances can start from terpenes which can also serve as excellent solvents or diluting agents for dyes and varnishes. Natural or synthetic resins of terpenes are used and also many pharmaceutical syntheses of vitamins and insecticides start from terpenes. As used herein, the term "terpene" or "sesquiterpene" (for example) includes corresponding terpenoid or sesquiterpenoid compounds.

As used herein, the term "oxygenated sesquiterpene" refers to a sesquiterpene scaffold having one or more oxygenation events, producing a corresponding alcohol, aldehyde, carboxylic acid and/or ketone. One or more oxygenated sesquiterpenes may be referred to herein as an "oxygenated product."

As used herein, the term "unoxygenated sesquiterpene" refers to a sesquiterpene scaffold that has not undergone any oxygenation events. An unoxygenated sesquiterpene may also be referred to herein as an "unoxygenated product."

As used herein, the term "oxygenated product titer" or "oxygenated titer" refers to the sum of titers of α-nootkatol, β-nootkatol, and (+)-nootkatone.

As used herein, the term "MEP pathway" refers to the (2-C-methyl-D-erythritol 4-phosphate) pathway, also called the MEP/DOXP (2-C-methyl-D-erythritol 4-phosphate/1-deoxy-D-xylulose 5-phosphate) pathway or the non-mevalonate pathway or the mevalonic acid-independent pathway. In the MEP pathway, pyruvate and D-glyceraldehyde-3-phosphate are converted via a series of reactions to IPP and DMAPP. The pathway typically involves action of the following enzymes: 1-deoxy-D-xylulose-5-phosphate synthase (Dxs), 1-deoxy-D-xylulose-5-phosphate reductoisomerase (IspC), 4-diphosphocytidyl-2-C-methyl-D-erythritol synthase (IspD), 4-diphosphocytidyl-2-C-methyl-D-erythritol kinase (IspE), 2C-methyl-D-erythritol 2,4-cyclodiphosphate synthase (IspF), 1-hydroxy-2-methyl-2-(E)-butenyl 4-diphosphate synthase (IspG), and isopentenyl diphosphate isomerase (IspH). The MEP pathway, and the genes and enzymes that make up the MEP pathway, are described in U.S. Pat. No. 8,512,988, which is hereby incorporated by reference in its entirety. For example, genes that make up the MEP pathway include dxs, ispC, ispD, ispE, ispF, ispG, ispH, idi, and ispA.

As used herein, the "MVA pathway" refers to the biosynthetic pathway that converts acetyl-CoA to IPP. The mevalonate pathway typically comprises enzymes that catalyze the following steps: (a) condensing two molecules of acetyl-CoA to acetoacetyl-CoA (e.g., by action of acetoacetyl-CoA thiolase); (b) condensing acetoacetyl-CoA with acetyl-CoA to form hydroxymethylglutaryl-CoenzymeA (HMG-CoA) (e.g., by action of HMG-CoA synthase (HMGS)); (c) converting HMG-CoA to mevalonate (e.g., by action of HMG-CoA reductase (HMGR)); (d) phosphorylating mevalonate to mevalonate 5-phosphate (e.g., by action of mevalonate kinase (MK)); (e) converting mevalonate 5-phosphate to mevalonate 5-pyrophosphate (e.g., by action of phosphomevalonate kinase (PMK)); and (f) converting mevalonate 5-pyrophosphate to isopentenyl pyrophosphate (e.g., by action of mevalonate pyrophosphate decarboxylase (MPD)). The MVA pathway, and the genes and enzymes that make up the MEP pathway, are described in U.S. Pat. No. 7,667,017, which is hereby incorporated by reference in its entirety.

As used herein, the term "cytochrome P450 reductase partner" or "CPR partner" refers to a cytochrome P450 reductase capable of regenerating the cofactor component of the cytochrome P450 oxidase of interest (e.g., SrKO) for oxidative chemistry. For example, SrCPR is a natural CPR partner for SrKO. In some embodiments, the CPR partner is not the natural CPR partner for SrKO. In some embodiments employing in vivo production of oxygenated sesquiterpene, the SrKO and SrCPR are co-expressed as separate proteins, or in some embodiments are expressed as a fusion protein.

As used herein, the term "natural product" refers to a product obtained, at least in part, from plant and/or animal material or obtained from microbial enzymatic biotransformations/bioconversions/biocatalysis and/or biosynthesis.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The similarity of nucleotide and amino acid sequences, i.e., the percentage of sequence identity, can be determined via sequence alignments. Such alignments can be carried out with several art-known algorithms, such as with the mathematical algorithm of Karlin and Altschul (Karlin & Altschul (1993) Proc. Natl. Acad. Sci. USA 90: 5873-5877), with hmmalign (HMMER package, hmmer.wustl.edu/) or with the CLUSTAL algorithm (Thompson, J. D., Higgins, D. G. & Gibson, T. J. (1994) Nucleic Acids Res. 22, 4673-80). The grade of sequence identity (sequence matching) may be calculated using e.g. BLAST, BLAT or BlastZ (or BlastX). A similar algorithm is incorporated into the BLASTN and BLASTP programs of Altschul et al (1990) J. Mol. Biol. 215: 403-410. BLAST polynucleotide searches can be performed with the BLASTN program, score=100, word length=12.

BLAST protein searches may be performed with the BLASTP program, score=50, word length=3. To obtain gapped alignments for comparative purposes, Gapped BLAST is utilized as described in Altschul et al (1997) Nucleic Acids Res. 25: 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:154-162) or Markov random fields.

"Conservative substitutions" may be made, for instance, on the basis of similarity in polarity, charge, size, solubility, hydrophobicity, hydrophilicity, and/or the amphipathic nature of the amino acid residues involved. The 20 naturally occurring amino acids can be grouped into the following six standard amino acid groups:

(1) hydrophobic: Met, Ala, Val, Leu, He;
(2) neutral hydrophilic: Cys, Ser, Thr; Asn, Gin;
(3) acidic: Asp, Glu;
(4) basic: His, Lys, Arg;
(5) residues that influence chain orientation: Gly, Pro; and
(6) aromatic: Trp, Tyr, Phe.

As used herein, "conservative substitutions" are defined as exchanges of an amino acid by another amino acid listed within the same group of the six standard amino acid groups shown above. For example, the exchange of Asp by Glu retains one negative charge in the so modified polypeptide. In addition, glycine and proline may be substituted for one another based on their ability to disrupt a-helices. Some preferred conservative substitutions within the above six groups are exchanges within the following sub-groups: (i) Ala, Val, Leu and He; (ii) Ser and Thr; (ii) Asn and Gin; (iv) Lys and Arg; and (v) Tyr and Phe.

As used herein, "non-conservative substitutions" or "non-conservative amino acid exchanges" are defined as exchanges of an amino acid by another amino acid listed in a different group of the six standard amino acid groups (1) to (6) shown above.

In one aspect, the disclosure provides a method for making an oxygenated product of a sesquiterpene. In various embodiments, the sesquiterpene substrate is (or the predominant sesquiterpene substrate is) valencene, germacrene (A, B, C, D, or E), farnesene, farnesol, nootkatol, patchoulol, cadinene, cedrol, humulene, longifolene, and/or. bergamotene, β-ylangene, β-santalol, β-santalene, α-santalene, α-santalol, β-vetivone, a-vetivone, khusimol, bisabolene, β-aryophyllene, Longifolene; α-sinensal; α-bisabolol, (−)-β-copaene, (−)-α-copaene, 4(Z),7(Z)-ecadienal, cedrol, cedrene, cedrol, guaiol, (−)-6,9-guaiadiene, bulnesol, guaiol, ledene, ledol, lindestrene, and alpha-bergamotene. In some embodiments, the predominant sesquiterpene substrate is valencene, and the predominant oxygenated product is nootkatone and/or nootkatol, which in some embodiments comprises both α and β nootkatol. In this context, the term "predominant" means that the particular sesquiterpene is present at a level higher than all other terpene or terpenoid species individually. In some embodiments, the predominant sesquiterpene (either the substrate or the oxygenated product after the reaction) makes up at least 25%, at least 40%, at least 50%, or at least 75% of the terpene or terpenoid component of the composition. In various embodiments involving in vivo production of oxygenated sesquiterpenes, the oxygenated product is recovered from the culture media, and can be fractionated to isolate or enrich for various components of the product, such as nootkatone, nootkatol, and/or other components.

In various embodiments, the disclosure comprises contacting a sesquiterpene with a terpene oxidizing P450 enzyme, or a derivative thereof. The contacting may take place in a host cell or in a cell free system. The substrate for oxidation (e.g., the sesquiterpene), may be produced by the cells (e.g., through metabolic flux through the MEP or MVA pathways), or alternatively fed to the host cells expressing the P450 enzyme. The oxygenated product may be recovered, or be the substrate for further chemical transformation either in the cellular system or cell free system. Table 1 below provides a list of exemplary P450 enzymes. While in certain embodiments the disclosure involves the use of the following P450 enzymes (optionally engineered to increase the oxygenation of valencene to nootkatone and/or nootkatol), a preferred enzyme in accordance with this disclosure is SrKO. Exemplary oxygenated sesquiterpene products obtained by these reactions in accordance with the disclosure are shown in Table 4.

TABLE 1

| # | Species | Name | Native Substrate | Native Reaction Product |
|---|---|---|---|---|
| 1 | *Zingiber zerumbet* | zzHO | a-humulene | 8-hydroxy-α-humulene |
| 2 | *Barnadesia spinosa* | BsGAO | germacrene A | germacra-1(10),4,11(13)-trien-12-ol |
| 3 | *Hyoscyamus muticus* | HmPO | premnaspirodiene | solavetivol |
| 4 | *Latuca spicata* | LsGAO | germacrene A | germacra-1(10),4,11(13)-trien-12-ol |
| 5 | *Nicotiana tabacum* | NtEAO | 5-epi-aristolochene | capsidiol |

TABLE 1-continued

| # | Species | Name | Native Substrate | Native Reaction Product |
|---|---|---|---|---|
| 6 | *Citrus × paradisi* | CpVO | valencene | nootkatol |
| 7 | *Artemesia annua* | AaAO | amorphadiene | artemisinic acid |
| 8 | *Arabidopsis thaliana* | AtKO | kaurene | kaurenoic acid |
| 9 | *Stevia rebaudiana* | SrKO | kaurene | kaurenoic acid |
| 10 | *Pseudomonas putida* | PpKO | kaurene | kaurenoic acid |
| 11 | *Bacillus megaterium* | BmVO | fatty acids | hydroxylated FAs |
| 12 | *Pleurotus sapidus* | PsVO | valencene | nootkatone |
| 13 | *Pleurotus ostreatus* | PoLO | unknown | unknown |
| 14 | *Cichorium intybus* | CiVO | valencene | nootkatone |
| 15 | *Helianthus annuus* | HaGAO | germacrene A | germacrene A acid |

In various embodiments, the method comprises contacting the sesquiterpene with a protein comprising *Stevia rebaudiana* Kaurene Oxidase (SrKO) or derivative thereof. In some embodiments the SrKO is expressed in a host cell as described below, or is provided in a cell free system. For example, certain in vitro and in vivo systems for oxidizing terpenes with P450 enzymes are disclosed in U.S. Pat. No. 7,211,420, which are hereby incorporated by reference. McDougle D R, Palaria A, Magnetta E, Meling D D, Das A. *Functional Studies of N-terminally modified CYP*2J2 epoxygenase in Model Lipid Bilayers, Protein Sci. 2013 22:964-79; Luthra, A., Gregory, M., Grinkova, Y. V., Denisov, I. G., Sligar, S. G. (2013) "Nanodiscs in the studies of membrane-bound cytochrome P450 enzymes." Methods Mol. Biol., 987, 115-127).

In some embodiments, the SrKO derivative comprises an amino acid sequence that has from about 1 to about 50 mutations independently selected from substitutions, deletions, or insertions relative to SrKO (SEQ ID NO: 37 or 38), or relative to an SrKO enzyme modified at its N-terminus for functional expression in *E. coli* (SEQ ID NO: 38 or 55). In various embodiments, the mutation or combination of mutations enhances the activity of the enzyme for oxygenation of valencene, such as the production of nootkatone and/or nootkatol. Protein modeling as described herein may be used to guide such substitutions, deletions, or insertions in the SrKO sequence. For example, a structural model of the SrKO amino acid sequence may be created using the coordinates for P45017A1. As demonstrated herein, such a homology model is useful for directing improvement of SrKO for valencene oxygenation. Thus, in various embodiments, the SrKO derivative may have from about 1 to about 45 mutations, about 1 to about 40 mutations, about 1 to about 35 mutations, from about 1 to about 30 mutations, about 1 to about 25 mutations, from about 1 to about 20 mutations, about 1 to about 15 mutations, about 1 to about 10 mutations, or from about 1 to about 5 mutations relative to SrKO (SEQ ID NO: 37, 38, or 55). In various embodiments, the SrKO comprises a sequence having at least 5 or at least 10 mutations with respect to SEQ ID NO: 37, 38, or 55, but not more than about 20 or 30 mutations. In various embodiments, the SrKO derivative may have about 1 mutation, about 2 mutations, about 3 mutations, about 4 mutations, about 5 mutations, about 6 mutations, about 7 mutations, about 8 mutations, about 9 mutations, about 10 mutations, about 11 mutations, about 12 mutations, about 13 mutations, about 14 mutations, about 15 mutations, about 16 mutations, about 17 mutations, about 18 mutations, about 19 mutations, about 20 mutations, about 21 mutations, about 22 mutations, about 23 mutations, about 24 mutations, about 25 mutations, about 26 mutations, about 27 mutations, about 28 mutations, about 29 mutations, about 30 mutations, about 31 mutations, about 32 mutations, about 33 mutations, about 34 mutations, about 35 mutations, about 36 mutations, about 37 mutations, about 38 mutations, about 39 mutations, about 40 mutations, about 41 mutations, about 42 mutations, about 43 mutations, about 44 mutations, about 45 mutations, about 46 mutations, about 47 mutations, about 48 mutations, about 49 mutations, or about 50 mutations relative to SrKO (SEQ ID NO: 37, 38, or 55). SEQ ID NO: 37, and other WT enzymes disclosed herein, can optionally contain an Ala inserted at position 2 where not present in the wild-type.

In these or other embodiments, the SrKO derivative may comprise an amino acid sequence having at least about 50% sequence identity, at least about 55% sequence identity, at least about 60% sequence identity, at least about 65% sequence identity, at least about 70% sequence identity, at least about 75% sequence identity, at least about 80% sequence identity, at least about 85% sequence identity, or at least 90% sequence identity, or at least 91% sequence identity, or at least 92% sequence identity, or at least 93% sequence identity, or at least 94% sequence identity, or at least 95% sequence identity, or at least 96% sequence identity, or at least 97% sequence identity, or at least 98% sequence identity, or at least 99% sequence identity, to SrKO (SEQ ID NO: 37, 38, or 55). In various embodiments, the SrKO derivative has higher activity for the oxygenation of valencene than the wild type enzyme, such as a higher production of oxygenated oil upon contact with valencene substrate than the wild type enzyme (SEQ ID NO: 37) or the wild type enzyme as modified for functional expression in *E. coli* (e.g., SEQ ID NO: 38). For example, the SrKO derivative may comprise an amino acid sequence having at least: about 50% identity, about 51% identity, about 52% identity, about 53% identity, about 54% identity, about 55% identity, about 56% identity, about 57% identity, about 58% identity, about 59% identity, about 60% identity, about 61% identity, about 62% identity, about 63% identity, about 64% identity, about 65% identity, about 66% identity, about 67% identity, about 68% identity, about 69% identity, about 70% identity, about 71% identity, about 72% identity, about 73% identity, about 74% identity, about 75% identity, about 76% identity, about 77% identity, about 78% identity, about 79% identity, about 80% identity, about 81% identity, about 82% identity, about 83% identity, about 84% identity, about 85% identity, about 86% identity, about 87% identity, about 88% identity, about 89% identity, about 90% identity, about 91% sequence identity, about 92% sequence identity, about 93% sequence identity, about 94% sequence identity, about 95% sequence identity, about 96% sequence identity, about 97% sequence identity, about 98% sequence identity, or about 99% sequence identity to SrKO (SEQ ID NO: 37, 38, or 55).

In some embodiments, mutants are selected for an increase in production of oxygenated valencene, such as nootkatone, α-nootkatol, and/or β-nootkatol. For example, the SrKO derivative may have one or more mutations at positions selected from 46, 76, 94, 131, 231, 284, 383, 390, 400, 444, 468, 488 and 499, numbered according to SEQ ID NO: 37. For example, in some embodiments, the SrKO is a derivative comprising an amino acid sequence having one or more (or all) of the mutations selected from H46R, R76K, M94V, T131Q, F231L, H284Q, R383K, I390L, V400Q, I444A, T468I, T488D, and T499N, numbered according to SEQ ID NO: 37. In certain embodiments, the SrKO is a derivative comprising an amino acid sequence having one or more (or all) of the mutations selected from R76K, M94V, T131Q, F231L, H284Q, R383K, I390L, T468I, and T499N, numbered according to SEQ ID NO: 37. In some embodiments, the SrKO derivative comprises an amino acid sequence selected from SEQ ID NOS: 55-61, which were engineered according to this disclosure to improve activity for oxygenation of valencene (e.g., production of nootkatone). In some embodiments, the derivative comprises an amino acid sequence having from one to twenty mutations relative to a sequence selected from SEQ ID NOS: 55-61, with the proviso that the amino acid sequence has one or more mutations at positions selected from 46, 76, 94, 131, 231, 284, 383, 390, 400, 444, 468, 488, and 499 (numbered according to SEQ ID NO: 37), or the proviso that the SrKO derivative comprises an amino acid sequence having one or more (or all) of the mutations selected from H46R, R76K, M94V, T131Q, F231L, H284Q, R383K, I390L, V400Q, I444A, T468I, T488D, and T499N (numbered according to SEQ ID NO: 37). In certain embodiments, the derivative comprises an amino acid sequence having from one to twenty mutations relative to a sequence selected from SEQ ID NOS: 55-61, with the proviso that the amino acid sequence has one or more mutations at positions selected from 46, 76, 94, 131, 231, 284, 383, 390, 400, 444, 468, 488, and 499 (numbered according to SEQ ID NO: 37), or the proviso that the SrKO derivative comprises an amino acid sequence having one or more (or all) of the mutations selected from R76K, M94V, T131Q, F231L, H284Q, R383K, I390L, T4681, and T499N (numbered according to SEQ ID NO: 37).

In some embodiments, the disclosure provides a recombinant polynucleotide encoding the SrKO derivative described above, which may be inserted into expression vectors for expression and optional purification. In some embodiments, the polynucleotide is incorporated into the genome of valencene-producing cells, such as valencene-producing *E. coli* cells.

The SrKO or derivative in various embodiments has valencene oxidase activity. Assays for determining and quantifying valencene oxidase activity are described herein and are known in the art. Assays include expressing the SrKO (or derivative) in valencene-producing cells (e.g., *E. coli* expressing FPPS and valencene synthase), and extracting the oxygenated oil from the aqueous reaction media. The profile of terpenoid product can be determined quantitatively by GC/MS. Various mutations of SrKO tested for effect on valencene oxidase activity are listed in Tables 2.1, 2.2, 2.3 and/or 6. Thus, in various embodiments, the SrKO may have at least about 1, at least about 2, at least about 3, at least about 4, at least about 5, at least about 6, at least about 7, at least about 8, at least about 9, or at least about 10 mutations selected from Tables 2.1, 2.2, 2.3 and/or 6. In some embodiments, the SrKO derivative is a modified SrKO polypeptide comprising an amino acid sequence which has up to 25 mutations compared to the wild type protein according to SEQ ID NO: 37 (or its counterpart that is modified for expression in *E. coli*), and comprises at least the substitutions I310V, V375I or T487N in combination with at least any one or more of V375F, V375A, V375M, M120L, M1201, M120V, F129L, F1291, L114V, L114F and V121A (numbered according to SEQ ID NO: 38) (see Table 6), and optionally comprises a leader sequence (as shown in SEQ ID NO: 38) supporting functional expression in *E. coli*.

TABLE 2.1

Summary of some *Stevia rebaudiana* kaurene oxidase mutations tested, numbered according to wild type SrKO (SEQ ID NOS: 37 and 108), 8rp-t20SrKO (SEQ ID NOS: 38 and 106), n22yhcB-t30VO1 (SEQ ID NO: 104), and n22yhcB-t30VO2 (SEQ ID NOS: 61 and 105).

| No. | WT | Position SEQ ID NO: 37 (SEQ ID NO: 108)/ SEQ ID NO: 38 (SEQ ID NO: 106) | Position SEQ ID NO: 104/ SEQ ID NO: 105 (SEQ ID NO: 61) | Mutation (relative to SEQ ID NO: 37 (SEQ ID NO: 108)/SEQ ID NO: 38 (SEQ ID NO: 106) |
|---|---|---|---|---|
| 1 | L | 59/47 | 51 | I |
| 2 | Y | 71/59 | 63 | H |
| 3 | M | 72/60 | 64 | K |
| 4 | T | 75/63 | 67 | A |
| 5 | A | 79/67 | 71 | E |
| 6 | K | 88/76 | 80 | R |
| 7 | T | 92/80 | 84 | C |
| 8 | M | 94/82 | 86 | V |
| 9 | V | 97/85 | 89 | L |
| 10 | V | 97/85 | 89 | I |
| 11 | S | 98/86 | 90 | N |
| 12 | Q | 112/100 | 104 | S |
| 13 | N | 118/106 | 110 | K |
| 14 | K | 124/112 | 116 | T |
| 15 | A | 128/116 | 120 | R |
| 16 | T | 131/119 | 123 | S |
| 17 | M | 135/123 | 127 | T |
| 18 | M | 135/123 | 127 | Q |
| 19 | M | 135/123 | 127 | F |
| 20 | M | 135/123 | 127 | T |
| 21 | D | 139/127 | 131 | G |
| 22 | Y | 141/129 | 133 | F |
| 23 | A | 152/140 | 144 | R |
| 24 | K | 161/149 | 153 | R |
| 25 | H | 162/150 | 154 | F |
| 26 | N | 183/171 | 175 | D |
| 27 | L | 192/180 | 184 | F |
| 28 | I | 195/183 | 187 | V |
| 29 | D | 220/208 | 212 | E |
| 30 | D | 244/232 | 236 | E |
| 31 | S | 279/267 | 271 | A |
| 32 | H | 284/272 | 276 | Q |
| 33 | S | 296/284 | 288 | C |
| 34 | I | 298/286 | 290 | L |
| 35 | Q | 306/294 | 298 | K |
| 36 | Q | 311/299 | 303 | E |
| 37 | I | 322/310 | 314 | T |

TABLE 2.1-continued

Summary of some *Stevia rebaudiana* kaurene oxidase mutations tested, numbered according to wild type SrKO (SEQ ID NOS: 37 and 108), 8rp-t20SrKO (SEQ ID NOS: 38 and 106), n22yhcB-t30VO1 (SEQ ID NO: 104), and n22yhcB-t30VO2 (SEQ ID NOS: 61 and 105).

| No. | WT | Position SEQ ID NO: 37 (SEQ ID NO: 108)/ SEQ ID NO: 38 (SEQ ID NO: 106) | Position SEQ ID NO: 104/ SEQ ID NO: 105 (SEQ ID NO: 61) | Mutation (relative to SEQ ID NO: 37 (SEQ ID NO: 108)/SEQ ID NO: 38 (SEQ ID NO: 106) |
|---|---|---|---|---|
| 38 | I | 322/310 | 314 | V |
| 39 | R | 383/371 | 375 | K |
| 40 | R | 383/371 | 375 | I |
| 41 | V | 387/375 | 379 | T |
| 42 | V | 387/375 | 379 | I |
| 43 | V | 387/375 | 379 | L |
| 44 | I | 390/378 | 382 | V |
| 45 | H | 394/382 | 386 | Y |
| 46 | V | 400/388 | 392 | Q |
| 47 | V | 400/388 | 392 | M |
| 48 | H | 405/393 | 397 | D |
| 49 | L | 412/400 | 404 | I |
| 50 | V | 425/413 | 417 | D |
| 51 | V | 425/413 | 417 | K |
| 52 | F | 446/434 | 438 | L |
| 53 | G | 454/442 | 446 | A |
| 54 | S | 462/450 | 454 | A |
| 55 | L | 466/454 | 458 | M |
| 56 | G | 472/460 | 464 | A |
| 57 | M | 476/464 | 468 | L |
| 58 | M | 487/475 | 479 | G |
| 59 | T | 499/487 | 491 | N |
| 60 | P | 504/492 | 496 | K |
| 61 | I | 509/497 | 501 | L |
| | T | 499/487 | 491 | S |
| 62 | M | 135/123 | 127 | Q |
| | T | 499/487 | 491 | V |
| 63 | M | 135/123 | 127 | F |
| | T | 499/487 | 491 | V |
| 64 | M | 135/123 | 127 | F |
| | T | 499/487 | 491 | F |
| 65 | M | 135/123 | 127 | F |
| | T | 499/487 | 491 | M |
| 66 | M | 135/123 | 127 | F |
| | T | 499/487 | 491 | G |

TABLE 2.2

The following mutants were evaluated in the VO1 background (n22-yhcB-t30-VO1, SEQ ID NO: 110) according to wild type SrKO (SEQ ID NOS: 37 and 108), 8rp-t20SrKO (SEQ ID NOS: 38 and 106), n22yhcB-t30VO1 (SEQ ID NO: 104) and n22yhcB-t30VO2 (SEQ ID NOS: 61 and 105).

| No. | WT | Position SEQ ID NO: 37 (SEQ ID NO: 108)/ SEQ ID NO: 38 (SEQ ID NO: 106) | Position SEQ ID NO: 104/ SEQ ID NO: 105 (SEQ ID NO: 61) | Mutation (relative to SEQ ID NO: 37 (SEQ ID NO: 108)/ SEQ ID NO: 38 (SEQ ID NO: 106) |
|---|---|---|---|---|
| 1 | A | 2 | | T |
| 2 | H | 46/34 | 38 | R |
| 3 | E | 52/40 | 44 | A |
| 4 | R | 76/64 | 68 | K |
| 5 | M | 94/82 | 86 | V |
| 6 | T | 131/119 | 123 | K |
| 7 | T | 131/119 | 123 | Q |
| 8 | L | 150/138 | 142 | M |
| 9 | D | 191/179 | 183 | N |
| 10 | L | 231/219 | 223 | M |
| 11 | Q | 268/256 | 260 | T |
| 12 | E | 323/311 | 315 | L |
| 13 | K | 344/332 | 336 | D |
| 14 | R | 351/339 | 343 | Q |
| 15 | I | 389/377 | 381 | L |
| 16 | I | 389/377 | 381 | V |
| 17 | I | 389/377 | 381 | A |
| 18 | I | 390/378 | 382 | L |
| 19 | I | 390/378 | 382 | M |
| 20 | V | 400/388 | 392 | Q |
| 21 | I | 444/432 | 436 | A |
| 22 | T | 468/456 | 460 | I |
| 23 | T | 488/476 | 480 | D |
| 24 | E | 491/479 | 483 | K |
| 25 | I | 495/483 | 487 | V |

TABLE 2.3

Summary of mutations of several engineered SrKO derivatives based on alignments relative to wild type Sr KO (SEQ ID NOS: 37 and 108). The point mutations for each of the SrKO derivatives (SEQ ID NOS: 38, 61, 104, 105, 106, and 107) are identified based on the shift value for each sequence relative to wild type SrKO. 8rp-t20SrKO (SEQ ID NOS: 38 and 106) is the SrKO sequence with a 20-amino acid truncation at the N-terminus, and the addition of an 8-amino acid membrane anchor. 8rp-t20VO0 (SEQ ID NO: 107) has a truncation of 20 amino acids of the SrKO N-terminus, the addition of an 8-amino acid N-terminal anchor, and a single mutation at position 487. n22yhcB-t30VO1 (SEQ ID NO: 104) has a 30-amino acid truncation of the SrKO N-terminus, a membrane anchor based on 22 amino acids from *E. coli* yhcB, and eight point mutations at positions 38, 223, 276, 375, 392, 436, 480, and 491, and a n22t30-yhcB mutation. n22yhcB-t30VO2 (SEQ ID NOS: 61 and 105) has a 30-amino acid truncation of the SrKO N-terminus, a membrane anchor based on 22 amino acids from *E. coli* yhcB, and nine point mutations at positions 68, 86, 123, 223, 276, 375, 382, 460, and 491, and a n22t30-yhcB mutation.

| Wild Type SrKO (SEQ ID NOS: 37 and 108) (Shift Value: 0) | 8rp-t20SrKO (SEQ ID NOS: 38 and 106) (Shift Value: −12) | 8rp-t20VO0 (SEQ ID NO: 107) (Shift Value: −12) | n22yhcB-t30VO1 (SEQ ID NO: 104) (Shift Value: −8) | n22yhcB-t30VO2 (SEQ ID NOS: 61 and 105) (Shift Value: −8) |
|---|---|---|---|---|
| H46 | H34 | | H38R | |
| R76 | R64 | | | R68K |
| M94 | M82 | | | M86V |
| T131 | T119 | | | T123Q |
| F231 | F219 | | F223L | F223L |
| H284 | H272 | | H276Q | H276Q |
| R383 | R371 | | R375K | R375K |
| I390 | 1378 | | | I382L |
| V400 | V388 | | V392Q | |
| I444 | I432 | | I436A | |
| T468 | T456 | | | T460I |
| T488 | T476 | | T480D | |
| T499 | T487 | T487N | T491N | T491N |

The SrKO may be expressed in a variety of host cells, either for recombinant protein production, or for sesquiterpene (e.g., valencene) oxidation. For example, the host cells include those described in US 8,512,988, which is hereby incorporated by reference in its entirety. The host cell may be a prokaryotic or eukaryotic cell. In some embodiments the cell is a bacterial cell, such as *Escherichia* spp., *Streptomyces* spp., *Zymonas* spp., *Acetobacter* spp., *Citrobacter* spp., *Synechocystis* spp., *Rhizobiwn* spp., *Clostridium* spp., *Cory nebacterium* spp., *Streptococcus* spp., *Xanthomonas* spp., *Lactobacillus* .spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp., and *Pantoea* spp. The bacterial cell can be a Gram-negative cell such as an *Escherichia coli* (*E. coli*) cell, or a Gram-positive cell such as a species of *Bacillus*. In other embodiments, the cell is a fungal cell such as a yeast cell, such as, for example, *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., *Yarrowia* spp., and industrial polyploid yeast strains. In an embodiment, the host cell is a bacterium selected from *E. coli, Bacillus subtillus*, or *Pseudomonas putida*. In an embodiment, the host cell is a yeast, and may be a species of *Saccharomyces, Pichia*, or *Yarrowia*, including *Saccharomyces cerevisiae, Pichia pastoris*, and *Yarrowia lipolytica*.

In some embodiments, the host cell produces isopentyl pyrophosphate (IPP), which acts as a substrate for the synthesis of the sesquiterpene. In some embodiments, the IPP is produced by metabolic flux (e.g., starting with a carbon source supplied to the cell) through an endogenous or heterologous methylerythritol phosphate (MEP) or mevalonic acid (MVA) pathway. In certain embodiments, the MEP or MVA pathway may be enhanced through expression of heterologous enzymes or duplication of certain enzymes in the pathway.

The MEP (2-C-methyl-D-erythritol 4-phosphate) pathway, also called the MEP/DOXP (2-C-methyl-D-erythritol 4-phosphate/1-deoxy-D-xylulose 5-phosphate) pathway or the non-mevalonate pathway or the mevalonic acid-independent pathway refers to the pathway that converts glyceraldehyde-3-phosphate and pyruvate to IPP and DMAPP. The pathway typically involves action of the following enzymes: 1-deoxy-D-xylulose-5-phosphate synthase (Dxs), 1-deoxy-D-xylulose-5-phosphate reductoisomerase (IspC), 4-diphosphocytidyl-2-C-methyl-D-erythritol synthase (IspD), 4-diphosphocytidyl-2-C-methyl-D-erythritol kinase (IspE), 2C-methyl-D-erythritol 2,4-cyclodiphosphate synthase (IspF), 1-hydroxy-2-methyl-2-(E)-butenyl 4-diphosphate synthase (IspG), and isopentenyl diphosphate isomerase (IspH). The MEP pathway, and the genes and enzymes that make up the MEP pathway, are described in US 8,512,988, which is hereby incorporated by reference in its entirety. For example, genes that make up the MEP pathway include dxs, ispC, ispD, ispE, ispF, ispG, ispH, idi, and ispA. In some embodiments, the sesquiterpene is produced at least in part by metabolic flux through an MEP pathway, and wherein the host cell has at least one additional copy of a dxs, ispD, ispF, and/or idi gene (e.g., dxs and idi; or dxs, ispD, ispF, and/or idi).

The MVA pathway refers to the biosynthetic pathway that converts acetyl-CoA to IPP. The mevalonate pathway typically comprises enzymes that catalyze the following steps: (a) condensing two molecules of acetyl-CoA to acetoacetyl-CoA (e.g., by action of acetoacetyl-CoA thiolase); (b) condensing acetoacetyl-CoA with acetyl-CoA to form hydroxymethylglutaryl-CoenzymeA (HMG-CoA) (e.g., by action of HMG-CoA synthase (HMGS)); (c) converting HMG-CoA to mevalonate (e.g., by action of HMG-CoA reductase (HMGR)); (d) phosphorylating mevalonate to mevalonate 5-phosphate (e.g., by action of mevalonate kinase (MK)); (e) converting mevalonate 5-phosphate to mevalonate 5-pyrophosphate (e.g., by action of phosphomevalonate kinase (PMK)); and (f) converting mevalonate 5-pyrophosphate to isopentenyl pyrophosphate (e.g., by action of mevalonate pyrophosphate decarboxylase (MPD)). The MVA pathway, and the genes and enzymes that make up the MEP pathway, are described in U.S. Pat. No. 7,667,017, which is hereby incorporated by reference in its entirety.

In some embodiments, the host cell expresses a farnesyl pyrophosphate synthase (FPPS), which produces farnesyl pyrophosphate from IPP or DMAPP. As shown in FIG. 1, farnesyl pyrophosphate is an intermediate for production of valencene. An exemplary farnesyl pyrophosphate synthase is ERG20 of *Saccharomyces cerevisiae* (NCBI accession P08524) and *E. coli* ispA. Various other prokaryotic, yeast, plant, and mammalian FPPS enzymes are known, and may be used in accordance with this aspect.

The host cell may further express a heterologous sesquiterpene synthase to produce the desired sesquiterpene, such as a valencene synthase. Several valencene synthase enzymes are known including valencene synthase from *Citrus x paradisi* or from *Citrus sinensis. Citrus sinensis* VS (e.g., AAQ04608.1) as well as various derivatives thereof are described in US 2012/0246767, which is hereby incorporated by reference. For example, the disclosure may employ an amino acid sequence of *Citrus sinensis* valencene synthase (CsVS) (SEQ ID NO: 12), or a derivative, having from 1 to 30 mutations or from 1 to 20 or from 1 to 10 mutations with respect to the wild type amino acid sequence (SEQ ID NO: 12). Such sequences may have at least 60% sequence identity, at least 70% sequence identity, at least 80% sequence identity, at least 90% sequence identity, at least 95% sequence identity, or at least about 96%, about 97%, about 98%, or about 99% sequence identity with the wild type sequence (SEQ ID NO: 12). Further, valencene synthase from *Vitis vinifera* (VvVS) (SEQ ID NO: 1) has been described by Licker et al. (Phytochemistry (2004) 65: 2649-2659). In an embodiment, a valencene synthase comprising the amino acid sequence of VvVS (SEQ ID NO: 1) or an engineered derivative thereof may be employed with the present disclosure. Various sesquiterpene synthase enzymes such as valencene synthase are known and are described in, for example, US 2012/0107893, US 2012/0246767, and U.S. Pat. No. 7,273,735, which are hereby incorporated by reference in their entireties.

For example, in some embodiments, the valencene synthase is a VvVS derivative that comprises an amino acid sequence having from about 1 to about 40 mutations, from about 1 to about 35 mutations, from about 1 to about 30 mutations, about 1 to about 25 mutations, from about 1 to about 20 mutations, about 1 to about 15 mutations, or from about 1 to about 10 mutations independently selected from substitutions, deletions, or insertions with respect to VvVS (SEQ ID NO: 1). For example, the VvVS derivative may comprise an amino acid sequence having at least about 5 or at least about 10, but less than about 30 or about 20 mutations with respect to SEQ ID NO: 1. In various embodiments, the VvVS derivative comprises an amino acid sequence that has about 1 mutation, about 2 mutations, about 3 mutations, about 4 mutations, about 5 mutations, about 6 mutations, about 7 mutations, about 8 mutations, about 9 mutations, about 10 mutations, about 11 mutations, about 12 mutations, about 13 mutations, about 14 mutations, about 15 mutations, about 16 mutations, about 17 mutations, about 18 mutations, about 19 mutations, about 20 mutations, about 21 mutations, about 22 mutations, about 23 mutations, about 24 mutations, about 25 mutations, about 26 mutations, about 27 mutations, about 28 mutations, about 29 mutations, about 30 mutations, about 31 mutations, about 32 mutations, about 33 mutations, about 34 mutations, about 35 mutations, about 36 mutations, about 37 mutations, about 38 mutations, about 39 mutations, or about 40 mutations relative to VvVS (SEQ ID NO: 1). Such sequences may have at least 60% sequence identity, at least 70% sequence identity, at least 80% sequence identity, at least 90% sequence identity, at least 95% sequence identity, or at least about 96%, about 97%, about 98%, or about 99% sequence identity with SEQ ID NO:1. Exemplary mutations of VvVS are shown in Table 3. Mutations can be guided by a homology model of *Vitis vinifera* valencene synthase (VvVS) based on the 5-epi-aristolochene synthase crystal structure as a template (PDB: SEAT).

TABLE 3.1

Summary of *Vitis vinifera* valencene synthase mutations with respect to wild type (SEQ ID NO: 1)

| No. | WT | Position | Mutation |
|---|---|---|---|
| 1 | N | 23 | D |
| 2 | T | 37 | R |
| 3 | P | 38 | S |
| 4 | V | 42 | R |
| 5 | A | 45 | E |
| 6 | C | 46 | K |
| 7 | Q | 50 | R |
| 8 | K | 56 | E |
| 9 | K | 59 | R |
| 10 | R | 60 | K |
| 11 | K | 61 | M |
| 12 | T | 63 | R |
| 13 | T | 63 | K |
| 14 | N | 69 | Q |
| 15 | N | 69 | K |
| 16 | S | 71 | I |
| 17 | Q | 72 | R |
| 18 | L | 73 | K |
| 19 | N | 75 | E |
| 20 | F | 76 | M |
| 21 | F | 76 | L |
| 22 | V | 80 | M |
| 23 | V | 80 | L |
| 24 | V | 85 | I |
| 25 | A | 86 | S |
| 26 | Q | 91 | D |
| 27 | A | 96 | I |
| 28 | Q | 98 | E |
| 29 | Q | 98 | D |
| 30 | C | 101 | Y |
| 31 | N | 102 | H |
| 32 | S | 103 | D |
| 33 | F | 104 | D |
| 34 | F | 104 | N |
| 35 | D | 111 | E |
| 36 | N | 116 | T |
| 37 | I | 117 | S |

TABLE 3.1-continued

Summary of *Vitis vinifera* valencene synthase mutations with respect to wild type (SEQ ID NO: 1)

| No. | WT | Position | Mutation |
|---|---|---|---|
| 38 | I | 117 | V |
| 39 | I | 117 | T |
| 40 | G | 120 | R |
| 41 | Q | 127 | H |
| 42 | T | 130 | N |
| 43 | I | 131 | V |
| 44 | I | 135 | V |
| 45 | T | 140 | K |
| 46 | E | 142 | K |
| 47 | E | 148 | D |
| 48 | A | 149 | S |
| 49 | A | 149 | D |
| 50 | I | 151 | S |
| 51 | R | 155 | K |
| 52 | M | 157 | L |
| 53 | G | 159 | S |
| 54 | G | 159 | N |
| 55 | E | 162 | Q |
| 56 | E | 162 | K |
| 57 | A | 164 | S |
| 58 | V | 168 | T |
| 59 | G | 170 | D |
| 60 | L | 174 | M |
| 61 | A | 175 | E |
| 62 | A | 175 | D |
| 63 | K | 176 | E |
| 64 | T | 183 | K |
| 65 | A | 187 | S |
| 66 | M | 188 | L |
| 67 | E | 190 | N |
| 68 | G | 193 | K |
| 69 | A | 201 | S |
| 70 | N | 205 | E |
| 71 | R | 206 | Q |
| 72 | I | 208 | L |
| 73 | R | 209 | H |
| 74 | G | 211 | R |
| 75 | L | 212 | M |
| 76 | E | 213 | P |
| 77 | I | 221 | L |
| 78 | V | 223 | R |
| 79 | Q | 225 | D |
| 80 | Q | 225 | E |
| 81 | D | 226 | K |
| 82 | D | 226 | E |
| 83 | A | 228 | E |
| 84 | F | 229 | I |
| 85 | H | 230 | V |
| 86 | D | 231 | N |
| 87 | K | 232 | E |
| 88 | T | 233 | A |
| 89 | T | 233 | V |
| 90 | S | 247 | D |
| 91 | L | 248 | M |
| 92 | L | 248 | K |
| 93 | K | 250 | Q |
| 94 | E | 251 | K |
| 95 | S | 254 | K |
| 96 | N | 255 | E |
| 97 | A | 257 | S |
| 98 | K | 261 | A |
| 99 | E | 262 | D |
| 100 | D | 264 | G |
| 101 | Y | 280 | F |
| 102 | M | 283 | I |
| 103 | H | 284 | M |
| 104 | H | 284 | A |
| 105 | G | 285 | A |
| 106 | Y | 287 | F |
| 107 | Q | 291 | N |
| 108 | R | 294 | L |
| 109 | R | 297 | I |
| 110 | L | 299 | M |
| 111 | M | 305 | A |
| 112 | M | 305 | L |

TABLE 3.1-continued

Summary of *Vitis vinifera* valencene synthase mutations with respect to wild type (SEQ ID NO: 1)

| No. | WT | Position | Mutation |
|---|---|---|---|
| 113 | I | 308 | M |
| 114 | T | 318 | S |
| 115 | P | 319 | L |
| 116 | P | 319 | I |
| 117 | K | 323 | Q |
| 118 | R | 331 | K |
| 119 | D | 333 | E |
| 120 | I | 334 | E |
| 121 | I | 334 | V |
| 122 | N | 335 | K |
| 123 | N | 335 | Q |
| 124 | N | 335 | S |
| 125 | S | 336 | A |
| 126 | Y | 343 | W |
| 127 | Y | 348 | F |
| 128 | V | 349 | L |
| 129 | L | 352 | I |
| 130 | D | 353 | E |
| 131 | D | 353 | N |
| 132 | V | 354 | T |
| 133 | Y | 355 | F |
| 134 | K | 356 | E |
| 135 | K | 356 | N |
| 136 | I | 358 | V |
| 137 | E | 359 | D |
| 138 | E | 360 | Y |
| 139 | E | 363 | K |
| 140 | E | 363 | L |
| 141 | G | 366 | A |
| 142 | Y | 369 | N |
| 143 | R | 370 | V |
| 144 | V | 371 | I |
| 145 | H | 372 | E |
| 146 | H | 372 | P |
| 147 | A | 374 | G |
| 148 | A | 374 | L |
| 149 | E | 376 | D |
| 150 | M | 378 | I |
| 151 | N | 380 | I |
| 152 | N | 380 | K |
| 153 | R | 383 | Q |
| 154 | E | 394 | Q |
| 155 | E | 394 | D |
| 156 | E | 395 | N |
| 157 | E | 395 | G |
| 158 | H | 396 | Y |
| 159 | H | 396 | Q |
| 160 | E | 402 | D |
| 161 | R | 405 | E |
| 162 | C | 414 | R |
| 163 | L | 415 | M |
| 164 | A | 417 | L |
| 165 | T | 418 | V |
| 166 | T | 419 | H |
| 167 | V | 422 | L |
| 168 | M | 424 | V |
| 169 | A | 428 | V |
| 170 | T | 429 | S |
| 171 | T | 437 | F |
| 172 | S | 438 | G |
| 173 | D | 439 | Y |
| 174 | K | 441 | R |
| 175 | I | 442 | M |
| 176 | I | 442 | L |
| 177 | M | 443 | V |
| 178 | S | 444 | R |
| 179 | N | 447 | S |
| 180 | F | 448 | T |
| 181 | M | 453 | A |
| 182 | G | 466 | E |
| 183 | T | 469 | A |
| 184 | Q | 478 | E |
| 185 | Y | 479 | F |
| 186 | G | 480 | A |
| 187 | V | 481 | A |

TABLE 3.1-continued

Summary of *Vitis vinifera* valencene synthase mutations with respect to wild type (SEQ ID NO: 1)

| No. | WT | Position | Mutation |
|---|---|---|---|
| 188 | S | 482 | T |
| 189 | Y | 487 | C |
| 190 | S | 488 | E |
| 191 | E | 489 | H |
| 192 | F | 490 | I |
| 193 | F | 490 | L |
| 194 | Q | 491 | K |
| 195 | Q | 491 | N |
| 196 | Q | 493 | L |
| 197 | I | 494 | M |
| 198 | N | 496 | D |
| 199 | D | 500 | E |
| 200 | L | 506 | M |
| 201 | T | 509 | S |
| 202 | V | 511 | M |
| 203 | S | 512 | P |
| 204 | S | 512 | T |
| 205 | M | 513 | K |
| 206 | P | 514 | D |
| 207 | L | 519 | A |
| 208 | D | 527 | E |
| 209 | V | 528 | F |
| 210 | E | 532 | D |
| 211 | Q | 533 | E |
| 212 | Q | 533 | G |
| 213 | S | 535 | G |
| 214 | V | 539 | S |
| 215 | V | 542 | L |
| 216 | V | 542 | T |
| 217 | M | 543 | I |
| 218 | N | 546 | H |
| 219 | V | 550 | L |
| 220 | F | 551 | L |
| 221 | I | 552 | V |
| 222 | N | 553 | D |
| 223 | N | 553 | E |
| 224 | A | 554 | P |
| 225 | V | 555 | I |

TABLE 3.2

Summary of mutations evaluated in the Vv2M5 background (SEQ ID NO: 9).

| No. | WT | Position | Mutation |
|---|---|---|---|
| 226 | N | 18 | V |
| 227 | V | 21 | S |
| 228 | N | 23 | D |
| 229 | N | 27 | S |
| 230 | Q | 32 | H |
| 231 | I | 34 | L |
| 232 | T | 35 | S |
| 233 | T | 37 | S |
| 234 | K | 41 | S |
| 235 | V | 42 | E |
| 236 | A | 45 | E |
| 237 | K | 46 | C |
| 238 | K | 47 | M |
| 239 | Q | 50 | R |
| 240 | I | 51 | V |
| 241 | D | 53 | E |
| 242 | K | 56 | E |
| 243 | V | 67 | A |
| 244 | A | 68 | N |
| 245 | N | 69 | D |
| 246 | N | 69 | Q |
| 247 | S | 71 | L |
| 248 | Q | 72 | R |
| 249 | V | 80 | I |
| 250 | A | 86 | S |
| 251 | Q | 91 | K |

TABLE 3.2-continued

Summary of mutations evaluated in the Vv2M5 background (SEQ ID NO: 9).

| No. | WT | Position | Mutation |
|---|---|---|---|
| 252 | C | 101 | Y |
| 253 | N | 102 | D |
| 254 | N | 102 | H |
| 255 | M | 110 | D |
| 256 | D | 111 | E |
| 257 | G | 112 | D |
| 258 | I | 117 | S |
| 259 | T | 130 | N |
| 260 | R | 143 | E |
| 261 | R | 145 | N |
| 262 | A | 149 | S |
| 263 | S | 152 | N |
| 264 | G | 159 | N |
| 265 | G | 159 | S |
| 266 | V | 168 | T |
| 267 | K | 176 | E |
| 268 | K | 186 | E |
| 269 | A | 187 | S |
| 270 | S | 191 | H |
| 271 | Y | 194 | P |
| 272 | H | 195 | P |
| 273 | N | 205 | E |
| 274 | L | 212 | M |
| 275 | E | 213 | P |
| 276 | W | 219 | H |
| 277 | V | 223 | I |
| 278 | D | 226 | E |
| 279 | A | 228 | E |
| 280 | F | 229 | S |
| 281 | T | 233 | V |
| 282 | V | 245 | L |
| 283 | L | 248 | M |
| 284 | L | 256 | I |
| 285 | K | 261 | A |
| 286 | E | 262 | D |
| 287 | C | 347 | F |
| 288 | E | 363 | A |
| 289 | H | 372 | E |
| 290 | V | 377 | A |
| 291 | E | 395 | G |
| 292 | E | 395 | N |
| 293 | H | 396 | Y |
| 294 | A | 399 | T |
| 295 | C | 414 | R |
| 296 | E | 426 | D |
| 297 | S | 438 | G |
| 298 | M | 443 | I |
| 299 | T | 469 | A |
| 300 | S | 488 | E |
| 301 | K | 491 | R |
| 302 | M | 513 | K |
| 303 | A | 517 | E |
| 304 | L | 519 | V |
| 305 | E | 532 | D |
| 306 | V | 550 | L |
| 307 | N | 553 | D |

TABLE 3.3

Summary of mutations evaluated in VS2 background (SEQ ID NO: 11).

| No. | WT | Position | Mutation |
|---|---|---|---|
| 308 | P | 20 | R |
| 309 | N | 23 | D |
| 310 | I | 28 | F |
| 311 | K | 41 | P |
| 312 | K | 41 | S |
| 313 | V | 42 | D |
| 314 | R | 44 | H |
| 315 | Q | 50 | D |

TABLE 3.3-continued

Summary of mutations evaluated in VS2 background (SEQ ID NO: 11).

| No. | WT | Position | Mutation |
|---|---|---|---|
| 316 | Q | 50 | R |
| 317 | E | 52 | R |
| 318 | K | 61 | M |
| 319 | N | 69 | Q |
| 320 | Q | 72 | R |
| 321 | L | 73 | K |
| 322 | A | 79 | I |
| 323 | A | 86 | S |
| 324 | H | 88 | L |
| 325 | Q | 91 | H |
| 326 | A | 96 | I |
| 327 | Q | 98 | R |
| 328 | C | 101 | Y |
| 329 | N | 102 | H |
| 330 | C | 107 | F |
| 331 | I | 117 | S |
| 332 | G | 120 | L |
| 333 | T | 140 | K |
| 334 | R | 145 | N |
| 335 | S | 152 | V |
| 336 | V | 154 | I |
| 337 | V | 154 | P |
| 338 | R | 155 | K |
| 339 | M | 157 | L |
| 340 | G | 159 | M |
| 341 | A | 175 | D |
| 342 | K | 176 | E |
| 343 | A | 177 | P |
| 344 | L | 178 | I |
| 345 | H | 184 | Y |
| 346 | H | 184 | Q |
| 347 | A | 187 | S |
| 348 | S | 191 | H |
| 349 | H | 195 | N |
| 350 | L | 196 | P |
| 351 | A | 201 | R |
| 352 | L | 212 | M |
| 353 | E | 213 | P |
| 354 | A | 217 | Q |
| 355 | A | 228 | E |
| 356 | D | 231 | N |
| 357 | K | 232 | P |
| 358 | T | 233 | V |
| 359 | E | 236 | D |
| 360 | D | 241 | E |
| 361 | N | 255 | D |
| 362 | A | 257 | M |
| 363 | L | 276 | P |
| 364 | Y | 280 | F |
| 365 | M | 283 | I |
| 366 | V | 286 | A |
| 367 | T | 300 | M |
| 368 | T | 300 | I |
| 369 | T | 306 | L |
| 370 | T | 306 | I |
| 371 | L | 309 | I |
| 372 | A | 315 | V |
| 373 | E | 320 | D |
| 374 | K | 323 | R |
| 375 | S | 336 | T |
| 376 | E | 342 | D |
| 377 | C | 347 | L |
| 378 | A | 350 | I |
| 379 | N | 356 | H |
| 380 | E | 363 | G |
| 381 | Q | 368 | P |
| 382 | N | 380 | D |
| 383 | Q | 381 | L |
| 384 | E | 395 | G |
| 385 | A | 407 | G |
| 386 | A | 407 | S |
| 387 | C | 414 | P |
| 388 | A | 417 | I |
| 389 | A | 432 | I |
| 390 | V | 436 | L |
| 391 | I | 442 | P |
| 392 | I | 442 | L |
| 393 | S | 445 | R |
| 394 | S | 446 | M |
| 395 | T | 450 | C |
| 396 | S | 458 | T |
| 397 | H | 459 | Y |
| 398 | H | 459 | M |
| 399 | H | 467 | Q |
| 400 | T | 469 | A |
| 401 | E | 484 | P |
| 402 | Q | 485 | H |
| 403 | Q | 485 | E |
| 404 | V | 486 | A |
| 405 | Y | 487 | L |
| 406 | S | 488 | E |
| 407 | I | 494 | V |
| 408 | N | 496 | D |
| 409 | N | 496 | K |
| 410 | M | 513 | T |
| 411 | T | 523 | I |
| 412 | D | 527 | L |
| 413 | I | 529 | L |
| 414 | I | 529 | M |
| 415 | E | 532 | H |
| 416 | E | 532 | Y |
| 417 | S | 535 | A |
| 418 | R | 544 | H |
| 419 | N | 546 | Y |
| 420 | N | 546 | F |
| 421 | A | 548 | I |
| 422 | V | 550 | L |
| 423 | V | 555 | I |

Thus, in various embodiments, the engineered VvVS may have at least about 1 mutation, about 2 mutations, about 3 mutations, about 4 mutations, about 5 mutations, about 6 mutations, about 7 mutations, about 8 mutations, about 9 mutations, about 10 mutations, about 11 mutations, about 12 mutations, about 13 mutations, about 14 mutations, about 15 mutations, about 16 mutations, about 17 mutations, about 18 mutations, about 19 mutations, about 20 mutations, about 21 mutations, about 22 mutations, about 23 mutations, about 24 mutations, about 25 mutations, about 26 mutations, about 27 mutations, about 28 mutations, about 29 mutations, about 30 mutations, about 31 mutations, about 32 mutations, about 33 mutations, about 34 mutations, about 35 mutations, about 36 mutations, about 37 mutations, about 38 mutations, about 39 mutations, or about 40 mutations selected from Table 3. Exemplary recombinant valencene synthases Vv1M1 (SEQ ID NO: 3), Vv2M1 (SEQ ID NO: 5), Vv1M5 (SEQ ID NO: 7), Vv2M5 (SEQ ID NO: 9), and VS2 (SEQ ID NO: 11) are further depicted in FIG. 3, including an alignment in FIG. 3B. A further exemplary recombinant valencene synthase VS3 (SEQ ID NO: 129) is also depicted herein.

In certain aspects, the disclosure provides polynucleotides comprising a nucleotide sequence encoding a valencene synthase modified for increased expression of valencene as described above. Such polynucleotides may be expressed in host cells, either on extrachromosomal elements such as plasmids, or may be chromosomally integrated.

In various embodiments, the SrKO is expressed alongside a P450 reductase to regenerate the enzyme, or alternatively, the SrKO or derivative is expressed with the P450 reductase as a chimeric P450 enzyme. Functional expression of cytochrome P450 has been considered challenging due to the inherent limitations of bacterial platforms, such as the absence of electron transfer machinery and cytochrome P450 reductases, and translational incompatibility of the membrane signal modules of P450 enzymes due to the lack of an endoplasmic reticulum.

Accordingly, in some embodiments the SrKO is expressed as a fusion protein with a cytochrome P450 reductase partner. Cytochrome P450 reductase is a membrane protein found in the endoplasmic reticulum. It catalyzes pyridine nucleotide dehydration and electron transfer to membrane bound cytochrome P450s. Isozymes of similar structure are found in humans, plants, other mammals, and insects. Exemplary P450 reductase partners include, for example, *Stevia rebaudiana* (Sr)CPR (SEQ ID NOS: 62 and 63), *Stevia rebaudiana* (Sr)CPR1 (SEQ ID NOS: 76 and 77), *Arabidopsis thaliana* (At)CPR (SEQ ID NOS: 64 and 65), *Taxus cuspidata* (Tc) CPR (SEQ ID NOS: 66 and 67), *Artemisia annua* (Aa)CPR (SEQ ID NOS: 68 and 69), *Arabidopsis thaliana* (At)CPR1 (SEQ ID NOS: 70 and 71), *Arabidopsis thaliana* (At)CPR2 (SEQ ID NOS: 72 and 73), *Arabidopsis thaliana* (At)R2 (SEQ ID NOS: 74 and 75); *Stevia rebaudiana* (Sr)CPR2 (SEQ ID NOS: 78 and 79); *Stevia rebaudiana* (Sr)CPR3 (SEQ ID NOS: 80 and 81); *Pelargonium graveolens* (Pg)CPR (SEQ ID NO: 82 and 83). Any of these P450s can be derivatized in some embodiments, for example, to introduce from 1 to about 20 mutations, or from about 1 to about 10 mutations. FIG. 6B shows an alignment of amino acid sequences for *Arabidopsis thaliana* and *Arternisia annua* CPR sequences (SEQ ID NOS: 72, 74, 68, 64, and 70). FIG. 6C shows an alignment of *Stevia rebaudiana* CPR sequences (SEQ ID NOS: 78, 80, 62, and 76). FIG. 6D shows an alignment of eight CPR amino acid sequences (SEQ ID NOS: 74, 72, 82, 68, 80, 62, 78, and 76).

Engineering of P450 fusion proteins is disclosed, for example, in US 2012/0107893 and US 2012/0164678, both of which are hereby incorporated by reference in their entireties. In certain embodiments, the Si-KO is fused to the cytochrome P450 reductase partner through a linker. Exemplary linker sequences, which are predominantly serine, glycine, and/or alanine, and optionally from one to five charged amino acids such as lysine or arginine, include, for example, GSG, GSGGGGS (SEQ ID NO: 113), GSGEAAAK (SEQ ID NO: 114), GSGEAAAKEAAAK (SEQ ID NO: 115), GSGMGSSSN (SEQ ID NO: 116), and GSTGS (SEQ ID NO: 117). The linker is generally flexible, and contains no more than one, two, or three hydrophobic residues, and is generally from three to fifty amino acids in length, such as from three to twenty amino acids in length. In other embodiments, a P450 reductase is expressed in the host cell separately, and may be expressed in the same operon as the SrKO in some embodiments. In some embodiments, the P450 reductase enzyme is expressed separately in the host cell, and the gene is optionally integrated into the genome or expressed from a plasmid.

In certain embodiments the N-terminus of the P450 enzymes may be engineered to increase their functional expression. The N-terminus of membrane-bound P450 plays important roles in enzyme expression, membrane association and substrate access. It has been reported that the use of rare codons in the N-terminus of P450 significantly improved the expression level of P450. Further, since most plant P450 enzymes are membrane-bound and hydrophobic substrates are thought to enter the enzymes through channels dynamically established between the P450 and membrane, N-terminal engineering can affect the association of the membrane and P450 and therefore the access of substrate to the enzyme. Accordingly, in an embodiment, N-terminal engineering of SrKO generates an SrKO derivative that either maintains or shows enhanced valencene oxidase activity in a host system such as *E. coli* or yeast. An exemplary N-terminal sequence is 8rp or MALLLAVF (SEQ ID NO: 112), and other exemplary sequences include sequences of from four to twenty amino acids (such as from four to fifteen amino acids, or from four to ten amino acids, or about eight amino acids) that are predominately hydrophobic, for example, constructed predominately of (at least 50%, or at least 75%) amino acids selected from leucine, valine, alanine, isoleucine, and phenylalanine.

In some embodiments, the SrKO is a derivative having a deletion of at least a portion of its N-terminal transmembrane region, and the addition of an inner membrane transmembrane domain from *E. coli* yhcB or derivative thereof. In these embodiments, the P450 enzyme has a more stable and/or productive association with the *E. coli* inner membrane, which reduces cell stress otherwise induced by the expression of a membrane-associated P450 enzyme. In some embodiments, the SrKO is a derivative having a deletion of from 15 to 35 amino acids of its N-terminal transmembrane domain, and the addition of from 15 to 25 amino acids of the transmembrane domain from *E. coli* yhcB or derivative thereof. In some embodiments, the N-terminal transmembrane domain of the derivative comprises the amino acid sequence MAWEYALIGLVVGIIIGAVA (SEQ ID NO: 118), or an amino acid sequence having from 1 to 10 or from 1 to 5 amino acid mutations with respect to SEQ ID NO: 118.

In some embodiments, the host cell further expresses one or more enzymes, such as an alcohol dehydrogenase (ADH). In certain embodiments, the host cell may express an ADH enzyme producing nootkatone from nootkatol, examples of which include *Rhodococcus erythropolis* CDH (SEQ ID NO: 84), *Citrus sinensis* DH (SEQ ID NO: 86), *Citrus sinensis* DH1 (SEQ ID NO: 88), *Citrus sinensis* DH2 (SEQ ID NO: 90), *Citrus sinensis* DH3 (SEQ ID NO: 92), *Vitis vinifera* DH (SEQ ID NO: 94), *Vitis vinifera* DH1 (SEQ ID NO: 96), *Citrus sinensis* ABA2 (SEQ ID NO: 98), *Brachypodiuni distachyon* DH (SEQ ID NO: 100), and *Zingiber zerunibet* SDR (SEQ ID NO: 102). The ADH may comprise an amino acid sequence having at least 70%, at least 80%, or at least 90% sequence identity to one or more of the enzymes described in this paragraph, and with the activity of converting nootkatol to nootkatone.

Sesquiterpenes valencene and its oxygenated products) can be produced as biosynthetic products of the non-mevalonate pathway in *E. coli* comprising two modules: the native upstream pathway forming Isopentenyl Pyrophosphate (IPP) and a heterologous downstream terpenoid-forming pathway. A multivariate-modular approach to metabolic pathway engineering can be employed to optimize the production of sesquiterpenes in an engineered *E. coli*. The multivariate-modular pathway engineering approach is based on a systematic multivariate search to identify conditions that optimally balance the two pathway modules to minimize accumulation of inhibitory intermediates and flux diversion to side products.

WO 2011/060057, US 2011/0189717, US 2012/107893, and U.S. Pat. No. 8,512,988 (each of which are hereby incorporated by reference) describe methods and compositions for optimizing production of terpenoids in cells by controlling expression of genes or proteins participating in an upstream pathway and a downstream pathway. This can be achieved by grouping the enzyme pathways into two modules: an upstream (MEP) pathway module (e.g., containing one or more genes of the MEP pathway) and a downstream, heterologous pathway to sesquiterpene production. Using this basic configuration, parameters such as the effect of plasmid copy number on cell physiology, gene order and promoter strength in an expression cassette, and chromosomal integration are evaluated with respect to their effect on terpene and terpenoid (e.g., sesquiterpene) production. Expression of genes within the MEP pathway can thus be regulated in a modular method. As used herein, regulation by a modular method refers to regulation of multiple genes together. By way of example, multiple genes within the MEP pathway can be recombinantly expressed on a contiguous region of DNA, such as an operon. It should be appreciated that modules of genes within the MEP pathway, consistent with aspects of the disclosure, can contain any of the genes within the MEP pathway, in any order. In some embodiments, a gene within the MEP pathway is one of the following: dxs, ispC, ispD, ispE, ispF, ispG, ispH, idi, ispA or ispB. A non-limiting example of a module of genes within the MEP pathway is a module containing the genes dxs, idi, ispD and ispF, and referred to as dxs-idi-ispDF.

The manipulation of the expression of genes and/or proteins, including modules such as the dxs-idi-ispDF operon, and a FPPS-VS operon, can be achieved through methods known to one of ordinary skill in the art. For example, expression of the genes or operons can be regulated through selection of promoters, such as inducible promoters, with different strengths. Several non-limiting examples of promoters include Trc, T5 and T7. Additionally, expression of genes or operons can be regulated through manipulation of the copy number of the gene or operon in the cell.

The expression of one or more genes and/or proteins within the MEP pathway can be upregulated and/or downregulated. In certain embodiments, upregulation of one or more genes and/or proteins within the MEP pathway can be combined with downregulation of one or more genes and/or proteins within the MEP pathway. By way of example, in some embodiments, a cell that overexpresses one or more components of the non-mevalonate (MEP) pathway is used, at least in part, to amplify isopentyl diphosphate (IPP) and dimethylallyl diphosphate (DMAPP), substrates of GGPPS. In some embodiments, overexpression of one or more components of the non-mevalonate (MEP) pathway is achieved by increasing the copy number of one or more components of the non-mevalonate (MEP) pathway. In this regards, copy numbers of components at rate-limiting steps in the MEP pathway such as (dxs, ispD, ispF, idi) can be amplified, such as by additional episomal expression.

In some embodiments, the production of indole is used as a surrogate marker for sesquiterpene production, and/or the accumulation of indole in the culture is controlled to increase sesquiterpene production. For example, in various embodiments, accumulation of indole in the culture is controlled to below about 100 mg/L, or below about 75 mg/L, or below about 50 mg/L, or below about 25 mg/L, or below about 10 mg/L. The accumulation of indole can be controlled by balancing protein expression and activity using the multivariate modular approach described above, and/or is controlled by chemical means.

In other aspects, the disclosure provides a method for making a product containing an oxygenated sesquiterpene (as described), which comprises incorporating the oxygenated sesquiterpene prepared and recovered according to the method described above into a consumer or industrial product. For example, the product may be a flavor product, a fragrance product, a cosmetic, a cleaning product, a detergent or soap, or a pest control product (e.g., an insect repellant). In some embodiments, the oxygenated product recovered and optionally enriched by fractionation is nootkatol (e.g., α and β nootkatol) and/or nootkatone, and the product is a flavor product selected from a beverage, a chewing gum, a candy, or a flavor additive, or is a pest control product (e.g., an insect repellant).

The oxygenated product can be recovered by any suitable process, including partitioning the desired product into an organic phase. The production of the desired product can be determined and/or quantified, for example, by gas chromatography (e.g., GC-MS). The desired product can be produced in batch or continuous bioreactor systems. Production of product, recovery, and/or analysis of the product can be done as described in US 2012/0246767, which is hereby incorporated by reference in its entirety. For example, in some embodiments, oxygenated oil is extracted from aqueous reaction medium, which may be done by using an organic solvent, such as an alkane such as heptane, followed by fractional distillation. Sesquiterpene and sesquiterpenoid components of fractions may be measured quantitatively by GC/MS, followed by blending of the fractions to generate a desired nootkatone-containing ingredient for flavour (or other) applications.

In other aspects, the disclosure provides polynucleotides comprising a nucleotide sequence encoding a P450 derivative described herein. The polynucleotide may be codon optimized for expression in *E. coli* or yeast in some embodiments. In another example, the polynucleotide may comprise a nucleotide sequence encoding a SrKO fusion protein, optionally with a P450 reductase partner as described herein. In other embodiments, the disclosure provides polynucleotides comprising a nucleotide sequence encoding a sesquiterpene synthase variant described herein, which may likewise be codon optimized for expression in *E. coli* or yeast. Such polynucleotides may further comprise, in addition to sequences encoding the P450 or sesquiterpene synthase, one or more expression control elements. For example, the polynucleotide may comprise one or more promoters or transcriptional enhancers, ribosomal binding sites, transcription termination signals, and polyadenylation signals, as expression control elements. The polynucleotide may be inserted within any suitable vector, including an expression vector, and which may be contained within any suitable host cell for expression. The polynucleotide may be designed for introduction and/or protein expression in any suitable host cell, including bacterial cells and yeast cells, and may be expressed from a plasmid, or may be chromosomally integrated. In some embodiments, the recombinant nucleic acid molecule encodes an SrKO derivative with a higher activity for oxidation of valencene than the wild type enzyme (SEQ ID NO: 37), and having a leader sequence as described, such as the leader sequence MALLLAVF (SEQ ID NO: 112) or leader sequence derived from *E. coli* yhcB. In certain embodiments, the recombinant nucleic acid molecules further encodes either as an operon or as a fusion in frame with the SrKO derivative, an SrCPR or derivative thereof capable of regenerating the SrKO enzyme. When present as a fusion protein, the SrKO derivative and the SrCPR may be connected by a linking sequence of from 3 to 10 amino acids (e.g., 5 amino acids). In some embodiments, the linking sequence is predominately glycine, serine, and/or alanine and may comprise the sequence GSTGS.

In other aspects, the disclosure provides host cells producing an oxygenated sesquiterpene as described herein, and which express all of the enzyme components for producing the desired oxygenated sesquiterpene from isopentyl pyrophosphate (IPP). For example, the host cell in various embodiments expresses a famesyl pyrophosphate synthase, a sesquiterpene synthase, and the SrKO or derivative thereof. IPP may be produced through the MEP and/or MVA pathway, which may be endogenous to the host cell or modified through expression of heterologous enzymes or duplication of certain enzymes in the pathway. Host cells include various bacteria and yeast as described herein.

In still other aspects, the disclosure provides sesquiterpene products produced by the methods and host cells described herein. As disclosed herein, SrKO enzyme showed unique activities by creating different stereoisomers of the hydroxylated product (alpha and beta nootkatol and further oxidizing to ketone, nootkatone), and produced different oxygenated terpene products including hydroxygermacra-1(10)5-diene, and murolan-3,9(11) diene-10-peroxy. This activity provides for the incorporation of a unique valencene oxidation profile into an oil suitable for flavouring applications.

In certain embodiments, the processes and methods disclosed herein provide compositions and formulations comprising an oxygenated product. In some embodiments, said compositions and formulations may further comprise an unoxygenated product, a sesquiterpene, valencene, a non-sesquiterpene component, and/or one or more additional ingredients. In particular embodiments, the compositions and formulations disclosed herein comprise at least one of valencene, hydroxygermacra-1(10)5-diene, murolan-3,9(11) diene-10-peroxy, α-nootkatol, β-nootkatol, and nootkatone. In certain embodiments of the compositions and formulations disclosed herein, the compositions and formulations comprise at least one of nootkatone, α-nootkatol, β-nootkatol, and valencene. For example, in certain such embodiments, the nootkatone content may be selected from about 50% to about 65% (w/w), about 52.5% to about 62.5% (w/w), and about 55% to about 60% (w/w); the α-nootkatol content may be selected from about 15% to about 30% (w/w), about 17.5% to about 27.5% (w/w), and about 20% to about 25% (w/w); the β-nootkatol content may be selected from about 1% to about 15% (w/w), about 3% to about 12% (w/w), and about 5% to about 10% (w/w); and the valencene content may be selected from about 1% to about 15% (w/w), about 3% to about 12% (w/w), and about 5% to about 10% (w/w).

In specific embodiments of the compositions and formulations disclosed herein, the compositions and formulations comprise at least one of nootkatone, α-nootkatol, and β-nootkatol. For example, in certain such embodiments, the nootkatone content may be selected from about 50% to about 65% (w/w), about 52.5% to about 62.5% (w/w), and about 55% to about 60% (w/w); the α-nootkatol content may be selected from about 15% to about 30% (w/w), about 17.5% to about 27.5% (w/w), and about 20% to about 25% (w/w); and the β-nootkatol content may be selected from about 1% to about 15% (w/w), about 3% to about 12% (w/w), and about 5% to about 10% (w/w).

In one embodiment, the composition or formulation comprise nootkatone, α-nootkatol, and β-nootkatol, wherein the nootkatone is present in an amount ranging from about 55% to about 60% (w/w), the α-nootkatol is present in an amount ranging from about 20% to about 25% (w/w), and the β-nootkatol is present in an amount ranging from about 5% to about 10% (w/w).

In another embodiment, the composition or formulation comprise valencene, nootkatone, α-nootkatol, and β-nootkatol, wherein the valencene is present in an amount ranging from about 5% to about 10% (w/w), the nootkatone is present in an amount ranging from about 55% to about 60% (w/w), the α-nootkatol is present in an amount ranging from about 20% to about 25% (w/w), and the β-nootkatol is present in an amount ranging from about 5% to about 10% (w/w).

Figure 7:
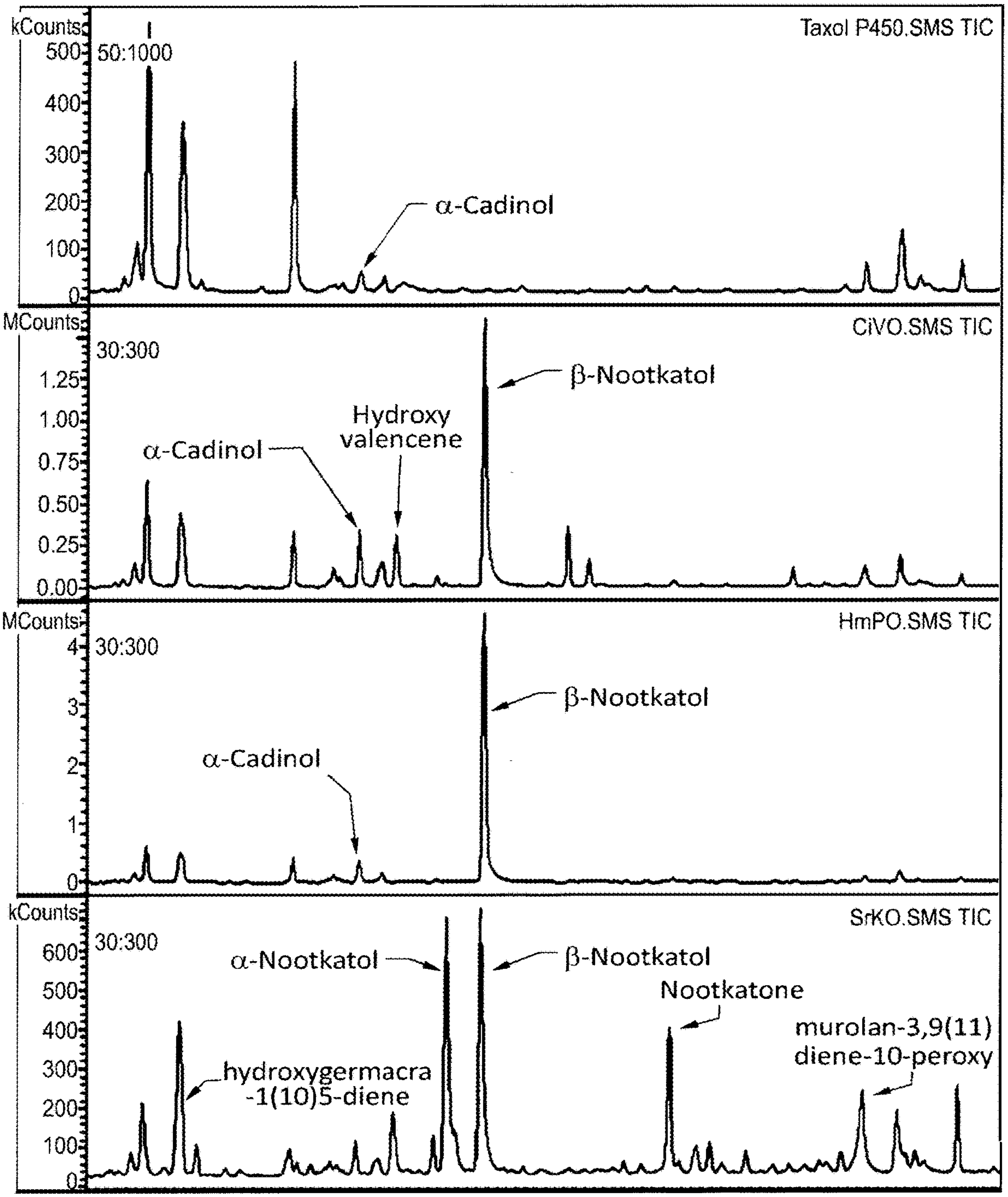
FIG. 7 provides GC-chromatographs which show the different activities of various CYP450 enzymes, as expressed in valencene-producing *E. coli* along with CPR partners as described in Example 2. Strains were cultured for four days and extracted with Methyl Tert-Butyl Ether (MTBE). 1 µl of MTBE was injected through GC-MS and the product profiles were monitored by comparing with a MS library. From top to bottom: Taxus 5-alpha hydroxylase, Cichorium intybus (CiVO) P450 (SEQ ID NO:50), Hyoscyamus muticus (HmPO) P450 (SEQ ID NO:20), and SrKO (SEQ ID NO:38).

Further, other P450 enzymes tested, including previously known sesquiterpene CYP450's or P450's having hydroxylating activity on the valencene substrate produced one of the stereoisomers (beta nootkatol) and only minor amounts of the ketone (nootkatone). Specifically, the other sesquiterpene CYP450 enzymes produced beta-nootkatol and hydroxyl valencene as major products, while Taxol CYP450 enzyme did not produce any oxygenated valencene (Table 4 and FIG. 7). The different blend of sesquiterpene products produced by SrKO provides a unique profile with a unique sensory/taste profile.

In certain aspects, the disclosure relates to SrKO derivative enzymes. In certain embodiments, the SrKO derivative polypeptide comprises an amino acid sequence that has up to 25 mutations compared to the wild type protein according to SEQ ID NO: 37. For example, the SrKO derivative may comprise an amino acid sequence that has one or more mutations at positions selected from 46, 76, 94, 131, 231, 284, 383, 390, 400, 444, 468, 488 and 499, numbered according to SEQ ID NO: 37. For example, in some embodiments, the SrKO is a derivative comprising an amino acid sequence having one or more (or all) of the mutations selected from H46R, R76K, M94V, T131Q, F231L, H284Q, R383K, I390L, V400Q, I444A, T4681, T488D, and T499N, numbered according to SEQ ID NO:37. In certain embodiments, the SrKO is a derivative comprising an amino acid sequence having one or more (or all) of the mutations selected from R76K, M94V, T131Q, F231L, H284Q, R383K, I390L, T468I, and T499N, numbered according to SEQ ID NO: 37. In some embodiments, the SrKO derivative comprises an amino acid sequence selected from SEQ ID NOS: 55-61, which were engineered according to this disclosure to improve activity for oxygenation of valencene (e.g., production of nootkatone and/or nootkatol). In some embodiments, the derivative comprises an amino acid sequence having from one to twenty mutations relative to a sequence selected from SEQ ID NOS: 55-61, with the proviso that the amino acid sequence has one or more mutations at positions selected from 46, 76, 94, 131, 231, 284, 383, 390, 400, 444, 468, 488 and 499 (numbered according to SEQ ID NO: 37), or the proviso that the SrKO derivative comprises an amino acid sequence having one or more (or all) of the mutations selected from H46R, R76K, M94V, T131Q, F231L, H284Q, R383K, I390L, V400Q, I444A, T468I, T488D, and T499N (numbered according to SEQ ID NO: 37). In certain embodiments, the derivative comprises an amino acid sequence having from one to twenty mutations relative to a sequence selected from SEQ ID NOS: 55-61, with the proviso that the amino acid sequence has one or more mutations at positions selected from 46, 76, 94, 131, 231, 284, 383, 390, 400, 444, 468, 488 and 499 (numbered according to SEQ ID NO: 37), or the proviso that the SrKO derivative comprises an amino acid sequence having one or more (or all) of the mutations selected from R76K, M94V, T131Q, F231L, H284Q, R383K, I390L, T468I, and T499N (numbered according to SEQ ID NO: 37). As shown herein, these mutations increase the level of SrKOs valencene oxidation activity.

In these or other embodiments, the SrKO is a derivative having a deletion of at least a portion of its N-terminal transmembrane region, and the addition of an inner membrane transmembrane domain from *E. coli* yhcB or derivative thereof. In some embodiments, the SrKO is a derivative having a deletion of from 15 to 35 amino acids of its N-terminal transmembrane domain, and the addition of from 15 to 25 amino acids of the transmembrane domain from *E. coli* yhcB or derivative thereof. In some embodiments, the N-terminal transmembrane domain of the derivative comprises the amino acid sequence MAWEYALIGLVVGIII-GAVA (SEQ ID NO:118), or an amino acid sequence having from 1 to 10 or from 1 to 5 amino acid mutations with respect to SEQ ID NO:118.

In still other aspects, the disclosure provides a method of preparing the modified SrKO polypeptide, wherein the method comprises the steps of: (i) culturing a host cell expressing the modified polypeptide under conditions which permit expression of the polypeptide; and (ii) optionally recovering the polypeptide.

In still other aspects, the disclosure provides a method of producing an oxygenated sesquiterpene comprising the steps of: (i) providing the modified SrKO polypeptide, (ii) contacting a sesquiterpene with the modified SrKO polypeptide, and (iii) recovering the produced oxygenated sesquiterpene. The method may further comprise providing a CPR enzyme for regenerating the SrKO cofactor (e.g., SrCPR). In some embodiments, the oxygenated sesquiterpene is recovered as an oil. In some embodiments, the sesquiterpene is valencene. In some embodiments, the oxygenated sesquiterpene comprises hydroxygermacra-1(10)5-diene, murolan-3,9(11) diene-10-peroxy, alpha-nootkatol, beta-nootkatol, and nootkatone. In some embodiments, the predominant oxygenated product is nootkatone and/or nootkatol. In some embodiments, the oxygenated product comprises both alpha and beta nootkatol.

Figure 8A:
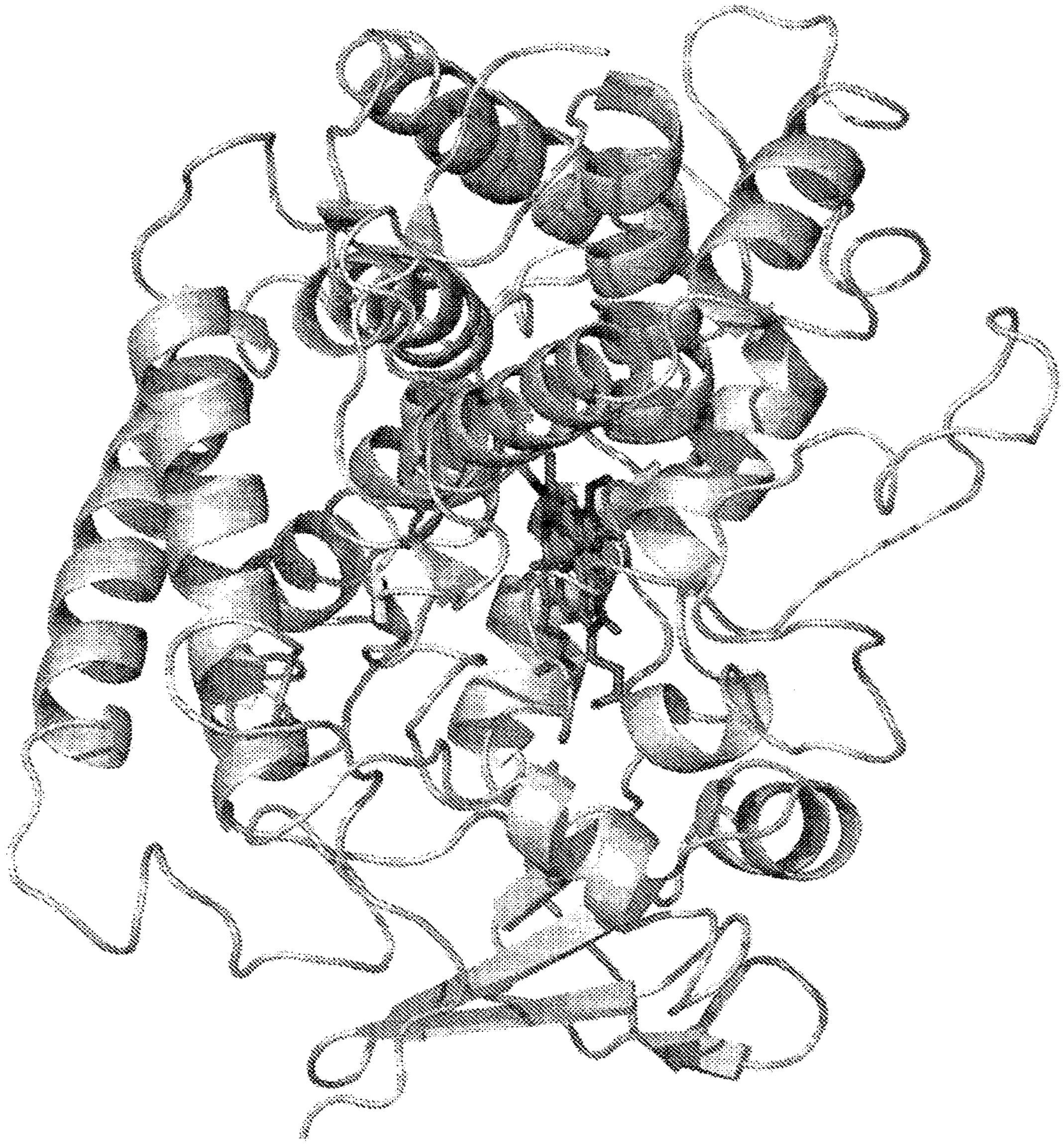
FIGS. 8A and 8B illustrate a homology model of SrKO and its active site. The SrKO homology model is based on the known mutant P45017A1 (the crystal structure of membrane-bound cytochrome P450 17 A1 as disclosed in DeVore N M and Scott E E (*Nature,* 482, 116-119, 2012), which catalyzes the biosynthesis of androgens in human. The position of the heme is shown as sticks.
Figure 8B:
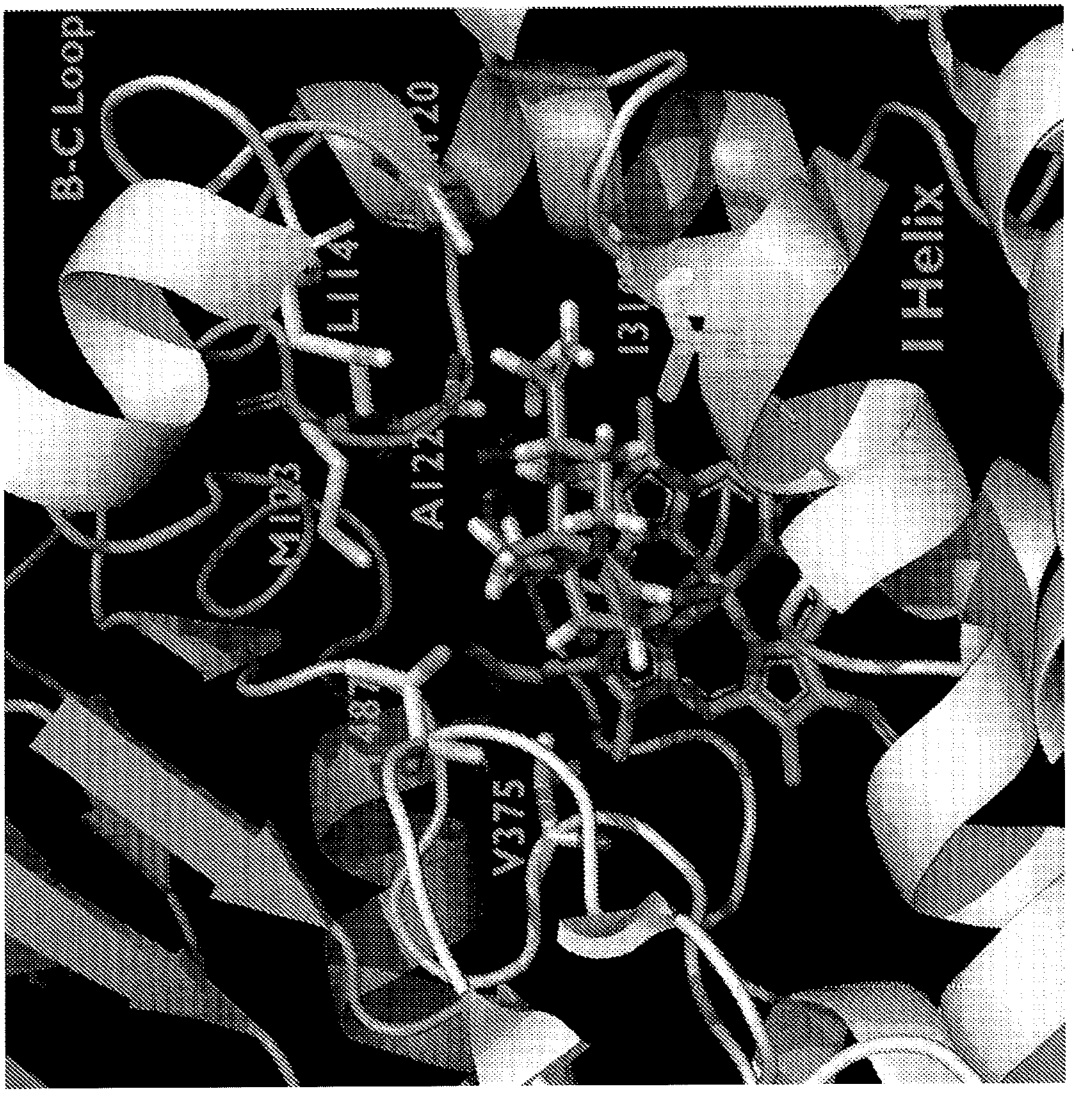

In another aspect, there is provided an SrKO crystal model structure (CMS) based on the structural coordinates of P45017A1, with an amino acid sequence of SrKO or derivative described herein. The CMS comprises a terpene binding pocket domain (TBD) that comprises a terpene binding pocket (TBP) and a terpene (e.g., valencene) bound to the TBD. FIGS. 8A and 8B. This SrKO crystal model structure (CMS) facilitates in-silico testing of SrKO derivatives.

Thus, in still other embodiments, the disclosure provides a method of screening for a terpene capable of binding to a TBD wherein the method comprises the use of the SrKO CMS. In another aspect, the disclosure provides a method for screening for a terpene capable of binding to the TBP, and the method comprises contacting the TBP with a test compound, and determining if said test compound binds to said TBP. In some embodiments, the method is to screen for a test compound (e.g., terpenes) useful in modulating the activity of a SrKO enzyme.

In another aspect, the disclosure provides a method for predicting, simulating or modelling the molecular characteristics and/or molecular interactions of a terpene binding domain (TBD) comprising the use of a computer model, said computer model comprising, using or depicting the structural coordinates of a terpene binding domain as defined above to provide an image of said ligand binding domain and to optionally display said image.

EXAMPLES

Example 1: Construction of Sesquiterpene Precursor (Valencene) Producing *E. Coli* Strain

*E. coli* overexpressing upstream MEP pathway genes dxs, ispD, ispF, and idi was created, which facilitates flux to the isoprenoid precursor isopentyl-pyrophosphate (IPP) supporting more than 1 g/L titers of a heterologous diterpenoid product (3). Strains were constructed producing a variety of terpenoids including mono- and sesquiterpenes by replacing the geranylgeranyl pyrophosphate synthase (GGPS) and diterpene synthase with a famesyl pyrophosphate synthase (FPPS) and sesquiterpene synthase or a geranyl pyrophosphate synthase (GPPS) and monoterpene synthase. For developing a sesquiterpene producing strain to test the CYP450s for novel oxygenated terpenes, a valencene synthase enzyme was cloned and expressed in the MEP pathway overexpressed *E. coli* strain. The high substrate flux helps identify the activity of the CYP450. Previously, research on an oxygenated taxadiene producing strain showed a significant drop in the productivity upon transferring the CYP450 pathway to the taxadiene producing strain (300 mg/L to ~10 mg/L).

Further, multivariate modular metabolic engineering (MMME) was applied for balancing the pathway for high level production of valencene. Naturally occurring valencene synthases, such as that from *Vitis vinifera*, often perform sub-optimally (~5 mg/L) even after MMME optimization, compared to previous results obtaining 100's of mg/L diterpenoids. Enzymes involved in the sesquiterpene biosynthesis can be difficult to express in *E. coli*, and also are deficient in kinetics relative to those involved in primary metabolism (17).

A homology model for the *Vitis vinifera* valencene synthase (VvVS) was constructed using the BioLuminate software package (Schrodinger, Inc.) with the 5-epi-aristolochene synthase crystal structure as a template (PDB: SEAT). Further, to identify the natural mutational landscape of terpene synthases, an extensive multiple sequence alignment incorporating hundreds of related terpene synthase sequences was created. Using this information, mutations were designed using a combination of back-to-consensus, in silky energetics, and structural analysis. Back-to-consensus mutations have been shown to be an important tool for improving stability (19,20) and expression (21). Energetics calculations based on atomic force-field models in BioLuminate were used to assess the $\Delta\Delta G$ of folding for individual mutations predicted for positions with low solvent-accessible surface area, which were predicted to affect folding and stability.

By applying the MMME approach, a balanced upstream and downstream valencene production strain was identified incorporating a codon-optimized version of VvVS on a plasmid with a p15A origin of replication and a T7 promoter. This strain background was then used to screen designed synthase enzyme mutations. Using the aforementioned protein engineering tools we designed over 200 unique point mutations (Table 3) which were then constructed in the p15A-T7 screening plasmid using site-directed mutagenesis. Mutated enzyme variants were transformed into the screening strain, triplicate colonies were cultured in selective LB cell culture medium overnight, and then inoculated into a minimal R-medium and cultured for four days at 22° C. Cultures were extracted using methyl tert-butyl ether (MTBE) and analyzed by combined gas chromatography/mass spectrometry for productivity of valencene.

Figure 2:
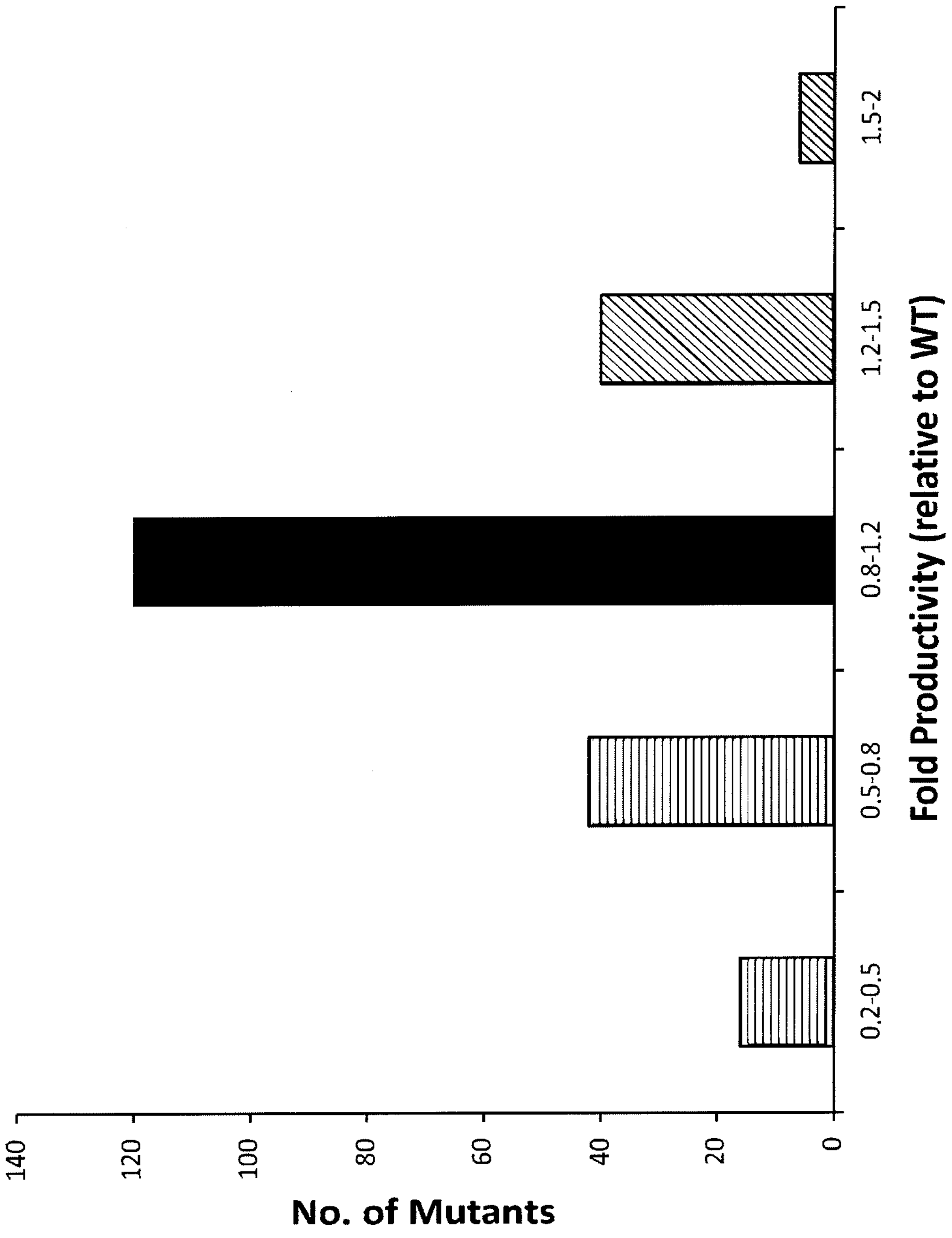
FIG. 2 depicts the fold productivities for site-directed mutants made to VvVS. 46 of the 225 point mutations convey an average improvement in productivity of valencene of at least 20% compared to the wild-type WT VvVS.

Approximately one-fifth of the designed point mutations increased valencene productivity in our screening strain by at least 20% (FIG. 2). Beneficial point mutations were then strategically combined to confer increasingly advantageous phenotypes. Recombined valencene synthase sequences are provided as Vv1M1 (Mutations—R331K, I334E, N335S, V371I, A374L, T418V, S482T, S512P, K356N, Q491K, E394D, A428V, Y348F, T318S, L352I, I442L, A554P), Vv2M1 (Mutations—R331K, I334E, N335S, V371I, A374L, T418V, S482T, S512P, K356N, Q491K, E394D, A428V, V542T, G480A, M305L, K441R, A554P), Vv1M5 (Mutations—R331K, 1334E, N335S, V371I, A374L, T418V, S482T, S512P, K356N, Q491K, E394D, A428V, Y348F, T318S, L352I, I442L, A554P, H284M, C46K, F448T, Q533E), and Vv2M5 (Mutations—R331K, I334E, N335S, V371I, A374L, T418V, S482T, S512P, K356N, Q491K, E394D, A428V, V542T, G480A, M305L, K441R, A554P, H284M, C46K, F448T, Q533E) (FIG. 3). When either of these enzymes was overexpressed in our MEP pathway strain with dxs-idi-ispDF overexpressed, and balanced using MMME, the titers of valencene obtained were sufficient to motivate incorporation of P450 enzymes to test their ability to catalyze the formation of oxygenated valencene. Titers of valencene before P450 incorporation were about 30 mg/L.

Example 2: Functional Activity of CYP450 Library on Valencene Scaffold

Valencene was used as a model system to validate the power of CYP450-based oxygenation chemistry for production terpene chemicals.

Figure 5A:
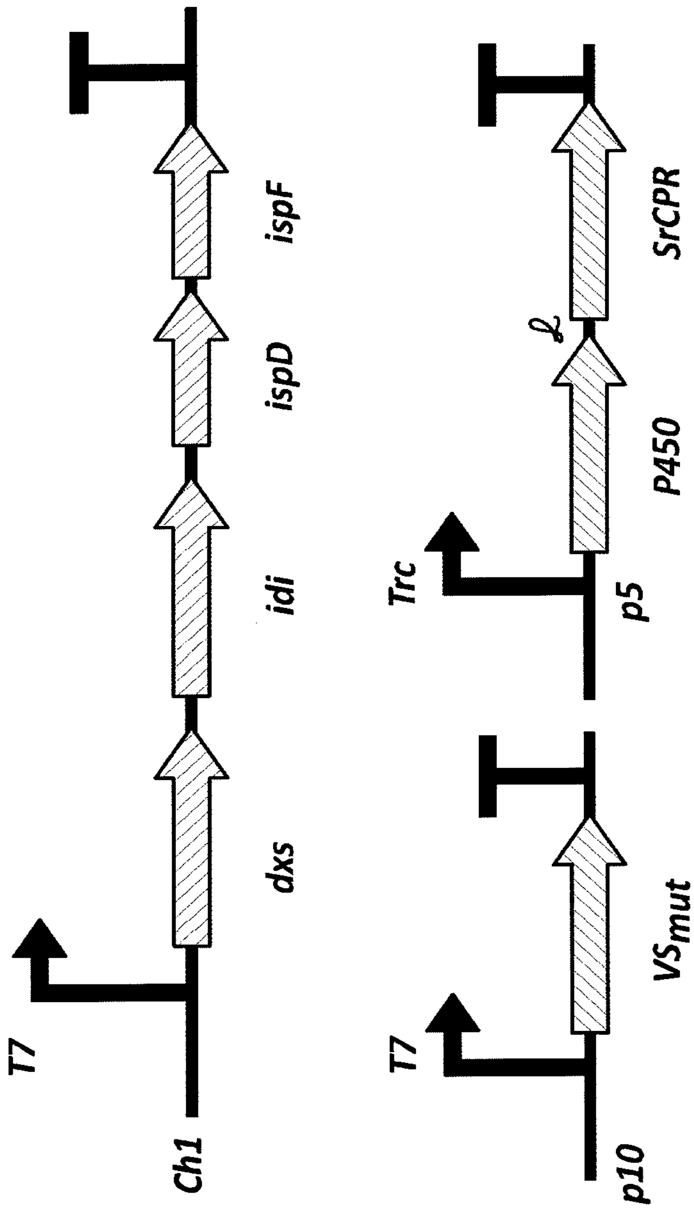
FIGS. 5A and 5B depict construct designs for expression of MEP, terpene and terpenoid synthases, and P450 enzymes in *E. coli*.
Figure 5B:
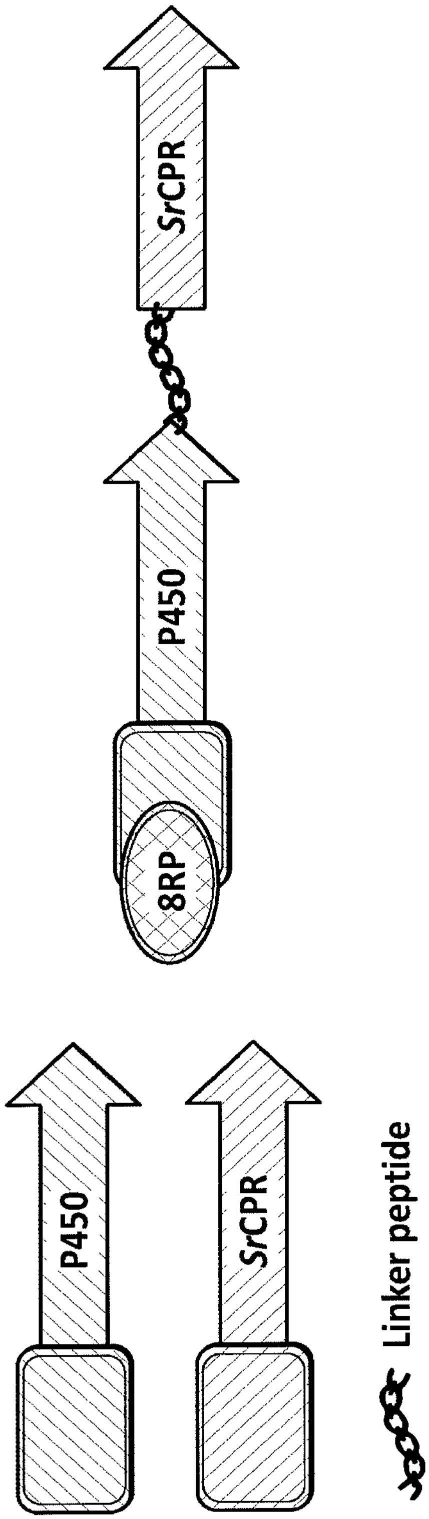

The CYPP450 candidate screening was conducted using the valencene producing *E. coli* strains as host background. For constructing the CYP450 for functional expression, a proprietary plasmid system, p5Trc (plasmid derived from pSC101) was used to construct a plasmid containing the candidate P450 fused to an N-terminal truncated *Stevia rebaudiana* cytochrome P450 reductase (SrCPR) through a flexible 5-amino acid linker (GSTGS, SEQ ID NO: 117). The sequences of the various candidate P450s are shown in FIG. 4. The candidate CYP450's were analyzed for N-terminal membrane associating regions which were truncated and a 8-amino acid leader sequence (MALLLAVF, SEQ ID NO: 112) was added to the fusion (FIGS. 5A and SB). CPR red/ox partners from *Arabidopsis thaliana* and *Taxus euspidata* were also prepared in similar genetic constructions. Since the native SrCPR was effective, the level of activity of these constructs was not determined. The sequences of the various CPR red/ox partners are shown in FIG. 6. Following transformation of p5Trc-CYP450-L-SrCPR to valencene producing strain, the strains were cultured overnight at 30° C. in antibiotic selective LB media. These cultures were then used to inoculate 2 mL antibiotic selective R-media cultures in hungate tubes with 15 g/L glycerol and 0.1 mM IPTG which were subsequently cultured for 4-days at 22° C. before being extracted with methyl tert-butyl ether (MTBE).

A set of CYP450 enzymes, from those listed in Table 4, was selected and classified for both sesqui- and diterpene oxygenation in this *E. coli* system. Among the various CYP450 enzymes tested for oxygenation on valencene, kaurene oxidase from *Stevia rebaudiana* (SrKO) (16) was discovered to have a unique oxygenation chemistry on the valencene scaffold. SrKO natively oxidizes the diterpene (−)-kaurene at the C19 position to (−)-kaurenoic acid. SrKO enzyme showed unique activities in the present studies by creating different stereoisomers of the hydroxylated product (alpha and beta nootkatol and further oxidizing to the ketone, nootkatone), and produced different oxygenated terpene products including hydroxygermacra-1(10)5-diene, murolan-3,9(11) diene-10-peroxy, in addition to the alpha-nootkatol, beta-nootkatol, and nootkatone. Other P450's, including the previously known sesquiterpene CYP450's for hydroxylating valencene produced only one of the isomers (beta nootkatol) and only detectable amounts of ketone (nootkatone). Specifically, the other sesquiterpene CYP450 enzymes produced beta-nootkatol and hydroxyl valencene as major products, while another diterpene CYP450 enzymes (e.g., Taxus 5-alpha hydroxylase) produced nootkatol as only a minor (detectable) product (Table 4 and FIG. 7).

TABLE 4

Major Products Formed From Valencene by Select P450 Enzymes in *E. coli*

| SPECIES | NAME | MAJOR PRODUCTS |
|---|---|---|
| *Cichorium intybus* | CiVO | β-nootkatol, α-cadinol, hydroxyl valencene. |
| *Hyoscyamus muticus* | HmPO | β-nootkatol, a-cadinol, hydroxyl valencene, nootkatone |
| *Latuca spicata* | LsGAO | β-nootkatol, α-cadinol, isovalencenol, nootkat-11-en-10-ol. |
| *Bamadesia spinosa* | BsGAO | β-nootkatol, α-cadinol, isovalencenol. |
| *Nicotiana tabacum* | NtEAO | α-cadinol, nootkat-11-en-10-ol. |
| *Stevia rebaudiana* | SrKO | α-nootkatol, hydroxygermacra-1(10)5-diene, β-nootkatol, nootkatone, murolan-3,9(11) diene-10-peroxy |
| *Zingiber zerumbet* | ZzHO | α-cadinol, nootkat-11-en-10-ol. |
| *Citrus × paradisi* | CpVO | α-cadinol, nootkat-11-en-10-ol. |
| *Mentha spicata* | MsL6OH | α-cadinol. |
| *Nicotiana tabacum* | NtVO | α-cadinol, nootkat-11-en-10-ol. |
| *Solanum tuberosum* | StVO | α-cadinol, β-nootkatol, globulol. |
| *Arabidopsis thaliana* | AtKO | α-cadinol, nootkat-11-en-10-ol. |
| *Cichorium intybus* | Ci2VO | β-nootkatol, α-cadinol, isovalencenol. |
| *Artemesia annua* | AaAO | α-cadinol, murolol, nootkat-11-en-10-ol. |
| Taxus 5-alpha hydroxylase P450 | | α-cadinol |

Example 3: Structural and Mutational Studies of SrKO

Once the unique activities of SrKO were identified, experiments were conducted to improve its ability to conduct its diverse oxidation of valencene. The crystal structure for SrKO has not been described. Blast search of SrKO against RCSB Protein Data Bank shows the sequence identity of SrKO to P450 enzymes with crystal structures are low (~20%). Given the conservative folding structures of P450s regardless of its low sequence identity, state-of-the-art protein modeling tools were used to build on SrKO. The crystal structure of membrane-bound cytochrome P450 17 Al (see DeVore N. M., Scott E. E., *Nature,* 482, 116-119, 2012) which catalyses the biosynthesis of androgens in human was selected as the template for model development. Using BioLuminate protein modeling software, a homology model was developed (FIG. 8A) such that the positioning of key residues and characteristic motifs (see Gotoh O., *J. Biol Chem,* 267, 83-90, 1992) aligned well with the template. Furthermore, a homology model for SrKO which included the prosthetic heme-iron complex was also constructed. AutoDock VINA was then used to create an ensemble of possible binding modes for valencene in the SrKO active site (FIG. 8B) (29).

In addition, a Blast search of SrKO against NCBI non-redundant protein sequence library returned no orthologs with sequence identity greater than 80% (except the SrKO itself). The top hits are listed in the Table 5.

TABLE 5

BLAST search with SrKO in preparation of Homology Model

| Enzyme Name | Species | Sequence Identity | Accession |
|---|---|---|---|
| kaurene oxidase | *Stevia rebaudiana* | 99% | AAQ63464.1 |
| ent-kaurene oxidase 2 | *Lactuca sativa* | 79% | BAG71198.1 |
| ent-kaurene oxidase 1 | *Lactuca sativa* | 71% | BAG71197.1 |
| ent-kaurene oxidase | *Ricinus communis* | 63% | XP_002510288.1 |

Once the unique activities of SrKO were identified, experiments were conducted to improve its ability to conduct its diverse oxidation of valencene. Using the back-to-consensus mutagenesis strategy, a multiple sequence alignment of P450 enzymes was constructed including sequences (after clustering and elimination of sequences with greater than 90% identity) from a BLAST search of the Unirefl 00 database using 4 seed kaurene oxidase genes, from a BLAST search of the bacterial proteome using $P450_{BM3}$, $P450_{CAM}$, and $P450_{eryF}$ as seed genes, and the most closely related SrKO homologs. Based on the homology model, the multiple sequence alignment, and the literature, various point mutations and double mutations were designed and tested. These cytochrome P450 derivatives were assessed for improvements in total oxygenated terpene productivity (e.g., total of the major peaks observed by GC/MS) in the in vivo testing system described above. Mutagenesis on active site positions guided by the model revealed several variants with significantly improved oxygenated products (Table 6 and Table 7 below).

TABLE 6

Binding pocket mutations and their fold productivity of total oxygenated oil according to wild type SrKO (SEQ ID NOS: 37 and 108), 8rp-t20SrKO (SEQ ID NOS: 38 and 106), n22yhcB-t30VO1 (SEQ ID NO: 104) and n22yhcB-t30VO2 (SEQ ID NOS: 61 and 105).

| Mutant # (Table 2.1) | Mutants (numbered according to SEQ ID NO: 38) (SEQ ID NO: 106) | Mutants (numbered according to SEQ ID NO: 37) (SEQ ID NO: 108) (Shift value relative to SEQ ID NO: 38: +12) | Mutants (numbered according to SEQ ID NO: 104/ SEQ ID NO: 105 (SEQ ID NO: 61)) (Shift value relative to SEQ ID NO.: 38: +4) | Fold productivity (as measured in mg/L) |
|---|---|---|---|---|
| 38 | I310V | I322V | I314V | 1.5 |
| 37 | I310T | I322T | I3I4T | 0.0 |
| 42 | V375I | V387I | V379I | 1.4 |
| 41 | V375T | V387T | V379T | 0.0 |
| 19 | M123F | M135F | M127F | 0.0 |
| 20 | M123T | M135T | M127T | 0.3 |
| 18 | M123Q | M135Q | M127Q | 0.0 |
| 59 | T487N | T499N | T491N | 2.5 |
| 66 | M123F_T487G | M135F_T499G | M127F_T491G | 0.0 |
| 63 | M123F_T487V | M135F_T499V | M127F_T491V | 0.0 |
| 62 | M123Q_T487V | M135Q_T499V | M127Q_T491V | 0.0 |
| 59 | T487N_V375F | T499N_V387F | T491N_V379F | 2.2 |
| 59 | T487N_V375A | T499N_V387A | T491N_V379F | 1.8 |
| 59 | T487N_V121A | T499N_V133A | T491N_V125A | 2.0 |
| 59 | T487N_V375M | T499N_V387M | T491N_V379M | 1.9 |
| 59 | T487N_M120L | T499N_M132L | T491N_M124L | 1.8 |
| 59 | T487N_M120I | T499N_M132I | T491N_M124I | 1.8 |
| 59 | T487N_L114V | T499N_L126V | T491N_L118V | 1.4 |
| 59 | T487N_F219L | T499N_F231L | T491N_F223L | 3.5 |
| 59 | T487N_M120V | T499N_M132V | T491N_M124V | 1.1 |
| 59 | T487N_F219I | T499N_F231I | T491N_F223I | 3.3 |
| 59 | T487N_L114F | T499N_L126F | T491N_L118F | 1.2 |

TABLE 7

Non-binding pocket point mutations and productivity of total oxygenated oil compared to the wild type SrKO (SEQ ID NOS: 38 and 106).

| Mutant # (Table 2.1) | Mutants (numbered according to SEQ ID NOS: 38 and 106) | Mutants (numbered according to SEQ ID NO: 37) (SEQ ID NO: 108) (Shift value relative to SEQ ID NO: 38: +12) | Mutants (numbered according to SEQ ID NO: 104/ SEQ ID NO: 105 (SEQ ID NO: 61)) (Shift value relative to SEQ ID NO: 38: +4) | Fold productivity (as measured in mg/L) |
|---|---|---|---|---|
| 53 | G442A | G454A | G446A | 0.849153 |
| 55 | L454M | L466M | L458M | 0.717318 |
| 44 | I378V | I390V | I382V | 0.349005 |
| 47 | V388M | V400M | V392M | 0.792428 |
| 9 | V85I | V97I | V89I | 0.795913 |
| 51 | V413K | V425K | V417K | 0.902039 |
| 60 | P492K | P504K | P496K | 0.131657 |
| 40 | R371I | R383I | R375I | 0.657808 |
| 7 | T80C | T92C | T84C | 0.342501 |
| 23 | A140R | A152R | A144R | 0.014872 |
| 2 | Y59H | Y71H | Y63H | 0.406787 |
| 5 | A67E | A78E | A71E | 0.937429 |
| 8 | M82V | M94V | M86V | 1.585588 |
| 11 | S86N | S98N | S90N | 0.977752 |
| 22 | Y129F | Y141F | Y133F | 0.686276 |
| 24 | K149R | K161R | K153R | 0.990776 |
| 29 | D208E | D220E | D212E | 0.853446 |
| 31 | S267A | S279A | S271A | 0.79152 |
| 32 | H272Q | H284Q | H276Q | 0.958227 |
| 33 | S284C | S296C | S288C | 0.652348 |
| 39 | R371K | R383K | R375K | 1.443497 |
| 45 | H382Y | H394Y | H386Y | 0.609951 |
| 46 | V388Q | V400Q | V392Q | 0.924043 |
| 49 | L400I | L412I | K4041 | 0.682775 |
| 50 | V413D | V425D | V417D | 0.039261 |
| 52 | F434L | F446L | F438L | 0.793926 |
| 57 | M464L | M476L | M468L | 0.689696 |
| 58 | M475G | M487G | M479G | 0.573906 |
| 61 | I497L | I509L | I501L | 0.679949 |
| 15 | A116R | A128R | A120R | 0.216353 |
| 1 | L47I | L59I | L51I | 0.88992 |
| 25 | H150F | H162F | H154F | 0.666723 |

Example 4: Isolation and Evaluation of Oxygenated Product

The product derived from oxidation of valencene by the cytochrome P450 enzyme SrKO (SEQ ID NO: 38) was analysed by GC/MS (Agilent 6800; Column: Rtx-5, 0.32 mm×60 m×1.0 μm film thickness; GC Temp. Program: 40° C. for 5 min, increased at 4° C./min to 300° C. and held for 30 min.) resulting in the data provided in Table 8A and 8B.

TABLE 8A

SrKO oxidation of valencene

| Ret. Time | Compound Name | CAS # | GC-FID Area % |
|---|---|---|---|
| 33.762 | dodecane | 112-40-3 | 6.70 |
| 35.440 | glyceryl diacetate I | | 5.26 |
| 38.767 | triacetin | 102-76-1 | 4.48 |
| 39.518 | unknown | | 10.17 |
| 40.176 | unknown | | 7.52 |
| 42.012 | unknown | | 2.53 |
| 44.437 | unknown | | 20.25 |
| 44.816 | valencene | 4630-07-3 | 1.97 |
| 45.546 | nootkatene | 5090-61-9 | 1.09 |
| 46.260 | unknown | | 2.14 |
| 46.395 | unknown | | 6.77 |
| 46.869 | unknown | | 4.01 |

TABLE 8A-continued

SrKO oxidation of valencene

| Ret. Time | Compound Name | CAS # | GC-FID Area % |
|---|---|---|---|
| 47.394 | germacrene D-4-ol | 74841-87-5 | 1.23 |
| 48.273 | unknown | | 1.86 |
| 49.659 | T-muurolol | 19912-62-0 | 0.69 |
| 49.753 | an unknown sesquiterpene | | 0.56 |
| 50.336 | an unknown sesquiterpene | | 0.58 |
| 51.025 | epinootkatol (or alpha nootkatol) | 50763-66-1 | 1.96 |
| 51.430 | Nootkatol (or beta nootkatol) | 50763-67-2 | 3.54 |
| 54.138 | nootkatone | 4674-50-4 | 15.87 |
| 54.501 | 6-isopropenyl-4,8a-dimethyl-4a,5,6,7,8,8a-hexahydro-2(1H)-naphthalenone | 76784-84-4 | 0.84 |
| | | TOTAL | 100.00 |

TABLE 8B

| SrKO oxidation of valencene | | | |
|---|---|---|---|
| Ret. Time | Compound Name | CAS # | GC-FID Area % |
| 33.763 | dodecane | 112-40-3 | 7.26 |
| 35.470 | glyceryl diacetate I | | 7.07 |
| 38.773 | triacetin | 102-76-1 | 6.19 |
| 39.526 | unknown | | 11.56 |
| 40.179 | unknown | | 8.10 |
| 44.440 | unknown | | 23.95 |
| 44.821 | valencene | 4630-07-3 | 6.88 |
| 45.545 | nootkatene | 5090-61-9 | 2.22 |
| 46.404 | unknown | | 5.08 |
| 46.879 | unknown | | 3.66 |
| 47.399 | germacrene D-4-ol | 74841-87-5 | 2.89 |
| 48.279 | unknown | | 2.27 |
| 49.665 | T-muurolol | 19912-62-0 | 0.94 |
| 50.342 | an unknown sesquiterpene | | 1.71 |
| 51.027 | epinootkatol | 50763-66-1 | 2.48 |
| 51.444 | nootkatol | 50763-67-2 | 5.24 |
| 54.152 | nootkatone | 4674-50-4 | 2.49 |
| | | TOTAL | 100.00 |

Similar analysis was conducted on the product produced by SrKO derivatives. It was confirmed that product profiles are comparable, and that the major products of nootkatone, α-nootkatol, and β-nootkatol can be produced at higher levels based on mutagenesis of SrKO.

The oxygenated oil product can then be extracted from the aqueous reaction medium using an appropriate solvent (e.g., heptane) followed by fractional distillation. The chemical composition of each fraction can be measured quantitatively by GC/MS. Fractions can be blended to generate the desired alpha/beta nootkatol and/or nootkatone ingredients for use in flavour or other applications.

Verification of acceptability can be carried out by direct comparison to a reference nootkatone flavouring product (for example, an existing natural flavouring commercial product obtained from Frutarom) with analysis provided in Table 9.

TABLE 9

| Analysis of commercially available natural flavouring nootkatone from Frutarom | | | |
|---|---|---|---|
| Ret. Time | Compound Name | CAS # | GC-FID Area % |
| 42.307 | limonene glycol | 1946-00-5 | 0.201 |
| 42.792 | decanoic acid | 334-48-5 | 0.115 |
| 49.405 | valencene | 4630-07-3 | 0.039 |
| 50.362 | delta-cadinene | 483-76-1 | 0.268 |
| 52.757 | alpha-elemol | 639-99-6 | 2.178 |
| 53.11 | spathulenol | 6750-60-3 | 0.264 |
| 53.423 | caryophyllene oxide | 1139-30-6 | 0.394 |
| 53.748 | viridiflorol | 552-02-3 | 0.061 |
| 54.225 | unknown sesquiterpenoid (MW = 220, tent) | | 0.113 |
| 54.853 | unknown | | 2.985 |
| 55.386 | unknown | | 2.251 |
| 55.97 | T-muurolol | 19912-62-0 | 0.399 |
| 56.192 | bulnesol | 22451-73-6 | 0.722 |
| 56.523 | 7(11), 4b-selinenol; tentative | | 1.425 |
| 56.65 | unknown (MW = 232, tent) | | 0.663 |
| 56.937 | beta-sinensal | 3779-62-2 | 0.914 |
| 57.449 | unknown | | 0.285 |
| 57.589 | cedrenal; tentative | | 0.438 |
| 58.189 | unknown sesquiterpenoid(s) | | 1.077 |
| 58.73 | unknown sesquiterpenoids (MW = 220, 222, tent) | | 0.537 |

TABLE 9-continued

| Analysis of commercially available natural flavouring nootkatone from Frutarom | | | |
|---|---|---|---|
| Ret. Time | Compound Name | CAS # | GC-FID Area % |
| 59.102 | beta, gamma-nootkatone | 35936-67-5 | 1.805 |
| 59.32 | myristic acid | 544-63-8 | 0.058 |
| 59.537 | 1,10-dihydronootkatone | 20489-53-6 | 0.582 |
| 59.75 | a nootkatone isomer | | 0.442 |
| 60.507 | nootkatone isomers (2); tentative | | 0.812 |
| 60.782 | unknowns (2) | | 0.605 |
| 61.034 | hexadecanal | 629-80-1 | 0.302 |
| 62.93 | nootkatone | 4674-50-4 | 74.287 |
| 63.057 | 3,11-eudesmadiene-2-one (5S,7R,10R) | 86917-81-9 | 1.909 |
| 63.14 | unknown (MW = 234, tent) | | 0.18 |
| 63.26 | unknown (MW = 232, tent) | | 0.105 |
| 64.112 | heptadecanal | 629-90-3 | 0.344 |
| 64.403 | unknown sesquiterpenoid | | 0.446 |
| 65.16 | unknown sesquiterpenoid | | 0.147 |
| 65.384 | palmitic acid | 57-10-3 | 0.154 |
| 65.599 | alpha-camphorene | 532-87-6 | 0.249 |
| 65.75 | unknown(s) | | 0.054 |
| 65.878 | dehydro-alpha-vetivenone; tentative | | 0.115 |
| 66.056 | nootkatone, 9-oxo | 86925-44-2 | 0.172 |
| 66.371 | ethyl palmitate | 628-97-7 | 0.185 |
| 66.856 | cis-9-octadecenal | 2423-10-1 | 0.239 |
| 66.986 | unknown sesquiterpenoids | | 0.114 |
| 67.556 | octadecanal | 638-66-4 | 0.096 |
| 74.551 | osthol | 484-12-8 | 0.367 |
| 80.543 | isomerazin | 1088-17-1 | 0.112 |
| 84.671 | unknown (MW = 298) | | 0.07 |
| | | TOTAL | 99.28 |

Two exemplary methods of verification are: 1) Duo-Trio Test, 2) Forced-Choice Preference Test. In one method, the SrKO derived product can be compared to the reference product (for example a commercial Frutarom sourced nootkatone ingredient) in a duo-trio test to determine if the ingredients can be distinguished with statistical significance. This test will determine if the two nootkatone containing ingredients at least match one another based on perception of overall taste and aroma profiles. In the second test, assuming the two products are determined to be distinguishable in a duo trio test, one could determine if the SrKO derived nootkatone is preferred by conducting a forced-choice preference test. More details on these tests are provided as follows.

Duo-Trio Test:

A Duo-Trio Test can be conducted to determine if the blended fractions obtained from the SrKO derived nootkatone flavouring can be distinguished with statistical significance from a reference nootkatone product (for example, a commercially available nootkatone flavouring sourced from Frutarom). The test will determine if the nootkatone flavouring ingredients at least match in terms of overall taste and aroma profile typically conducted in a sugar/acid solution but could also be evaluated in water or sugar water.

TABLE 10

| Name | Finished Beverage |
|---|---|
| Spring Water | 1000 g |
| Citric Acid | 0.1% |
| Sucrose | 8% |
| Nootkatone flavouring | 2.5 ppm |

Methodology: One ounce of the reference sample, labelled "REF" is presented first followed by a one ounce sample of the reference and a one ounce sample of the test sample presented blindly in random order to a minimum of 15 discriminator panellists. The panellists are asked which blind sample is the same as the reference sample. The data are subjected to a statistical analysis to determine the degree of difference between the test sample and the reference control.

Forced-Choice Preference Test:

Assuming a difference is observed between nootkatone flavouring derived from SrKO oxidation and the reference nootkatone product (for example, a Frutarom nootkatone flavouring), a Forced-Choice Preference Test can be conducted to determine if one sample is preferred over the other as a nootkatone flavouring ingredient. The test can be conducted in sugar/acid solution, sugar water or water.

TABLE 11

| Name | Finished Beverage |
|---|---|
| Spring Water | 1000 g |
| Citric Acid | 0.1% |
| Sucrose | 8% |
| Nootkatone flavouring | 2.5 ppm |

Methodology: One ounce of each test sample is presented blindly in random order to a minimum of 40 discriminator panellists. The panellists are asked which blind sample is preferred based on aroma and taste when consumed orally and are forced to make a decision. The data are subjected to a statistical analysis to determine the degree of preference for one sample over the other.

Example 5: N-Terminal Anchor Engineering

Figure 9:
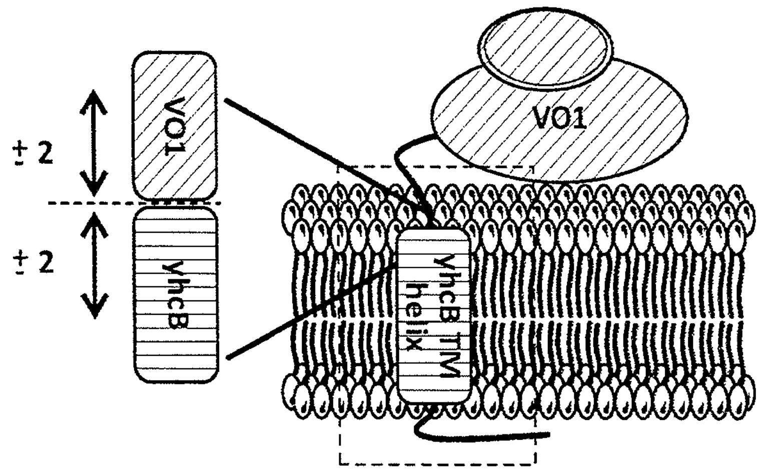
FIG. 9 shows optimizing the valencene oxidase (VO) N-terminal membrane anchor. The N-terminus of *E. coli* yhcB was selected as a membrane anchor sequence, which provides a single-pass transmembrane helix. The length of the anchor (from 20 to 24 amino acids) and the VO N-terminal truncation length (from 28 to 32 amino acids) were screened for improvements in oxygenation titer.

To optimize membrane interaction of the initial SrKO variants (referred to in these examples as Valencene Oxidase 1, or VO1), *E. coli* proteins anchored in the inner membrane with a cytoplasmic C-terminus were identified. An N-terminal sequence of *E. coli* yhcB was selected, which provides a single-pass transmembrane domain. 20-24 amino acids from the N-terminus of yhcB was exchanged for the original membrane anchor sequence MALLLAVF (SEQ ID NO:112), and the size of the SrKO N-terminal truncation was varied from 28 to 32. See FIG. 9. VO1 was expressed under control of a T7 promoter on a p5 plasmid. SrCPR was expressed independently from the chromosome. Strains were cultured in 96 deepwell plates at 30° C. for 48 hours, in R-medium plus glycerol and dodecane overlay as already described.

Figure 10:
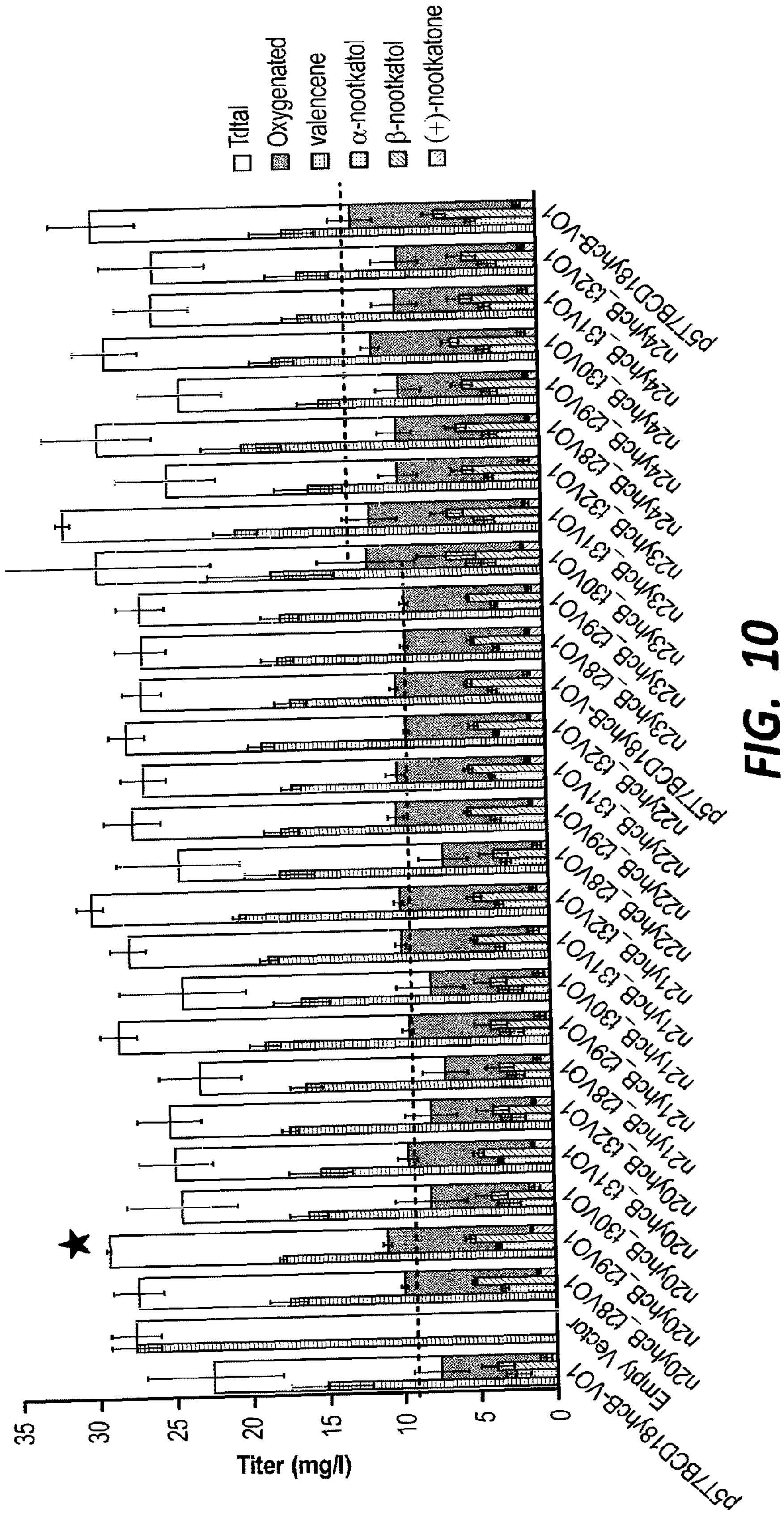
FIG. 10 shows that a truncation length of 29, and a 20 amino acid N-terminal anchor based on *E. coli* yhcB, led to a 1.2-fold increase in total oxygenated titer compared to the average of controls.
Figure 11:
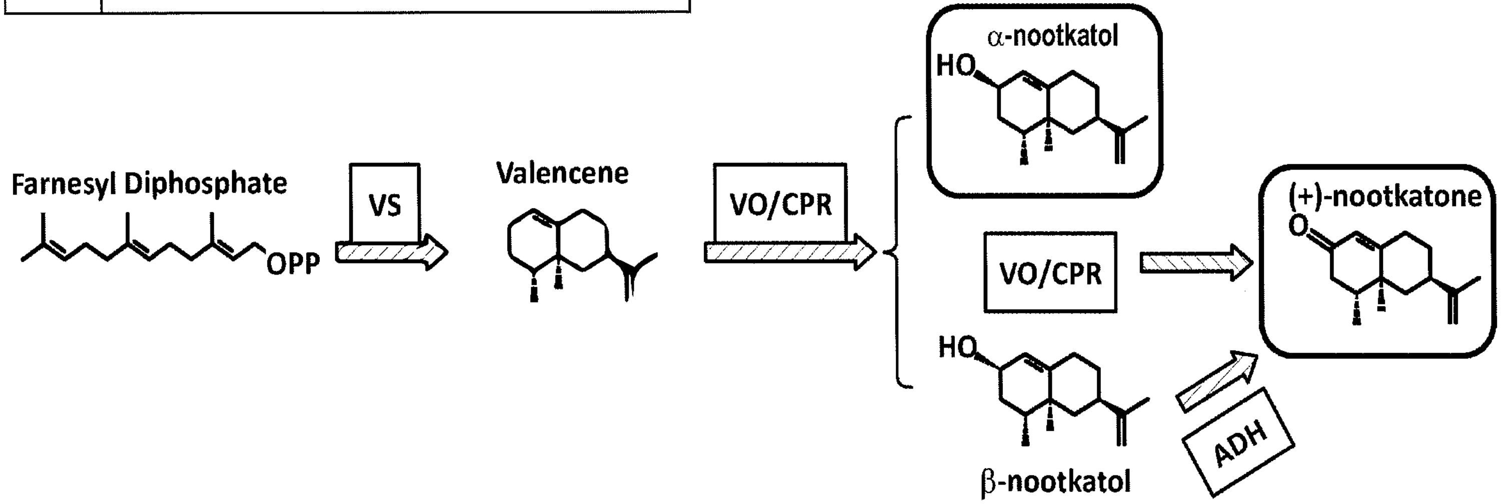
FIG. 11 illustrates an exemplary downstream pathway for expression in the host cell, for conversion of farnesyl diphosphate to nootkatone. Farnesyl diphosphate (produced from IPP/DMAPP by an expressed Farnesyl Pyrophosphate Synthase) is converted to valencene by the action of a Valencene Synthase (VS), which is oxidized by a Valencene Oxidase (VO), such as SrKO or an SrKO derivative described herein. The VO cofactor is regenerated by a cytochrome P450 reductase (CPR). The products of oxidation by VO can include nootkatol (α and β) and nookatone, which can be further directed to nootkatone by the action of an Alcohol Dehydrogenase (ADH).
Figure 12A:
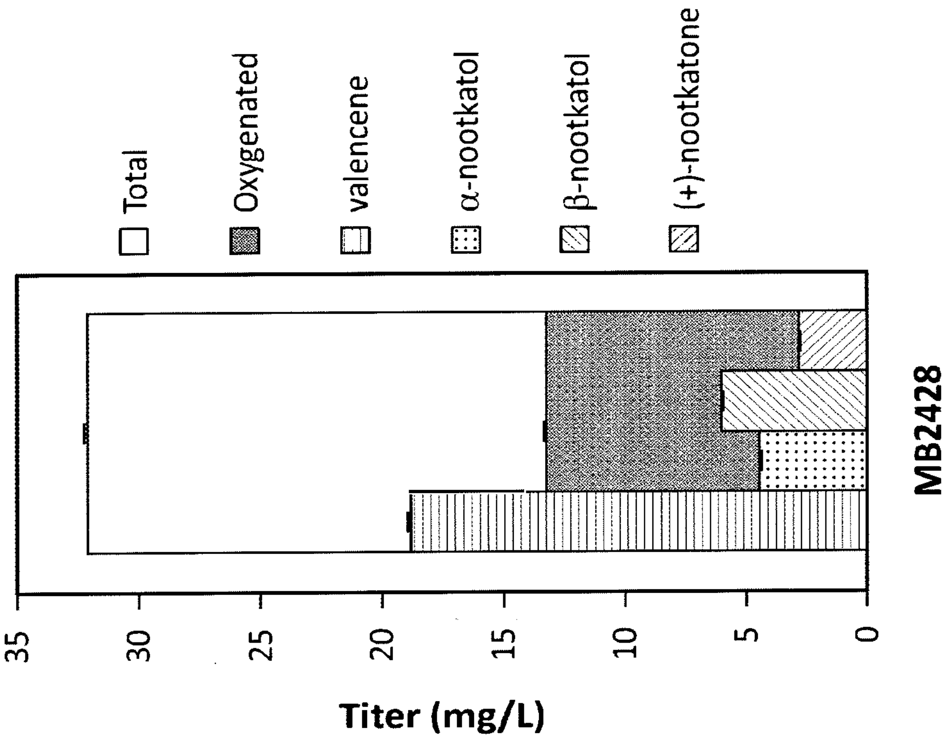
FIG. 12 (A and B) shows the oxygenation profile for a strain expressing VO1-L-SrCPR. The oxygenation profile includes the single oxygenation products of β-nootkatol and α-nootkatol along with the two-step oxygenation product, nootkatone. Panel (A) shows the profile in mg/L. Panel (B) shows the profile by percent of total oxygenated product (the legend for panels (A) and (B) are the same).
Figure 12B:
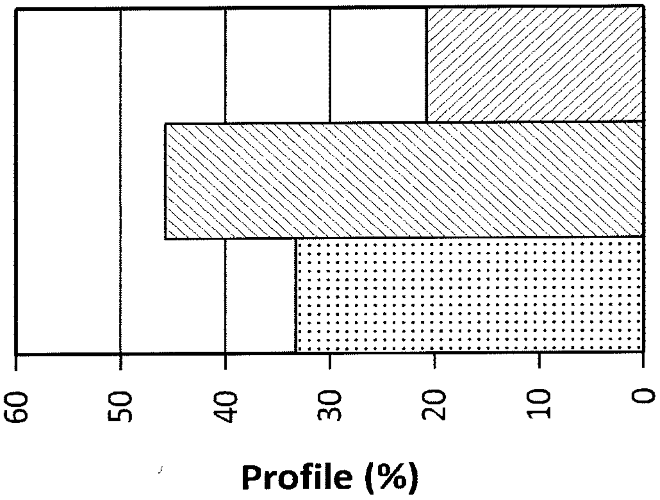

As shown in FIG. 10, n20yhcB_t29VO1 exhibited 1.2-fold productivity in total oxygenated titer compared to the average of controls. N20yhcB_t29VO1 exhibited a total oxygentated titer approximately 1.8 fold of the original 8RP anchor (not shown).

Example 6: Mutational Analysis of VO1

Mutational analysis of VO1 was conducted in an effort to increase oxygenated titers, as well as to produce altered product profiles. Strain MB2509 (MP6-MEP MP1-ScFPPS Fab46-VS2 MP6-ScCPR) was used as the background, which when transformed with a p5-T7-yhcB-VO1 plasmid produces about 18% nootkatone, about 35% α-nootkatol, and about 47% β-nootkatol, with a complete conversion of valencene. Strains were evaluated for higher production of nootkatone and α-nootkatol.

Guided by the homology model based on P450 17A1 (Example 3) site-saturation mutagenesis of the VO active site was conducted at 18 positions, and 5 paired position libraries were constructed. First shell residues were identified through substrate docking, and non-conserved first shell residues were selected based on relative proximity and position for altering the binding pocket geometry. Paired position libraries were constructed by overlap extension PCR and Gibson assembly.

TABLE 12

| Paired Position Libraries (numbered according to SEQ ID NOS: 37 and 108) | | | | |
|---|---|---|---|---|
| Library | Pos. 1 | Allowed AA | Pos. 2 | Allowed AA |
| 1 | V387 | F, L, I, S, P, T, A, M | P388 | S, T, A |
| 2 | M132 | F, L, I, V, S, P, T, A | V133 | F, L, I, S, P, T, A, M |
| 3 | L123 | F, I, V, S, T, A, P, M | L126 | F, I, V, S, T, A, P, M |
| 4 | V387 | F, L, I, S, P, T, A, M | I322 | F, L, V, S, P, A, M, T |
| 5 | I322 | F, L, V, S, P, A, M, T | V133 | F, L, I, S, P, T, A, M |

Strains were evaluated as in Example 4 for total oxygenation of valencene, and ratio of α- to β-nootkatol. Strains were evaluated at 30° C. and 22° C.

Primary screening of paired position libraries revealed that many of the variants lost activity. Library 3 contained variants with improved activity at 22° C. but not 30° C. Thus, introducing two or more mutations simultaneously in the first shell residues can be determimental to activity.

TABLE 13

| The following single position SSM was conducted (numbered according to SEQ ID NOS: 37 and 108) | | |
|---|---|---|
| Residue | Location | |
| I390 | Channel | |
| L392 | Channel | |
| V387 | 1st Shell | |
| E323 | 1st Shell | I helix |
| I322 | 1st Shell | I helix |
| T499 | 1st Shell | |
| Q500 | 1st Shell | |
| L231 | 1st Shell | F helix |
| L123 | 1st Shell | B-C loop |
| L126 | 1st Shell | B-C loop |
| V125 | 1st Shell | B-C loop |
| V133 | 1st Shell | F87 on BM3 |
| T131 | Channel | |
| M135 | 1st Shell | |
| L234 | 1st Shell | F helix |
| P238 | 1st Shell | F-G loop |
| M132 | 1st Shell | B-C loop |
| P388 | 1st Shell | |

Several variants improved oxygenated titers up to 1.7-fold or improved α/β-LGN ratios up to 3.8-fold. Mutations at positions E323, 1390, and Q500 showed several hits with improved oxygenation titer and/or improved α/β profile, and these positions were selected for secondary screening.

Figure 13A:
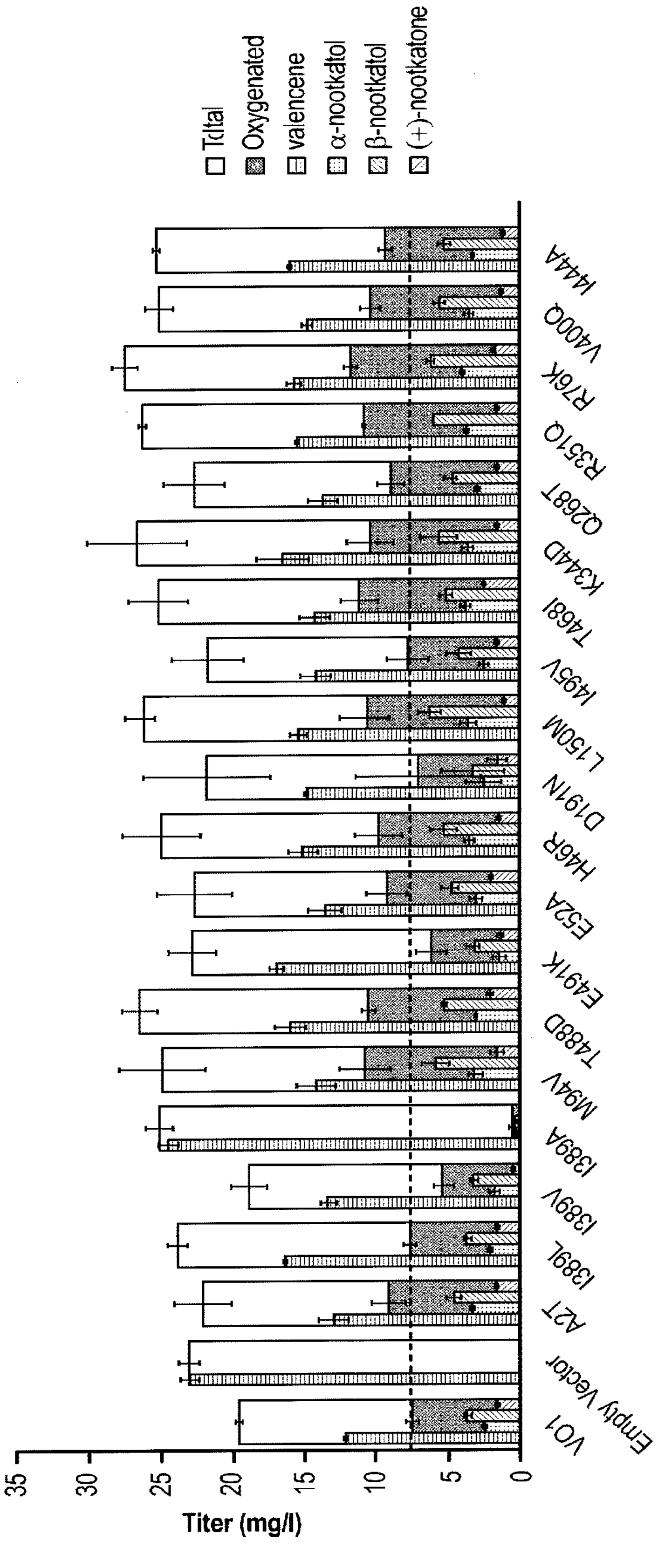
FIG. 13 (A and B) shows evaluation of mutations identified using a back-to-consensus strategy in wild-type SrKO, translated into an engineered valencene oxidase background (n22yhcB_t30VO1 (SEQ ID NO: 104)). More than 50% of the mutations resulted in a 1.2 to 1.45 fold improvement in total oxygenated titers. Panel (A) shows titer in mg/L. Panel (B) shows fold change in oxygenated titer and ratio of α/βnootkatol.
Figure 13B:
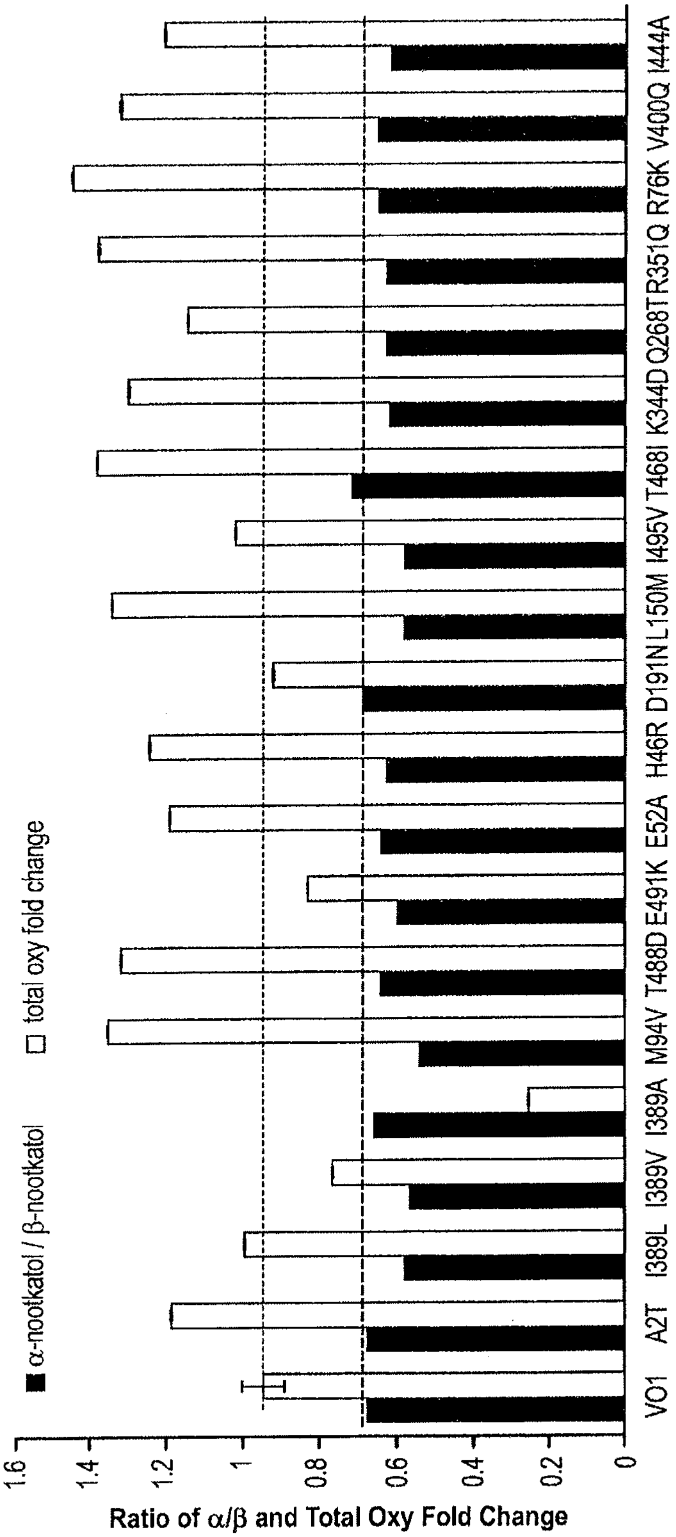

Next, back-to-consensusmutations (19 mutants) were screened in the VO1 background. Using the screening process described in Example 3, the following mutations were screened: A2T, 1389L, I389V, I389A, M94V, T488D, E491 K, E52A, H46R, D 191N, L150M, 1495V, T468I, K344D, Q268T, R351Q, R76K, V400Q, and I444A (numbered according to SEQ ID NO: 37). As shown in FIG. 13A, more than 50% of the mutations resulted in 1.2 to 1.45 times oxygenated titers (shown as mg/L), without dramatic shifts in product profile. Improvements were seen with A2T, M94V, T488D, E52A, H46R, L150M, T468I, K344D, Q268T, R351Q, R76K, V400Q, and I444A, which were selected for secondary screening. FIG. 13B shows the same screen plotted versus fold total oxygenated product change and α-/β-nootkatol ratio.

Figure 14:
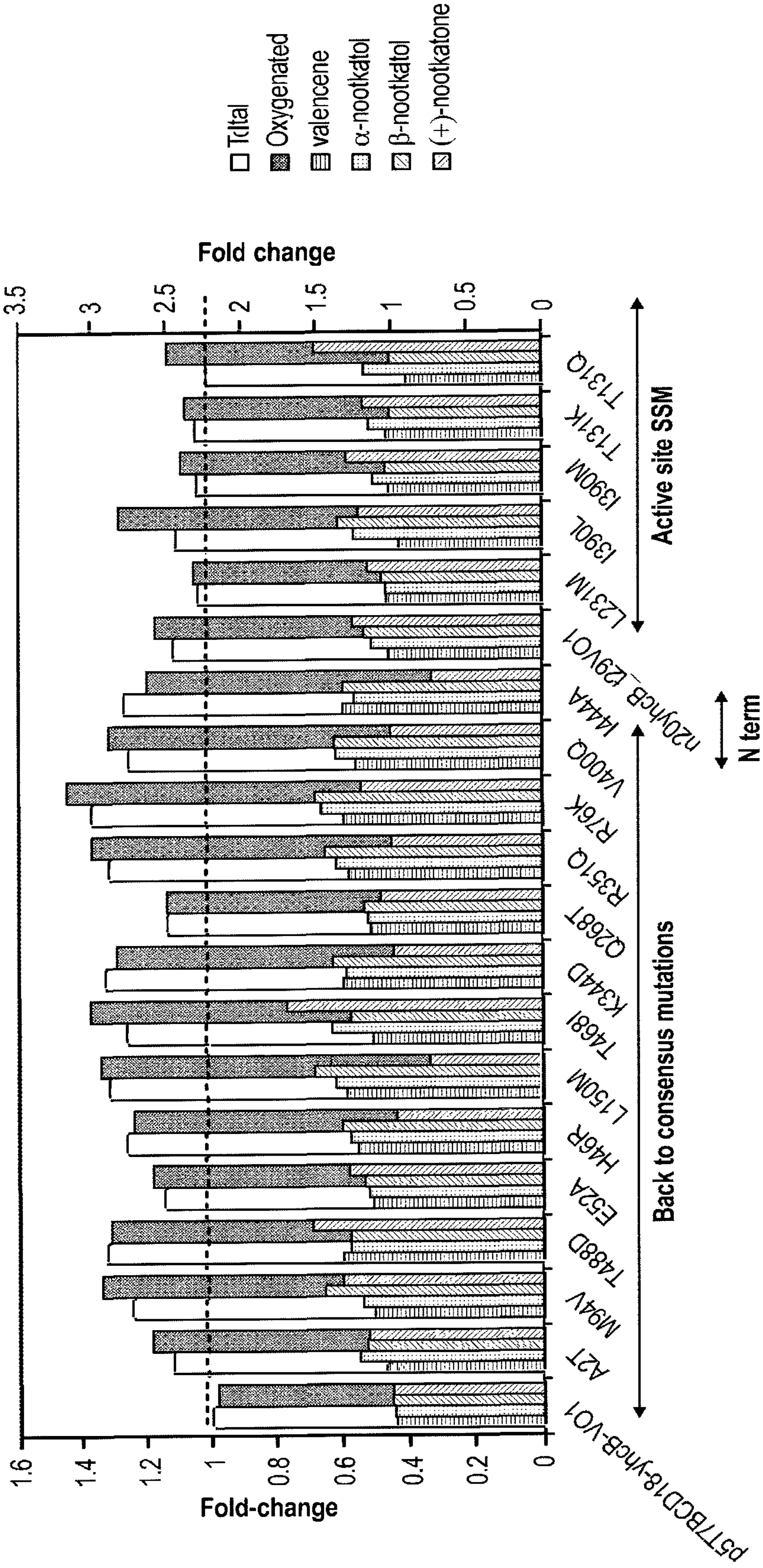
FIG. 14 shows results of secondary screening of back-to-consensus mutations, N-terminal anchor optimization, and site-saturation mutagenesis (SSM). Several mutations were identified that show a 1.1 to 1.4-fold improvement in oxygenated titers.
Figure 15:
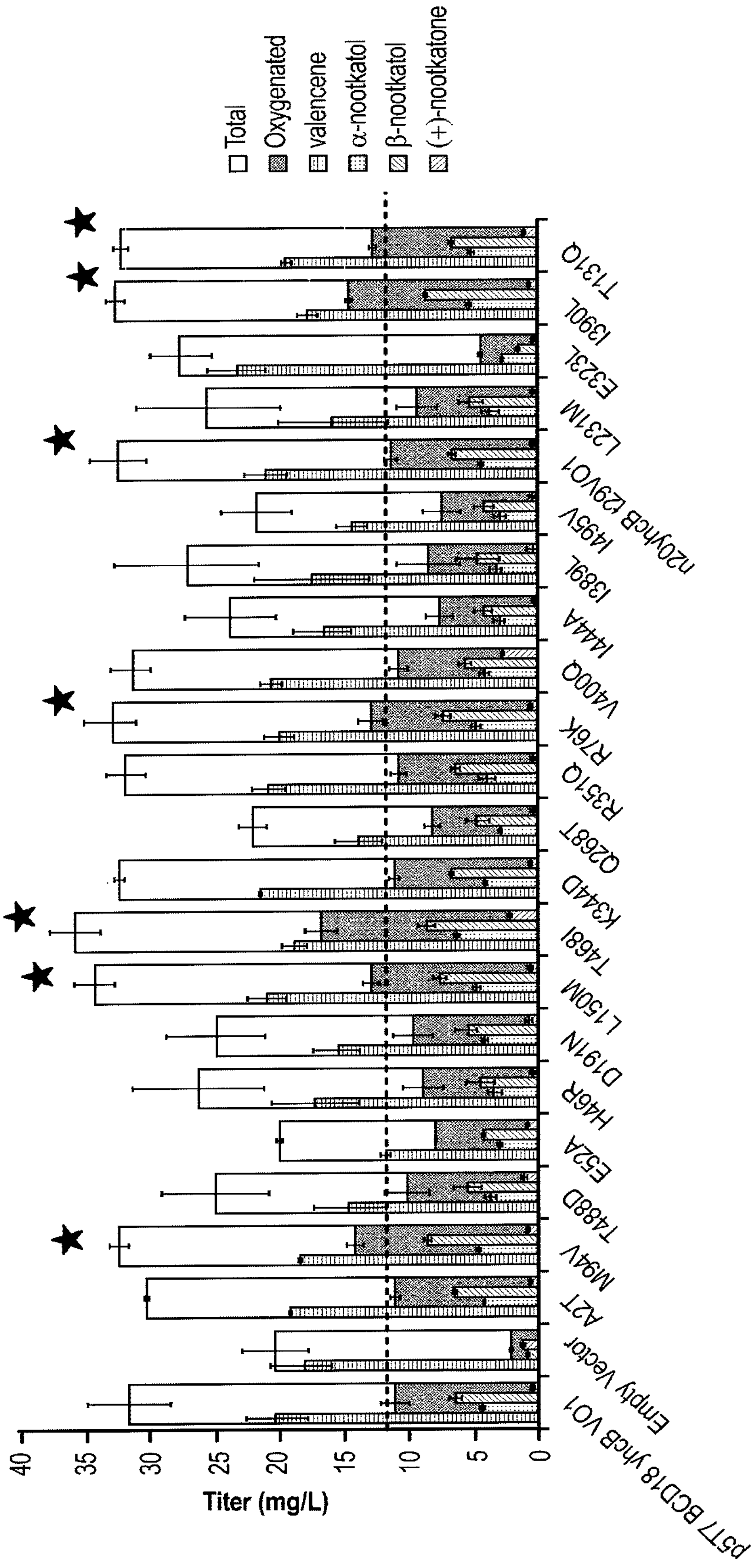
FIG. 15 shows performance of select VO1 variants at 33° C. Six mutations were identified that maintained improved productivities at 33° C.

Lead variants from active site SSM (L231M, I390L, 1390M, T131K, and T131Q), the N-terminal anchor variant n20yhcB_t29VO1, and back-to-consensus mutagenesis were selected, and re-screened. The results of this secondary screen are shown in FIG. 14. Several mutations showed a 1.1-1.4-fold improvement in oxygenated titers. To narrow the list of mutations for recombination, the same mutations were screened at 33° C. to differentiate stabilizing mutations which could enable a process shift to higher temperature. As shown in FIG. 15, six mutations (M94V, L150M, T468I, R76K, I390L, and T131Q) maintained improved productivities at 33° C. These six mutations, in addition to the lead N-terminal anchor, were selected for recombination.

Example 7: SrKO Recombination Library Screening

The seven mutations selected after secondary screening (Example 6) were randomly incorporated into a VO recombination library by allowing either the variant or wild type at each site. The background strain was MB2509 (EGV G2 MP6-CPR)+pBAC-T7-BCD7-yhcB-VO.

Figure 16A:
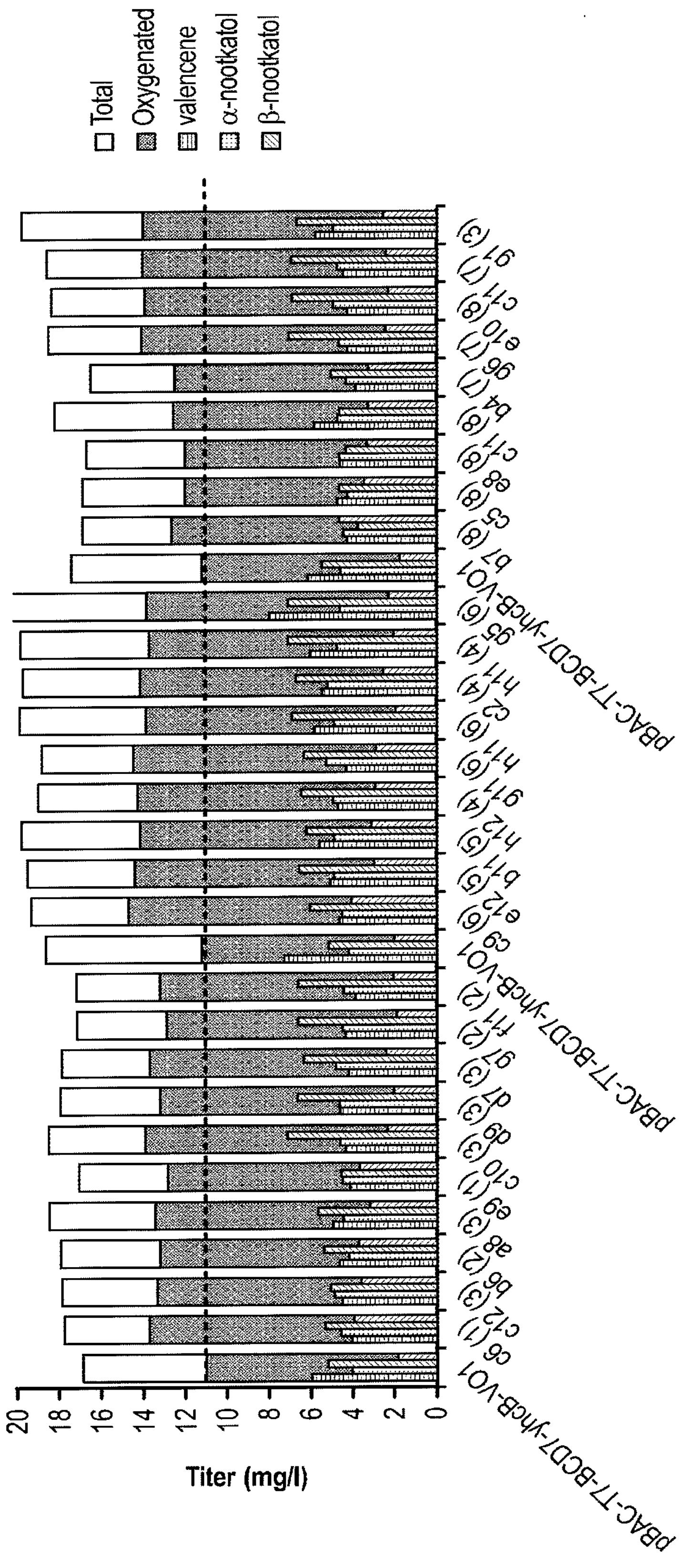
FIG. 16 (A and B) shows results from primary screening of the recombination library. Several variants (shown) exhibited up to 1.35-fold improvement in oxygenated product titer. There was a shift in profile to more (+)-nootkatone and higher oxygenation capacity for select variants. Panel (A) shows oxygenated product in mg/L. Panel (B) plots the fold change in oxygenation capacity (nootkatols require only one oxygenation cycle from valencene, while nootkatone requires two oxygenation cycles).
Figure 16B:
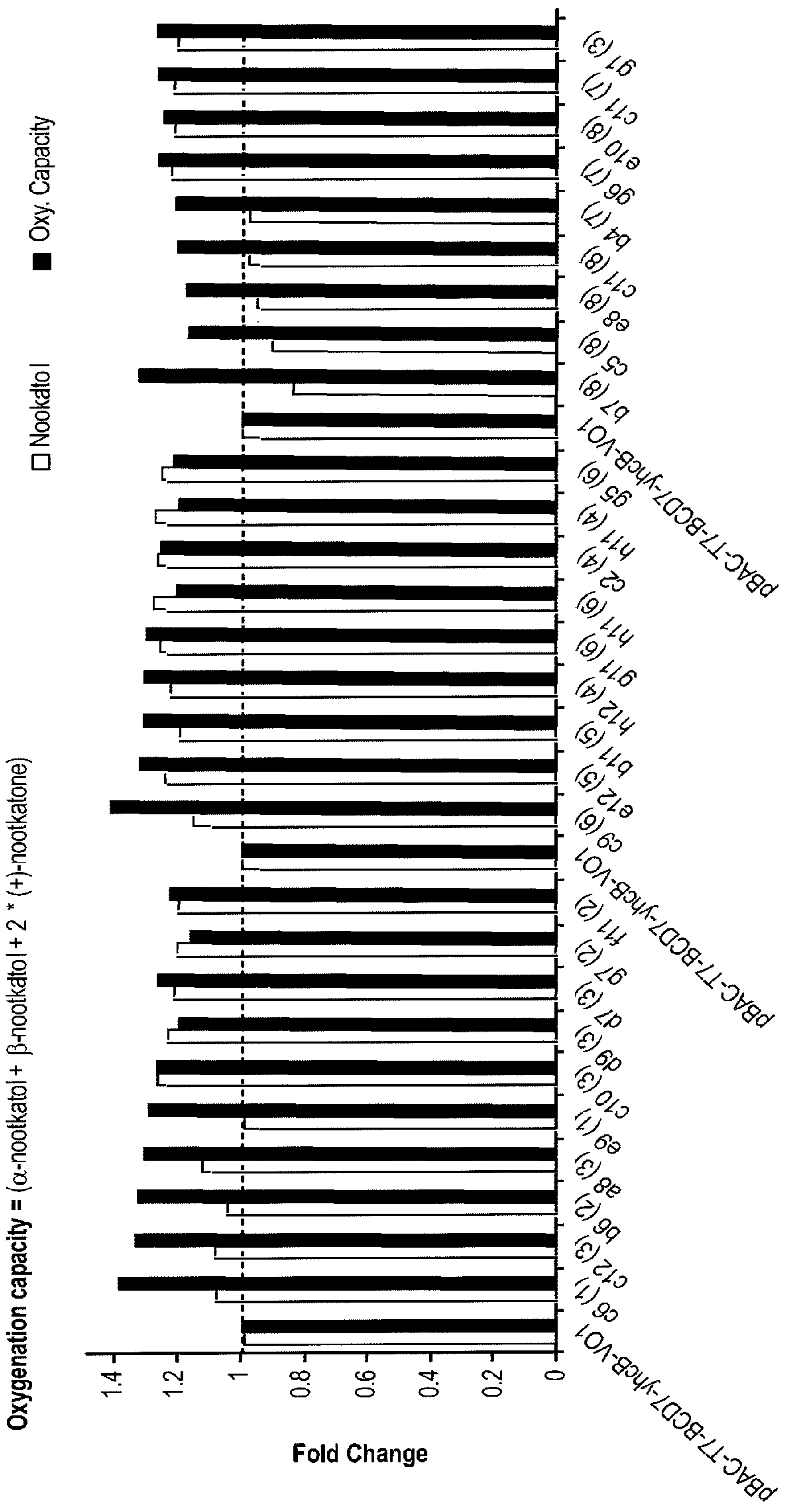

Primary screening at 30° C. (using the same process described in Example 5) identified several variants with up to 1.35-fold improvement in oxygenated product titers, compared to VO1. Further, select variants showed a shift in production to nootkatone, suggesting higher P450 activity (since production of nootkatone requires two oxygenation cycles). Results of primary screening are shown in FIG. 16A (strain versus titer in mg/L). FIG. 16B presents the same screen shown based on oxygenation capacity (total of nootkatone, α-nootkatol, and β-nootkatol).

Figure 17:
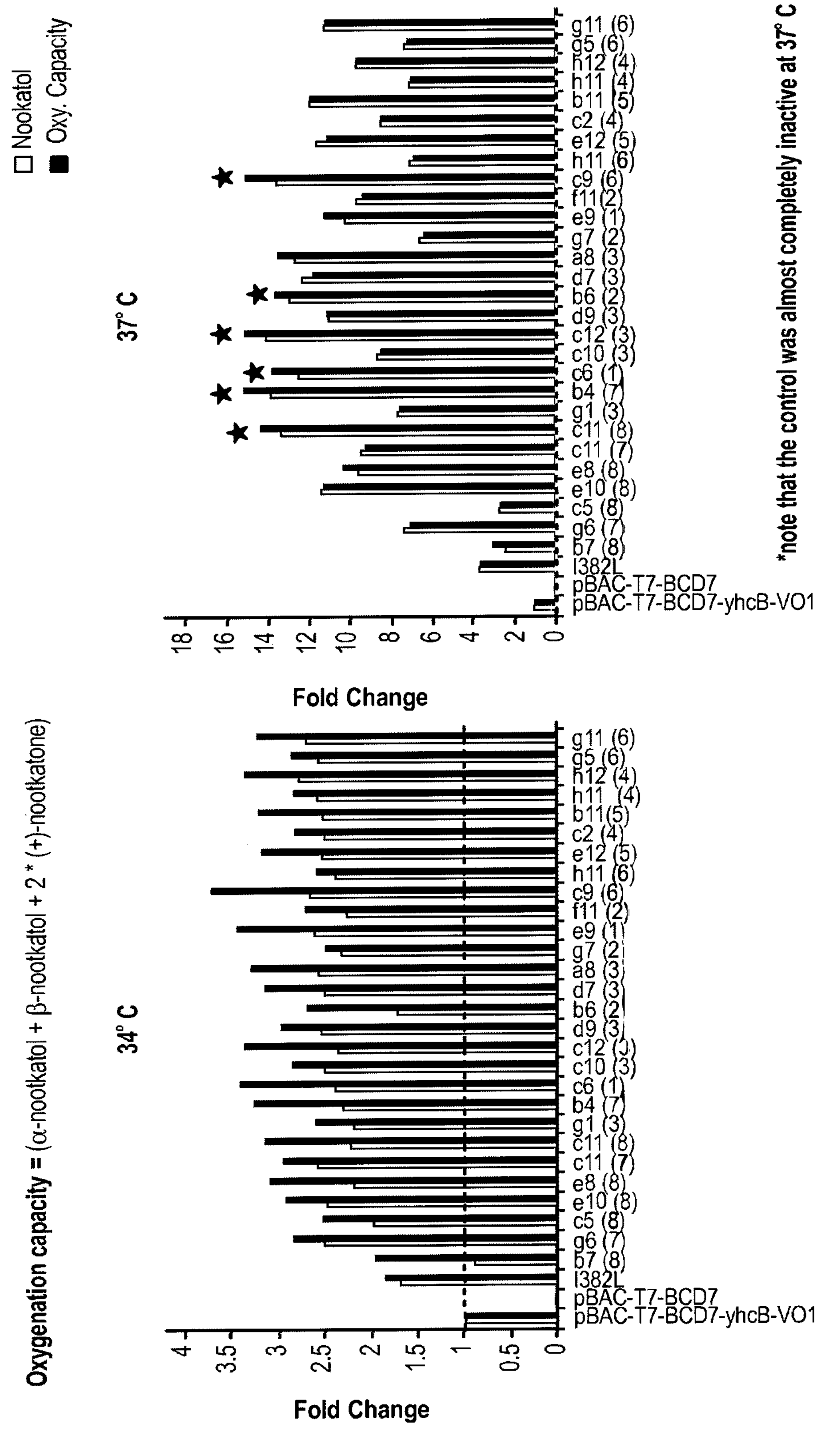
FIG. 17 shows oxygenation capacity at 34° C. and 37° C. for select VO recombination library variants.
Figure 18:
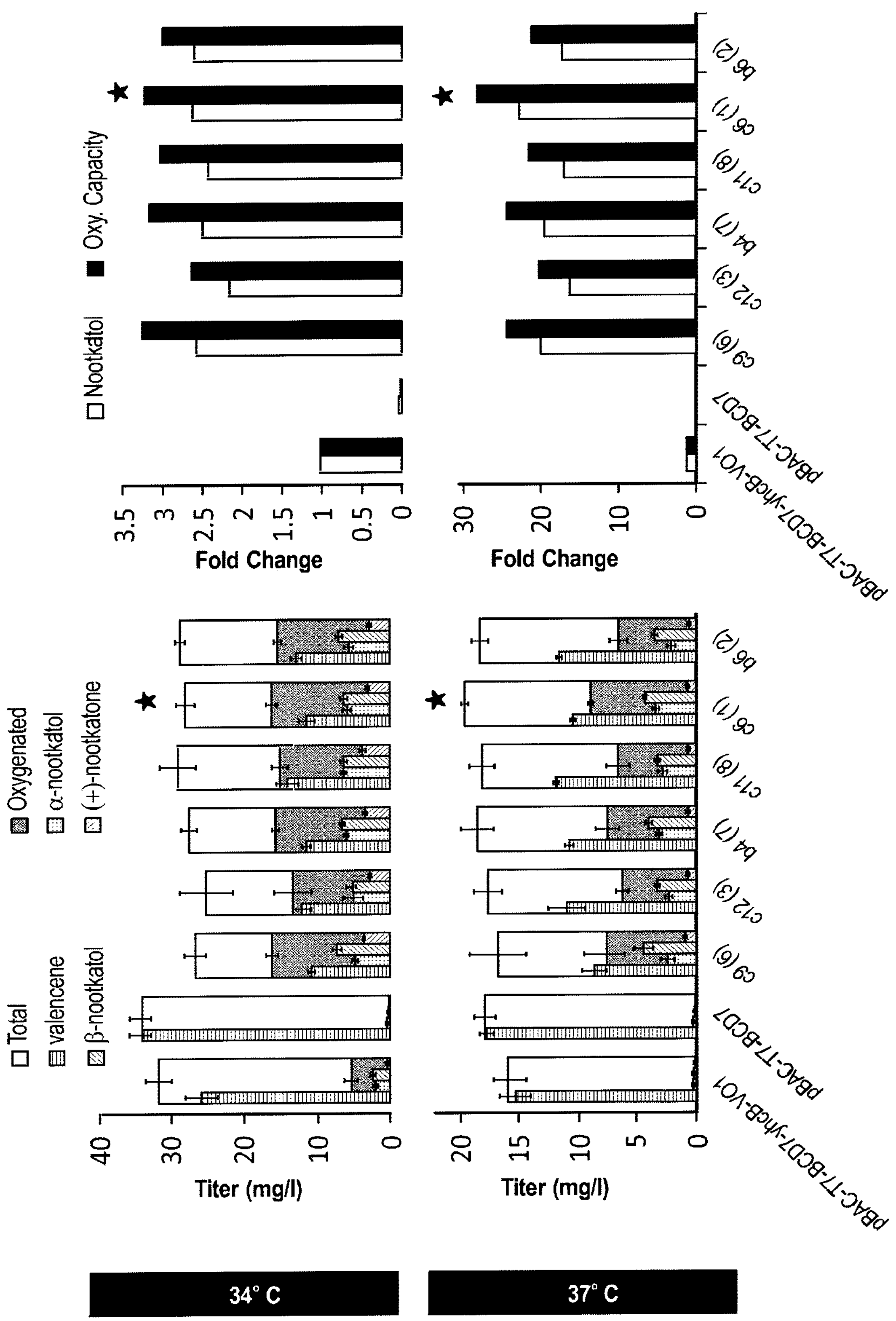
FIG. 18 shows oxygenation titer at 34° C. and 37° C. after re-screen of lead VO variants. C6(1) (R76K, M94V, T131Q, I390L, T468I) had the highest oxygenation capacity at 37° C., and was designated VO2 (SEQ ID NO: 111).
Figure 19:
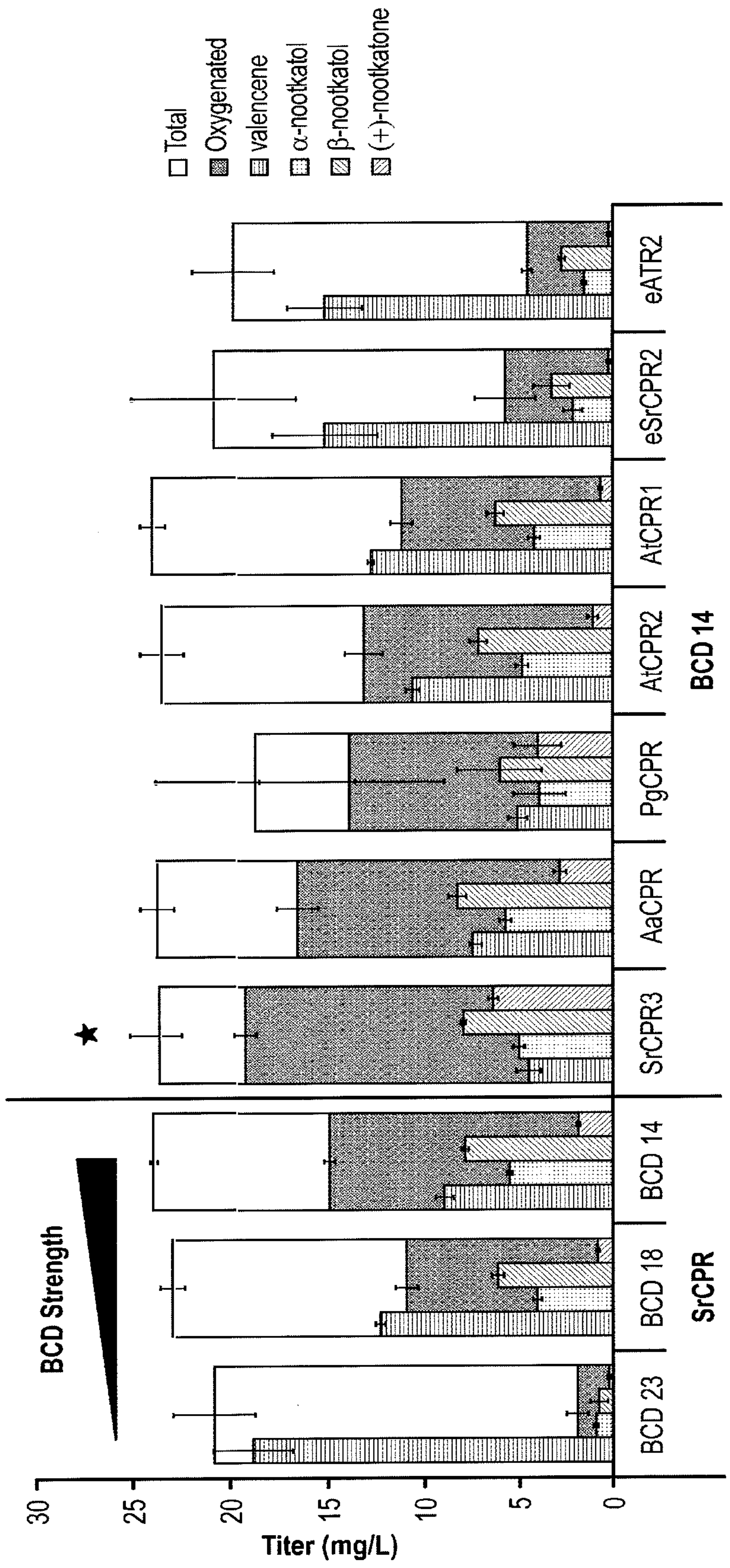
FIG. 19 shows screening of cytochrome P450 reductase (CPR) orthologs for enhanced valencene oxidase activity (30° C.). SrCPR3 shows increased oxygenation titer and higher production of Nootkatone.

The recombination variants were then screened at 34° C. and 37° C. to select leads with improved activity and stability at higher temperature. The results of the secondary screen are shown in FIG. 17. While the control was almost completely inactive at 37° C., six leads showed promising activity at the higher temperatures, and were selected for further screening (c11(8), b4(7), c6(1), c12(3), b6(2), and c9(6)). Based on this further screening (FIG. 18) c6(1) was selected as the best variant based on oxygenation capacity. Variant c6(1) was further modified to generate VO2 (SEQ ID NO: 111). The six leads contain the following sets of mutations.

TABLE 14

Sets of mutations in lead variants from recombination library (shown relative to SEQ ID NOS: 37 and 108).

| | N20_t29yhcB | R76K | M94V | T131Q | L150M | I390L | T468I | A39H | Others |
|---|---|---|---|---|---|---|---|---|---|
| c9(6) | | | X | | | X | X | | V146L |
| c12(3) | | X | | X | | X | X | | |
| b4(7) | | | X | X | | X | X | X | |
| c11(8) | X | X | | X | | X | X | X | |
| c6(1) | | X | X | X | | X | X | | |
| b6(2) | | X | X | | | | X | | |

FIG. 23 (A and B) shows alignments of several engineered valencene oxidase (VO) variants as described herein, and highlights select mutations evaluated in the screening process. In FIG. 23A: 8rp-t20SrK0 (SEQ ID NO: 106) is the SrKO sequence with a 20-amino acid truncation at the N-terminus, and the addition of an 8-amino acid membrane anchor. 8rp-t20VO0 (SEQ ID NO: 107) has a truncation of 20 amino acids of the SrKO N-terminus, the addition of an 8-amino acid N-terminal anchor, and a single mutation at position 499 (numbered according to wild-type SrKO). n22yhcB-t30V01 (SEQ ID NO: 104) has a 30-amino acid truncation of the Si-KO N-terminus, a membrane anchor based on 22 amino acids from *E. coli* yhcB, and eight point mutations at positions 46, 231, 284, 383, 400, 444, 488, and 499 (with respect to SrKO wild-type). n22yhcB-t30V02 (SEQ ID NOS: 61 and 105) has a 30-amino acid truncation of the SrKO N-terminus, a membrane anchor based on 22 amino acids from *E. coli* yhcB, and nine point mutations at positions 76, 94, 131, 231, 284, 383, 390, 468, and 499 (with respect to SrKO wild-type). In FIG. 23B, point mutations in VO0 (SEQ ID NO: 109), VO1 (SEQ ID NO: 110), and VO2 (SEQ ID NO: 111) are shown against wild-type SrKO (SEQ ID NO: 108) (all shown with the wild-type SrKO N-terminus for convenience).

Example 8: Cytochrome P450 Reductase Screening

A set of cytochrome P450 reductases were screened for improved activity with VO1. This example was done using the strain MB2459 as the background, with pBAC-T7-BCD7-VO1(I382L)-T7BCDx-CPRx. BCD stands for BiCistronic Design, and is described in Mutalik et. al. *Nature Methods* 2013(10)4:354. Lower BCD numbers refer to higher translation rate. CPRs included SrCPR (SEQ ID NO: 62), SrCPR3 (SEQ ID NO: 80), AaCPR (SEQ ID NO: 68), PgCPR (SEQ ID NO: 82), AtCPR2 (SEQ ID NO: 72), AtCPR1 (SEQ ID NO: 70), eSrCPR1 (SEQ ID NO: 76), and eATR2 (SEQ ID NO: 74). Strains were tested as in Example 5, at 30° C.

Figure 20:
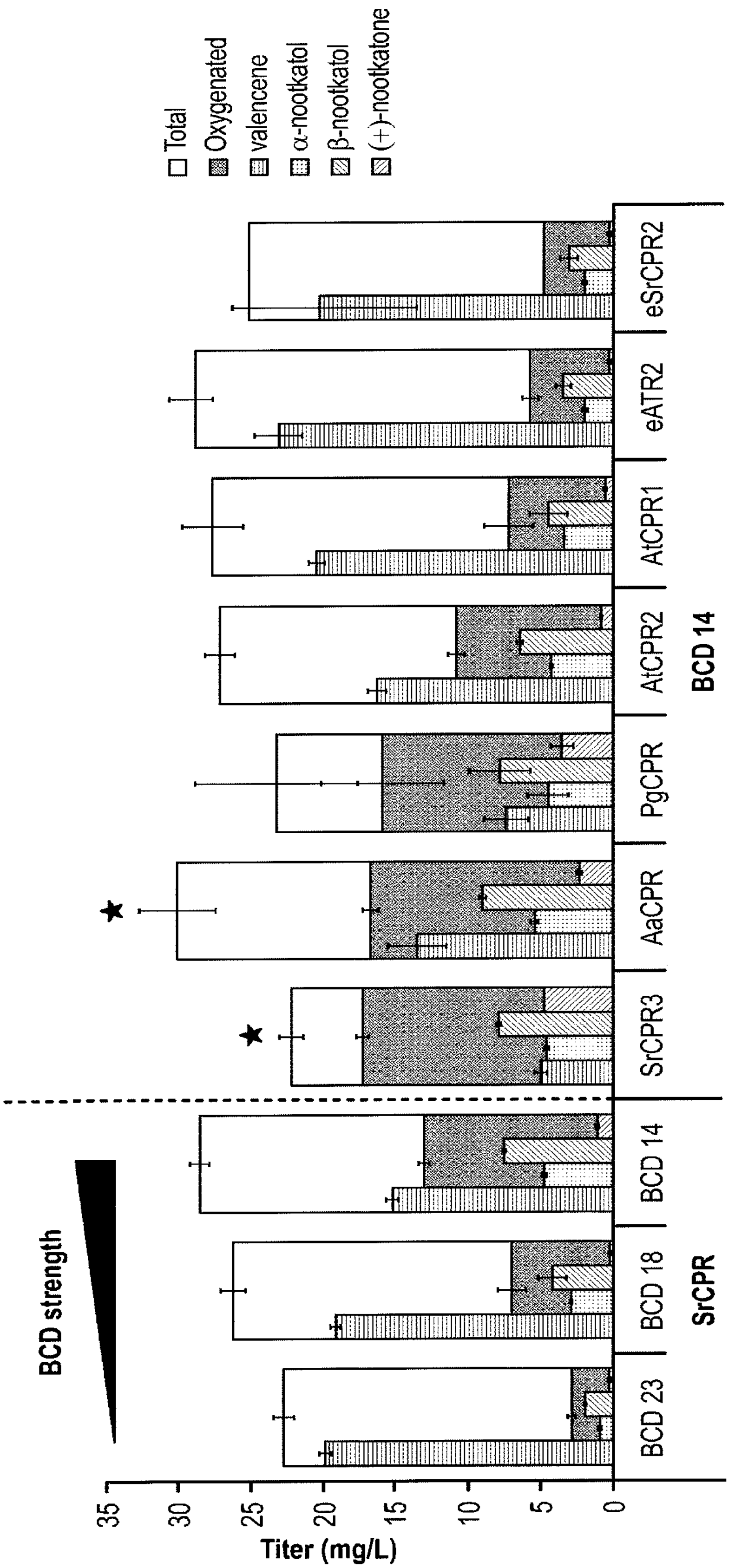
FIG. 20 shows screening of CPR orthologs at 34° C. SrCPR3 and AaCPR exhibit ~1.3-fold improvement in oxygenated titer, even at the higher temperature.

As shown in FIG. 20, SrCPR3, which was obtained through RNA sequencing studies, exhibited a 1.3-fold improvement in oxygenated titer.

The CPR orthologs were retested at 34° C. The results are shown in FIG. 20. Both SrCPR3 (SEQ ID NO: 80) and AaCPR (SEQ ID NO: 68) exhibited a 1.3-fold improvement in oxygenated titer, even at the higher temperature. Oxygenated titers are comparable to those obtained at 30° C.

Example 9: Alcohol Dehydrogenase Enzymes to Alter Product Profile

The ability of alcohol dehydrogenases to convert nootkatols to nootkatone was evaluated. The following ADH enzymes were evaluated:

TABLE 15

| CPR enzymes | | |
|---|---|---|
| Gene | UniProtID | Organism |
| reCDH | Q9RA05 | *Rhodococcus erythropolis* |
| csDH1 | A0A067H4B8 | *Citrus sinensis* |
| csDH2 | A0A067H4S0 | *Citrus sinensis* |
| csDH3 | | *Citrus sinensis* |
| vvDH | F6GX78 | *Vitis vinifera* |
| voDH1 | | |
| csABA2 | A0A067DRA0 | *Citrus sinensis* |
| csDH | A0A0A0KNF1 | *Cucumis sativus* |
| bdDH | I1GLS4 | *Brachypodium distachyon* |
| zzSDR | F1SWA0 | *Zingiber zerumbet* |

Strains were evaluated as in Example 5, using MB2490 as the background strain (MP6-MEP FAB46-ScFPPS-L-VS1 MP6-VO1-o-SrCPR+p5-T7-BCD14-ADH). Briefly, MP6, Fab46 and T7 refer to the promoter for the attached gene or operon. Here MEP is an operon overexpressing *E. coli* dxs, idi, and ispDF genes. The L between ScFPPS and VS1 refers to a short polypeptide linker encoding (GSTGS) while -o-between VO1 and SrCPR refers to an operonic construction in which an RBS sequence is inserted between the two genes. The plus denotes a plasmid following which is described as a p5 (five copy) plasmid with a promoter, BCD (described above) and the ADH in question.

Figure 21:
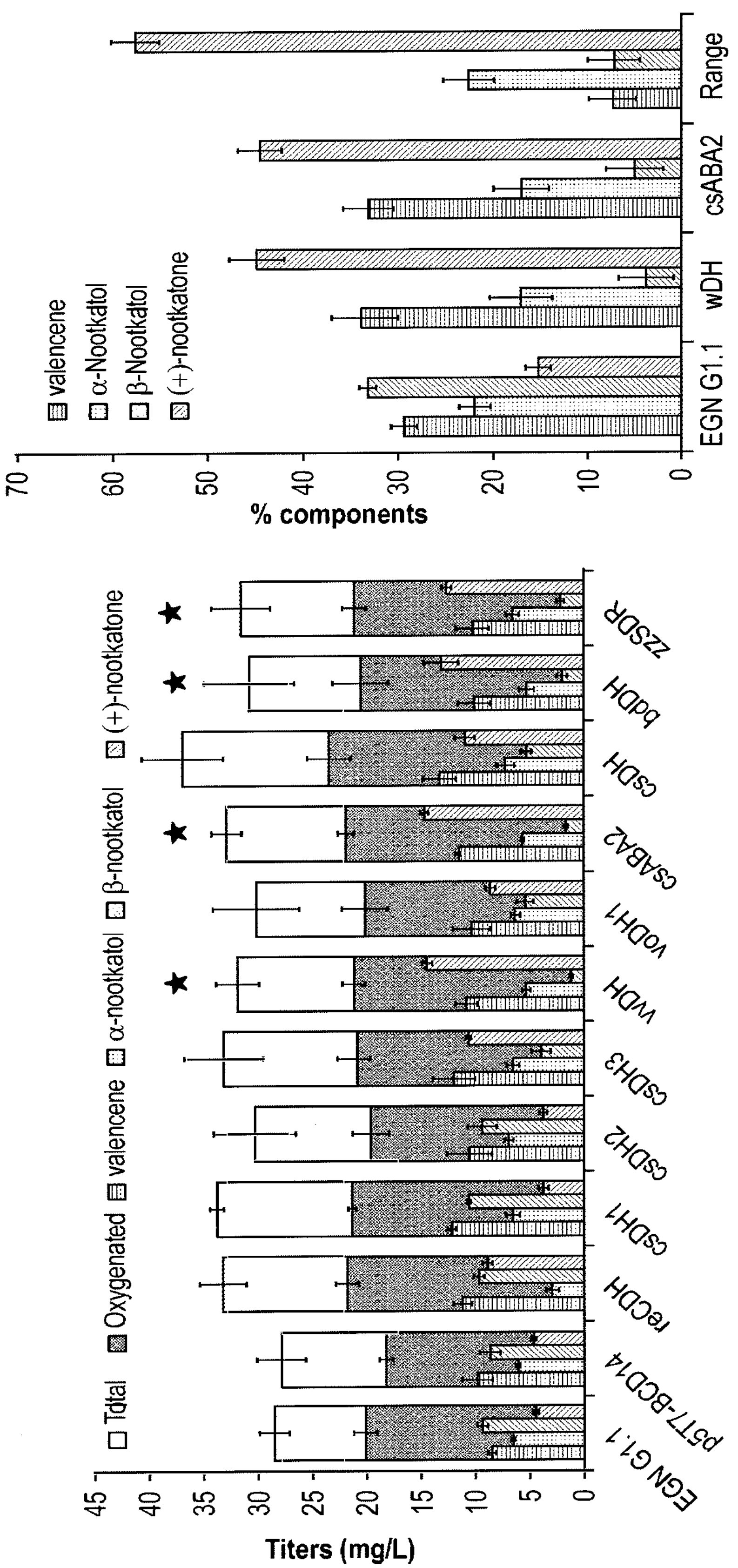
FIG. 21 shows conversion of nootkatols to nootkatone with an alcohol dehydrogenase (ADH). Four ADH orthologs (vvDH, csABA2, bdDH, and zzSDR) were identified that convert f3-nootkatol to (+)-nootkatone, resulting in a 3-fold increase in (+)-nootkatone titers and an increase in proportion of α-nootkatol.

Four orthologs were identified (vvDH, csABA2, bdDH, and zzSDR) that convert β-nootkatol to nootkatone, resulting in more than a 3-fold increase in nootkatone titers. FIG. 21.

REFERENCES

1. Qualley A, Dudareva N. Plant Volatiles. Encycl. Life Sci. 2010; 1-9.
2. Ajikumar P, Tyo K, Carlsen S. Terpenoids: opportunities for biosynthesis of natural product drugs using engineered microorganisms. Mol. Pharm. [Internet]. 2008 [cited 2013 May 16]; 5(2):167-90.
3. Ajikumar P K, Xiao W-H, Tyo K E J, Wang Y, Simeon F, Leonard E, et al. Isoprenoid pathway optimization for Taxol precursor overproduction in *Escherichia coli*. Science [Internet]. 2010 Oct. 1 [cited 2013 May 22]; 330 (6000):70-4.
4. Ro D-K, Paradise E M, Ouellet M, Fisher K J, Newman K L, Ndungu J M, et al. Production of the antimalarial drug precursor artemisinic acid in engineered yeast. Nature [Internet]. 2006 Apr. 13 [cited 2013 Mar. 1]; 440(7086):940-3.
5. Sevrioukova I F, Li H, Zhang H, Peterson J a, Poulos T L. Structure of a cytochrome P450-redox partner electron-transfer complex. Proc. Natl. Acad. Sci. U.S.A. [Internet]. 1999 Mar. 2; 96(5):1863-8.
6. Sevrioukova I F, Poulos T L. Structural biology of redox partner interactions in P450cam monooxygenase: a fresh look at an old system. Arch. Biochem. Biophys. [Internet]. Elsevier Inc.; 2011 Mar. 1 [cited 2013 Mar. 26]; 507(1):66-74.
7. Ekroos M, Sjögren T. Structural basis for ligand promiscuity in cytochrome P450 3A4. Proc. Natl. Acad. Sci. U.S.A. [Internet]. 2006 Sep. 12; 103(37):13682-7.
8. Takahashi S, Yeo Y-S, Zhao Y, O'Maille P E, Greenhagen B T, Noel J P, et al. Functional characterization of premnaspirodiene oxygenase, a cytochrome P450 catalyzing regio- and stereo-specific hydroxylations of diverse sesquiterpene substrates. J. Biol. Chem. [Internet]. 2007 Oct. 26 [cited 2013 Mar. 10]; 282(43):31744-54.
9. Morrone D, Chen X, Coates R M, Peters R J. Characterization of the kaurene oxidase CYP701A3, a multifunctional cytochrome P450 from gibberellin biosynthesis. Biochem. J. [Internet]. 2010 Nov. 1 [cited 2013 Feb. 6]; 431(3):337-44.
10. Zhang Z, Sibbesen O. The substrate specificity of cytochrome P450 cam. Bioorganic Med. . . . [Internet]. 1998 [cited 2013 Sep. 24]; 6:1501-8.
11. Stjernschantz E, van Vugt-Lussenburg B M a, Bonifacio A, de Beer S B a, van der Zwan G, Gooijer C, et al. Structural rationalization of novel drug metabolizing mutants of cytochrome P450 BM3. Proteins [Internet]. 2008 April [cited 2013 May 16]; 71(1):336-52.
12. Chen M M Y, Snow C D, Vizcarra C L, Mayo S L, Arnold F H. Comparison of random mutagenesis and semi-rational designed libraries for improved cytochrome P450 BM3-catalyzed hydroxylation of small alkanes. Protein Eng. Des. Sel. [Internet]. 2012 April [cited 2013 Mar. 11]; 25(4):171-8.
13. Harford-Cross C F, Carmichael a B, Allan F K, England P a, Rouch D a, Wong L L. Protein engineering of cytochrome p450(cam) (CYP101) for the oxidation of polycyclic aromatic hydrocarbons. Protein Eng. [Internet]. 2000 February; 13(2):121-8.
14. Bell S G, Chen X, Sowden R J, Xu F, Williams J N, Wong L, et al. Molecular Recognition in (+)-r-Pinene Oxidation by Cytochrome P450cam. J. Am. Chem. Soc. 2003; 125:705-14.
15. Sowden R, Yasmin S, Rees N, Bell S G, Wong L-L. Biotransformation of the sesquiterpene (+)-valencene by cytochrome P450cam and P450BM-3. Org. Biomol. Chem. [Internet]. 2005 [cited 2013 May 16]; 3:57-64.
16. Brandle J E, Richman A, Swanson A K, Chapman B P. Leaf Ests from *Stevia rebaudiana*: a resource for gene discovery in diterpene synthesis. Plant Mol. Biol. [Internet]. 2002 November [cited 2013 Feb. 12]; 50(4-5):613-22.
17. Bar-even A, Noor E, Savir Y, Liebermeister W, Davidi D, Tawfik D S, et al. The Moderately Efficient Enzyme: Evolutionary and Physicochemical Trends Shaping Enzyme Parameters. Biochemistry. 2011;
18. Pleiss J. Protein design in metabolic engineering and synthetic biology. Curr. Opin. Biotechnol. [Internet]. 2011 October [cited 2013 Mar. 5]; 22(5):611-7.
19. Lehmann M, Pasamontes L, Lassen S F, Wyss M. The consensus concept for thermostability engineering of proteins. Biochim. Biophys. Acta [Internet]. 2000 Dec. 29 [cited 2013 Oct. 17]; 1543(2):408-15.
20. Vazquez-Figueroa E, Yeh V, Broering J M, Chaparro-Riggers J F, Bommarius A S. Thermostable variants constructed via the structure-guided consensus method also show increased stability in salts solutions and homogeneous aqueous-organic media. Protein Eng. Des. Sel. [Internet]. 2008 November [cited 2013 Oct. 17]; 21(11): 673-80.

21. Dai M, Fisher H E, Temirov J, Kiss C, Phipps M E, Pavlik P, et al. The creation of a novel fluorescent protein by guided consensus engineering. Protein Eng. Des. Sel. [Internet]. 2007 February [cited 2013 Sep. 19]; 20(2):69-79.
22. Fraatz M a., Riemer S J L, Stober R, Kaspera R, Nimtz M, Berger R G, et al. A novel oxygenase from Pleurotus sapidus transforms valencene to nootkatone. J. Mol. Catal. B Enzym. [Internet]. 2009 December [cited 2013 Apr. 17]; 61(3-4):202-7.
23. Kriigener S, Krings U, Zorn H, Berger R G. A dioxygenase of Pleurotus sapidus transforms (+)-valencene regio-specifically to (+)-nootkatone via a stereo-specific allylic hydroperoxidation. Bioresour. Technol. [Internet]. Elsevier Ltd; 2010 January [cited 2013 Apr. 12]; 101(2): 457-62.
24. Zorn H, Fraatz M A, Riemer S J L, Takenberg M. Enzymatic synthesis of nootkatone. GERMANY; 2010.
25. Kaspera R, Krings U, Nanzad T, Berger R G. Bioconversion of (+)-valencene in submerged cultures of the ascomycete Chaetomium globosum. Appl. Microbiol. Biotechnol. [Internet]. 2005 June [cited 2013 May 16]; 67(4):477-83.
26. Cankar K, van Houwelingen A, Bosch D, Sonke T, Bouwmeester H, Beekwilder J. A chicory cytochrome P450 mono-oxygenase CYP71AV8 for the oxidation of (+)-valencene. FEBS Lett. [Internet]. Federation of European Biochemical Societies; 2011 Jan. 3 [cited 2013 Mar. 6]; 585(1):178-82.
27. Girhard M, Machida K, Itoh M, Schmid R D, Arisawa A, Urlacher V B. Regioselective biooxidation of (+)-valencene by recombinant *E. coli* expressing CYP109B1 from *Bacillus subtilis* in a two-liquid-phase system. Microb. Cell Fact. [Internet]. 2009 January [cited 2013 May 16]; 8(4):36.
28. Bm-P, Sowden R J, Yasmin S, Rees N H, Bell S G, Wong L. Biotransformation of the sesquiterpene (+)-valencene by cytochrome P450.2005; 57-64.
29. Trott O, Olson A. AutoDock Vina: improving the speed and accuracy of docking with a new scoring function, efficient optimization, and multithreading. J. Comput. Chem. [Internet]. 2010 [cited 2013 Jul. 26]; 31(2):455-61.1

The invention claimed is:

1. A method of making a formulation comprising nootkatone, α-nootkatol, and β-nootkatol, the method comprising:

contacting valencene with *Stevia rebaudiana* Kaurene Oxidase (SrKO) or an SrKO derivative comprising a sequence having at least 70% sequence identity to SEQ ID NO: 37, SEQ ID NO: 38, or SEQ ID NO: 55, and having valencene oxidizing activity in an in vitro or in vivo system to produce an oxygenated product comprising nootkatone, α-nootkatol, and β-nootkatol.

2. The method of claim 1, further comprising processing the oxygenated product by fractional distillation to yield two or more fractions of the oxygenated product.

3. The method of claim 2, further comprising blending the two or more fractions of the oxygenated product.

4. The method of claim 1, further comprising adding an unoxygenated product to the oxygenated product, one or more fractions of the oxygenated product, or the formulation.

5. The method of claim 1, wherein the nootkatone is present in the formulation in an amount ranging from about 55% to about 60% (w/w), the α-nootkatol is present in the formulation in an amount ranging from about 20% to about 25% (w/w), and the β-nootkatol is present in the formulation an amount ranging from about 5% to about 10% (w/w).

6. The method of claim 4, wherein the unoxygenated product comprises valencene.

7. The method of claim 6, wherein the valencene is present in the formulation in an amount ranging from about 5% to about 10% (w/w).

8. The method of claim 1, wherein the SrKO derivative comprises a sequence having at least 90% sequence identity to SEQ ID NO: 55; wherein the SrKO derivative has one or more mutations relative to SEQ ID NO: 37, 38, or 55; or wherein the SrKO derivative has a deletion of at least a portion of its N-terminal transmembrane region, and the addition of an inner membrane transmembrane domain from *E. coli* yhcB.

9. The method of claim 1, wherein the SrKO derivative is SrKO comprising at least one of:

at least one substitution mutation located at a position selected from a group of 46, 76, 94, 131, 231, 284, 383, 390, 400, 444, 468, 488 and 499, relative to SEQ ID NO: 37;

at least one substitution mutation selected from a group of I310V, V375I and T487N, relative to SEQ ID NO: 38;

a 15 to 35 amino acid deletion of an N-terminal transmembrane domain in the SrKO and addition of 15 to 25 amino acids of *E. coli* yhcB transmembrane domain; or a linker comprising amino acids and cytochrome P450 reductase truncated at its N-terminus.

10. The method of claim 9, wherein the SrKO derivative comprising the substitution mutation T487N further comprises at least one substitution mutation selected from V375F, V375A, V375M, M120L, M1201, M120V, F129L, F1291, L114V, L114F, and V121A relative to SEQ ID NO: 38.

11. The method of claim 1, wherein the SrKO derivative comprises at least one substitution mutation selected from R76K, M94V, T131Q, I390L, and T468I relative to SEQ ID NO: 37.

12. The method of claim 1, wherein the SrKO derivative comprises:

an amino acid sequence selected from SEQ ID NOS: 55-61, 104, and 105; or an amino acid sequence having from one to twenty mutations relative to a sequence selected from SEQ ID NOS: 55-61, 104, and 105.

13. The method of claim 1, wherein the SrKO derivative comprises:

a 20-amino acid truncation of the SrKO N-terminus and an addition of an 8-amino acid membrane anchor of *E. coli* yhcB; or a 30-amino acid truncation of the SrKO N-terminus and an addition of a membrane anchor based on 22 amino acids of *E. coli* yhcB.

14. The method of claim 1 wherein the contacting takes place in a host cell, which is a bacterium or yeast.

15. The method of claim 14, wherein the host cell is a bacterium selected from *E. coli, Bacillus subtilis*, or *Pseudomonas putida*; or a yeast selected from a species of *Saccharomyces, Pichia*, or *Yarrowia.*

16. The method of claim 14, wherein the host cell produces isopentenyl pyrophosphate (IPP) through an endogenous or heterologous MEP or MVA pathway, and optionally through an endogenous MEP pathway having at least one additional copy of a dxs, ispD, ispF, and/or idi gene.

17. The method of claim 16, wherein the host cell further expresses a farnesyl pyrophosphate synthase and a heterologous valencene synthase.

18. The method of claim 17, wherein the valencene synthase is *Citrus sinensis* of SEQ ID NO: 12 or *Vitis vinifera* valencene synthase of SEQ ID NO:1 or derivative thereof having at least 70% sequence identity to SEQ ID NO: 12 or SEQ ID NO: 1.

19. The method of claim 1 wherein the SrKO is expressed in a host cell that co-expresses a cytochrome P450 reductase, which is optionally from *Stevia* sp.

20. The method of claim 19, wherein the host cell further expresses an alcohol dehydrogenase producing nootkatone from nootkatol, which is optionally an alcohol dehydrogenase selected from *Rhodococcus erythropolis* CDH of SEQ ID NO: 84, *Citrus sinensis* DH3 of SEQ ID NO: 92, *Vitis vinifera* DH of SEQ ID NO: 94, *Citrus sinensis* ABA2 of SEQ ID NO: 98, *Brachypodium distachyon* DH of SEQ ID NO: 100, and *Zingiber zerumbet* SDR of SEQ ID NO: 102, or a derivative thereof having at least 70% sequence identity thereto.

* * * * *